United States Patent
Yamamoto et al.

(10) Patent No.: US 10,053,468 B2
(45) Date of Patent: Aug. 21, 2018

(54) HETEROCYCLIC COMPOUND

(71) Applicant: TAKEDA PHARMACEUTICAL COMPANY LIMITED, Osaka-shi, Osaka (JP)

(72) Inventors: Satoshi Yamamoto, Fujisawa (JP); Junya Shirai, Fujisawa (JP); Hiroyuki Watanabe, Kobe (JP); Shoji Fukumoto, Kobe (JP); Tsuneo Oda, Fujisawa (JP); Hidekazu Tokuhara, Fujisawa (JP); Yoshihide Tomata, San Diego, CA (US); Naoki Ishii, Fujisawa (JP); Michiko Tawada, Fujisawa (JP); Mitsunori Kono, Fujisawa (JP); Atsuko Ochida, Fujisawa (JP); Takashi Imada, Fujisawa (JP); Yoshiyuki Fukase, New York, NY (US); Tomoya Yukawa, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/902,309

(22) PCT Filed: Jul. 2, 2014

(86) PCT No.: PCT/JP2014/067650
§ 371 (c)(1),
(2) Date: Dec. 30, 2015

(87) PCT Pub. No.: WO2015/002231
PCT Pub. Date: Jan. 8, 2015

(65) Prior Publication Data
US 2017/0050974 A1    Feb. 23, 2017

(30) Foreign Application Priority Data

Jul. 3, 2013  (JP) ................. 2013-140210

(51) Int. Cl.
| | |
|---|---|
| *C07D 491/056* | (2006.01) |
| *C07D 217/26* | (2006.01) |
| *C07D 401/06* | (2006.01) |
| *C07D 405/06* | (2006.01) |
| *C07D 409/06* | (2006.01) |
| *C07D 413/06* | (2006.01) |
| *C07D 417/06* | (2006.01) |
| *C07D 471/04* | (2006.01) |
| *C07D 491/048* | (2006.01) |
| *C07D 401/12* | (2006.01) |
| *C07D 413/12* | (2006.01) |
| *C07D 491/04* | (2006.01) |
| *C07D 413/14* | (2006.01) |
| *C07D 401/04* | (2006.01) |
| *C07D 405/12* | (2006.01) |
| *C07F 7/08* | (2006.01) |

(52) U.S. Cl.
CPC ....... *C07D 491/056* (2013.01); *C07D 217/26* (2013.01); *C07D 401/04* (2013.01); *C07D 401/06* (2013.01); *C07D 401/12* (2013.01); *C07D 405/06* (2013.01); *C07D 405/12* (2013.01); *C07D 409/06* (2013.01); *C07D 413/06* (2013.01); *C07D 413/12* (2013.01); *C07D 413/14* (2013.01); *C07D 417/06* (2013.01); *C07D 471/04* (2013.01); *C07D 491/04* (2013.01); *C07D 491/048* (2013.01); *C07F 7/0812* (2013.01)

(58) Field of Classification Search
CPC .................................. C07D 491/056
USPC ......................................... 546/112
See application file for complete search history.

(56) References Cited

U.S. PATENT DOCUMENTS

| | | | |
|---|---|---|---|
| 6,066,649 | A | 5/2000 | Podzuweit |
| 6,245,746 | B1 | 6/2001 | Chamberland et al. |
| 7,135,498 | B1 | 11/2006 | Chopp |
| 9,187,453 | B2 | 11/2015 | Tsukamoto |
| 9,365,530 | B2 * | 6/2016 | Nicewicz ............. B01J 31/0239 |

(Continued)

FOREIGN PATENT DOCUMENTS

| | | |
|---|---|---|
| EP | 1341035 | 9/2003 |
| EP | 2873669 | 5/2015 |

(Continued)

OTHER PUBLICATIONS

Largeron Tetrahedron (1994), 50(21), 6307-32.*

(Continued)

*Primary Examiner* — Nizal S Chandrakumar
(74) *Attorney, Agent, or Firm* — Anne M. Reynolds; Casimir Jones, S.C.

(57) ABSTRACT

The present invention relates to compound (I) or a salt thereof which has a RORγt inhibitory action.

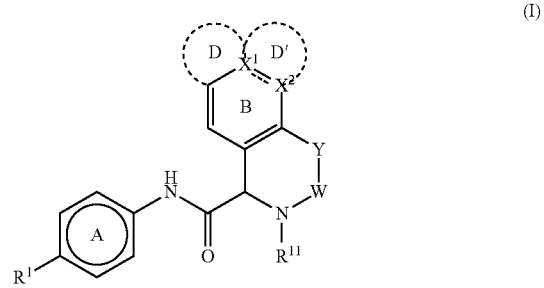

wherein each symbol is as defined in the specification.

18 Claims, No Drawings

(56) References Cited

U.S. PATENT DOCUMENTS

| | | |
|---|---|---|
| 9,573,903 B2* | 2/2017 | Yamamoto .......... C07D 217/26 |
| 2002/0032203 A1 | 3/2002 | Swope |
| 2002/0119978 A1 | 8/2002 | Swope |
| 2002/0132754 A1 | 9/2002 | Boss |
| 2002/0155173 A1 | 10/2002 | Chopp |
| 2002/0198377 A1 | 12/2002 | Niewohner et al. |
| 2004/0127538 A1 | 7/2004 | Oinuma |
| 2005/0143388 A1 | 6/2005 | Chopp |
| 2005/0282880 A1 | 12/2005 | Oinuma |
| 2006/0106037 A1 | 5/2006 | Baer |
| 2006/0128695 A1 | 6/2006 | Bourguignon |
| 2006/0135557 A1 | 6/2006 | Nan et al. |
| 2006/0148802 A1 | 7/2006 | Niewohner et al. |
| 2007/0135457 A1 | 6/2007 | Beyer |
| 2007/0299079 A1 | 12/2007 | Norbert et al. |
| 2008/0027064 A1 | 1/2008 | Hofgen et al. |
| 2008/0280907 A1 | 11/2008 | Schmidt et al. |
| 2008/0312225 A1 | 12/2008 | Schmidt et al. |
| 2009/0163552 A1 | 6/2009 | Benson et al. |
| 2009/0203691 A1 | 8/2009 | Oinuma |
| 2009/0239874 A1 | 9/2009 | Hofgen et al. |
| 2010/0035882 A1 | 2/2010 | Ellinghaus |
| 2010/0063063 A1 | 3/2010 | Benbow et al. |
| 2010/0120762 A1 | 5/2010 | Stange |
| 2010/0120763 A1 | 5/2010 | Stange |
| 2010/0150839 A1 | 6/2010 | Kelleher |
| 2011/0071168 A1 | 3/2011 | Chopp |
| 2011/0136803 A1 | 6/2011 | Schmidt et al. |
| 2011/0144153 A1 | 6/2011 | Nozawa |
| 2012/0009152 A1 | 1/2012 | Chopp |
| 2012/0136012 A1 | 5/2012 | Breslin et al. |
| 2012/0136064 A1 | 5/2012 | Nixon |
| 2012/0252780 A1 | 10/2012 | Ng |
| 2012/0322837 A1 | 12/2012 | Maeba et al. |
| 2013/0115194 A1 | 5/2013 | Long et al. |
| 2013/0115404 A1 | 5/2013 | Goehlich |
| 2014/0088080 A1 | 3/2014 | Koga |
| 2015/0105373 A1 | 4/2015 | Mikami et al. |
| 2015/0158863 A1 | 6/2015 | Nakamura |
| 2016/0229814 A1 | 8/2016 | Yamamoto et al. |
| 2017/0107240 A1 | 4/2017 | Yamamoto et al. |

FOREIGN PATENT DOCUMENTS

| | | |
|---|---|---|
| FR | 2860793 | 4/2005 |
| GB | 2404658 | 2/2005 |
| JP | H06-145169 | 5/1994 |
| JP | H09-221423 | 8/1997 |
| JP | H11-292877 | 10/1999 |
| JP | 2001-512137 | 8/2001 |
| JP | 2004-525098 | 8/2004 |
| JP | 2005-145840 | 6/2005 |
| JP | 2006-519243 | 8/2006 |
| JP | 2007-513996 | 5/2007 |
| JP | 2008-526716 | 7/2008 |
| JP | 2008-526717 | 7/2008 |
| JP | 2009-538853 | 11/2009 |
| WO | WO 92/01938 | 2/1992 |
| WO | WO 99/06435 | 2/1999 |
| WO | WO 99/37667 | 7/1999 |
| WO | WO 00/23091 | 4/2000 |
| WO | WO 00/32575 | 6/2000 |
| WO | WO 01/09125 | 2/2001 |
| WO | WO 01/44228 | 6/2001 |
| WO | WO 01/44266 | 6/2001 |
| WO | WO 01/55106 | 8/2001 |
| WO | WO 02/50078 | 6/2002 |
| WO | WO 2004/037784 | 5/2004 |
| WO | WO 2004/044234 | 5/2004 |
| WO | WO 2004/056823 | 7/2004 |
| WO | WO 2004/060872 | 7/2004 |
| WO | WO 2004/108892 | 12/2004 |
| WO | WO 2005/035534 | 4/2005 |
| WO | WO 2005/037839 | 4/2005 |
| WO | WO 2005/058892 | 6/2005 |
| WO | WO 2005/120497 | 12/2005 |
| WO | WO 2006/015159 | 2/2006 |
| WO | WO 2006/064286 | 6/2006 |
| WO | WO 2006/128129 | 11/2006 |
| WO | WO 2006/128172 | 11/2006 |
| WO | WO 2007/020521 | 2/2007 |
| WO | WO 2007/125405 | 11/2007 |
| WO | WO 2007/137819 | 12/2007 |
| WO | WO 2007/146230 | 12/2007 |
| WO | WO 2008/016659 | 2/2008 |
| WO | WO 2008/043461 | 4/2008 |
| WO | WO 2008/044700 | 4/2008 |
| WO | WO 2008/085302 | 7/2008 |
| WO | WO 2008/121602 | 10/2008 |
| WO | WO 2009/019508 | 2/2009 |
| WO | WO 2009/026276 | 2/2009 |
| WO | WO 2009/095324 | 8/2009 |
| WO | WO 2009/138338 | 11/2009 |
| WO | WO 2010/013161 | 2/2010 |
| WO | WO 2010/054253 | 5/2010 |
| WO | WO 2010/054260 | 5/2010 |
| WO | WO 2010/090290 | 8/2010 |
| WO | WO 2010/097410 | 9/2010 |
| WO | WO 2010/142752 | 12/2010 |
| WO | WO 2011/022213 | 2/2011 |
| WO | WO 2011/044157 | 4/2011 |
| WO | WO 2011/059839 | 5/2011 |
| WO | 2012/027965 | 3/2012 |
| WO | WO 2012/042541 | 4/2012 |
| WO | WO 2012/051036 | 4/2012 |
| WO | 2012/064744 A2 | 5/2012 |
| WO | WO 2012/087861 | 6/2012 |
| WO | 2012/100734 | 8/2012 |
| WO | WO 2012/165399 | 12/2012 |
| WO | WO 2012/178124 | 12/2012 |
| WO | 2013/019682 | 2/2013 |
| WO | WO 2013/018695 | 2/2013 |
| WO | WO 2013/042782 | 3/2013 |
| WO | WO 2013/055984 | 4/2013 |
| WO | 2013/064231 A1 | 5/2013 |
| WO | WO 2013/100027 | 7/2013 |
| WO | WO 2013/146963 | 10/2013 |
| WO | WO 2013/161913 | 10/2013 |
| WO | WO 2014/142255 | 9/2014 |
| WO | WO 2015/002230 | 1/2015 |
| WO | WO 2015/002231 | 1/2015 |
| WO | WO 2015/012328 | 1/2015 |
| WO | WO 2015/016206 | 2/2015 |

OTHER PUBLICATIONS

Montalbetti et al. Tetrahedron 61 (2005) 10827-10852.*
Venkatesh et al., J. Pharm. Sci. 89, 145-54 (2000).*
Dorwald F. A. Side Reactions in Organic Synthesis, 2005, Wiley: VCH, Weinheim p. IX of Preface p. 1-15.*
Akdis, M. et al., "Interleukins, from 1 to 37, and interferon-γ: Receptors, functions, and roles in diseases," Journal of Allergy and Clinical Immunology, 2011, 127, 3,701-721.e70.
Banerjee, B. et al., "Second-generation DBFOX ligands for the synthesis of beta-substituted alpha-amino acids via enantioselective radical conjugate additions," J. Org. Chem. (2008) 73:8973-8978.
Beavo, J.A. et al., "Stimulation of adenosine 3',5'-monophosphate hydrolysis by guanosine 3',5'-monophosphate," J. Biol. Chem. (1971) 246(12):3841-3846.
Bender, A.T. et al., "Differentiation of human monocytes in vitro with granulocyte-macrophage colony-stimulating factor and macrophage colony-stimulating factor produces distinct changes in cGMP phosphodiesterase expression," Cell. Signalling (2004) 16:365-374.
Benton, H.P., "Cytokines and their receptors," Curr Opin Cell Biol. 1991, 3(2):171-5.
Blanco, P. et al., "Dendritic cells and cytokines in human inflammatory and autoimmune diseases," Cytokine Growth Factor Rev., Feb. 2008, 19(1):41-52.
Boess, F.G. et al., "Inhibition of phosphodiesterase 2 increases neuronal cGMP, synaptic plasticity and memory performance," Neuropharmacology (2004) 47:1081-1092.

(56) References Cited

OTHER PUBLICATIONS

Chemical Abstracts 1422576-26-8, Imidazo[1,2-a]pyridine-2-carboxamide, N-[2-methoxy-1-(2-pyridinyl)ethyl]-6-methyl-, (2016) ChemBridge Corporation.
Chemical Abstracts 1422628-80-5, "Imidazo[1,2-a]pyridine-6-carboxamide, N-[1-(3,5-dichlorophenyl)-2-hydroxyethyl]-" (2013) ChemBridge Corporation.
Chen, Y. et al., "Design, Synthesis, and Biological Evaluation of Isoquinoline-1, 3, 4-trione Derivatives as Potent Caspase-3 Inhibitors," Journal of Medicinal Chemistry, 2006, vol. 49, No. 5, p. 1613-1623.
Chl W. et al., "Upregulated IL-23 and IL-17 in Behçet patients with active uveitis," Invest Ophthalmol Vis Sci., 2008, 49(7):3058-64.
Domek-Lopacinska, K.U. et al., "Cyclic GMP and nitric oxide synthase in aging and Alzheimer's disease," Mol. Neurobiol. (2010) 41:129-137.
Dorwald, F.Z., Side Reactions in Organic Synthesis. A Guide to Successful Synthesis Design, (2005) Wiley-VCH Verlag, Weinheim, 6 pages.
Du, J. et al., "Isoquinoline-1, 3, 4-trione Derivates Inactivate Caspase-3 by Generation of Reactive Oxygen Species," Journal of Biological Chemistry, 2008, vol. 283, No. 44, p. 30205-30215.
Ghoreschi, K. et al., "Selective and therapeutic inhibition of kinases: to be or not to be?," Nat Immunol. Apr. 2009, 10(4):356-360.
Harada, S. et al., "Inclusion Compounds of Lankacidin-Group Antibiotics with Cyclodextrins," The Journal of Antibiotics, 1985, vol. 38, No. 7, pp. 877-885.
Houslay, M.D. et al., "cAMP-specific phosphodiesterase-4 enzymes in the cardiovascular system—A molecular toolbox for generating compartmentalized cAMP signaling," Cir. Res. (2007) 100:950-966.
Imramovsky, A. et al., "Synthetic Route for the Preparation of 2-Hydroxy-N-[1-(2-hydroxyphenylamino)-1-oxoalkan-2-yl] benzamides," J. Comb. Chem., 2010, 12, 414-416.
Jaeger, R. et al., "Activation of PDE2 and PDE5 by specific GAF ligands: delayed activation of PDE5," British J. Pharmacol. (2010) 161:1645-1660.
Jiang, Z. et al., "IL-23R gene confers susceptibility to Behcet's disease in a Chinese Han population," Ann Rheum Dis, 2010, 69(7):1325-8.
Jones, G. H., "Inhibitors of cyclic AMP phosphodiesterase. 1. Analogues of Cilostamide and Anagrelide," Journal of Medicinal Chemistry, 1987, vol. 30, No. 2, p. 295-303.
Jordan, V.C., "Tamoxifen: a most unlikely pioneering medicine," Nature Rev. Drug Disc. (2003) 2:205-213.
Juilfs, D.M. et al., "Cyclic GMP as substrate and regulator of cyclic nucleotide phosphodiesterases (PDEs)," in Rev. Physiol. Biochem. Pharmacol. (1999) 135:67-104.
Klimkowski, V.J. et al., "D-phenylglycinol-derived non-covalent factor Xa inhibitors: effect of non-peptidic S4 linkage elements on affinity and anticoagulant activity," Biorg. Med. Chem. Lett (2007) 17:5801-5805.
Lakics, V. et al., "Quantitative comparison of phosphodiesterase mRNA distribution in human brain and peripheral tissues," Neuropharmacology (2010) 59:367-374.
Martinez, S.E. et al., "The two GAF domains in phosphodiesterase 2A have distinct roles in dimerization and in cGMP binding," Proc. Natl. Acad. Sci. (2002) 99(20):13260-13265.
Martins, T.J. et al., "Purification and characterization of a cyclic GMP-stimulated cyclic nucleotide phosphodiesterase from Bovine Tissues," J. Biol. Chem. (1982) 257(4):1973-1979.
Masood, A. et al., "Anxiolytic effects of phosphodiesterase-2 inhibitors associated with increased cGMP signaling," J. Pharmacology and Exp. Ther. (2009) 331(2):690-699.
Masood, A. et al., "Reversal of oxidative stress-induced anxiety by inhibition of phosphodiesterase-2 in mice," J. Pharm. Exp. Thera. (2008) 326(2):369-379.
Menniti, F.S. et al., "Phosphodiesterases in the CNS: targets for drug development," Nature Rev. Drug Discov. (2006) 5:660-670.

Minegishi, Y. et al., "Molecular mechanisms of the immunological abnormalities in hyper-IgE, syndrome," New York Academy of Science, 2011, 1246:34-40.
Pfefferkorn, J.A. et al., "Pyridones as glucokinase activators: Identification of a unique metabolic liability of the 4-sulfonyl-2-pyridone heterocycle," Bioorganic & Medicinal Chemistry Letters 19, 2009, 3247-3252.
Rodefer, J.S. et al., "Selective phosphodiesterase inhibitors improve performance on the ED/ID cognitive task in rats," Neuropharmacology (2012) 62:1182-1190.
Russell, T.R. et al., "Separate phosphodiesterases for the hydrolysis of cyclic adenosine 3',5'-monophosphate and cyclic guanosine 3',5'-monophosphate in rat liver," J. Biol. Chem. (1973) 248(4):1334-1340.
Sheridan, J., "The Most Common Chemical Replacements in Drug-Like Compounds," Chem Int Comput. Sci., 2002, 42, 103-108.
Shen, H.C. et al., "Discovery of pyrazolopyrimidines as the first class of allosteric agonists for the high affinity nicotinic acid receptor GPR109A," Bioorg. Med. Chem. Lett. (2008) 18:4948-4951.
Stephenson, D.T. et al., "Immunohistochemical localization of phosphodiesterase 2A in multiple mammalian species," J. Histochem. Cytochem. (2009) 57(10):933-949.
Strobl, B. et al., "Tyrosine kinase 2 (TYK2) in cytokine signalling and host immunity," Front Biosci, 2011, 16:3214-32.
Tenor, H. et al., "2. Analysis of PDE isoenzyme profiles in cells and tissues by pharmacological methods," in Phosphodiesterase Inhibitors (1996) Academic Press Limited, pp. 21-40.
Toguchi, H. et al., "Gastro-Intestinal Absorption of Ethyl 2-Chloro-3-[4-(2-methyl-2-phenylpropyloxy)phenyl]propionate from Different Dosage Forms in Rats and Dogs," Chemical and Pharmaceutical Bulletin, 1990, vol. 38, No. 10, pp. 2792-2796.
Venuti, M.C. et al., "Inhibitors of cyclic AMP phosphodiesterase. 4. Synthesis and evaluation of potential prodrugs of lixazinone (N-cyclohexyl-N-methyl-4-[(1, 2, 3, 5-tetrahydro-2-oxoimidazo [2,1-b] quinazolin-7-ypoxy] butyramide, RS-82856)," Journal of Medicinal Chemistry, 1988, vol. 31, No. 11, p. 2145-2152.
Wong, J.C. et al., "Application of p21 and klf2 reporter gene assays to identify selective histone deacetylase inhibitors for cancer therapy," Bioorganic & Medicinal Chemistry Letters, 2011, 21(1), 110-116.
Wong, J.C. et al., "Pharmacokinetic Optimization of Class-Selective Histone Deacetylase Inhibitors and Identification of Associated Candidate Predictive Biomarkers of Hepatocellular Carcinoma Tumor Response," Journal of Medicinal Chemistry, 2012, 55(20), 8903-8925.
Wu, A.Y. et al., "Molecular determinants for cyclic nucleotide binding to the regulatory domains of phosphodiesterase 2A," J. Biol. Chem. (2004) 279(36):37928-37938.
Yamagata, K. et al., "Synthesis of 1-acyl-2-oxo-3-pyrrolidinecarbonitriles by the reaction of 2-acylamino-4,5-dihydro-3-furancarbonitriles with sodium iodide," Journal of Heterocyclic Chemistry, 2005, vol. 42, Issue 4, pp. 543-549.
Yamamoto, T. et al., "Purification and characterization of cyclic GMP-stimulated cyclic nucleotide phosphodiesterase from calf liver. Effects of divalent cations on activity," J. Biol. Chem. (1983) 258(20):12526-12533.
International Search Report for Application No. PCT/JP2014/056721 dated May 27, 2014.
Written Opinion for Application No. PCT/JP2014/056721 dated May 27, 2014.
International Search Report for Application No. PCT/JP2014/067650 dated Aug. 19, 2014.
Written Opinion for Application No. PCT/JP2014/067650 dated Aug. 19, 2014.
International Search Report for Application No. PCT/JP2014/067649 dated Sep. 30, 2014.
Written Opinion for Application No. PCT/JP2014/067649 dated Sep. 30, 2014.
International Search Report for Application No. PCT/JP2014/069907 dated Aug. 26, 2014.
Written Opinion for Application No. PCT/JP2014/069907 dated Aug. 26, 2014.

(56) References Cited

OTHER PUBLICATIONS

International Search Report for Application No. PCT/JP2014/069494 dated Sep. 24, 2014.
Written Opinion for Application No. PCT/JP2014/069494 dated Sep. 24, 2014.
United States Patent Office Action for U.S. Appl. No. 14/909,427 dated Oct. 20, 2016.
European Patent Office Supplementary Search Report for Application No. 14820366.4 dated Nov. 10, 2016.
European Patent Office Supplementary Search Report for Application No. 14762328.4 dated Nov. 3, 2016.
Fauber, B. P et al., "Modulators of the Nuclear Receptor Retinoic Acid Receptor-Related Orphan Receptor-y (RORy or RORc)," Journal of Medicinal Chemistry, 2014, vol. 57, No. 14, pp. 5871-5892.

* cited by examiner

HETEROCYCLIC COMPOUND

CROSS-REFERENCE TO RELATED APPLICATIONS

This is a U.S. national stage entry of International Patent Application No. PCT/JP2014/067650, filed on Jul. 2, 2014, which claims priority to Japanese Patent Application No. 2013-140210, filed on Jul. 3, 2013, the entire contents of all of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 616 Byte ASCII (Text) file named "202877-PCT-US-029998-1164- US00-SEQ-LIST-11-09-16.txt" created on Dec. 31, 2015.

TECHNICAL FIELD

The present invention relates to a heterocyclic compound having an RORγt inhibitory action, a medicament containing the compound, and the like.

BACKGROUND OF THE INVENTION

Th17 cell and inflammatory cytokine (IL-17A, IL-17F, etc.) produced thereby cause a decrease in QOL as a severe etiology cell and factor accompanying enhancement of a systemic new immune response, in various autoimmune disease such as inflammatory bowel disease (IBD), rheumatoid arthritis, multiple sclerosis or psoriasis. However, the existing therapeutic drugs show only limited effects, and therefore, the earliest possible development of a novel therapeutic drug has been desired.

Involvement of T cells, inter alia, Th17 cell and inflammatory cytokines (IL-17A, IL-17F, etc.) produced thereby, in the pathology of these immune disease has been drawing attention in recent years.

Moreover, it has been recently clarified that a Retinoid-related Orphan Receptor (ROR) γt, which is one of the orphan nuclear receptors, plays an important role in the differentiation of Th17 cells and production of IL-17A/IL-17F. That is, it has been reported that RORγt is mainly expressed in Th17 cells and functions as a transcription factor of IL-17A and IL-17F, as well as a master regulator of Th17 cell differentiation.

Therefore, a medicament that inhibits the action of RORγt is expected to show a treatment effect on various immune disease by suppressing differentiation and activation of Th17 cells.

Patent Document 1 reports the following compound represented by the general formula:

P-M-M₁ wherein
M is a 3- to 8-membered linear chain consisting of carbon atoms, 0-3 carbonyl groups, 0-1 thiocarbonyl group, and 0-4 heteroatoms selected from O, N and $S(O)_p$,
one of P and $M_1$ is -G, and the other is -A-B;
G is a group represented by the formula (IIa) or formula (IIb):

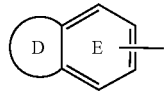

IIa

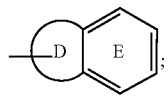

IIb

Ring D, including the two atoms of Ring E to which it is attached, is a 5- or 6-membered ring consisting of carbon atoms and 0-3 heteroatoms selected from N, O and $S(O)_p$;
Ring D is substituted with 0-2 R or 0-2 carbonyl, and there are 0-3 ring double bonds;
E is selected from phenyl, pyridyl, pyrimidyl, pyrazinyl and pyridazinyl, which is substituted with 1-3 R;
A is selected from a $C_{3-10}$ carbocycle substituted with 0-2 $R^4$, and a 5-12-membered heterocycle consisting of carbon atoms and 1-4 heteroatoms selected from N, O and $S(O)_p$, and substituted with 0-2 $R^4$;
B is $X-Y-R^{4a}$ or the like;
X is absent, $-(CR^2R^{2a})_{1-4}-$ or the like;
Y is selected from a $C_{3-10}$ carboncycle and a 3-10-membered heterocycle; and
$R^{4a}$ is a $C_{1-6}$ alkyl substituted with 0-2 $R^{4c}$, or the like, which has a Xa factor inhibitory action, and is useful for the treatment of thromboembolism.

Patent Document 2 discloses, as a fused heterocyclic compound, a compound represented by the formula:

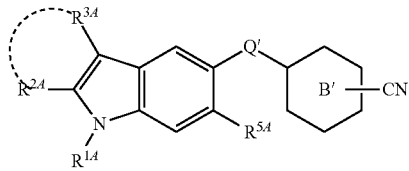

wherein
$R^{1A}$ is an optionally substituted hydrocarbon group or an optionally substituted hydrocarbon-oxy group,
$R^{2A}$ and $R^{3A}$ are each independently a hydrogen atom, an optionally substituted hydrocarbon group or the like, or
$R^{2A}$ and $R^{3A}$ in combination optionally form, together with the carbon atoms which they are bonded to, an optionally substituted hydrocarbon ring,
$R^{5A}$ is a hydrogen atom or a halogen atom,
Q' is

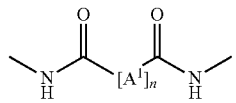

wherein
[$A^1$] are the same or different and each is a methylene group optionally substituted by $C_{1-6}$ alkyl group(s) optionally substituted by hydroxy group(s) and the like, wherein the two substituents bonded to the single carbon atom are optionally combined to each other to form a hydrocarbon ring, and
n is an integer of 1 to 5, or the like, and
Ring B' is a benzene ring optionally further having substituent(s), or the like, which has a RORγt inhibitory action, and is useful for the treatment of inflammatory bowel disease (IBD) and the like.

Patent Document 3 discloses a compound represented by the formula:

wherein

Ring A is a $C_{3-10}$ carbocycle;

L is a group selected from a bond, $-CHR^{10}CHR^{10}-$, $-CR^{10}=CR^{10}-$ and $-C\equiv C-$;

$R^{10}$ is H, halogen, OH or $C_{1-4}$ alkyl;

Q is selected from C, CH and N;

- - - - is an optional bond; provided that when Q is N, then the optional bond is absent;

Ring B is a 5- to 6-membered heterocycle containing heteroatoms selected from N, $NR^6$, O and $S(O)_p$, and substituted by 0-3 $R^5$;

optionally, Ring B is further fused with phenyl substituted with 0-2 $R^5$ or a 5- to 6-membered aromatic heterocycle containing 1 to 2 heteroatoms selected from N, $NR^6$, O and $S(O)_p$, and substituted with 0-2 $R^5$;

$R^1$ are each independently H, halo, $C_{1-2}$ alkyl, $-O(C_{1-4}$ alkyl), CN, $-CH_2NH_2$ or $-C(=NH)NH_2$;

$R^2$ is H, halo, CN, OH, $C_{1-6}$ alkyl, $C_{1-4}$ alkoxy, $C_{1-6}$ haloalkyl, $C_{1-6}$ haloalkoxy, $CO(C_{1-4}$ alkyl), $CONH_2$, $CO_2H$, and, a 5- to 7-membered heterocycle containing 1 to 4 heteroatoms selected from N, NH, $N(C_{1-4}$ alkyl), O and $S(O)_p$, and substituted with 1-2 $R^{2a}$; and $R^3$ is a $C_{1-6}$ alkyl group substituted with 1-3 $R^{3a}$, a $C_{3-10}$ carboncycle substituted with 1-3 $R^3$, or a 5- to 10-membered heterocycle containing 1 to 4 heteroatoms selected from N, $NR^7$, O and $S(O)_p$, and substituted with 1-3 $R^{3a}$, which is a Factor XIIa, and is useful for the treatment of thromboembolism and inflammatory disease.

Patent Document 4 discloses a compound represented by the formula:

wherein $A^1$ is $CR^{41}$ wherein $R^{41}$ is a hydrogen atom or a substituent, or a nitrogen atom, $A^2$ is $CR^{42}$ wherein $R^{42}$ is a hydrogen atom or a substituent, or a nitrogen atom, $A^3$ is $CR^{43}$ wherein $R^{43}$ is a hydrogen atom or a substituent, or a nitrogen atom, or, provided that when $A^2$ is $CR^{42}$ wherein $R^{42}$ is a substituent, and $A^3$ is $CR^{43}$ wherein $R^{43}$ is a substituent, then $R^{42}$ and $R^{43}$ in combination optionally form, together with the carbon atoms which they are bonded to, a carbocycle or a heterocycle, $R^1$ is an optionally substituted carbocyclic group or the like, $R^2$ is a hydrogen atom or a substituent, one of $R^3$ or $R^4$ is an optionally substituted carbocyclic group, an optionally substituted aromatic nitrogen-containing heterocyclic group or an optionally substituted fused non-aromatic heterocyclic group, and the other is a hydrogen atom or a substituent, $R^5$ is a hydrogen atom or a substituent, and $R^9$ is a hydrogen atom or a hydroxy group, provided that when $R^9$ is a hydroxy group, then $A^1$, $A^2$ and $A^3$ are $CR^{41}$, $CR^{42}$ and $CR^{43}$, respectively.

Patent Document 5 discloses a compound represented by the formula:

wherein $R^1$ is $C_{1-2}$ alkyl, halogen or $CF_3$;

$R^2$ is H, Cl, F or methyl;

$R^3$ is H, methyl;

$R^4$ is H, $C_{1-6}$ alkyl or benzyl optionally substituted by $CF_3$;

$R^5$ is methyl, nitro, halogen, CN, $CF_3$ or $-C(O)OCH_2CH_3$;

$R^6$ is Cl, F or $CF_3$; and m is 0 or 1, as a non-steroidal compound which is an androgen receptor modulator.

DOCUMENT LIST

Patent Document

[Patent Document 1] WO 2004/108892
[Patent Document 2] WO 2013/042782
[Patent Document 3] WO 2013/055984
[Patent Document 4] WO 2013/100027
[Patent Document 5] WO 2008/121602

SUMMARY OF THE INVENTION

Problems to be Solved by the Invention

The present invention aims to provide a compound having a superior RORγt inhibitory action, and useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

Means of Solving the Problems

The present inventors have found that a compound represented by the following formula (I) (including a compound represented by the formula (Ia)) or a salt thereof has a superior RORγt inhibitory action based on the specific chemical structure thereof and affords superior efficacy as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like. The present inventors have conducted intensive studies based on the finding and completed the present invention.

Accordingly, the present invention relates to the followings.

[1] A compound represented by the following formula (I):

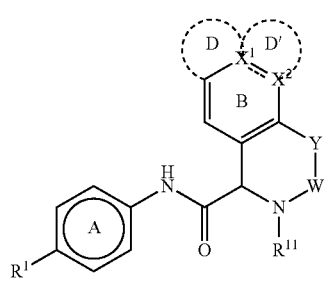

(I)

wherein

Ring A is an optionally further substituted 6-membered aromatic ring, $R^1$ is (1) a group represented by the formula: -Q($R^{1a}$) ($R^{1b}$) ($R^{1c}$) wherein Q is a carbon atom, a silicon atom or a germanium atom, and $R^{1a}$, $R^{1b}$ and $R^{1c}$ are each independently a substituent, or $R^{1a}$ and $R^{1b}$ in combination optionally form, together with the adjacent Q, an optionally further substituted ring, and $R^{1c}$ is optionally bonded to one substituent for Ring A to form an optionally further substituted ring, (2) a neo-pentyl group, or (3) a trimethylsilylmethyl group, $R^{11}$ is —$CR^{12}R^{12\prime}$—$R^{12\prime\prime}$, —C(=O)—$R^4$ or —$SO_2$—$R^{13}$, $R^{12}$, $R^{12}$ and $R^{12\prime}$ are each independently a hydrogen atom, a halogen atom, a cyano group, a nitro group, an optionally substituted $C_{1-6}$ alkyl group, an optionally substituted $C_{2-6}$ alkenyl group, an optionally substituted $C_{2-6}$ alkynyl group, an optionally substituted heterocyclic group or an optionally substituted thiocarbamoyl group, $R^4$ is an optionally substituted $C_{1-6}$ alkyl group, an optionally substituted $C_{2-6}$ alkenyl group, an optionally substituted $C_{2-6}$ alkynyl group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl(SH) group or an optionally substituted silyl group, wherein the "$C_{1-6}$ alkyl group", the "$C_{2-6}$ alkenyl group" and the "$C_{2-6}$ alkynyl group" of the "optionally substituted $C_{1-6}$ alkyl group", the "optionally substituted $C_{2-6}$ alkenyl group" and the "optionally substituted $C_{2-6}$ alkynyl group" for $R^4$ are each optionally substituted by 1 to 5 substituents selected from (1) a halogen atom, (2) a nitro group, (3) a cyano group, (4) an oxo group, (5) a hydroxy group, (6) a $C_{1-6}$ alkoxy group optionally substituted by substituent(s) selected from a halogen atom and a carboxy group, (7) a $C_{6-14}$ aryloxy group, (8) a $C_{7-16}$ aralkyloxy group, (9) a 5- to 14-membered aromatic heterocyclyloxy group, (10) a 3- to 14-membered non-aromatic heterocyclyloxy group, (11) a $C_{1-6}$ alkyl-carbonyloxy group, (12) a $C_{6-14}$ aryl-carbonyloxy group, (13) a $C_{1-6}$ alkoxy-carbonyloxy group, (14) a mono- or di-$C_{1-6}$ alkyl-carbamoyloxy group, (15) a $C_{6-14}$ aryl-carbamoyloxy group, (16) a 5- to 14-membered aromatic heterocyclylcarbonyloxy group, (17) a 3- to 14-membered non-aromatic heterocyclylcarbonyloxy group, (18) an optionally halogenated $C_{1-6}$ alkylsulfonyloxy group, (19) a $C_{6-14}$ arylsulfonyloxy group optionally substituted by $C_{1-6}$ alkyl group(s), (20) an optionally halogenated $C_{1-6}$ alkylthio group, (21) a 5- to 14-membered aromatic heterocyclic group optionally substituted by substituent(s) selected from a hydroxy group, a $C_{1-6}$ alkyl group, a $C_{1-6}$ alkoxy group and a carboxy group, (22) a 3- to 14-membered non-aromatic heterocyclic group optionally substituted by substituent(s) selected from an oxo group and a $C_{1-6}$ alkyl group, (23) a formyl group, (24) a carboxy group, (25) an optionally halogenated $C_{1-6}$ alkyl-carbonyl group, (26) a $C_{6-14}$ aryl-carbonyl group, (27) a 5- to 14-membered aromatic heterocyclylcarbonyl group, (28) a 3- to 14-membered non-aromatic heterocyclylcarbonyl group, (29) a $C_{1-6}$ alkoxy-carbonyl group, (30) a $C_{6-14}$ aryloxy-carbonyl group, (31) a $C_{7-16}$ aralkyloxy-carbonyl group, (32) a carbamoyl group, (33) a thiocarbamoyl group, (34) a mono- or di-$C_{1-6}$ alkyl-carbamoyl group, (35) a $C_{6-14}$ aryl-carbamoyl group, (36) a 5- to 14-membered aromatic heterocyclylcarbamoyl group, (37) a 3- to 14-membered non-aromatic heterocyclylcarbamoyl group, (38) an optionally halogenated $C_{1-6}$ alkylsulfonyl group, (39) a $C_{6-14}$ arylsulfonyl group, (40) a 5- to 14-membered aromatic heterocyclylsulfonyl group, (41) an optionally halogenated $C_{1-6}$ alkylsulfinyl group, (42) a $C_{6-14}$ arylsulfinyl group, (43) a 5- to 14-membered aromatic heterocyclylsulfinyl group, (44) an amino group, (45) a mono- or di-$C_{1-6}$ alkylamino group (the $C_{1-6}$ alkyl is optionally substituted by carboxy group(s)), (46) a mono- or di-$C_{6-14}$ arylamino group, (47) a 5- to 14-membered aromatic heterocyclylamino group, (48) a $C_{7-16}$ aralkylamino group, (49) a formylamino group, (50) a $C_{1-6}$ alkyl-carbonylamino group, (51) a ($C_{1-6}$ alkyl) ($C_{1-6}$ alkyl-carbonyl)amino group, (52) a $C_{6-14}$ aryl-carbonylamino group, (53) a $C_{1-6}$ alkoxy-carbonylamino group, (54) a $C_{7-16}$ aralkyloxy-carbonylamino group, (55) a $C_{1-6}$ alkylsulfonylamino group, (56) a $C_{6-14}$ arylsulfonylamino group optionally substituted by $C_{1-6}$ alkyl group(s), (57) an optionally halogenated $C_{1-6}$ alkyl group, (58) a $C_{2-6}$ alkenyl group, and (59) a $C_{2-6}$ alkynyl group, $R^{13}$ is a substituent, Ring B is a benzene ring, a pyridine ring or a dihydropyridine ring, each of which is optionally further substituted, the partial structure represented by the formula:

$X^1\text{-----}X^2$ is $CR^{5a}$=$CR^6$, $CR^{5b}$=N or C(=O)—$NR^7$, $R^{5a}$ and $R^{5b}$ are each independently an optionally substituted alkyl group, an optionally substituted alkoxy group, an optionally substituted alkylsulfonyl group, a cyano group, an optionally substituted cyclic amino group or an oxetan-3-yloxy group, and $R^6$ and $R^7$ are each independently a hydrogen atom or a substituent, or the substituent that Ring B optionally further has and $R^{5a}$ or $R^{5b}$ in combination optionally form Ring D, wherein Ring D is a 5- or 6-membered oxygen-containing heterocycle containing 1 to 2 oxygen atoms as heteroatoms in addition to carbon atoms, and is fused at the ring forming position, or $R^{5a}$ and $R^6$ in combination optionally form Ring D', wherein Ring D' is a 5- or 6-membered oxygen-containing heterocycle containing 1 to 2 oxygen atoms as heteroatoms in addition to carbon atoms, and is fused at the ring forming position, Y is an optionally substituted methylene group or an oxygen atom, and W is an optionally substituted $C_{1-2}$ alkylene group, or a salt thereof (hereinafter sometimes to be referred to as compound (I)).

[2] The compound or salt of the above-mentioned [1], wherein $R^1$ is a trimethylsilyl group, an ethyldimethylsilyl group or an optionally substituted tert-butyl group, or a group represented by the formula: —$C(R^{1a})(R^{1b})(R^{1c})$ wherein $R^{1a}$ and $R^{1b}$ are each independently a substituent, or $R^{1a}$ and $R^{1b}$ in combination optionally form, together with the adjacent carbon atom, an optionally further substituted ring, and $R^{1c}$ is bonded to one substituent for Ring A to form an optionally further substituted ring.

[3] The compound or salt of the above-mentioned [1], wherein Ring A is a benzene ring optionally further substituted by a halogen atom or a cyano group.

[4] The compound or salt of the above-mentioned [1], wherein $R^4$ is (1) a $C_{1-6}$ alkyl group optionally substituted by 1 to 3 substituents selected from (a) a halogen atom, (b) a cyano group, (c) a hydroxy group, (d) a 5- to 6-membered monocyclic aromatic heterocyclic group, (e) a 4- to 6-membered monocyclic non-aromatic heterocyclic group, and (f) a carboxy group, or (2) an optionally substituted heterocyclic group.

[5] The compound or salt of the above-mentioned [1], wherein Ring D' is a dioxole ring.

[6] The compound or salt of the above-mentioned [1], wherein Y and W are both methylene groups.

[7] The compound or salt of the above-mentioned [1], wherein $R^{5a}$ is (1) an optionally substituted $C_{1-6}$ alkyl group, (2) an optionally substituted $C_{1-6}$ alkoxy group, or (3) an optionally substituted $C_{1-6}$ alkylsulfonyl group.

[8] The compound or salt of the above-mentioned [1], wherein $R^{5b}$ is (1) an optionally substituted $C_{1-4}$ alkoxy group, or (2) an optionally substituted $C_{1-4}$ alkyl group.

[9] The compound or salt of the above-mentioned [1], wherein $R^6$ is a hydrogen atom.

[10] The compound or salt of the above-mentioned [1], wherein Ring B is a benzene ring or a pyridine ring, each of which is optionally further substituted.

[11] 5-((5R)-5-((7-Fluoro-1,1-dimethyl-2,3-dihydro-1H-inden-5-yl)carbamoyl)-2-methoxy-7,8-dihydro-1,6-naphthyridin-6(5H)-yl)-5-oxopentanoic acid or a salt thereof.

[12] (1-(((6R)-6-((3,5-Difluoro-4-(trimethylsilyl)phenyl)carbamoyl)-8,9-dihydro[1,3]dioxolo[4,5-f]isoquinolin-7(6H)-yl)carbonyl)azetidin-3-yl)acetic acid or a salt thereof.

[13] (1-(((5R)-5-((3,5-Difluoro-4-(trimethylsilyl)phenyl)carbamoyl)-2-methoxy-7,8-dihydro-1,6-naphthyridin-6(5H)-yl)carbonyl)azetidin-3-yl)acetic acid or a salt thereof.

[14] A medicament comprising the compound or salt of the above-mentioned [1].

[15] The medicament of the above-mentioned [14], which is a RORγt inhibitor.

[16] The medicament of the above-mentioned [14], which is an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

[17] A method of inhibiting RORγt, which comprises administering an effective amount of the compound or salt of the above-mentioned [1] to a mammal.

[18] A method for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE), which comprises administering an effective amount of the compound or salt of the above-mentioned [1] to a mammal.

[19] Use of the compound or salt of the above-mentioned [1] for the production of an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

[20] The compound or salt of the above-mentioned [1] for use in the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

[1a] A compound represented by the formula (Ia):

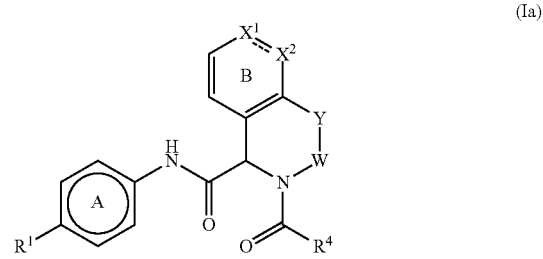

(Ia)

wherein

Ring A is an optionally further substituted 6-membered aromatic ring, $R^1$ is (1) a group represented by the formula: -$Q(R^{1a})(R^{1b})(R^{1c})$ wherein Q is a carbon atom, a silicon atom or a germanium atom, and $R^{1a}$, $R^{1b}$ and $R^{1c}$ are each independently a substituent, or $R^{1a}$ and $R^{1b}$ in combination optionally form, together with the adjacent Q, an optionally further substituted ring, and $R^{1c}$ is optionally bonded to one substituent for Ring A to form an optionally further substituted ring, (2) a neo-pentyl group, or (3) a trimethylsilylmethyl group, $R^4$ is a halogen atom, a cyano group, a nitro group, an optionally substituted $C_{1-6}$ alkyl group, an optionally substituted $C_{2-6}$ alkenyl group, an optionally substituted $C_{2-6}$ alkynyl group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl(SH) group or an optionally substituted silyl group, wherein the "optionally substituted $C_{1-6}$ alkyl group", the "optionally substituted $C_{2-6}$ alkenyl group" and the "optionally substituted $C_{2-6}$ alkynyl group" for $R^4$ are each optionally substituted by 1 to 5 substituents selected from (1) a halogen atom, (2) a nitro group, (3) a cyano group, (4) an oxo group, (5) a hydroxy group, (6) an optionally halogenated $C_{1-6}$ alkoxy group, (7) a $C_{6-14}$ aryloxy group, (8) a $C_{7-16}$ aralkyloxy group, (9) a 5- to 14-membered aromatic heterocyclyloxy group, (10) a 3- to 14-membered non-aromatic heterocyclyloxy group, (11) a $C_{1-6}$ alkyl-carbonyloxy group, (12) a $C_{6-14}$ aryl-carbonyloxy group, (13) a $C_{1-6}$ alkoxy-carbonyloxy group, (14) a mono- or di-$C_{1-6}$ alkyl-carbamoyloxy group, (15) a $C_{6-14}$ aryl-carbamoyloxy group, (16) a 5- to 14-membered aromatic heterocyclylcarbonyloxy group, (17) a 3- to 14-membered non-aromatic heterocyclylcarbonyloxy group, (18) an optionally halogenated $C_{1-6}$ alkylsulfonyloxy group, (19) a $C_{6-14}$ arylsulfonyloxy group optionally substituted by $C_{1-6}$ alkyl group(s), (20) an optionally halogenated $C_{1-6}$ alkylthio group, (21) a 5- to 14-membered aromatic heterocyclic group, (22) a 3- to 14-membered non-aromatic heterocyclic group, (23) a formyl group, (24) a carboxy group, (25) an optionally halogenated $C_{1-6}$ alkyl-carbonyl group, (26) a $C_{6-14}$ aryl-carbonyl group, (27) a 5- to 14-membered aromatic heterocyclylcarbonyl group, (28) a 3- to 14-membered non-aromatic heterocyclylcarbonyl group, (29) a $C_{1-6}$ alkoxy-carbonyl group, (30) a $C_{6-14}$ aryloxy-carbonyl group, (31) a $C_{7-16}$ aralkyloxy-carbonyl group, (32) a carbamoyl group, (33) a thiocarbamoyl group, (34) a mono- or di-$C_{1-6}$ alkyl-carbamoyl group, (35) a $C_{6-14}$ aryl-carbamoyl group, (36) a 5- to 14-membered aromatic heterocyclylcarbamoyl group, (37) a 3- to 14-membered non-aromatic heterocyclylcarbamoyl group, (38) an optionally halogenated $C_{1-6}$ alkylsulfonyl group, (39) a $C_{6-14}$ arylsulfonyl group, (40) a 5- to 14-membered aromatic heterocyclylsulfonyl group, (41) an optionally halogenated $C_{1-6}$ alkylsulfinyl group, (42) a $C_{6-14}$ arylsulfinyl group, (43) a 5-to 14-membered aromatic heterocyclylsulfinyl group, (44) an amino group, (45) a mono- or di-$C_{1-6}$ alkylamino group, (46) a mono- or di-$C_{6-14}$ arylamino group, (47) a 5- to 14-membered aromatic heterocyclylamino group, (48) a $C_{7-16}$ aralkylamino group, (49) a formylamino group, (50) a $C_{1-6}$ alkyl-carbonylamino group, (51) a ($C_{1-6}$ alkyl) ($C_{1-6}$ alkyl-carbonyl)amino group, (52) a $C_{6-14}$ aryl-carbonylamino group, (53) a $C_{1-6}$ alkoxy-carbonylamino group, (54) a $C_{7-16}$ aralkyloxy-carbonylamino group, (55) a $C_{1-6}$ alkylsulfonylamino group, (56) a $C_{6-14}$ arylsulfonylamino group optionally substituted by $C_{1-6}$ alkyl group(s), (57) an optionally halogenated $C_{1-6}$ alkyl group, (58) a $C_{2-6}$ alkenyl group, and (59) a $C_{2-6}$ alkynyl group, Ring B is a benzene ring, a pyridine ring or a dihydropyridine ring, each of which is optionally further substituted, the partial structure represented by the formula:

is $CR^{5a}=CR^6$, $CR^{5b}=N$ or $C(=O)-NR^7$,
$R^{5a}$ and $R^{5b}$ are each independently an optionally substituted alkyl group or an optionally substituted alkoxy group,
$R^6$ and $R^7$ are each independently a hydrogen atom or a substituent,
Y is an optionally substituted methylene group or an oxygen atom, and
W is an optionally substituted $C_{1-2}$ alkylene group, or a salt thereof (hereinafter sometimes to be referred to as compound (Ia)).

[2a] A compound represented by the formula (Ia):

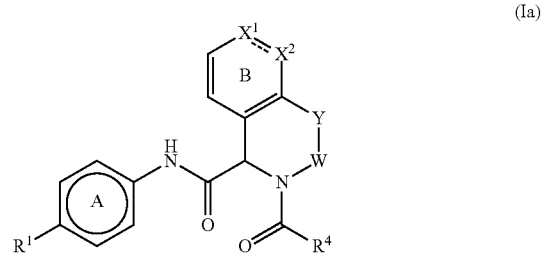

wherein
Ring A is an optionally further substituted 6-membered aromatic ring,
$R^1$ is a group represented by the formula: -Q($R^{1a}$) ($R^{1b}$) ($R^{1c}$) wherein Q is a carbon atom or a silicon atom, and $R^{1a}$, $R^{1b}$ and $R^{1c}$ are each independently a substituent, or $R^{1a}$ and $R^{1b}$ in combination optionally form, together with the adjacent Q, an optionally further substituted ring, and $R^{1c}$ is optionally bonded to one substituent for Ring A to form an optionally further substituted ring, or neo-pentyl group,
$R^4$ is a halogen atom, a cyano group, a nitro group, an optionally substituted $C_{1-6}$ alkyl group, an optionally substituted $C_{2-6}$ alkenyl group, an optionally substituted $C_{2-6}$ alkynyl group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl(SH) group or an optionally substituted silyl group,
wherein the "optionally substituted $C_{1-6}$ alkyl group", the "optionally substituted $C_{2-6}$ alkenyl group" and the "optionally substituted $C_{2-6}$ alkynyl group" for $R^4$ are each optionally substituted by 1 to 5 substituents selected from (1) a halogen atom, (2) a nitro group, (3) a cyano group, (4) an oxo group, (5) a hydroxy group, (6) an optionally halogenated $C_{1-6}$ alkoxy group, (7) a $C_{6-14}$ aryloxy group, (8) a $C_{7-16}$ aralkyloxy group, (9) a 5- to 14-membered aromatic heterocyclyloxy group, (10) a 3- to 14-membered non-aromatic heterocyclyloxy group, (11) a $C_{1-6}$ alkyl-carbonyloxy group, (12) a $C_{6-14}$ aryl-carbonyloxy group, (13) a $C_{1-6}$ alkoxy-carbonyloxy group, (14) a mono- or di-$C_{1-6}$ alkyl-carbamoyloxy group, (15) a $C_{6-14}$ aryl-carbamoyloxy group, (16) a 5- to 14-membered aromatic heterocyclylcarbonyloxy group, (17) a 3- to 14-membered non-aromatic heterocyclylcarbonyloxy group, (18) an optionally halogenated $C_{1-6}$ alkylsulfonyloxy group, (19) a $C_{6-14}$ arylsulfonyloxy group optionally substituted by $C_{1-6}$ alkyl group(s), (20) an optionally halogenated $C_{1-6}$ alkylthio group, (21) a 5- to 14-membered aromatic heterocyclic group, (22) a 3- to 14-membered non-aromatic heterocyclic group, (23) a formyl group, (24) a carboxy group, (25) an optionally halogenated $C_{1-6}$ alkyl-carbonyl group, (26) a $C_{6-14}$ aryl-carbonyl group, (27) a 5- to 14-membered aromatic heterocyclylcarbonyl group, (28) a 3- to 14-membered non-aromatic heterocyclylcarbonyl group, (29) a $C_{1-6}$ alkoxy-carbonyl group, (30) a $C_{6-14}$ aryloxy-carbonyl group, (31) a $C_{7-16}$ aralkyloxy-carbonyl group, (32) a carbamoyl group, (33) a thiocarbamoyl group, (34) a mono- or di-$C_{1-6}$ alkyl-carbamoyl group, (35) a $C_{6-14}$ aryl-carbamoyl group, (36) a 5- to 14-membered aromatic heterocyclylcarbamoyl group, (37) a 3- to 14-membered non-aromatic heterocyclylcarbamoyl group, (38) an optionally halogenated $C_{1-6}$ alkylsulfonyl group, (39) a $C_{6-14}$ arylsulfonyl group, (40) a 5- to 14-membered aromatic heterocyclylsulfonyl group, (41) an optionally halogenated $C_{1-6}$ alkylsulfinyl group, (42) a $C_{6-14}$ arylsulfinyl group, (43) a 5-to 14-membered aromatic heterocyclylsulfinyl group, (44) an amino group, (45) a mono- or di-$C_{1-6}$ alkylamino group, (46) a mono- or di-$C_{6-14}$ arylamino group, (47) a 5- to 14-membered aromatic heterocyclylamino group, (48) a $C_{7-16}$ aralkylamino group, (49) a formylamino group, (50) a $C_{1-6}$ alkyl-carbonylamino group, (51) a ($C_{1-6}$ alkyl) ($C_{1-6}$ alkyl-carbonyl)amino group, (52) a $C_{6-14}$ aryl-carbonylamino group, (53) a $C_{1-6}$ alkoxy-carbonylamino group, (54) a $C_{7-16}$ aralkyloxy-carbonylamino group, (55) a $C_{1-6}$ alkylsulfonylamino group, (56) a $C_{6-14}$ arylsulfonylamino group optionally substituted by $C_{1-6}$ alkyl group(s), (57) an optionally halogenated $C_{1-6}$ alkyl group, (58) a $C_{2-6}$ alkenyl group, and (59) a $C_{2-6}$ alkynyl group, Ring B is a benzene ring, a pyridine ring or a dihydropyridine ring, each of which is optionally further substituted, the partial structure represented by the formula:

is $CR^{5a}\!=\!CR^6$, $CR^{5b}\!=\!N$ or $C(\!=\!O)\!-\!NR^7$, $R^{5a}$ and $R^{5b}$ are each independently an optionally substituted alkyl group or an optionally substituted alkoxy group, $R^6$ and $R^7$ are each independently a hydrogen atom or a substituent, Y is an optionally substituted methylene group or an oxygen atom, and W is an optionally substituted $C_{1-2}$ alkylene group, or a salt thereof.

Effect of the Invention

The compound of the present invention has a superior RORγt inhibitory action, and useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, a halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, a halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, a halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, a halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, a halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkyl-sulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, a halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) an amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, 3-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbonsulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxycarbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkyl-sulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) an amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) an amino group (e.g., methylcarbamoylamino), a (mono- or di-$C_{7-16}$ aralkyl-carbamoyl) an amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl) an amino group (e.g., N-acetyl-N-methylamino) and a ($C_{1-6}$ alkyl) ($C_{6-14}$ aryl-carbonyl) an amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-C$_{2-6}$ alkenyl-thiocarbamoyl group (e.g., diallylthiocarbamoyl), a mono- or di-C$_{3-10}$ cycloalkyl-thiocarbamoyl group (e.g., cyclopropylthiocarbamoyl, cyclohexylthiocarbamoyl), a mono- or di-C$_{6-14}$ aryl-thiocarbamoyl group (e.g., phenylthiocarbamoyl), a mono- or di-C$_{7-16}$ aralkyl-thiocarbamoyl group (e.g., benzylthiocarbamoyl, phenethylthiocarbamoyl), a mono- or di-C$_{1-6}$ alkyl-carbonyl-thiocarbamoyl group (e.g., acetylthiocarbamoyl, propionylthiocarbamoyl), a mono- or di-C$_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a C$_{1-6}$ alkyl group, a C$_{2-6}$ alkenyl group, a C$_{3-10}$ cycloalkyl group, a C$_{6-14}$ aryl group, a C$_{7-16}$ aralkyl group, a C$_{1-6}$ alkyl-carbonyl group, a C$_{6-14}$ aryl-carbonyl group, a C$_{7-16}$ aralkyl-carbonyl group, a 5-to 14-membered aromatic heterocyclylcarbonyl group, a 3- to 14-membered non-aromatic heterocyclylcarbonyl group, a C$_{1-6}$ alkoxy-carbonyl group, a 5- to 14-membered aromatic heterocyclic group, a carbamoyl group, a mono- or di-C$_{1-6}$ alkyl-carbamoyl group and a mono- or di-C$_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-C$_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-C$_{2-6}$ alkenyl-sulfamoyl group (e.g., diallylsulfamoyl), a mono- or di-C$_{3-10}$ cycloalkyl-sulfamoyl group (e.g., cyclopropylsulfamoyl, cyclohexylsulfamoyl), a mono- or di-C$_{6-14}$ aryl-sulfamoyl group (e.g., phenylsulfamoyl), a mono- or di-C$_{7-16}$ aralkyl-sulfamoyl group (e.g., benzylsulfamoyl, phenethylsulfamoyl), a mono- or di-C$_{1-6}$ alkyl-carbonyl-sulfamoyl group (e.g., acetylsulfamoyl, propionylsulfamoyl), a mono- or di-C$_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a C$_{1-6}$ alkyl group, a C$_{2-6}$ alkenyl group, a C$_{3-10}$ cycloalkyl group, a C$_{6-14}$ aryl group, a C$_{7-16}$ aralkyl group, a C$_{1-6}$ alkyl-carbonyl group, a C$_{6-14}$ aryl-carbonyl group, a C$_{7-16}$ aralkyl-carbonyl group, a 5- to 14-membered aromatic heterocyclylcarbonyl group, a 3- to 14-membered non-aromatic heterocyclylcarbonyl group, a C$_{1-6}$ alkoxy-carbonyl group, a 5- to 14-membered aromatic heterocyclic group, a carbamoyl group, a mono- or di-C$_{1-6}$ alkyl-carbamoyl group, a mono- or di-C$_{7-16}$ aralkyl-carbamoyl group, a C$_{1-6}$ alkylsulfonyl group and a C$_{6-14}$ arylsulfonyl group, each of which optionally has 1 to 3 substituents selected from Substituent group A".

Preferable examples of the optionally substituted hydroxy group include a hydroxy group, a C$_{1-6}$ alkoxy group, a C$_{2-6}$ alkenyloxy group (e.g., allyloxy, 2-butenyloxy, 2-pentenyloxy, 3-hexenyloxy), a C$_{3-10}$ cycloalkyloxy group (e.g., cyclohexyloxy), a C$_{6-14}$ aryloxy group (e.g., phenoxy, naphthyloxy), a C$_{7-16}$ aralkyloxy group (e.g., benzyloxy, phenethyloxy), a C$_{1-6}$ alkyl-carbonyloxy group (e.g., acetyloxy, propionyloxy, butyryloxy, isobutyryloxy, pivaloyloxy), a C$_{6-14}$ aryl-carbonyloxy group (e.g., benzoyloxy), a C$_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a C$_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a C$_{1-6}$ alkyl-carbamoyloxy group (e.g., methylcarbamoyloxy), a C$_{7-16}$ aralkyl-carbamoyloxy group (e.g., benzylcarbamoyloxy), a C$_{1-6}$ alkylsulfonyloxy group (e.g., methylsulfonyloxy, ethylsulfonyloxy) and a C$_{6-14}$ arylsulfonyloxy group (e.g., phenylsulfonyloxy).

In the present specification, examples of the "optionally substituted sulfanyl group" include a sulfanyl group optionally having "a substituent selected from a C$_{1-6}$ alkyl group, a C$_{2-6}$ alkenyl group, a C$_{3-10}$ cycloalkyl group, a C$_{6-14}$ aryl group, a C$_{7-16}$ aralkyl group, a C$_{1-6}$ alkyl-carbonyl group, a C$_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a C$_{1-6}$ alkylthio group, a C$_{2-6}$ alkenylthio group (e.g., allylthio, 2-butenylthio, 2-pentenylthio, 3-hexenylthio), a C$_{3-10}$ cycloalkylthio group (e.g., cyclohexylthio), a C$_{6-14}$ arylthio group (e.g., phenylthio, naphthylthio), a C$_{7-16}$ aralkylthio group (e.g., benzylthio, phenethylthio), a C$_{1-6}$ alkyl-carbonylthio group (e.g., acetylthio, propionylthio, butyrylthio, isobutyrylthio, pivaloylthio), a C$_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a C$_{1-6}$ alkyl group, a C$_{2-6}$ alkenyl group, a C$_{3-10}$ cycloalkyl group, a C$_{6-14}$ aryl group and a C$_{7-16}$ aralkyl group, each of which optionally has 1 to 3 substituents selected from Substituent group A".

Preferable examples of the optionally substituted silyl group include a tri-C$_{1-6}$ alkylsilyl group (e.g., trimethylsilyl, tert-butyl(dimethyl)silyl).

In the present specification, examples of the "C$_{1-6}$ alkylene group" include —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(C$_2$H$_5$)—, —CH(C$_3$H$_7$)—, —CH(CH(CH$_3$)$_2$)—, —(CH(CH$_3$))$_2$—, —CH$_2$—CH(CH$_3$)—, —CH(CH$_3$)—CH$_2$—, —CH$_2$—CH$_2$—C(CH$_3$)$_2$—, —C(CH$_3$)$_2$—CH$_2$—CH$_2$—, and —C(CH$_3$)$_2$—CH$_2$—CH$_2$—CH$_2$—.

In the present specification, examples of the "C$_{2-6}$ alkenylene group" include —CH=CH—, —CH$_2$—CH=CH—, —CH=CH—CH$_2$—, —C(CH$_3$)$_2$—CH=CH—, —CH=CH—C(CH$_3$)$_2$—, —CH$_2$—CH=CH—CH$_2$—, —CH$_2$—CH$_2$—CH=CH—, —CH=CH—CH$_2$—CH$_2$—, —CH=CH—CH$_2$—CH$_2$—CH$_2$— and —CH$_2$—CH$_2$—CH$_2$—CH=CH—.

In the present specification, examples of the "C$_{2-6}$ alkynylene group" include —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—, —C≡C—CH$_2$—CH$_2$—, —C≡C—C≡C—, —C≡C—CH$_2$—CH$_2$—CH$_2$— and —CH$_2$—CH$_2$—CH$_2$—C≡C—.

As shown in the formula:

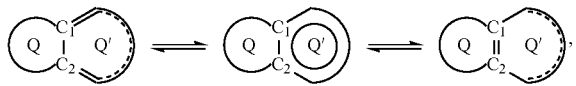

in the present specification, when the non-aromatic Ring Q, which is fused with the aromatic Ring Q', is present, then the non-aromatic Ring Q is expressed as a ring wherein the bond $C^1C^2$ is a double bond.

For example, when the above-mentioned fused Ring QQ' is an indane ring, then the non-aromatic Ring Q is expressed as a cyclopentene ring, and the aromatic Ring Q' is expressed as a benzene ring.

For example, when the above-mentioned fused Ring QQ' is a 2,3-dihydrobenzofuran ring, then the non-aromatic Ring Q is expressed as a dihydrofuran ring (e.g., 2,3-dihydrofuran), and the aromatic Ring Q' is expressed as a benzene ring.

For example, when the above-mentioned fused Ring QQ' is a 1,3-benzodioxole ring, then the non-aromatic Ring Q is expressed as a dioxole ring (e.g., 1,3-dioxole), and the aromatic Ring Q' is expressed as a benzene ring.

For example, when the above-mentioned fused Ring QQ' is a 2,3-dihydro-1,4-benzodioxin ring, then the non-aromatic Ring Q is expressed as a dihydrodioxin ring (e.g., 2,3-dihydro-1,4-dioxin), and the aromatic Ring Q' is expressed as a benzene ring.

The definition of each symbol in the formulas (I) and (Ia) is explained in detail in the following.

Ring A is an optionally further substituted 6-membered aromatic ring.

Examples of the "6-membered aromatic ring" of the "optionally further substituted 6-membered aromatic ring" for Ring A include a benzene ring, a pyridine ring, a pyridazine ring, a pyrimidine ring, a pyrazine ring and a triazine ring.

The "6-membered aromatic ring" is optionally further substituted, for example, by substituent(s) selected from the above-mentioned Substituent Group A. The number of the substituents is, for example, 1 to 3. When the number of the substituents is 2 or more, the respective substituents may be the same or different.

Ring A is preferably a 6-membered aromatic ring (e.g., a benzene ring, a pyridine ring) optionally further substituted by 1 to 3 (preferably 1 or 2) substituents selected from
(1) a halogen atom (e.g., a fluorine atom, a chlorine atom),
(2) a $C_{1-6}$ alkoxy group (e.g., methoxy, ethoxy) optionally substituted by 1 to 3 halogen atoms (e.g., a fluorine atom), and
(3) a cyano group.

Ring A is more preferably a benzene ring optionally further substituted by 1 to 3 (preferably 1 or 2) substituents selected from
(1) a halogen atom (e.g., a fluorine atom, a chlorine atom), and
(2) a cyano group.

Ring A is still more preferably a benzene ring optionally further substituted by 1 to 3 (preferably 1 or 2) halogen atoms (e.g., a fluorine atom).

In another embodiment, Ring A is more preferably a benzene ring optionally further substituted by halogen atom(s) (e.g., a fluorine atom, a chlorine atom) or cyano group(s).

Ring A is still more preferably a benzene ring optionally further substituted by halogen atom(s) (e.g., a fluorine atom).

$R^1$ is
(1) a group represented by the formula: -Q($R^{1a}$) ($R^{1b}$) ($R^{1c}$)
wherein Q is a carbon atom, a silicon atom or a germanium atom, and $R^{1a}$, $R^{1b}$ and $R^{1c}$ are each independently a substituent, or $R^{1a}$ and $R^{1b}$ in combination optionally form, together with the adjacent Q, an optionally further substituted ring, and $R^{1c}$ is optionally bonded to one substituent for Ring A to form an optionally further substituted ring,
(2) a neo-pentyl group, or
(3) a trimethylsilylmethyl group.

Examples of the "optionally substituted ring" formed by $R^{1a}$ and $R^{1b}$ in combination together with the adjacent Q include a $C_{3-10}$ cycloalkane ring, a $C_{3-10}$ cycloalkene ring and a non-aromatic heterocycle (including a 3- to 14-membered non-aromatic heterocycle), each of which is optionally further substituted by substituent(s) selected from the above-mentioned Substituent Group A. The number of the substituents in the "optionally substituted ring" is, for example, 1 to 3. When the number of the substituents is 2 or more, the respective substituents may be the same or different.

Examples of the "$C_{3-10}$ cycloalkane ring" exemplified as the "optionally substituted ring" formed by $R^{1a}$ and $R^{1b}$ in combination together with the adjacent Q include a ring corresponding to the above-mentioned "$C_{3-10}$ cycloalkyl group".

Examples of the "$C_{3-10}$ cycloalkene ring" exemplified as the "optionally substituted ring" formed by $R^{1a}$ and $R^{1b}$ in combination together with the adjacent Q include a ring corresponding to the above-mentioned "$C_{3-10}$ cycloalkenyl group".

Examples of the "non-aromatic heterocycle" exemplified as the "optionally substituted ring" formed by $R^{1a}$ and $R^{1b}$ in combination together with the adjacent Q include a ring corresponding to the above-mentioned "non-aromatic heterocyclic group".

Examples of the "optionally further substituted ring" formed by $R^{1c}$ and one substituent for Ring A in combination include a $C_{3-10}$ cycloalkene ring and a non-aromatic heterocycle (including a 3- to 14-membered non-aromatic heterocycle), each of which is optionally further substituted by substituent(s) selected from the above-mentioned Substituent Group A. The number of the substituents in the "optionally substituted ring" is, for example, 1 to 3. When the number of the substituents is 2 or more, the respective substituents may be the same or different.

Examples of the "$C_{3-10}$ cycloalkene ring" exemplified as the "optionally further substituted ring" formed by $R^{1c}$ and one substituent for Ring A in combination include a ring corresponding to the above-mentioned "$C_{3-10}$ cycloalkenyl group".

Examples of the "non-aromatic heterocycle" exemplified as the "optionally further substituted ring" formed by $R^{1c}$ and one substituent for Ring A in combination include a ring corresponding to the above-mentioned "non-aromatic heterocyclic group".

When $R^{1c}$ is bonded to one substituent for Ring A to form an "optionally further substituted ring", in the formula (I) or formula (Ia), the partial structure represented by the formula:

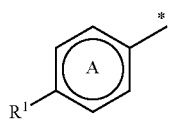

wherein * is a binding site, and the other symbols are as defined above, is preferably the partial structure represented by the formula:

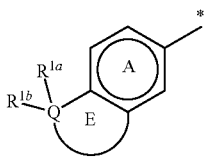

wherein Ring E is a "optionally further substituted ring" formed by $R^{1c}$ and one substituent for Ring A, and the other symbols are as defined above,
more preferably the partial structure represented by the formula:

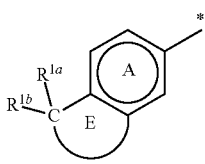

wherein each symbol is as defined above,
still more preferably the partial structure represented by the formula:

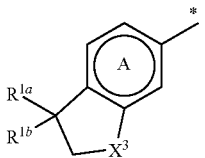

wherein $X^3$ is a methylene group or an oxygen atom, and the other symbols are as defined above,
(which is the partial structure wherein $R^{1c}$ is bonded to one substituent for Ring A to form a dihydrofuran ring (one example) or a cyclopentene ring),
particularly preferably the partial structure represented by the formula:

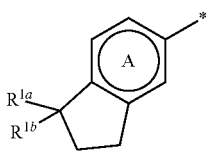

(which is the partial structure wherein $R^{1c}$ is bonded to one substituent for Ring A to form a cyclopentene ring).
Q is preferably a carbon atom or a silicon atom.
$R^{1a}$ and $R^{1b}$ is preferably each independently a $C_{1-6}$ alkyl group (e.g., methyl).
$R^{1c}$ is preferably
(a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from
  (i) a halogen atom (e.g., a fluorine atom),
  (ii) a $C_{3-10}$ cycloalkyl group (e.g., cyclopropyl), and
  (iii) a $C_{1-6}$ alkoxy group (e.g., methoxy),
(b) a $C_{1-6}$ alkoxy-carbonyl group (e.g., ethoxycarbonyl),
(c) a carbamoyl group optionally mono- or di-substituted by substituent(s) selected from
  (i) a $C_{1-6}$ alkyl group (e.g., ethyl), and
  (ii) a $C_{3-10}$ cycloalkyl group (e.g., cyclopropyl),
(d) a 5- or 6-membered monocyclic aromatic heterocyclic group (e.g., oxadiazolyl (1,3,4-oxadiazolyl)) optionally substituted by 1 to 3 $C_{1-6}$ alkyl groups (e.g., methyl), or
(e) a 3- to 8-membered monocyclic non-aromatic heterocyclylcarbonyl group (e.g., pyrrolidinylcarbonyl).
$R^{1c}$ is more preferably
(a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from
  (i) a halogen atom (e.g., a fluorine atom),
  (ii) a $C_{3-10}$ cycloalkyl group (e.g., cyclopropyl), and
  (iii) a $C_{1-6}$ alkoxy group (e.g., methoxy),
(b) a $C_{1-6}$ alkoxy-carbonyl group (e.g., ethoxycarbonyl), or
(c) a 3- to 8-membered monocyclic non-aromatic heterocyclylcarbonyl group (e.g., pyrrolidinylcarbonyl).
$R^{1c}$ is particularly preferably a $C_{1-6}$ alkyl group (e.g., methyl).
Alternatively, $R^{1c}$ is bonded to one substituent for Ring A to form preferably
(a) a $C_{3-10}$ cycloalkene ring (e.g., cyclopentene), or
(b) a 3- to 14-membered non-aromatic heterocycle (e.g., dihydrofuran), more preferably a $C_{3-10}$ cycloalkene ring (e.g., cyclopentene).
$R^1$ is preferably
(1) a group represented by the formula: $-Q(R^{1a})(R^{1b})(R^{1c})$
wherein
Q is a carbon atom or a silicon atom, and
$R^{1a}$, $R^{1b}$ and $R^{1c}$ are each independently
  (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 halogen atoms (e.g., a fluorine atom),
  (b) a $C_{1-6}$ alkoxy-carbonyl group (e.g., ethoxycarbonyl),
  (c) a carbamoyl group optionally mono- or di-substituted by substituent(s) selected from
    (i) a $C_{1-6}$ alkyl group (e.g., ethyl), and
    (ii) a $C_{3-10}$ cycloalkyl group (e.g., cyclopropyl),
  (d) a 5- or 6-membered monocyclic aromatic heterocyclic group (e.g., oxadiazolyl (1,3,4-oxadiazolyl)) optionally substituted by 1 to 3 $C_{1-6}$ alkyl groups (e.g., methyl), or
  (e) a 3- to 8-membered monocyclic non-aromatic heterocyclylcarbonyl group (e.g., pyrrolidinylcarbonyl), or
  $R^{1c}$ is bonded to one substituent for Ring A to form
  (a) a $C_{3-10}$ cycloalkene ring (e.g., cyclopentene), or
  (b) a 3- to 14-membered non-aromatic heterocycle (e.g., dihydrofuran), or
(2) a neo-pentyl group.
$R^1$ is more preferably a group represented by the formula:

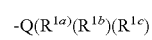

wherein
Q is a carbon atom or a silicon atom, and
$R^{1a}$, $R^{1b}$ and $R^{1c}$ are each independently
  (a) a $C_{1-6}$ alkyl group (e.g., methyl), or
  (b) a $C_{1-6}$ alkoxy-carbonyl group (e.g., ethoxycarbonyl), or
$R^{1c}$ is bonded to one substituent for Ring A to form a $C_{3-10}$ cycloalkene ring (e.g., cyclopentene).

In another embodiment, $R^1$ is preferably
(1) a group represented by the formula: $-Q(R^{1a})(R^{1b})(R^{1c})$
  wherein
  Q is a carbon atom or a silicon atom, and
  $R^{1a}$, $R^{1b}$ and $R^{1c}$ are each independently
    (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from
      (i) a halogen atom (e.g., a fluorine atom),
      (ii) a $C_{3-10}$ cycloalkyl group (e.g., cyclopropyl), and
      (iii) a $C_{1-6}$ alkoxy group (e.g., methoxy),
    (b) a $C_{1-6}$ alkoxy-carbonyl group (e.g., ethoxycarbonyl),
    (c) a carbamoyl group optionally mono- or di-substituted by substituent(s) selected from
      (i) a $C_{1-6}$ alkyl group (e.g., ethyl), and
      (ii) a $C_{3-10}$ cycloalkyl group (e.g., cyclopropyl),
    (d) a 5- or 6-membered monocyclic aromatic heterocyclic group (e.g., oxadiazolyl (1,3,4-oxadiazolyl)) optionally substituted by 1 to 3 $C_{1-6}$ alkyl groups (e.g., methyl), or
    (e) a 3- to 8-membered monocyclic non-aromatic heterocyclylcarbonyl group (e.g., pyrrolidinylcarbonyl), or
  $R^{1c}$ is bonded to one substituent for Ring A to form
    (a) a $C_{3-10}$ cycloalkene ring (e.g., cyclopentene), or
    (b) a 3- to 14-membered non-aromatic heterocycle (e.g., dihydrofuran), or
(2) a neo-pentyl group.
$R^1$ is more preferably a group represented by the formula:

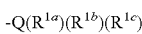

wherein
Q is a carbon atom or a silicon atom, and
$R^{1a}$, $R^{1b}$ and $R^{1c}$ are each independently
  (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from
    (i) a halogen atom (e.g., a fluorine atom),
    (ii) a $C_{3-10}$ cycloalkyl group (e.g., cyclopropyl), and
    (iii) a $C_{1-6}$ alkoxy group (e.g., methoxy),
  (b) a $C_{1-6}$ alkoxy-carbonyl group (e.g., ethoxycarbonyl), or
  (c) a 3- to 8-membered monocyclic non-aromatic heterocyclylcarbonyl group (e.g., pyrrolidinylcarbonyl), or
$R^{1c}$ is bonded to one substituent for Ring A to form a $C_{3-10}$ cycloalkene ring (e.g., cyclopentene).

$R^1$ is particularly preferably a group represented by the formula: $-Q(R^{1a})(R^{1b})(R^{1c})$
wherein
Q is a carbon atom or a silicon atom, and
$R^{1a}$, $R^{1b}$ and $R^{1c}$ are each independently a $C_{1-6}$ alkyl group (e.g., methyl), or
$R^{1c}$ is bonded to one substituent for Ring A to form a $C_{3-10}$ cycloalkene ring (e.g., cyclopentene).

In another embodiment, $R^1$ is preferably
(1) a group represented by the formula: $-Q(R^{1a})(R^{1b})(R^{1c})$
  wherein
  Q is a carbon atom or a silicon atom,
  $R^{1a}$ and $R^{1b}$ are each independently a $C_{1-6}$ alkyl group (e.g., methyl), and
  $R^{1c}$ is
    (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from
      (i) a halogen atom (e.g., a fluorine atom),
      (ii) a $C_{3-10}$ cycloalkyl group (e.g., cyclopropyl), and
      (iii) a $C_{1-6}$ alkoxy group (e.g., methoxy),
    (b) a $C_{1-6}$ alkoxy-carbonyl group (e.g., ethoxycarbonyl),
    (c) a carbamoyl group optionally mono- or di-substituted by substituent(s) selected from
      (i) a $C_{1-6}$ alkyl group (e.g., ethyl), and
      (ii) a $C_{3-10}$ cycloalkyl group (e.g., cyclopropyl),
    (d) a 5- or 6-membered monocyclic aromatic heterocyclic group (e.g., oxadiazolyl (1,3,4-oxadiazolyl)) optionally substituted by 1 to 3 $C_{1-6}$ alkyl groups (e.g., methyl), or
    (e) a 3- to 8-membered monocyclic non-aromatic heterocyclylcarbonyl group (e.g., pyrrolidinylcarbonyl), or
  $R^{1c}$ is bonded to one substituent for Ring A to form
    (a) a $C_{3-10}$ cycloalkene ring (e.g., cyclopentene), or
    (b) a 3- to 14-membered non-aromatic heterocycle (e.g., dihydrofuran), or
(2) a neo-pentyl group.

$R^1$ is more preferably a group represented by the formula:

$-Q(R^{1a})(R^{1b})(R^{1c})$ wherein
Q is a carbon atom or a silicon atom,
$R^{1a}$ and $R^{1b}$ are each independently a $C_{1-6}$ alkyl group (e.g., methyl), and
$R^{1c}$ is
  (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from
    (i) a halogen atom (e.g., a fluorine atom),
    (ii) a $C_{3-10}$ cycloalkyl group (e.g., cyclopropyl), and
    (iii) a $C_{1-6}$ alkoxy group (e.g., methoxy),
  (b) a $C_{1-6}$ alkoxy-carbonyl group (e.g., ethoxycarbonyl), or
  (c) a 3- to 8-membered monocyclic non-aromatic heterocyclylcarbonyl group (e.g., pyrrolidinylcarbonyl), or
$R^{1c}$ is bonded to one substituent for Ring A to form a $C_{3-10}$ cycloalkene ring (e.g., cyclopentene).

In another embodiment, $R^1$ is preferably a trimethylsilyl group, an ethyldimethylsilyl group or an optionally substituted tert-butyl group, or a group represented by the formula: $-C(R^{1a})(R^{1b})(R^{1c})$ wherein $R^{1a}$ and $R^{1b}$ are each independently a substituent, or $R^{1a}$ and $R^{1b}$ in combination optionally form, together with the adjacent carbon atom, an optionally further substituted ring, and $R^{1c}$ is bonded to one substituent for Ring A to form an optionally further substituted ring.

Examples of the "optionally substituted tert-butyl group" for $R^1$ include a tert-butyl group optionally substituted by substituent(s) selected from the above-mentioned Substituent Group A. The number of the substituents in the "optionally substituted tert-butyl group" is, for example, 1 to 5, preferably 1 to 3. When the number of the substituents is 2 or more, the respective substituents may be the same or different.

$R^1$ is more preferably
(1) (a) a trimethylsilyl group,
  (b) an ethyldimethylsilyl group, or
  (c) a tert-butyl group optionally substituted by 1 to 3 $C_{1-6}$ alkoxy groups (e.g., methoxy, ethoxy) optionally substituted by 1 to 3 substituents selected from
    (i) a halogen atom (e.g., a fluorine atom),
    (ii) a $C_{3-10}$ cycloalkyl group (e.g., cyclopropyl), and
    (iii) a $C_{1-6}$ alkoxy group (e.g., methoxy), or
(2) a group represented by the formula: $-C(R^{1a})(R^{1b})(R^{1c})$
wherein
$R^{1a}$ and $R^{1b}$ are each independently a $C_{1-6}$ alkyl group (e.g., methyl), and $R^{1c}$ is bonded to one substituent for Ring A to form a $C_{3-10}$ cycloalkene ring (e.g., cyclopentene).

In one embodiment, in formula (I) or formula (Ia), the partial structure represented by the formula:

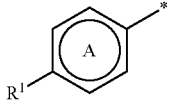

wherein each symbol is as defined above,
is preferably the partial structure selected from the formula:

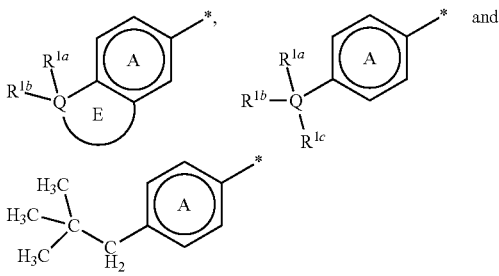

wherein each symbol is as defined above,
more preferably the partial structure selected from the formula:

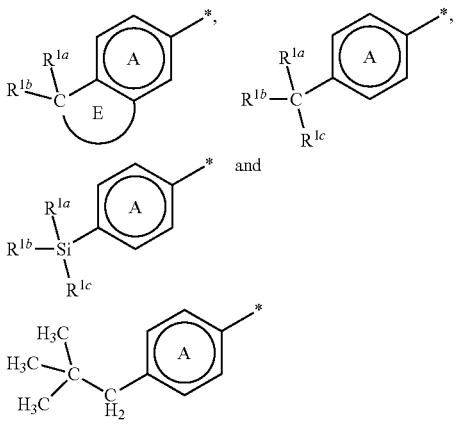

wherein each symbol is as defined above,
still more preferably the partial structure selected from the formula:

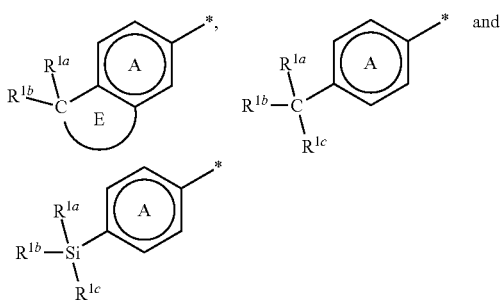

wherein each symbol is as defined above, particularly preferably the partial structure selected from the formula:

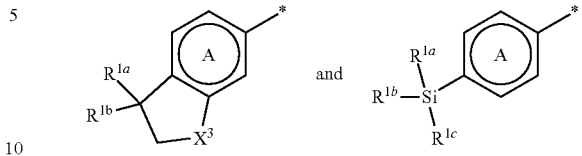

wherein each symbol is as defined above.

$R^{11}$ is —$CR^{12}R^{12'}$—$R^{12''}$, —$C(=O)$—$R^4$ or —$SO_2$—$R^{13'}$
$R^{11}$ is preferably —$C(=O)$—$R^4$.

$R^{12}$, $R^{12'}$ and $R^{12''}$ are each independently a hydrogen atom, a halogen atom, a cyano group, a nitro group, an optionally substituted $C_{1-6}$ alkyl group, an optionally substituted $C_2$-6 alkenyl group, an optionally substituted $C_{2-6}$ alkynyl group, an optionally substituted heterocyclic group or an optionally substituted thiocarbamoyl group.

The "optionally substituted $C_{1-6}$ alkyl group", "optionally substituted $C_{2-6}$ alkenyl group", "optionally substituted $C_{2-6}$ alkynyl group", "optionally substituted heterocyclic group" and the "optionally substituted thiocarbamoyl group" for $R^{12}$, $R^{12'}$ or $R^{12''}$ are each optionally substituted by 1 to 5 (preferably 1 to 3) substituents selected from Substituent Group A. When the number of the substituents is 2 or more, the respective substituents may be the same or different.

Preferably, $R^{12}$ is a hydrogen atom, a halogen atom, a cyano group, a nitro group, an optionally substituted $C_{1-6}$ alkyl group, an optionally substituted $C_{2-6}$ alkenyl group, an optionally substituted $C_{2-6}$ alkynyl group, an optionally substituted heterocyclic group or an optionally substituted thiocarbamoyl group, and $R^{12'}$ and $R^{12''}$ are hydrogen atoms.

More preferably, $R^{12}$ is an optionally substituted $C_{1-6}$ alkyl group, and $R^{12'}$ and $R^{12''}$ are hydrogen atoms.

Still more preferably, $R^{12}$ is a $C_{1-6}$ alkyl group (e.g., ethyl) optionally substituted by 1 to 3 $C_{1-6}$ alkoxy-carbonyl groups (e.g., methoxycarbonyl), and $R^{12'}$ and $R^{12''}$ are hydrogen atoms.

$R^4$ is a halogen atom, a cyano group, a nitro group, an optionally substituted $C_{1-6}$ alkyl group, an optionally substituted $C_{2-6}$ alkenyl group, an optionally substituted $C_{2-6}$ alkynyl group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl(SH) group or an optionally substituted silyl group, wherein the "$C_{1-6}$ alkyl group", "$C_{2-6}$ alkenyl group" and "$C_{2-6}$ alkynyl group" of the "optionally substituted $C_{1-6}$ alkyl group", "optionally substituted $C_{2-6}$ alkenyl group" and "optionally substituted $C_{2-6}$ alkynyl group" for $R^4$ are each optionally substituted by 1 to 5 (preferably 1 to 3) substituents selected from (1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),

(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group (e.g., phenylsulfonyloxy, toluenesulfonyloxy) optionally substituted by $C_{1-6}$ alkyl group(s),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group (e.g., phenylsulfonylamino, toluenesulfonylamino) optionally substituted by $C_{1-6}$ alkyl group(s),
(57) an optionally halogenated $C_{1-6}$ alkyl group,
(58) a $C_{2-6}$ alkenyl group, and
(59) a $C_{2-6}$ alkynyl group.
When the number of the substituents is 2 or more, the respective substituents may be the same or different.

In another embodiment, $R^4$ is an optionally substituted $C_{1-6}$ alkyl group, an optionally substituted $C_{2-6}$ alkenyl group, an optionally substituted $C_{2-6}$ alkynyl group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl(SH) group or an optionally substituted silyl group,
wherein the "$C_{1-6}$ alkyl group", "$C_{2-6}$ alkenyl group" and "$C_{2-6}$ alkynyl group" of the "optionally substituted $C_{1-6}$ alkyl group", "optionally substituted $C_{2-6}$ alkenyl group" and "optionally substituted $C_{2-6}$ alkynyl group" for $R^4$ are each optionally substituted by 1 to 5 (preferably 1 to 3) substituents selected from
(1) a halogen atom,
(2) a nitro group,
(3) a cyano group,
(4) an oxo group,
(5) a hydroxy group,
(6) a $C_{1-6}$ alkoxy group optionally substituted by substituent(s) selected from a halogen atom and a carboxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),

(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group (e.g., phenylsulfonyloxy, toluenesulfonyloxy) optionally substituted by $C_{1-6}$ alkyl group(s),
(20) an optionally halogenated $C_{1-6}$ alkylthio group,
(21) a 5- to 14-membered aromatic heterocyclic group optionally substituted by substituent(s) selected from a hydroxy group, a $C_{1-6}$ alkyl group, a $C_{1-6}$ alkoxy group and a carboxy group,
(22) a 3- to 14-membered non-aromatic heterocyclic group optionally substituted by substituent(s) selected from an oxo group and a $C_{1-6}$ alkyl group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (the $C_{1-6}$ alkyl is optionally substituted by carboxy group(s)) (e.g., methylamino, ethylamino, propylamino, isopropylamino, butylamino, dimethylamino, diethylamino, dipropylamino, dibutylamino, N-ethyl-N-methylamino, N-(carboxymethyl)-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group (e.g., phenylsulfonylamino, toluenesulfonylamino) optionally substituted by $C_{1-6}$ alkyl group(s),
(57) an optionally halogenated $C_{1-6}$ alkyl group,
(58) a $C_{2-6}$ alkenyl group, and
(59) a $C_{2-6}$ alkynyl group.
When the number of the substituents is 2 or more, the respective substituents may be the same or different.

In another embodiment, $R^4$ is a halogen atom, a cyano group, a nitro group, an optionally substituted $C_{1-6}$ alkyl group, an optionally substituted $C_{2-6}$ alkenyl group, an optionally substituted $C_{2-6}$ alkynyl group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group or an optionally substituted silyl group, wherein the substituents which the "optionally substituted $C_{1-6}$ alkyl group", "optionally substituted $C_{2-6}$ alkenyl group", "optionally substituted $C_{2-6}$ alkynyl group" and "optionally substituted heterocyclic group" for $R^4$ optionally have are each selected from
(1) a halogen atom,
(2) a nitro group,
(3) a cyano group,
(4) an oxo group,
(5) a hydroxy group,
(6) an optionally halogenated $C_{1-6}$ alkoxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,

(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino), (53) a $C_{1-6}$ alkoxy-carbonylamino group (e.g.,
methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) an optionally halogenated $C_{1-6}$ alkyl group,
(58) a $C_{2-6}$ alkenyl group, and
(59) a $C_{2-6}$ alkynyl group.
The number of the substituents is 1 to 5 (preferably 1 to 3). When the number of the substituents is 2 or more, the respective substituents may be the same or different.

In another embodiment, $R^4$ is an optionally substituted $C_{1-6}$ alkyl group, an optionally substituted $C_{2-6}$ alkenyl group, an optionally substituted $C_{2-6}$ alkynyl group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl(SH) group or an optionally substituted silyl group, Wherein the substituents for the "$C_{1-6}$ alkyl group", "$C_{2-6}$ alkenyl group" and "$C_{2-6}$ alkynyl group" of the "optionally substituted $C_{1-6}$ alkyl group", "optionally substituted $C_{2-6}$ alkenyl group" and "optionally substituted $C_{2-6}$ alkynyl group" for $R^4$ are each selected from
(1) a halogen atom,
(2) a nitro group,
(3) a cyano group,
(4) an oxo group,
(5) a hydroxy group,
(6) a $C_{1-6}$ alkoxy group optionally substituted by substituent(s) selected from a halogen atom and a carboxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group optionally substituted by substituent(s) selected from a hydroxy group, a $C_{1-6}$ alkyl group, a $C_{1-6}$ alkoxy group and a carboxy group,
(22) a 3- to 14-membered non-aromatic heterocyclic group optionally substituted by substituent(s) selected from an oxo group and a $C_{1-6}$ alkyl group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (the $C_{1-6}$ alkyl is optionally substituted by carboxy group(s)) (e.g., methylamino, ethylamino, propylamino, isopropylamino, butylamino, dimethylamino, diethylamino, dipropylamino, dibutylamino, N-ethyl-N-methylamino, N-(carboxymethyl)-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),

(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) an optionally halogenated $C_{1-6}$ alkyl group,
(58) a $C_{2-6}$ alkenyl group, and
(59) a $C_{2-6}$ alkynyl group.

The number of the substituents is 1 to 5 (preferably 1 to 3). When the number of the substituents is 2 or more, the respective substituents may be the same or different.

The substituent which the "optionally substituted heterocyclic group" for $R^4$ optionally has is selected from
(1) a halogen atom,
(2) a nitro group,
(3) a cyano group,
(4) an oxo group,
(5) a hydroxy group,
(6) a $C_{1-6}$ alkoxy group optionally substituted by substituent(s) selected from a halogen atom and a carboxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) a $C_{1-6}$ alkyl group optionally substituted by substituent(s) selected from a halogen atom, a carboxy group, and a "$C_{1-6}$ alkoxy-carbonyl optionally substituted by $C_{6-14}$ aryl group(s)",
(58) a $C_{2-6}$ alkenyl group, and
(59) a $C_{2-6}$ alkynyl group.

The number of the substituents is 1 to 5 (preferably 1 to 3). When the number of the substituents is 2 or more, the respective substituents may be the same or different.

In one embodiment, examples of the "acyl group" for $R^4$ include a formyl group, a carboxy group, a carbamoyl group, a thiocarbamoyl group, a sulfino group, a sulfo group, a sulfamoyl group and a phosphono group, each of which has "1 or 2 substituents selected from a $C_{1-6}$ alkyl group, a $C_{2-6}$ alkenyl group, a 5- to 14-membered aromatic heterocyclic group and a 3- to 14-membered non-aromatic heterocyclic group, each of which has 1 to 3 substituents selected from a halogen atom, an optionally halogenated $C_{1-6}$ alkoxy group, a hydroxy group, a nitro group, a cyano group, an amino group, a carboxy group and a carbamoyl group".

In one embodiment, examples of the "optionally substituted amino group" for $R^4$ include an amino group optionally having 1 or 2 substituents selected from a $C_{1-6}$ alkyl group, a $C_{2-6}$ alkenyl group, a $C_{1-6}$ alkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a $C_{1-6}$ alkylsulfonyl group, each of which has 1 to 3 substituents selected from
(1) a halogen atom,
(2) a nitro group,
(3) a cyano group,
(4) an oxo group,
(5) a hydroxy group,
(6) an optionally halogenated $C_{1-6}$ alkoxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),

(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group optionally substituted by $C_{6-14}$ aryl group(s),
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) an optionally halogenated $C_{1-6}$ alkyl group,
(58) a $C_{2-6}$ alkenyl group, and
(59) a $C_{2-6}$ alkynyl group.

When the number of the substituents is 2, the respective substituents may be the same or different.

In one embodiment, examples of the "optionally substituted carbamoyl group" for $R^4$ include a carbamoyl group optionally having 1 or 2 substituents selected from a $C_{1-6}$ alkyl group, a $C_{2-6}$ alkenyl group, a $C_{1-6}$ alkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group and a mono- or di-$C_{1-6}$ alkyl-carbamoyl group, each of which has 1 to 3 substituents selected from
(1) a halogen atom,
(2) a nitro group,
(3) a cyano group,
(4) an oxo group,
(5) a hydroxy group,
(6) an optionally halogenated $C_{1-6}$ alkoxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),

(51) a ($C_{1-6}$ alkyl) ($C_{1-6}$ alkyl-carbonyl)amino group (e.g., N-acetyl-N-methylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) an optionally halogenated $C_{1-6}$ alkyl group,
(58) a $C_{2-6}$ alkenyl group, and
(59) a $C_{2-6}$ alkynyl group.

When the number of the substituents is 2, the respective substituents may be the same or different.

In one embodiment, examples of the "optionally substituted thiocarbamoyl group" for $R^4$ include a thiocarbamoyl group optionally having 1 or 2 substituents selected from a $C_{1-6}$ alkyl group, a $C_{2-6}$ alkenyl group, a $C_{1-6}$ alkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group and a mono- or di-$C_{1-6}$ alkyl-carbamoyl group, each of which has 1 to 3 substituents selected from (1) a halogen atom,
(2) a nitro group,
(3) a cyano group,
(4) an oxo group,
(5) a hydroxy group,
(6) an optionally halogenated $C_{1-6}$ alkoxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) an optionally halogenated $C_{1-6}$ alkyl group,
(58) a $C_{2-6}$ alkenyl group, and
(59) a $C_{2-6}$ alkynyl group.

When the number of the substituents is 2, the respective substituents may be the same or different.

In one embodiment, examples of the "optionally substituted sulfamoyl group" for $R^4$ include a sulfamoyl group optionally having 1 or 2 substituents selected from a $C_{1-6}$ alkyl group, a $C_{2-6}$ alkenyl group, a $C_{1-6}$ alkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group and a mono- or di-$C_{1-6}$ alkyl-carbamoyl group, each of which has 1 to 3 substituents selected from (1) a halogen atom,
(2) a nitro group,
(3) a cyano group,
(4) an oxo group,
(5) a hydroxy group,
(6) an optionally halogenated $C_{1-6}$ alkoxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),

(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) an optionally halogenated $C_{1-6}$ alkyl group,
(58) a $C_{2-6}$ alkenyl group, and
(59) a $C_{2-6}$ alkynyl group.

When the number of the substituents is 2, the respective substituents may be the same or different.

In one embodiment, examples of the "optionally substituted hydroxy group" for $R^4$ include a hydroxy group optionally having a substituent selected from a $C_{1-6}$ alkyl group, a $C_{2-6}$ alkenyl group, a $C_{1-6}$ alkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a $C_{1-6}$ alkylsulfonyl group, each of which has 1 to 3 substituents selected from
(1) a halogen atom,
(2) a nitro group,
(3) a cyano group,
(4) an oxo group,
(5) a hydroxy group,
(6) an optionally halogenated $C_{1-6}$ alkoxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),

(57) an optionally halogenated $C_{1-6}$ alkyl group,
(58) a $C_{2-6}$ alkenyl group, and
(59) a $C_{2-6}$ alkynyl group.

In one embodiment, examples of the "optionally substituted sulfanyl(SH) group" for $R^4$ include a sulfanyl group optionally having a substituent selected from a $C_{1-6}$ alkyl group, a $C_{2-6}$ alkenyl group, a $C_{1-6}$ alkyl-carbonyl group and a 5- to 14-membered aromatic heterocyclic group, each of which has 1 to 3 substituents selected from
(1) a halogen atom,
(2) a nitro group,
(3) a cyano group,
(4) an oxo group,
(5) a hydroxy group,
(6) an optionally halogenated $C_{1-6}$ alkoxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) an optionally halogenated $C_{1-6}$ alkyl group,
(58) a $C_{2-6}$ alkenyl group, and
(59) a $C_{2-6}$ alkynyl group,
and halogenated sulfanyl group.

In one embodiment, examples of the "optionally substituted silyl group" for $R^4$ include a silyl group optionally having 1 to 3 substituents selected from a $C_{1-6}$ alkyl group and a $C_{2-6}$ alkenyl group, each of which has 1 to 3 substituents selected from
(1) a halogen atom,
(2) a nitro group,
(3) a cyano group,
(4) an oxo group,
(5) a hydroxy group,
(6) an optionally halogenated $C_{1-6}$ alkoxy group,
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(32) a carbamoyl group,
(33) a thiocarbamoyl group,
(34) a mono- or di-$C_{1-6}$ alkyl-carbamoyl group,
(36) a 5- to 14-membered aromatic heterocyclylcarbamoyl group (e.g., pyridylcarbamoyl, thienylcarbamoyl),

(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(47) a 5- to 14-membered aromatic heterocyclylamino group (e.g., pyridylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(55) a $C_{1-6}$ alkylsulfonylamino group (e.g., methylsulfonylamino, ethylsulfonylamino),
(57) an optionally halogenated $C_{1-6}$ alkyl group,
(58) a $C_{2-6}$ alkenyl group, and
(59) a $C_{2-6}$ alkynyl group.
When the number of the substituents is 2 or more, the respective substituents may be the same or different.
$R^4$ is preferably
(1) a 5- or 6-membered monocyclic aromatic heterocyclic group (e.g., isoxazolyl) optionally substituted by 1 to 3 hydroxy groups,
(2) a 3- to 8-membered monocyclic non-aromatic heterocyclic group (e.g., dihydropyridyl (1,2-dihydropyridyl), pyrrolidinyl) optionally substituted by 1 to 3 oxo groups,
(3) a $C_{1-6}$ alkyl group (e.g., methyl, ethyl, propyl, butyl, isobutyl, neo-pentyl) optionally substituted by 1 to 5 substituents selected from
  (a) a 3- to 8-membered monocyclic non-aromatic heterocyclic group (e.g., thiazolidinyl, piperidyl, imidazolidinyl, pyrrolidinyl, oxazolidinyl, tetrahydropyrimidinyl (1,2,3,4-tetrahydropyrimidinyl), dihydropyrimidinyl (3,4-dihydropyrimidinyl), dihydropyridyl (1,2-dihydropyridyl), 1,1-dioxidotetrahydrothiopyranyl) optionally substituted by 1 to 5 substituents selected from
    (i) an oxo group, and
    (ii) a $C_{1-6}$ alkyl group (e.g., methyl),
  (b) a 5- or 6-membered monocyclic aromatic heterocyclic group (e.g., isoxazolyl, oxadiazolyl (1,3,4-oxadiazolyl), pyridyl, tetrazolyl) optionally substituted by 1 to 3 substituents selected from
    (i) a hydroxy group,
    (ii) a $C_{1-6}$ alkyl group (e.g., methyl), and
    (iii) a $C_{1-6}$ alkoxy group (e.g., methoxy),
  (c) a hydroxy group,
  (d) a $C_{1-6}$ alkylsulfonyl group (e.g., methylsulfonyl),
  (e) a carboxy group,
  (f) a 8- to 14-membered fused polycyclic (preferably bi- or tri-cyclic) aromatic heterocyclic group (e.g., indazolyl),
  (g) a halogen atom (e.g., a fluorine atom),
  (h) a cyano group, and
  (i) a $C_{1-6}$ alkoxy group (e.g., methoxy) optionally substituted by 1 to 3 carboxy groups,
(4) an amino group optionally mono- or di-substituted by 5- or 6-membered monocyclic aromatic heterocyclic group (s) (e.g., pyridazinyl, pyrazolyl) optionally substituted by 1 to 3 $C_{1-6}$ alkyl groups (e.g., methyl),
(5) a carboxy group, or
(6) a carbamoyl group.
$R^4$ is more preferably
(1) a 5- or 6-membered monocyclic aromatic heterocyclic group (e.g., isoxazolyl) optionally substituted by 1 to 3 hydroxy groups,
(2) a 3- to 8-membered monocyclic non-aromatic heterocyclic group (e.g., dihydropyridyl (1,2-dihydropyridyl), pyrrolidinyl) optionally substituted by 1 to 3 oxo groups, or
(3) a $C_{1-6}$ alkyl group (e.g., methyl, ethyl) optionally substituted by 1 to 5 substituents selected from
  (a) a 3- to 8-membered monocyclic non-aromatic heterocyclic group (e.g., dihydropyrimidinyl (3,4-dihydropyrimidinyl)) optionally substituted by 1 to 3 oxo groups,
  (b) a 5- or 6-membered monocyclic aromatic heterocyclic group (e.g., isoxazolyl, oxadiazolyl (1,3,4-oxadiazolyl), pyridyl) optionally substituted by 1 to 3 substituents selected from
    (i) a hydroxy group,
    (ii) a $C_{1-6}$ alkyl group (e.g., methyl), and
    (iii) a $C_{1-6}$ alkoxy group (e.g., methoxy), and
  (c) a hydroxy group.
In another embodiment, $R^4$ is preferably
(1) a 5- or 6-membered monocyclic aromatic heterocyclic group (e.g., isoxazolyl, pyrazolyl) optionally substituted by 1 to 5 (preferably 1 to 3) substituents selected from
  (a) a hydroxy group,
  (b) a carboxy group, and
  (c) a $C_{1-6}$ alkyl group (e.g., methyl),
(2) a 3- to 8-membered monocyclic non-aromatic heterocyclic group (e.g., dihydropyridyl (1,2-dihydropyridyl), pyrrolidinyl, azetidinyl, morpholinyl) optionally substituted by 1 to 3 substituents selected from
  (a) an oxo group,
  (b) a $C_{1-6}$ alkyl group (e.g., methyl) optionally substituted by 1 to 3 substituents selected from
    (i) a carboxy group, and
    (ii) a $C_{1-6}$ alkoxy-carbonyl (e.g., methoxycarbonyl) optionally substituted by 1 to 3 $C_{6-14}$ aryl groups (e.g., phenyl),
  (c) a carboxy group,
  (d) a hydroxy group, and
  (e) a $C_{1-6}$ alkoxy group (e.g., methoxy) optionally substituted by 1 to 3 carboxy groups,
(3) a $C_{1-6}$ alkyl group (e.g., methyl, ethyl, propyl, butyl, isobutyl, sec-butyl, neo-pentyl, isopentyl) optionally substituted by 1 to 5 (preferably 1 to 3) substituents selected from
  (a) a 3- to 8-membered monocyclic non-aromatic heterocyclic group (e.g., thiazolidinyl, piperidyl, imidazolidinyl, pyrrolidinyl, oxazolidinyl, tetrahydropyrimidinyl (1,2,3,4-tetrahydropyrimidinyl), dihydropyrimidinyl (3,4-dihydropyrimidinyl), dihydropyridyl (1,2-dihydropyridyl), 1,1-dioxidotetrahydrothiopyranyl, 1,1-dioxidothiadiazolidinyl (1,1-dioxido-1,2,5-thiadiazolidinyl)) optionally substituted by 1 to 5 (preferably 1 to 3) substituents selected from
    (i) an oxo group, and
    (ii) a $C_{1-6}$ alkyl group (e.g., methyl),
  (b) a 5- or 6-membered monocyclic aromatic heterocyclic group (e.g., isoxazolyl, oxadiazolyl (1,3,4-oxadiazolyl), pyridyl, tetrazolyl) optionally substituted by 1 to 3 substituents selected from
  (i) a hydroxy group,
  (ii) a $C_{1-6}$ alkyl group (e.g., methyl),
  (iii) a $C_{1-6}$ alkoxy group (e.g., methoxy), and
  (iv) a carboxy group,
(c) a hydroxy group,
(d) a $C_{1-6}$ alkylsulfonyl group (e.g., methylsulfonyl),
(e) a carboxy group,
(f) a 8- to 14-membered fused polycyclic (preferably bi- or tri-cyclic) aromatic heterocyclic group (e.g., indazolyl),
(g) a halogen atom (e.g., a fluorine atom),
(h) a cyano group,
(i) a $C_{1-6}$ alkoxy group (e.g., methoxy) optionally substituted by 1 to 3 carboxy groups,
(j) an amino group optionally mono- or di-substituted by $C_{1-6}$ alkyl group(s) (e.g., methyl) optionally substituted by 1 to 3 carboxy groups, and
(k) a carbamoyl group,
(4) an amino group optionally mono- or di-substituted by substituent(s) selected from
  (a) a 5- or 6-membered monocyclic aromatic heterocyclic group (e.g., pyridazinyl, pyrazolyl) optionally substituted by 1 to 3 $C_{1-6}$ alkyl groups (e.g., methyl), and
  (b) a $C_{1-6}$ alkyl group (e.g., methyl, ethyl, propyl, isopropyl) optionally substituted by 1 to 3 substituents selected from
    (i) a $C_{1-6}$ alkoxy-carbonyl group (e.g., methoxycarbonyl, ethoxycarbonyl) optionally substituted by 1 to 3 $C_{6-14}$ aryl groups (e.g., phenyl), and
    (ii) a carboxy group,
(5) a carboxy group,
(6) a carbamoyl group,
(7) a $C_{2-6}$ alkenyl group (e.g., vinyl) optionally substituted by 1 to 3 carboxy groups,
(8) a $C_{1-6}$ alkyl-carbonyl group (e.g., propionyl) optionally substituted by 1 to 3 carboxy groups, or
(9) a $C_{1-6}$ alkoxy group (e.g., ethoxy, propoxy) optionally substituted by 1 to 3 carboxy groups.

$R^4$ is more preferably
(1) a 5- or 6-membered monocyclic aromatic heterocyclic group (e.g., isoxazolyl) optionally substituted by 1 to 3 hydroxy groups,
(2) a 3- to 8-membered monocyclic non-aromatic heterocyclic group (e.g., dihydropyridyl (1,2-dihydropyridyl), pyrrolidinyl, azetidinyl) optionally substituted by 1 to 3 substituents selected from
  (a) an oxo group, and
  (b) a $C_{1-6}$ alkyl group (e.g., methyl) optionally substituted by 1 to 3 carboxy groups,
(3) a $C_{1-6}$ alkyl group (e.g., methyl, ethyl, propyl, butyl, isobutyl, neo-pentyl) optionally substituted by 1 to 5 (preferably 1 to 3) substituents selected from
  (a) a 3- to 8-membered monocyclic non-aromatic heterocyclic group (e.g., thiazolidinyl, dihydropyrimidinyl (3,4-dihydropyrimidinyl)) optionally substituted by 1 to 3 oxo groups,
  (b) a 5- or 6-membered monocyclic aromatic heterocyclic group (e.g., isoxazolyl, oxadiazolyl (1,3,4-oxadiazolyl), pyridyl) optionally substituted by 1 to 3 substituents selected from
    (i) a hydroxy group,
    (ii) a $C_{1-6}$ alkyl group (e.g., methyl), and
    (iii) a $C_{1-6}$ alkoxy group (e.g., methoxy),
  (c) a hydroxy group,
  (d) a carboxy group,
  (e) a halogen atom (e.g., a fluorine atom),
  (f) a cyano group, and
  (g) a carbamoyl group,
(4) an amino group optionally mono- or di-substituted by substituent(s) selected from a $C_{1-6}$ alkyl group (e.g., ethyl, propyl) optionally substituted by 1 to 3 carboxy groups, or
(5) a $C_{2-6}$ alkenyl group (e.g., vinyl) optionally substituted by 1 to 3 carboxy groups.

$R^4$ is still more preferably
(1) a 3- to 8-membered monocyclic non-aromatic heterocyclic group (e.g., azetidinyl) optionally substituted by 1 to 3 substituents selected from a $C_{1-6}$ alkyl group (e.g., methyl) optionally substituted by 1 to 3 carboxy groups, or
(2) a $C_{1-6}$ alkyl group (e.g., propyl) optionally substituted by 1 to 3 carboxy groups.

In another embodiment, $R^4$ is preferably
(1) a $C_{1-6}$ alkyl group (e.g., methyl, ethyl, propyl, butyl, isobutyl, sec-butyl, neo-pentyl, isopentyl) optionally substituted by 1 to 3 substituents selected from
  (a) a halogen atom,
  (b) a cyano group,
  (c) a hydroxy group,
  (d) a 5- to 6-membered monocyclic aromatic heterocyclic group (e.g., isoxazolyl, oxadiazolyl (1,3,4-oxadiazolyl), pyridyl, tetrazolyl),
  (e) a 4- to 6-membered monocyclic non-aromatic heterocyclic group (e.g., thiazolidinyl, piperidyl, imidazolidinyl, pyrrolidinyl, oxazolidinyl, tetrahydropyrimidinyl (1,2,3,4-tetrahydropyrimidinyl), dihydropyrimidinyl (3,4-dihydropyrimidinyl), dihydropyridyl (1,2-dihydropyridyl), 1,1-dioxidotetrahydrothiopyranyl, 1,1-dioxidothiadiazolidinyl (1,1-dioxido-1,2,5-thiadiazolidinyl)), and
  (f) a carboxy group, or
(2) an optionally substituted heterocyclic group (e.g., a 5- or 6-membered monocyclic aromatic heterocyclic group (e.g., isoxazolyl), a 3- to 8-membered monocyclic non-aromatic heterocyclic group (e.g., dihydropyridyl (1,2-dihydropyridyl), pyrrolidinyl, azetidinyl, morpholinyl)).

$R^4$ is more preferably
(1) a $C_{1-6}$ alkyl group (e.g., methyl, ethyl, propyl, butyl, isobutyl, sec-butyl, neo-pentyl, isopentyl) optionally substituted by 1 to 3 substituents selected from
  (a) a halogen atom,
  (b) a cyano group,
  (c) a hydroxy group,
  (d) a 5- to 6-membered monocyclic aromatic heterocyclic group (e.g., isoxazolyl, oxadiazolyl (1,3,4-oxadiazolyl), pyridyl, tetrazolyl),
  (e) a 4- to 6-membered monocyclic non-aromatic heterocyclic group (e.g., thiazolidinyl, piperidyl, imidazolidinyl, pyrrolidinyl, oxazolidinyl, tetrahydropyrimidinyl (1,2,3,4-tetrahydropyrimidinyl), dihydropyrimidinyl (3,4-dihydropyrimidinyl), dihydropyridyl (1,2-dihydropyridyl), 1,1-dioxidotetrahydrothiopyranyl, 1,1-dioxidothiadiazolidinyl (1,1-dioxido-1,2,5-thiadiazolidinyl)), and
  (f) a carboxy group,
(2) a 5- or 6-membered monocyclic aromatic heterocyclic group (e.g., isoxazolyl) optionally substituted by 1 to 3 hydroxy groups, or
(3) a 3- to 8-membered monocyclic non-aromatic heterocyclic group (e.g., dihydropyridyl (1,2-dihydropyridyl), pyrrolidinyl, azetidinyl) optionally substituted by 1 to 3 substituents selected from (a) an oxo group, and
(b) a $C_{1-6}$ alkyl group (e.g., methyl) optionally substituted by 1 to 3 carboxy groups.

Examples of the above-mentioned "4- to 6-membered monocyclic non-aromatic heterocyclic group" include a 4- to 6-membered monocyclic non-aromatic heterocyclic group containing, as a ring-constituting atom besides carbon atoms, 1 to 4 heteroatoms selected from a nitrogen atom, a sulfur atom and an oxygen atom. Preferable examples of the "4- to 6-membered monocyclic non-aromatic heterocyclic group" include those similar to a 4- to 6-membered ring, from among the above-mentioned "3- to 8-membered monocyclic non-aromatic heterocyclic group".

$R^{13}$ is a substituent.

$R^{13}$ is preferably an optionally substituted hydrocarbon group or an optionally substituted amino group.

$R^{13}$ is more preferably
(1) an amino group optionally mono- or di-substituted by substituent(s) selected from
    (a) a $C_{1-6}$ alkoxy-carbonyl group (e.g., tert-butoxycarbonyl), and
    (b) a $C_{1-6}$ alkyl group (e.g., propyl) optionally substituted by 1 to 3 carboxy groups, or
(2) a $C_{1-6}$ alkyl group (e.g., propyl) optionally substituted by 1 to 3 substituents selected from a $C_{1-6}$ alkoxy-carbonyl group (e.g., methoxycarbonyl).

Ring B is a benzene ring, a pyridine ring or a dihydropyridine ring, each of which is optionally further substituted.

Ring B is preferably a benzene ring, a pyridine ring or a 1,2-dihydropyridine ring.

Ring B is more preferably a benzene ring or a pyridine ring.

In another embodiment, Ring B is preferably a benzene ring or a pyridine ring, each of which is optionally further substituted.

Examples of the "additional substituent" of the "optionally further substituted" for Ring B include the substituents selected from the above-mentioned Substituent Group A. The number of the substituents is 1 or 2. When the to number of the substituents is 2, the respective substituents may be the same or different.

The partial structure represented by the formula:

$X^1\text{-----}X^2$ is $CR^{5a}=CR^6$, $CR^{5b}=N$ or $C(=O)-NR^7$, $R^{5a}$ and $R^{5b}$ are each independently an optionally substituted alkyl group or an optionally substituted alkoxy group, and $R^6$ and $R^7$ are each independently a hydrogen atom or a substituent.

In another embodiment, the partial structure represented by the formula:

$X^1\text{-----}X^2$ is $CR^{5a}=CR^6$, $CR^{5b}=N$ or $C(=O)-NR^7$, $R^{5a}$ and $R^{5b}$ are each independently an optionally substituted alkyl group, an optionally substituted alkoxy group, an optionally substituted alkylsulfonyl group, a cyano group, an optionally substituted cyclic amino group or an oxetan-3-yloxy group, and $R^6$ and $R^7$ are each independently a hydrogen atom or a substituent, or the substituent that Ring B optionally further has and $R^{5a}$ or $R^{5b}$ in combination optionally form Ring D, wherein Ring D is a 5- or 6-membered oxygen-containing heterocycle containing 1 to 2 oxygen atoms as heteroatoms in addition to carbon atoms, and is fused at the ring forming position, or $R^{5a}$ and $R^6$ in combination optionally form Ring D', wherein Ring D' is a 5- or 6-membered oxygen-containing heterocycle containing 1 to 2 oxygen atoms as heteroatoms in addition to carbon atoms, and is fused at the ring forming position.

Examples of the "cyclic amino group" for $R^{5a}$ and $R^{5b}$ include a 3- to 14-membered (preferably 4- to 10-membered) cyclic amino group (which is a group formed by removing one hydrogen atom from the nitrogen atom) optionally further containing, as a ring-constituting atom besides carbon atoms and one nitrogen atom, 1 to 4 heteroatoms selected from a nitrogen atom, a sulfur atom and an oxygen atom.

Preferable examples of the "cyclic amino group" include 4-to 10-membered cyclic amino groups such as azetidino, pyrrolidino, imidazolidino, pyrazolidino, piperidino, piperazino, oxazolidino, isoxazolidino, thiazolidino, thiazolidino, morpholino, thiomorpholino, azepano and the like, and the like.

Examples of the "optionally substituted alkyl group" for $R^{5a}$ or $R^{5b}$ include a $C_{1-6}$ alkyl group optionally substituted by substituent(s) selected from the above-mentioned Substituent Group A.

Examples of the "optionally substituted alkoxy group" for $R^{5a}$ or $R^{5b}$ include a "$C_{1-6}$ alkoxy group" optionally substituted by substituent(s) selected from the above-mentioned Substituent Group A.

Examples of the "optionally substituted alkylsulfonyl group" for $R^{5a}$ or $R^{5b}$ include a "$C_{1-6}$ alkylsulfonyl group" optionally substituted by substituent(s) selected from the above-mentioned Substituent Group A.

Examples of the "optionally substituted cyclic amino group" for $R^{5a}$ or $R^{5b}$ include a "cyclic amino group" optionally substituted by substituent(s) selected from the above-mentioned Substituent Group A.

The number of the above-mentioned substituents in the "optionally substituted alkyl group", "optionally substituted alkoxy group", "optionally substituted alkylsulfonyl group" and "optionally substituted cyclic amino group" is, for example, 1 to 5, preferably 1 to 3. When the number of the substituents is 2 or more, the respective substituents may be the same or different.

In another embodiment, examples of the "optionally substituted alkoxy group" for $R^{5a}$ or $R^{5b}$ include a group represented by the formula: $-OR^9$ wherein $R^9$ is an optionally substituted $C_{1-6}$ alkyl group.

Examples of the "5- or 6-membered oxygen-containing heterocycle" for Ring D or Ring D' include a 5- or 6-membered unsaturated non-aromatic heterocyclic group or a 5-membered aromatic heterocyclic group, each of which optionally further contains, as a ring-constituting atom besides carbon atoms and 1 to 2 oxygen atoms, 1 to 2 heteroatoms selected from a sulfur atom and a nitrogen atom.

Preferable examples of the "5- or 6-membered oxygen-containing heterocycle" include 5- or 6-membered unsaturated non-aromatic heterocyclic groups such as dihydrofuran (e.g., 2,3-dihydrofuran, 2,5-dihydrofuran), dioxole (e.g., 1,3-dioxole), dihydrooxazole (e.g., 2,3-dihydrooxazole), dihydroisoxazole (e.g., 2,3-dihydroisoxazole), pyran (e.g., 2H-pyran), dihydropyran (e.g., 3,4-dihydro-2H-pyran), dihydrodioxin (e.g., 2,3-dihydro-1,4-dioxin) and the like; 5-membered aromatic heterocyclic groups such as furan, oxazole, isoxazole and the like.

In the partial structure represented by the formula:

$X^1\text{-----}X^2$ $X^1$ and $X^2$ are present in this order starting from the left, and they are not revised. The same applies to $CR^{5a}=CR^6$, $CR^{5b}=N$ and $C(=O)-NR^7$.

The partial structure represented by the formula:

is preferably $CR^{5a}=CR^6$, $CR^{5b}=N$ or $C(=O)-NR^7$; and
$R^{5a}$ and $R^{5b}$ are each independently a $C_{1-6}$ alkyl group (e.g., methyl) optionally substituted by 1 to 3 $C_{1-6}$ alkoxy groups (e.g., methoxy, ethoxy), or a $C_{1-6}$ alkoxy group (e.g., methoxy, ethoxy);
$R^6$ is a hydrogen atom; and
$R^7$ is a $C_{1-6}$ alkyl group (e.g., methyl).

The partial structure represented by the formula:

is more preferably $CR^{5a}=CR^6$ or $CR^{5b}=N$; and
$R^{5a}$ is a $C_{1-6}$ alkyl group (e.g., methyl) optionally substituted by 1 to 3 $C_{1-6}$ alkoxy groups (e.g., methoxy, ethoxy), or a $C_{1-6}$ alkoxy group (e.g., methoxy, ethoxy);
$R^{5b}$ is a $C_{1-6}$ alkoxy group (e.g., methoxy, ethoxy); and
$R^6$ is a hydrogen atom.

In another embodiment, the partial structure represented by the formula:

is preferably $CR^{5a}=CR^6$ or $CR^{5b}=N$.

$R^{5a}$ and $R^{5b}$ are preferably each independently
(1) a $C_{1-6}$ alkyl group (e.g., methyl, propyl, isopropyl) optionally substituted by 1 to 3 substituents selected from a $C_{1-6}$ alkoxy group (e.g., methoxy) optionally substituted by 1 to 3 halogen atoms (e.g., a fluorine atom),
(2) a $C_{1-6}$ alkoxy group (e.g., methoxy, ethoxy, propoxy, isopropoxy) optionally substituted by 1 to 3 substituents selected from
  (a) a halogen atom (e.g., a fluorine atom), and
  (b) a $C_{3-10}$ cycloalkyl group (e.g., cyclopropyl),
(3) a $C_{1-6}$ alkylsulfonyl group (e.g., methylsulfonyl),
(4) a cyano group,
(5) a cyclic amino group (e.g., azetidino) optionally substituted by 1 to 3 halogen atoms (e.g., a fluorine atom), or
(6) an oxetan-3-yloxy group.

$R^{5a}$ and $R^{5b}$ are more preferably each independently
(1) a $C_{1-6}$ alkyl group (e.g., methyl) optionally substituted by 1 to 3 $C_{1-6}$ alkoxy groups (e.g., methoxy),
(2) a $C_{1-6}$ alkoxy group (e.g., methoxy, ethoxy) optionally substituted by 1 to 3 halogen atoms (e.g., a fluorine atom), or
(3) a $C_{1-6}$ alkylsulfonyl group (e.g., methylsulfonyl).

$R^{5a}$ and $R^{5b}$ are still more preferably each independently a $C_{1-6}$ alkoxy group (e.g., methoxy).

In another embodiment, $R^{5a}$ is preferably
(1) a $C_{1-6}$ alkyl group (e.g., methyl, propyl) optionally substituted by 1 to 3 substituents selected from a $C_{1-6}$ alkoxy group (e.g., methoxy) optionally substituted by 1 to 3 halogen atoms (e.g., a fluorine atom),
(2) a $C_{1-6}$ alkoxy group (e.g., methoxy, ethoxy, propoxy, isopropoxy) optionally substituted by 1 to 3 substituents selected from
  (a) a halogen atom (e.g., a fluorine atom), and
  (b) a $C_{3-10}$ cycloalkyl group (e.g., cyclopropyl),
(3) a $C_{1-6}$ alkylsulfonyl group (e.g., methylsulfonyl),
(4) a cyano group,
(5) a cyclic amino group (e.g., azetidino) optionally substituted by 1 to 3 halogen atoms (e.g., a fluorine atom), or
(6) an oxetan-3-yloxy group.

$R^{5a}$ is more preferably
(1) a $C_{1-6}$ alkyl group (e.g., methyl) optionally substituted by 1 to 3 $C_{1-6}$ alkoxy groups (e.g., methoxy),
(2) a $C_{1-6}$ alkoxy group (e.g., methoxy, ethoxy) optionally substituted by 1 to 3 halogen atoms (e.g., a fluorine atom), or
(3) a $C_{1-6}$ alkylsulfonyl group (e.g., methylsulfonyl).

In another embodiment, $R^{5a}$ is preferably
(1) an optionally substituted $C_{1-6}$ alkyl group,
(2) an optionally substituted $C_{1-6}$ alkoxy group, or
(3) an optionally substituted $C_{1-6}$ alkylsulfonyl group.

Examples of the "optionally substituted $C_{1-6}$ alkyl group" include a "$C_{1-6}$ alkyl group" optionally substituted by substituent(s) selected from the above-mentioned Substituent Group A.

Examples of the "optionally substituted $C_{1-6}$ alkoxy group" include a "$C_{1-6}$ alkoxy group" optionally substituted by substituent(s) selected from the above-mentioned Substituent Group A.

Examples of the "optionally substituted $C_{1-6}$ alkylsulfonyl group" include a "$C_{1-6}$ alkylsulfonyl group" optionally substituted by substituent(s) selected from the above-mentioned Substituent Group A.

The number of the above-mentioned substituents in the "optionally substituted $C_{1-6}$ alkyl group", "optionally substituted $C_{1-6}$ alkoxy group" and "optionally substituted $C_{1-6}$ alkylsulfonyl group" is, for example, 1 to 5, preferably 1 to 3. When the number of the substituents is 2 or more, the respective substituents may be the same or different.

$R^{5b}$ is preferably
(1) a $C_{1-6}$ alkyl group (e.g., methyl, propyl, isopropyl) optionally substituted by 1 to 3 $C_{1-6}$ alkoxy groups (e.g., methoxy), or
(2) a $C_{1-6}$ alkoxy group (e.g., methoxy, ethoxy) optionally substituted by 1 to 3 halogen atoms (e.g., a fluorine atom).

$R^{5b}$ is more preferably
(1) a $C_{1-6}$ alkyl group (e.g., methyl) optionally substituted by 1 to 3 $C_{1-6}$ alkoxy groups (e.g., methoxy), or
(2) a $C_{1-6}$ alkoxy group (e.g., methoxy, ethoxy).

$R^{5b}$ is still more preferably a $C_{1-6}$ alkoxy group (e.g., methoxy).

In another embodiment, $R^{5b}$ is preferably
(1) an optionally substituted $C_{1-4}$ alkoxy group, or
(2) an optionally substituted $C_{1-4}$ alkyl group.

Specific examples of the "$C_{1-4}$ alkoxy group" of the "optionally substituted $C_{1-4}$ alkoxy group" for $R^{5b}$ include methoxy, ethoxy, propoxy, isopropoxy, butoxy, isobutoxy, sec-butoxy and tert-butoxy.

Specific examples of the "$C_{1-4}$ alkyl group" of the "optionally substituted $C_{1-4}$ alkyl group" for $R^{5b}$ include methyl, ethyl, propyl, isopropyl, butyl, isobutyl, sec-butyl and tert-butyl.

Examples of the "optionally substituted $C_{1-4}$ alkoxy group" include a "$C_{1-4}$ alkoxy group" optionally substituted by substituent(s) selected from the above-mentioned Substituent Group A.

Examples of the "optionally substituted $C_{1-4}$ alkyl group" include a "$C_{1-4}$ alkyl group" optionally substituted by substituent(s) selected from the above-mentioned Substituent Group A.

The number of the above-mentioned substituents in the "optionally substituted $C_{1-4}$ alkoxy group" and "optionally substituted $C_{1-4}$ alkyl group" is, for example, 1 to 5, preferably 1 to 3. When the number of the substituents is 2 or more, the respective substituents may be the same or different.

$R^6$ is preferably a hydrogen atom or an optionally substituted hydrocarbon group.

$R^6$ is more preferably a hydrogen atom or a $C_{1-6}$ alkyl group (e.g., methyl).

$R^6$ is still more preferably a hydrogen atom.

$R^7$ is preferably a hydrogen atom or an optionally substituted hydrocarbon group.

$R^7$ is more preferably a $C_{1-6}$ alkyl group (e.g., methyl).

Preferably, the substituent that Ring B optionally further has and $R^{5a}$ or $R^{5b}$ in combination optionally form Ring D wherein the Ring D is a dihydrofuran ring (e.g., 2,3-dihydrofuran) and is fused at the ring forming position.

Preferably, $R^{5a}$ and $R^6$ in combination optionally form Ring D' wherein Ring D' is a dihydrofuran ring (e.g., 2,3-dihydrofuran), a dioxole ring (e.g., 1,3-dioxole) or a dihydrodioxin ring (e.g., 2,3-dihydro-1,4-dioxin), and each is fused at the ring forming position.

More preferably, $R^{5a}$ and $R^6$ in combination optionally form Ring D' wherein Ring D' is a dioxole ring (e.g., 1,3-dioxole), and is fused at the ring forming position.

In another embodiment, the partial structure represented by the formula:

is preferably $CR^{5a}=CR^6$, $CR^{5b}=N$ or $C(=O)-NR^7$,
$R^{5a}$ and $R^{5b}$ are each independently
(1) a $C_{1-6}$ alkyl group (e.g., methyl, propyl, isopropyl) optionally substituted by 1 to 3 substituents selected from a $C_{1-6}$ alkoxy group (e.g., methoxy) optionally substituted by 1 to 3 halogen atoms (e.g., a fluorine atom),
(2) a $C_{1-6}$ alkoxy group (e.g., methoxy, ethoxy, propoxy, isopropoxy) optionally substituted by 1 to 3 substituents selected from
  (a) a halogen atom (e.g., a fluorine atom), and
  (b) a $C_{3-10}$ cycloalkyl group (e.g., cyclopropyl),
(3) a $C_{1-6}$ alkylsulfonyl group (e.g., methylsulfonyl),
(4) a cyano group,
(5) a cyclic amino group (e.g., azetidino) optionally substituted by 1 to 3 halogen atoms (e.g., a fluorine atom), or
(6) an oxetan-3-yloxy group,
$R^6$ is a hydrogen atom or a $C_{1-6}$ alkyl group (e.g., methyl), and
$R^7$ is a $C_{1-6}$ alkyl group (e.g., methyl), or
the substituent that Ring B optionally further has and $R^{5a}$ or $R^{5b}$ in combination optionally form Ring D wherein the Ring D is a dihydrofuran ring (e.g., 2,3-dihydrofuran) and is fused at the ring forming position, or
$R^{5a}$ and $R^6$ in combination optionally form Ring D' wherein Ring D' is a dihydrofuran ring (e.g., 2,3-dihydrofuran), a dioxole ring (e.g., 1,3-dioxole) or a dihydrodioxin ring (e.g., 2,3-dihydro-1,4-dioxin), and each is fused at the ring forming position.

The partial structure represented by the formula:

is more preferably $CR^{5a}=CR^6$ or $CR^{5b}=N$,
$R^{5a}$ and $R^{5b}$ are each independently
(1) a $C_{1-6}$ alkyl group (e.g., methyl) optionally substituted by 1 to 3 $C_{1-6}$ alkoxy groups (e.g., methoxy),
(2) a $C_{1-6}$ alkoxy group (e.g., methoxy, ethoxy) optionally substituted by 1 to 3 halogen atoms (e.g., a fluorine atom), or
(3) a $C_{1-6}$ alkylsulfonyl group (e.g., methylsulfonyl), and
$R^6$ is a hydrogen atom, or
$R^{5a}$ and $R^6$ in combination optionally form Ring D' wherein Ring D' is a dioxole ring (e.g., 1,3-dioxole), and is fused at the ring forming position.

The partial structure represented by the formula:

is still more preferably $CR^{5a}=CR^6$ or $CR^{5b}=N$;
$R^{5a}$ and $R^{5b}$ are each independently a $C_{1-6}$ alkoxy group (e.g., methoxy), and
$R^6$ is a hydrogen atom, or
$R^{5a}$ and $R^6$ in combination optionally form Ring D' wherein Ring D' is a dioxole ring (e.g., 1,3-dioxole), and is fused at the ring forming position.

In another embodiment, the partial structure represented by the formula:

is preferably $CR^{5a}=CR^6$, $CR^{5b}=N$ or $C(=O)-NR^7$,
$R^{5a}$ is
(1) a $C_{1-6}$ alkyl group (e.g., methyl, propyl) optionally substituted by 1 to 3 substituents selected from a $C_{1-6}$ alkoxy group (e.g., methoxy) optionally substituted by 1 to 3 halogen atoms (e.g., a fluorine atom),
(2) a $C_{1-6}$ alkoxy group (e.g., methoxy, ethoxy, propoxy, isopropoxy) optionally substituted by 1 to 3 substituents selected from
  (a) a halogen atom (e.g., a fluorine atom), and
  (b) a $C_{3-10}$ cycloalkyl group (e.g., cyclopropyl),
(3) a $C_{1-6}$ alkylsulfonyl group (e.g., methylsulfonyl),
(4) a cyano group,
(5) a cyclic amino group (e.g., azetidino) optionally substituted by 1 to 3 halogen atoms (e.g., a fluorine atom), or
(6) an oxetan-3-yloxy group,
$R^{5b}$ is
(1) a $C_{1-6}$ alkyl group (e.g., methyl, propyl, isopropyl) optionally substituted by 1 to 3 $C_{1-6}$ alkoxy groups (e.g., methoxy), or
(2) a $C_{1-6}$ alkoxy group (e.g., methoxy, ethoxy) optionally substituted by 1 to 3 halogen atoms (e.g., a fluorine atom),
$R^6$ is a hydrogen atom or a $C_{1-6}$ alkyl group (e.g., methyl), and
$R^7$ is a $C_{1-6}$ alkyl group (e.g., methyl), or
the substituent that Ring B optionally further has and $R^{5a}$ or $R^{5b}$ in combination optionally form Ring D wherein the Ring D is a dihydrofuran ring (e.g., 2,3-dihydrofuran) and is fused at the ring forming position, or
$R^{5a}$ and $R^6$ in combination optionally form Ring D' wherein Ring D' is a dihydrofuran ring (e.g., 2,3-dihydrofuran), a dioxole ring (e.g., 1,3-dioxole) or a dihydrodioxin ring (e.g., 2,3-dihydro-1,4-dioxin), and each is fused at the ring forming position.

The partial structure represented by the formula:

is more preferably $CR^{5a}=CR^6$ or $CR^{5b}=N$,
$R^{5a}$ is
(1) a $C_{1-6}$ alkyl group (e.g., methyl) optionally substituted by 1 to 3 $C_{1-6}$ alkoxy groups (e.g., methoxy),
(2) a $C_{1-6}$ alkoxy group (e.g., methoxy, ethoxy) optionally substituted by 1 to 3 halogen atoms (e.g., a fluorine atom), or
(3) a $C_{1-6}$ alkylsulfonyl group (e.g., methylsulfonyl),
$R^{5b}$ is
(1) a $C_{1-6}$ alkyl group (e.g., methyl) optionally substituted by 1 to 3 $C_{1-6}$ alkoxy groups (e.g., methoxy), or
(2) a $C_{1-6}$ alkoxy group (e.g., methoxy, ethoxy), and
$R^6$ is a hydrogen atom, or
$R^{5a}$ and $R^6$ in combination optionally form Ring D' wherein Ring D' is a dioxole ring (e.g., 1,3-dioxole), and is fused at the ring forming position.

In the formula (I), the partial structure represented by the formula:

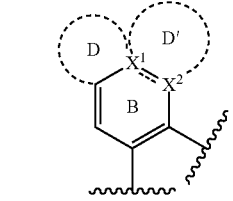

wherein each symbol is as defined above, encompasses the partial structure selected from the formulas:

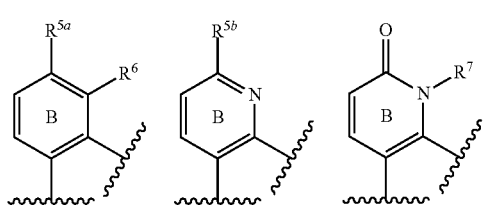

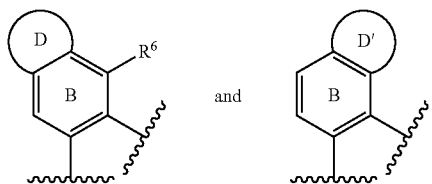

wherein each symbol is as defined above.

In one embodiment, it is preferably the partial structure selected from the formulas:

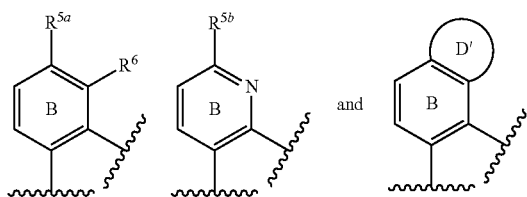

wherein each symbol is as defined above, more preferably the partial structure selected from the formulas:

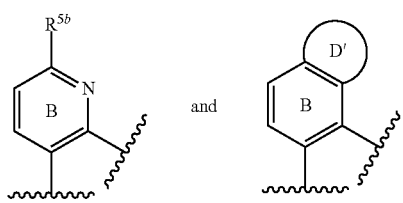

wherein each symbol is as defined above.

Specific examples of the partial structure represented by the formula:

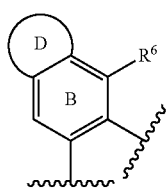

wherein each symbol is as defined above, include the partial structure represented by the formula:

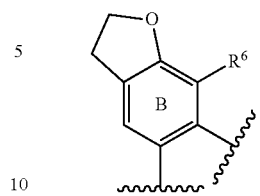

wherein each symbol is as defined above.

Specific examples of the partial structure represented by the formula:

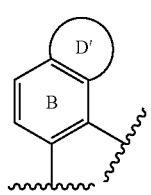

wherein each symbol is as defined above, include the partial structure selected from the formulas:

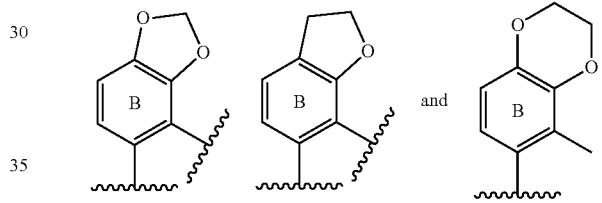

wherein each symbol is as defined above.

Y is an optionally substituted methylene group or an oxygen atom.

Examples of the "optionally substituted methylene group" include a "methylene group" optionally substituted by substituent(s) selected from the above-mentioned Substituent Group A.

Y is preferably a methylene group or an oxygen atom, more preferably a methylene group.

W is an optionally substituted $C_{1-2}$ alkylene group.

Examples of the "optionally substituted $C_{1-2}$ alkylene group" include a "$C_{1-2}$ alkylene group" optionally substituted by substituent(s) selected from the above-mentioned Substituent Group A.

W is preferably a $C_{1-2}$ alkylene group (e.g., methylene, ethylene (—CH$_2$—CH$_2$—)), more preferably a methylene group.

In one embodiment, in formula (I) or formula (Ia), the partial structure represented by the formula —Y—W— is preferably —CH$_2$—CH$_2$— or —O—CH$_2$—CH$_2$—, more preferably —CH$_2$—CH$_2$—.

Preferable examples of the ring, group, substituent and the like explained in the present specification are more preferably used in combination.

Preferable examples of compound (I) include the following compounds.

[Compound I-A1]
A compound wherein
Ring A is a 6-membered aromatic ring (e.g., a benzene ring, a pyridine ring) optionally further substituted by 1 to 3 (preferably 1 or 2) substituents selected from (1) a halogen atom (e.g., a fluorine atom, a chlorine atom),
(2) a $C_{1-6}$ alkoxy group (e.g., methoxy, ethoxy) optionally substituted by 1 to 3 halogen atoms (e.g., a fluorine atom), and
(3) a cyano group;

$R^1$ is
(1) a group represented by the formula: -Q($R^{1a}$)($R^{1b}$)($R^{1c}$) wherein
Q is a carbon atom or a silicon atom, and
$R^{1a}$, $R^{1b}$ and $R^{1c}$ are each independently
  (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from
    (i) a halogen atom (e.g., a fluorine atom),
    (ii) a $C_{3-10}$ cycloalkyl group (e.g., cyclopropyl), and
    (iii) a $C_{1-6}$ alkoxy group (e.g., methoxy),
  (b) a $C_{1-6}$ alkoxy-carbonyl group (e.g., ethoxycarbonyl),
  (c) a carbamoyl group optionally mono- or di-substituted by substituent(s) selected from
    (i) a $C_{1-6}$ alkyl group (e.g., ethyl), and
    (ii) a $C_{3-10}$ cycloalkyl group (e.g., cyclopropyl),
  (d) a 5- or 6-membered monocyclic aromatic heterocyclic group (e.g., oxadiazolyl (1,3,4-oxadiazolyl)) optionally substituted by 1 to 3 $C_{1-6}$ alkyl groups (e.g., methyl), or
  (e) a 3- to 8-membered monocyclic non-aromatic heterocyclylcarbonyl group (e.g., pyrrolidinylcarbonyl), or
  $R^{1c}$ is bonded to one substituent for Ring A to form
  (a) a $C_{3-10}$ cycloalkene ring (e.g., cyclopentene), or
  (b) a 3- to 14-membered non-aromatic heterocycle (e.g., dihydrofuran), or
(2) a neo-pentyl group;

$R^{11}$ is $-CR^{12}R^{12'}-R^{12''}$, $-C(=O)-R^4$ or $-SO_2-R^{13}$;

$R^{12}$ is a $C_{1-6}$ alkyl group (e.g., ethyl) optionally substituted by 1 to 3 $C_{1-6}$ alkoxy-carbonyl groups (e.g., methoxycarbonyl), and $R^{12'}$ and $R^{12'}$ are hydrogen atoms;

$R^4$ is
(1) a 5- or 6-membered monocyclic aromatic heterocyclic group (e.g., isoxazolyl, pyrazolyl) optionally substituted by 1 to 5 (preferably 1 to 3) substituents selected from
  (a) a hydroxy group,
  (b) a carboxy group, and
  (c) a $C_{1-6}$ alkyl group (e.g., methyl),
(2) a 3- to 8-membered monocyclic non-aromatic heterocyclic group (e.g., dihydropyridyl (1,2-dihydropyridyl), pyrrolidinyl, azetidinyl, morpholinyl) optionally substituted by 1 to 3 substituents selected from
  (a) an oxo group,
  (b) a $C_{1-6}$ alkyl group (e.g., methyl) optionally substituted by 1 to 3 substituents selected from
    (i) a carboxy group, and
    (ii) a $C_{1-6}$ alkoxy-carbonyl (e.g., methoxycarbonyl) optionally substituted by 1 to 3 $C_{6-14}$ aryl groups (e.g., phenyl),
  (c) a carboxy group,
  (d) a hydroxy group, and
  (e) a $C_{1-6}$ alkoxy group (e.g., methoxy) optionally substituted by 1 to 3 carboxy groups,
(3) a $C_{1-6}$ alkyl group (e.g., methyl, ethyl, propyl, butyl, isobutyl, sec-butyl, neo-pentyl, isopentyl) optionally substituted by 1 to 5 (preferably 1 to 3) substituents selected from
  (a) a 3- to 8-membered monocyclic non-aromatic heterocyclic group (e.g., thiazolidinyl, piperidyl, imidazolidinyl, pyrrolidinyl, oxazolidinyl, tetrahydropyrimidinyl (1,2,3,4-tetrahydropyrimidinyl), dihydropyrimidinyl (3,4-dihydropyrimidinyl), dihydropyridyl (1,2-dihydropyridyl), 1,1-dioxidotetrahydrothiopyranyl, 1,1-dioxidothiadiazolidinyl (1,1-dioxido-1,2,5-thiadiazolidinyl)) optionally substituted by 1 to 5 (preferably 1 to 3) substituents selected from
    (i) an oxo group, and
    (ii) a $C_{1-6}$ alkyl group (e.g., methyl),
  (b) a 5- or 6-membered monocyclic aromatic heterocyclic group (e.g., isoxazolyl, oxadiazolyl (1,3,4-oxadiazolyl), pyridyl, tetrazolyl) optionally substituted by 1 to 3 substituents selected from
    (i) a hydroxy group,
    (ii) a $C_{1-6}$ alkyl group (e.g., methyl),
    (iii) a $C_{1-6}$ alkoxy group (e.g., methoxy), and
    (iv) a carboxy group,
  (c) a hydroxy group,
  (d) a $C_{1-6}$ alkylsulfonyl group (e.g., methylsulfonyl),
  (e) a carboxy group,
  (f) a 8- to 14-membered fused polycyclic (preferably bi- or tri-cyclic) aromatic heterocyclic group (e.g., indazolyl),
  (g) a halogen atom (e.g., a fluorine atom),
  (h) a cyano group,
  (i) a $C_{1-6}$ alkoxy group (e.g., methoxy) optionally substituted by 1 to 3 carboxy groups,
  (j) an amino group optionally mono- or di-substituted by $C_{1-6}$ alkyl group(s) (e.g., methyl) optionally substituted by 1 to 3 carboxy groups, and
  (k) a carbamoyl group,
(4) an amino group optionally mono- or di-substituted by substituent(s) selected from
  (a) a 5- or 6-membered monocyclic aromatic heterocyclic group (e.g., pyridazinyl, pyrazolyl) optionally substituted by 1 to 3 $C_{1-6}$ alkyl groups (e.g., methyl), and
  (b) a $C_{1-6}$ alkyl group (e.g., methyl, ethyl, propyl, isopropyl) optionally substituted by 1 to 3 substituents selected from
    (i) a $C_{1-6}$ alkoxy-carbonyl group (e.g., methoxycarbonyl, ethoxycarbonyl) optionally substituted by 1 to 3 $C_{6-14}$ aryl groups (e.g., phenyl), and
    (ii) a carboxy group,
(5) a carboxy group,
(6) a carbamoyl group,
(7) a $C_{2-6}$ alkenyl group (e.g., vinyl) optionally substituted by 1 to 3 carboxy groups,
(8) a $C_{1-6}$ alkyl-carbonyl group (e.g., propionyl) optionally substituted by 1 to 3 carboxy groups, or
(9) a $C_{1-6}$ alkoxy group (e.g., ethoxy, propoxy) optionally substituted by 1 to 3 carboxy groups;

$R^{13}$ is
(1) an amino group optionally mono- or di-substituted by substituent(s) selected from
  (a) a $C_{1-6}$ alkoxy-carbonyl group (e.g., tert-butoxycarbonyl), and
  (b) a $C_{1-6}$ alkyl group (e.g., propyl) optionally substituted by 1 to 3 carboxy groups, or
(2) a $C_{1-6}$ alkyl group (e.g., propyl) optionally substituted by 1 to 3 substituents selected from a $C_{1-6}$ alkoxy-carbonyl group (e.g., methoxycarbonyl);

Ring B is a benzene ring, a pyridine ring or a dihydropyridine ring, each of which is optionally further substituted;

the partial structure represented by the formula:

is $CR^{5a}=CR^6$, $CR^{5b}=N$ or $C(=O)-NR$; and
$R^{5a}$ and $R^{5b}$ are each independently
(1) a $C_{1-6}$ alkyl group (e.g., methyl, propyl, isopropyl) optionally substituted by 1 to 3 substituents selected from a $C_{1-6}$ alkoxy group (e.g., methoxy) optionally substituted by 1 to 3 halogen atoms (e.g., a fluorine atom),
(2) a $C_{1-6}$ alkoxy group (e.g., methoxy, ethoxy, propoxy, isopropoxy) optionally substituted by 1 to 3 substituents selected from
  (a) a halogen atom (e.g., a fluorine atom), and
  (b) a $C_{3-10}$ cycloalkyl group (e.g., cyclopropyl),
(3) a $C_{1-6}$ alkylsulfonyl group (e.g., methylsulfonyl),
(4) a cyano group,
(5) a cyclic amino group (e.g., azetidino) optionally substituted by 1 to 3 halogen atoms (e.g., a fluorine atom), or
(6) an oxetan-3-yloxy group;
$R^6$ is a hydrogen atom or a $C_{1-6}$ alkyl group (e.g., methyl); and
$R^7$ is a $C_{1-6}$ alkyl group (e.g., methyl); or
the substituent that Ring B optionally further has and $R^{5a}$ or $R^{5b}$ in combination optionally form Ring D wherein the Ring D is a dihydrofuran ring (e.g., 2,3-dihydrofuran) and is fused at the ring forming position; or
$R^{5a}$ and $R^6$ in combination optionally form Ring D' wherein Ring D' is a dihydrofuran ring (e.g., 2,3-dihydrofuran), a dioxole ring (e.g., 1,3-dioxole) or a dihydrodioxin ring (e.g., 2,3-dihydro-1,4-dioxin), and each is fused at the ring forming position;
Y is a methylene group or an oxygen atom; and
W is a $C_{1-2}$ alkylene group (e.g., methylene, ethylene ($-CH_2-CH_2-$))
or a salt thereof.

[Compound I-A2]
A compound wherein
Ring A is a 6-membered aromatic ring (e.g., a benzene ring, a pyridine ring) optionally further substituted by 1 to 3 (preferably 1 or 2) substituents selected from
  (1) a halogen atom (e.g., a fluorine atom, a chlorine atom),
  (2) a $C_{1-6}$ alkoxy group (e.g., methoxy, ethoxy) optionally substituted by 1 to 3 halogen atoms (e.g., a fluorine atom), and
  (3) a cyano group;
$R^1$ is
(1) a group represented by the formula: $-Q(R^{1a})(R^{1b})(R^{1c})$ wherein
  Q is a carbon atom or a silicon atom,
  $R^{1a}$ and $R^{1b}$ are each independently a $C_{1-6}$ alkyl group (e.g., methyl), and
  $R^{1c}$ is
  (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from
    (i) a halogen atom (e.g., a fluorine atom),
    (ii) a $C_{3-10}$ cycloalkyl group (e.g., cyclopropyl), and
    (iii) a $C_{1-6}$ alkoxy group (e.g., methoxy),
  (b) a $C_{1-6}$ alkoxy-carbonyl group (e.g., ethoxycarbonyl),
  (c) a carbamoyl group optionally mono- or di-substituted by substituent(s) selected from
    (i) a $C_{1-6}$ alkyl group (e.g., ethyl), and
    (ii) a $C_{3-10}$ cycloalkyl group (e.g., cyclopropyl),
  (d) a 5- or 6-membered monocyclic aromatic heterocyclic group (e.g., oxadiazolyl (1,3,4-oxadiazolyl)) optionally substituted by 1 to 3 $C_{1-6}$ alkyl groups (e.g., methyl), or
  (e) a 3- to 8-membered monocyclic non-aromatic heterocyclylcarbonyl group (e.g., pyrrolidinylcarbonyl), or
  $R^{1c}$ is bonded to one substituent for Ring A to form
    (a) a $C_{3-10}$ cycloalkene ring (e.g., cyclopentene), or
    (b) a 3- to 14-membered non-aromatic heterocycle (e.g., dihydrofuran), or
(2) a neo-pentyl group;
$R^{11}$ is $-CR^{12}R^{12'}-R^{12''}$, $-C(=O)-R^4$ or $-SO_2-R^{13}$;
$R^{12}$ is a $C_{1-6}$ alkyl group (e.g., ethyl) optionally substituted by 1 to 3 $C_{1-6}$ alkoxy-carbonyl groups (e.g., methoxycarbonyl), and $R^{12'}$ and $R^{12''}$ are hydrogen atoms;
$R^4$ is
(1) a 5- or 6-membered monocyclic aromatic heterocyclic group (e.g., isoxazolyl, pyrazolyl) optionally substituted by 1 to 5 (preferably 1 to 3) substituents selected from
  (a) a hydroxy group,
  (b) a carboxy group, and
  (c) a $C_{1-6}$ alkyl group (e.g., methyl),
(2) a 3- to 8-membered monocyclic non-aromatic heterocyclic group (e.g., dihydropyridyl (1,2-dihydropyridyl), pyrrolidinyl, azetidinyl, morpholinyl) optionally substituted by 1 to 3 substituents selected from
  (a) an oxo group,
  (b) a $C_{1-6}$ alkyl group (e.g., methyl) optionally substituted by 1 to 3 substituents selected from
    (i) a carboxy group, and
    (ii) a $C_{1-6}$ alkoxy-carbonyl (e.g., methoxycarbonyl) optionally substituted by 1 to 3 $C_{6-14}$ aryl groups (e.g., phenyl),
  (c) a carboxy group,
  (d) a hydroxy group, and
  (e) a $C_{1-6}$ alkoxy group (e.g., methoxy) optionally substituted by 1 to 3 carboxy groups,
(3) a $C_{1-6}$ alkyl group (e.g., methyl, ethyl, propyl, butyl, isobutyl, sec-butyl, neo-pentyl, isopentyl) optionally substituted by 1 to 5 (preferably 1 to 3) substituents selected from
  (a) a 3- to 8-membered monocyclic non-aromatic heterocyclic group (e.g., thiazolidinyl, piperidyl, imidazolidinyl, pyrrolidinyl, oxazolidinyl, tetrahydropyrimidinyl (1,2,3,4-tetrahydropyrimidinyl), dihydropyrimidinyl (3,4-dihydropyrimidinyl), dihydropyridyl (1,2-dihydropyridyl), 1,1-dioxidotetrahydrothiopyranyl, 1,1-dioxidothiadiazolidinyl (1,1-dioxido-1,2,5-thiadiazolidinyl)) optionally substituted by 1 to 5 (preferably 1 to 3) substituents selected from
    (i) an oxo group, and
    (ii) a $C_{1-6}$ alkyl group (e.g., methyl),
  (b) a 5- or 6-membered monocyclic aromatic heterocyclic group (e.g., isoxazolyl, oxadiazolyl (1,3,4-oxadiazolyl), pyridyl, tetrazolyl) optionally substituted by 1 to 3 substituents selected from
    (i) a hydroxy group,
    (ii) a $C_{1-6}$ alkyl group (e.g., methyl),
    (iii) a $C_{1-6}$ alkoxy group (e.g., methoxy), and
    (iv) a carboxy group,
  (c) a hydroxy group,
  (d) a $C_{1-6}$ alkylsulfonyl group (e.g., methylsulfonyl),
  (e) a carboxy group,
  (f) a 8- to 14-membered fused polycyclic (preferably bi- or tri-cyclic) aromatic heterocyclic group (e.g., indazolyl),
  (g) a halogen atom (e.g., a fluorine atom),
  (h) a cyano group,
  (i) a $C_{1-6}$ alkoxy group (e.g., methoxy) optionally substituted by 1 to 3 carboxy groups, (j) an amino group optionally mono- or di-substituted by $C_{1-6}$ alkyl group(s) (e.g., methyl) optionally substituted by 1 to 3 carboxy groups, and (k) a carbamoyl group, (4) an amino group optionally mono- or di-substituted by substituent(s) selected from (a) a 5- or 6-membered monocyclic aromatic heterocyclic group (e.g., pyridazinyl, pyrazolyl) optionally substituted by 1 to 3 $C_{1-6}$ alkyl groups (e.g., methyl), and (b) a $C_{1-6}$ alkyl group (e.g., methyl, ethyl, propyl, isopropyl) optionally substituted by 1 to 3 substituents selected from (i) a $C_{1-6}$ alkoxy-carbonyl group (e.g., methoxycarbonyl, ethoxycarbonyl) optionally substituted by 1 to 3 $C_{6-14}$ aryl groups (e.g., phenyl), and (ii) a carboxy group, (5) a carboxy group, (6) a carbamoyl group, (7) a $C_{2-6}$ alkenyl group (e.g., vinyl) optionally substituted by 1 to 3 carboxy groups, (8) a $C_{1-6}$ alkyl-carbonyl group (e.g., propionyl) optionally substituted by 1 to 3 carboxy groups, or (9) a $C_{1-6}$ alkoxy group (e.g., ethoxy, propoxy) optionally substituted by 1 to 3 carboxy groups;

$R^{13}$ is (1) an amino group optionally mono- or di-substituted by substituent(s) selected from (a) a $C_{1-6}$ alkoxy-carbonyl group (e.g., tert-butoxycarbonyl), and (b) a $C_{1-6}$ alkyl group (e.g., propyl) optionally substituted by 1 to 3 carboxy groups, or (2) a $C_{1-6}$ alkyl group (e.g., propyl) optionally substituted by 1 to 3 substituents selected from a $C_{1-6}$ alkoxy-carbonyl group (e.g., methoxycarbonyl);

Ring B is a benzene ring, a pyridine ring or a dihydropyridine ring, each of which is optionally further substituted;

the partial structure represented by the formula:

$X^1\text{-----}X^2$ is $CR^{5a}=CR^6$, $CR^{5b}=N$ or $C(=O)-NR$; and $R^{5a}$ is (1) a $C_{1-6}$ alkyl group (e.g., methyl, propyl) optionally substituted by 1 to 3 substituents selected from a $C_{1-6}$ alkoxy group (e.g., methoxy) optionally substituted by 1 to 3 halogen atoms (e.g., a fluorine atom), (2) a $C_{1-6}$ alkoxy group (e.g., methoxy, ethoxy, propoxy, isopropoxy) optionally substituted by 1 to 3 substituents selected from (a) a halogen atom (e.g., a fluorine atom), and (b) a $C_{3-10}$ cycloalkyl group (e.g., cyclopropyl), (3) a $C_{1-6}$ alkylsulfonyl group (e.g., methylsulfonyl), (4) a cyano group, (5) a cyclic amino group (e.g., azetidino) optionally substituted by 1 to 3 halogen atoms (e.g., a fluorine atom), or (6) an oxetan-3-yloxy group;

$R^{5b}$ is (1) a $C_{1-6}$ alkyl group (e.g., methyl, propyl, isopropyl) optionally substituted by 1 to 3 $C_{1-6}$ alkoxy groups (e.g., methoxy), or (2) a $C_{1-6}$ alkoxy group (e.g., methoxy, ethoxy) optionally substituted by 1 to 3 halogen atoms (e.g., a fluorine atom);

$R^6$ is a hydrogen atom or a $C_{1-6}$ alkyl group (e.g., methyl); and $R^7$ is a $C_{1-6}$ alkyl group (e.g., methyl); or the substituent that Ring B optionally further has and $R^{5a}$ or $R^{5b}$ in combination optionally form Ring D wherein the Ring D is a dihydrofuran ring (e.g., 2,3-dihydrofuran) and is fused at the ring forming position; or $R^{5a}$ and $R^6$ in combination optionally form Ring D' wherein Ring D' is a dihydrofuran ring (e.g., 2,3-dihydrofuran), a dioxole ring (e.g., 1,3-dioxole) or a dihydrodioxin ring (e.g., 2,3-dihydro-1,4-dioxin), and each is fused at the ring forming position;

Y is a methylene group or an oxygen atom; and

W is a $C_{1-2}$ alkylene group (e.g., methylene, ethylene ($-CH_2-CH_2-$))

or a salt thereof.

[Compound I-B1]

A compound wherein

Ring A is a benzene ring optionally further substituted by 1 to 3 (preferably 1 or 2) substituents selected from (1) a halogen atom (e.g., a fluorine atom, a chlorine atom), and (2) a cyano group;

$R^1$ is a group represented by the formula: $-Q(R^{1a})(R^{1b})(R^{1c})$ wherein Q is a carbon atom or a silicon atom, and $R^{1a}$, $R^{1b}$ and $R^{1c}$ are each independently (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from (i) a halogen atom (e.g., a fluorine atom), (ii) a $C_{3-10}$ cycloalkyl group (e.g., cyclopropyl), and (iii) a $C_{1-6}$ alkoxy group (e.g., methoxy), (b) a $C_{1-6}$ alkoxy-carbonyl group (e.g., ethoxycarbonyl), or (c) a 3- to 8-membered monocyclic non-aromatic heterocyclylcarbonyl group (e.g., pyrrolidinylcarbonyl), or $R^{1c}$ is bonded to one substituent for Ring A to form a $C_{3-10}$ cycloalkene ring (e.g., cyclopentene);

$R^{11}$ is $-C(=O)-R^4$;

$R^4$ is (1) a 5- or 6-membered monocyclic aromatic heterocyclic group (e.g., isoxazolyl) optionally substituted by 1 to 3 hydroxy groups, (2) a 3- to 8-membered monocyclic non-aromatic heterocyclic group (e.g., dihydropyridyl (1,2-dihydropyridyl), pyrrolidinyl, azetidinyl) optionally substituted by 1 to 3 substituents selected from (a) an oxo group, and (b) a $C_{1-6}$ alkyl group (e.g., methyl) optionally substituted by 1 to 3 carboxy groups, (3) a $C_{1-6}$ alkyl group (e.g., methyl, ethyl, propyl, butyl, isobutyl, neo-pentyl) optionally substituted by 1 to 5 (preferably 1 to 3) substituents selected from (a) a 3- to 8-membered monocyclic non-aromatic heterocyclic group (e.g., thiazolidinyl, dihydropyrimidinyl (3,4-dihydropyrimidinyl)) optionally substituted by 1 to 3 oxo groups, (b) a 5- or 6-membered monocyclic aromatic heterocyclic group (e.g., isoxazolyl, oxadiazolyl (1,3,4-oxadiazolyl), pyridyl) optionally substituted by 1 to 3 substituents selected from (i) a hydroxy group, (ii) a $C_{1-6}$ alkyl group (e.g., methyl), and (iii) a $C_{1-6}$ alkoxy group (e.g., methoxy), (c) a hydroxy group, (d) a carboxy group, (e) a halogen atom (e.g., a fluorine atom), (f) a cyano group, and (g) a carbamoyl group, (4) an amino group optionally mono- or di-substituted by substituent(s) selected from a $C_{1-6}$ alkyl group (e.g., ethyl, propyl) optionally substituted by 1 to 3 carboxy groups, or (5) a $C_{2-6}$ alkenyl group (e.g., vinyl) optionally substituted by 1 to 3 carboxy groups;

the partial structure represented by the formula:

$X^1\text{------}X^2$ is $CR^{5a}=CR^6$ or $CR^{5b}=N$, and $R^{5a}$ and $R^{5b}$ are each independently (1) a $C_{1-6}$ alkyl group (e.g., methyl) optionally substituted by 1 to 3 $C_{1-6}$ alkoxy groups (e.g., methoxy), (2) a $C_{1-6}$ alkoxy group (e.g., methoxy, ethoxy) optionally substituted by 1 to 3 halogen atoms (e.g., a fluorine atom), or (3) a $C_{1-6}$ alkylsulfonyl group (e.g., methylsulfonyl); and $R^6$ is a hydrogen atom; or $R^{5a}$ and $R^6$ in combination optionally form Ring D' wherein Ring D' is a dioxole ring (e.g., 1,3-dioxole), and is fused at the ring forming position;

Y is a methylene group or an oxygen atom; and

W is a $C_{1-2}$ alkylene group (e.g., methylene, ethylene ($-CH_2-CH_2-$))

or a salt thereof.

[Compound I-B2]

A compound wherein

Ring A is a benzene ring optionally further substituted by 1 to 3 (preferably 1 or 2) substituents selected from (1) a halogen atom (e.g., a fluorine atom, a chlorine atom), and (2) a cyano group;

$R^1$ is a group represented by the formula: $-Q(R^{1a})(R^{1b})(R^{1c})$ wherein Q is a carbon atom or a silicon atom, $R^{1a}$ and $R^{1b}$ are each independently a $C_{1-6}$ alkyl group (e.g., methyl), and $R^{1c}$ is (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 substituents selected from (i) a halogen atom (e.g., a fluorine atom), (ii) a $C_{3-10}$ cycloalkyl group (e.g., cyclopropyl), and (iii) a $C_{1-6}$ alkoxy group (e.g., methoxy), (b) a $C_{1-6}$ alkoxy-carbonyl group (e.g., ethoxycarbonyl), or (c) a 3- to 8-membered monocyclic non-aromatic heterocyclylcarbonyl group (e.g., pyrrolidinylcarbonyl), or $R^{1c}$ is bonded to one substituent for Ring A to form a $C_{3-10}$ cycloalkene ring (e.g., cyclopentene);

$R^{11}$ is $-C(=O)-R^4$;

$R^4$ is (1) a 5- or 6-membered monocyclic aromatic heterocyclic group (e.g., isoxazolyl) optionally substituted by 1 to 3 hydroxy groups, (2) a 3- to 8-membered monocyclic non-aromatic heterocyclic group (e.g., dihydropyridyl (1,2-dihydropyridyl), pyrrolidinyl, azetidinyl) optionally substituted by 1 to 3 substituents selected from (a) an oxo group, and (b) a $C_{1-6}$ alkyl group (e.g., methyl) optionally substituted by 1 to 3 carboxy groups, (3) a $C_{1-6}$ alkyl group (e.g., methyl, ethyl, propyl, butyl, isobutyl, neo-pentyl) optionally substituted by 1 to 5 (preferably 1 to 3) substituents selected from (a) a 3- to 8-membered monocyclic non-aromatic heterocyclic group (e.g., thiazolidinyl, dihydropyrimidinyl (3,4-dihydropyrimidinyl)) optionally substituted by 1 to 3 oxo groups, (b) a 5- or 6-membered monocyclic aromatic heterocyclic group (e.g., isoxazolyl, oxadiazolyl (1,3,4-oxadiazolyl), pyridyl) optionally substituted by 1 to 3 substituents selected from (i) a hydroxy group, (ii) a $C_{1-6}$ alkyl group (e.g., methyl), and (iii) a $C_{1-6}$ alkoxy group (e.g., methoxy), (c) a hydroxy group, (d) a carboxy group, (e) a halogen atom (e.g., a fluorine atom), (f) a cyano group, and (g) a carbamoyl group, (4) an amino group optionally mono- or di-substituted by substituent(s) selected from a $C_{1-6}$ alkyl group (e.g., ethyl, propyl) optionally substituted by 1 to 3 carboxy groups, or (5) a $C_{2-6}$ alkenyl group (e.g., vinyl) optionally substituted by 1 to 3 carboxy groups;

the partial structure represented by the formula:

$X^1\text{------}X^2$ is $CR^{5a}=CR^6$ or $CR^{5b}=N$; and $R^{5a}$ is (1) a $C_{1-6}$ alkyl group (e.g., methyl) optionally substituted by 1 to 3 $C_{1-6}$ alkoxy groups (e.g., methoxy), (2) a $C_{1-6}$ alkoxy group (e.g., methoxy, ethoxy) optionally substituted by 1 to 3 halogen atoms (e.g., a fluorine atom), or (3) a $C_{1-6}$ alkylsulfonyl group (e.g., methylsulfonyl);

$R^{5b}$ is (1) a $C_{1-6}$ alkyl group (e.g., methyl) optionally substituted by 1 to 3 $C_{1-6}$ alkoxy groups (e.g., methoxy), or (2) a $C_{1-6}$ alkoxy group (e.g., methoxy, ethoxy); and $R^6$ is a hydrogen atom; or $R^{5a}$ and $R^6$ in combination optionally form Ring D' wherein Ring D' is a dioxole ring (e.g., 1,3-dioxole), and is fused at the ring forming position;

Y is a methylene group or an oxygen atom; and

W is a $C_{1-2}$ alkylene group (e.g., methylene, ethylene ($-CH_2-CH_2-$)

or a salt thereof.

[Compound I-C1]

A compound wherein

Ring A is a benzene ring optionally further substituted by 1 to 3 (preferably 1 or 2) halogen atoms (e.g., a fluorine atom);

$R^1$ is a group represented by the formula: $-Q(R^{1a})(R^{1b})(R^{1c})$ wherein Q is a carbon atom or a silicon atom, and $R^{1a}$, $R^{1b}$ and $R^{1c}$ are each independently a $C_{1-6}$ alkyl group (e.g., methyl), or $R^{1c}$ is bonded to one substituent for Ring A to form a $C_{3-10}$ cycloalkene ring (e.g., cyclopentene);

$R^{11}$ is $-C(=O)-R^4$;

$R^4$ is (1) a 3- to 8-membered monocyclic non-aromatic heterocyclic group (e.g., azetidinyl) optionally substituted by 1 to 3 substituents selected from a $C_{1-6}$ alkyl group (e.g., methyl) optionally substituted by 1 to 3 carboxy groups, or (2) a $C_{1-6}$ alkyl group (e.g., propyl) optionally substituted by 1 to 3 carboxy groups;

the partial structure represented by the formula:

$X^1\text{------}X^2$ is $CR^{5a}=CR^6$ or $CR^{5b}=N$; and $R^{5a}$ and $R^{5b}$ are each independently a $C_{1-6}$ alkoxy group (e.g., methoxy); and $R^6$ is a hydrogen atom; or $R^{5a}$ and $R^6$ in combination optionally form Ring D' wherein Ring D' is a dioxole ring (e.g., 1,3-dioxole), and is fused at the ring forming position;

Y is a methylene group; and

W is a methylene group or a salt thereof.

[Compound I-D1]

5-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)-5-oxopentanoic acid or a salt thereof.

[Compound I-D2]

(1-(((6R)-6-((3,5-difluoro-4-(trimethylsilyl)phenyl)carbamoyl)-8, 9-dihydro[1,3]dioxolo[4,5-f]isoquinolin-7(6H)-yl)carbonyl)azetidin-3-yl)acetic acid or a salt thereof.

[Compound I-D3]

(1-(((5R)-5-((3,5-difluoro-4-(trimethylsilyl)phenyl)carbamoyl)-2-methoxy-7,8-dihydro-1,6-naphthyridin-6(5H)-yl)carbonyl)azetidin-3-yl)acetic acid or a salt thereof.

Specific examples of compound (I) include the compounds of Examples 1 to 293, which are the compound of formula (I) or a salt thereof or a solvate thereof (e.g., a hydrate (e.g., monohydrate, dihydrate, etc.)).

Among compound (I), examples of compound (Ia) include the following compounds.

[Compound Ia-A1]

A compound wherein

Ring A is a 6-membered aromatic ring (e.g., a benzene ring, a pyridine ring) optionally further substituted by 1 to 3 (preferably 1 or 2) substituents selected from (1) a halogen atom (e.g., a fluorine atom, a chlorine atom), (2) a $C_{1-6}$ alkoxy group (e.g., methoxy, ethoxy) optionally substituted by 1 to 3 halogen atoms (e.g., a fluorine atom), and (3) a cyano group;

$R^1$ is (1) a group represented by the formula: -Q($R^{1a}$) ($R^{1b}$) ($R^{1c}$) wherein Q is a carbon atom or a silicon atom, and $R^{1a}$, $R^{1b}$ and $R^{1c}$ are each independently (a) a $C_{1-6}$ alkyl group (e.g., methyl, ethyl) optionally substituted by 1 to 3 $C_{1-6}$ alkoxy groups (e.g., methoxy, ethoxy) optionally substituted by 1 to 3 halogen atoms (e.g., a fluorine atom), (b) a $C_{1-6}$ alkoxy-carbonyl group (e.g., ethoxycarbonyl), (c) a carbamoyl group optionally mono- or di-substituted by substituent(s) selected from (i) a $C_{1-6}$ alkyl group (e.g., ethyl), and (ii) a $C_{3-10}$ cycloalkyl group (e.g., cyclopropyl), (d) a 5- or 6-membered monocyclic aromatic heterocyclic group (e.g., oxadiazolyl (1,3,4-oxadiazolyl)) optionally substituted by 1 to 3 $C_{1-6}$ alkyl groups (e.g., methyl), or (e) a 3- to 8-membered monocyclic non-aromatic heterocyclylcarbonyl group (e.g., pyrrolidinylcarbonyl), or $R^{1c}$ is bonded to one substituent for Ring A to form (a) a $C_{3-10}$ cycloalkene ring (e.g., cyclopentene), or (b) a 3- to 14-membered non-aromatic heterocycle (e.g., dihydrofuran), or (2) a neo-pentyl group;

$R^4$ is (1) a 5- or 6-membered monocyclic aromatic heterocyclic group (e.g., isoxazolyl) optionally substituted by 1 to 3 hydroxy groups, (2) a 3- to 8-membered monocyclic non-aromatic heterocyclic group (e.g., dihydropyridyl (1,2-dihydropyridyl), pyrrolidinyl) optionally substituted by 1 to 3 oxo groups, (3) a $C_{1-6}$ alkyl group (e.g., methyl, ethyl, propyl, butyl, isobutyl, neo-pentyl) optionally substituted by 1 to 5 (preferably 1 to 3) substituents selected from (a) a 3- to 8-membered monocyclic non-aromatic heterocyclic group (e.g., thiazolidinyl, piperidyl, imidazolidinyl, pyrrolidinyl, oxazolidinyl, tetrahydropyrimidinyl (1,2,3,4-tetrahydropyrimidinyl), dihydropyrimidinyl (3,4-dihydropyrimidinyl), dihydropyridyl (1,2-dihydropyridyl), 1,1-dioxidotetrahydrothiopyranyl) optionally substituted by 1 to 5 (preferably 1 to 3) substituents selected from (i) an oxo group, and (ii) a $C_{1-6}$ alkyl group (e.g., methyl), (b) a 5- or 6-membered monocyclic aromatic heterocyclic group (e.g., isoxazolyl, oxadiazolyl (1,3,4-oxadiazolyl), pyridyl, tetrazolyl (5-tetrazolyl)) optionally substituted by 1 to 3 substituents selected from (i) a hydroxy group, (ii) a $C_{1-6}$ alkyl group (e.g., methyl), and (iii) a $C_{1-6}$ alkoxy group (e.g., methoxy), (c) a hydroxy group, (d) a $C_{1-6}$ alkylsulfonyl group (e.g., methylsulfonyl), (e) a carboxy group, (f) a 8- to 14-membered fused polycyclic (preferably bi- or tri-cyclic) aromatic heterocyclic group (e.g., indazolyl (1H-indazolyl)), (g) a halogen atom (e.g., a fluorine atom), (h) a cyano group, and (i) a $C_{1-6}$ alkoxy group (e.g., methoxy) optionally substituted by 1 to 3 carboxy groups, (4) an amino group optionally mono- or di-substituted by 5- or 6-membered monocyclic aromatic heterocyclic group(s) (e.g., pyridazinyl, pyrazolyl) optionally substituted by 1 to 3 $C_{1-6}$ alkyl groups (e.g., methyl), (5) a carboxy group, or (6) a carbamoyl group;

Ring B is a benzene ring, a pyridine ring or a 1,2-dihydropyridine ring;

the partial structure represented by the formula:

$X^1\text{------}X^2$ is $CR^{5a}=CR^6$, $CR^{5b}=N$ or $C(=O)-NR$; and $R^{5a}$ is a $C_{1-6}$ alkyl group (e.g., methyl) optionally substituted by 1 to 3 $C_{1-6}$ alkoxy groups (e.g., methoxy, ethoxy), or a $C_{1-6}$ alkoxy group (e.g., methoxy, ethoxy);

$R^{5b}$ is a $C_{1-6}$ alkoxy group (e.g., methoxy, ethoxy);

$R^6$ is a hydrogen atom; and $R^7$ is a $C_{1-6}$ alkyl group (e.g., methyl);

Y is a methylene group or an oxygen atom; and

W is a $C_{1-2}$ alkylene group (e.g., methylene, ethylene) or a salt thereof.

[Compound Ia-B1]

A compound wherein

Ring A is a benzene ring optionally further substituted by 1 to 3 (preferably 1 or 2) substituents selected from (1) a halogen atom (e.g., a fluorine atom, a chlorine atom), and (2) a cyano group;

$R^1$ is a group represented by the formula: -Q($R^{1a}$) ($R^{1b}$) ($R^{1c}$) wherein Q is a carbon atom or a silicon atom, and $R^{1a}$, $R^{1b}$ and $R^{1c}$ are each independently (a) a $C_{1-6}$ alkyl group (e.g., methyl), or (b) a $C_{1-6}$ alkoxy-carbonyl group (e.g., ethoxycarbonyl), or $R^{1c}$ is bonded to one substituent for Ring A to form a $C_{3-10}$ cycloalkene ring (e.g., cyclopentene);

R[4] is
(1) a 5- or 6-membered monocyclic aromatic heterocyclic group (e.g., isoxazolyl) optionally substituted by 1 to 3 hydroxy groups,
(2) a 3- to 8-membered monocyclic non-aromatic heterocyclic group (e.g., dihydropyridyl (1,2-dihydropyridyl), pyrrolidinyl) optionally substituted by 1 to 3 oxo groups, or
(3) a $C_{1-6}$ alkyl group (e.g., methyl, ethyl) optionally substituted by 1 to 5 (preferably 1 to 3) substituents selected from
    (a) a 3- to 8-membered monocyclic non-aromatic heterocyclic group (e.g., dihydropyrimidinyl (3,4-dihydropyrimidinyl)) optionally substituted by 1 to 3 oxo groups,
    (b) a 5- or 6-membered monocyclic aromatic heterocyclic group (e.g., isoxazolyl, oxadiazolyl (1,3,4-oxadiazolyl), pyridyl) optionally substituted by 1 to 3 substituents selected from
        (i) a hydroxy group,
        (ii) a $C_{1-6}$ alkyl group (e.g., methyl), and
        (iii) a $C_{1-6}$ alkoxy group (e.g., methoxy), and
    (c) a hydroxy group;
Ring B is a benzene ring or a pyridine ring;
the partial structure represented by the formula:

is $CR^{5a}=CR^6$ or $CR^{5b}=N$; and
$R^{5a}$ is a $C_{1-6}$ alkyl group (e.g., methyl) optionally substituted by 1 to 3 $C_{1-6}$ alkoxy groups (e.g., methoxy), or a $C_{1-6}$ alkoxy group (e.g., methoxy, ethoxy);
$R^{5b}$ is a $C_{1-6}$ alkoxy group (e.g., methoxy); and
$R^6$ is a hydrogen atom;
Y is a methylene group or an oxygen atom; and
W is a $C_{1-2}$ alkylene group (e.g., methylene, ethylene) or a salt thereof.

Examples of salts of compound (I) and (Ia) include metal salts, ammonium salts, salts with organic base, salts with inorganic acid, salts with organic acid, salts with basic or acidic amino acids, and the like. Preferable examples of the metal salt include alkaline metal salts such as sodium salt, potassium salt and the like; alkaline earth metal salts such as calcium salt, magnesium salt, barium salt and the like; aluminum salts, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salt with aspartic acid, glutamic acid and the like.

Among them, pharmaceutically acceptable salts are preferable. For example, if the compound has an acidic functional group therein, examples of the salt include inorganic salts such as alkaline metal salts (e.g., sodium salt, potassium salt and the like), alkaline earth metal salts (e.g., calcium salt, magnesium salt, barium salt and the like) and the like; ammonium salt, and the like. If the compound has a basic functional group therein, examples of the salt thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

The production method of the compound (I) or (Ia) of the present invention is explained below.

The intermediates produced in the following production methods may be isolated and purified according to methods such as column chromatography, recrystallization, distillation and the like, or may be directly used without isolation for the next step.

Ring A represented by the formula:

in the following production methods is used for the same meaning as Ring A represented by the formula:

which is defined in compounds (I) and (Ia) of the present invention.

Compound (Ia) or a salt thereof of the present invention can be produced according to the following Method A.

[Method A]

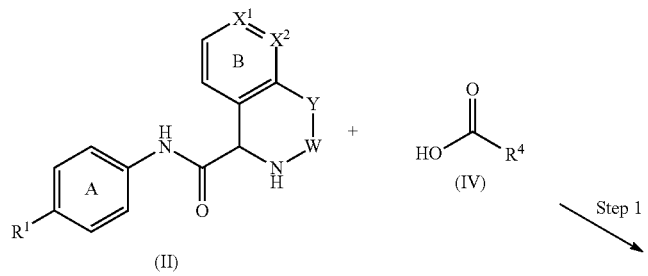

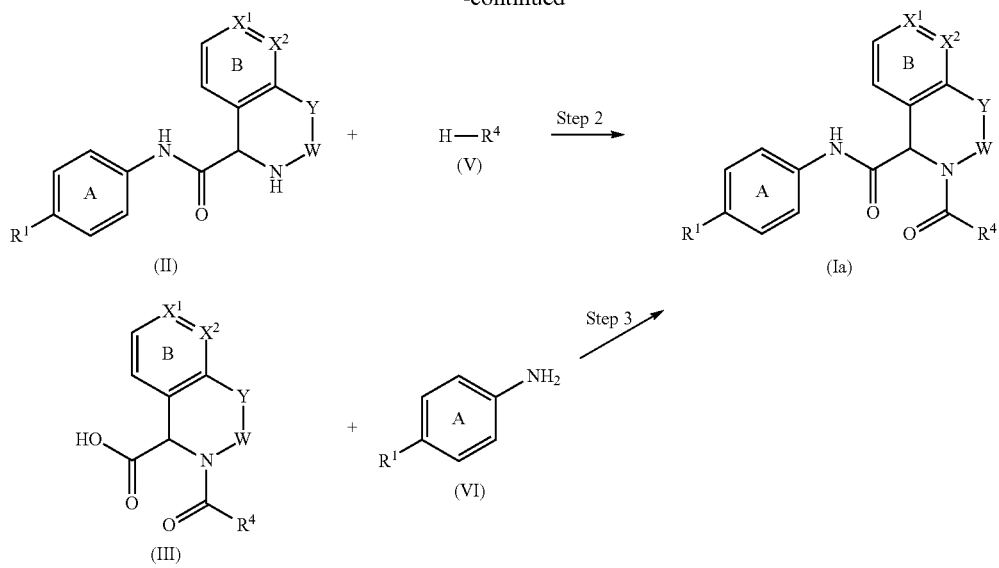

wherein each symbol is as defined above.
(Step 1)

This step is a step of subjecting compound (II) or a salt thereof to an acylation reaction to convert compound (II) or a salt thereof to compound (Ia) or a salt thereof.

In the acylation reaction, compound (Ia) or a salt thereof can be produced by reacting compound (II) or a salt thereof with a compound represented by the formula:

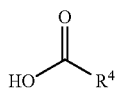
(IV)

wherein the symbol is as defined above (hereinafter to be referred to as compound (IV)) or a salt thereof.

Compound (IV) or a salt thereof may be a commercially available product, or can also be produced according to a method known per se or a method analogous thereto.

The acylation reaction can be carried out according to a method known per se, for example, the method described in Jikken Kagaku Kouza, 4th Edition, 1991, vol. 22, organic synthesis IV (the Chemical Society of Japan ed.) and the like, or a method analogous thereto. Examples of the method include a method using a condensing agent, a method via a reactive derivative, and the like.

Examples of the condensing agent to be used for the "method using a condensing agent" include (dimethylamino)-N,N-dimethyl(3H-[1,2,3]triazolo[4,5-b]pyridin-3-yloxy)methaneiminium hexafluorophosphate (HATU), 1-[(1-(cyano-2-ethoxy-2-oxoethylideneaminooxy)-dimethylamino-morpholino)]carbenium hexafluorophosphorate (COMU), 2,4,6-tripropyl-1,3,5,2,4,6-trioxatriphosphorinane-2,4,6-trioxide (T3P), dicyclohexylcarbodiimide (DCC), diisopropylcarbodiimide (DIC), N-ethyl-N'-3-dimethylaminopropylcarbodiimide and a hydrochloride thereof (WSC, WSC.HCl, EDCI), benzotriazol-1-yl-tris(dimethylamino)phosphonium hexafluorophosphorate (BOP), diphenylphosphorylazide(DPPA) and the like. They can be used alone or in combination with an additive (e.g., N-hydroxysuccinimide, 1-hydroxybenzotriazole or 3-hydroxy-4-oxo-3,4-dihydro-1,2,3-benzotriazine, etc.). The amount of the condensing agent to be used is about 1 to 10 mol equivalent, preferably about 1 to 2 mol equivalent, per 1 mol of compound (II). The amount of the additive to be used is about 1 to 10 mol equivalent, preferably about 1 to 2 mol equivalent, per 1 mol of compound (II).

The above-mentioned reaction is generally carried out in a solvent that does not adversely influence the reaction, and a base may be added for the progress of the reaction. Examples of the solvent include hydrocarbons (benzene, toluene, etc.), ethers (diethyl ether, 1,4-dioxane, tetrahydrofuran, etc.), esters (ethyl acetate, etc.), halogenated hydrocarbons (chloroform, dichloromethane, etc.), amides (N,N-dimethylformamide, etc.), aromatic amines (pyridine, etc.), water and the like, and they may be mixed as appropriate. Examples of the base include alkali metal hydroxides (sodium hydroxide, potassium hydroxide, etc.), hydrogen carbonates (sodium hydrogen carbonate, potassium hydrogen carbonate, etc.), carbonates (sodium carbonate, potassium carbonate, etc.), acetates (sodium acetate, etc.), tertiary amines (trimethylamine, triethylamine, N-methylmorpholine, diisopropylamine, etc.), aromatic amines (pyridine, picoline, N,N-dimethylaniline, 4-dimethylaminopyridine, etc.) and the like. The amount of the base to be used is generally about 1 to 100 mol equivalent, preferably about 1 to 5 mol equivalent, per 1 mol of compound (II). The reaction temperature is generally about −80 to 150° C., preferably about 0 to 50° C., and the reaction time is generally about 0.5 to 48 hr, preferably 0.5 to 16 hr.

Examples of the reactive derivative in the "method via a reactive derivative" include a compound represented by the formula:

(IVa)

wherein LG is a leaving group, and the other symbols are as defined above (hereinafter to be referred to as compound (IVa)) or a salt thereof (e.g., acid halides, anhydrides, mixed anhydrides, activated esters, etc.) or chemical equivalents thereof (isocyanates, thioisocyanates, etc.) and the like.

Examples of the leaving group for LG include halogen atoms (a chlorine atom, a bromine atom, an iodine atom, etc.), substituted sulfonyloxy groups ($C_{1-6}$ alkylsulfonyloxy groups such as methanesulfonyloxy, ethanesulfonyloxy and the like; $C_{6-14}$ arylsulfonyloxy groups such as benzenesulfonyloxy, p-toluenesulfonyloxy and the like; $C_{7-16}$ aralkylsulfonyloxy groups such as benzylsulfonyloxy group and the like, etc.), acyloxy groups (acetoxy, benzoyloxy, etc.), an oxy group substituted by a heterocyclic group or an aryl group (2,5-dioxo-1-pyrrolidinyl, benzotriazolyl, quinolyl, 4-nitrophenyl, etc.), heterocyclic groups (imidazolyl, etc.) and the like. LG is optionally bonded to $R^4$ to form a ring, and compound (IVa) may be, for example, anhydrides (dihydro-2H-pyran-2,6(3H)-dione, oxepane-2,7-dione, 4-methyldihydro-2H-pyran-2,6(3H)-dione, 4,4-dimethyldihydro-2H-pyran-2,6(3H)-dione, 4-methylmorpholine-2,6-dione, 4-hydroxy-4-methyldihydro-2H-pyran-2,6(3H)-dione, succinic anhydride, etc.).

The conversion of compound (IV) to the reactive derivative (compound (IVa)) can be carried out according to a method known per se. For example, The conversion to the acid halide can be carried out by employing a method using an acid halide (e.g., thionyl chloride, oxalyl chloride, etc.), a method using a halide of phosphorus and phosphoric acid (e.g., phosphorus trichloride, phosphorus pentachloride, etc.), and the like. The method using a reactive derivative is generally carried out in a solvent that does not adversely influence the reaction, which varies depending on the kind of compound (IVa), and a base may be added for the progress of the reaction. The kind and amount of the solvent and base to be used for the reaction, the reaction temperature and the reaction time are the same as in the above-mentioned "method using a condensing agent".

(Step 2)

This step is a step of subjecting compound (II) or a salt thereof to an ureation reaction to convert compound (II) or a salt thereof to compound (Ia) or a salt thereof.

In the ureation reaction, compound (Ia) or a salt thereof can be produced by reacting a compound represented by the formula:

$$R^4—H \quad (V)$$

wherein the symbol is as defined above (hereinafter to be referred to as compound (V)) or a salt thereof with a carbonylating agent, and then reacting the resulting reactive intermediate with compound (II) or a salt thereof, or by reacting compound (II) or a salt thereof with a carbonylating agent, and then reacting the resulting reactive intermediate with compound (V) or a salt thereof.

Compound (V) may be a commercially available product, or can also be produced according to a method known per se or a method analogous thereto.

Examples of the carbonylating agent to be used in this step include triphosgene, chloroformic acid 4-nitrophenyl or carbonyldiimidazole and the like. The amount of the carbonylating agent to be used is about 1 to 10 mol equivalent, preferably about 1 to 2 mol equivalent, per 1 mol of compound (II).

The above-mentioned reaction is generally carried out in a solvent that does not adversely influence the reaction, and a base may be added for the progress of the reaction. Examples of the solvent include hydrocarbons (benzene, toluene, etc.), ethers (diethyl ether, 1,4-dioxane, tetrahydrofuran, etc.), esters (ethyl acetate, etc.), halogenated hydrocarbons (chloroform, dichloromethane, etc.), amides (N,N-dimethylformamide, etc.) and the like, and they may be mixed as appropriate. Examples of the base include alkali metal hydroxides (sodium hydroxide, potassium hydroxide, etc.), hydrogen carbonates (sodium hydrogen carbonate, potassium hydrogen carbonate, etc.), carbonates (sodium carbonate, potassium carbonate, etc.), acetates (sodium acetate, etc.), tertiary amines (trimethylamine, triethylamine, N-methylmorpholine, etc.), aromatic amines (pyridine, picoline, N,N-dimethylaniline, etc.) and the like. The amount of the base to be used is generally about 1 to 100 mol equivalent, preferably about 1 to 5 mol equivalent, per 1 mol of compound (II). The reaction temperature is generally about −80 to 150° C., preferably about 0 to 50° C., and the reaction time is generally about 0.5 to 100 hr, preferably 0.5 to 60 hr.

The reactive intermediate obtained by the reaction of compound (V) or a salt thereof with a carbonylating agent may be reacted with compound (II) or a salt thereof after isolation.

The reactive intermediate obtained by the reaction of compound (II) or a salt thereof with a carbonylating agent may be reacted with compound (V) or a salt thereof after isolation.

(Step 3)

This step is a step of reacting compound (III) or a salt thereof with a compound represented by the formula:

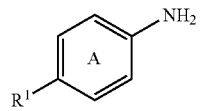

wherein each symbol is as defined above (hereinafter to be referred to as compound (VI)) or a salt thereof in the presence of a condensing agent to produce compound (Ia) or a salt thereof.

Compound (VI) or a salt thereof may be a commercially available product, or can also be produced according to a method known per se or a method analogous thereto, or the below-mentioned method.

This step can be performed in the same manner as in the method described in Step 1 of Method A.

The raw material used in Method A can be produced according to the following Methods B-D.

[Method B]

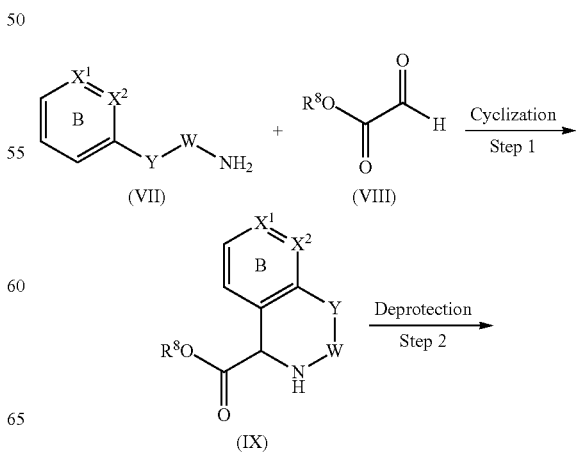

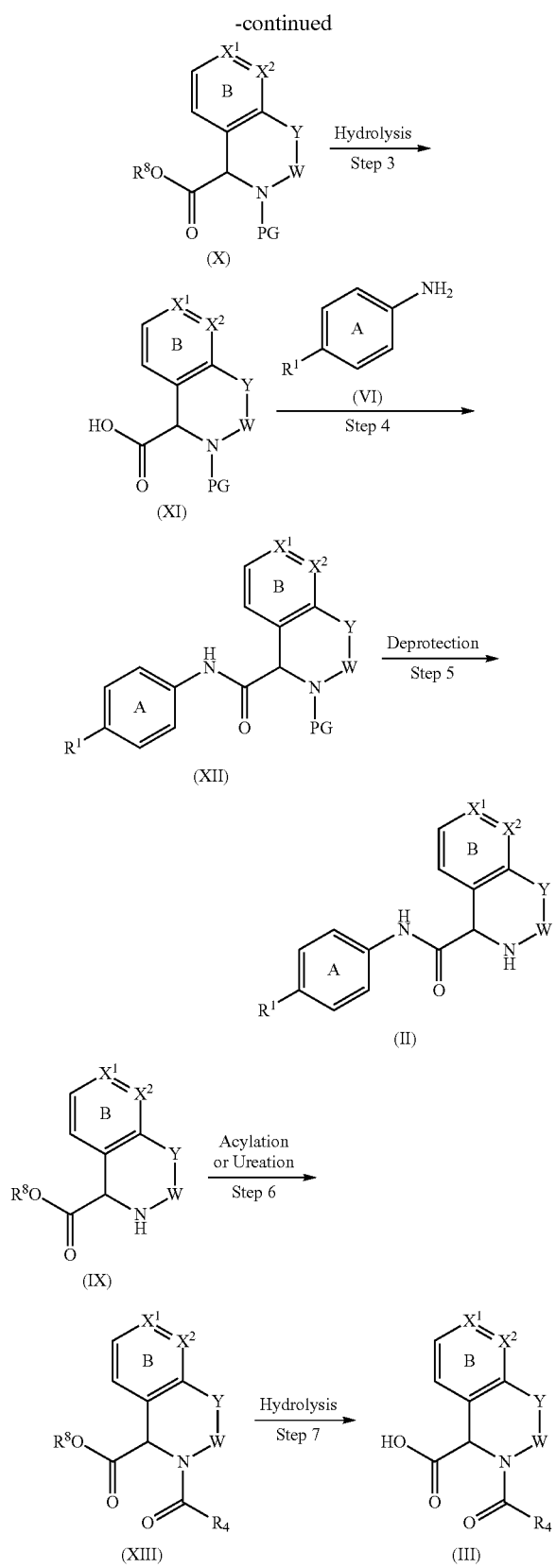

wherein $R^8$ is a hydrocarbon group optionally having substituent(s), PG is an amino-protecting group, and the other symbols are as defined above.

Examples of the amino-protecting group for PG include a tert-butoxycarbonyl (Boc) group, a benzyl (Bn) group, a 4-methoxybenzyl (PMB) group, a trifluoroacetyl ($CF_3CO$) group and the like.

Compound (II) or a salt thereof of the present invention can be produced according to the following Step 1 to Step 5.

(Step 1)

This step is a step of subjecting compound (VII) or a salt thereof and compound (VIII) or a salt thereof to a cyclization reaction using an acid to produce compound (IX) or a salt thereof.

Examples of the acid to be used for this reaction include mineral acids (hydrochloric acid, hydrobromic acid, sulfuric acid, etc.), Lewis acids (aluminium chloride, tin chloride, zinc bromide, etc.) and the like. Among them, hydrochloric acid, hydrobromic acid and aluminium chloride are preferable. While the amount of the acid to be used varies depending on the kind of the solvent and the other reaction condition, it is generally about 1 mol equivalent or more per 1 mol of compound (VII).

Compound (VII) or a salt thereof and compound (VIII) or a salt thereof to be used for this reaction may be a commercially available product, or can also be produced according to a method known per se or a method analogous thereto.

The amount of compound (VIII) to be used is generally about 1 to 10 mol equivalent, preferably about 1 to 2 mol equivalent, per 1 mol of compound (VII).

This step is performed in a solvent that does not adversely influence the reaction. Examples of the solvent that does not adversely influence the reaction include alcohols (methanol, ethanol, propanol, 2-propanol, butanol, isobutanol, tert-butanol, etc.), aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), esters (ethyl acetate, etc.) and the like.

The reaction temperature is, for example, within about 0 to 200° C., preferably about 25 to 100° C. While the reaction time varies depending on the kind of compound (VII) or a salt thereof, the reaction temperature and the like, it is, for example, about 0.5 to 100 hr, preferably about 0.5 to 24 hr.

(Step 2)

This step is a step of subjecting compound (IX) or a salt thereof to an amino-protecting reaction to produce compound (X) or a salt thereof.

When the amino group is protected by a Boc group, the reaction is carried out by reacting compound (IX) or a salt thereof with di-tert-butyl dicarbonate ($Boc_2O$) in the presence of a base, in a solvent that does not adversely influence the reaction.

Examples of the base to be used in this step include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, alkali metal alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. Among them, sodium hydride and triethylamine are preferable. While the amount of the base to be used varies depending on the kind of the solvent and the other reaction condition, it is generally about 1 to 10 mol equivalent, preferably about 1 to 5 mol equivalent, per 1 mol of compound (IX).

Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), esters (ethyl acetate, etc.), amides (N,N-dimethylformamide, etc.), sulfoxides (dimethyl sulfoxide, etc.), and water and the like. These solvent may be used in a mixture of two or more kinds thereof in an appropriate ratio.

The amount of the $Boc_2O$ to be used in this step is about 1 to 10 mol equivalent, preferably about 1 to 2 mol equivalent, per 1 mol of compound (IX).

The reaction temperature is, for example, within about −10 to 100° C. While the reaction time varies depending on the kind of compound (IX) or a salt thereof, the reaction temperature and the like, it is, for example, about 0.5 to 100 hr, preferably about 0.5 to 24 hr.

When the amino group is protected by a Bn group, the reaction is carried out by reacting compound (IX) or a salt thereof with benzaldehyde in a solvent that does not adversely influence the reaction, and then treating the resulting compound with a reducing agent, or by reacting compound (IX) or a salt thereof with benzyl bromide in the presence of a base, in a solvent that does not adversely influence the reaction.

When compound (IX) or a salt thereof is reacted with benzaldehyde, examples of the solvent that does not adversely influence the reaction include hydrocarbons (heptane, hexane, toluene, xylene, etc.), halogenated hydrocarbons (chloroform, dichloromethane, 1,2-dichloroethane, etc.), ethers (diethyl ether, tetrahydrofuran, 1,4-dioxane, etc.), esters (ethyl acetate, tert-butyl acetate, etc.), alcohols (methanol, ethanol, 2-propanol, etc.), nitriles (acetonitrile, butyronitrile, etc.), amides (N,N-dimethylformamide, N,N-dimethylacetamide, etc.), sulfoxides (dimethyl sulfoxide, etc.), and mixed solvents thereof.

Examples of the reducing agent to be used for this reaction include metal hydrides (e.g., sodium borohydride, lithium borohydride, zinc borohydride, sodium cyanoborohydride, sodium triacetoxyborohydride, lithium cyanoborohydride, diisobutylaluminium hydride, aluminium hydride, lithium aluminium hydride, borane complex (borane-THF complex, catecholborane, etc.) and the like. The amount of the metal hydride to be used is about 1 to about 50 mol per 1 mol of compound (IX).

In this reaction, a catalyst may be added for the progress of the reaction, if necessary. Examples of the catalyst include mineral acids (hydrochloric acid, hydrobromic acid, sulfuric acid, etc.), carboxylic acids (formic acid, acetic acid, propionic acid, trifluoroacetic acid, etc.), sulfonic acids (methanesulfonic acid, p-toluenesulfonic acid, etc.), Lewis acids (aluminium chloride, zinc chloride, zinc bromide, boron trifluoride, titanium chloride, etc.), acetates (sodium acetate, potassium acetate, etc.), molecular sieves (molecular sieves 3A, 4A, 5A, etc.), dehydrating agents (magnesium sulfate, etc.) and the like. The amount of the catalyst to be used is generally about 0.01 to 50 mol equivalent, preferably about 0.1 to 10 mol equivalent, per 1 mol of compound (IX).

The amount of the benzaldehyde to be used is generally about 1 to 10 mol equivalent, preferably about 1 to 2 mol equivalent, per 1 mol of compound (IX).

The reaction temperature is generally about 0° C.-200° C., preferably about 20° C. to 150° C., and the reaction time is generally about 0.5 hr to 48 hr, preferably about 0.5 hr to 24 hr.

When compound (IX) or a salt thereof is reacted with benzyl bromide, examples of the base to be used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, alkali metal alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. Among them, potassium carbonate is preferable. While the amount of the base to be used varies depending on the kind of the solvent and the other reaction condition, it is generally about 1 to 10 mol equivalent, preferably about 1 to 5 mol equivalent, per 1 mol of compound (IX).

The amount of the benzyl bromide to be used is generally about 1 to 10 mol equivalent, preferably about 1 to 2 mol equivalent, per 1 mol of compound (IX).

Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), esters (ethyl acetate, etc.), amides (N,N-dimethylformamide, etc.), sulfoxides (dimethyl sulfoxide, etc.) and the like. Among them, acetonitrile is preferable. These solvent may be used in a mixture of two or more kinds thereof in an appropriate ratio.

The reaction temperature is, for example, within about 0 to 200° C., preferably about 25 to 100° C. While the reaction time varies depending on the kind of compound (IX), the reaction temperature and the like, it is, for example, about 0.5 to 100 hr, preferably about 0.5 to 24 hr.

When the amino group is protected by a PMB group, the reaction is carried out by reacting compound (IX) or a salt thereof with 4-methoxybenzaldehyde in a solvent that does not adversely influence the reaction, and then treating the resulting compound with a reducing agent.

The kind and amount of the solvent, reducing agent, reagent and additive to be used in this step, the reaction temperature and the reaction time are the same as in the reaction of the amino group with a Bn group.

When the amino group is protected by a $CF_3CO$ group, the reaction is carried out by reacting compound (IX) or a salt thereof with trifluoroacetic anhydride in the presence of a base, in a solvent that does not adversely influence the reaction. The kind and amount of the solvent, reducing agent, reagent and additive to be used in this step, the reaction temperature and the reaction time are the same as in the reaction of the amino group with a Bn group.

(Step 3)

This step is a step of subjecting compound (X) or a salt thereof to hydrolysis to convert compound (X) or a salt thereof to compound (XI) or a salt thereof. This reaction can be carried out according to a method known per se, generally in the presence of an acid or a base, in a solvent that does not adversely influence the reaction, if necessary.

Examples of the acid include mineral acids (hydrochloric acid, hydrobromic acid, sulfuric acid, etc.), carboxylic acids (acetic acid, trifluoroacetic acid, trichloroacetic acid, etc.), sulfonic acids (methanesulfonic acid, p-toluenesulfonic acid, etc.), Lewis acids (aluminium chloride, tin chloride, zinc bromide, etc.) and the like. Where necessary, they may be used in a mixture of two or more kinds thereof. While the amount of the acid to be used varies depending on the kind of the solvent and the other reaction condition, it is generally about 0.1 mol equivalent or more per 1 mol of compound (X), The acid may be used as a solvent.

Examples of the base include inorganic bases (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate and the like, alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. Among them, sodium hydroxide is preferable. While the amount of the base to be used varies depending on the kind of the solvent and the other reaction condition, it is generally about 0.1 to 10 mol equivalent, preferably about 1 to 5 mol equivalent, per 1 mol of compound (X).

Examples of the solvent that does not adversely influence the reaction include alcohols (methanol, ethanol, propanol, 2-propanol, butanol, isobutanol, tert-butanol, etc.), hydrocarbons (benzene, toluene, xylene, hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), carboxylic acids (acetic acid, etc.), amides (N,N-dimethylformamide, N,N-dimethylacetamide, etc.), sulfoxides (dimethyl sulfoxide, etc.), water and the like. Among them, ethanol, tetrahydrofuran and water are preferable. These solvent may be used in a mixture of two or more kinds thereof in an appropriate ratio.

The reaction temperature is, for example, within about −50 to 200° C., preferably about 0 to 100° C. While the reaction time varies depending on the kind of compound (X) or a salt thereof, the reaction temperature and the like, it is, for example, about 0.5 to 100 hr, preferably about 0.5 to 24 hr.

(Step 4)

This step is a step of reacting compound (XI) or a salt thereof with compound (VI) or a salt thereof in the presence of a condensing agent to produce compound (XII) or a salt thereof.

This step can be performed in the same manner as in the method described in Step 3 of Method A or Step 1 of Method A.

(Step 5)

This step is a step of subjecting compound (XII) or a salt thereof to a deprotection reaction to produce compound (II) or a salt thereof.

The deprotection reaction can be carried out according to a method known per se (e.g., the method described in "Protective Groups in Organic Synthesis, 3rd Ed", Wiley-Interscience, Inc. (1999) (Theodora W. Greene, Peter G. M. Wuts)).

When PG is a Boc group, the deprotection reaction can be carried out in the presence of an acid, in a solvent that does not adversely influence the reaction.

Examples of the acid include mineral acids (hydrochloric acid, hydrobromic acid, sulfuric acid, etc.), carboxylic acids (acetic acid, trifluoroacetic acid, trichloroacetic acid, etc.), sulfonic acids (methanesulfonic acid, p-toluenesulfonic acid, etc.), Lewis acids (aluminium chloride, tin chloride, zinc bromide, etc.) and the like. Where necessary, they may be used in a mixture of two or more kinds thereof. While the amount of the acid to be used varies depending on the kind of the solvent and the other reaction condition, it is generally about 0.1 mol equivalent or more per 1 mol of compound (XII). The acid may be used as a solvent.

Examples of the solvent that does not adversely influence the reaction include alcohols (methanol, ethanol, propanol, 2-propanol, butanol, isobutanol, tert-butanol, etc.), aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), esters (ethyl acetate, etc.), carboxylic acids (acetic acid, etc.), amides (N,N-dimethylformamide, etc.), sulfoxides (dimethyl sulfoxide, etc.), water and mixed solvents thereof.

The reaction temperature is, for example, within about −50 to 200° C., preferably about 0 to 100° C. While the reaction time varies depending on the kind of compound (XII), the reaction temperature and the like, it is, for example, about 0.5 to 100 hr, preferably about 0.5 to 24 hr.

When PG is a Bn group or a PMB group, the deprotection reaction can be carried out by a catalytic hydrogenation reaction, an oxidation reaction or an acid hydrolysis.

The catalytic hydrogenation reaction can be carried out in the presence of a catalyst under hydrogen atmosphere. Examples of the catalyst include palladiums such as palladium on carbon, palladium hydroxide on carbon, palladium oxide and the like; nickels such as Raney-nickel catalyst and the like; platinums such as platinum oxide, platinum on carbon and the like; rhodiums such as rhodium on carbon and the like, and the like. The amount thereof to be used is generally about 0.001 to 1 mol, preferably about 0.01 to 0.5 mol, per 1 mol of compound (XII).

The catalytic hydrogenation reaction is generally carried out in a solvent inert to the reaction. Examples of the solvent include alcohols such as methanol, ethanol, propanol, butanol and the like; hydrocarbons such as benzene, toluene, xylene and the like; halogenated hydrocarbons such as dichloromethane, chloroform and the like; ethers such as diethyl ether, 1,4-dioxane, tetrahydrofuran and the like; esters such as ethyl acetate and the like; amides such as N,N-dimethylformamide and the like; carboxylic acids such as acetic acid and the like; water and mixtures thereof.

The hydrogen pressure for the reaction is generally about 1 to 50 atm, preferably about 1 to 10 atm. The reaction temperature is generally about 0° C. to 150° C., preferably about 20° C. to 100° C., and the reaction time is generally about 5 min to 72 hr, preferably about 0.5 hr to 40 hr.

Examples of the oxidizing agent to be used for the oxidation reaction include ammonium cerium(IV) nitrate. The amount thereof to be used is about 1 to about 50 mol per 1 mol of compound (XII).

The oxidation reaction is carried out in a solvent that does not adversely influence the reaction. Examples of the solvent include nitriles (e.g., acetonitrile), hydrocarbons (e.g., benzene, toluene, xylene), halogenated hydrocarbons (e.g., dichloromethane, chloroform), ethers (e.g., diethyl ether, 1,4-dioxane, tetrahydrofuran), amides (e.g., N,N-dimethylformamide), water and mixtures thereof.

The reaction temperature is generally about 0° C. to 150° C., preferably about 20° C. to 100° C., and the reaction time is generally about 5 min to 72 hr, preferably about 0.5 hr to 40 hr.

Examples of the acid to be used for the acid hydrolysis include trifluoroacetic acid. The acid may be used as a solvent. The reaction temperature is generally about 0° C. to 150° C., preferably about 0° C. to 30° C., and the reaction time is generally about 5 min to 72 hr, preferably about 0.5 hr to 40 hr.

When PG is a CF$_3$CO group, the deprotection reaction can be carried out in the presence of a base, in a solvent that does not adversely influence the reaction.

Examples of the base include inorganic bases (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate and the like, alkoxides such as sodium methoxide, sodium ethoxide and the like, etc.) and the like. The amount of the base to be used is about 1 to 100 mol equivalent, preferably about 1 to 20 mol equivalent, per 1 mol of compound (XII).

Examples of the solvent that does not adversely influence the reaction include hydrocarbons (benzene, toluene, xylene, hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), amides (N,N-dimethylformamide, N,N-dimethylacetamide, etc.), sulfoxides (dimethyl sulfoxide, etc.), water and the like. These solvent may be used in a mixture of two or more kinds thereof in an appropriate ratio.

The reaction temperature is, for example, within about −50 to 200° C., preferably about 0 to 100° C. While the reaction time varies depending on the kind of compound (XII), the reaction temperature and the like, it is, for example, about 0.5 to 24 hr, preferably about 0.5 to 2 hr.

Compound (III) or a salt thereof of the present invention can be produced according to the following Step 6 and Step 7.

(Step 6)

This step is a step of subjecting compound (IX) or a salt thereof to an acylation reaction with compound (IV) or a salt thereof to convert compound (IX) or a salt thereof to compound (XIII) or a salt thereof, or a step of subjecting compound (IX) or a salt thereof to an ureation reaction with compound (V) or a salt thereof to convert compound (IX) or a salt thereof to compound (XIII) or a salt thereof.

This step can be performed in the same manner as in the method described in Step 1 or Step 2 of Method A.

(Step 7)

This step is a step of subjecting compound (XIII) or a salt thereof to hydrolysis to convert compound (XIII) or a salt thereof to compound (III) or a salt thereof.

This step can be performed in the same manner as in the method described in Step 3 of Method B.

A compound wherein
X$^1$------X$^2$
is CR$^{5a}$=CR$^6$, R$^{5a}$ is a C$_{1-6}$ alkoxy group (e.g., methoxy, ethoxy), and R$^6$ is a hydrogen atom in formula (Ia), which is a raw material compound in Method A, can be produced according to Method C.

[Method C]

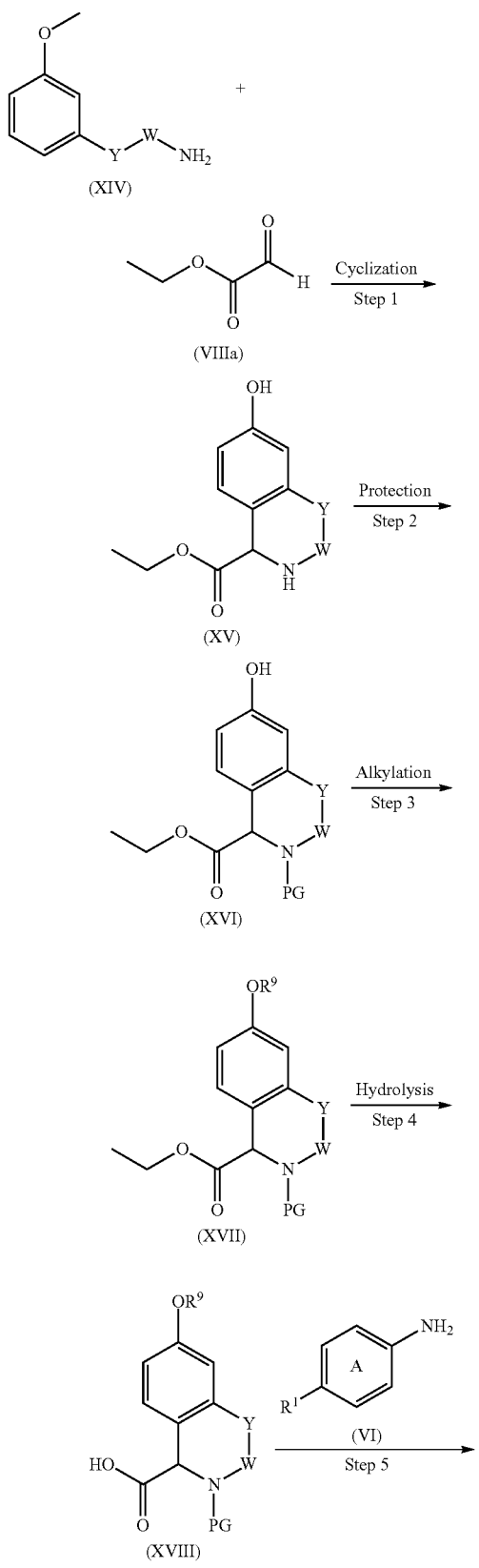

-continued

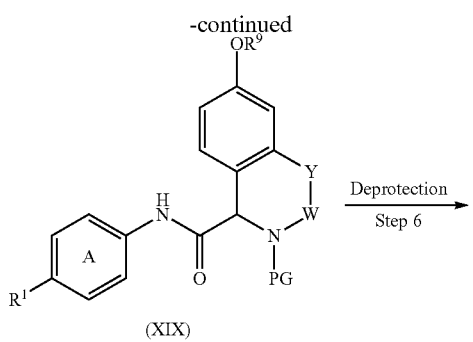

(XIX)

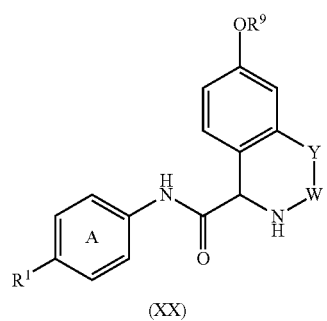

(XX)

wherein $R^9$ is an optionally substituted $C_{1-6}$ alkyl group, and the other symbols are as defined above.

(Step 1)

This step is a step of subjecting compound (XIV) or a salt thereof and compound (VIIIa) to a cyclization reaction using an acid to produce compound (XV) or a salt thereof.

This step can be performed in the same manner as in the method described in Step 1 of Method B.

(Step 2)

This step is a step of subjecting compound (XV) or a salt thereof to an amino-protecting reaction to produce compound (XVI) or a salt thereof.

This step can be performed in the same manner as in the method described in Step 2 of Method B.

(Step 3)

This step is a step of subjecting compound (XVI) or a salt thereof to an alkylation reaction with a compound represented by the formula:

$$R^9\text{-LG} \quad (XXXV)$$

wherein each symbol is as defined above (hereinafter to be referred to as compound (XXXV)) or a salt thereof in the presence of a base to produce compound (XVII) or a salt thereof.

Compound (XXXV) may be a commercially available product, or can also be produced according to a method known per se or a method analogous thereto.

Examples of the base to be used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, and the like. While the amount of the base to be used varies depending on the kind of the solvent and the other reaction condition, it is generally about 1 to 10 mol equivalent, preferably about 1 to 5 mol equivalent, per 1 mol of compound (XVI).

The amount of compound (XXXV) to be used is generally about 1 to 10 mol equivalent, preferably about 1 to 3 mol equivalent, per 1 mol of compound (XVI).

This step is performed in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), esters (ethyl acetate, etc.), amides (N,N-dimethylformamide, etc.), sulfoxides (dimethyl sulfoxide, etc.) and the like. These solvent may be used in a mixture of two or more kinds thereof in an appropriate ratio.

The reaction temperature is, for example, within about −75 to 200° C., preferably about −10 to 30° C. While the reaction time varies depending on the kind of compound (XVI) or a salt thereof, the reaction temperature and the like, it is, for example, about 0.5 to 100 hr, preferably about 0.5 to 24 hr.

When $R^9O$ of compound (XVII) is $F_2HCO$, sodium 2-chloro-2,2-difluoroacetate can be preferably used as compound (XXXV).

(Step 4)

This step is a step of subjecting compound (XVII) or a salt thereof to hydrolysis to convert compound (XVII) or a salt thereof to compound (XVIII) or a salt thereof.

This step can be performed in the same manner as in the method described in Step 3 of Method B.

(Step 5)

This step is a step of reacting compound (XVIII) or a salt thereof with compound (VI) or a salt thereof in the presence of a condensing agent to produce compound (XIX) or a salt thereof.

This step can be performed in the same manner as in the method described in Step 3 of Method A or Step 1 of Method A.

(Step 6)

This step is a step of subjecting compound (XIX) or a salt thereof to a deprotection reaction to produce compound (XX) or a salt thereof.

This step can be performed in the same manner as in the method described in Step 5 of Method B.

A compound wherein

is $CR^{5b}$=N, and $R^{5b}$ is a $C_{1-6}$ alkoxy group (e.g., methoxy, ethoxy) in formula (Ia), which is a raw material compound in Method A, can be produced according to Method D.

[Method D]
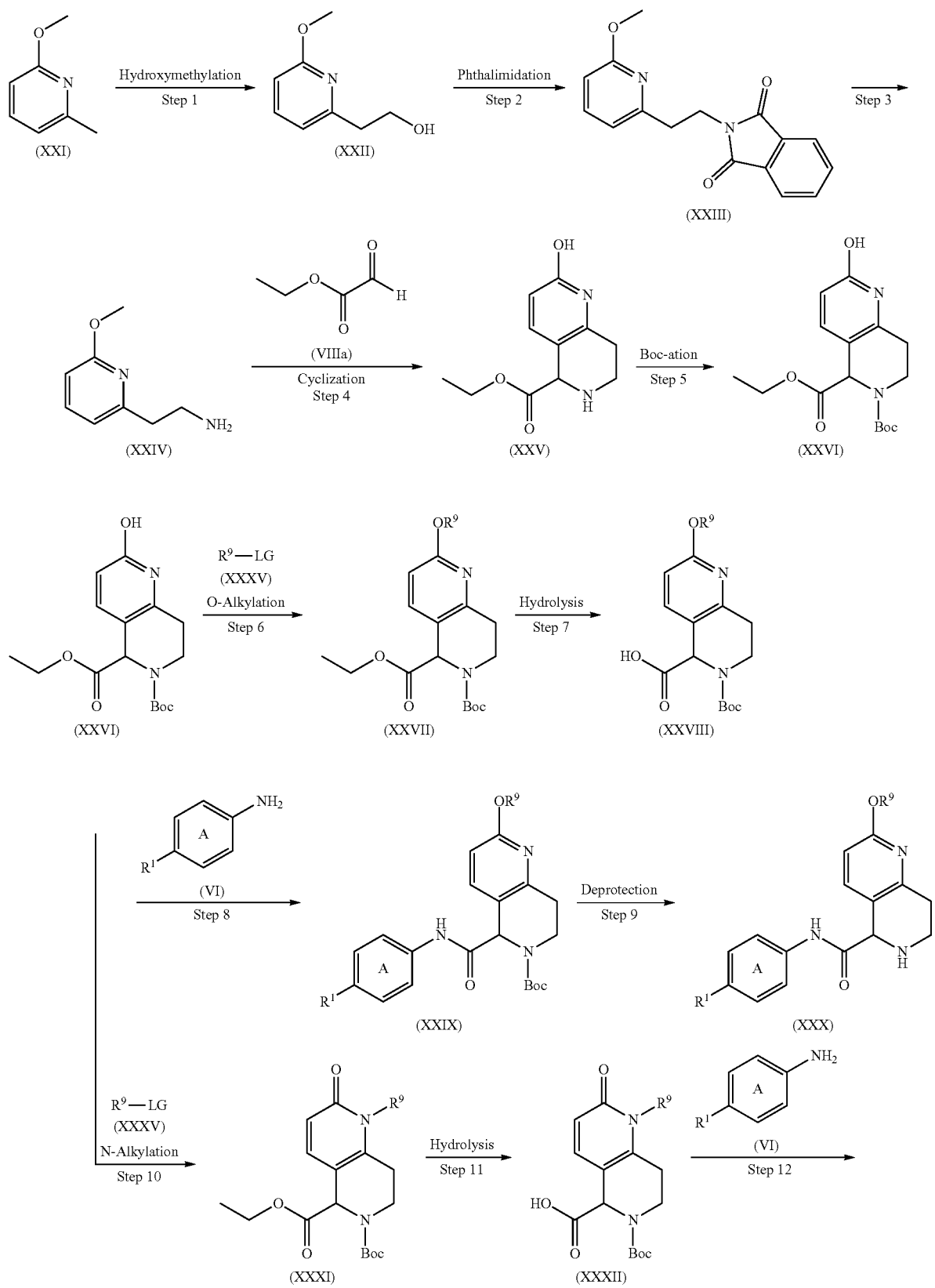

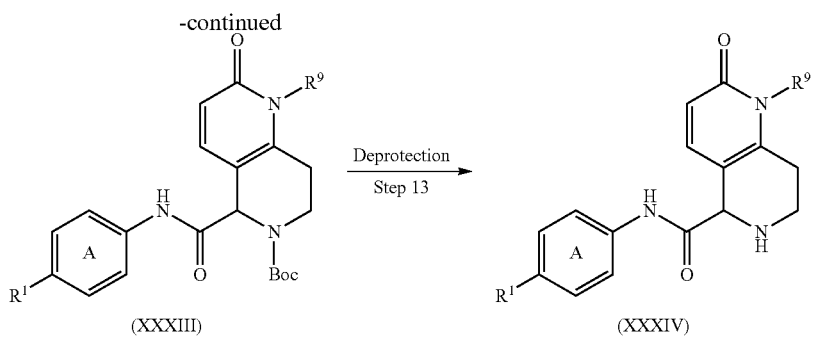

(XXXIII) → (XXXIV)

wherein each symbol is as defined above.

(Step 1)

This step is a step of subjecting compound (XXI) or a salt thereof to a hydroxymethylation reaction to convert compound (XXI) or a salt thereof to compound (XXII) or a salt thereof.

In this reaction, compound (XXII) or a salt thereof can be produced by reacting compound (XXI) or a salt thereof with paraformaldehyde in the presence of a base.

Examples of the base to be used for this reaction include organic lithium reagents (e.g., n-butyllithium, phenyllithium, lithium diisopropylamide), alkali metal hydrides (e.g., sodium hydride, lithium hydride) and the like. While the amount of the base to be used varies depending on the kind of the solvent and the other reaction condition, it is generally about 1 to 10 mol equivalent, preferably about 1 to 2 mol equivalent, per 1 mol of compound (XXI).

The amount of the paraformaldehyde to be used for this reaction is about 1 to 10 mol equivalent, preferably about 1 to 5 mol equivalent, per 1 mol of compound (XXI).

This step is performed in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.) and the like. These solvent may be used in a mixture of two or more kinds thereof in an appropriate ratio.

The reaction temperature is, for example, within about −100 to 50° C., preferably about −78 to 25° C., and the reaction time is, for example, about 0.5 to 100 hr, preferably about 0.5 to 24 hr.

(Step 2)

This step is a step of subjecting compound (XXII) or a salt thereof to a phthalimidation reaction to convert compound (XXII) or a salt thereof to compound (XXIII) or a salt thereof.

In this reaction, compound (XXIII) or a salt thereof can be produced by reacting compound (XXII) or a salt thereof with phthalimide in the presence of an azodicarboxylate reagent and triphenylphosphine.

Examples of the azodicarboxylate reagent to be used for this reaction include diethyl azodicarboxylate (DEAD) and diisopropyl azodicarboxylate (DIAD). While the amount of the azodicarboxylate reagent to be used varies depending on the kind of the solvent and the other reaction condition, it is generally about 1 to 5 mol equivalent, preferably about 1 to 2 mol equivalent, per 1 mol of compound (XXII).

The amount of the triphenylphosphine to be used for this reaction is about 1 to 5 mol equivalent, preferably about 1 to 2 mol equivalent, per 1 mol of compound (XXII).

The amount of the phthalimide to be used for this reaction is about 1 to 5 mol equivalent, preferably about 1 to 2 mol equivalent, per 1 mol of compound (XXII).

This step is performed in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.) and the like. These solvent may be used in a mixture of two or more kinds thereof in an appropriate ratio.

The reaction temperature is, for example, within about −50 to 50° C., preferably about 0 to 25° C., and the reaction time is, for example, about 0.5 to 100 hr, preferably about 0.5 to 24 hr.

(Step 3)

This step is a step of reacting compound (XXIII) or a salt thereof with hydrazine to convert to compound (XXIII) or a salt thereof to compound (XXIV) or a salt thereof.

The amount of the hydrazine to be used for this reaction is about 1 to 20 mol equivalent, preferably about 3 to 7 mol equivalent, per 1 mol of compound (XXIII).

This step is performed in a solvent that does not adversely influence the reaction. Examples of the solvent that does not adversely influence the reaction include alcohols (methanol, ethanol, propanol, 2-propanol, butanol, isobutanol, tert-butanol, etc.), water, nitriles (acetonitrile, etc.), amides (N,N-dimethylformamide, N,N-dimethylacetamide, etc.), sulfoxides (dimethyl sulfoxide, etc.), ethers (diethyl ether, diisopropyl ether, tert-butyl methyl ether, tetrahydrofuran, 1,4-dioxane, 1,2-dimethoxyethane, etc.) and the like. These solvent may be used in a mixture of two or more kinds thereof in an appropriate ratio.

The reaction temperature is, for example, within about 0 to 200° C., preferably about 0 to 100° C., and the reaction time is, for example, about 0.5 to 100 hr, preferably about 0.5 to 24 hr.

(Step 4)

This step is a step of subjecting compound (XXIV) or a salt thereof and compound (VIIIa) to a cyclization reaction using an acid to produce compound (XXV) or a salt thereof.

This step can be performed in the same manner as in the method described in Step 1 of Method B.

(Step 5)

This step is a step of subjecting compound (XXV) or a salt thereof to an amino-protecting reaction with a tert-butoxycarbonyl (Boc) group to produce compound (XXVI) or a salt thereof.

This step can be performed in the same manner as in the method described in Step 2 of Method B.
(Step 6)
This step is a step of subjecting compound (XXVI) or a salt thereof to an O-alkylation reaction to produce compound (XXVII) or a salt thereof.

In this reaction, compound (XXVI) or a salt thereof can be produced by reacting compound (XXVI) or a salt thereof with compound (XXXV) in the presence of a base.

Examples of the base to be used for this reaction include silver salts (e.g., silver carbonate, silver nitrate, silver sulfate, silver acetate, silver chloride).

The amount of the silver salt to be used for this reaction is about 1 to 5 mol equivalent, preferably about 1 to 2 mol equivalent, per 1 mol of compound (XXVI).

This step can be performed in the same manner as in the method described in Step 3 of Method C.
(Step 7)
This step is a step of subjecting compound (XXVII) or a salt thereof to hydrolysis to convert compound (XXVII) or a salt thereof to compound (XXVIII) or a salt thereof.

This step can be performed in the same manner as in the method described in Step 3 of Method B.
(Step 8)
This step is a step of reacting compound (XXVIII) or a salt thereof with compound (VI) or a salt thereof in the presence of a condensing agent to produce compound (XXIX) or a salt thereof.

This step can be performed in the same manner as in the method described in Step 3 of Method A or Step 1 of Method A.
(Step 9)
This step is a step of subjecting compound (XXIX) or a salt thereof to a deprotection reaction to produce compound (XXX) or a salt thereof.

This step can be performed in the same manner as in the method described in Step 5 of Method B.
(Step 10)
This step is a step of subjecting compound (XXVI) or a salt thereof to an N-alkylation reaction to produce compound (XXXI) or a salt thereof.

In this reaction, compound (XXXI) or a salt thereof can be produced by reacting compound (XXVI) or a salt thereof with compound (XXXV) in the presence of a base.

Examples of the base to be used for this reaction include cesium salts (e.g., cesium carbonate, cesium nitrate, cesium sulfate, cesium acetate, cesium chloride).

The amount of the cesium salt to be used for this reaction is about 1 to 5 mol equivalent, preferably about 1 to 2 mol equivalent, per 1 mol of compound (XXVI).

This step can be performed in the same manner as in the method described in Step 3 of Method C.
(Step 11)
This step is a step of subjecting compound (XXXI) or a salt thereof to hydrolysis to convert compound (XXXI) or a salt thereof to compound (XXXII) or a salt thereof.

This step can be performed in the same manner as in the method described in Step 3 of Method B.
(Step 12)
This step is a step of reacting compound (XXXII) or a salt thereof with compound (VI) or a salt thereof in the presence of a condensing agent to produce compound (XXXIII) or a salt thereof.

This step can be performed in the same manner as in the method described in Step 3 of Method A or Step 1 of Method A.
(Step 13)
This step is a step of subjecting compound (XXXIII) or a salt thereof to a deprotection reaction to produce compound (XXXIV) or a salt thereof.

This step can be performed in the same manner as in the method described in Step 5 of Method B.

A compound wherein
$X^1\text{-----}X^2$
is $CR^{5a}=CR^6$, $R^{5a}$ is a $C_{1-6}$ alkoxy group (e.g., methoxy, ethoxy), $R^6$ is a hydrogen atom, Y is an oxygen atom, and W is a methylene group in formula (Ia), which is a raw material compound in Method A, can be produced according to Method E.

[Method E]

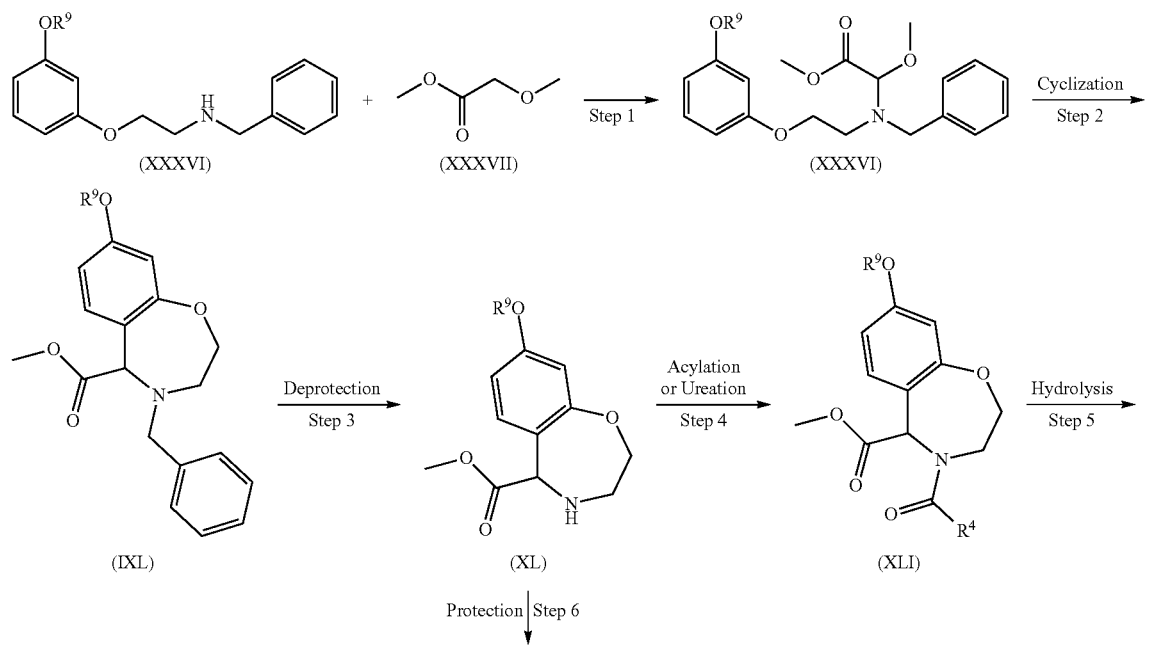

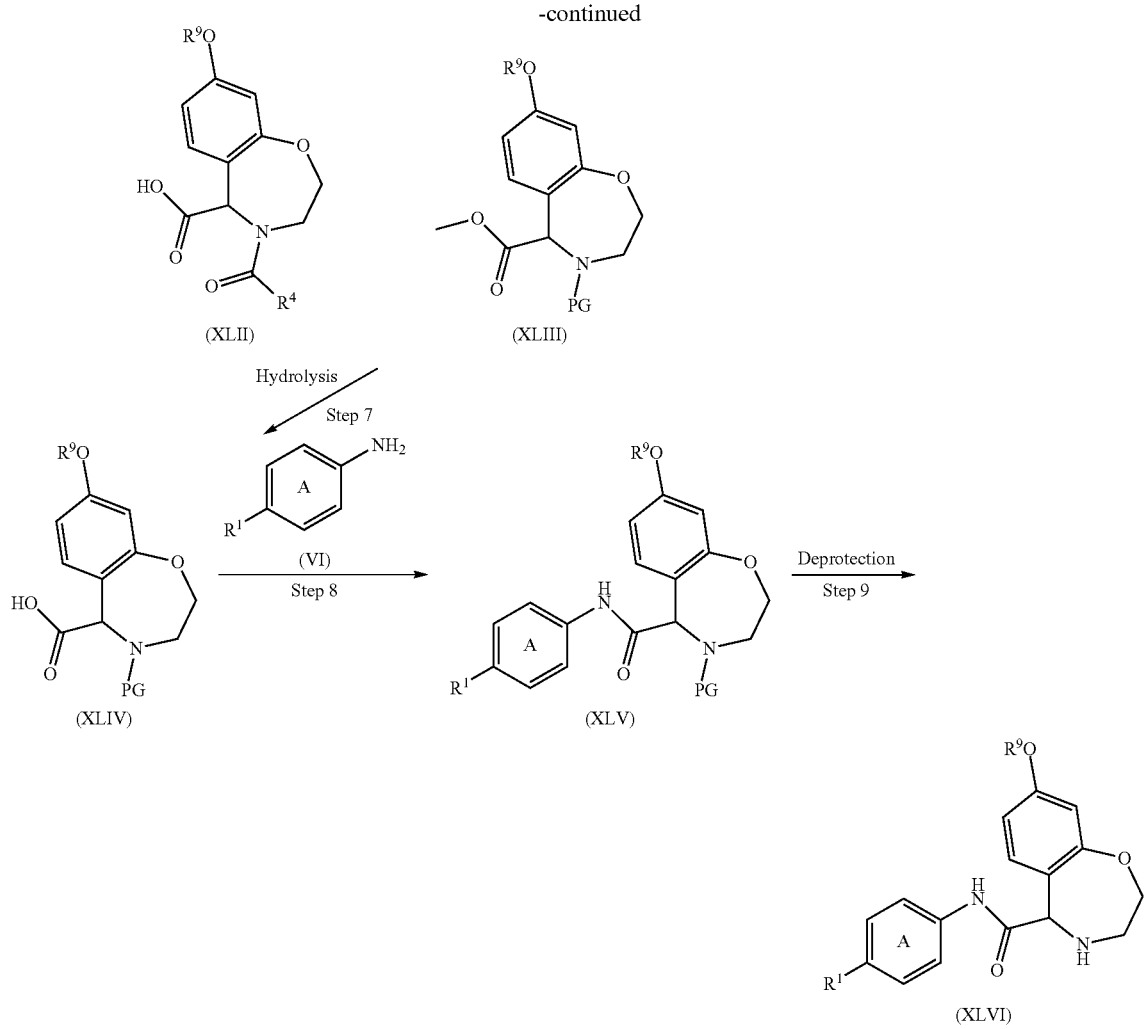

wherein each symbol is as defined above.

(Step 1)

This step is a step of subjecting compound (XXXVI) or a salt thereof to an alkylation reaction to produce compound (XXXVIII) or a salt thereof.

In this reaction, compound (XXXVIII) or a salt thereof can be produced by reacting compound (XXXVII) with N-bromosuccinimide (NBS) in the presence of 2,2'-azobis (isobutyronitrile) (AIBN) (Step 1-1), and then reacting the obtained compound with compound (XXXVI) or a salt thereof in the presence of a base (Step 1-2).

The amount of the AIBN to be used in Step 1-1 is about 0.001 to 0.5 mol equivalent, preferably about 0.01 to 0.1 mol equivalent, per 1 mol of compound (XXXVII).

Compound (XXXVII) may be a commercially available product. The amount thereof to be used is about 1 to 5 mol equivalent, preferably about 1 to 2 mol equivalent, per 1 mol of compound (XXXVI).

The amount of the NBS to be used in Step 1-1 is about 1 to 5 mol equivalent, preferably about 1 to 2 mol equivalent, per 1 mol of compound (XXXVII).

The solvent to be used in Step 1-1 is not particularly limited as long as it does not adversely influence the reaction, and examples thereof include hydrocarbons (benzene, toluene, xylene, etc.) and halogenated hydrocarbons (trifluoromethylbenzene, chloroform, 1,2-dichloroethane, etc.) The reaction temperature is generally about 0 to 200° C., preferably about 25 to 150° C., and the reaction time is generally about 0.5 to 48 hr, preferably about 0.5 to 24 hr.

Examples of the base to be used in Step 1-2 include organic amines (trimethylamine, triethylamine, diisopropylethylamine, N-methylmorpholine, 1,8-diazabicyclo[5,4,0]undec-7-ene, pyridine, N,N-dimethylaniline, etc.). The amount thereof to be used is about 1 to 5 mol equivalent, preferably about 1 to 2 mol equivalent, per 1 mol of compound (XXXVI).

The solvent to be used in Step 1-2 is not particularly limited as long as it does not adversely influence the reaction, and examples thereof include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), aprotic polar solvents (N,N-dimethylformamide, dimethyl sulfoxide, hexamethylphosphoroamide, etc.) and mixtures thereof. The reaction temperature is generally about −10 to 200° C., preferably about 0 to 50° C., and the reaction time is generally about 0.5 to 48 hr, preferably about 0.5 to 24 hr.

(Step 2)

This step is a step of subjecting compound (XXXVIII) or a salt thereof to a cyclization reaction using chlorotrimethylsilane to produce compound (IXL) or a salt thereof.

The amount of the chlorotrimethylsilane to be used for this reaction is about 1 to 5 mol equivalent, preferably about 1 to 2 mol equivalent, per 1 mol of compound (XXXVIII).

The solvent to be used for this reaction is not particularly limited as long as it does not adversely influence the reaction, and examples thereof include hydrocarbons (benzene, toluene, xylene, etc.), halogenated hydrocarbons (chloroform, 1,2-dichloroethane, etc.), nitriles (acetonitrile, etc.) and ethers (dimethoxyethane, tetrahydrofuran). The reaction temperature is generally about 0 to 200° C., preferably about 25 to 100° C., and the reaction time is generally about 0.5 to 48 hr, preferably about 0.5 to 24 hr.

(Step 3)

This step is a step of subjecting compound (IXL) or a salt thereof to a debenzylation reaction to produce compound (XL) or a salt thereof.

The debenzylation reaction can be carried out in the presence of a palladium catalyst (e.g., palladium on carbon, palladium hydroxide, palladium oxide), in a solvent that does not adversely influence the reaction, under hydrogen atmosphere.

The amount of the palladium catalyst to be used is generally about 0.01 to 1 mol equivalent, preferably about 0.05 to 0.2 mol equivalent, per 1 mol of compound (IXL).

Examples of the solvent that does not adversely influence the reaction include alcohols (methanol, ethanol, propanol, 2-propanol, etc.), ethers (diethyl ether, 1,4-dioxane, tetrahydrofuran, etc.), nitriles (acetonitrile, etc.), hydrocarbons (benzene, toluene, etc.), esters (ethyl acetate, etc.) and the like, and they may be mixed as appropriate. The hydrogen pressure for the reaction is generally about 1 to 50 atm, preferably about 1 to 10 atm. The reaction temperature is generally about 0 to 150° C., preferably about 10 to 30° C., and the reaction time is generally about 0.5 to 100 hr, preferably about 0.5 to 60 hr.

(Step 4)

This step is a step of subjecting compound (XL) or a salt thereof to an acylation reaction or an ureation reaction to convert compound (XL) or a salt thereof to compound (XLI) or a salt thereof.

This step can be performed in the same manner as in the method described in Steps 1 and 2 of Method A.

(Step 5)

This step is a step of subjecting compound (XLI) or a salt thereof to hydrolysis to convert compound (XLI) or a salt thereof to compound (XLII) or a salt thereof.

This step can be performed in the same manner as in the method described in Step 3 of Method B.

(Step 6)

This step is a step of subjecting compound (XL) or a salt thereof to an amino-protecting reaction to produce compound (XLIII) or a salt thereof.

This step can be performed in the same manner as in the method described in Step 2 of Method B.

(Step 7)

This step is a step of subjecting compound (XLIII) or a salt thereof to hydrolysis to convert compound (XLIII) or a salt thereof to compound (XLIV) or a salt thereof.

This step can be performed in the same manner as in the method described in Step 3 of Method B.

(Step 8)

This step is a step of reacting compound (XLIV) or a salt thereof with compound (VI) or a salt thereof in the presence of a condensing agent to produce compound (XLV) or a salt thereof.

This step can be performed in the same manner as in the method described in Step 3 of Method A or Step 1 of Method A.

(Step 9)

This step is a step of subjecting compound (XLV) or a salt thereof to a deprotection reaction to produce compound (XLVI) or a salt thereof.

This step can be performed in the same manner as in the method described in Step 5 of Method B.

When compound (VI) is a compound represented by the formula:

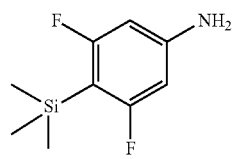

(hereinafter to be referred to as compound (XLVII)) or a salt thereof, the compound can be produced according to Method F.

[Method F]

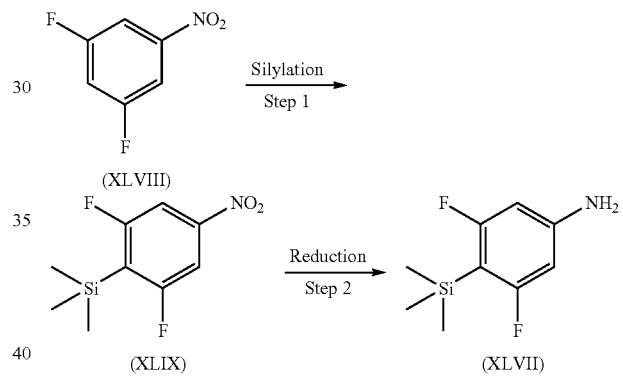

(Step 1)

This step is a step of reacting compound (XLVIII) with a silylating agent in the presence of or without a transition metal catalyst to produce compound (XLIX).

Compound (XLVIII) may be a commercially available product.

Examples of the transition metal catalyst to be used for this reaction include palladium catalysts (palladium acetate, palladium chloride, tetrakistriphenylphosphinepalladium, etc.), nickel catalysts (nickel chloride, etc.) and the like. Where necessary, a ligand (triphenylphosphine, tri-tert-butylphosphine, S-Phos, BINAP, etc.) and a base (e.g., organic amines (trimethylamine, triethylamine, diisopropylamine, N-methylmorpholine, 1,8-diazabicyclo[5,4,0]undec-7-ene, pyridine, N,N-dimethylaniline, etc.), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide, etc.), metal hydrides (potassium hydride, sodium hydride, etc.), alkali metal alkoxides (sodium methoxide, sodium ethoxide, sodium tert-butoxide, potassium tert-butoxide, etc.), alkali disilazides (lithium disilazide, sodium disilazide, potassium disilazide, etc.)) may be added, or a metal oxide (copper oxide, silver oxide, etc.) and the like my be used as a co-catalyst. The amount of the catalyst to be used is about 0.0001 to 1 mol equivalent, preferably about 0.01 to 0.5 mol equivalent, per 1 mol of compound (XLVIII). The amount of the ligand to be used is about 0.0001 to 4 mol equivalent, preferably about 0.01 to 2 mol equivalent, per 1 mol of compound (XLVIII). The amount of the base to be used is about 1 to 10 mol equivalent, preferably about 1 to 2 mol equivalent, per 1 mol of compound (XLVIII). The amount of the co-catalyst to be used is about 0.0001 to 4 mol equivalent, preferably about 0.01 to 2 mol equivalent, per 1 mol of compound (XLVIII).

Examples of the silylating agent include 1,1,1,2,2,2-hexamethyldisilane and chlorotrimethylsilane.

The solvent to be used is not particularly limited as long as it does not adversely influence the reaction, and examples thereof include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), alcohols (methanol, ethanol, etc.), aprotic polar solvents (N,N-dimethylformamide, dimethyl sulfoxide, hexamethylphosphoroamide, etc.), water and mixtures thereof. The reaction temperature is generally about −100 to 200° C., preferably about −80 to 150° C., and the reaction time is generally about 0.5 to 48 hr, preferably about 0.5 to 24 hr. The reaction may be carried out under microwave irradiation, if necessary.

(Step 2)

This step is a step of subjecting compound (XLIX) to a reduction reaction using a transition metal catalyst to produce compound (XLVII).

Examples of the transition metal catalyst to be used for this reaction include palladiums (palladium on carbon, palladium hydroxide, palladium oxide, etc.), nickels (Raney nickel, etc.), platinums (platinum oxide, platinum on carbon, etc.), rhodiums (rhodium acetate, rhodium on carbon, etc.) and the like. The amount thereof to be used is, for example, about 0.001 to 1 equivalent, preferably about 0.01 to 0.5 equivalent, per 1 mol of compound (XLIX). The catalytic hydrogenation reaction is generally carried out in a solvent inert to the reaction. Examples of the solvent include alcohols (methanol, ethanol, propanol, butanol, etc.), hydrocarbons (benzene, toluene, xylene, etc.), halogenated hydrocarbons (dichloromethane, chloroform, etc.), ethers (diethyl ether, 1,4-dioxane, tetrahydrofuran, etc.), esters (ethyl acetate, etc.), amides (N,N-dimethylformamide, etc.), carboxylic acids (acetic acid, etc.), water and mixtures thereof. The hydrogen pressure for the reaction is generally about 1 to 50 atm, preferably about 1 to 10 atm. The reaction temperature is generally about 0 to 150° C., preferably about 20 to 100° C., and the reaction time is generally about 5 min to 72 hr, preferably about 0.5 to 40 hr.

When compound (VI) is a compound represented by the formula:

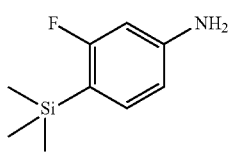

(hereinafter to be referred to as compound (L)) or a salt thereof, the compound can be produced according to Method G.

[Method G]

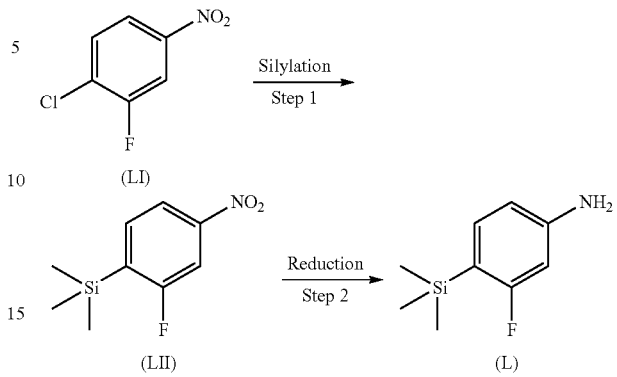

(Step 1)

This step is a step of reacting compound (LI) with a silylating agent in the presence of a transition metal catalyst to produce compound (LII).

Compound (LI) may be a commercially available product.

This step can be performed in the same manner as in the method described in Step 1 of Method F.

(Step 2)

This step is a step of subjecting compound (LII) to a reduction reaction using a transition metal catalyst to produce compound (L).

This step can be performed in the same manner as in the method described in Step 2 of Method F.

When compound (X) is a compound represented by the formula:

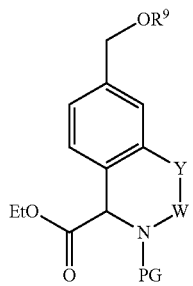

wherein each symbol is as defined above (hereinafter to be referred to as compound (LIII)) or a salt thereof, the compound can be produced according to Method H.

[Method H]

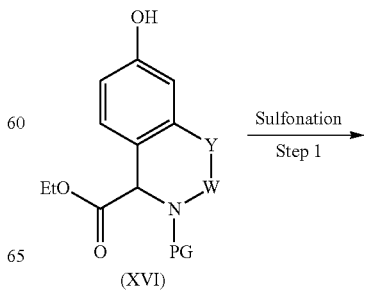

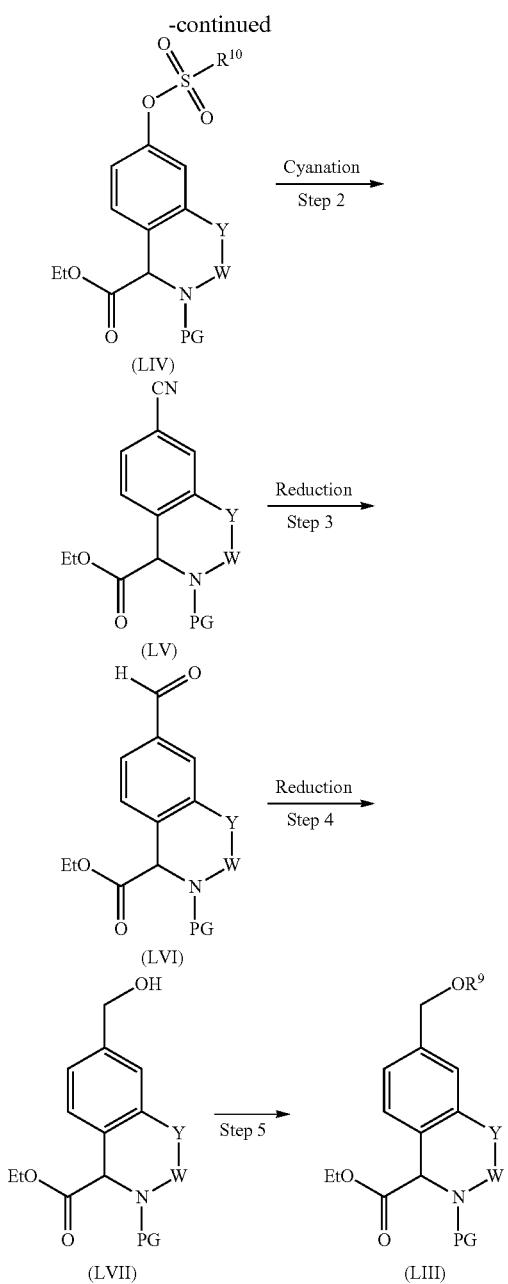

wherein $R^{10}$ is a trifluoromethyl group or a p-tolyl group, and the other symbols are as defined above.

(Step 1)

This step is a step of subjecting compound (XVI) or a salt thereof to a sulfonation reaction to produce compound (LIV) or a salt thereof.

Compound (XVI) may be a commercially available product, or can be produced according to the above-mentioned Method B, a method known per se or a method analogous thereto.

This reaction can be carried out in the presence of a base and a sulfonating agent.

Examples of the base to be used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, etc.), organic bases (amines such as trimethylamine, triethylamine, diisopropylethylamine, 1,8-diazabicyclo[5,4,0]undec-7-ene and the like, cyclic amines such as pyridine, 4-dimethylaminopyridine and the like, etc.) and the like. While the amount of the base to be used varies depending on the kind of the solvent and the other reaction condition, it is generally about 1 to 10 mol equivalent, preferably about 1 to 5 mol equivalent, per 1 mol of compound (XVI).

Examples of the sulfonating agent to be used for this reaction include sulfonyl chlorides (e.g., trifluoromethanesulfonyl chloride, p-tosyl chloride), sulfonic anhydrides (e.g., trifluoromethanesulfonic anhydride, p-toluenesulfonic anhydride), sulfonimides (e.g., N-phenylbis(trifluoromethanesulfonimide), N-(5-chloro-2-pyridyl)triflimide) and the like. While the amount of the sulfonating agent to be used varies depending on the kind of the solvent and the other reaction condition, it is generally about 1 to 10 mol equivalent, preferably about 1 to 5 mol equivalent, per 1 mol of compound (XVI).

This step is performed in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), esters (ethyl acetate, etc.), amides (N,N-dimethylformamide, etc.), sulfoxides (dimethyl sulfoxide, etc.) and the like. These solvent may be used in a mixture of two or more kinds thereof in an appropriate ratio.

The reaction temperature is, for example, within about −10 to 100° C. While the reaction time varies depending on the kind of compound (XVI) or a salt thereof, the reaction temperature and the like, it is, for example, about 0.5 to 100 hr, preferably about 0.5 to 24 hr.

(Step 2)

This step is a step of subjecting compound (LIV) or a salt thereof to a cyanation reaction to produce compound (LV) or a salt thereof.

The this reaction can be carried out using a cyanating agent in the presence of a transition metal catalyst, in a solvent that does not adversely influence the reaction.

Examples of the transition metal catalyst to be used for this reaction include palladium catalysts (palladium acetate, palladium chloride, tetrakistriphenylphosphinepalladium, etc.), nickel catalysts (nickel chloride, etc.) and the like. Where necessary, a ligand (triphenylphosphine, tri-tert-butylphosphine, S-Phos, BINAP, etc.) can be used. The amount of the transition metal catalyst to be used varies depending on the kind of the solvent and the other reaction condition, it is generally about 0.001 to 1 mol equivalent, preferably about 0.1 to 0.5 mol equivalent, per 1 mol of compound (LIV). The amount of the ligand to be used is about 0.001 to 1 mol equivalent per 1 mol of compound (LIV).

Examples of the cyanating agent to be used for this reaction include zinc cyanide, copper cyanide and the like. The amount thereof to be used varies depending on the kind of the solvent and the other reaction condition, it is generally about 0.5 to 10 mol equivalent, preferably about 0.5 to 2 mol equivalent, per 1 mol of compound (LIV).

Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), esters (ethyl acetate, etc.), amides (N,N-dimethylformamide, etc.), sulfoxides (dimethyl sulfoxide, etc.) and the like. These solvent may be used in a mixture of two or more kinds thereof in an appropriate ratio.

The reaction temperature is, for example, within about −10 to 200° C. While the reaction time varies depending on the kind of compound (LIV) or a salt thereof, the reaction temperature and the like, it is, for example, about 0.5 to 100 hr, preferably about 0.5 to 24 hr. Where necessary, the reaction may be carried out under microwave irradiation.
(Step 3)

This step is a step of subjecting compound (LV) or a salt thereof to a reduction reaction to produce compound (LVI) or a salt thereof.

The reduction reaction can be carried out in the presence of a Raney-nickel catalyst, under hydrogen atmosphere or using a hydrogen donor.

The amount of the Raney-nickel catalyst to be used is generally about 0.001 to 10 mol, preferably about 0.01 to 2 mol, per 1 mol of compound (LV).

The hydrogen pressure for the reaction is generally about 1 to 50 atm, preferably about 1 to 10 atm.

Examples of the hydrogen donor include sodium hypophosphite. The amount thereof to be used is generally about 1 to 100 mol, preferably about 1 to 20 mol, per 1 mol of compound (LV).

This reaction is carried out in a solvent inert to the reaction. Examples of the solvent include alcohols such as methanol, ethanol, propanol, butanol and the like; hydrocarbons such as benzene, toluene, xylene and the like; halogenated hydrocarbons such as dichloromethane, chloroform and the like; ethers such as diethyl ether, 1,4-dioxane, tetrahydrofuran and the like; esters such as ethyl acetate and the like; amides such as N,N-dimethylformamide and the like; carboxylic acids such as acetic acid and the like; bases such as pyridine, triethylamine and the like; water and mixtures thereof.

The reaction temperature is generally about 0° C. to 150° C., preferably about 20° C. to 100° C., and the reaction time is generally about 5 min to 72 hr, preferably about 0.5 hr to 40 hr.
(Step 4)

This step is a step of treating compound (LVI) or a salt thereof with a reducing agent to produce compound (LVII) or a salt thereof.

Examples of the reducing agent to be used for this reaction include metal hydrides (e.g., sodium borohydride, lithium borohydride, zinc borohydride, sodium cyanoborohydride, sodium triacetoxyborohydride, lithium cyanoborohydride) and the like. The amount of the metal hydride to be used is about 1 to 50 mol per 1 mol of compound (LVI).

This reaction is carried out in a solvent that does not adversely influence the reaction. Examples of the solvent include alcohols such as methanol, ethanol, propanol, butanol and the like; hydrocarbons such as benzene, toluene, xylene and the like; halogenated hydrocarbons such as dichloromethane, chloroform and the like; ethers such as diethyl ether, 1,4-dioxane, tetrahydrofuran and the like; esters such as ethyl acetate and the like; amides such as N,N-dimethylformamide and the like; carboxylic acids such as acetic acid and the like; water and mixtures thereof.

The reaction temperature is, for example, within about −50 to 200° C., preferably about 0 to 50° C. While the reaction time varies depending on the kind of compound (LVI), the reaction temperature and the like, it is, for example, about 0.1 to 100 hr, preferably about 0.1 to 6 hr.
(Step 5)

This step is a step of converting compound (LVII) or a salt thereof to compound (LIII) or a salt thereof.

This step is a step of "reacting compound (LVII) or a salt thereof with compound (XXXV) in the presence of a base to produce compound (LIII) or a salt thereof" or a step of "subjecting compound (LVII) or a salt thereof to a sulfonation reaction to convert compound (LVII) or a salt thereof to a compound represented by the formula:

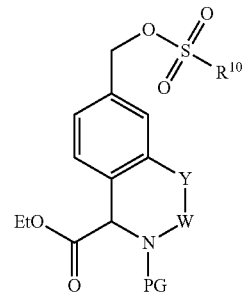

wherein each symbol is as defined above (hereinafter to be referred to as compound (LVIIa)) or a salt thereof, and then reacting the compound with a compound represented by the formula:

$$R^9\text{—OH}$$

wherein the symbol is as defined above (hereinafter to be referred to as compound (XXXVa)) or a salt thereof in the presence of a base to produce compound (LIII) or a salt thereof".

The method of "reacting compound (LVII) or a salt thereof with compound (XXXV) in the presence of a base to produce compound (LIII) or a salt thereof" can be carried out in the same manner as in the method described in Step 3 of Method C.

The sulfonation reaction in the method of "subjecting compound (LVII) or a salt thereof to a sulfonation reaction to convert compound (LVII) or a salt thereof to compound (LVIIa) or a salt thereof, and then reacting compound (LVIIa) or a salt thereof with compound (XXXVa) or a salt thereof in the presence of a base to produce compound (LIII) or a salt thereof" can be carried out in the same manner as in the method described in Step 1 of Method H.

Examples of the base to be used for the reaction of compound (LVIIa) or a salt thereof with compound (XXXVa) or a salt thereof in the presence of a base include organic amines (trimethylamine, triethylamine, diisopropylamine, N-methylmorpholine, 1,8-diazabicyclo[5,4,0]undec-7-ene, pyridine, N,N-dimethylaniline, etc.), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide, lithium acetate, etc.), metal hydrides (potassium hydride, sodium hydride, etc.) and the like. The amount of the base to be used is about 1 to 10 mol equivalent per 1 mol of compound (LVIIa).

This step is performed in a solvent that does not adversely influence the reaction. Examples of the solvent that does not adversely influence the reaction include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), aprotic polar solvents (N,N-dimethylformamide, dimethyl sulfoxide, hexamethylphosphoroamide, etc.) and mixtures thereof. Compound (XXXVa) itself may be used as a solvent. The reaction temperature is generally about −100 to 200° C., preferably about −20 to 100° C., and the reaction time is generally about 0.5 to 48 hr, preferably about 0.5 to 24 hr.

When compound (VI) is a compound represented by the formula:

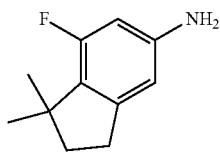

(hereinafter to be referred to as compound (LVIII)) or a salt thereof, the compound can be produced according to Method I.

[Method I]

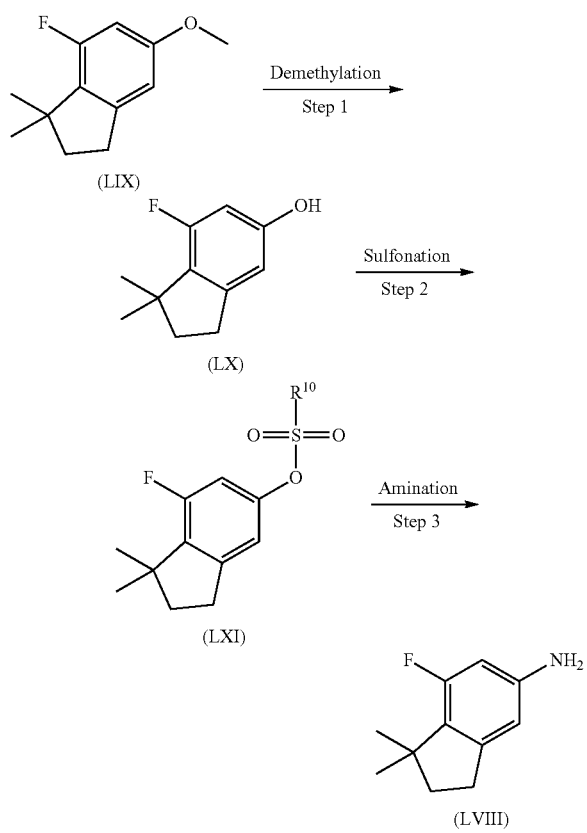

wherein the symbol is as defined above.

(Step 1)

This step is a step of subjecting compound (LIX) to a demethylation reaction to produce compound (LX).

Compound (LIX) may be a commercially available product, or can also be produced according to a method known per se or a method analogous thereto.

The demethylation reaction can be carried out according to a method known per se (e.g., the method described in "Protective Groups in Organic Synthesis, 3rd Ed", Wiley-Interscience, Inc. (1999) (Theodora W. Greene, Peter G. M. Wuts)). For example, compound (LX) can be produced by treating compound (LIX) with aluminium chloride in the presence of 1-dodecanethiol.

The amount of the 1-dodecanethiol to be used is about 1 to 10 mol equivalent per 1 mol of compound (LIX). The amount of the aluminium chloride to be used is about 1 to 10 mol equivalent per 1 mol of compound (LIX).

This reaction is carried out in a solvent that does not adversely influence the reaction. Examples of the solvent include hydrocarbons such as benzene, toluene, xylene and the like; halogenated hydrocarbons such as dichloromethane, chloroform and the like; ethers such as diethyl ether, 1,4-dioxane, tetrahydrofuran and the like; and the like.

The reaction temperature is, for example, within about −50 to 100° C., preferably about −10 to 50° C. While the reaction time varies depending on the reaction temperature and the like, it is, for example, about 0.1 to 100 hr, preferably about 0.1 to 6 hr.

(Step 2)

This step is a step of subjecting compound (LX) or a salt thereof to a sulfonation reaction to produce compound (LXI) or a salt thereof.

This step can be performed in the same manner as in the method described in Step 1 of Method H.

(Step 3)

This step is a step of reacting compound (LXI) with an aminating agent in the presence of a transition metal catalyst and a base, and then treating the resulting compound with an acid or a combination of hydroxyamine hydrochloride and sodium acetate to produce compound (LVIII).

Examples of the transition metal catalyst to be used for this reaction include palladium catalysts (palladium acetate, palladium chloride, tetrakistriphenylphosphinepalladium, tris(dibenzylideneacetone)dipalladium (0), etc.), nickel catalysts (nickel chloride, etc.) and the like. Where necessary, a ligand (triphenylphosphine, tri-tert-butylphosphine, S-Phos, BINAP, 2'-(di-tert-butylphosphino)-N,N-dimethyl-[1,1'-biphenyl]-2-amine, XANTPHOS, etc.) or a base (e.g., organic amines (trimethylamine, triethylamine, diisopropylamine, N-methylmorpholine, 1,8-diazabicyclo[5,4,0]undec-7-ene, pyridine, N,N-dimethylaniline, etc.), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide, lithium acetate, etc.), metal hydrides (potassium hydride, sodium hydride, etc.), alkali metal alkoxides (sodium methoxide, sodium ethoxide, sodium tert-butoxide, potassium tert-butoxide, etc.) and alkali disilazides (lithium disilazide, sodium disilazide, potassium disilazide, etc.)) may be added. A metal oxide (copper oxide, silver oxide, etc.) and the like may be used as a co-catalyst. The amount of the catalyst to be used is about 0.0001 to 1 mol equivalent, preferably about 0.01 to 0.5 mol equivalent, per 1 mol of compound (LXI). The amount of the ligand to be used is about 0.0001 to 4 mol equivalent, preferably about 0.01 to 2 mol equivalent, per 1 mol of compound (LXI). The amount of the base to be used is about 1 to 10 mol equivalent, preferably about 1 to 2 mol equivalent, per 1 mol of compound (LXI). The amount of the co-catalyst to be used is about 0.0001 to 4 mol equivalent, preferably about 0.01 to 2 mol equivalent, per 1 mol of compound (LXI).

This step is performed in a solvent that does not adversely influence the reaction. Examples of the solvent that does not adversely influence the reaction include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), alcohols (methanol, ethanol, etc.), aprotic polar solvents (N,N-dimethylformamide, dimethyl sulfoxide, hexamethylphosphoroamide, etc.), water and mixtures thereof. The reaction temperature is generally about −100 to 200° C., preferably about −80 to 150° C., and the reaction time is generally about 0.5 to 48 hr, preferably about 0.5 to 24 hr.

Preferable examples of the aminating agent to be used include diphenylmethanimine. The amount of the aminating agent to be used is about 1 to 5 mol equivalent, preferably about 1 to 2 mol equivalent, per 1 mol of compound (LXI).

Examples of the acid to be used include mineral acids (hydrochloric acid, hydrobromic acid, sulfuric acid, etc.). While the amount of the acid to be used varies depending on the kind of the solvent and the other reaction condition, it is generally about 0.1 mol equivalent or more per 1 mol of compound (LXI). Preferable examples of the solvent to be used include THF and water. The reaction temperature is about −20 to 100° C., preferably about 0 to 30° C., and the reaction time is generally about 1 to 100 hr, preferably about 1 to 72 hr.

The amount of the hydroxyamine hydrochloride and sodium acetate to be used is about 1 to 5 mol equivalent, preferably about 1 to 2 mol equivalent, per 1 mol of compound (LXI), respectively.

Preferable examples of the solvent to be used for the treatment with hydroxyamine hydrochloride and sodium acetate include methanol. The reaction temperature is about −20 to 100° C., preferably about 0 to 30° C., and the reaction time is generally about 1 to 100 hr, preferably about 1 to 72 hr.

When compound (VI) is a compound represented by the formula:

(hereinafter to be referred to as compound (LXII)) or a salt thereof, the compound can be produced according to Method J.

[Method J]

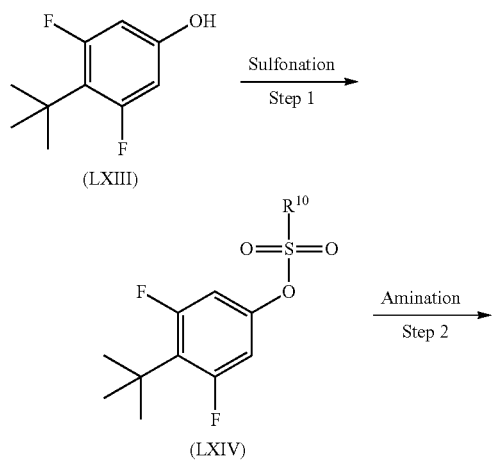

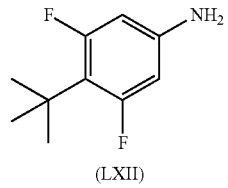

(LXII)

wherein the symbol is as defined above.

(Step 1)

This step is a step of subjecting compound (LXIII) or a salt thereof to a sulfonation reaction to produce compound (LXIV) or a salt thereof.

Compound (LXIII) can be produced according to a method known per se or a method analogous thereto.

This step can be performed in the same manner as in the method described in Step 2 of Method H.

(Step 2)

This step is a step of reacting compound (LXIV) with an aminating agent in the presence of a transition metal catalyst and a base, and then treating the resulting compound with an acid or a combination of hydroxyamine hydrochloride and sodium acetate to produce compound (LXII).

This step can be performed in the same manner as in the method described in Step 3 of Method I.

When compound (VI) is a compound represented by the formula:

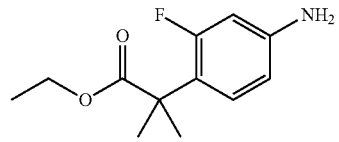 [SMILES: CCOC(=O)C(C)(C)c1ccc(N)cc1F]

(hereinafter to be referred to as compound (LXV)) or a salt thereof, the compound can be produced according to Method K.

[Method K]

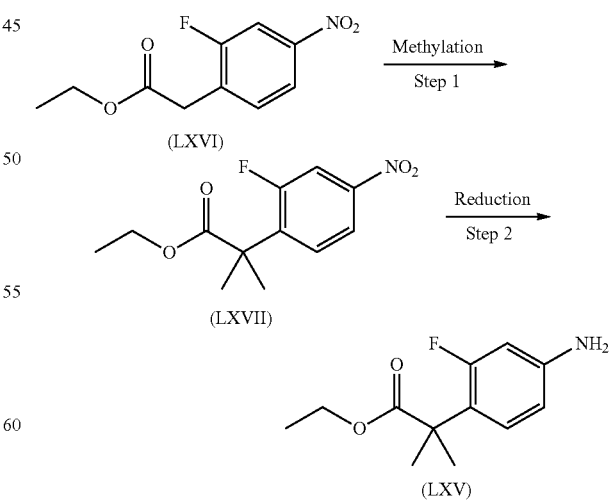

(Step 1)

This step is a step of subjecting compound (LXVI) to methylation to produce compound (LXVII).

In this reaction, compound (LXVII) can be produced by reacting compound (LXVI) with iodomethane in the presence of a base.

Compound (LXVI) may be a commercially available product, or can also be produced according to a method known per se or a method analogous thereto.

Examples of the base to be used for this reaction include alkali metal hydrides (e.g., sodium hydride, lithium hydride). While the amount of the base to be used varies depending on the kind of the solvent and the other reaction condition, it is generally about 2 to 10 mol equivalent, preferably about 2 to 5 mol equivalent, per 1 mol of compound (LXVI).

The amount of the iodomethane to be used is generally about 2 to 10 mol equivalent, preferably about 2 to 3 mol equivalent, per 1 mol of compound (LXVI).

This step is performed in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), nitriles (acetonitrile, etc.), esters (ethyl acetate, etc.), amides (N,N-dimethylformamide, etc.), sulfoxides (dimethyl sulfoxide, etc.) and the like. These solvent may be used in a mixture of two or more kinds thereof in an appropriate ratio.

The reaction temperature is, for example, within about −75 to 100° C., preferably about −10 to 30° C. While the reaction time varies depending on the reaction temperature and the like, it is, for example, about 0.5 to 100 hr, preferably about 0.5 to 24 hr.

(Step 2)

This step is a step of subjecting compound (LXVII) to a reduction reaction using a transition metal catalyst to produce compound (LXV).

This step can be performed in the same manner as in the method described in Step 2 of Method F.

When compound (VI) is a compound represented by the formula:

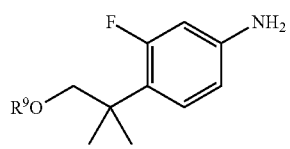

wherein the symbol is as defined above (hereinafter to be referred to as compound (LXVIII)) or a salt thereof, the compound can be produced according to Method L.

[Method L]

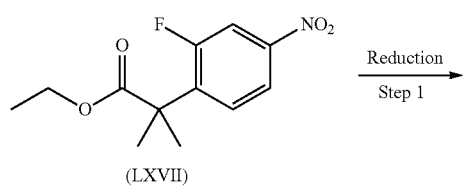

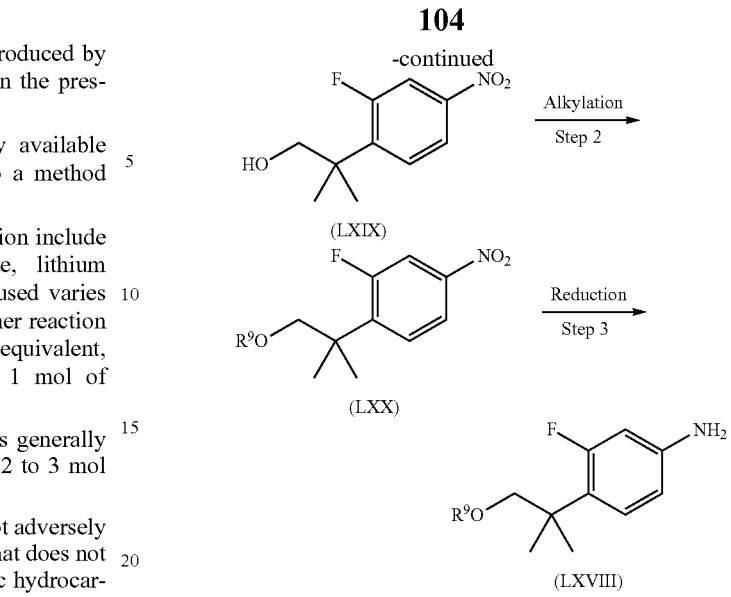

wherein the symbol is as defined above.

(Step 1)

This step is a step of treating compound (LXVII) with a reducing agent to produce compound (LXIX).

Compound (LXVII) may be a commercially available product, or can also be produced according to a method known per se or a method analogous thereto.

Examples of the reducing agent to be used for this reaction include metal hydrides (e.g., lithium borohydride, diisobutylaluminium hydride, aluminium hydride, lithium aluminium hydride). The amount of the metal hydride to be used is about 0.5 to 50 mol per 1 mol of compound (LXVII).

This step is performed in a solvent that does not adversely influence the reaction, and examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.) and the like. These solvent may be used in a mixture of two or more kinds thereof in an appropriate ratio.

The reaction temperature is generally about −20 to 100° C., preferably about 0 to 30° C., and the reaction time is generally about 1 to 100 hr, preferably about 1 to 72 hr.

(Step 2)

This step is a step of subjecting compound (LXIX) to an alkylation reaction with compound (XXXV) in the presence of a base to produce compound (LXX) or a salt thereof.

This step can be performed in the same manner as in the method described in Step 3 of Method C.

(Step 3)

This step is a step of subjecting compound (LXX) to a reduction reaction using a transition metal catalyst to produce compound (LXVIII).

This step can be performed in the same manner as in the method described in Step 2 of Method F.

When compound (VI) is a compound represented by the formula:

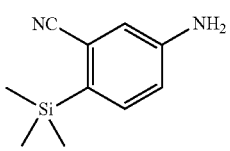

(hereinafter to be referred to as compound (LXXI)) or a salt thereof, the compound can be produced according to Method M.

[Method M]

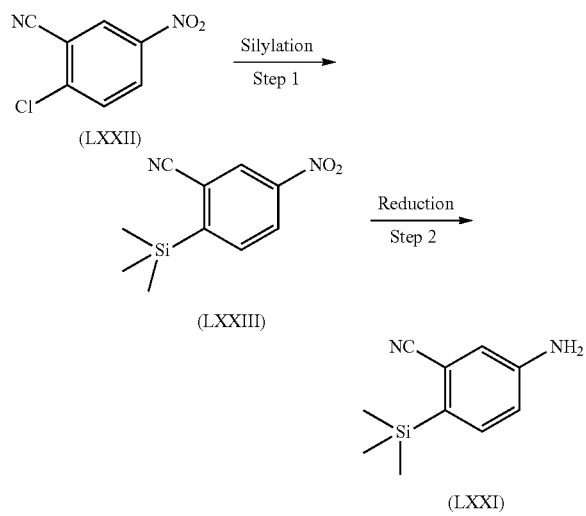

(Step 1)

This step is a step of reacting compound (LXXII) with a silylating agent in the presence of a transition metal catalyst to produce compound (LXXIII).

Compound (LXXII) may be a commercially available product.

This step can be performed in the same manner as in the method described in Step 1 of Method G.

(Step 2)

This step is a step of subjecting compound (LXXIII) to a reduction reaction using a transition metal catalyst to produce compound (LXXI).

This step can be performed in the same manner as in the method described in Step 2 of Method G.

When compound (VI) is a compound represented by the formula:

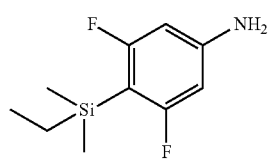

(hereinafter to be referred to as compound (LXXIV)) or a salt thereof, the compound can be produced according to Method N.

[Method N]

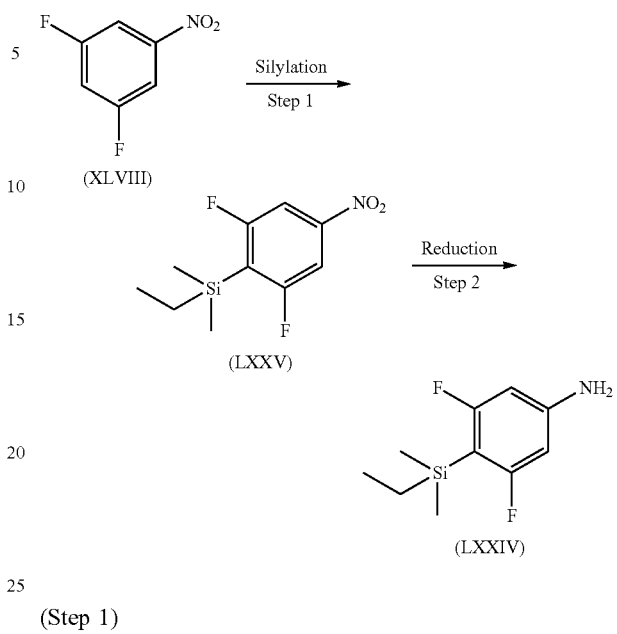

(Step 1)

This step is a step of reacting compound (XLVIII) with a silylating agent in the presence of or without a transition metal catalyst to produce compound (LXXV).

Compound (XLVIII) may be a commercially available product.

This step can be performed in the same manner as in the method described in Step 1 of Method F.

Examples of the silylating agent include chloro(ethyl)dimethylsilane.

(Step 2)

This step is a step of subjecting compound (LXXV) to a reduction reaction using a transition metal catalyst to produce compound (LXXIV).

This step can be performed in the same manner as in the method described in Step 2 of Method G.

When compound (VI) is a compound represented by the formula:

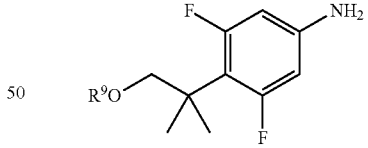

(hereinafter to be referred to as compound (LXXVI)) or a salt thereof, the compound can be produced according to Method O.

[Method O]

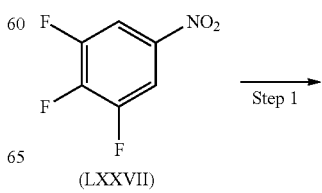

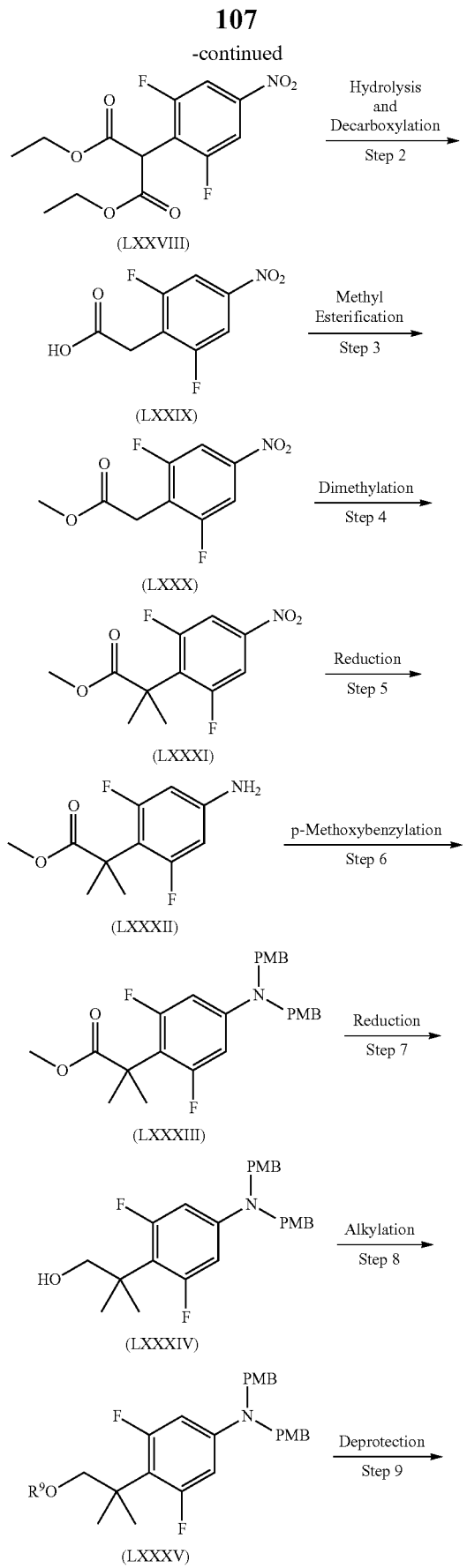

wherein PMB is a 4-methoxybenzyl group, and the other symbols are as defined above.

(Step 1)

This step is a step of subjecting compound (LXXVII) to a coupling reaction with diethyl malonate in the presence of a base to convert compound (LXXVII) to compound (LXXVIII).

Compound (LXXVII) may be a commercially available product.

Examples of the base to be used for this reaction include organic lithium reagents (e.g., n-butyllithium, phenyllithium, lithium diisopropylamide), alkali metal hydrides (e.g., sodium hydride, lithium hydride) and the like. While the amount of the base to be used varies depending on the kind of the solvent and the other reaction condition, it is generally about 1 to 10 mol equivalent, preferably about 1 to 2 mol equivalent, per 1 mol of compound (LXXVII).

The amount of the diethyl malonate to be used for this reaction is about 1 to 10 mol equivalent, preferably about 1 to 5 mol equivalent, per 1 mol of compound (LXXVII).

This step is performed in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), amides (N,N-dimethylformamide, etc.) and the like. These solvent may be used in a mixture of two or more kinds thereof in an appropriate ratio.

The reaction temperature is, for example, within about −100 to 50° C., preferably about −78 to 25° C., and the reaction time is, for example, about 0.5 to 100 hr, preferably about 0.5 to 24 hr.

(Step 2)

This step is a step of subjecting compound (LXXVIII) to a hydrolysis reaction and decarboxylation reaction to convert compound (LXXVIII) to compound (LXXIX) or a salt thereof.

The hydrolysis reaction can be carried out in the same manner as in the method described in Step 3 of Method B. The decarboxylation reaction progresses rapidly without stopping halfway after the hydrolysis reaction.

(Step 3)

This step is a step of subjecting compound (LXXIX) or a salt thereof to methyl esterification to produce compound (LXXX).

This reaction can be carried out according to a method known per se (e.g., the method described in "Protective Groups in Organic Synthesis, 3rd Ed", Wiley-Interscience, Inc. (1999) (Theodora W. Greene, Peter G. M. Wuts)). For example, compound (LXXX) can be produced by heating compound (LXXIX) or a salt thereof in methanol, in the presence of an acid catalyst.

Examples of the acid catalyst to be used for this reaction include mineral acids (hydrochloric acid, sulfuric acid, etc.), organic sulfonic acids (methanesulfonic acid, p-toluenesulfonic acid, etc.), Lewis acids (boron fluoride etherate, etc.), thionyl chloride and the like. While the amount of the acid catalyst to be used varies depending on the kind of the solvent and the other reaction condition, it is generally about 0.0001 to 10 mol equivalent, preferably about 0.01 to 0.1 mol equivalent, per 1 mol of compound (LXXIX).

In this reaction, methanol may be used as a solvent. The reaction temperature is, for example, within about 0 to 120° C., preferably about 25 to 80° C., and the reaction time is, for example, about 0.5 to 100 hr, preferably about 0.5 to 24 hr.

(Step 4)
This step is a step of subjecting compound (LXXX) to methylation to produce compound (LXXXI).
This step can be performed in the same manner as in the method described in Step 1 of Method K.

(Step 5)
This step is a step of subjecting compound (LXXXI) to a reduction reaction using a transition metal catalyst to produce compound (LXXXII).
This step can be performed in the same manner as in the method described in Step 2 of Method G.

(Step 6)
This step is a step of reacting compound (LXXXII) with α-chloro-4-methoxytoluene in the presence of a base to produce compound (LXXXIII).

Examples of the base to be used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, alkali metal alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. While the amount of the base to be used varies depending on the kind of the solvent and the other reaction condition, it is generally about 2 to 10 mol equivalent, preferably about 2 to 5 mol equivalent, per 1 mol of compound (LXXXII).

The amount of the α-chloro-4-methoxytoluene to be used is about 2 to 10 mol equivalent, preferably about 2 to 5 mol equivalent, per 1 mol of compound (LXXXII).

This step is performed in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, tert-butyl methyl ether, tetrahydrofuran, 1,4-dioxane, 1,2-dimethoxyethane, etc.), amides (N,N-dimethylformamide, etc.) and the like. These solvent may be used in a mixture of two or more kinds thereof in an appropriate ratio.

The reaction temperature is, for example, within about −100 to 150° C., preferably about −78 to 50° C., and the reaction time is, for example, about 0.5 to 100 hr, preferably about 0.5 to 24 hr.

This reaction can also be carried out under the condition described in "when the amino group is protected by a PMB group" in Step 2 of Method B.

(Step 7)
This step is a step of treating compound (LXXXIII) with a reducing agent to produce compound (LXXXIV).
This step can be performed in the same manner as in the method described in Step 1 of Method L.

(Step 8)
This step is a step of subjecting compound (LXXXIV) to an alkylation reaction with compound (XXXV) in the presence of a base to produce compound (LXXXV) or a salt thereof.
This step can be performed in the same manner as in the method described in Step 3 of Method C.

(Step 9)
This step is a step of subjecting compound (LXXXV) or a salt thereof to a deprotection reaction to produce compound (LXXV) or a salt thereof.
This step can be performed in the same manner as in the method described in Step 5 of Method B.

When compound (VI) is a compound represented by the formula:

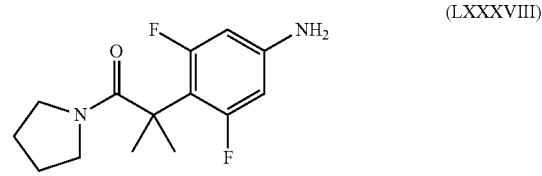 [SMILES: CC(C)(C(=O)N1CCCC1)c1c(F)cc(N)cc1F]

(LXXXVIII)

(hereinafter to be referred to as compound (LXXXVIII)) or a salt thereof, the compound can be produced according to Method P.

[Method P]

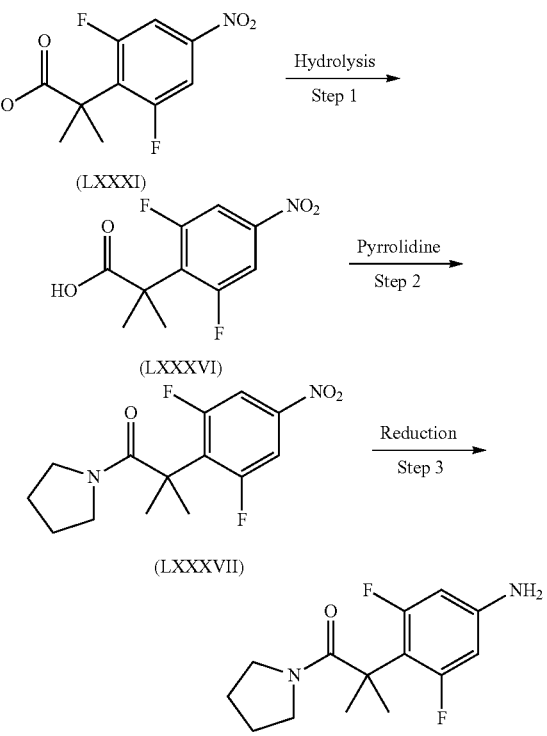

(Step 1)

This step is a step of subjecting compound (LXXXI) or a salt thereof to hydrolysis to convert compound (LXXXI) or a salt thereof to compound (LXXXVI) or a salt thereof.

This step can be performed in the same manner as in the method described in Step 3 of Method B.

(Step 2)

This step is a step of reacting compound (LXXXVI) or a salt thereof with pyrrolidine or a salt thereof in the presence of a condensing agent to produce compound (LXXXVII) or a salt thereof.

This step can be performed in the same manner as in the method described in Step 3 of Method A or Step 1 of Method A.

(Step 3)

This step is a step of subjecting compound (LXXXVII) to a reduction reaction using a transition metal catalyst to produce compound (LXXXVIII).

This step can be performed in the same manner as in the method described in Step 2 of Method G.

When compound (XII) is a compound represented by the formula:

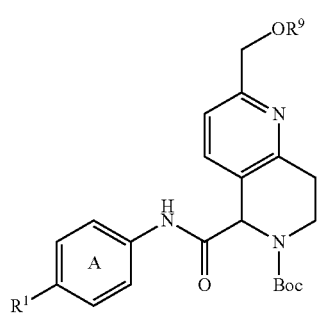

(LXLIV)

wherein each symbol is as defined above (hereinafter to be referred to as compound (LXLIV)) or a salt thereof, the compound can be produced according to Method Q.

[Method Q]

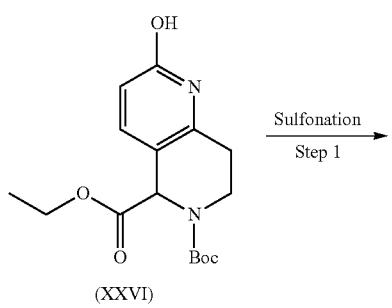

(XXVI)

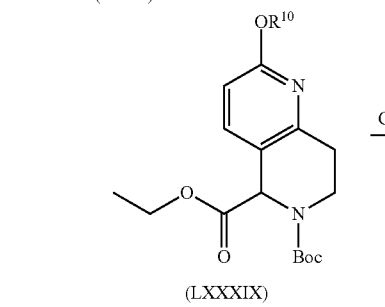

(LXXXIX)

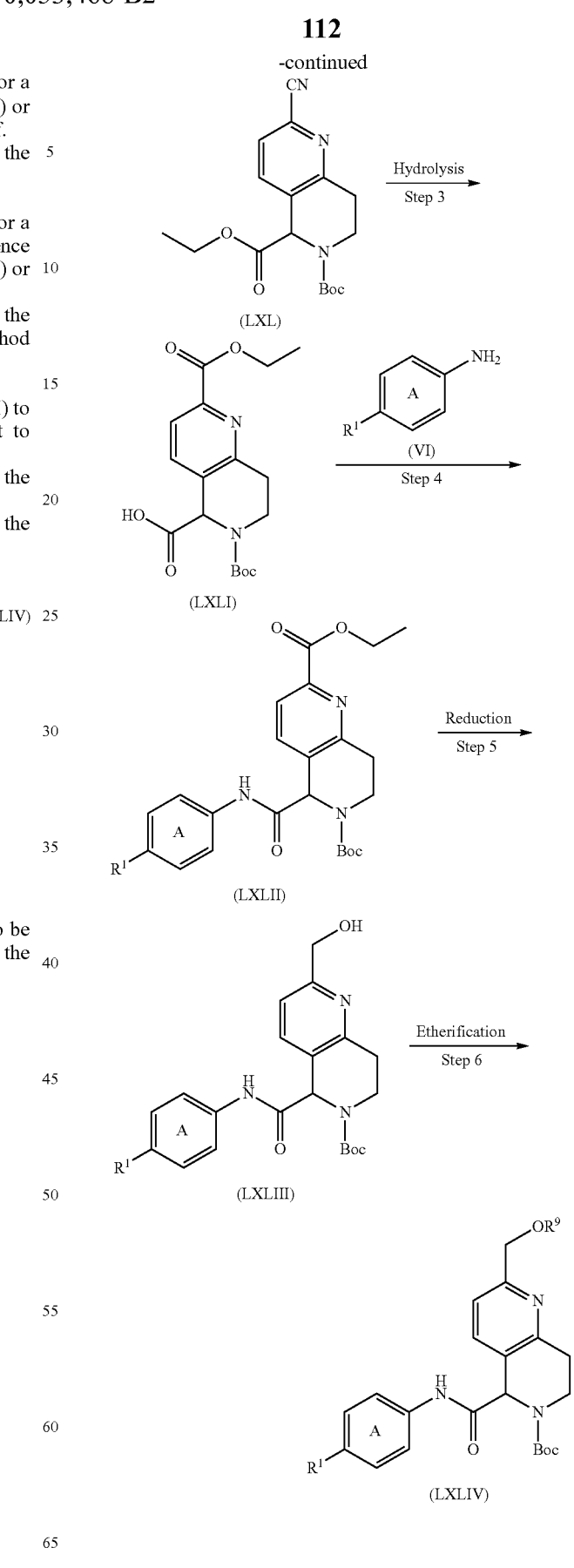

wherein the symbol is as defined above.

(Step 1)

This step is a step of subjecting compound (XXVI) or a salt thereof to a sulfonation reaction to produce compound (LXXXIX) or a salt thereof.

This step can be performed in the same manner as in the method described in Step 1 of Method H.

(Step 2)

This step is a step of subjecting compound (LXXXIX) or a salt thereof to a cyanation reaction to produce compound (LXL) or a salt thereof.

This step can be performed in the same manner as in the method described in Step 2 of Method H.

(Step 3)

This step is a step of subjecting compound (LXL) or a salt thereof to hydrolysis to produce compound (LXLI) or a salt thereof.

This step can be performed in the same manner as in the method described in Step 3 of Method B.

(Step 4)

This step is a step of reacting compound (LXLI) or a salt thereof with compound (VI) or a salt thereof in the presence of a condensing agent to produce compound (LXLII) or a salt thereof.

This step can be performed in the same manner as in the method described in Step 3 of Method A or Step 1 of Method A.

(Step 5)

This step is a step of treating compound (LXLII) or a salt thereof with a reducing agent to produce compound (LXLIII) or a salt thereof.

This step can be performed in the same manner as in the method described in Step 1 of Method L.

(Step 6)

This step is a step of converting compound (LXLIII) or a salt thereof to compound (LXLIV) or a salt thereof.

This step is a step of "reacting compound (LXLIII) or a salt thereof with compound (XXXV) in the presence of a base to produce compound (LXLIV) or a salt thereof" or a step of "subjecting compound (LXLIII) or a salt thereof to a sulfonation reaction to convert compound (LXLIII) or a salt thereof to a compound represented by the formula:

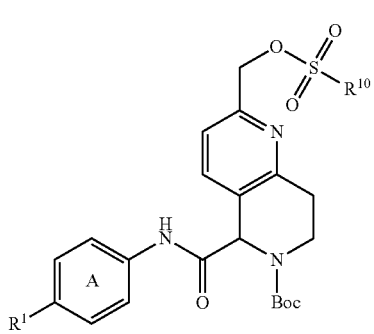

(LXLIIIa)

wherein each symbol is as defined above (hereinafter to be referred to as compound (LXLIIIa)) or a salt thereof, and reacting the compound with a compound represented by the formula:

R$^9$—OH wherein the symbol is as defined above (hereinafter to be referred to as compound (XXXVa)) or a salt thereof in the presence of a base to produce compound (LXLIV) or a salt thereof".

This step can be performed in the same manner as in the method described in Step 5 of Method H.

When compound (VI) is a compound represented by the formula:

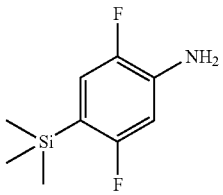

(hereinafter to be referred to as compound (LXLVIII)) or a salt thereof, the compound can be produced according to Method R.

[Method R]

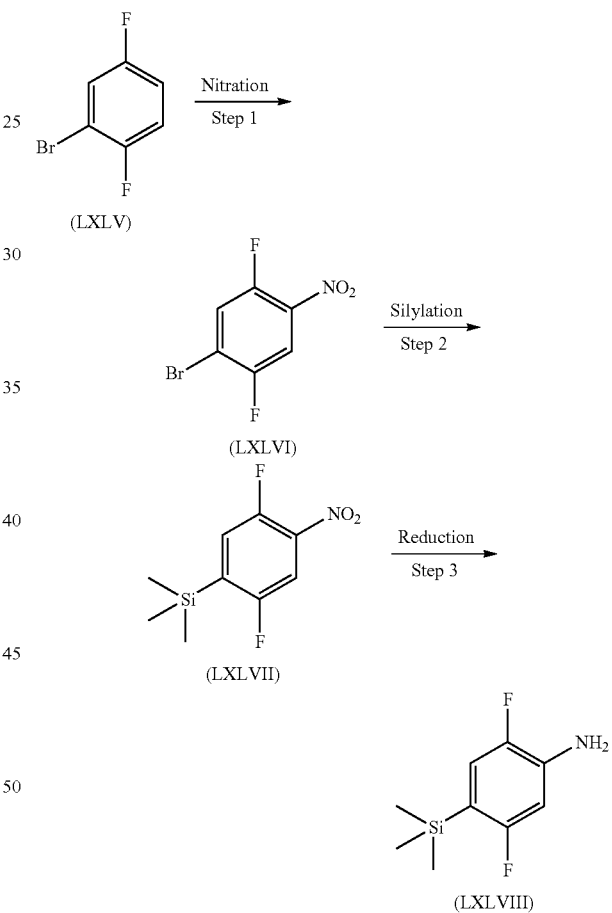

(Step 1)

This step is a step of subjecting compound (LXLV) to a nitration reaction to produce compound (LXLVI)

Compound (LXLV) may be a commercially available product, or can also be produced according to a method known per se or a method analogous thereto.

In this reaction, compound (LXLVI) can be produced by reacting compound (LXLV) with conc. nitric acid in the presence of conc. sulfuric acid.

The conc. sulfuric acid to be used for this reaction is used as a solvent, and the amount thereof is generally about 1 to 10 mol equivalent per 1 mol of compound (LXLV). The amount of the conc. nitric acid is generally about 1 to 2 mol equivalent, preferably about 1 to 1.1 mol equivalent, per 1 mol of compound (LXLV). The reaction temperature is, for example, −10° C. to 50° C., preferably 0 to 25° C. The reaction time is, for example, 0.5 to 24 hr, preferably 0.5 to 2 hr.

(Step 2)

This step is a step of reacting compound (LXLVI) with a silylating agent in the presence of or without a transition metal catalyst to produce compound (LXLVII).

This step can be performed in the same manner as in the method described in Step 1 of Method F.

Examples of the silylating agent include chlorotrimethylsilane.

(Step 3)

This step is a step of subjecting compound (LXLVII) to a reduction reaction using a transition metal catalyst to produce compound (LXLVIII).

This step can be performed in the same manner as in the method described in Step 2 of Method G.

When compound (X) is a compound represented by the formula:

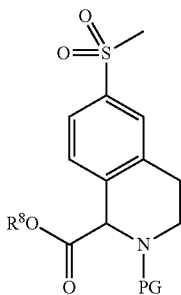

(Xa)

wherein each symbol is as defined above (hereinafter to be referred to as compound (Xa)) or a salt thereof, the compound can be produced according to Method S.

[Method S]

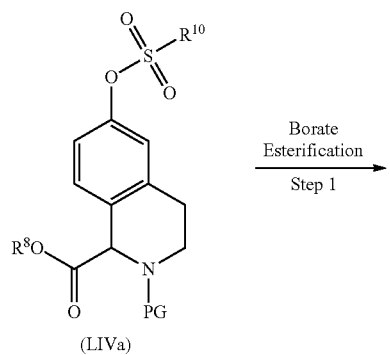

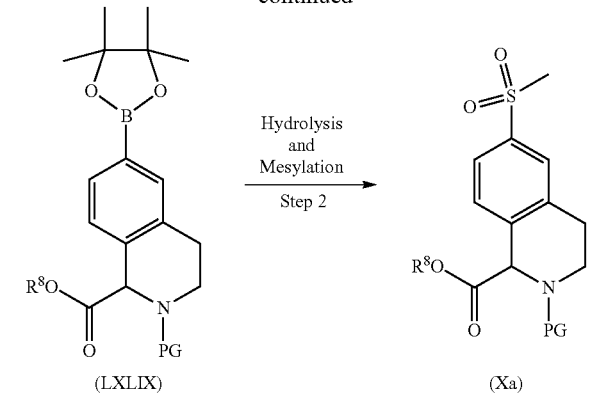

wherein the symbol is as defined above.

(Step 1)

This step is a step of subjecting compound (LIVa) or a salt thereof to a borate esterification reaction to convert compound (LIVa) or a salt thereof to compound (LXLIX) or a salt thereof.

This reaction can be carried out in the presence of a transition metal catalyst, bis(pinacolato)diboron and a base, in a solvent that does not adversely influence the reaction.

Examples of the transition metal catalyst to be used include palladium catalysts (1,1'-bis(diphenylphosphino)ferrocene-palladium(II) dichloride-dichloromethane complex, palladium acetate, palladium chloride, tetrakistriphenylphosphinepalladium, etc.), nickel catalysts (nickel chloride, etc.) and the like. Where necessary, a ligand (triphenylphosphine, tri-tert-butylphosphine, S-Phos, etc.) may be added. A metal oxide (copper oxide, silver oxide, etc.) and the like may be used as a co-catalyst. While the amount of the catalyst to be used varies depending on the kind of the catalyst, it is generally about 0.0001 to 1 mol equivalent, preferably about 0.01 to 0.5 mol equivalent, per 1 mol of compound (LIVa). The amount of the ligand to be used is generally about 0.0001 to 4 mol equivalent, preferably about 0.01 to 2 mol equivalent, per 1 mol of compound (LIVa). The amount of the co-catalyst to be used is about 0.0001 to 4 mol equivalent, preferably about 0.01 to 2 mol equivalent, per 1 mol of compound (LIVa).

The amount of the bis(pinacolato)diboron to be used is about 1 to 5 mol equivalent, preferably about 1 to 2 mol equivalent, per 1 mol of compound (LIVa).

Examples of the base to be used include organic amines (trimethylamine, triethylamine, diisopropylamine, N-methylmorpholine, 1,8-diazabicyclo[5,4,0]undec-7-ene, pyridine, N,N-dimethylaniline, etc.), alkali metal salts (sodium hydrogen carbonate, potassium hydrogen carbonate, sodium carbonate, potassium carbonate, cesium carbonate, sodium phosphate, potassium acetate, potassium phosphate, sodium hydroxide, potassium hydroxide, etc.), metal hydrides (potassium hydride, sodium hydride, etc.), alkali metal alkoxides (sodium methoxide, sodium ethoxide, sodium tert-butoxide, potassium tert-butoxide, etc.), alkali disilazides (lithium disilazide, sodium disilazide, potassium disilazide, etc.) and the like. Among them, alkali metal salts such as potassium acetate and the like are preferable. The amount of the base to be used is about 0.1 to 10 mol equivalent, preferably about 1 to 5 mol equivalent, per 1 mol of compound (LIVa).

The solvent to be used is not particularly limited as long as it does not adversely influence the reaction, and examples thereof include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), alcohols (methanol, ethanol, etc.), aprotic polar solvents (N,N-dimethylformamide, dimethyl sulfoxide, hexamethylphosphoroamide, etc.), water and mixtures thereof. The reaction temperature is generally −10 to 200° C., preferably about 0 to 150° C., and the reaction time is generally 0.5 to 48 hr, preferably 0.5 to 24 hr.

(Step 2)

This step is a step of subjecting compound (LXLIX) or a salt thereof to hydrolysis, and then subjecting the resulting compound to a mesylation reaction to convert compound (LXLIX) or a salt thereof to compound (Xa) or a salt thereof. The reaction of subjecting compound (LXLIX) or a salt thereof to hydrolysis can be carried out using sodium periodate in a solvent that does not adversely influence the reaction.

The amount of the sodium periodate to be used is about 1 to 10 mol equivalent, preferably about 1 to 3 mol equivalent, per 1 mol of compound (LXLIX).

The solvent to be used is not particularly limited as long as it does not adversely influence the reaction, and examples thereof include water, ketones (acetone, methylethylketone, etc.), nitriles (acetonitrile, etc.), ethers (dimethoxyethane, tetrahydrofuran), alcohols (methanol, ethanol, etc.), aprotic polar solvents (N,N-dimethylformamide, dimethyl sulfoxide, hexamethylphosphoroamide, etc.) and mixtures thereof. The reaction temperature is generally −10 to 100° C., preferably about 0 to 25° C., and the reaction time is generally 0.5 to 48 hr, preferably 0.5 to 24 hr.

The mesylation reaction can be carried out in the presence of copper(II) acetate and sodium methanesulfinate, in 1-butyl-3-methylimidazolium trifluoromethylsulfonate.

The amount of the copper(II) acetate to be used is about 0.01 to 1 mol equivalent, preferably about 0.01 to 0.1 mol equivalent, per 1 mol of compound (LXLIX).

The amount of the sodium methanesulfinate to be used is about 1 to 5 mol equivalent, preferably about 1 to 2 mol equivalent, per 1 mol of compound (LXLIX). The amount of the 1-butyl-3-methylimidazolium trifluoromethylsulfonate to be used is about 1 to 10 mol equivalent, preferably about 1 to 5 mol equivalent, per 1 mol of compound (LXLIX). The reaction temperature is generally −10 to 150° C., preferably about 0 to 100° C., and the reaction time is generally 0.5 to 48 hr, preferably 0.5 to 24 hr.

When compound (I) is a compound represented by the formula

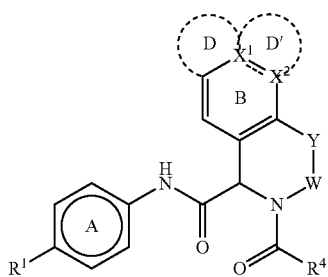

wherein each symbol is as defined above (hereinafter to be referred to as compound (Ib)), or a compound represented by the formula

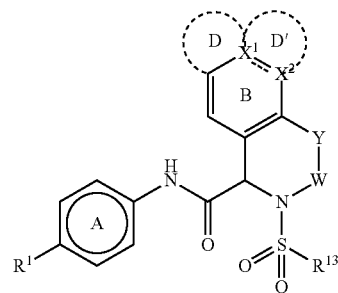

wherein each symbol is as defined above (hereinafter to be referred to as compound (Ic)), or a compound represented by the formula:

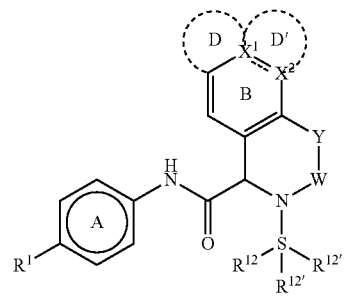

wherein each symbol is as defined above (hereinafter to be referred to as compound (Id)), or a compound represented by the formula:

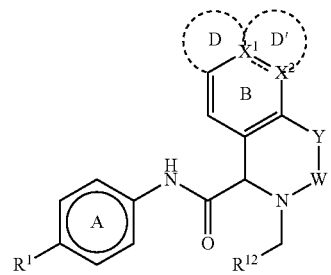

wherein each symbol is as defined above (hereinafter to be referred to as compound (Ie)), compounds (Ib), (Ic), (Id) and (Ie) or a salt thereof of the present invention can be produced according to the following Method T.

[Method T]

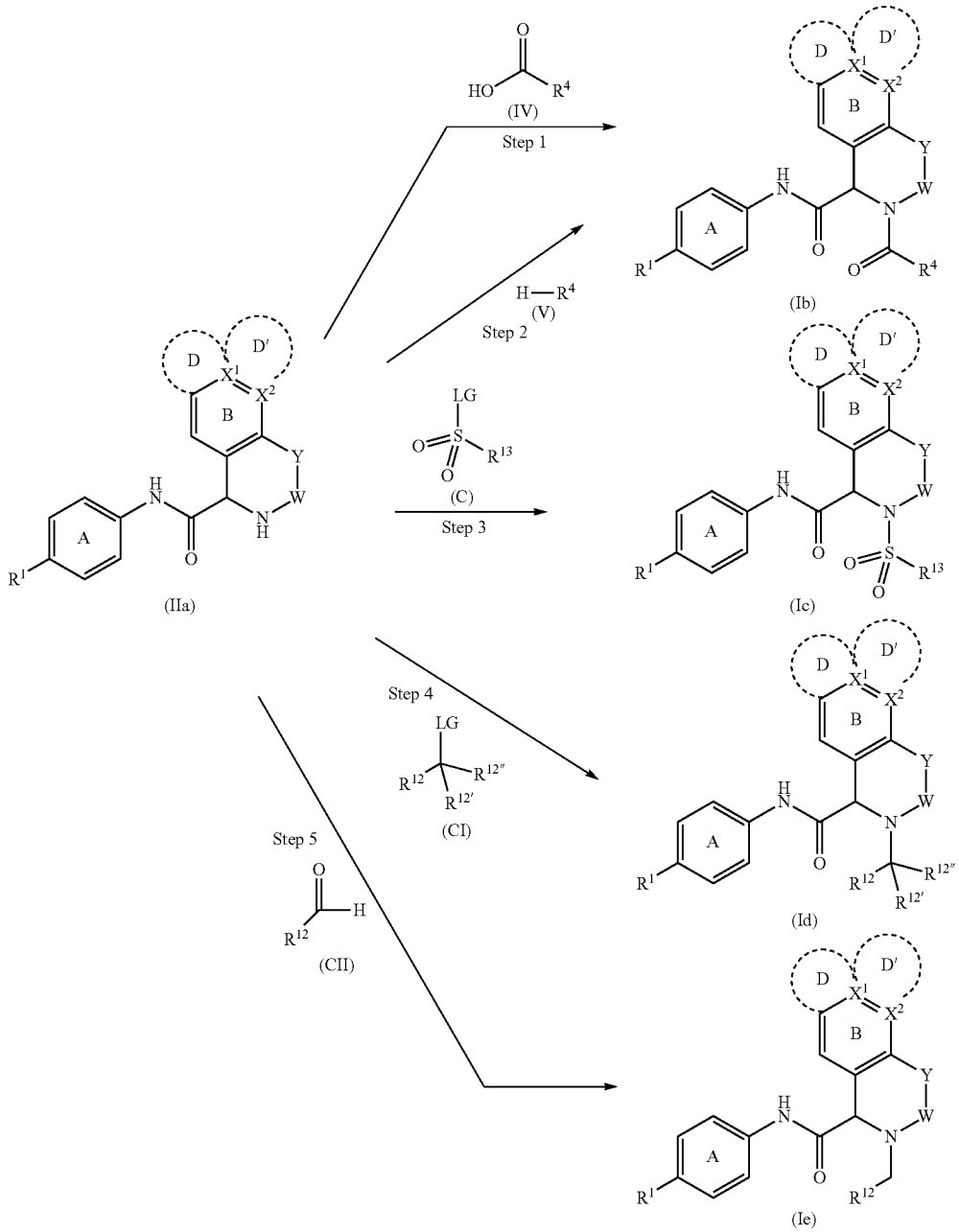

wherein each symbol is as defined above.

Compound (IIa) can be produced according to the below-mentioned Method U.

(Step 1)

This step is a step of subjecting compound (IIa) or a salt thereof to an acylation reaction to convert compound (IIa) or a salt thereof to compound (Ib) or a salt thereof.

This step can be performed in the same manner as in the method described in Step 1 of Method A.

(Step 2)

This step is a step of subjecting compound (IIa) or a salt thereof to an ureation reaction to convert compound (IIa) or a salt thereof to compound (Ib) or a salt thereof.

This step can be performed in the same manner as in the method described in Step 2 of Method A.

(Step 3)

This step is a step of reacting compound (IIa) or a salt thereof with a compound represented by the formula

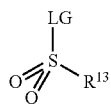

wherein each symbol is as defined above (hereinafter to be referred to as compound (C)) or a salt thereof in the presence of a base to produce compound (Ic) or a salt thereof.

Compound (C) or a salt thereof may be a commercially available product, or can also be produced according to a method known per se or a method analogous thereto.

In this reaction, the amount of compound (C), the kind and amount of the base to be used, the kind and amount of the solvent to be used, the reaction temperature and the reaction time can be selected from those described in Step 1 of Method A.

(Step 4)

This step is a step of subjecting compound (IIa) or a salt thereof to an alkylation reaction to convert compound (IIa) or a salt thereof to compound (Id) or a salt thereof.

This step is a step of subjecting compound (IIa) or a salt thereof to an alkylation reaction with a compound represented by the formula

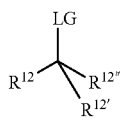

wherein each symbol is as defined above (hereinafter to be referred to as compound (CI)) or a salt thereof in the presence of a base to produce compound (Id) or a salt thereof.

Compound (CI) may be a commercially available product, or can also be produced according to a method known per se or a method analogous thereto.

This step can be performed in the same manner as in the method described in Step 3 of Method C.

(Step 5)

This step is a step of subjecting compound (IIa) or a salt thereof to a reductive alkylation reaction to convert compound (IIa) or a salt thereof to compound (Ie) or a salt thereof.

This step is a step of reacting compound (IIa) or a salt thereof with a compound represented by the formula

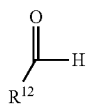

wherein each symbol is as defined above (hereinafter to be referred to as compound (CII)) or a salt thereof in the presence of a reducing agent to produce compound (Ie) or a salt thereof.

The reductive alkylation reaction in this step can be carried out according to a method known per se. For example, the reaction can be carried out by reacting compound (IIa) or a salt thereof with compound (CII) or a salt thereof, and then subjecting the resulting imine or iminium ion to a reduction reaction.

The amount of compound (CII) to be used is generally about 1 to 10 mol equivalent, preferably about 1 to 3 mol equivalent, per 1 mol of compound (IIa).

The solvent to be used for the production reaction of the imine or iminium ion is not particularly limited as long as the reaction proceeds, and examples thereof include hydrocarbons (heptane, hexane, toluene, xylene, etc.), halogenated hydrocarbons (chloroform, dichloromethane, 1,2-dichloroethane, etc.), ethers (diethyl ether, tetrahydrofuran, 1,4-dioxane, etc.), esters (ethyl acetate, tert-butyl acetate, etc.), alcohols (methanol, ethanol, 2-propanol, etc.), nitriles (acetonitrile, butyronitrile, etc.), amides (N,N-dimethylformamide, N,N-dimethylacetamide, etc.), sulfoxides (dimethyl sulfoxide, etc.) and mixed solvents thereof.

In this step, the reaction can advantageously proceeds by the addition of a catalyst, if necessary. Examples of the catalyst include mineral acids (hydrochloric acid, hydrobromic acid, sulfuric acid, etc.), carboxylic acids (formic acid, acetic acid, propionic acid, trifluoroacetic acid, etc.), sulfonic acids (methanesulfonic acid, p-toluenesulfonic acid, etc.), Lewis acids (aluminium chloride, zinc chloride, zinc bromide, boron trifluoride, titanium chloride, etc.), acetates (sodium acetate, potassium acetate, etc.), molecular sieves (molecular sieves 3A, 4A, 5A, etc.), dehydrating agents (magnesium sulfate, etc.) and the like. The amount of the catalyst to be used is generally 0.01 to 50 mol equivalent, preferably about 0.1 to about 10 mol, per 1 mol of compound (IIa).

The reaction temperature is generally about 0° C. to about 200° C., preferably about 20° C. to about 150° C., and the reaction time is generally about 0.5 hr to about 48 hr, preferably about 0.5 hr to about 24 hr.

The conversion to the imine or iminium ion can be carried out according to various reduction reactions in a solvent. The reduction reaction can be carried out according to a method known per se, and examples thereof include a method using a metal hydride, and method employing catalytic hydrogenation reaction.

Examples of the metal hydride include sodium borohydride, lithium borohydride, zinc borohydride, sodium cyanoborohydride, sodium triacetoxyborohydride, lithium cyanoborohydride, dibutylaluminium hydride, aluminium hydride, lithium aluminium hydride, borane complex (borane-THF complex, catecholborane, etc.) and the like. Among them, sodium borohydride, sodium cyanoborohydride, sodium triacetoxyborohydride and the like are preferable. The amount of the metal hydride to be used is, for example, about 1 to about 50 mol, preferably about 1 to about 10 mol, per 1 mol of the imine.

The reduction reaction using a metal hydride is generally carried out in a solvent inert to the reaction. Examples of the solvent include aromatic hydrocarbons (toluene, xylene, etc.), aliphatic hydrocarbons (heptane, hexane, etc.), halogenated hydrocarbons (chloroform, dichloromethane, etc.), ethers (diethyl ether, tetrahydrofuran, 1,4-dioxane, etc.), alcohols (methanol, ethanol, 2-propanol, butanol, benzyl alcohol, etc.), nitriles (acetonitrile, etc.), N,N-dimethylformamide, dimethyl sulfoxide and the like. These solvent may be used in a mixture thereof in an appropriate ratio.

The reaction temperature is generally about −80° C. to about 80° C., preferably about −40° C. to about 40° C., and the reaction time is generally about 5 min to about 48 hr, preferably about 1 hr to about 24 hr.

The catalytic hydrogenation reaction can be carried out in the presence of a catalyst, under hydrogen atmosphere. Examples of the catalyst include palladiums such as palladium on carbon, palladium hydroxide on carbon, palladium oxide and the like; nickels such as Raney-nickel catalyst and the like; platinums such as platinum oxide, platinum on carbon and the like; rhodiums such as rhodium on carbon and the like, and the like. The amount thereof to be used is generally about 0.001 to about 1 mol, preferably about 0.01 to about 0.5 mol, per 1 mol of the imine or iminium ion.

The catalytic hydrogenation reaction is generally carried out in a solvent inert to the reaction. Examples of the solvent include alcohols (methanol, ethanol, propanol, butanol, etc.), hydrocarbons (benzene, toluene, xylene, etc.), halogenated hydrocarbons (dichloromethane, chloroform, etc.), ethers (diethyl ether, 1,4-dioxane, tetrahydrofuran, etc.), esters (ethyl acetate, etc.), amides (N,N-dimethylformamide, etc.), carboxylic acids (acetic acid, etc.), water and mixtures thereof.

The hydrogen pressure for the reaction is generally about 1 to about 50 atm, preferably about 1 to about 10 atm. The reaction temperature is generally about 0° C. to about 150° C., preferably about 20° C. to about 100° C., and the reaction time is generally about 5 min to about 72 hr, preferably about 0.5 hr to about 40 hr.

In this step, the imine or iminium ion, which is an intermediate, can also be used without isolation for the next reduction reaction to produce compound (Ie) directly from compound (IIa). In this case, the pH of the reaction mixture is preferably adjusted to about 4 to about 5.

Compound (IIa) used in Method T can be produced according to the following Method U.

[Method U]

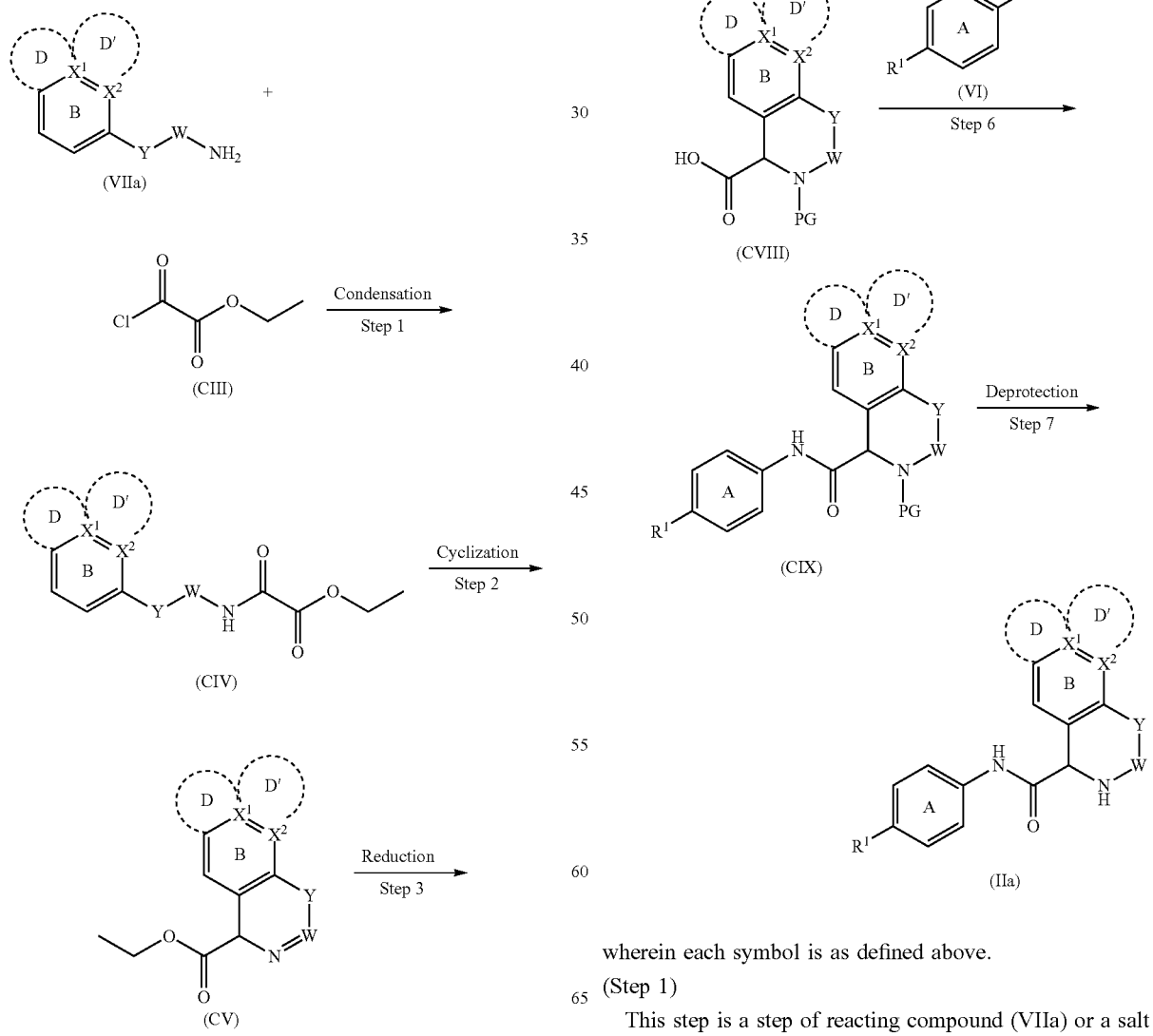

wherein each symbol is as defined above.

(Step 1)

This step is a step of reacting compound (VIIa) or a salt thereof with a compound represented by the formula:

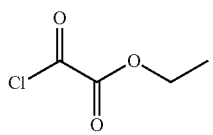

(hereinafter to be referred to as compound (CIII)) or a salt thereof in the presence of a base to produce compound (CIV) or a salt thereof.

This step can be performed in the same manner as in the method described in Step 1 of Method A.

(Step 2)

This step is a step of treating compound (CIV) or a salt thereof with phosphorus oxychloride and zinc(II) chloride to produce compound (CV) or a salt thereof.

The amount of the phosphorus oxychloride to be used is generally about 1 to 10 mol equivalent, preferably about 1 to mol equivalent, per 1 mol of compound (CIV).

The amount of the zinc(II) chloride to be used is generally about 0.1 to 2 mol equivalent, preferably about 0.1 to 1 mol equivalent, per 1 mol of compound (CIV).

The above-mentioned reaction is generally carried out in a solvent that does not adversely influence the reaction. Examples of the solvent include hydrocarbons (benzene, toluene, etc.), ethers (diethyl ether, 1,4-dioxane, tetrahydrofuran, etc.), nitriles (acetonitrile, etc.), halogenated hydrocarbons (chloroform, dichloromethane, etc.) and the like, and they may be mixed as appropriate. The reaction temperature is generally about −80 to 150° C., preferably about 0 to 10° C., and the reaction time is generally about 0.5 to 100 hr, preferably 0.5 to 10 hr.

(Step 3)

This step is a step of subjecting compound (CV) or a salt thereof to a reduction reaction to produce compound (CVI) or a salt thereof.

This step can be performed in the same manner as in the method described in the "subjecting the imine or iminium ion to a reduction reaction" in Step 5 of Method T.

(Step 4)

This step is a step of subjecting compound (CVI) or a salt thereof to an amino-protecting reaction to produce compound (CVII) or a salt thereof.

This step can be performed in the same manner as in the method described in Step 2 of Method B.

(Step 5)

This step is a step of subjecting compound (CVII) or a salt thereof to hydrolysis to convert compound (CVII) or a salt thereof to compound (CVIII) or a salt thereof.

This step can be performed in the same manner as in the method described in Step 3 of Method B.

(Step 6)

This step is a step of reacting compound (CVIII) or a salt thereof with compound (VI) or a salt thereof in the presence of a condensing agent to produce compound (CIX) or a salt thereof.

This step can be performed in the same manner as in the method described in Step 3 of Method A or Step 1 of Method A.

(Step 7)

This step is a step of subjecting compound (CIX) or a salt thereof to a deprotection reaction to produce compound (IIa) or a salt thereof.

This step can be performed in the same manner as in the method described in Step 5 of Method B.

Compound (LVIII) can also be produced according to Method V.

[Method V]

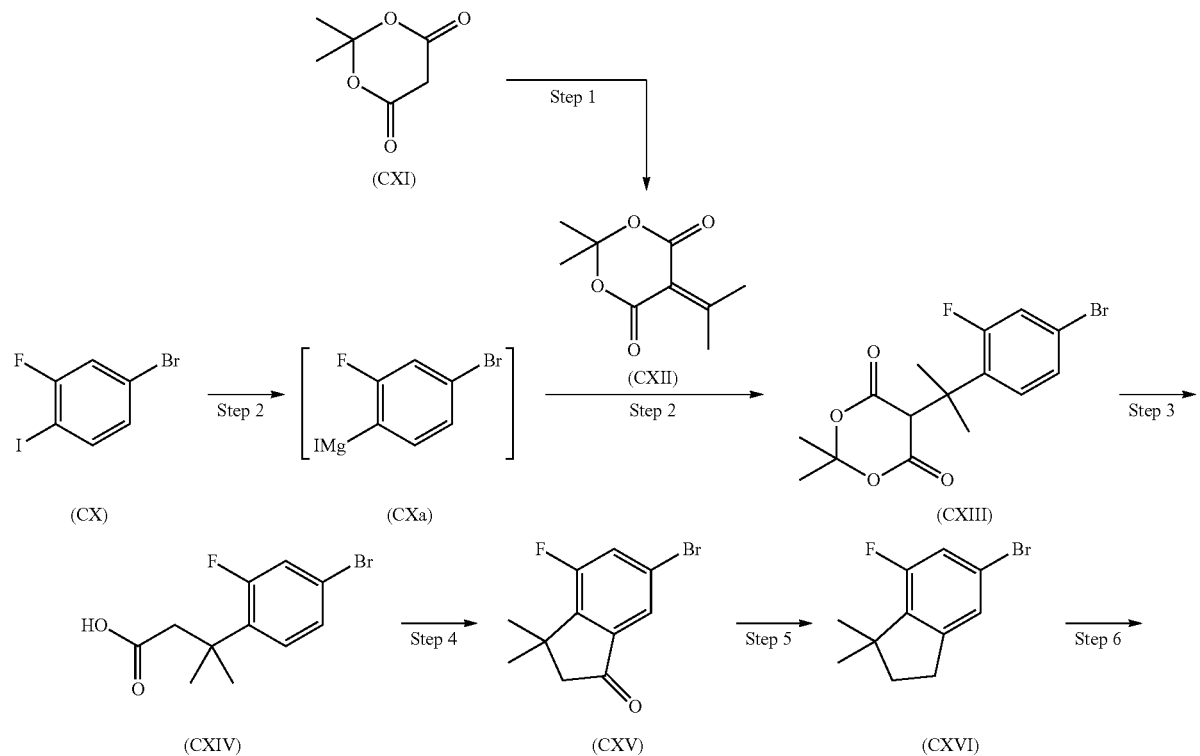

-continued

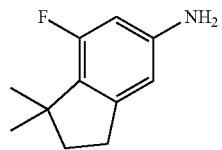

(LVIII)

(Step 1)

This step is a step of subjecting compound (CXI) (2,2-dimethyl-1,3-dioxane-4,6-dione) to a dehydration condensation with acetone in the presence of morpholine and acetic acid to produce compound (CXII).

Compound (CXI) may be a commercially available product.

The amount of the morpholine and acetic acid to be used is about 0.01 to 1 mol equivalent, preferably about 0.01 to 0.05 mol equivalent, per 1 mol of compound (CXI), respectively.

The amount of the acetone to be used is about 1 to 100 mol equivalent per 1 mol of compound (CXI). Acetone may be used as a solvent.

The reaction temperature is generally about 0 to 50° C., preferably about 0 to 30° C., and the reaction time is generally about 0.5 to 48 hr, preferably 1 to 24 hr.

(Step 2)

This step is a step of converting compound (CX) to Grignard reagent (CXa), and then coupling Grignard reagent (CXa) with compound (CXII) to produce compound (CXIII).

Compound (CX) may be a commercially available product.

The step of converting compound (CX) to Grignard reagent (CXa) can be performed by reacting compound (CX) with isopropylmagnesium chloride.

Isopropylmagnesium chloride may be a commercially available product. The amount thereof to be used is about 1 to 2 mol equivalent, preferably about 1 to 1.2 mol equivalent, per 1 mol of compound (CX).

This reaction is generally carried out in a solvent that does not adversely influence the reaction. Examples of the solvent include hydrocarbons (benzene, toluene, etc.), ethers (diethyl ether, 1,4-dioxane, tetrahydrofuran, etc.) and the like, and they may be mixed as appropriate.

The reaction temperature is generally about −80 to 30° C., preferably about −50 to 0° C., and the reaction time is generally about 0.5 to 2 hr, preferably 0.5 to 1 hr.

Grignard reagent (CXa) can be used without isolation for the coupling reaction with compound (CXII).

In the coupling reaction with compound (CXII), the amount of compound (CXII) to be used is about 1 to 2 mol equivalent, preferably about 1 to 1.2 mol equivalent, per 1 mol of compound (CXa).

This reaction is generally carried out in a solvent that does not adversely influence the reaction, and the solvent used for the above-mentioned conversion of compound (CX) to Grignard reagent (CXa) can be used.

The reaction temperature is generally about −80 to 30° C., preferably about −50 to 0° C., and the reaction time is generally about 0.5 to 2 hr, preferably 0.5 to 1 hr.

(Step 3)

This step is a step of treating compound (CXIII) with hydrochloric acid to produce compound (CXIV) or a salt thereof.

The amount of the hydrochloric acid to be used is about 1 to 50 mol equivalent, preferably about 1 to 5 mol equivalent, per 1 mol of compound (CXIII).

This reaction is generally carried out in a solvent that does not adversely influence the reaction. Examples of the solvent include ethers (diethyl ether, tetrahydrofuran, 1,4-dioxane, etc.), alcohols (methanol, ethanol, 2-propanol, etc.), nitriles (acetonitrile, butyronitrile, etc.), amides (N,N-dimethylformamide, N,N-dimethylacetamide, etc.), sulfoxides (dimethyl sulfoxide, etc.), water and the like, and they may be mixed as appropriate.

The reaction temperature is generally about 0 to 150° C., preferably about 20 to 100° C., and the reaction time is generally about 0.5 to 48 hr, preferably 0.5 to 24 hr.

(Step 4)

This step is a step of treating compound (CXIV) with polyphosphoric acid to produce compound (CXV).

The amount of the polyphosphoric acid to be used is about 1 to 50 mol equivalent, preferably about 1 to 5 mol equivalent, per 1 mol of compound (CXIV).

The reaction temperature is generally about 20 to 150° C., preferably about 50 to 100° C., and the reaction time is generally about 0.5 to 24 hr, preferably 0.5 to 10 hr.

(Step 5)

This step is a step of treating compound (CXV) with triethylsilane in trifluoroacetic acid solvent to produce compound (CXVI).

The amount of the triethylsilane to be used is about 1 to 10 mol equivalent, preferably about 1 to 2 mol equivalent, per 1 mol of compound (CXV).

The reaction temperature is generally about −20 to 100° C., preferably about 0 to 30° C., and the reaction time is generally about 0.5 to 100 hr, preferably 1 to 50 hr.

(Step 6)

This step is a step of subjecting compound (CXVI) to an amination reaction to produce compound (LVIII).

This step can be performed in the same manner as in the method described in Step 3 of Method I.

When the object product is obtained in a free form by the above-mentioned reaction, it may be converted to a salt by a conventional method. When it is obtained as a salt, it can also be converted to a free form or other salt by a conventional method. The thus-obtained compound (I) can be isolated and purified from the reaction solution by a known means, for example, phase transfer, concentration, solvent extraction, fractionation, crystallization, recrystallization, chromatography and the like.

When compound (I) contains an isomer such as a tautomer, an optical isomer, a stereoisomer, a regioisomer, a rotamer and the like, any isomer and a mixture thereof are also encompassed in the compound of the present invention. Furthermore, when compound (I) has an optical isomer, an optical isomer resolved from this compound is also encompassed in compound (I).

The compound (I) may be a crystal. Even if compound (I) is in a single crystal form or mixed crystal form, it can be provided as compound (I) of the present invention.

Compound (I) may be a pharmaceutically acceptable co-crystal or co-crystal salt. Here, the co-crystal or co-crystal salt means a crystalline substance consisting of two or more particular substances which are solids at room temperature, each of which has different physical properties (e.g., structure, melting point, heat of melting, hygroscopicity, solubility, stability etc.). The cocrystal and cocrystal salt can be produced by cocrystallization known per se.

The compound (I) may be a solvate (e.g., a hydrate (e.g., monohydrate, dihydrate, etc.)) or a nonsolvate (e.g., nonhydrate, etc.). Any of them can be provided as compound (I) of the present invention.

Any of the above compounds may be labeled or substituted with an isotope (e.g., $^2H$, $^3H$, $^{11}C$, $^{14}C$, $^{18}F$, $^{35}S$, or $^{125}I$) and provided as compound (I) of the present invention. Compound (I) labeled or substituted with an isotope can be used, for example, as a tracer (PET tracer) used for positron emission tomography (PET), and is useful in the field such as medical diagnosis and the like.

The prodrug of compound (I) means a compound which can be converted into compound (I) by reaction with an enzyme, gastric acid, or the like under physiological conditions in the living body. In other words, it means a compound which can be converted into compound (I) by enzymatic oxidation, reduction, hydrolysis or the like, or a compound which can be converted into compound (I) by hydrolysis with gastric acid or the like. Examples of the prodrug of compound (I) include a compound in which amino of compound (I) is acylated, alkylated, or phosphorylated (e.g., the amino of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); a compound in which hydroxyl of compound (I) is acylated, alkylated, phosphorylated, or borated (e.g., hydroxyl of compound (I) is acetylated, palmitoylated, propanoylated, pivaloylated, succinylated, fumarylated, alanylated, or dimethylaminomethylcarbonylated); a compound in which carboxy of compound (I) is esterified or amidated (e.g., a compound in which carboxy of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, or methylamidated). These compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

Since compound (I) and a prodrug thereof [hereinafter sometimes to be abbreviated as the compound of the present invention] show superior RORγt inhibitory activity, they are also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for RORγt associated diseases, Th17 cell associated diseases and IL-17A or IL-17F associated diseases, more specifically, the diseases described in (1)-(4) below.

(1) inflammatory diseases (e.g., rheumatoid arthritis, acute pancreatitis, chronic pancreatitis, asthma, bronchial asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, uveitis etc.), (2) autoimmune diseases (e.g., rheumatoid arthritis, ankylosing spondylitis, psoriasis, multiple sclerosis (MS), polymyositis, dermatomyositis (DM), polyarteritis nodosa (PN), mixed connective tissue disease (MCTD), Sjogren's syndrome, systemic lupus erythematosus (SLE), scleroderma, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, inflammatory bowel disease (IBD), ulcerative colitis (UC), Crohn's disease, graft versus host disease, Addison's disease, abnormal immunoresponse, arthritis, dermatitis, radiodermatitis etc.), (3) bone or joint degenerative diseases (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor and the like), lung cancer (e.g., non-small cell lung cancer, small cell lung cancer, malignant mesothelioma and the like), mesothelioma, pancreatic cancer (e.g., pancreatic duct cancer and the like), gastric cancer (e.g., papillary adenocarcinoma, mucinous adenocarcinoma, adenosquamous carcinoma and the like), breast cancer (e.g., invasive ductal carcinoma, ductal carcinoma in situ, inflammatory breast cancer and the like), ovarian cancer (e.g., ovarian epithelial carcinoma, extragonadal germ cell tumor, ovarian germ cell tumor, ovarian low malignant potential tumor and the like), prostate cancer (e.g., hormone-dependent prostate cancer, non-hormone dependent prostate cancer and the like), liver cancer (e.g., primary liver cancer, extrahepatic bile duct cancer and the like), thyroid cancer (e.g., medullary thyroid carcinoma and the like), kidney cancer (e.g., renal cell carcinoma, transitional cell carcinoma in kidney and urinary duct and the like), uterine cancer, endometrial cancer, brain tumor (e.g., pineal astrocytoma, pilocytic astrocytoma, diffuse astrocytoma, anaplastic astrocytoma and the like), melanoma (melanoma), sarcoma, urinary bladder cancer, hematologic cancer and the like including multiple myeloma, hypophyseal adenoma, glioma, acoustic neurinoma, retinoblastoma, head and neck cancer, pharyngeal cancer, laryngeal cancer, cancer of the tongue, thymoma, esophagus cancer, duodenal cancer, colorectal cancer, rectal cancer, hepatoma, pancreatic endocrine tumor, cancer of the bile duct, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary).

The medicament of the present invention can be preferably used as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

In another embodiment, the medicament of the present invention can be preferably used as an agent for the prophylaxis or treatment of autoimmune disease, inflammatory disease, bone or articular disease, or neoplastic disease, particularly preferably psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE), chronic obstructive pulmonary diseases, ovarian cancer, non small cell lung cancer, breast cancer, stomach cancer, head and neck cancer, prostate cancer or endometrial cancer.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. In addition, the medicament of the present invention shows particularly superior pharmacokinetics in oral administration, and therefore, it shows superior in vivo activity. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. While the dose varies depending on the subject of administration, administration route, disease and the like, for example, for oral administration to an adult inflammatory bowel disease (IBD) patient (body weight about 60 kg), it is about 0.1 mg/kg body weight to 30 mg/kg body weight, preferably about 1 mg/kg body weight to 20 mg/kg body weight as an active ingredient (compound (I)) for one day, which is administered once to several times, preferably once or two to three times.

The pharmaceutically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as an RORγt inhibitor, Th17 cell inhibitor, IL-17A or IL-17F inhibitor, it can be used in combination with the following drugs.

(1) Non-steroidal Anti-inflammatory Drug (NSAIDs)
(i) Classical NSAIDs
alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.
(ii) cyclooxygenase inhibitor (COX-1 selective inhibitor, COX-2 selective inhibitor and the like)
salicylic acid derivatives (e.g., celecoxib, aspirin), etoricoxib, valdecoxib, diclofenac, indomethacin, loxoprofen and the like.
(iii) nitric oxide-releasing NSAIDs
(2) disease-modifying Anti-rheumatic Drugs (DMARDs)
(i) Gold preparation
auranofin and the like.
(ii) penicillamine
D-penicillamine.
(iii) aminosalicylic acid preparation
sulfasalazine, mesalazine, olsalazine, balsalazide.
(iv) antimalarial drug
chloroquine and the like.
(v) pyrimidine synthesis inhibitor
leflunomide and the like.
(vi) tacrolimus
(3) Anti-cytokine Drug
(I) protein drug
(i) Tnf inhibitor
etanercept, infliximab, adalimumab, certolizumab pegol, golimumab, PASSTNF-α, soluble TNF-α receptor, TNF-α binding protein, anti-TNF-α antibody and the like.
(ii) interleukin-1 inhibitor
anakinra (interleukin-1 receptor antagonist), soluble interleukin-1 receptor and the like.
(iii) interleukin-6 inhibitor
tocilizumab (anti-interleukin-6 receptor antibody), anti-interleukin-6 antibody and the like.
(iv) interleukin-10 drug
interleukin-10 and the like.
(v) interleukin-12/23 inhibitor
ustekinumab, briakinumab (anti-interleukin-12/23 antibody) and the like.
(vi) B cell activation inhibitor
rituxan, benrista and the like.
(vii) co-stimulatory molecules related protein drug
abatacept and the like.
(II) non-protein drug
(i) MAPK inhibitor
BMS-582949 and the like.
(ii) gene modulator
inhibitor of molecule involved in signal transduction, such as NF-κ, NF-κB, IKK-1, IKK-2, AP-1 and the like, and the like.
(iii) cytokine production inhibitor
iguratimod, tetomilast and the like.
(iv) TNF-α converting enzyme inhibitor
(v) interleukin-1β converting enzyme inhibitor
belnacasan and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (vercirnon (vercirnon sodium), CCX025, N-{4-chloro-2-[(1-oxidepyridin-4-yl)carbonyl]phenyl}-4-(propan-2-yloxy)benzenesulfonamide), MCP-1 antagonist and the like.
(ix) interleukin-2 receptor antagonist
denileukin, diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor, soluble TNF-α receptor and the like.
(xii) antisense compound
ISIS 104838 and the like.
(4) Integrin Inhibitor
natalizumab, vedolizumab, AJM300, TRK-170, E-6007 and the like.
(5) Immunomodulator (Immunosuppressant)
methotrexate, cyclophosphamide, MX-68, atiprimod dihydrochloride, abatacept, CKD-461, rimexolone, cyclosporine, tacrolimus, gusperimus, azathiopurine, anti-lymphocyte serum, freeze-dried sulfonated normal immunoglobulin, erythropoietin, colony stimulating factor, interleukin, interferon and the like.
(6) Proteasome Inhibitor
velcade and the like.
(7) JAK Inhibitor
tofacitinib and the like.
(8) Steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(9) Angiotensin Converting Enzyme Inhibitor
enalapril, captopril, ramipril, lisinopril, cilazapril, perindopril and the like.
(10) Angiotensin II Receptor Antagonist
candesartan cilexetil, valsartan, irbesartan, olmesartan, eprosartan and the like.

(11) Diuretic Drug
   hydrochlorothiazide, spironolactone, furosemide, indapamide, bendrofluazide, cyclopenthiazide and the like.
(12) Cardiotonic Drug
   digoxin, dobutamine and the like.
(13) β Receptor Antagonist
   carvedilol, metoprolol, atenolol and the like.
(14) Ca Sensitizer
   caldaret hydrate and the like.
(15) Ca Channel Antagonist
   nifedipine, diltiazem, verapamil and the like.
(16) Anti-platelet Drug, Anticoagulator
   heparin, aspirin, warfarin and the like.
(17) HMG-CoA Reductase Inhibitor
   atorvastatin, simvastatin and the like.
(18) Contraceptive
(i) sex hormone or derivatives thereof
   gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, tosagestin, TX-525, ethinylestradiol/TX525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
   ormeloxifene, mifepristone, Org-33628 and the like.
(iii) spermatocide
   ushercell and the like.
(19) Others
(i) T cell inhibitors
(ii) inosine monophosphate dehydrogenase (IMPDH) inhibitor
   mycophenolate mofetil and the like.
(iii) adhesion molecule inhibitor
   alicaforsen sodium, selectin inhibitor, ELAM-1 inhibitor, VCAM-1 inhibitor, ICAM-1 inhibitor and the like.
(iv) thalidomide
(v) cathepsin inhibitor
(vi) matrix metalloprotease (MMPs) inhibitor
   V-85546 and the like.
(vii) glucose-6-phosphate dehydrogenase inhibitor
(viii) dihydroorotate dehydrogenase (DHODH) inhibitor
(ix) phosphodiesterase IV (PDE IV) inhibitor
   roflumilast, apremilast, CG-1088 and the like.
(x) phospholipase $A_2$ inhibitor
(xi) iNOS inhibitor
   VAS-203 and the like.
(xii) microtubule stimulating drug
   paclitaxel and the like.
(xiii) microtuble inhibitor
   reumacon and the like.
(xiv) MHC class II antagonist
(xv) prostacyclin agonist
   iloprost and the like.
(xvi) CD4 antagonist
   zanolimumab and the like.
(xvii) CD23 antagonist
(xviii) LTB4 receptor antagonist
   DW-1350 and the like.
(xix) 5-lipoxygenase inhibitor
   zileuton and the like.
(xx) cholinesterase inhibitor
   galanthamine and the like.
(xxi) tyrosine kinase inhibitor
   Tyk2 inhibitor (WO2010/142752) and the like.
(xxii) cathepsin B inhibitor
(xxiii) adenosine deaminase inhibitor
   pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
   synvisc (hylan G-F 20), orthovisc and the like.
(xxix) glucosamine sulfate
(xxx) amiprilose
(xxxi) CD-20 inhibitor
   rituximab, ibritumomab, tositumomab, ofatumumab and the like.
(xxxii) BAFF inhibitor
   belimumab, tabalumab, atacicept, blisibimod and the like.
(xxxiii) CD52 inhibitor
   alemtuzumab and the like.

Other concomitant drugs besides the above-mentioned include for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, therapeutic drug for diabetes, antinarcotic, vitamin, vitamin derivative, antiasthmatic, therapeutic agent for pollakisuria/anischuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial Agent
(i) sulfa drug
   sulfamethizole, sulfisoxazole, sulfamonomethoxine, salazosulfapyridine, silver sulfadiazine and the like.
(ii) quinolone antibacterial agent
   nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
   isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
   diaphenylsulfone, rifampicin and the like.
(v) antiviral drug
   idoxuridine, acyclovir, vidarabine, gancyclovir and the like.

(vi) anti-HIV agent
   zidovudine, didanosine, zalcitabine, indinavir sulfate ethanolate, ritonavir and the like.
(vii) antispirochetele
(viii) antibiotic
   tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885(1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H, 4H)-1,2,4-triazolone, fluconazole, itraconazole and the like] and the like.

(2) Antifungal Agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) Antiprotozoal Agent
   metronidazole, tinidazole, diethylcarbamazine citrate, quinine hydrochloride, quinine sulfate and the like.

(4) Antitussive and Expectorant Drug
   ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline oxymetebanol, morphine hydrochloride, dextromethorfan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) Sedative
   chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic
(6-1) Local Anesthetic
   cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.
(6-2) General Anesthetic
(i) inhalation anesthetic (e.g., ether, halothane, nitrous oxide, isoflurane, enflurane),
(ii) intravenous anesthetic (e.g., ketamine hydrochloride, droperidol, thiopental sodium, thiamylal sodium, pentobarbital) and the like.

(7) Antiulcer Drug
   histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(8) Antiarrhythmic Agent
(i) sodium channel blocker (e.g., quinidine, procainamide, disopyramide, ajmaline, lidocaine, mexiletine, phenytoin),
(ii) β-blocker (e.g., propranolol, alprenolol, bufetolol hydrochloride, oxprenolol, atenolol, acebutolol, metoprolol, bisoprolol, pindolol, carteolol, arotinolol hydrochloride),
(iii) potassium channel blocker (e.g., amiodarone),
(iv) calcium channel blocker (e.g., verapamil, diltiazem) and the like.

(9) Hypotensive Diuretic Drug
   hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) Anticoagulant
   heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) Tranquilizer
   diazepam, lorazepam, oxazepam, chlordiazepoxide, medazepam, oxazolam, cloxazolam, clotiazepam, bromazepam, etizolam, fludiazepam, hydroxyzine and the like.

(12) Antipsychotic
   chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) Antitumor Drug
   6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) Hypolipidemic Drug
   clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], pravastatin, simvastatin, probucol, bezafibrate, clinofibrate, nicomol, cholestyramine, dextran sulfate sodium and the like.

(15) Muscle Relaxant
  pridinol, tubocurarine, pancuronium, tolperisone hydrochloride, chlorphenesin carbamate, baclofen, chlormezanone, mephenesin, chlorzoxazone, eperisone, tizanidine and the like.
(16) Antiepileptic Drug
  phenytoin, ethosuximide, acetazolamide, chlordiazepoxide, trimethadione, carbamazepine, phenobarbital, primidone, sulthiame, sodium valproate, clonazepam, diazepam, nitrazepam and the like.
(17) Antidepressant
  imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.
(18) Antiallergic drug
  diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.
(19) Cardiac Stimulants
  trans-n-oxocamphor, terephyllol, aminophylline, etilefrine, dopamine, dobutamine, denopamine, aminophylline, vesnarinone, amrinone, pimobendan, ubidecarenone, digitoxin, digoxin, methyldigoxin, lanatoside C, G-strophanthin and the like.
(20) Vasodilator
  oxyfedrine, diltiazem, tolazoline, hexobendine, bamethan, clonidine, methyldopa, guanabenz and the like.
(21) Vasoconstrictor
  dopamine, dobutamine denopamine and the like.
(22) Hypotensive Diuretic
  hexamethonium bromide, pentolinium, mecamylamine, ecarazine, clonidine, diltiazem, nifedipine and the like.
(23) Therapeutic Drug for Diabetes
  tolbutamide, chlorpropamide, acetohexamide, glibenclamide, tolazamide, acarbose, epalrestat, troglitazone, glucagon, glymidine, glipizide, phenformin, buformin, metformin and the like.
(24) Antinarcotic
  levallorphan, nalorphine, naloxone or a salt thereof and the like.
(25) Liposoluble Vitamins
(i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, 5-tocopherol, dl-α-tocopherol nicotinate
(iv) vitamin K: vitamin $K_1$, $K_2$, $K_3$ and $K_4$
(v) folic acid (vitamin M) and the like.
(26) Vitamin Derivative
  various derivatives of vitamins, for example, vitamin $D_3$ derivatives such as 5,6-trans-cholecalciferol, 2,5-hydroxycholecalciferol, 1-α-hydroxycholecalciferol, calcipotriol and the like, vitamin $D_2$ derivatives such as 5,6-trans-ergocalciferol and the like, and the like.
(27) Antiasthmatic
  isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate, ciclesonide and the like.
(28) Therapeutic Agent for Pollakisuria/anischuria
  flavoxate hydrochloride and the like.
(29) Therapeutic Agent for Atopic Dermatitis
  sodium cromoglicate and the like.
(30) Therapeutic Agent for Allergic Rhinitis
  sodium cromoglicate, chlorpheniramine maleate, alimemazine tartrate, clemastine fumarate, homochlorcyclizine hydrochloride, fexofenadine, mequitazine, ketotifen fumarate, cetirizine hydrochloride, oxatomide, azelastine, ebastine, epinastine hydrochloride, loratadine and the like.
(31) Hypertensor
  dopamine, dobutamine, denopamine, digitoxin, digoxin, methyldigoxin, lanatoside C, G-strophanthin and the like.
(32) Others
  hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose varies depending on the kind of the compound of the present invention, administration route, symptom, age of patients and the like. For example, for oral administration to patients (body weight about 60 kg) with inflammatory bowel disease (IBD), about 0.1 mg/kg body weight—about 30 mg/kg body weight, preferably about 1 mg/kg body weight—20 mg/kg body weight, of compound (I) can be administered once to several portions per day.

The dose of the medicament of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human and the like), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in more detail in the following by referring to Examples, Formulation Examples and Experimental Examples, which are not to be construed as limitative and may be modified without departing from the scope of the invention.

Unless particularly specified, the elution in column chromatography in the Examples was performed under observation by TLC (Thin Layer Chromatography). For TLC observation, 60F254 manufactured by Merck was used as a TLC plate, and the solvent used as an elution solvent for column chromatography was used as a developing solvent. For detection, a UV detector was adopted. In silica gel column chromatography, NH means use of aminopropylsilane-bonded silica gel, and Diol means use of 3-(2,3-dihydroxypropoxy)propylsilane-bonded silica gel. In preparative HPLC (high performance liquid chromatography), C18 means use of octadecyl-bonded silica gel. The ratios of elution solvents are volume mixing ratios, unless otherwise specified. The room temperature generally means a temperature about 10° C. to 35° C. For drying extracts, sodium sulfate or magnesium sulfate was used.

In the chemical structure formulas described in Examples, the wavy line bonded to the asymmetric carbon

∼∼∼ means one stereochemical structure which is not determined, and the solid line

――――――― means a mixture of two stereochemical structure.

The abbreviations in the present specification or the Examples mean as follows.
LC: liquid chromatography
MS: mass analysis spectrum
API: atmospheric pressure ionization method
M: molecular weight of the compound
NMR: nuclear magnetic resonance spectrum
Hz: hertz
J: coupling constant
m: multiplet
q: quartet
t: triplet
d: doublet
s: singlet
dt: double triplet
sxt: sextet
brs: broad singlet
quant.: quantitative
ADDP: 1,1'-(azodicarbonyl)dipiperidine
AIBN: 2,2'-azobis(isobutyronitrile)
BINAP: 2,2'-bis(diphenylphosphino)-1,1'-binaphthyl
Boc: tert-butyloxycarbonyl group
Boc$_2$O: di-tert-butyl dicarbonate
CDI: carbonyldiimidazole
COMU: 1-[(1-(cyano-2-ethoxy-2-oxoethylideneaminooxy)-dimethylamino-morpholino)]carbenium hexafluorophosphate
CPME: cyclopentyl methyl ether
DBU: 1,8-diazabicyclo[5.4.0]undec-7-ene
DEAD: diethyl azodicarboxylate
DIAD: diisopropyl azodicarboxylate
DIBAL-H: diisobutylaluminium hydride
DIEA: diisopropylethylamine
DMA: N,N-dimethylacetamide
DMAP: 4-dimethylaminopyridine
DME: dimethoxyethane
DMF: N,N-dimethylformamide
DMSO: dimethyl sulfoxide
DPPA: diphenylphosphoryl azide
Et$_2$O: diethyl ether
EtOH: ethanol
HATU: 2-(1H-7-azabenzotriazol-1-yl)-1,1,3,3-tetramethyluronium hexafluorophosphate
HMDS: 1,1,1,2,2,2-hexamethyldisilane HOBt: 1H-benzo[d][1,2,3]triazol-1-ol hydrate
IPE: diisopropyl ether
MeOH: methanol
M: mol concentration
N: normal concentration
NaHMDS: sodium bis(trimethylsilyl)amide
NBS: N-bromosuccinimide
n-BuLi: 1.6M n-butyllithium/hexane solution
NMP: N-methyl-2-pyrrolidone
Pd(PPh$_3$)$_4$: tetrakis(triphenylphosphine)palladium(0)
Pd$_2$(dba)$_3$: tris(dibenzylideneacetone)dipalladium(0)
PdCl$_2$(dppf): 1,1'-bis(diphenylphosphino)ferrocene-palladium(II) dichloride-dichloromethane complex
PPA: polyphosphoric acid
PPh$_3$: triphenylphosphine
t-: tert-
T3P: 1.6M 2,4,6-tripropyl-1,3,5,2,4,6-trioxatriphosphorinane-2,4,6-trioxide/ethyl acetate solution, or DMF solution
TEA: triethylamine
TFA: trifluoroacetic acid
THF: tetrahydrofuran
TMSCl: trimethylsilyl chloride or trimethylsilane chloride
WSC: N$^1$-((ethylimino)methylene)-N$^3$,N$^3$-dimethylpropane-1,3-diamine hydrochloride
XANTPHOS: 4,5-bis(diphenylphosphino)-9,9-dimethylxanthene Example 1

2-((3-hydroxy-1,2-oxazol-5-yl)carbonyl)-6-methoxy-N-(4-(trimethylsilyl)phenyl)-1,2,3,4-tetrahydroisoquinoline-1-carboxamide (Step 1)

To a 0.5M (4-(bis(trimethylsilyl)amino)phenyl)magnesium chloride/THF solution (100 mL, 50.00 mmol) was added trimethylsilyl chloride (7.03 mL, 55.00 mmol), and the mixture was stirred at room temperature for 30 min. To the reaction mixture was added 0.1N hydrochloric acid with cooling, and the mixture was stirred for 10 min. Then, aqueous sodium hydrogen carbonate solution and ethyl acetate were added thereto, and the organic layer was separated. The organic layer was washed with brine, and dried over magnesium sulfate, and the solvent was evaporated under reduced pressure. The obtained residue was purified by silica gel column chromatography (solvent gradient; 5→30% ethyl acetate/hexane) to give 4-(trimethylsilyl)aniline (6.51 g, 39.4 mmol, 79%) as a pale yellow oil.

$^1$H NMR (300 MHz, DMSO-d$_6$): δ 0.09-0.19 (9H, m), 5.14 (2H, s), 6.49-6.60 (2H, m), 7.09-7.19 (2H, m).

(Step 2)

A solution of 3-(2-aminoethyl)phenol hydrochloride (4.60 g, 26.49 mmol) and 47% ethyl glyoxylate (6.15 mL, 29.14 mmol) in a mixed solvent of toluene/EtOH (50 mL) was heated under reflux for 18 hr. The reaction mixture was concentrated under reduced pressure. The precipitate was collected by filtration, and washed with ethyl acetate/diethyl ether to give ethyl 6-hydroxy-1,2,3,4-tetrahydroisoquinoline-1-carboxylate hydrochloride (6.15 g, 23.86 mmol, 90%) as white crystals.

$^1$H NMR (300 MHz, DMSO-d$_6$): δ 1.25 (3H, t, J=7.0 Hz), 2.94 (2H, t, J=6.2 Hz), 3.35 (1H, brs), 3.38-3.52 (2H, m), 4.26 (2H, q, J=7.1 Hz), 5.27 (1H, s), 6.64 (1H, d, J=2.3 Hz), 6.73 (1H, dd, J=8.7, 2.6 Hz), 7.21 (1H, d, J=8.7 Hz), 9.77 (1H, s), 9.99 (1H, brs) (The exchangeable 1H was not observed)

(Step 3)

Boc$_2$O (5.47 g, 25.06 mmol) was added to a solution of ethyl 6-hydroxy-1,2,3,4-tetrahydroisoquinoline-1-carboxylate hydrochloride (6.15 g, 23.86 mmol) and TEA (3.33 mL, 23.86 mmol) in a mixed solvent of THF (65 mL) and water (25 mL) at room temperature, and the mixture was stirred for 2 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 5-30% ethyl acetate/hexane) to give 1-ethyl 2-tert-butyl 6-hydroxy-3,4-dihydroisoquinoline-1,2(1H)-dicarboxylate (7.85 g, 24.43 mmol, quant.) as a colorless oil.

$^1$H NMR (300 MHz, CDCl$_3$): δ 1.19-1.29 (3H, m), 1.45-1.52 (9H, m), 2.72-2.96 (2H, m), 3.65-3.83 (2H, m), 4.08-4.19 (2H, m), 5.16-5.50 (2H, m), 6.63 (1H, s), 6.67-6.73 (1H, m), 7.31-7.37 (1H, m).

(Step 4)

Iodomethane (3.04 mL, 48.85 mmol) was added to a solution of 1-ethyl 2-tert-butyl 6-hydroxy-3,4-dihydroisoquinoline-1,2(1H)-dicarboxylate (7.85 g, 24.43 mmol) and cesium carbonate (10.35 g, 31.75 mmol) in DMF (50 mL) at room temperature, and the mixture was stirred for 2.5 hr. To the reaction mixture was added water, and the mixture was extracted three times with ethyl acetate. The organic layer was washed with 0.1% aqueous sodium thiosulfate solution and brine, and dried over magnesium sulfate, and the solvent was evaporated under reduced pressure to give 1-ethyl 2-tert-butyl 6-methoxy-3,4-dihydroisoquinoline-1,2(1H)-dicarboxylate (8.23 g, 24.54 mmol, 100%) as a colorless oil.

$^1$H NMR (300 MHz, CDCl$_3$): δ 1.20-1.29 (3H, m), 1.46-1.51 (9H, m), 2.75-2.99 (2H, m), 3.69-3.81 (5H, m), 4.08-4.19 (2H, m), 5.33-5.51 (1H, m), 6.68 (1H, s), 6.77 (1H, dd, J=8.3, 2.6 Hz), 7.36-7.43 (1H, m).

(Step 5)

2N Aqueous lithium hydroxide solution (73.6 mL, 147.23 mmol) was added to a solution of 1-ethyl 2-tert-butyl 6-methoxy-3,4-dihydroisoquinoline-1,2(1H)-dicarboxylate (8.23 g, 24.54 mmol) in a mixed solvent of EtOH (35 mL) and THF (35 mL) at room temperature, and the mixture was stirred for 2 hr. To the reaction mixture was added water, 2N hydrochloric acid was added thereto until the pH of the mixture became 3, and the mixture was extracted three times with ethyl acetate. The organic layer was washed with brine, and dried over magnesium sulfate, and the solvent was evaporated under reduced pressure to give 2-(tert-butoxycarbonyl)-6-methoxy-1,2,3,4-tetrahydroisoquinoline-1-carboxylic acid (7.59 g, 24.70 mmol, quant.) as a colorless oil.

$^1$H NMR (300 MHz, CDCl$_3$): δ 1.41-1.52 (9H, m), 2.72-3.00 (2H, m), 3.56-3.67 (1H, m), 3.71-3.87 (4H, m), 5.33-5.53 (1H, m), 6.68 (1H, d, J=2.3 Hz), 6.77 (1H, dd, J=8.7, 2.3 Hz), 7.37 (1H, d, J=8.7 Hz) (The exchangeable 1H was not observed).

(Step 6)

HATU (2.281 g, 6.00 mmol) was added to a solution of 2-(tert-butoxycarbonyl)-6-methoxy-1,2,3,4-tetrahydroisoquinoline-1-carboxylic acid (1.537 g, 5 mmol), 4-(trimethylsilyl)aniline (0.827 g, 5.00 mmol) and DIEA (1.742 mL, 10.00 mmol) in DMF (20 mL) at room temperature, and the mixture was stirred at room temperature for 15 hr. To the reaction mixture was added aqueous sodium hydrogen carbonate solution, and the mixture was extracted three times with ethyl acetate. The organic layer was washed with brine, and dried over magnesium sulfate, and the solvent was evaporated under reduced pressure. The precipitate was washed with IPE/hexane to give tert-butyl 6-methoxy-1-((4-(trimethylsilyl)phenyl)carbamoyl)-3,4-dihydroisoquinoline-2(1H)-carboxylate (1.86 g, 4.09 mmol, 82%) as white crystals.

$^1$H NMR (300 MHz, CDCl$_3$): δ 0.23 (9H, s), 1.52 (9H, s), 2.79-3.02 (3H, m), 3.51-3.87 (5H, m), 5.62 (1H, brs), 6.72 (1H, d, J=2.3 Hz), 6.81 (1H, dd, J=8.3, 2.6 Hz), 7.41-7.54 (4H, m), 8.82 (1H, brs).

(Step 7)

Cooled TFA (25 mL) was added to tert-butyl 6-methoxy-1-((4-(trimethylsilyl)phenyl)carbamoyl)-3,4-dihydroisoquinoline-2(1H)-carboxylate (1.86 g, 4.09 mmol), and the mixture was stirred at room temperature for 5 min. The reaction mixture was added to ice and aqueous sodium hydrogen carbonate solution, and potassium carbonate was added thereto until the pH of the mixture became 8. Then, the mixture was extracted three times with a mixed solvent of ethyl acetate/THF (3:1). The organic layer was washed with brine, and dried over magnesium sulfate, and the solvent was evaporated under reduced pressure. The precipitate was washed with IPE/hexane to give 6-methoxy-N-(4-(trimethylsilyl)phenyl)-1,2,3,4-tetrahydroisoquinoline-1-carboxamide (1.12 g, 3.16 mmol, 77%) as white crystals.

$^1$H NMR (300 MHz, CDCl$_3$): δ 0.23 (9H, s), 1.83 (1H, brs), 2.70-2.81 (1H, m), 2.84-2.96 (1H, m), 3.14 (2H, t, J=5.7 Hz), 3.78 (3H, s), 4.63 (1H, s), 6.64 (1H, s), 6.78 (1H, dd, J=8.7, 2.3 Hz), 7.44 (2H, d), 7.51-7.59 (3H, m), 9.33 (1H, brs).

(Step 8)

HATU (319 mg, 0.84 mmol) was added to a solution of 6-methoxy-N-(4-(trimethylsilyl)phenyl)-1,2,3,4-tetrahydroisoquinoline-1-carboxamide (248 mg, 0.70 mmol), 3-hydroxy-1,2-oxazole-5-carboxylic acid (95 mg, 0.73 mmol) and DIEA (244 μL, 1.40 mmol) in DMF (3.5 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 30→100% ethyl acetate/hexane), and the precipitate was washed with IPE/hexane to give the title compound (109.1 mg, 0.234 mmol, 33.5%) as white crystals.

MS(API): Calculated 465.6. Found 466.1 (M+H).

$^1$H NMR (300 MHz, CDCl$_3$): δ 0.23 (9H, s), 1.25-1.30 (1H, m), 3.04-3.12 (2H, m), 3.82 (3H, s), 3.85-3.97 (1H, m), 4.08-4.18 (1H, m), 6.00 (1H, s), 6.54 (1H, s), 6.77 (1H, d, J=2.6 Hz), 6.85 (1H, dd, J=8.7, 2.6 Hz), 7.17 (1H, d, J=8.7 Hz), 7.45 (2H, d), 7.52 (2H, d), 8.68 (1H, s).

Example 2

6-methoxy-2-((6-oxo-1,6-dihydropyridin-3-yl)carbonyl)-N-(4-(trimethylsilyl)phenyl)-1,2,3,4-tetrahydroisoquinoline-1-carboxamide HATU (319 mg, 0.84 mmol) was added to a solution of 6-methoxy-N-(4-(trimethylsilyl)phenyl)-1,2,3,4-tetrahydroisoquinoline-1-carboxamide (248 mg, 0.70 mmol), 6-oxo-1,6-dihydropyridine-3-carboxylic acid (102 mg, 0.73 mmol) and DIEA (244 μL, 1.40 mmol) in DMF (3.5 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 0→8% MeOH/ethyl acetate), and the precipitate was washed with ethyl acetate/IPE to give the title compound (58.2 mg, 0.122 mmol, 17.49%) as white crystals.

MS(API): Calculated 475.6. Found 474.2 (M−H).

$^1$H NMR (300 MHz, DMSO-d$_6$): δ 0.21 (9H, s), 2.83-2.94 (1H, m), 3.03-3.15 (1H, m), 3.70-3.81 (4H, m), 3.98-4.08 (1H, m), 5.63 (1H, s), 6.36 (1H, d, J=9.4 Hz), 6.81-6.86 (2H, m), 7.43 (2H, d, J=8.3 Hz), 7.49-7.60 (4H, m), 7.67 (1H, brs), 10.45 (1H, brs), 11.89 (1H, brs).

Example 3

N-(3-fluoro-4-(trimethylsilyl)phenyl)-2-((3-hydroxy-1,2-oxazol-5-yl)carbonyl)-6-methoxy-1,2,3,4-tetrahydroisoquinoline-1-carboxamide (Step 1)

A solution of 1-chloro-2-fluoro-4-nitrobenzene (2.63 g, 15 mmol), HMDS (8.12 g, 55.50 mmol) and Pd(PPh$_3$)$_4$ (0.433 g, 0.38 mmol) in xylene (6.5 mL) was stirred under microwave irradiation at 200° C. for 1 hr. To the reaction mixture was added ethyl acetate (about 150 mL), and the insoluble substance was removed by filtration. The filtrate was concentrated under reduced pressure, and the obtained residue was purified by NH-silica gel column chromatography (solvent gradient; 2→5% ethyl acetate/hexane) to give (2-fluoro-4-nitrophenyl)trimethylsilane (3.22 g, 15.10 mmol, 101%) as a yellow oil.

$^1$H NMR (300 MHz, CDCl$_3$): δ 0.36 (9H, d, J=1.1 Hz), 7.57 (1H, dd, J=8.1, 5.5 Hz), 7.82 (1H, dd, J=8.1, 2.1 Hz), 7.99 (1H, dd, J=8.1, 2.1 Hz).

(Step 2)

A solution of (2-fluoro-4-nitrophenyl)trimethylsilane (3.22 g, 15.10 mmol) and 10% palladium-carbon (1.0 g, 0.47 mmol, 50% wet) in MeOH (65 mL) was stirred at room temperature for 3.5 hr under hydrogen atmosphere (1 atm). The catalyst was removed by filtration, and the filtrate was concentrated under reduced pressure. The obtained residue was purified by silica gel column chromatography (solvent gradient; 2-15% MeOH/ethyl acetate) to give 3-fluoro-4-(trimethylsilyl)aniline (1.89 g, 10.31 mmol, 68.3%) as a colorless oil.

$^1$H NMR (300 MHz, CDCl$_3$): δ 0.26 (9H, d, J=0.8 Hz), 3.79 (2H, brs), 6.31 (1H, dd, J=10.6, 2.3 Hz), 6.44 (1H, dd, J=7.9, 1.9 Hz), 7.13 (1H, dd, J=7.9, 6.8 Hz).

(Step 3)

T3P (4.46 mL, 7.50 mmol) was added to a solution of 2-(tert-butoxycarbonyl)-6-methoxy-1,2,3,4-tetrahydroisoquinoline-1-carboxylic acid (1.537 g, 5 mmol), 3-fluoro-4-(trimethylsilyl)aniline (0.916 g, 5.00 mmol), DIEA (4.35 mL, 25.00 mmol) and DMAP (0.672 g, 5.50 mmol) in ethyl acetate (35 mL), and the mixture was stirred at 70° C. for 18 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 2→20% ethyl acetate/hexane), and the precipitate was washed with IPE/hexane to give tert-butyl 1-((3-fluoro-4-(trimethylsilyl)phenyl)carbamoyl)-6-methoxy-3,4-dihydroisoquinoline-2(1H)-carboxylate (1.85 g, 3.91 mmol, 78%) as white crystals.

$^1$H NMR (300 MHz, CDCl$_3$): δ 0.27 (9H, s), 1.52 (9H, s), 2.80-2.96 (2H, m), 3.55-3.76 (2H, m), 3.80 (3H, s), 5.61 (1H, brs), 6.72 (1H, d, J=2.3 Hz), 6.81 (1H, dd, J=8.3, 2.6

Hz), 7.09 (1H, d, J=7.9 Hz), 7.24-7.30 (2H, m), 7.39 (1H, dd, J=10.6, 1.9 Hz), 9.00 (1H, brs).

(Step 4)

Cooled TFA (25 mL) was added to tert-butyl 1-((3-fluoro-4-(trimethylsilyl)phenyl)carbamoyl)-6-methoxy-3,4-dihydroisoquinoline-2(1H)-carboxylate (1.85 g, 3.91 mmol), and the mixture was stirred at room temperature for 2 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The precipitate was washed with ethyl acetate. The filtrate was concentrated, the obtained residue was purified by silica gel column chromatography (solvent gradient; 0-5% MeOH/ethyl acetate), and the precipitate was combined with the previously-obtained precipitate, and washed with IPE/hexane to give N-(3-fluoro-4-(trimethylsilyl)phenyl)-6-methoxy-1,2,3,4-tetrahydroisoquinoline-1-carboxamide (919 mg, 2.467 mmol, 63.0%) as white crystals.

$^1$H NMR (300 MHz, CDCl$_3$): δ 0.27 (9H, d, J=1.1 Hz), 2.23 (1H, brs), 2.69-2.80 (1H, m), 2.84-2.94 (1H, m), 3.14 (2H, t, J=5.9 Hz), 3.78 (3H, s), 4.63 (1H, s), 6.64 (1H, d, J=2.6 Hz), 6.78 (1H, dd, J=8.7, 2.6 Hz), 7.17 (1H, dd), 7.24-7.30 (1H, m), 7.45 (1H, dd, J=10.6, 1.9 Hz), 7.53 (1H, d, J=8.7 Hz), 9.45 (1H, s)

(Step 5)

HATU (561 mg, 1.48 mmol) was added to a solution of N-(3-fluoro-4-(trimethylsilyl)phenyl)-6-methoxy-1,2,3,4-tetrahydroisoquinoline-1-carboxamide (458 mg, 1.23 mmol), 3-hydroxy-1,2-oxazole-5-carboxylic acid (167 mg, 1.29 mmol) and DIEA (428 μL, 2.46 mmol) in DMF (6 mL) at room temperature, and the mixture was stirred at room temperature for 15 hr. To the reaction mixture was added water, and the mixture was extracted three times with a mixed solvent of ethyl acetate/THF (3:1). The organic layer was washed with brine, and dried over magnesium sulfate, and the solvent was evaporated under reduced pressure. The obtained residue was purified by silica gel column chromatography (solvent gradient; 30→100% ethyl acetate/hexane), and the precipitate was washed with IPE/hexane to give the title compound (272.4 mg, 0.563 mmol, 45.8%) as white crystals.

MS(API): Calculated 483.6. Found 484.2 (M+H).

$^1$H NMR (300 MHz, CDCl$_3$): δ 0.27 (9H, s), 1.72 (1H, brs), 3.08 (2H, t, J=5.7 Hz), 3.82 (3H, s), 3.87-3.97 (1H, m), 4.09-4.19 (1H, m), 5.98 (1H, s), 6.56 (1H, s), 6.77 (1H, d, J=2.3 Hz), 6.85 (1H, dd, J=8.5, 2.5 Hz), 7.12-7.20 (2H, m), 7.25-7.31 (1H, m), 7.39 (1H, dd, J=10.6, 1.5 Hz), 8.85 (1H, s).

Example 4

N-(3-fluoro-4-(trimethylsilyl)phenyl)-6-methoxy-2-((6-oxo-1,6-dihydropyridin-3-yl)carbonyl)-1,2,3,4-tetrahydroisoquinoline-1-carboxamide HATU (561 mg, 1.48 mmol) was added to a solution of N-(3-fluoro-4-(trimethylsilyl)phenyl)-6-methoxy-1,2,3,4-tetrahydroisoquinoline-1-carboxamide (458 mg, 1.23 mmol), 6-oxo-1,6-dihydropyridine-3-carboxylic acid (180 mg, 1.29 mmol) and DIEA (428 μL, 2.46 mmol) in DMF (6 mL) at room temperature, and the mixture was stirred for 15 hr. To the reaction mixture was added water, and the mixture was extracted three times with a mixed solvent of ethyl acetate/THF (3:1). The organic layer was washed with brine, and dried over magnesium sulfate, and the solvent was evaporated under reduced pressure to give a precipitate. The precipitate was washed with IPE/hexane, and recrystallized from MeOH/ethyl acetate to give the title compound (394.6 mg, 0.799 mmol, 65.0%) as white crystals.

MS(API): Calculated 493.6. Found 492.2 (M–H).

$^1$H NMR (300 MHz, DMSO-d$_6$): δ 0.25 (9H, s), 2.83-2.94 (1H, m), 3.03-3.15 (1H, m), 3.66-3.81 (4H, m), 3.98-4.08 (1H, m), 5.60 (1H, s), 6.36 (1H, d, J=9.8 Hz), 6.81-6.87 (2H, m), 7.28-7.39 (2H, m), 7.44-7.53 (2H, m), 7.58 (1H, d, J=9.1 Hz), 7.68 (1H, brs), 10.69 (1H, brs), 11.91 (1H, brs).

Example 5

4-((3-hydroxy-1,2-oxazol-5-yl)carbonyl)-8-methoxy-N-(4-(trimethylsilyl)phenyl)-2,3,4,5-tetrahydro-1,4-benzoxazepine-5-carboxamide (Step 1)

Boc$_2$O (16.67 g, 76.39 mmol) was added to a solution of 2-(benzylamino)ethanol (11.00 g, 72.75 mmol) in THF (220 mL) at room temperature, and the mixture was stirred at room temperature for 16 hr. The reaction mixture was concentrated under reduced pressure. The obtained residue was purified by silica gel column chromatography (solvent gradient; 10→60% ethyl acetate/hexane) to give tert-butyl benzyl(2-hydroxyethyl)carbamate (18.26 g, 72.7 mmol, 100%) as a colorless oil.

$^1$H NMR (300 MHz, CDCl$_3$): δ 1.47 (9H, s), 3.03 (1H, brs), 3.40 (2H, brs), 3.65-3.75 (2H, m), 4.48 (2H, brs), 7.21-7.37 (5H, m).

(Step 2)

1.9 M DIAD toluene solution (47.8 mL, 90.87 mmol) was added to a solution of tert-butyl benzyl(2-hydroxyethyl)carbamate (18.27 g, 72.69 mmol), 3-methoxyphenol (7.52 g, 60.58 mmol) and triphenylphosphine (23.83 g, 90.87 mmol) in THF (250 mL) at 0° C. under argon gas atmosphere, and the mixture was stirred at room temperature for 3 days. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 2→15% ethyl acetate/hexane) to give tert-butyl benzyl(2-(3-methoxyphenoxy)ethyl)carbamate (8.83 g, 24.70 mmol, 40.8%) as a colorless oil.

$^1$H NMR (300 MHz, CDCl$_3$): δ 1.41-1.53 (9H, m), 3.47-3.63 (2H, m), 3.78 (3H, s), 3.97-4.14 (2H, m), 4.57 (2H, brs), 6.39-6.53 (3H, m), 7.16 (1H, t, J=8.1 Hz), 7.22-7.36 (5H, m).

(Step 3)

Cooled TFA (30 mL) was added to tert-butyl benzyl(2-(3-methoxyphenoxy)ethyl)carbamate (8.83 g, 24.70 mmol), and the mixture was stirred at room temperature for 15 min. The reaction mixture was added to ice and aqueous sodium hydrogen carbonate solution, and 8N aqueous sodium hydroxide solution and potassium carbonate were added thereto until the pH of the mixture became 8. Then, the mixture was extracted three times with ethyl acetate. The organic layer was washed with brine, and dried over magnesium sulfate, and the solvent was evaporated under reduced pressure to give N-benzyl-2-(3-methoxyphenoxy)ethanamine (6.34 g, 24.64 mmol, 100%) as a colorless oil.

¹H NMR (300 MHz, CDCl₃): δ 1.71 (1H, brs), 3.02 (2H, t, J=5.3 Hz), 3.78 (3H, s), 3.88 (2H, s), 4.08 (2H, t, J=5.3 Hz), 6.46-6.53 (3H, m), 7.17 (1H, t, J=8.1 Hz), 7.27-7.38 (5H, m).

(Step 4)

A solution of methyl 2-methoxyacetate (2.82 g, 27.10 mmol), NBS (5.04 g, 28.33 mmol) and AIBN (0.081 g, 0.49 mmol) in trifluoromethylbenzene (50 mL) was stirred at 80° C. for 5 hr. The reaction solution was cooled, and the precipitate was removed by filtration. The filtrate was concentrated under reduced pressure to give an oil. The obtained oil was added to a solution of N-benzyl-2-(3-methoxyphenoxy)ethanamine (6.34 g, 24.64 mmol) and DIEA (5.15 mL, 29.57 mmol) in THF (60 mL) at room temperature, and the mixture was stirred at room temperature for 1 hr. The reaction mixture was added to aqueous sodium hydrogen carbonate solution, and the mixture was extracted three times with ethyl acetate. The organic layer was washed with brine, and dried over magnesium sulfate, and the solvent was evaporated under reduced pressure. The obtained residue was purified by NH-silica gel column chromatography (solvent gradient; 2→20% ethyl acetate/hexane) to give methyl 2-(benzyl(2-(3-methoxyphenoxy)ethyl)amino)-2-methoxyacetate (6.72 g, 18.70 mmol, 76%) as a colorless oil.

¹H NMR (300 MHz, CDCl₃): δ 3.12 (2H, td, J=5.9, 1.5 Hz), 3.39 (3H, s), 3.77 (3H, s), 3.77 (3H, s), 3.87-4.08 (4H, m), 4.48 (1H, s), 6.38-6.53 (3H, m), 7.15 (1H, t, J=8.1 Hz), 7.24-7.39 (5H, m).

(Step 5)

Chlorotrimethylsilane (2.85 mL, 22.44 mmol) was added to a solution of methyl 2-(benzyl(2-(3-methoxyphenoxy)ethyl)amino)-2-methoxyacetate (6.72 g, 18.70 mmol) in acetonitrile (75 mL) at 0° C., and the mixture was stirred at room temperature for 1 hr. The reaction mixture was added to aqueous sodium hydrogen carbonate solution, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 3-80% ethyl acetate/hexane) to give methyl 4-benzyl-8-methoxy-2,3,4,5-tetrahydrobenzo[f][1,4]oxazepine-5-carboxylate (3.65 g, 11.15 mmol, 59.6%) as a colorless oil.

¹H NMR (300 MHz, CDCl₃): δ 2.97 (1H, ddd), 3.56 (1H, ddd, J=14.5, 8.7, 2.5 Hz), 3.67-3.82 (7H, m), 3.95 (1H, d, J=13.6 Hz), 3.98-4.06 (1H, m), 4.12-4.20 (1H, m), 4.49 (1H, s), 6.58 (1H, dd), 6.61 (1H, d), 6.87 (1H, d, J=8.3 Hz), 7.23-7.38 (5H, m).

(Step 6)

A solution of methyl 4-benzyl-8-methoxy-2,3,4,5-tetrahydrobenzo[f][1,4]oxazepine-5-carboxylate (3.65 g, 11.15 mmol) and 10% palladium-carbon (1.2 g, 0.56 mmol, 50% wet) in MeOH (75 mL) was stirred at room temperature for 3 hr under hydrogen atmosphere (1 atm). The catalyst was removed by filtration, and the filtrate was concentrated under reduced pressure to give methyl 8-methoxy-2,3,4,5-tetrahydrobenzo[f][1,4]oxazepine-5-carboxylate (2.54 g, 10.71 mmol, 96%) as a colorless oil.

¹H NMR (300 MHz, CDCl₃): δ 2.13 (1H, brs), 3.16 (1H, ddd), 3.35 (1H, ddd), 3.78 (3H, s), 3.78 (3H, s), 3.99 (1H, ddd), 4.05-4.12 (1H, m), 4.70 (1H, s), 6.59 (1H, dd), 6.62 (1H, d), 6.95 (1H, d, J=8.3 Hz).

(Step 7)

HATU (2.442 g, 6.42 mmol) was added to a solution of methyl 8-methoxy-2,3,4,5-tetrahydrobenzo[f][1,4]oxazepine-5-carboxylate (1.27 g, 5.35 mmol), 3-hydroxy-1,2-oxazole-5-carboxylic acid (0.725 g, 5.62 mmol) and DIEA (1.865 mL, 10.71 mmol) in DMF (25 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane) to give methyl 4-(3-hydroxy-1,2-oxazole-5-carbonyl)-8-methoxy-2,3,4,5-tetrahydrobenzo[f][1,4]oxazepine-5-carboxylate (1.80 g, 5.17 mmol, 97%) as a colorless oil.

¹H NMR (300 MHz, CDCl₃): δ 1.35 (1H, s), 3.71-3.77 (3H, m), 3.79-3.83 (3H, m), 3.96-4.23 (3H, m), 4.38-4.47 (1H, m), 5.75-6.24 (1H, m), 6.46-6.50 (1H, m), 6.60 (1H, d, J=2.6 Hz), 6.67 (1H, dd, J=8.3, 2.6 Hz), 7.07-7.29 (1H, m).

(Step 8)

2N Aqueous lithium hydroxide solution (10.28 mL, 20.56 mmol) was added to a solution of methyl 4-(3-hydroxy-1,2-oxazole-5-carbonyl)-8-methoxy-2,3,4,5-tetrahydrobenzo[f][1,4]oxazepine-5-carboxylate (1.79 g, 5.14 mmol) in a mixed solvent of MeOH (7.5 mL) and THF (7.5 mL) at room temperature, and the mixture was stirred at room temperature for 1.5 hr. To the reaction mixture was added water, 2N hydrochloric acid was added thereto until the pH of the mixture became 2, and the mixture was extracted three times with a mixed solvent of ethyl acetate/THF. The organic layer was washed with brine, and dried over magnesium sulfate, and the solvent was evaporated under reduced pressure. The precipitate was washed with IPE/hexane to give 4-(3-hydroxy-1,2-oxazole-5-carbonyl)-8-methoxy-2,3,4,5-tetrahydrobenzo[f][1,4]oxazepine-5-carboxylic acid (1.07 g, 3.20 mmol, 62.3%) as white crystals.

¹H NMR (300 MHz, DMSO-d₆): δ 3.74 (3H, s), 3.88-4.18 (3H, m), 4.26-4.35 (1H, m), 5.73-6.14 (1H, m), 6.33-6.53 (1H, m), 6.56 (1H, d, J=2.3 Hz), 6.66 (1H, dd, J=8.3, 2.6 Hz), 7.18-7.37 (1H, m), 11.77 (1H, brs), 13.23 (1H, brs).

(Step 9)

HATU (274 mg, 0.72 mmol) was added to a solution of 4-(3-hydroxy-1,2-oxazole-5-carbonyl)-8-methoxy-2,3,4,5-tetrahydrobenzo[f][1,4]oxazepine-5-carboxylic acid (201 mg, 0.60 mmol), 4-(trimethylsilyl)aniline (104 mg, 0.63 mmol) and DIEA (209 μL, 1.20 mmol) in DMF (3 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 30→100% ethyl acetate/hexane), and the precipitate was washed with IPE/hexane to give the title compound (81.7 mg, 0.170 mmol, 28.2%) as pale yellow crystals.

MS(API): Calculated 481.6. Found 482.1 (M+H).

¹H NMR (300 MHz, CDCl₃): δ 0.22 (9H, s), 1.83 (1H, brs), 3.73-4.24 (6H, m), 4.34-4.60 (1H, m), 5.87-6.41 (1H, m), 6.49 (1H, s), 6.68-6.77 (2H, m), 7.15-7.34 (2H, m), 7.36 (2H, d, J=8.3 Hz), 7.43 (2H, d).

Example 6

8-methoxy-4-((6-oxo-1,6-dihydropyridin-3-yl)carbonyl)-N-(4-(trimethylsilyl)phenyl)-2,3,4,5-tetrahydro-1,4-benzoxazepine-5-carboxamide The title compound was obtained using methyl 8-methoxy-2,3,4,5-tetrahydrobenzo[f][1,4]oxazepine-5-carboxylate and 6-oxo-1,6-dihydropyridine-3-carboxylic acid, by the reaction and purification in the same manner as in Steps 7 to 9 of Example 5.

MS(API): Calculated 491.6. Found 490.2 (M−H).

$^1$H NMR (300 MHz, CDCl$_3$): δ 0.23 (9H, s), 1.60 (1H, brs), 3.84 (3H, s), 3.87-4.02 (3H, m), 4.33-4.43 (2H, m), 6.59 (1H, d, J=9.4 Hz), 6.69 (1H, s), 6.73 (1H, dd), 7.26 (1H, s), 7.35 (2H, d), 7.43 (2H, d), 7.64 (1H, dd, J=9.4, 2.3 Hz), 7.74 (1H, d, J=1.5 Hz), 12.15 (1H, brs).

Example 7

(1R)-N-(3-fluoro-4-(trimethylsilyl)phenyl)-2-((3-hydroxy-1,2-oxazol-5-yl)carbonyl)-6-methoxy-1,2,3,4-tetrahydroisoquinoline-1-carboxamide N-(3-Fluoro-4-(trimethylsilyl)phenyl)-2-((3-hydroxy-1,2-oxazol-5-yl)carbonyl)-6-methoxy-1,2,3,4-tetrahydroisoquinoline-1-carboxamide (220 mg) was resolved by chiral column chromatography. The fraction having a shorter retention time was concentrated to give the title compound (105.5 mg, >99% ee) as a white solid.

MS(API): Calculated 483.6. Found 484.2 (M+H).

purification condition by chiral column chromatography
  column: CHIRALPAK IA(MB001) 20 mmID×250 mmL
  solvent: CO$_2$/MeOH=600/400
  backpressure: 100 bar
  temperature: 35° C.
  detection method: UV 220 nm
  $[α]_D^{20}$-18.0 (c 0.2500, MeOH)

Example 8

(1R)-N-(3-fluoro-4-(trimethylsilyl)phenyl)-6-methoxy-2-((6-oxo-1,6-dihydropyridin-3-yl)carbonyl)-1,2,3,4-tetrahydroisoquinoline-1-carboxamide N-(3-Fluoro-4-(trimethylsilyl)phenyl)-6-methoxy-2-((6-oxo-1,6-dihydropyridin-3-yl)carbonyl)-1,2,3,4-tetrahydroisoquinoline-1-carboxamide (290 mg) was resolved by chiral column chromatography. The fraction having a shorter retention time was concentrated to give the title compound (137.0 mg, >99% ee) as a white solid.

MS(API): Calculated 493.6. Found 492.2 (M−H).

purification condition by chiral column chromatography
  column: CHIRALPAK ASH(LA005) 20 mmID×250 mmL
  solvent: CO$_2$/MeOH/acetonitrile=600/200/200
  backpressure: 100 bar
  temperature: 35° C.
  detection method: UV 220 nm
  $[α]_D^{25}$−16.1 (c 0.2500, MeOH)

Example 9

N-(4-tert-butyl-3-fluorophenyl)-2-((3-hydroxy-1,2-oxazol-5-yl)carbonyl)-6-methoxy-1,2,3,4-tetrahydroisoquinoline-1-carboxamide (Step 1)

2-(tert-Butyl)aniline (10 g, 67.01 mmol) was slowly added dropwise to sulfuric acid (63.8 mL, 670.09 mmol) while the mixture was maintained at 10° C. or below. Then, potassium nitrate (6.77 g, 67.01 mmol) was slowly added thereto while the mixture was maintained at 10° C. or below. The reaction mixture was stirred at 5° C. for 30 min, and then at room temperature for 1 hr. The reaction mixture was poured into ice (about 500 g), and the mixture was extracted with diethyl ether. The organic layer was washed with brine, and dried over magnesium sulfate, and the solvent was evaporated under reduced pressure. The obtained residue was purified by silica gel column chromatography (solvent; 20% ethyl acetate/hexane), and crystallized from hexane to give 2-(tert-butyl)-5-nitroaniline (12.26 g, 63.1 mmol, 94%) as a pale yellow solid.

$^1$H NMR (300 MHz, CDCl$_3$): δ 1.44 (9H, s), 3.81-4.32 (2H, m), 7.34 (1H, d, J=8.7 Hz), 7.46 (1H, d, J=2.3 Hz), 7.49-7.59 (1H, m).

(Step 2)

A solution of 2-(tert-butyl)-5-nitroaniline (2054 mg, 10.58 mmol) and nitrosonium tetrafluoroborate (0.920 mL, 17.21 mmol) in o-dichlorobenzene (20 mL) was stirred at 0° C. for 1 hr. The reaction mixture was stirred at 110° C. for 1 hr, cooled, and poured into water. The mixture was extracted with ethyl acetate. The organic layer was washed with brine, and dried over magnesium sulfate, and the solvent was evaporated under reduced pressure. The obtained residue was purified by silica gel column chromatography (solvent gradient; 0→10% ethyl acetate/hexane) to give 1-(tert-butyl)-2-fluoro-4-nitrobenzene (1600 mg, 8.11 mmol, 60.4%) as a brown oil.

$^1$H NMR (300 MHz, CDCl$_3$): δ 1.42 (9H, d, J=1.1 Hz), 7.48 (1H, t, J=8.3 Hz), 7.87 (1H, dd, J=11.9, 2.5 Hz), 7.96 (1H, dd, J=8.7, 2.3 Hz).

(Step 3)

A solution of 1-(tert-butyl)-2-fluoro-4-nitrobenzene (1.6 g, 8.11 mmol) and 10% palladium-carbon (0.432 g, 0.20 mmol, 50% wet) in EtOH (20 mL) was stirred under hydrogen atmosphere (1 atm) at room temperature for 5 hr. The catalyst was removed by filtration, and the filtrate was concentrated under reduced pressure. The obtained residue was purified by silica gel column chromatography (solvent gradient; 0→20% ethyl acetate/hexane) to give 4-(tert-butyl)-3-fluoroaniline (1.310 g, 7.83 mmol, 97%) as a brown oil.

$^1$H NMR (300 MHz, CDCl$_3$): δ 1.32 (9H, d, J=1.1 Hz), 3.61 (2H, brs), 6.26-6.46 (2H, m), 6.95-7.12 (1H, m).

(Step 4)

T3P (12.06 mL, 20.27 mmol) was added to a solution of 2-(tert-butoxycarbonyl)-6-methoxy-1,2,3,4-tetrahydroisoquinoline-1-carboxylic acid (4.15 g, 13.51 mmol), 4-(tert-butyl)-3-fluoroaniline (2.26 g, 13.51 mmol), DIEA (11.77 mL, 67.57 mmol) and DMAP (1.816 g, 14.87 mmol) in ethyl acetate (95 mL), and the mixture was stirred at 70° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with IPE/hexane to give tert-butyl 1-((4-(tert-butyl)-3-fluorophenyl)carbamoyl)-6-methoxy-3,4-dihydroisoquinoline-2(1H)-carboxylate (5.22 g, 11.43 mmol, 85%) as white crystals.

$^1$H NMR (300 MHz, CDCl$_3$): δ 1.33 (9H, s), 1.52 (9H, s), 2.80-2.97 (2H, m), 3.52-3.77 (2H, m), 3.80 (3H, s), 5.61 (1H, brs), 6.72 (1H, d, J=2.3 Hz), 6.81 (1H, dd, J=8.3, 2.6 Hz), 7.03 (1H, d, J=7.6 Hz), 7.14-7.22 (2H, m), 7.39 (1H, dd, J=14.4, 2.3 Hz), 8.88 (1H, brs).

(Step 5)

TFA (3 mL) was added to tert-butyl 1-((4-(tert-butyl)-3-fluorophenyl)carbamoyl)-6-methoxy-3,4-dihydroisoquinoline-2(1H)-carboxylate (214 mg, 0.47 mmol), and the mixture was stirred at room temperature for 30 min. The reaction mixture was added to aqueous sodium hydrogen carbonate solution, and potassium carbonate was added thereto until the pH of the mixture became 8. Then, the mixture was extracted three times with a mixed solvent of ethyl acetate/THF. The organic layer was washed with brine, and dried over magnesium sulfate, and the solvent was evaporated under reduced pressure to give N-(4-(tert-butyl)-3-fluorophenyl)-6-methoxy-1,2,3,4-tetrahydroisoquinoline-1-carboxamide (155 mg, 0.435 mmol, 93%) as a white solid.

$^1$H NMR (300 MHz, CDCl$_3$): δ 1.34 (9H, s), 2.20 (1H, brs), 2.69-2.80 (1H, m), 2.83-2.95 (1H, m), 3.14 (2H, t), 3.78 (3H, s), 4.62 (1H, s), 6.63 (1H, d, J=2.6 Hz), 6.78 (1H, dd, J=8.7, 2.6 Hz), 7.10 (1H, dd), 7.18 (1H, t), 7.44 (1H, dd, J=14.4, 2.3 Hz), 7.53 (1H, d, J=8.7 Hz), 9.35 (1H, brs).

(Step 6)

HATU (195 mg, 0.51 mmol) was added to a solution of N-(4-(tert-butyl)-3-fluorophenyl)-6-methoxy-1,2,3,4-tetrahydroisoquinoline-1-carboxamide (152 mg, 0.43 mmol), 3-hydroxy-1,2-oxazole-5-carboxylic acid (57.8 mg, 0.45 mmol) and DIEA (149 μL, 0.86 mmol) in DMF (2 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 30→100% ethyl acetate/hexane), and the precipitate was washed with diethyl ether to give the title compound (102.4 mg, 0.219 mmol, 51.4%) as white crystals.

MS(API): Calculated 467.5. Found 468.2 (M+H).

$^1$H NMR (300 MHz, CDCl$_3$): δ 1.33 (9H, s), 3.04-3.12 (2H, m), 3.82 (3H, s), 3.86-3.96 (1H, m), 4.08-4.19 (1H, m), 5.97 (1H, s), 6.55 (1H, s), 6.77 (1H, d, J=2.3 Hz), 6.85 (1H, dd, J=8.5, 2.5 Hz), 7.09 (1H, dd), 7.14-7.23 (2H, m), 7.40 (1H, dd, J=14.4, 1.9 Hz), 8.72 (1H, s), 10.24 (1H, brs).

Example 10

N-(4-tert-butyl-3-chlorophenyl)-2-((3-hydroxy-1,2-oxazol-5-yl)carbonyl)-6-methoxy-1,2,3,4-tetrahydroisoquinoline-1-carboxamide (Step 1)

A solution of 2-(tert-butyl)-5-nitroaniline (4 g, 20.59 mmol), pentyl nitrite (3.62 g, 30.89 mmol) and copper(I) chloride (2.039 g, 20.59 mmol) in acetonitrile (100 mL) was stirred at 50° C. for 2 hr. To the reaction mixture was added 1N hydrochloric acid at room temperature, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0-5% ethyl acetate/hexane) to give 1-(tert-butyl)-2-chloro-4-nitrobenzene (1.760 g, 8.24 mmol, 40.0%) as a white solid.

$^1$H NMR (300 MHz, CDCl$_3$): δ 1.52 (9H, s), 7.60 (1H, d, J=9.1 Hz), 8.04 (1H, dd, J=8.9, 2.5 Hz), 8.22 (1H, d, J=2.6 Hz).

(Step 2)

A solution of 1-(tert-butyl)-2-chloro-4-nitrobenzene (1.76 g, 8.24 mmol), iron(II) chloride hexahydrate (0.045 g, 0.16 mmol) and activated carbon (300 mg) in a mixed solvent of THF (10 mL) and MeOH (10 mL) was heated under reflux for 15 min. Then, a solution of hydrazine monohydrate (2.474 g, 49.42 mmol) in MeOH (5 mL) was added thereto, and the mixture was heated under reflux for additional 40 min. The reaction mixture was cooled, and the insoluble substance was removed by filtration. To the filtrate were added water and ethyl acetate, and the organic layer was separated. The organic layer was washed with brine, and dried over sodium sulfate, and the solvent was evaporated under reduced pressure to give 4-(tert-butyl)-3-chloroaniline (1.420 g, 7.73 mmol, 94%) as a colorless oil.

$^1$H NMR (300 MHz, CDCl$_3$): δ 1.43 (9H, s), 3.58 (2H, brs), 6.51 (1H, dd, J=8.5, 2.5 Hz), 6.70 (1H, d, J=2.6 Hz), 7.18 (1H, d, J=8.3 Hz).

(Step 3)

T3P (0.729 mL, 1.22 mmol) was added to a solution of 2-(tert-butoxycarbonyl)-6-methoxy-1,2,3,4-tetrahydroisoquinoline-1-carboxylic acid (251 mg, 0.82 mmol), 4-(tert-butyl)-3-chloroaniline (150 mg, 0.82 mmol), DIEA (0.711 mL, 4.08 mmol) and DMAP (110 mg, 0.90 mmol) in ethyl acetate (6 mL), and the mixture was stirred at 70° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with IPE/hexane to give tert-butyl 1-((4-(tert-butyl)-3-chlorophenyl)carbamoyl)-6-methoxy-3,4-dihydroisoquinoline-2(1H)-carboxylate (331 mg, 0.700 mmol, 86%) as white crystals.

$^1$H NMR (300 MHz, CDCl$_3$): δ 1.44 (9H, s), 1.52 (9H, s), 2.83-2.97 (2H, m), 3.55-3.76 (2H, m), 3.80 (3H, s), 5.59 (1H, brs), 6.72 (1H, d, J=2.3 Hz), 6.81 (1H, dd, J=8.7, 2.6 Hz), 7.25-7.34 (3H, m), 7.60 (1H, brs), 8.81 (1H, brs).

(Step 4)

TFA (4.5 mL) was added to tert-butyl 1-((4-(tert-butyl)-3-chlorophenyl)carbamoyl)-6-methoxy-3,4-dihydroisoquinoline-2(1H)-carboxylate (327 mg, 0.69 mmol), and the mixture was stirred at room temperature for 30 min. The reaction mixture was added to ice and aqueous sodium hydrogen carbonate solution, and 8N aqueous sodium hydroxide solution and potassium carbonate were added thereto until the pH of the mixture became 8. Then, the mixture was extracted three times with ethyl acetate. The organic layer was washed with brine, and dried over magnesium sulfate, and the solvent was evaporated under reduced pressure. The precipitate was washed with IPE/hexane to give N-(4-(tert-butyl)-3-chlorophenyl)-6-methoxy-1,2,3,4-tetrahydroisoquinoline-1-carboxamide (224 mg, 0.601 mmol, 87%) as white crystals.

$^1$H NMR (300 MHz, CDCl$_3$): δ 1.44 (9H, s), 2.16 (1H, brs), 2.69-2.80 (1H, m), 2.83-2.94 (1H, m), 3.13 (2H, t, J=5.9 Hz), 3.78 (3H, s), 4.62 (1H, s), 6.63 (1H, d, J=2.6 Hz), 6.78 (1H, dd, J=8.3, 2.6 Hz), 7.32 (1H, d), 7.40 (1H, dd), 7.53 (1H, d, J=8.7 Hz), 7.60 (1H, d, J=2.3 Hz), 9.34 (1H, s).

(Step 5)

HATU (270 mg, 0.71 mmol) was added to a mixture of N-(4-(tert-butyl)-3-chlorophenyl)-6-methoxy-1,2,3,4-tetrahydroisoquinoline-1-carboxamide (221 mg, 0.59 mmol), 3-hydroxy-1,2-oxazole-5-carboxylic acid (80 mg, 0.62 mmol) and DIEA (206 μL, 1.18 mmol) at room temperature, and the mixture was stirred at room temperature for 15 hr. To the reaction mixture was added water, and the mixture was extracted three times with ethyl acetate. The organic layer was washed with brine, and the solvent was evaporated under reduced pressure. The obtained residue was purified by silica gel column chromatography (solvent gradient; 30→100% ethyl acetate/hexane), and the precipitate was washed with IPE/hexane to give the title compound (198.3 mg, 0.410 mmol, 69.1%) as white crystals.

MS(API): Calculated 483.9. Found 482.0 (M−H).

$^1$H NMR (300 MHz, CDCl$_3$): δ 1.43 (9H, s), 3.07 (2H, t, J=5.7 Hz), 3.82 (3H, s), 3.92 (1H, dt, J=12.9, 6.2 Hz), 4.06-4.18 (1H, m), 5.96 (1H, s), 6.55 (1H, s), 6.76 (1H, d, J=2.3 Hz), 6.85 (1H, dd, J=8.7, 2.3 Hz), 7.17 (1H, d, J=8.7 Hz), 7.32 (2H, s), 7.60 (1H, s), 8.73 (1H, s), 10.44 (1H, brs).

Example 11

N-(7-fluoro-1,1-dimethyl-2,3-dihydro-1H-inden-5-yl)-2-((3-hydroxy-1,2-oxazol-5-yl)carbonyl)-6-methoxy-1,2,3,4-tetrahydroisoquinoline-1-carboxamide (Step 1)

To a solution of 1-bromo-3-fluoro-5-methoxybenzene (15 g, 73.16 mmol), tris(2-methylphenyl)phosphane (1.781 g, 5.85 mmol) and ethyl acrylate (11.90 mL, 109.74 mmol) in TEA (135 mL) was added palladium(II) acetate (0.329 g, 1.46 mmol) under nitrogen gas atmosphere at room temperature, and the mixture was stirred at 90° C. for 2 days. The solvent was evaporated under reduced pressure, the residue was diluted with water, and the mixture was extracted with ethyl acetate. The organic layer was washed with water and brine, and dried over magnesium sulfate, and the solvent was evaporated under reduced pressure. The obtained residue was purified by silica gel column chromatography to give ethyl (E)-3-(3-fluoro-5-methoxyphenyl)acrylate (14.2 g, 63.3 mmol, 87%) as a colorless oil.

$^1$H NMR (300 MHz, CDCl$_3$): δ 1.34 (3H, t, J=7.2 Hz), 3.82 (3H, s), 4.27 (2H, q, J=7.2 Hz), 6.40 (1H, d, J=16.2 Hz), 6.64 (1H, dt, J=10.2, 2.3 Hz), 6.78-6.87 (2H, m), 7.58 (1H, d, J=16.2 Hz).

(Step 2)

A mixture of ethyl (E)-3-(3-fluoro-5-methoxyphenyl)acrylate (14.2 g, 63.33 mmol) and 10% palladium-carbon (1.4 g, 0.66 mmol, 50% wet) in EtOH (300 mL) was stirred under hydrogen atmosphere (1 atm) at room temperature for 5 hr. The catalyst was removed by filtration through Celite, and the filtrate was concentrated under reduced pressure to give ethyl 3-(3-fluoro-5-methoxyphenyl)propanoate (13.9 g, 61.4 mmol, 97%) as a colorless oil.

(Step 3)

To a solution of ethyl 3-(3-fluoro-5-methoxyphenyl)propanoate (13.9 g, 61.44 mmol) in anhydrous THF (200 mL) was added dropwise 3M methylmagnesium bromide/diethyl ether solution (61.4 mL, 184.31 mmol) at 0° C., and the mixture was stirred under nitrogen gas atmosphere at room temperature for 1 hr. To the reaction mixture were added water and ethyl acetate, and the organic layer was separated. The organic layer was dried over magnesium sulfate, and the solvent was evaporated under reduced pressure to give 4-(3-fluoro-5-methoxyphenyl)-2-methylbutan-2-ol (12.1 g, 57.01 mmol, 93%). This compound was used for the next step without purification.

(Step 4)

A mixture of 4-(3-fluoro-5-methoxyphenyl)-2-methylbutan-2-ol (12.1 g, 57.01 mmol) and PPA (100 g, 57.01 mmol) was stirred at 90° C. for 1 hr. The reaction mixture was added to ice-water, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give 7-fluoro-5-methoxy-1,1-dimethyl-2,3-dihydro-1H-indene (4.76 g, 24.51 mmol, 43%) as a colorless oil.

(Step 5)

To a solution of 7-fluoro-5-methoxy-1,1-dimethyl-2,3-dihydro-1H-indene (4.76 g, 24.51 mmol) and 1-dodecanethiol (17.71 mL, 73.52 mmol) in toluene (50 mL) was added aluminium chloride (9.80 g, 73.52 mmol) at 0° C., and the mixture was stirred at room temperature for 2 hr. To the reaction mixture was added 1N hydrochloric acid, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give 7-fluoro-1,1-dimethyl-2,3-dihydro-1H-inden-5-ol (4.17 g, 23.14 mmol, 94%) as a grayish white solid.

(Step 6)

To a solution of 7-fluoro-1,1-dimethyl-2,3-dihydro-1H-inden-5-ol (4.17 g, 23.14 mmol) in THF (80 mL) was added sodium hydride (60% oil, 1.111 g, 27.77 mmol) at 0° C., and the mixture was stirred at room temperature for 15 min. Then, 1,1,1-trifluoro-N-phenyl-N-(trifluoromethyl)sulfonylmethanesulfonamide (9.09 g, 25.45 mmol) was added thereto at 0° C., and the mixture was stirred at room temperature for 2 hr. The reaction mixture was added to ice-water, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give 7-fluoro-1,1-dimethyl-2,3-dihydro-1H-inden-5-yl trifluoromethanesulfonate (6.21 g, 19.89 mmol, 86%) as a colorless oil.

(Step 7)

A mixture of 7-fluoro-1,1-dimethyl-2,3-dihydro-1H-inden-5-yl trifluoromethanesulfonate (5.18 g, 16.59 mmol), diphenylmethanimine (3.61 g, 19.91 mmol), Pd$_2$(dba)$_3$ (0.759 g, 0.83 mmol), BINAP (1.033 g, 1.66 mmol), sodium t-butoxide (2.391 g, 24.88 mmol) and toluene (75 mL) was stirred at 80° C. for 2 hr. The reaction mixture was added to water, and the mixture was extracted with ethyl acetate. The organic layer was dried over magnesium sulfate, and the solvent was evaporated under reduced pressure. The obtained residue was dissolved in THF (200 mL), and 1N hydrochloric acid (83 mL, 82.94 mmol) was added thereto. The mixture was stirred at room temperature for 30 min, and 1N aqueous sodium hydroxide solution was added thereto until the mixture became basic. The mixture was extracted with ethyl acetate. The organic layer was washed with brine, and dried over magnesium sulfate, and the solvent was evaporated under reduced pressure. The obtained residue was purified by silica gel column chromatography (solvent gradient; 0→10% ethyl acetate/hexane) to give 7-fluoro-1,1-dimethyl-2,3-dihydro-1H-inden-5-amine (1.92 g, 10.71 mmol, 65%) as an orange oil.

$^1$H NMR (300 MHz, CDCl$_3$): δ 1.34 (6H, s), 1.89 (2H, t, J=7.4 Hz), 2.82 (2H, t, J=7.2 Hz), 3.61 (2H, brs), 6.13-6.21 (1H, m), 6.28-6.33 (1H, m).

(Step 8)

To a solution of 7-fluoro-1,1-dimethyl-2,3-dihydro-1H-inden-5-amine (100 mg, 0.56 mmol), 2-(tert-butoxycarbonyl)-6-methoxy-1,2,3,4-tetrahydroisoquinoline-1-carboxylic acid (206 mg, 0.67 mmol), DMAP (75.0 mg, 0.61 mmol) and DIEA (0.487 mL, 2.79 mmol) in ethyl acetate (3.0 mL) was added T3P (0.656 mL, 1.12 mmol), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→20% ethyl acetate/hexane) to give tert-butyl 1-((7-fluoro-1,1-dimethyl-2,3-dihydro-1H-inden-5-yl)carbamoyl)-6-methoxy-3,4-dihydroisoquinoline-2(1H)-carboxylate (139.7 mg, 0.298 mmol, 53.4%) as a white solid.

MS(API): Calculated 468.56. Found 467.3 (M−H).

(Step 9)

To a solution of tert-butyl 1-((7-fluoro-1,1-dimethyl-2,3-dihydro-1H-inden-5-yl)carbamoyl)-6-methoxy-3,4-dihydroisoquinoline-2(1H)-carboxylate (139 mg, 0.30 mmol) in ethyl acetate (2.0 mL) was added 4N hydrogen chloride/ethyl acetate (2.0 mL, 8.00 mmol), and the mixture was stirred overnight at room temperature. The precipitate was collected by filtration with ethyl acetate to give N-(7-fluoro-1,1-dimethyl-2,3-dihydro-1H-inden-5-yl)-6-methoxy-1,2,3,4-tetrahydroisoquinoline-1-carboxamide hydrochloride (102.2 mg, 0.252 mmol, 85%) as white crystals.

$^1$H NMR (300 MHz, DMSO-$d_6$): δ 1.32 (6H, s), 1.90 (2H, t, J=7.2 Hz), 2.91 (2H, t, J=7.2 Hz), 2.95-3.03 (1H, m), 3.04-3.19 (1H, m), 3.36-3.46 (1H, m), 3.64-3.73 (1H, m), 3.74 (3H, s), 5.23 (1H, s), 6.75-6.95 (2H, m), 7.20-7.45 (3H, m), 9.36 (1H, brs), 10.10 (1H, brs), 11.37 (1H, s).

(Step 10)

To a solution of N-(7-fluoro-1,1-dimethyl-2,3-dihydro-1H-inden-5-yl)-6-methoxy-1,2,3,4-tetrahydroisoquinoline-1-carboxamide hydrochloride (100 mg, 0.25 mmol), DIEA (0.127 mL, 0.74 mmol), 3-hydroxy-1,2-oxazole-5-carboxylic acid (35.1 mg, 0.27 mmol) and DIEA (0.127 mL, 0.74 mmol) in DMF (2.0 mL) was added HATU (113 mg, 0.30 mmol) at 0° C., and the mixture was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (78.2 mg, 0.163 mmol, 66.0%) as white crystals.

MS(API): Calculated 479.5. Found 480.1 (M+H).

$^1$H NMR (300 MHz, DMSO-$d_6$): δ 1.28 (6H, d, J=1.5 Hz), 1.87 (2H, t, J=7.4 Hz), 2.71-2.95 (3H, m), 3.01-3.24 (1H, m), 3.61-3.87 (4H, m), 4.03-4.24 (1H, m), 5.50-5.75 (1H, m), 6.32-6.64 (1H, m), 6.75-6.92 (2H, m), 7.05-7.30 (2H, m), 7.46-7.58 (1H, m), 10.22-10.66 (1H, m), 11.78 (1H, brs).

Example 12

N-(4-tert-butyl-3,5-difluorophenyl)-2-((3-hydroxy-1,2-oxazol-5-yl)carbonyl)-6-methoxy-1,2,3,4-tetrahydroisoquinoline-1-carboxamide (Step 1)

To a solution of 3,5-difluorophenol (17.0 g, 130.68 mmol) in 2-methoxy-2-methylpropane (34 mL, 285.43 mmol) was slowly added zirconium(IV) chloride (15.23 g, 65.34 mmol) so that the mixture was maintained at 30 to 40° C. The mixture was stirred at room temperature for 2 hr, and zirconium(IV) chloride (15.23 g, 65.34 mmol) was slowly added thereto. The mixture was stirred at room temperature for 2 hr, and the reaction mixture was poured into ice and 8N aqueous sodium hydroxide solution (90 mL). Diethyl ether (about 400 mL) was added thereto, and the insoluble substance was removed by filtration. The filtrate was washed with brine, and dried over magnesium sulfate, and the solvent was evaporated under reduced pressure. The obtained residue was purified by silica gel column chromatography (solvent gradient; 0-10% ethyl acetate/hexane) to give 4-(tert-butyl)-3,5-difluorophenol (16.80 g, 90 mmol, 69.0%) as a brown oil.

$^1$H NMR (300 MHz, CDCl$_3$): δ 1.42 (9H, t, J=2.3 Hz), 5.07-5.26 (1H, m), 6.24-6.42 (2H, m).

(Step 2)

To a solution of 4-(tert-butyl)-3,5-difluorophenol (16.8 g, 90.23 mmol) in THF (168 mL) was added sodium hydride (60% oil, 4.33 g, 108.27 mmol) at 0° C., and 1,1,1-trifluoro-N-phenyl-N-((trifluoromethyl)sulfonyl)methanesulfonamide (35.5 g, 99.25 mmol) was added thereto. The reaction mixture was stirred at room temperature for 2 hr, and poured into aqueous ammonium chloride solution. The mixture was extracted with ethyl acetate, the organic layer was washed with aqueous sodium hydrogen carbonate solution, and dried over magnesium sulfate, and the solvent was evaporated under reduced pressure. The obtained residue was purified by silica gel column chromatography (solvent; hexane) to give 4-(tert-butyl)-3,5-difluorophenyl trifluoromethanesulfonate (8.14 g, 25.6 mmol, 28.3%) as a pale yellow oil.

$^1$H NMR (300 MHz, CDCl$_3$): δ 1.46 (9H, t, J=2.3 Hz), 6.80 (2H, d, J=10.2 Hz).

(Step 3)

A solution of XANTPHOS (1.407 g, 2.43 mmol), diphenylmethanimine (4.06 mL, 24.32 mmol), cesium carbonate (15.85 g, 48.64 mmol), 4-(tert-butyl)-3,5-difluorophenyl trifluoromethanesulfonate (5.16 g, 16.21 mmol) and Pd$_2$(dba)$_3$ (0.742 g, 0.81 mmol) in THF (50 mL) was heated under reflux overnight. The reaction mixture was neutralized with aqueous sodium hydrogen carbonate solution. To the reaction mixture was added ethyl acetate, and the organic layer was separated. The organic layer was washed with brine, and dried over magnesium sulfate, and the solvent was evaporated under reduced pressure. The obtained residue were added THF (50.00 mL) and 6N hydrochloric acid (5 mL, 30 mmol), and the mixture was stirred at room temperature for 2 hr. The reaction mixture was neutralized with aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→15% ethyl acetate/hexane) to give 4-(tert-butyl)-3,5-difluoroaniline (2.100 g, 11.34 mmol, 69.9%) as a pale yellow oil.

$^1$H NMR (300 MHz, DMSO-$d_6$): δ 1.33 (9H, t, J=2.1 Hz), 5.46 (2H, s), 6.02-6.18 (2H, m).

(Step 4)

To a solution of 4-(tert-butyl)-3,5-difluoroaniline (150 mg, 0.81 mmol), 2-(tert-butoxycarbonyl)-6-methoxy-1,2,3,4-tetrahydroisoquinoline-1-carboxylic acid (299 mg, 0.97 mmol), DMAP (109 mg, 0.89 mmol) and DIEA (0.707 mL, 4.05 mmol) in ethyl acetate (3.0 mL) was added T3P (0.953 mL, 1.62 mmol), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0-20% ethyl acetate/hexane) to give tert-butyl 1-((4-(tert-butyl)-3,5-difluorophenyl)carbamoyl)-6-methoxy-3,4-dihydroisoquinoline-2(1H)-carboxylate (253.6 mg, 0.534 mmol, 66.0%) as white crystals.

MS(API): Calculated 474.54. Found 473.3 (M−H).

(Step 5)

To a solution of tert-butyl 1-((4-(tert-butyl)-3,5-difluorophenyl)carbamoyl)-6-methoxy-3,4-dihydroisoquinoline-2(1H)-carboxylate (250 mg, 0.53 mmol) in ethyl acetate (5.0 mL) was added 4N hydrogen chloride/ethyl acetate (5.0 mL, 20.00 mmol), and the mixture was stirred at room temperature for 5 hr. The precipitate was collected by filtration with ethyl acetate to give N-(4-(tert-butyl)-3,5-difluorophenyl)-6-methoxy-1,2,3,4-tetrahydroisoquinoline-1-carboxamide hydrochloride (135.2 mg, 0.329 mmol, 62.5%) as white crystals.

$^1$H NMR (300 MHz, DMSO-$d_6$): δ 1.41 (9H, t, J=1.9 Hz), 2.89-3.19 (2H, m), 3.38-3.51 (1H, m), 3.63-3.81 (4H, m), 5.24 (1H, s), 6.80-6.93 (2H, m), 7.22-7.42 (3H, m), 9.44 (1H, brs), 10.03 (1H, brs), 11.72 (1H, s).

(Step 6)

To a solution of N-(4-(tert-butyl)-3,5-difluorophenyl)-6-methoxy-1,2,3,4-tetrahydroisoquinoline-1-carboxamide hydrochloride (130 mg, 0.32 mmol), DIEA (0.162 mL, 0.95 mmol) and 3-hydroxy-1,2-oxazole-5-carboxylic acid (53.1 mg, 0.41 mmol) in DMF (2.0 mL) was added HATU (144 mg, 0.38 mmol), and the mixture was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (70.2 mg, 0.145 mmol, 45.7%) as white crystals.

MS(API): Calculated 485.5. Found 486.1 (M+H).

$^1$H NMR (300 MHz, DMSO-$d_6$): δ 1.38 (9H, t, J=1.9 Hz), 3.02-3.23 (1H, m), 3.64-3.83 (4H, m), 4.09-4.23 (1H, m), 5.52-5.69 (1H, m), 6.38-6.62 (1H, m), 6.79-6.92 (2H, m), 7.12-7.27 (2H, m), 7.46-7.56 (1H, m), 7.95 (1H, s), 10.44-10.87 (1H, m), 11.81 (1H, brs).

Example 13

(1R)-N-(4-tert-butyl-3-fluorophenyl)-2-((3-hydroxy-1,2-oxazol-5-yl) carbonyl)-6-methoxy-1,2,3,4-tetrahydroisoquinoline-1-carboxamide HATU (230 mg, 0.61 mmol) was added to a solution of (R)-N-(4-(tert-butyl)-3-fluorophenyl)-6-methoxy-1,2,3,4-tetrahydroisoquinoline-1-carboxamide (180 mg, 0.51 mmol), 3-hydroxy-1,2-oxazole-5-carboxylic acid (68.4 mg, 0.53 mmol) and DIEA (176 μL, 1.01 mmol) in DMF (2.5 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 30→100% ethyl acetate/hexane) to give the title compound (99.1 mg, 0.212 mmol, 42.0%) as a white solid.

MS(API): Calculated 467.5. Found 468.2 (M+H).

$^1$H NMR (300 MHz, CDCl$_3$): δ 1.32 (9H, s), 3.09 (2H, brs), 3.81 (3H, s), 3.92-4.03 (1H, m), 4.07-4.17 (1H, m), 5.98 (1H, s), 6.56 (1H, s), 6.77 (1H, s), 6.84 (1H, dd, J=8.7, 2.3 Hz), 7.07 (1H, dd), 7.13-7.22 (2H, m), 7.38 (1H, dd, J=14.4, 1.9 Hz), 8.84 (1H, s), 10.52 (1H, brs).

$[α]_D^{25}$ −13.4 (c 0.2500, MeOH)

Example 14

(1S)—N-(4-tert-butyl-3-fluorophenyl)-2-((3-hydroxy-1,2-oxazol-5-yl)carbonyl)-6-methoxy-1,2,3,4-tetrahydroisoquinoline-1-carboxamide The title compound was synthesized using (S)—N-(4-(tert-butyl)-3-fluorophenyl)-6-methoxy-1,2,3,4-tetrahydroisoquinoline-1-carboxamide, by the reaction and purification in the same manner as in Examples 1 and 25.

MS(API): Calculated 467.5. Found 468.1 (M+H).

The compounds described in Examples 15 to 24 were synthesized by the reaction and purification in the same manner as in Examples 1 and 25.

Example 15

(1R)-N-(4-tert-butyl-3-fluorophenyl)-2-((2,4-dioxo-1,3-thiazolidin-5-yl)acetyl)-6-methoxy-1,2,3,4-tetrahydroisoquinoline-1-carboxamide (a mixture of two diastereomers)

Example 16

(1R)-N-(4-tert-butyl-3-fluorophenyl)-2-((2,6-dioxopiperidin-4-yl)acetyl)-6-methoxy-1,2,3,4-tetrahydroisoquinoline-1-carboxamide Example 17

(1R)-N$^1$-(4-tert-butyl-3-fluorophenyl)-6-methoxy-N$^2$-(pyridazin-3-yl)-3,4-dihydroisoquinoline-1,2(1H)-dicarboxamide Example 18

(1R)-N-(4-tert-butyl-3-fluorophenyl)-2-((2,5-dioxoimidazolidin-4-yl)acetyl)-6-methoxy-1,2,3,4-tetrahydroisoquinoline-1-carboxamide (a mixture of two diastereomers)

Example 19

(1R)-N-(4-tert-butyl-3-fluorophenyl)-2-((2,4-dioxoimidazolidin-1-yl)acetyl)-6-methoxy-1,2,3,4-tetrahydroisoquinoline-1-carboxamide Example 20

(1R)-N-(4-tert-butyl-3-fluorophenyl)-6-methoxy-2-((5-oxopyrrolidin-3-yl)acetyl)-1,2,3,4-tetrahydroisoquinoline-1-carboxamide (a mixture of two diastereomers)

Example 21

(1R)-N-(4-tert-butyl-3-fluorophenyl)-6-methoxy-N$^2$-(1-methyl-1H-pyrazol-3-yl)-3,4-dihydroisoquinoline-1,2(1H)-dicarboxamide Example 22

(1R)-N-(4-tert-butyl-3-fluorophenyl)-2-((5,5-dimethyl-2,4-dioxo-1,3-oxazolidin-3-yl)acetyl)-6-methoxy-1,2,3,4-tetrahydroisoquinoline-1-carboxamide

Example 23

(1R)-N-(4-tert-butyl-3-fluorophenyl)-6-methoxy-2-((2-oxoimidazolidin-1-yl)acetyl)-1,2,3,4-tetrahydroisoquinoline-1-carboxamide

Example 24

(1R)-N-(4-tert-butyl-3-fluorophenyl)-2-((2,4-dioxo-3,4-dihydropyrimidin-1(2H)-yl)acetyl)-6-methoxy-1,2,3,4-tetrahydroisoquinoline-1-carboxamide

Example 25

(1R)-N-(4-tert-butyl-3-fluorophenyl)-6-methoxy-2-(((3S)-5-oxopyrrolidin-3-yl)carbonyl)-1,2,3,4-tetrahydroisoquinoline-1-carboxamide (Step 1)

tert-Butyl 1-((4-(tert-butyl)-3-fluorophenyl)carbamoyl)-6-methoxy-3,4-dihydroisoquinoline-2(1H)-carboxylate (5.00 g) was resolved by chiral column chromatography. The fraction having a shorter retention time was concentrated to give tert-butyl (R)-1-((4-(tert-butyl)-3-fluorophenyl)carbamoyl)-6-methoxy-3,4-dihydroisoquinoline-2(1H)-carboxylate (2.38 g, >99.9% ee) as a white solid.

purification condition by chiral column chromatography
    column: CHIRALCEL OD (NL001) 50 mmID×500 mmL
    solvent: hexane/EtOH=600/400
    flow rate: 80 mL/min
    temperature: 30° C.
    detection method: UV 220 nm (Step 2)

TFA (28 mL) was added to tert-butyl (R)-1-((4-(tert-butyl)-3-fluorophenyl)carbamoyl)-6-methoxy-3,4-dihydroisoquinoline-2(1H)-carboxylate (2.33 g, 5.10 mmol), and the mixture was stirred at room temperature for 30 min. The reaction mixture was added to ice and aqueous sodium hydrogen carbonate solution, and 8N aqueous sodium hydroxide solution and potassium carbonate were added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(4-(tert-butyl)-3-fluorophenyl)-6-methoxy-1,2,3,4-tetrahydroisoquinoline-1-carboxamide (1.69 g, 4.74 mmol, 93%) as a white solid.

$^1$H NMR (300 MHz, CDCl$_3$): δ 1.34 (9H, s), 2.05 (1H, brs), 2.69-2.80 (1H, m), 2.84-2.95 (1H, m), 3.14 (2H, t), 3.78 (3H, s), 4.64 (1H, s), 6.64 (1H, d, J=2.6 Hz), 6.78 (1H, dd, J=8.7, 2.6 Hz), 7.11 (1H, dd), 7.18 (1H, t), 7.44 (1H, dd, J=14.4, 2.3 Hz), 7.53 (1H, d, J=8.7 Hz), 9.36 (1H, s).

(Step 3)

HATU (77 mg, 0.20 mmol) was added to a solution of (R)-N-(4-(tert-butyl)-3-fluorophenyl)-6-methoxy-1,2,3,4-tetrahydroisoquinoline-1-carboxamide (60 mg, 0.17 mmol), (S)-5-oxopyrrolidine-3-carboxylic acid (22.82 mg, 0.18 mmol) and DIEA (59 μL, 0.34 mmol) in DMF (0.9 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 0→30% ethyl acetate/hexane), and the precipitate was washed with diethyl ether/IPE to give the title compound (65.9 mg, 0.141 mmol, 84%) as white crystals.

MS(API): Calculated 467.5. Found 466.0 (M–H).

$^1$H NMR (300 MHz, CDCl$_3$): δ 1.30 (9H, s), 2.61 (1H, dd, J=17.0, 9.1 Hz), 2.78-2.92 (2H, m), 3.14-3.25 (1H, m), 3.59-3.76 (4H, m), 3.79 (3H, s), 3.96 (1H, ddd, J=12.1, 7.6, 4.5 Hz), 5.98 (1H, s), 6.00 (1H, s), 6.74 (1H, d, J=2.6 Hz), 6.83 (1H, dd, J=8.5, 2.5 Hz), 6.96 (1H, dd, J=8.5, 2.1 Hz), 7.11 (1H, t), 7.24-7.28 (1H, m), 7.32 (1H, dd, J=14.4, 2.3 Hz), 9.06 (1H, s).

Example 26

(1R)-N-(4-tert-butyl-3-fluorophenyl)-6-methoxy-2-(((3R)-5-oxopyrrolidin-3-yl)carbonyl)-1,2,3,4-tetrahydroisoquinoline-1-carboxamide HATU (77 mg, 0.20 mmol) was added to a solution of (R)-N-(4-(tert-butyl)-3-fluorophenyl)-6-methoxy-1,2,3,4-tetrahydroisoquinoline-1-carboxamide (60 mg, 0.17 mmol), (R)-5-oxopyrrolidine-3-carboxylic acid (22.82 mg, 0.18 mmol) and DIEA (59 μL, 0.34 mmol) in DMF (0.9 mL) at room temperature, and the mixture was stirred for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 0→10% MeOH/ethyl acetate), and the precipitate was washed with diethyl ether/IPE to give the title compound (64.0 mg, 0.137 mmol, 81%) as white crystals.

MS(API): Calculated 467.5. Found 466.0 (M–H).

$^1$H NMR (300 MHz, CDCl$_3$): δ 1.30 (9H, s), 2.55-2.65 (1H, m), 2.70-2.80 (1H, m), 2.89 (1H, ddd, J=15.8, 7.1, 4.7 Hz), 3.15-3.26 (1H, m), 3.64-3.77 (4H, m), 3.80 (3H, s), 3.96 (1H, ddd, J=12.1, 7.4, 4.7 Hz), 5.82 (1H, s), 5.97 (1H, s), 6.74 (1H, d, J=2.3 Hz), 6.83 (1H, dd, J=8.5, 2.5 Hz), 6.97 (1H, dd, J=8.5, 2.1 Hz), 7.09 (1H, t), 7.23-7.31 (2H, m), 9.12 (1H, s).

Example 27

(1R)-N-(4-tert-butyl-3-fluorophenyl)-2-((3-hydroxy-1,2-oxazol-5-yl)acetyl)-6-methoxy-1,2,3,4-tetrahydroisoquinoline-1-carboxamide (Step 1)

n-BuLi (5.27 mL, 8.43 mmol) was added to a solution of diisopropylamine (1.301 mL, 9.20 mmol) in THF (40 mL) at −78° C. under argon gas atmosphere, and the mixture was stirred for 20 min. Then, a solution of 3-(benzyloxy)-5-methyl-1,2-oxazole (1450 mg, 7.66 mmol) in THF (10.0 mL) was added thereto at −78° C., and the mixture was stirred for 50 min. Then, a solution of ethyl chloroformate (0.875 mL, 9.20 mmol) in THF (5.0 mL) was added thereto at −78° C., and the mixture was stirred for 2 hr. To the reaction mixture was added aqueous ammonium chloride solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→20% ethyl acetate/hexane) to give diethyl 2-(3-(benzyloxy)-1,2-oxazol-5-yl)malonate (391 mg, 1.173 mmol, 15.31%) as a colorless oil.

¹H NMR (300 MHz, CDCl₃): δ 1.23-1.37 (6H, m), 4.19-4.33 (4H, m), 4.77 (1H, s), 5.27 (2H, s), 6.14 (1H, s), 7.29-7.50 (5H, m).

(Step 2)

2N Aqueous sodium hydroxide solution (3.52 mL, 7.04 mmol) was added to a solution of diethyl 2-(3-(benzyloxy)-1,2-oxazol-5-yl)malonate (391 mg, 1.17 mmol) in EtOH (3.5 mL), and the mixture was stirred at room temperature for 3 hr. THF (1.50 mL) was added thereto, and the mixture was stirred at room temperature for 1 hr, and then overnight at 50° C. The reaction mixture was neutralized with 1N hydrochloric acid, and the mixture was extracted with ethyl acetate. The organic layer was washed with brine, and dried over magnesium sulfate, and the solvent was evaporated under reduced pressure. The residue was crystallized from hexane/IPE to give 2-(3-(benzyloxy)-1,2-oxazol-5-yl)acetic acid (154 mg, 0.660 mmol, 56.3%) as a white solid.

¹H NMR (300 MHz, CDCl₃): δ 3.79 (2H, s), 5.26 (2H, s), 5.97 (1H, s), 7.30-7.50 (5H, m) (The peak derived from COOH was not observed).

(Step 3)

HATU (154 mg, 0.40 mmol) was added to a solution of (R)-N-(4-(tert-butyl)-3-fluorophenyl)-6-methoxy-1,2,3,4-tetrahydroisoquinoline-1-carboxamide (120 mg, 0.34 mmol), 2-(3-(benzyloxy)-1,2-oxazol-5-yl)acetic acid (82 mg, 0.35 mmol) and DIEA (117 µL, 0.67 mmol) in DMF (1.7 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 8→50% ethyl acetate/hexane), and the precipitate was washed with diethyl ether/IPE to give (R)-2-(2-(3-(benzyloxy)-1,2-oxazol-5-yl)acetyl)-N-(4-(tert-butyl)-3-fluorophenyl)-6-methoxy-1,2,3,4-tetrahydroisoquinoline-1-carboxamide (160 mg, 0.280 mmol, 83%) as white crystals.

¹H NMR (300 MHz, CDCl₃): δ 1.30 (9H, s), 2.81-2.91 (1H, m), 3.19 (1H, ddd, J=15.5, 7.7, 4.7 Hz), 3.67-3.75 (1H, m), 3.77 (3H, s), 3.89-4.03 (3H, m), 5.25 (2H, s), 5.99 (2H, d, J=5.7 Hz), 6.73 (1H, d, J=2.3 Hz), 6.83 (1H, dd, J=8.3, 2.6 Hz), 6.95 (1H, dd, J=8.5, 2.1 Hz), 7.09 (1H, t), 7.21-7.30 (2H, m), 7.33-7.45 (5H, m), 8.96 (1H, s).

(Step 4)

To a solution of (R)-2-(2-(3-(benzyloxy)-1,2-oxazol-5-yl)acetyl)-N-(4-(tert-butyl)-3-fluorophenyl)-6-methoxy-1,2,3,4-tetrahydroisoquinoline-1-carboxamide (157 mg, 0.27 mmol) in a mixed solvent of MeOH (2.8 mL) and THF (2.8 mL) was added 5% palladium-barium sulfate (200 mg, 0.094 mmol), and the mixture was stirred under hydrogen atmosphere (1 atm) at room temperature for 3 hr. The catalyst was removed by filtration, and the filtrate was concentrated under reduced pressure. The obtained residue was purified by silica gel column chromatography (solvent gradient; 30→100% ethyl acetate/hexane), and the precipitate was washed with IPE/hexane to give the title compound (103.1 mg, 0.214 mmol, 78%) as white crystals.

MS(API): Calculated 481.5. Found 480.0 (M−H).

¹H NMR (300 MHz, DMSO-d₆): δ 1.29 (9H, s), 2.77-2.89 (1H, m), 3.08-3.20 (1H, m), 3.55-3.67 (1H, m), 3.73 (3H, s), 3.91-4.14 (3H, m), 5.67 (1H, s), 5.91 (1H, s), 6.80-6.86 (2H, m), 7.18-7.29 (2H, m), 7.41-7.52 (2H, m), 10.54 (1H, s), 11.14 (1H, brs).

$[\alpha]_D^{25}$ +8.8 (c 0.2500, MeOH)

Example 28

(1R)-N-(4-tert-butyl-3-fluorophenyl)-6-methoxy-2-((5-methyl-1,3,4-oxadiazol-2-yl)acetyl)-1,2,3,4-tetrahydroisoquinoline-1-carboxamide (Step 1)

To a solution of ethyl 2-(5-methyl-1,3,4-oxadiazol-2-yl)acetate (279 mg, 1.64 mmol) in a mixed solvent of water (2 mL) and THF (1 mL) was added lithium hydroxide monohydrate (68.9 mg, 1.64 mmol), and the mixture was stirred at room temperature for 1 hr. The reaction mixture was concentrated under reduced pressure, and the residue was subjected to azeotropy with toluene to give lithium 2-(5-methyl-1,3,4-oxadiazol-2-yl)acetate (250 mg, 1.689 mmol, 103%) as a white solid.

¹H NMR (300 MHz, DMSO-d₆): δ 2.41 (3H, s), 3.35 (2H, s).

(Step 2)

HATU (77 mg, 0.20 mmol) was added to a solution of (R)-N-(4-(tert-butyl)-3-fluorophenyl)-6-methoxy-1,2,3,4-tetrahydroisoquinoline-1-carboxamide (60 mg, 0.17 mmol), lithium 2-(5-methyl-1,3,4-oxadiazol-2-yl)acetate (26.2 mg, 0.18 mmol) and DIEA (59 µL, 0.34 mmol) in DMF (0.9 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 30→100% ethyl acetate/hexane), and the precipitate was washed with diethyl ether/hexane to give the title compound (61.9 mg, 0.129 mmol, 77%) as white crystals.

MS(API): Calculated 480.5. Found 481.1 (M+H).

¹H NMR (300 MHz, CDCl₃): δ 1.31 (9H, s), 2.51 (3H, s), 2.83-2.93 (1H, m), 3.17 (1H, ddd, J=15.6, 7.8, 4.9 Hz), 3.71 (1H, ddd, J=12.1, 7.7, 4.7 Hz), 3.80 (3H, s), 3.96 (1H, ddd, J=12.0, 6.9, 4.9 Hz), 4.04-4.21 (2H, m), 6.00 (1H, s), 6.71 (1H, d, J=2.6 Hz), 6.84 (1H, dd, J=8.7, 2.6 Hz), 7.08-7.14 (2H, m), 7.23-7.28 (1H, m), 7.35-7.42 (1H, m), 9.21 (1H, s).

Example 29

(1R)-N-(4-tert-butyl-3-fluorophenyl)-6-methoxy-2-((6-oxopyrimidin-1(6H)-yl)acetyl)-1,2,3,4-tetrahydroisoquinoline-1-carboxamide HATU (77 mg, 0.20 mmol) was added to a solution of (R)-N-(4-(tert-butyl)-3-fluorophenyl)-6-methoxy-1,2,3,4-tetrahydroisoquinoline-1-carboxamide (60 mg, 0.17 mmol), 2-(6-oxopyrimidin-1(6H)-yl)acetic acid (27.2 mg, 0.18 mmol) and DIEA (59 µL, 0.34 mmol) in DMF (0.9 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 0→5% MeOH/ethyl acetate), and the precipitate was washed with diethyl ether/hexane to give the title compound (62.3 mg, 0.126 mmol, 75%) as white crystals.

MS(API): Calculated 492.5. Found 491.1 (M−H).
¹H NMR (300 MHz, CDCl₃): δ 1.31 (9H, s), 2.87-3.00 (1H, m), 3.16-3.28 (1H, m), 3.72-3.80 (1H, m), 3.81 (3H, s), 4.12 (1H, dt, J=11.5, 5.6 Hz), 4.71-4.90 (2H, m), 5.93 (1H, s), 6.51-6.56 (1H, m), 6.75 (1H, d, J=2.6 Hz), 6.82 (1H, dd, J=8.5, 2.5 Hz), 7.04 (1H, dd), 7.13 (1H, t), 7.22 (1H, d, J=8.3 Hz), 7.33 (1H, dd, J=14.5, 2.1 Hz), 7.98 (1H, d, J=6.8 Hz), 8.16 (1H, s), 8.65 (1H, s).

Example 30

(1R)-N-(4-tert-butyl-3-fluorophenyl)-2-(3-hydroxypropanoyl)-6-methoxy-1,2,3,4-tetrahydroisoquinoline-1-carboxamide HATU (77 mg, 0.20 mmol) was added to a solution of (R)-N-(4-(tert-butyl)-3-fluorophenyl)-6-methoxy-1,2,3,4-tetrahydroisoquinoline-1-carboxamide (60 mg, 0.17 mmol), 3.6M aqueous 3-hydroxypropanoic acid solution (51.4 μL, 0.19 mmol) and DIEA (59 μL, 0.34 mmol) in DMF (0.9 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 30→100% ethyl acetate/hexane) to give the title compound (53.6 mg, 0.125 mmol, 74.3%) as a white solid.
MS(API): Calculated 428.5. Found 427.1 (M−H).
¹H NMR (300 MHz, CDCl₃): δ 1.32 (9H, s), 2.59-2.79 (2H, m), 2.80 (1H, s), 2.83-2.93 (1H, m), 3.04-3.15 (2H, m), 3.66 (1H, ddd, J=12.2, 7.5, 4.9 Hz), 3.76-3.86 (4H, m), 3.92-4.02 (1H, m), 6.00 (1H, s), 6.75 (1H, d, J=2.6 Hz), 6.83 (1H, dd, J=8.5, 2.5 Hz), 7.02 (1H, dd), 7.11-7.22 (2H, m), 7.36 (1H, dd, J=14.4, 2.3 Hz), 8.80 (1H, s).

Example 31

(1R)-N-(4-tert-butyl-3-fluorophenyl)-6-methoxy-2-(3-(methylsulfonyl)propanoyl)-1,2,3,4-tetrahydroisoquinoline-1-carboxamide The title compound was synthesized by the reaction and purification in the same manner as in Examples 1 and 25.

Example 32

(1R)-N-(4-tert-butyl-3-fluorophenyl)-6-methoxy-2-((6-methoxypyridin-3-yl)acetyl)-1,2,3,4-tetrahydroisoquinoline-1-carboxamide HATU (154 mg, 0.40 mmol) was added to a solution of (R)-N-(4-(tert-butyl)-3-fluorophenyl)-6-methoxy-1,2,3,4-tetrahydroisoquinoline-1-carboxamide (120 mg, 0.34 mmol), 2-(6-methoxypyridin-3-yl)acetic acid (59.1 mg, 0.35 mmol) and DIEA (117 μL, 0.67 mmol) in DMF (1.7 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 20→80% ethyl acetate/hexane), and the precipitate was washed with diethyl ether/hexane to give the title compound (139.4 mg, 0.276 mmol, 82%) as white crystals.
MS(API): Calculated 505.6. Found 506.2 (M+H).
¹H NMR (300 MHz, CDCl₃): δ 1.30 (9H, s), 2.73-2.84 (1H, m), 3.11-3.23 (1H, m), 3.68-3.82 (6H, m), 3.91-4.01 (4H, m), 5.97 (1H, s), 6.70-6.76 (3H, m), 6.89 (1H, dd, J=8.7, 2.3 Hz), 7.04-7.12 (2H, m), 7.23 (1H, dd), 7.54 (1H, dd, J=8.5, 2.5 Hz), 8.05 (1H, d, J=2.3 Hz), 9.21 (1H, s).

Example 33

(1R)-N-(4-tert-butyl-3-fluorophenyl)-6-methoxy-2-((6-oxo-1,6-dihydropyridin-3-yl)acetyl)-1,2,3,4-tetrahydroisoquinoline-1-carboxamide Chlorotrimethylsilane (75 μL, 0.59 mmol) was added to a solution of (1R)-N-(4-tert-butyl-3-fluorophenyl)-6-methoxy-2-((6-methoxypyridin-3-yl)acetyl)-1,2,3,4-tetrahydroisoquinoline-1-carboxamide (100 mg, 0.20 mmol) and sodium iodide (89 mg, 0.59 mmol) in acetonitrile (2.5 mL), and the mixture was stirred at 70° C. for 4 hr. To the reaction mixture was added 2% aqueous Na₂SO₃ solution, and the mixture was extracted three times with a mixed solvent of ethyl acetate/THF. The organic layer was washed with brine, and dried over magnesium sulfate, and the solvent was evaporated under reduced pressure. The precipitate was washed with diethyl ether/hexane to give the title compound (47.8 mg, 0.097 mmol, 49.2%) as white crystals.
MS(API): Calculated 491.6. Found 492.2 (M+H).
¹H NMR (300 MHz, CDCl₃): δ 1.29 (9H, s), 2.82 (1H, dt, J=15.3, 5.0 Hz), 3.30-3.42 (1H, m), 3.55-3.66 (3H, m), 3.77 (3H, s), 4.05-4.15 (1H, m), 5.84 (1H, s), 6.61 (1H, d, J=9.4 Hz), 6.71 (1H, d, J=2.3 Hz), 6.76 (1H, dd, J=8.3, 2.6 Hz), 7.07-7.17 (2H, m), 7.29-7.44 (4H, m), 10.07 (1H, s), 12.00 (1H, brs).

Example 34

4-((1R)-1-((4-tert-butyl-3-fluorophenyl) carbamoyl)-6-methoxy-3,4-dihydroisoquinolin-2(1H)-yl)-4-oxobutanoic acid Succinic anhydride (17.69 mg, 0.18 mmol) was added to a solution of (R)-N-(4-(tert-butyl)-3-fluorophenyl)-6-methoxy-1,2,3,4-tetrahydroisoquinoline-1-carboxamide (60 mg, 0.17 mmol) and TEA (26 μL, 0.19 mmol) in THF (1.5 mL), and the mixture was stirred at room temperature for 4 hr. To the reaction mixture was added 0.1N hydrochloric acid, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (Diol, solvent gradient; 0→10% MeOH/ethyl acetate), and the precipitate was washed with diethyl ether/hexane to give the title compound (63.1 mg, 0.138 mmol, 82%) as white crystals.
MS(API): Calculated 456.5. Found 455.1 (M−H).
¹H NMR (300 MHz, CDCl₃): δ 1.30 (9H, s), 2.64-2.74 (1H, m), 2.76-2.93 (4H, m), 3.06-3.18 (1H, m), 3.68 (1H, ddd, J=12.2, 7.6, 5.1 Hz), 3.80 (3H, s), 3.81-3.92 (1H, m), 5.99 (1H, s), 6.74 (1H, d, J=2.6 Hz), 6.81 (1H, dd, J=8.5, 2.5 Hz), 7.03 (1H, dd), 7.12 (1H, t), 7.22 (1H, d, J=8.3 Hz), 7.31 (1H, dd, J=14.4, 2.3 Hz), 8.89 (1H, s) (The exchangeable 1H was not observed).

Example 35

N-(4-tert-butyl-3-fluorophenyl)-4-((3-hydroxy-1,2-oxazol-5-yl)carbonyl)-8-methoxy-2,3,4,5-tetrahydro-1,4-benzoxazepine-5-carboxamide (Step 1)

Boc$_2$O (2.415 g, 11.06 mmol) was added to a solution of methyl 8-methoxy-2,3,4,5-tetrahydrobenzo[f][1,4]oxazepine-5-carboxylate (2.50 g, 10.54 mmol) in THF (30 mL), and the mixture was stirred at room temperature for 3 hr. The reaction mixture was concentrated under reduced pressure, and the precipitate was crystallized from IPE/hexane to give 5-methyl 4-tert-butyl 8-methoxy-2,3-dihydrobenzo[f][1,4]oxazepine-4,5(5H)-dicarboxylate (2.97 g, 8.80 mmol, 84%) as white crystals.

$^1$H NMR (300 MHz, CDCl$_3$): δ 1.44-1.49 (9H, m), 3.69-3.73 (3H, m), 3.74-4.00 (6H, m), 4.23-4.38 (1H, m), 5.54-5.97 (1H, m), 6.53-6.59 (1H, m), 6.59-6.66 (1H, m), 7.09-7.24 (1H, m).

(Step 2)

2N Aqueous lithium hydroxide solution (26.3 mL, 52.64 mmol) was added to a solution of 5-methyl 4-tert-butyl 8-methoxy-2,3-dihydrobenzo[f][1,4]oxazepine-4,5(5H)-dicarboxylate (2.96 g, 8.77 mmol) in a mixed solvent of EtOH (14 mL) and THF (14 mL), and the mixture was stirred at room temperature for 1.5 hr. To the reaction mixture was added ice, and 2N hydrochloric acid was added thereto until the pH of the mixture became 3. Then, the mixture was extracted three times with a mixed solvent of ethyl acetate/THF. The organic layer was washed with brine, and dried over magnesium sulfate, and the solvent was evaporated under reduced pressure. The residue was crystallized from IPE/hexane to give 4-(tert-butoxycarbonyl)-8-methoxy-2,3,4,5-tetrahydrobenzo[f][1,4]oxazepine-5-carboxylic acid (2.77 g, 8.57 mmol, 98%) as white crystals.

$^1$H NMR (300 MHz, CDCl$_3$): δ 1.46 (9H, s), 3.71-3.81 (4H, m), 3.86-3.97 (2H, m), 4.23-4.39 (1H, m), 5.54-6.00 (1H, m), 6.54-6.67 (2H, m), 7.14-7.24 (1H, m) (The exchangeable 1H was not observed).

(Step 3)

T3P (1.909 mL, 3.21 mmol) was added to a solution of 4-(tert-butoxycarbonyl)-8-methoxy-2,3,4,5-tetrahydrobenzo[f][1,4]oxazepine-5-carboxylic acid (692 mg, 2.14 mmol), 4-(tert-butyl)-3-fluoroaniline (358 mg, 2.14 mmol), DIEA (1.864 mL, 10.70 mmol) and DMAP (288 mg, 2.35 mmol) in ethyl acetate (17 mL), and the mixture was stirred at 65° C. for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 30→50% ethyl acetate/hexane) to give tert-butyl 5-((4-(tert-butyl)-3-fluorophenyl)carbamoyl)-8-methoxy-2,3-dihydrobenzo[f][1,4]oxazepine-4(5H)-carboxylate (887 mg, 1.877 mmol, 88%) as a white solid.

$^1$H NMR (300 MHz, CDCl$_3$): δ 1.33 (9H, s), 1.47 (9H, s), 3.56-3.78 (1H, m), 3.81 (3H, s), 3.83-3.95 (2H, m), 4.31 (1H, brs), 5.46-6.00 (1H, m), 6.64 (1H, d, J=2.3 Hz), 6.69 (1H, dd, J=8.3, 2.3 Hz), 6.96 (1H, d, J=7.9 Hz), 7.13-7.24 (2H, m), 7.31 (1H, dd, J=14.4, 2.3 Hz), 7.71 (1H, brs).

(Step 4)

TFA (10 mL, 134.6 mmol) was added to tert-butyl 5-((4-(tert-butyl)-3-fluorophenyl) carbamoyl)-8-methoxy-2,3-dihydrobenzo[f][1,4]oxazepine-4(5H)-carboxylate (882 mg, 1.87 mmol), and the mixture was stirred at room temperature for 20 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The residue was crystallized from IPE/hexane to give N-(4-(tert-butyl)-3-fluorophenyl)-8-methoxy-2,3,4,5-tetrahydrobenzo[f][1,4]oxazepine-5-carboxamide (636 mg, 1.708 mmol, 91%) as white crystals.

$^1$H NMR (300 MHz, CDCl$_3$): δ 1.35 (9H, s), 1.81 (1H, brs), 3.13-3.31 (2H, m), 3.80 (3H, s), 3.96-4.14 (2H, m), 4.69 (1H, s), 6.61-6.66 (2H, m), 7.12 (1H, dd), 7.18-7.25 (2H, m), 7.46 (1H, dd, J=14.4, 2.3 Hz), 8.89 (1H, s)

(Step 5)

HATU (245 mg, 0.64 mmol) was added to a solution of N-(4-(tert-butyl)-3-fluorophenyl)-8-methoxy-2,3,4,5-tetrahydrobenzo[f][1,4]oxazepine-5-carboxamide (200 mg, 0.54 mmol), 3-hydroxy-1,2-oxazole-5-carboxylic acid (72.8 mg, 0.56 mmol) and DIEA (187 μL, 1.07 mmol) in DMF (2.6 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 30→100% ethyl acetate/hexane), and the precipitate was washed with diethyl ether/IPE to give the title compound (70.0 mg, 0.145 mmol, 27.0%) as white crystals.

MS(API): Calculated 483.5. Found 484.1 (M+H).

$^1$H NMR (300 MHz, CDCl$_3$): δ 1.32 (9H, s), 3.73-4.23 (6H, m), 4.40-4.59 (1H, m), 5.84-6.39 (1H, m), 6.49 (1H, s), 6.69-6.78 (2H, m), 6.89-6.98 (1H, m), 7.11-7.22 (2H, m), 7.23-7.30 (2H, m), 7.36 (1H, d, J=8.7 Hz)

Example 36

N-(3,5-difluoro-4-(trimethylsilyl)phenyl)-4-((3-hydroxy-1,2-oxazol-5-yl)carbonyl)-8-methoxy-2,3,4,5-tetrahydro-1,4-benzoxazepine-5-carboxamide (Step 1)

To a solution of 1,3-difluoro-5-nitrobenzene (3 g, 18.86 mmol) in THF (60 mL) was added trimethylsilyl chloride (7.23 mL, 56.57 mmol) under nitrogen atmosphere at −78° C. To the reaction solution was added sodium hexamethyldisilazide (19.85 mL, 37.71 mmol), and the mixture was maintained at −75° C. or below. The reaction solution was stirred for 1 hr, and water and ethyl acetate were added thereto. The organic layer was separated, and the aqueous layer was extracted with ethyl acetate. The organic layer was dried over magnesium sulfate, and the solvent was evaporated under reduced pressure. The obtained residue was purified by silica gel column chromatography (solvent; hexane) to give (2,6-difluoro-4-nitrophenyl)trimethylsilane (3.51 g, 15.18 mmol, 80%) as a colorless oil.

$^1$H NMR (300 MHz, CDCl$_3$): δ 0.42 (9H, s), 7.61-7.71 (2H, m).

(Step 2)

A solution of (2,6-difluoro-4-nitrophenyl)trimethylsilane (3.5 g, 15.13 mmol) and 10% palladium-carbon (350 mg, 0.16 mmol, 50% wet) in MeOH (70 mL) was stirred under hydrogen atmosphere (1 atm) at room temperature for 5 hr. The catalyst was filtered off, and the filtrate was concentrated under reduced pressure. The obtained residue was purified by silica gel column chromatography (solvent; ethyl acetate/hexane) to give 3,5-difluoro-4-(trimethylsilyl)aniline (2.50 g, 12.42 mmol, 82%) as a pale yellow oil.

$^1$H NMR (300 MHz, CDCl$_3$): δ 0.30 (9H, s), 3.88 (2H, brs), 5.99-6.16 (2H, m).

(Step 3)

T3P (1.909 mL, 3.21 mmol) was added to a solution of 4-(tert-butoxycarbonyl)-8-methoxy-2,3,4,5-tetrahydrobenzo[f][1,4]oxazepine-5-carboxylic acid (692 mg, 2.14 mmol), 3,5-difluoro-4-(trimethylsilyl)aniline (431 mg, 2.14 mmol), DIEA (1.864 mL, 10.70 mmol) and DMAP (288 mg, 2.35 mmol) in ethyl acetate (17 mL), and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The obtained residue was purified by silica gel column chromatography (solvent gradient; 5→30% ethyl acetate/hexane) to give tert-butyl 5-((3,5-difluoro-4-(trimethylsilyl)phenyl)carbamoyl)-8-methoxy-2,3-dihydrobenzo[f][1,4]oxazepine-4 (5H)-carboxylate (924 mg, 1.824 mmol, 85%) as a white solid.

$^1$H NMR (300 MHz, CDCl$_3$): δ 0.31 (9H, s), 1.47 (9H, s), 3.66-3.78 (1H, m), 3.81 (3H, s), 3.86-3.95 (2H, m), 4.33 (1H, brs), 5.38-5.98 (1H, m), 6.65 (1H, d, J=2.3 Hz), 6.70 (1H, dd, J=8.3, 2.3 Hz), 6.95 (2H, d, J=8.7 Hz), 7.19-7.25 (1H, m), 7.46-7.97 (1H, m).

(Step 4)

Cooled TFA (10 mL, 134.6 mmol) was added to tert-butyl 5-((3,5-difluoro-4-(trimethylsilyl)phenyl)carbamoyl)-8-methoxy-2,3-dihydrobenzo[f][1,4]oxazepine-4(5H)-carboxylate (919 mg, 1.81 mmol), and the mixture was stirred at room temperature for 2 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The precipitate was washed with hexane to give N-(3,5-difluoro-4-(trimethylsilyl)phenyl)-8-methoxy-2,3,4,5-tetrahydrobenzo [f][1,4]oxazepine-5-carboxamide (652 mg, 1.604 mmol, 88%) as white crystals.

$^1$H NMR (300 MHz, CDCl$_3$): δ 0.34 (9H, s), 1.74 (1H, brs), 3.13-3.29 (2H, m), 3.80 (3H, s), 3.96-4.13 (2H, m), 4.69 (1H, s), 6.62-6.67 (2H, m), 7.08-7.16 (2H, m), 7.17-7.21 (1H, m), 9.16 (1H, s).

(Step 5)

HATU (245 mg, 0.64 mmol) was added to a solution of N-(3,5-difluoro-4-(trimethylsilyl)phenyl)-8-methoxy-2,3,4, 5-tetrahydrobenzo[f][1,4]oxazepine-5-carboxamide (218 mg, 0.54 mmol), 3-hydroxy-1,2-oxazole-5-carboxylic acid (72.7 mg, 0.56 mmol) and DIEA (187 µL, 1.07 mmol) in DMF (2.6 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 30→100% ethyl acetate/hexane), and the precipitate was washed with IPE/hexane to give the title compound (114.5 mg, 0.221 mmol, 41.3%) as white crystals.

MS(API): Calculated 517.6. Found 518.1 (M+H).

$^1$H NMR (300 MHz, CDCl$_3$): δ 0.31 (9H, s), 3.73-3.88 (4H, m), 3.91-4.17 (3H, m), 4.40-4.53 (1H, m), 5.82-6.35 (1H, m), 6.51 (1H, s), 6.70 (1H, d), 6.75 (1H, dd, J=8.3, 2.3 Hz), 6.85-6.95 (2H, m), 7.13-7.23 (1H, m), 7.32-7.38 (1H, m).

Example 37 ethyl 2-(2-fluoro-4-(((2-((3-hydroxy-1,2-oxazol-5-yl)carbonyl)-6-methoxy-1,2,3,4-tetrahydroisoquinolin-1-yl)carbonyl)amino)phenyl)-2-methylpropanoate (Step 1)

Diethyl malonate (20.14 g, 125.71 mmol) was added to a suspension of sodium hydride (60% oil, 5.28 g, 132.00 mmol) in DMF (100 mL) at 0° C., and the mixture was stirred at 0° C. for 30 min. Then, 1,2-difluoro-4-nitrobenzene (10 g, 62.86 mmol) was slowly added thereto, and the mixture was stirred overnight at 70° C. To the reaction mixture were added aqueous ammonium chloride and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→40% ethyl acetate/hexane), and then silica gel column chromatography (NH, solvent gradient; 0-20% ethyl acetate/hexane) to give diethyl 2-(2-fluoro-4-nitrophenyl)malonate (16.20 g, 54.1 mmol, 86%) as a yellow oil.

$^1$H NMR (300 MHz, DMSO-d$_6$): δ 1.13-1.24 (6H, m), 4.19 (4H, q, J=7.2 Hz), 5.36 (1H, s), 7.67-7.82 (1H, m), 8.16 (2H, ddd, J=16.1, 9.1, 2.5 Hz).

(Step 2)

Lithium chloride (3.44 g, 81.20 mmol) was added to a solution of diethyl 2-(2-fluoro-4-nitrophenyl)malonate (16.2 g, 54.14 mmol) in a mixed solvent of water (0.975 mL, 54.14 mmol) and DMSO (20 mL), and the mixture was stirred overnight at 120° C. To the reaction mixture were added 0.1N hydrochloric acid and ethyl acetate, and the organic layer was separated. The organic layer was washed with brine, and dried over magnesium sulfate, and the solvent was evaporated under reduced pressure. The obtained residue was purified by silica gel column chromatography (NH, solvent gradient; 0→20% ethyl acetate/hexane) to give ethyl 2-(2-fluoro-4-nitrophenyl)acetate (7.38 g, 32.5 mmol, 60.0%) as a yellow oil.

$^1$H NMR (300 MHz, DMSO-d$_6$): δ 1.19 (3H, t, J=7.2 Hz), 3.91 (2H, d, J=1.1 Hz), 4.12 (2H, q, J=7.2 Hz), 7.62-776 (1H, m), 8.04-8.17 (2H, m).

(Step 3)

To a solution of ethyl 2-(2-fluoro-4-nitrophenyl)acetate (7.38 g, 32.48 mmol) and iodomethane (8.12 mL, 129.94 mmol) in DMF (150 mL) was added sodium hydride (60% oil, 3.25 g, 81.21 mmol) at 0° C., and the mixture was stirred at 0° C. for 4 hr. To the reaction mixture were added aqueous ammonium chloride solution and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 5-20% ethyl acetate/hexane) to give ethyl 2-(2-fluoro-4-nitrophenyl)-2-methylpropanoate (7.22 g, 28.3 mmol, 87%) as yellow crystals.

$^1$H NMR (300 MHz, DMSO-d$_6$): δ 1.11 (3H, t, J=7.0 Hz), 1.53 (6H, s), 4.09 (2H, q, J=6.9 Hz), 7.68-7.81 (1H, m), 8.03-8.18 (2H, m).

(Step 4)

A solution of ethyl 2-(2-fluoro-4-nitrophenyl)-2-methylpropanoate (2 g, 7.84 mmol) and 10% palladium-carbon (0.834 g, 0.39 mmol, 50% wet) in EtOH (50 mL) was stirred overnight under hydrogen atmosphere (1 atm) at room temperature. The catalyst was removed by filtration, and the filtrate was concentrated under reduced pressure to give ethyl 2-(4-amino-2-fluorophenyl)-2-methylpropanoate (1.770 g, 7.86 mmol, 100%) as a yellow oil.

$^1$H NMR (300 MHz, DMSO-d$_6$): δ 1.01-1.18 (3H, m), 1.38 (6H, s), 4.03 (2H, q, J=7.2 Hz), 5.26 (2H, s), 6.17-6.39 (2H, m), 6.98 (1H, dd, J=9.3, 8.5 Hz).

(Step 5)

T3P (7.01 mL, 11.79 mmol) was added to a solution of 2-(tert-butoxycarbonyl)-6-methoxy-1,2,3,4-tetrahydroisoquinoline-1-carboxylic acid (2.415 g, 7.86 mmol), ethyl 2-(4-amino-2-fluorophenyl)-2-methylpropanoate (1.77 g, 7.86 mmol), DIEA (6.86 mL, 39.29 mmol) and DMAP (1.056 g, 8.64 mmol) in ethyl acetate (100 mL), and the mixture was stirred at 70° C. for 15 hr. To the reaction mixture was added water, and the mixture was extracted twice with ethyl acetate. The organic layer was washed with aqueous sodium hydrogen carbonate solution and brine, and dried over magnesium sulfate, and the solvent was evaporated under reduced pressure. The obtained residue was purified by silica gel column chromatography (solvent gradient; 0→30% ethyl acetate/hexane) to give tert-butyl 1-((4-(1-ethoxy-2-methyl-1-oxopropan-2-yl)-3-fluorophenyl)carbamoyl)-6-methoxy-3,4-dihydroisoquinoline-2 (1H)-carboxylate (2.78 g, 5.40 mmol, 68.8%) as a pale yellow solid.

$^1$H NMR (300 MHz, DMSO-d$_6$): δ 1.08 (3H, t, J=7.0 Hz), 1.35 (6H, s), 1.44 (9H, s), 2.66-2.82 (1H, m), 3.05 (1H, brs), 3.35-3.50 (1H, m), 3.72 (3H, s), 3.87-4.01 (1H, m), 4.00-4.11 (2H, m), 5.21-5.50 (1H, m), 6.69-6.91 (2H, m), 7.22-7.39 (2H, m), 7.40-7.57 (2H, m), 10.35-10.62 (1H, m).

(Step 6)

4N hydrogen chloride/MeOH (5 mL, 20.00 mmol) was added to a solution of tert-butyl 1-((4-(1-ethoxy-2-methyl-1-oxopropan-2-yl)-3-fluorophenyl)carbamoyl)-6-methoxy-3,4-dihydroisoquinoline-2(1H)-carboxylate (1.74 g, 3.38 mmol) in MeOH (5 mL), and the mixture was stirred overnight at room temperature. The reaction mixture was concentrated under reduced pressure to give ethyl 2-(2-fluoro-4-(6-methoxy-1,2,3,4-tetrahydroisoquinoline-1-carboxamide)phenyl)-2-methylpropanoate hydrochloride (1.600 g, 3.55 mmol, 105%) as a white solid.

$^1$H NMR (300 MHz, DMSO-d$_6$): δ 1.10 (3H, t, J=7.0 Hz), 1.47 (6H, s), 2.87-3.04 (1H, m), 3.05-3.20 (1H, m), 3.43 (1H, brs), 3.62-3.85 (4H, m), 4.00-4.14 (2H, m), 5.24 (1H, brs), 6.84-6.94 (2H, m), 7.36 (1H, d, J=9.4 Hz), 7.40-7.49 (2H, m), 7.51-7.63 (1H, m), 9.37 (1H, brs), 10.09 (1H, brs), 11.51 (1H, s).

(Step 7)

HATU (1.096 g, 2.88 mmol) was added to a solution of DIEA (1.162 mL, 6.65 mmol), 3-hydroxy-1,2-oxazole-5-carboxylic acid (0.372 g, 2.88 mmol) and ethyl 2-(2-fluoro-4-(6-methoxy-1,2,3,4-tetrahydroisoquinoline-1-carboxamide)phenyl)-2-methylpropanoate hydrochloride (1 g, 2.22 mmol) in DMF (15 mL) at room temperature, and the mixture was stirred at room temperature for 5 hr. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane, 0-10% MeOH/ethyl acetate) to give the title compound (0.412 g, 0.784 mmol, 35.4%) as a white solid.

MS(API): Calculated 525.5. Found 524.1 (M−H).

$^1$H NMR (300 MHz, DMSO-d$_6$): δ 1.08 (3H, t, J=7.0 Hz), 1.43 (6H, s), 2.78-2.97 (1H, m), 3.05-3.26 (1H, m), 3.62-3.86 (4H, m), 3.96-4.10 (2H, m), 4.11-4.23 (1H, m), 5.69 (1H, s), 6.59 (1H, s), 6.77-6.97 (2H, m), 7.21-7.40 (2H, m), 7.43-7.60 (2H, m), 10.73 (1H, s), 11.76 (1H, s).

Example 38

N-(4-tert-butyl-3-fluorophenyl)-6-(1H-indazol-1-ylacetyl)-1-methyl-2-oxo-1,2,5,6,7,8-hexahydro-1,6-naphthyridine-5-carboxamide (Step 1)

Iodomethane (1.947 mL, 31.27 mmol) was added to a solution of 5-ethyl 6-tert-butyl 2-hydroxy-7,8-dihydro-1,6-naphthyridine-5,6(5H)-dicarboxylate (5.04 g, 15.63 mmol) and cesium carbonate (6.62 g, 20.33 mmol) in DMF (35 mL), and the mixture was stirred at room temperature for 3.5 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 10→100% ethyl acetate/hexane) to give 5-ethyl 6-tert-butyl 1-methyl-2-oxo-1,2,7,8-tetrahydro-1,6-naphthyridine-5,6(5H)-dicarboxylate (3.60 g, 10.70 mmol, 68.5%) as a colorless oil.

$^1$H NMR (300 MHz, CDCl$_3$): δ 1.25-1.33 (3H, m), 1.44-1.52 (9H, m), 2.64-2.88 (2H, m), 3.37-3.59 (4H, m), 4.17-4.37 (3H, m), 5.16-5.39 (1H, m), 6.52 (1H, d, J=9.4 Hz), 7.45-7.53 (1H, m).

(Step 2)

2N Aqueous lithium hydroxide solution (32.1 mL, 64.21 mmol) was added to a solution of 5-ethyl 6-tert-butyl 1-methyl-2-oxo-1,2,7,8-tetrahydro-1,6-naphthyridine-5,6(5H)-dicarboxylate (3.60 g, 10.70 mmol) in a mixed solvent of EtOH (15 mL) and THF (15 mL), and the mixture was stirred at room temperature for 2 hr. To the reaction mixture was added ice-water, and 2N hydrochloric acid was added thereto until the pH of the mixture became 4. Then, the mixture was extracted three times with a mixed solvent of ethyl acetate/THF. The organic layer was washed with brine, and dried over magnesium sulfate, and the solvent was evaporated under reduced pressure. The precipitate was washed with IPE/hexane to give 6-(tert-butoxycarbonyl)-1-methyl-2-oxo-1,2,5,6,7,8-hexahydro-1,6-naphthyridine-5-carboxylic acid (2.82 g, 9.15 mmol, 85%) as white crystals.

$^1$H NMR (300 MHz, DMSO-d$_6$): δ 1.36-1.47 (9H, m), 2.75-2.86 (2H, m), 3.15-3.27 (1H, m), 3.39 (3H, s), 4.03-4.14 (1H, m), 5.09-5.23 (1H, m), 6.34 (1H, d, J=9.4 Hz), 7.50 (1H, d, J=9.4 Hz), 13.17 (1H, brs)

(Step 3)

T3P (1.047 mL, 1.76 mmol) was added to a solution of 6-(tert-butoxycarbonyl)-1-methyl-2-oxo-1,2,5,6,7,8-hexahydro-1,6-naphthyridine-5-carboxylic acid (362 mg, 1.17 mmol), 4-(tert-butyl)-3-fluoroaniline (196 mg, 1.17 mmol), DIEA (1.023 mL, 5.87 mmol) and DMAP (158 mg, 1.29 mmol) in ethyl acetate (9.5 mL), and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The obtained residue was purified by silica gel column chromatography (solvent gradient; 0→10% MeOH/ethyl acetate) to give tert-butyl 5-((4-(tert-butyl)-3-fluorophenyl)carbamoyl)-1-methyl-2-oxo-1,2,7,8-tetrahydro-1,6-naphthyridine-6(5H)-carboxylate (494 mg, 1.080 mmol, 92%) as a white solid.

$^1$H NMR (300 MHz, CDCl$_3$): δ 1.35 (9H, s), 1.54 (9H, s), 2.67-2.90 (2H, m), 3.22-3.34 (1H, m), 3.52 (3H, s), 4.23 (1H, dd, J=13.6, 4.9 Hz), 5.44 (1H, brs), 6.56 (1H, d, J=9.4 Hz), 7.06 (1H, dd, J=8.3, 2.3 Hz), 7.13-7.25 (2H, m), 7.38 (1H, dd, J=14.4, 2.3 Hz), 8.79 (1H, brs).

(Step 4)

TFA (5.5 mL, 74.0 mmol) was added to tert-butyl 5-((4-(tert-butyl)-3-fluorophenyl)carbamoyl)-1-methyl-2-oxo-1,2,7,8-tetrahydro-1,6-naphthyridine-6(5H)-carboxylate (491 mg, 1.07 mmol), and the mixture was stirred at room temperature for 20 min. The reaction mixture was added to ice and aqueous sodium hydrogen carbonate solution, and potassium carbonate was added thereto until the pH of the mixture became 8. Then, the mixture was extracted three times with a mixed solvent of ethyl acetate/THF. The organic layer was washed with brine, and dried over magnesium sulfate, and the solvent was evaporated under reduced pressure. The precipitate was washed with IPE/hexane to give N-(4-(tert-butyl)-3-fluorophenyl)-1-methyl-2-oxo-1,2,5,6,7,8-hexahydro-1,6-naphthyridine-5-carboxamide (325 mg, 0.909 mmol, 85%) as white crystals.

$^1$H NMR (300 MHz, CDCl$_3$): δ 1.35 (9H, s), 2.13 (1H, brs), 2.60-2.77 (2H, m), 3.06-3.17 (1H, m), 3.22-3.31 (1H, m), 3.49 (3H, s), 4.41 (1H, s), 6.52 (1H, d, J=9.4 Hz), 7.12 (1H, dd), 7.21 (1H, t), 7.42 (1H, dd, J=14.4, 2.3 Hz), 7.58 (1H, d, J=9.4 Hz), 9.25 (1H, s).

(Step 5)

HATU (102 mg, 0.27 mmol) was added to a solution of N-(4-(tert-butyl)-3-fluorophenyl)-1-methyl-2-oxo-1,2,5,6,7,8-hexahydro-1,6-naphthyridine-5-carboxamide (80 mg, 0.22 mmol), 2-(1H-indazol-1-yl)acetic acid (41.4 mg, 0.24 mmol) and DIEA (78 μL, 0.45 mmol) in DMF (1.2 mL) at room temperature, and the mixture was stirred at room temperature for 15 hr. To the reaction mixture was added water, and the mixture was extracted three times with a mixed solvent of ethyl acetate/THF. The organic layer was washed with brine, and dried over magnesium sulfate, and the solvent was evaporated under reduced pressure. The precipitate was washed with IPE/hexane to give the title compound (93.8 mg, 0.182 mmol, 81%) as white crystals.

MS(API): Calculated 515.6. Found 516.3 (M+H).

$^1$H NMR (300 MHz, DMSO-d$_6$): δ 1.29 (9H, s), 3.01-3.08 (2H, m), 3.46 (3H, s), 4.14 (2H, t, J=5.7 Hz), 5.54 (1H, s), 5.57-5.73 (2H, m), 6.38 (1H, d, J=9.4 Hz), 7.13 (1H, t), 7.21 (1H, dd), 7.26 (1H, t), 7.35 (1H, t, J=7.7 Hz), 7.42-7.46 (1H, m), 7.48 (1H, s), 7.56 (1H, d, J=8.3 Hz), 7.76 (1H, d, J=7.9 Hz), 8.08 (1H, s), 10.48 (1H, s).

Example 39

N-(3,5-difluoro-4-(trimethylsilyl)phenyl)-6-(1H-indazol-1-ylacetyl)-1-methyl-2-oxo-1,2,5,6,7,8-hexahydro-1,6-naphthyridine-5-carboxamide The title compound was synthesized by the reaction and purification in the same manner as in Example 38.

Example 40

(1R)-N-(4-tert-butyl-3-fluorophenyl)-6-methoxy-2-(2H-tetrazol-5-ylacetyl)-1,2,3,4-tetrahydroisoquinoline-1-carboxamide The title compound was synthesized by the reaction and purification in the same manner as in Examples 1 and 25.

Example 41

N-(4-tert-butyl-3-fluorophenyl)-6-((3-hydroxy-1,2-oxazol-5-yl)acetyl)-2-methoxy-5,6,7,8-tetrahydro-1,6-naphthyridine-5-carboxamide (Step 1)

n-BuLi (84 mL, 133.98 mmol) was slowly added to a solution of 2-methoxy-6-methylpyridine (15.00 g, 121.80 mmol) in THF (200 mL) under argon gas atmosphere at −78° C., and the mixture was stirred at −78° C. for 25 min. Then, paraformaldehyde (14.63 g, 487.20 mmol) was added thereto at −78° C., and the mixture was stirred at room temperature for 4 hr. To the reaction mixture were added ice water and sodium chloride, and the mixture was extracted four times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 5→40% ethyl acetate/hexane) to give 2-(6-methoxypyridin-2-yl)ethanol (7.93 g, 51.8 mmol, 42.5%) as a colorless oil.

(Step 2)

2.2M DEAD/toluene solution (30.6 mL, 67.22 mmol) was added to a solution of 2-(6-methoxypyridin-2-yl)ethanol (7.92 g, 51.70 mmol), PPh$_3$ (17.63 g, 67.22 mmol) and phthalimide (8.37 g, 56.87 mmol) in THF (120 mL) under argon gas atmosphere at 0° C., and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 2-20% ethyl acetate/hexane) to give 2-(2-(6-methoxypyridin-2-yl)ethyl)isoindoline-1,3-dione (12.45 g, 44.1 mmol, 85%) as a colorless oil.

(Step 3)

Hydrazine monohydrate (10.95 mL, 225.83 mmol) was added to a solution of 2-(2-(6-methoxypyridin-2-yl)ethyl)isoindoline-1,3-dione (12.75 g, 45.17 mmol) in EtOH (125 mL), and the mixture was heated under reflux for 1 hr. The reaction mixture was cooled, and the insoluble substance was removed by filtration. The filtrate was concentrated under reduced pressure, and the obtained residue was purified by silica gel column chromatography (NH, solvent gradient; 30→100% ethyl acetate/hexane) to give 2-(6-methoxypyridin-2-yl)ethanamine (6.53 g, 42.9 mmol, 95%) as a colorless oil.

(Step 4)

A solution of 2-(6-methoxypyridin-2-yl)ethanamine (6.53 g, 42.91 mmol), 4N hydrogen chloride/CPME solution (23.60 mL, 94.39 mmol) and 47% ethyl glyoxylate/toluene solution (27.1 mL, 128.72 mmol) in EtOH (75 mL) was heated under reflux for 20 hr. The reaction mixture was concentrated under reduced pressure, and the precipitate was washed with EtOH/diethyl ether to give ethyl 2-hydroxy-5, 6,7,8-tetrahydro-1,6-naphthyridine-5-carboxylate hydrochloride (8.89 g, 34.4 mmol, 80%) as a white solid.
(Step 5)

Boc$_2$O (7.87 g, 36.08 mmol) was added to a solution of ethyl 2-hydroxy-5,6,7,8-tetrahydro-1,6-naphthyridine-5-carboxylate hydrochloride (8.89 g, 34.36 mmol) and TEA (5.03 mL, 36.08 mmol) in a mixed solvent of THF (95 mL) and water (35 mL), and the mixture was stirred at room temperature for 15 hr. To the reaction mixture was added brine, and the mixture was extracted three times with a mixed solvent of ethyl acetate/THF. The organic layer was washed with brine, and dried over magnesium sulfate, and the solvent was evaporated under reduced pressure. The precipitate was washed with IPE/hexane to give 5-ethyl 6-tert-butyl 2-hydroxy-7,8-dihydro-1,6-naphthyridine-5,6(5H)-dicarboxylate (6.85 g, 21.25 mmol, 61.8%) as a white solid.
(Step 6)

Iodomethane (7.94 mL, 127.50 mmol) was added to a solution of 5-ethyl 6-tert-butyl 2-hydroxy-7,8-dihydro-1,6-naphthyridine-5,6(5H)-dicarboxylate (6.85 g, 21.25 mmol) and silver(I) carbonate (7.62 g, 27.62 mmol) in THF (140 mL), and the mixture was stirred at room temperature for 15 hr, and then at 50° C. for 8 hr. The reaction mixture was cooled, and the insoluble substance was removed by filtration. The filtrate was concentrated under reduced pressure, and the obtained residue was purified by silica gel column chromatography (solvent gradient; 5→30% ethyl acetate/hexane) to give 5-ethyl 6-tert-butyl 2-methoxy-7,8-dihydro-1,6-naphthyridine-5,6(5H)-dicarboxylate (6.41 g, 19.06 mmol, 90%) as a colorless oil.
(Step 7)

2N Aqueous lithium hydroxide solution (6.29 mL, 12.57 mmol) was added to a solution of 5-ethyl 6-tert-butyl 2-methoxy-7,8-dihydro-1,6-naphthyridine-5,6(5H)-dicarboxylate (705 mg, 2.10 mmol) in a mixed solvent of EtOH (3 mL) and THF (3 mL), and the mixture was stirred at room temperature for 2 hr. To the reaction mixture was added ice water, and 2N hydrochloric acid was added thereto until the pH of the mixture became 4. Then, the mixture was extracted three times with a mixed solvent of ethyl acetate/THF. The organic layer was washed with brine, and dried over magnesium sulfate, and the solvent was evaporated under reduced pressure to give 6-(tert-butoxycarbonyl)-2-methoxy-5,6,7,8-tetrahydro-1,6-naphthyridine-5-carboxylic acid (643 mg, 2.085 mmol, 100%) as a white solid.
(Step 8)

T3P (1.227 mL, 2.06 mmol) was added to a solution of 6-(tert-butoxycarbonyl)-2-methoxy-5,6,7,8-tetrahydro-1,6-naphthyridine-5-carboxylic acid (424 mg, 1.38 mmol), 4-(tert-butyl)-3-fluoroaniline (230 mg, 1.38 mmol), DIEA (1.198 mL, 6.88 mmol) and DMAP (185 mg, 1.51 mmol) in ethyl acetate (11 mL) at room temperature, and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with hexane to give tert-butyl 5-((4-(tert-butyl)-3-fluorophenyl)carbamoyl)-2-methoxy-7,8-dihydro-1,6-naphthyridine-6(5H)-carboxylate (471 mg, 1.029 mmol, 74.9%) as white crystals.

$^1$H NMR (300 MHz, CDCl$_3$): δ 1.34 (9H, s), 1.53 (9H, s), 2.83-3.03 (2H, m), 3.47 (1H, brs), 3.92 (3H, s), 4.02-4.12 (1H, m), 5.59 (1H, brs), 6.64 (1H, d, J=8.7 Hz), 7.05 (1H, d, J=8.7 Hz), 7.16-7.31 (2H, m), 7.39 (1H, dd, J=14.4,2.3 Hz), 7.48 (1H, brs).
(Step 9)

TFA (5.5 mL, 74.0 mmol) was added to tert-butyl 5-((4-(tert-butyl)-3-fluorophenyl)carbamoyl)-2-methoxy-7,8-dihydro-1,6-naphthyridine-6(5H)-carboxylate (469 mg, 1.03 mmol), and the mixture was stirred at room temperature for 20 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The precipitate was washed with IPE/hexane to give N-(4-(tert-butyl)-3-fluorophenyl)-2-methoxy-5,6,7,8-tetrahydro-1,6-naphthyridine-5-carboxamide (321 mg, 0.898 mmol, 88%) as white crystals.

$^1$H NMR (300 MHz, CDCl$_3$): δ 1.34 (9H, d, J=0.8 Hz), 2.17 (1H, brs), 2.74-2.85 (1H, m), 2.87-2.98 (1H, m), 3.13-3.29 (2H, m), 3.90 (3H, s), 4.58 (1H, s), 6.60 (1H, d, J=8.3 Hz), 7.11 (1H, dd), 7.20 (1H, t), 7.44 (1H, dd, J=14.4,2.3 Hz), 7.83 (1H, d, J=8.7 Hz), 9.44 (1H, s).
(Step 10)

HATU (174 mg, 0.46 mmol) was added to a solution of N-(4-(tert-butyl)-3-fluorophenyl)-2-methoxy-5,6,7,8-tetrahydro-1,6-naphthyridine-5-carboxamide (136 mg, 0.38 mmol), 2-(3-hydroxy-1,2-oxazol-5-yl)acetic acid (57.2 mg, 0.40 mmol) and DIEA (133 µL, 0.76 mmol) in DMF (1.9 mL) at room temperature, and the mixture was stirred for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 30→100% ethyl acetate/hexane), and the precipitate was washed with diethyl ether/hexane to give the title compound (59.5 mg, 0.123 mmol, 32.4%) as white crystals.

MS(API): Calculated 482.5. Found 483.1 (M+H).

$^1$H NMR (300 MHz, CDCl$_3$): δ 1.31 (9H, s), 2.89-3.14 (2H, m), 3.87-3.99 (7H, m), 5.95 (1H, s), 5.97 (1H, brs), 6.64 (1H, d, J=8.7 Hz), 6.98 (1H, d, J=8.3 Hz), 7.10-7.20 (2H, m), 7.32 (1H, dd, J=14.4,1.9 Hz), 7.42 (1H, d, J=8.3 Hz), 8.94 (1H, brs).

Example 42

N-(4-(1-(ethylamino)-2-methyl-1-oxopropan-2-yl)-3-fluorophenyl)-6-methoxy-2-propionyl-1,2,3,4-tetrahydroisoquinoline-1-carboxamide The title compound was synthesized by the reaction and purification in the same manner as in Examples 1 and 25.

Example 43

(1R)-N-(4-tert-butyl-3,5-difluorophenyl)-2-((3-hydroxy-1,2-oxazol-5-yl)acetyl)-6-methoxy-1,2,3,4-tetrahydroisoquinoline-1-carboxamide (Step 1)

tert-Butyl 1-((4-(tert-butyl)-3,5-difluorophenyl)carbamoyl)-6-methoxy-3,4-dihydroisoquinoline-2(1H)-carboxylate (2.080 g) was resolved by chiral column chromatography. The fraction having a shorter retention time was concentrated to give tert-butyl (R)-1-((4-(tert-butyl)-3,5-difluorophenyl)carbamoyl)-6-methoxy-3,4-dihydroisoquinoline-2(1H)-carboxylate (765 mg, >99.9% ee) as a white solid.

purification condition by chiral column chromatography column: CHIRALPAK AD (AF003) 50 mmID×500 mmL solvent: hexane/EtOH=850/150 flow rate: 80 mL/min temperature: 30° C.

detection method: UV 220 nm (Step 2)

4M Hydrogen chloride/ethyl acetate (5 mL, 20.00 mmol) was added to tert-butyl (R)-1-((4-(tert-butyl)-3,5-difluorophenyl)carbamoyl)-6-methoxy-3,4-dihydroisoquinoline-2(1H)-carboxylate (765 mg, 1.61 mmol), and the mixture was stirred overnight at room temperature. The reaction mixture was concentrated under reduced pressure, and the precipitate was washed with ethyl acetate/hexane to give (R)-N-(4-(tert-butyl)-3,5-difluorophenyl)-6-methoxy-1,2,3,4-tetrahydroisoquinoline-1-carboxamide hydrochloride (550 mg, 1.339 mmol, 83%) as a white solid.

$^1$H NMR (300 MHz, DMSO-$d_6$): δ 1.41 (9H, t, J=2.1 Hz), 2.87-3.03 (1H, m), 3.04-3.19 (1H, m), 3.36-3.48 (1H, m), 3.62-3.73 (1H, m), 3.75 (3H, s), 5.20 (1H, s), 6.70-7.02 (2H, m), 7.17-7.48 (3H, m), 8.87-10.47 (2H, m), 11.59 (1H, s).

(Step 3)

WSC (70.0 mg, 0.37 mmol) was added to a solution of DIEA (0.128 mL, 0.73 mmol), HOBt (44.7 mg, 0.29 mmol), 2-(3-hydroxy-1,2-oxazol-5-yl)acetic acid (38.3 mg, 0.27 mmol) and (R)-N-(4-(tert-butyl)-3,5-difluorophenyl)-6-methoxy-1,2,3,4-tetrahydroisoquinoline-1-carboxamide hydrochloride (100 mg, 0.24 mmol) in DMF (5 mL) at room temperature, and the mixture was stirred at room temperature for 5 hr. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 30→100% ethyl acetate/hexane) to give the title compound (61.0 mg, 0.122 mmol, 50.2%) as white crystals.

MS(API): Calculated 499.5. Found 497.8 (M−H).

$^1$H NMR (300 MHz, DMSO-$d_6$): δ 1.38 (9H, s), 2.69-2.90 (1H, m), 3.03-3.18 (1H, m), 3.49-3.62 (1H, m), 3.73 (3H, s), 3.88-4.16 (3H, m), 5.62 (1H, s), 5.90 (1H, s), 6.72-6.96 (2H, m), 7.18 (2H, d, J=13.2 Hz), 7.47 (1H, d, J=9.1 Hz), 10.69 (1H, s), 11.17 (1H, brs).

$[α]_D^{25}$+5.4 (c 0.2550, MeOH)

Example 45

(1R)-N-(7-fluoro-1,1-dimethyl-2,3-dihydro-1H-inden-5-yl)-2-((3-hydroxy-1,2-oxazol-5-yl)acetyl)-6-methoxy-1,2,3,4-tetrahydroisoquinoline-1-carboxamide (Step 1)

tert-Butyl 1-((7-fluoro-1,1-dimethyl-2,3-dihydro-1H-inden-5-yl)carbamoyl)-6-methoxy-3,4-dihydroisoquinoline-2(1H)-carboxylate (1.54 g) was resolved by chiral column chromatography. The fraction having a shorter retention time was concentrated to give tert-butyl (R)-1-((7-fluoro-1,1-dimethyl-2,3-dihydro-1H-inden-5-yl)carbamoyl)-6-methoxy-3,4-dihydroisoquinoline-2(1H)-carboxylate (562 mg, >99.9% ee) as a white solid.

purification condition by chiral column chromatography column: CHIRALCEL OD (NL001) 50 mmID×500 mmL solvent: hexane/EtOH=900/100 flow rate: 80 mL/min temperature: 30° C.

detection method: UV 220 nm (Step 2)

To a solution of tert-butyl (R)-1-((7-fluoro-1,1-dimethyl-2,3-dihydro-1H-inden-5-yl) carbamoyl)-6-methoxy-3,4-dihydroisoquinoline-2(1H)-carboxylate (750 mg, 1.60 mmol) in ethyl acetate (5.0 mL) was added 4M hydrogen chloride/ethyl acetate (7.0 mL, 28.00 mmol), and the mixture was stirred overnight at room temperature. The precipitate was collected by filtration, and washed with ethyl acetate to give (R)-N-(7-fluoro-1,1-dimethyl-2,3-dihydro-1H-inden-5-yl)-6-methoxy-1,2,3,4-tetrahydroisoquinoline-1-carboxamide hydrochloride (528.4 mg, 1.305 mmol, 82%) as white crystals.

(Step 3)

To a solution of (R)-N-(7-fluoro-1,1-dimethyl-2,3-dihydro-1H-inden-5-yl)-6-methoxy-1,2,3,4-tetrahydroisoquinoline-1-carboxamide hydrochloride (50 mg, 0.12 mmol), DIEA (0.042 mL, 0.25 mmol) and 2-(3-hydroxy-1,2-oxazol-5-yl)acetic acid (19.44 mg, 0.14 mmol) in DMF (2.0 mL) was added HATU (56.3 mg, 0.15 mmol), and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (32.5 mg, 0.066 mmol, 53.3%) as white crystals.

MS(API): Calculated 493.5. Found 492.1 (M−H).

$^1$H NMR (300 MHz, DMSO-$d_6$): δ 1.28 (6H, d, J=1.9 Hz), 1.86 (2H, t, J=7.2 Hz), 2.72-2.91 (3H, m), 3.05-3.22 (1H, m), 3.52-3.68 (1H, m), 3.69-3.76 (3H, m), 3.87-4.15 (3H, m), 5.61-5.71 (1H, m), 5.91 (1H, s), 6.74-6.89 (2H, m), 7.11-7.26 (2H, m), 7.42-7.53 (1H, m), 10.46 (1H, s), 11.16 (1H, brs).

$[α]_D^{25}$+15.2 (c 0.2550, MeOH)

The compounds described in Examples 44 and 46 to 48 were synthesized by the reaction and purification in the same manner as in Examples 1 and 25.

Example 44

(1R)-N-(4-tert-butyl-3-fluorophenyl)-2-((1,1-dioxidotetrahydro-2H-thiopyran-4-yl)acetyl)-6-methoxy-1,2,3,4-tetrahydroisoquinoline-1-carboxamide

Example 46

N-(3-fluoro-4-(2-(5-methyl-1,3,4-oxadiazol-2-yl)propan-2-yl)phenyl)-6-methoxy-2-propionyl-1,2,3,4-tetrahydroisoquinoline-1-carboxamide

Example 47

(1R)-N-(4-tert-butyl-3-fluorophenyl)-6-methoxy-2-propionyl-1,2,3,4-tetrahydroisoquinoinoline-1-carboxamide

Example 48

(1R)-N-(4-tert-butyl-3-fluorophenyl)-6-methoxy-2-(3,3,3-trifluoropropanoyl)-1,2,3,4-tetrahydroisoquinoline-1-carboxamide

Example 49

N-(4-tert-butyl-3-fluorophenyl)-4-((3-hydroxy-1,2-oxazol-5-yl)acetyl)-8-methoxy-2,3,4,5-tetrahydro-1,4-benzoxazepine-5-carboxamide The title compound was synthesized by the reaction and purification in the same manner as in Example 5.

Example 50

N-(3,5-difluoro-4-(trimethylsilyl)phenyl)-4-((3-hydroxy-1,2-oxazol-5-yl)acetyl)-8-methoxy-2,3,4,5-tetrahydro-1,4-benzoxazepine-5-carboxamide HATU (480 mg, 1.26 mmol) was added to a solution of N-(3,5-difluoro-4-(trimethylsilyl)phenyl)-8-methoxy-2,3,4,5-tetrahydrobenzo[f][1,4]oxazepine-5-carboxamide (428 mg, 1.05 mmol), 2-(3-hydroxy-1,2-oxazol-5-yl)acetic acid (158 mg, 1.11 mmol) and DIEA (367 µL, 2.11 mmol) in DMF (5.1 mL) at room temperature, and the mixture was stirred for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 20→90% ethyl acetate/hexane), and the precipitate was washed with IPE/hexane to give the title compound (141.7 mg, 0.267 mmol, 25.3%) as white crystals.

MS(API): Calculated 531.6. Found 530.0 (M−H).

$^1$H NMR (300 MHz, CDCl$_3$): δ 0.31 (9H, s), 3.83 (3H, s), 3.85-4.02 (5H, m), 4.31-4.40 (1H, m), 6.01 (1H, s), 6.41 (1H, s), 6.64 (1H, d, J=2.6 Hz), 6.68-6.74 (2H, m), 6.87-6.95 (2H, m), 7.28-7.38 (2H, m).

The compounds described in Examples 51 to 53 were synthesized by the reaction and purification in the same manner as in Examples 1 and 25.

Example 51

N-(4-tert-butyl-3-(difluoromethoxy)phenyl)-2-((3-hydroxy-1,2-oxazol-5-yl)acetyl)-6-methoxy-1,2,3,4-tetrahydroisoquinoline-1-carboxamide

Example 52

N-(4-tert-butyl-3-(2,2-difluoroethoxy)phenyl)-2-((3-hydroxy-1,2-oxazol-5-yl)acetyl)-6-methoxy-1,2,3,4-tetrahydroisoquinoline-1-carboxamide

Example 53

N-(4-tert-butyl-3-cyanophenyl)-2-((3-hydroxy-1,2-oxazol-5-yl)acetyl)-6-methoxy-1,2,3,4-tetrahydroisoquinoline-1-carboxamide

Example 54

N-(4-tert-butyl-3-fluorophenyl)-6-ethoxy-2-((3-hydroxy-1,2-oxazol-5-yl)acetyl)-1,2,3,4-tetrahydroisoquinoline-1-carboxamide (Step 1)

Iodoethane (7.12 mL, 88.37 mmol) was added to a solution of 1-ethyl 2-tert-butyl 6-hydroxy-3,4-dihydroisoquinoline-1,2(1H)-dicarboxylate (14.2 g, 44.19 mmol) and cesium carbonate (18.72 g, 57.44 mmol) in DMF (100 mL), and the mixture was stirred at room temperature for 2.5 hr. To the reaction mixture was added water, and the mixture was extracted with ethyl acetate. The organic layer was washed with brine, and dried over magnesium sulfate, and the solvent was evaporated under reduced pressure to give 1-ethyl 2-tert-butyl 6-ethoxy-3,4-dihydroisoquinoline-1,2(1H)-dicarboxylate (13.0 g, 37.2 mmol, 84%) as a colorless oil.

(Step 2)

2N Aqueous sodium hydroxide solution (55.8 mL, 111.61 mmol) was added to a solution of 1-ethyl 2-tert-butyl 6-ethoxy-3,4-dihydroisoquinoline-1,2(1H)-dicarboxylate (13.0 g, 37.20 mmol) in a mixed solvent of EtOH (100 mL) and THF (100 mL), and the mixture was stirred overnight at room temperature. To the reaction mixture was added ice water, and the mixture was washed with diethyl ether. 2N Hydrochloric acid was added thereto until the pH of the mixture became 4. Then, the mixture was extracted with ethyl acetate. The organic layer was washed with brine, and dried over magnesium sulfate, and the solvent was evaporated under reduced pressure to give 2-(tert-butoxycarbonyl)-6-ethoxy-1,2,3,4-tetrahydroisoquinoline-1-carboxylic acid (3.56 g, 11.08 mmol, 29.8%) as a colorless oil.

(Step 3)

To a solution of 4-(tert-butyl)-3-fluoroaniline (500 mg, 2.99 mmol), 2-(tert-butoxycarbonyl)-6-ethoxy-1,2,3,4-tetrahydroisoquinoline-1-carboxylic acid (1057 mg, 3.29 mmol), DMAP (402 mg, 3.29 mmol) and DIEA (2.61 mL, 14.95 mmol) in ethyl acetate (10 mL) was added T3P (3.52 mL, 5.98 mmol), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane), and crystallized from diethyl ether/hexane to give tert-butyl 1-((4-(tert-butyl)-3-fluorophenyl)carbamoyl)-6-ethoxy-3,4-dihydroisoquinoline-2 (1H)-carboxylate (689.3 mg, 1.465 mmol, 49.0%) as a white solid.

$^1$H NMR (300 MHz, CDCl$_3$): δ 1.33 (9H, d, J=0.8 Hz), 1.40 (3H, t, J=6.8 Hz), 1.52 (9H, s), 2.75-2.97 (2H, m), 3.53-3.78 (2H, m), 4.02 (2H, q, J=6.8 Hz), 5.59 (1H, brs), 6.67-6.83 (2H, m), 7.03 (1H, d, J=7.9 Hz), 7.12-7.22 (2H, m), 7.32-7.43 (1H, m), 8.87 (1H, brs).

(Step 4)

To a solution of tert-butyl 1-((4-(tert-butyl)-3-fluorophenyl)carbamoyl)-6-ethoxy-3,4-dihydroisoquinoline-2(1H)-carboxylate (680 mg, 1.45 mmol) in ethyl acetate (7.0 mL) was added 4N hydrogen chloride/ethyl acetate (7.0 mL, 28.00 mmol), and the mixture was stirred at room temperature for 5 hr. The precipitate was collected by filtration, and washed with ethyl acetate to give N-(4-(tert-butyl)-3-fluorophenyl)-6-ethoxy-1,2,3,4-tetrahydroisoquinoline-1-carboxamide hydrochloride (506.2 mg, 1.244 mmol, 86%) as white crystals.

$^1$H NMR (300 MHz, DMSO-d$_6$): δ 1.27-1.37 (12H, m), 2.88-3.19 (2H, m), 3.38-3.48 (1H, m), 3.70 (1H, dt, J=12.2, 5.8 Hz), 4.01 (2H, q, J=6.8 Hz), 5.25 (1H, s), 6.75-6.94 (2H, m), 7.26-7.44 (3H, m), 7.47-7.61 (1H, m), 9.37 (1H, brs), 10.20 (1H, brs), 11.51 (1H, s).

(Step 5)

To a solution of N-(4-(tert-butyl)-3-fluorophenyl)-6-ethoxy-1,2,3,4-tetrahydroisoquinoline-1-carboxamide hydrochloride (500 mg, 1.23 mmol), DIEA (0.420 mL, 2.46 mmol) and 2-(3-hydroxy-1,2-oxazol-5-yl)acetic acid (211 mg, 1.47 mmol) in DMF (10 mL) was added HATU (561 mg, 1.47 mmol) at room temperature, and the mixture was stirred for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (444.0 mg, 0.896 mmol, 72.9%) as white crystals.

MS(API): Calculated 495.5. Found 494.1 (M−H).

$^1$H NMR (300 MHz, DMSO-d$_6$): δ 1.24-1.34 (12H, m), 2.70-2.88 (1H, m), 3.06-3.20 (1H, m), 3.52-3.67 (1H, m), 3.91-4.14 (5H, m), 5.58-5.70 (1H, m), 5.82-5.94 (1H, m), 6.75-6.86 (2H, m), 7.15-7.29 (2H, m), 7.38-7.50 (2H, m), 10.54 (1H, s), 11.14 (1H, brs).

Example 55

6-ethoxy-N-(7-fluoro-1,1-dimethyl-2,3-dihydro-1H-inden-5-yl)-2-((3-hydroxy-1,2-oxazol-5-yl)acetyl)-1,2,3,4-tetrahydroisoquinoline-1-carboxamide (Step 1)

To a solution of 7-fluoro-1,1-dimethyl-2,3-dihydro-1H-inden-5-amine (365 mg, 2.04 mmol), 2-(tert-butoxycarbonyl)-6-ethoxy-1,2,3,4-tetrahydroisoquinoline-1-carboxylic acid (720 mg, 2.24 mmol), DMAP (274 mg, 2.24 mmol) and DIEA (1.778 mL, 10.18 mmol) in ethyl acetate (10 mL) was added T3P (2.396 mL, 4.07 mmol), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane), and washed with diethyl ether/hexane to give tert-butyl 6-ethoxy-1-((7-fluoro-1,1-dimethyl-2,3-dihydro-1H-inden-5-yl)carbamoyl)-3,4-dihydroisoquinoline-2(1H)-carboxylate (482.9 mg, 1.001 mmol, 49.1%) as white crystals.

$^1$H NMR (300 MHz, CDCl$_3$): δ 1.33 (6H, s), 1.40 (3H, t, J=7.0 Hz), 1.51 (9H, s), 1.90 (2H, t, J=7.4 Hz), 2.79-2.93 (4H, m), 3.48-3.78 (2H, m), 4.02 (2H, q, J=7.0 Hz), 5.54 (1H, brs), 6.66-6.83 (2H, m), 6.94-7.21 (3H, m), 8.76 (1H, brs).

(Step 2)

To a solution of tert-butyl 6-ethoxy-1-((7-fluoro-1,1-dimethyl-2,3-dihydro-1H-inden-5-yl)carbamoyl)-3,4-dihydroisoquinoline-2(1H)-carboxylate (480 mg, 0.99 mmol) in ethyl acetate (5.0 mL) was added 4N hydrogen chloride/ethyl acetate (5.0 mL, 20.00 mmol), and the mixture was stirred at room temperature for 5 hr. The precipitate was collected by filtration, and washed with ethyl acetate to give 6-ethoxy-N-(7-fluoro-1,1-dimethyl-2,3-dihydro-1H-inden-5-yl)-1,2,3,4-tetrahydroisoquinoline-1-carboxamide hydrochloride (360.5 mg, 0.861 mmol, 87%) as white crystals.

$^1$H NMR (300 MHz, DMSO-d$_6$): δ 1.26-1.36 (9H, m), 1.90 (2H, t, J=7.4 Hz), 2.85-3.17 (4H, m), 3.36-3.45 (1H, m), 3.56-3.77 (1H, m), 4.01 (2H, q, J=7.2 Hz), 5.27 (1H, s), 6.81-6.90 (2H, m), 7.26-7.40 (3H, m), 9.37 (1H, brs), 10.25 (1H, brs), 11.51 (1H, s).

(Step 3)

To a solution of 6-ethoxy-N-(7-fluoro-1,1-dimethyl-2,3-dihydro-1H-inden-5-yl)-1,2,3,4-tetrahydroisoquinoline-1-carboxamide hydrochloride (350 mg, 0.84 mmol), DIEA (0.286 mL, 1.67 mmol) and 2-(3-hydroxy-1,2-oxazol-5-yl) acetic acid (143 mg, 1.00 mmol) in DMF (7.0 mL) was added HATU (381 mg, 1.00 mmol), and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 00→50% ethyl acetate/hexane), and crystallized from ethyl acetate/hexane to give the title compound (225.1 mg, 0.444 mmol, 53.1%) as white crystals.

MS(API): Calculated 507.6. Found 506.1 (M−H).

$^1$H NMR (300 MHz, DMSO-d$_6$): δ 1.24-1.34 (9H, m), 1.86 (2H, t, J=7.4 Hz), 2.71-2.91 (3H, m), 3.05-3.05-3.18 (1H, m), 3.51-3.67 (1H, m), 3.95-4.11 (5H, m), 5.63-5.69 (1H, m), 5.84-5.93 (1H, m), 6.76-6.86 (2H, m), 7.13-7.27 (2H, m), 7.40-7.51 (1H, m), 10.42-10.52 (1H, m), 11.14 (1H, brs).

Example 56

(5R)-N-(3,5-difluoro-4-(trimethylsilyl)phenyl)-4-((3-hydroxy-1,2-oxazol-5-yl)acetyl)-8-methoxy-2,3,4,5-tetrahydro-1,4-benzoxazepine-5-carboxamide N-(3,5-Difluoro-4-(trimethylsilyl)phenyl)-4-((3-hydroxy-1,2-oxazol-5-yl)acetyl)-8-methoxy-2,3,4,5-tetrahydro-1,4-benzoxazepine-5-carboxamide (116.7 mg) was resolved by chiral column chromatography. The fraction having a shorter retention time was concentrated to give the title compound (48.6 mg, >99.9% ee) as a white solid.

MS(API): Calculated 531.6. Found 532.1 (M+H).

purification condition by chiral column chromatography
   column: CHIRALPAK IA (QK001) 50 mmID×500 mmL
   solvent: hexane/EtOH=500/500
   flow rate: 80 mL/min
   temperature: 30° C.
   detection method: UV 220 nm The compounds described in Examples 57 to 60 were synthesized by the reaction and purification in the same manner as in Examples 5 and 56.

Example 57

(5S)—N-(3,5-difluoro-4-(trimethylsilyl)phenyl)-4-((3-hydroxy-1,2-oxazol-5-yl)acetyl)-8-methoxy-2,3,4,5-tetrahydro-1,4-benzoxazepine-5-carboxamide Example 58

(5R)-N-(4-tert-butyl-3,5-difluorophenyl)-4-((3-hydroxy-1,2-oxazol-5-yl)carbonyl)-8-methoxy-2,3,4,5-tetrahydro-1,4-benzoxazepine-5-carboxamide Example 59

(5S)—N-(4-tert-butyl-3,5-difluorophenyl)-4-((3-hydroxy-1,2-oxazol-5-yl)carbonyl)-8-methoxy-2,3,4,5-tetrahydro-1,4-benzoxazepine-5-carboxamide Example 60

(5R)-N-(4-tert-butyl-3,5-difluorophenyl)-4-((3-hydroxy-1,2-oxazol-5-yl)acetyl)-8-methoxy-2,3,4,5-tetrahydro-1,4-benzoxazepine-5-carboxamide The compounds described in Examples 61 and 62 were synthesized by the reaction and purification in the same manner as in Examples 1 and 25.

Example 61

N-(4-(1-(cyclopropylamino)-2-methyl-1-oxopropan-2-yl)-3-fluorophenyl)-6-methoxy-2-(3,3,3-trifluoropropanoyl)-1,2,3,4-tetrahydroisoquinoline-1-carboxamide Example 62

N-(3-fluoro-4-(2-methyl-1-oxo-1-(pyrrolidin-1-yl)propan-2-yl)phenyl)-6-methoxy-2-(3,3,3-trifluoropropanoyl)-1,2,3,4-tetrahydroisoquinoline-1-carboxamide Example 63

(1R)-N-(7-fluoro-1,1-dimethyl-2,3-dihydro-1H-inden-5-yl)-2-(3-(3-hydroxy-1,2-oxazol-5-yl)propanoyl)-6-methoxy-1,2,3,4-tetrahydroisoquinoline-1-carboxamide To a solution of (R)-N-(7-fluoro-1,1-dimethyl-2,3-dihydro-1H-inden-5-yl)-6-methoxy-1,2,3,4-tetrahydroisoquinoline-1-carboxamide (70 mg, 0.19 mmol), DIEA (0.065 mL, 0.38 mmol) and 3-(3-hydroxy-1,2-oxazol-5-yl)propanoic acid (35.8 mg, 0.23 mmol) in DMF (2.0 mL) was added HATU (87 mg, 0.23 mmol) at 0° C., and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (37.9 mg, 0.075 mmol, 39.3%) as a white solid.

MS(API): Calculated 507.6. Found 508.2 (M+H).

$^1$H NMR (300 MHz, DMSO-d$_6$): δ 1.28 (6H, d, J=1.1 Hz), 1.81-1.91 (2H, m), 2.73-2.98 (7H, m), 3.06-3.21 (1H, m), 3.49-3.62 (1H, m), 3.73 (3H, s), 4.02-4.12 (1H, m), 5.59-5.81 (2H, m), 6.76-6.87 (2H, m), 7.15 (1H, s), 7.22 (1H, d, J=12.5 Hz), 7.47 (1H, d, J=8.7 Hz), 10.38 (1H, s), 11.01 (1H, brs).

Example 65

(1R)-N-(4-tert-butyl-3-cyanophenyl)-2-((3-hydroxy-1,2-oxazol-5-yl)acetyl)-6-methoxy-1,2,3,4-tetrahydroisoquinoline-1-carboxamide (Step 1)

To a mixture of 1-(tert-butyl)-4-nitrobenzene (1 g, 5.58 mmol) in conc. sulfuric acid (5 mL) was added silver(I) sulfate (1.11 g, 3.57 mmol). Then, bromine (0.286 mL, 5.58 mmol) was slowly added thereto at 0° C., and the mixture was stirred at room temperature for 3 hr. The reaction mixture was added to ice-water, and the mixture was extracted with ethyl acetate. The organic layer was washed with aqueous sodium hydrogen carbonate solution, and the insoluble substance was removed by filtration. The filtrate was dried over magnesium sulfate, and the solvent was evaporated under reduced pressure to give 2-bromo-1-(tert-butyl)-4-nitrobenzene (1.4 g, 5.42 mmol, 97%) as a yellow oil.

$^1$H NMR (300 MHz, CDCl$_3$): δ 1.55 (9H, s), 7.61 (1H, d, J=9.1 Hz), 8.04-8.11 (1H, m), 8.45 (1H, d, J=2.6 Hz).

(Step 2)

A solution of 2-bromo-1-(tert-butyl)-4-nitrobenzene (191 mg, 0.74 mmol), zinc cyanide (69.3 mg, 0.59 mmol) and Pd(Ph$_3$)$_4$ (42.8 mg, 0.04 mmol) in DMF (1 mL) was stirred under microwave irradiation at 200° C. for 3 hr. Similarly, a solution of 2-bromo-1-(tert-butyl)-4-nitrobenzene (1.2 g, 4.65 mmol), zinc cyanide (437 mg, 3.72 mmol) and Pd(Ph$_3$)$_4$ (0.269 g, 0.23 mmol) in DMF (4.65 mL) was stirred under microwave irradiation at 200° C. for 3 hr. To these reaction mixtures was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→40% ethyl acetate/hexane) to give 5-nitro-2-(tert-butyl)benzonitrile (223 mg, 1.280 mmol, 27.5%).

$^1$H NMR (300 MHz, CDCl$_3$): δ 1.58 (9H, s), 7.67 (1H, d, J=8.3 Hz), 8.05 (1H, dd, J=8.7,2.3 Hz), 8.24 (1H, d, J=2.3 Hz).

(Step 3)

A solution of 5-nitro-2-(tert-butyl)benzonitrile (3.81 g, 18.66 mmol), 10% palladium-carbon (1.985 g, 0.94 mmol, 50% wet) and ammonium formate (3.53 g, 55.97 mmol) in EtOH (100 mL) was stirred under nitrogen atmosphere at 80° C. for 1.5 hr. The catalyst was removed by filtration, and the filtrate was concentrated under reduced pressure. The obtained residue was purified by silica gel column chromatography (solvent gradient; 3→50% ethyl acetate/hexane), and then silica gel column chromatography (NH, solvent gradient; 3→60% ethyl acetate/hexane) to give 5-amino-2-(tert-butyl)benzonitrile (2.9 g, 16.64 mmol, 89%) as a colorless oil.

$^1$H NMR (300 MHz, CDCl$_3$): δ 1.46 (9H, s), 3.72 (2H, brs), 6.78 (1H, dd, J=8.7,2.6 Hz), 6.95 (1H, d, J=3.0 Hz), 7.23 (1H, d, J=8.3 Hz).

(Step 4)

T3P (6.66 mL, 11.19 mmol) was added to a solution of 2-(tert-butoxycarbonyl)-6-methoxy-1,2,3,4-tetrahydroisoquinoline-1-carboxylic acid (2.52 g, 8.21 mmol), 5-amino-2-(tert-butyl)benzonitrile (1.3 g, 7.46 mmol), DIEA (6.50 mL, 37.30 mmol) and DMAP (1.003 g, 8.21 mmol) in ethyl acetate (95 mL), and the mixture was stirred at 70° C. for 3 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent; ethyl acetate/hexane), and crystallized from diethyl ether/hexane, and washed to give tert-butyl 1-((4-(tert-butyl)-3-cyanophenyl)carbamoyl)-6-methoxy-3,4-dihydroisoquinoline-2(1H)-carboxylate (2.23 g, 4.81 mmol, 64.5%) as white crystals.

$^1$H NMR (300 MHz, CDCl$_3$): δ 1.47 (9H, s), 1.53 (9H, s), 2.75-3.03 (2H, m), 3.58-3.76 (2H, m), 3.80 (3H, s), 5.61 (1H, brs), 6.68-6.85 (2H, m), 7.18-7.26 (1H, m), 7.31-7.39 (1H, m), 7.54-7.61 (1H, m), 7.86 (1H, d, J=2.3 Hz), 9.14 (1H, brs).

(Step 5)

tert-Butyl 1-((4-(tert-butyl)-3-cyanophenyl)carbamoyl)-6-methoxy-3,4-dihydroisoquinoline-2(1H)-carboxylate (2.23 g) was resolved by chiral column chromatography. The fraction having a shorter retention time was concentrated to give tert-butyl (R)-1-((4-(tert-butyl)-3-cyanophenyl)carbamoyl)-6-methoxy-3,4-dihydroisoquinoline-2(1H)-carboxylate (0.90 g, >99.9% ee) as a white solid.

purification condition by chiral column chromatography
    column: CHIRALPAK OD (NL001) 50 mmID×500 mmL
    solvent: hexane/EtOH=900/100
    flow rate: 80 mL/min
    temperature: 30° C.
    detection method: UV 220 nm (Step 6)

To a solution of tert-butyl (R)-1-((4-(tert-butyl)-3-cyanophenyl)carbamoyl)-6-methoxy-3,4-dihydroisoquinoline-2(1H)-carboxylate (870 mg, 1.88 mmol) in ethyl acetate (8.0 mL) was added 4M hydrogen chloride/ethyl acetate solution (8.0 mL, 32.00 mmol), and the mixture was stirred overnight at room temperature. The reaction mixture was concentrated under reduced pressure, and to the obtained residue were added ethyl acetate and aqueous sodium hydrogen carbonate solution. The organic layer was washed with brine, and dried over magnesium sulfate, and the solvent was evaporated under reduced pressure to give (R)-N-(4-(tert-butyl)-3-cyanophenyl)-6-methoxy-1,2,3,4-tetrahydroisoquinoline-1-carboxamide (551.4 mg, 1.517 mmol, 81%) as a white solid.

$^1$H NMR (300 MHz, CDCl$_3$): δ 1.48 (9H, s), 2.67-2.95 (2H, m), 3.09-3.19 (2H, m), 3.78 (3H, s), 4.64 (1H, s), 6.64 (1H, d, J=2.6 Hz), 6.79 (1H, dd, J=8.5,2.6 Hz), 7.38 (1H, d, J=8.7 Hz), 7.52 (1H, d, J=8.7 Hz), 7.73 (1H, dd, J=8.7,2.3 Hz), 7.88 (1H, d, J=2.3 Hz), 9.50 (1H, s) (The exchangeable 1H was not observed).

(Step 7)

To a solution of (R)-N-(4-(tert-butyl)-3-cyanophenyl)-6-methoxy-1,2,3,4-tetrahydroisoquinoline-1-carboxamide (100 mg, 0.28 mmol), DIEA (0.094 mL, 0.55 mmol) and 2-(3-hydroxy-1,2-oxazol-5-yl)acetic acid (47.2 mg, 0.33 mmol) in DMF (2.0 mL) was added HATU (126 mg, 0.33 mmol), and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (38.7 mg, 0.079 mmol, 28.8%) as white crystals.

MS(API): Calculated 488.5. Found 487.0 (M−H).

$^1$H NMR (300 MHz, DMSO-d$_6$): δ 1.42 (9H, s), 2.72-2.90 (1H, m), 3.05-3.20 (1H, m), 3.52-3.65 (1H, m), 3.73 (3H, s), 3.93-4.14 (3H, m), 5.61-5.75 (1H, m), 5.82-5.96 (1H, m), 6.79-6.89 (2H, m), 7.42-7.55 (2H, m), 7.65-7.75 (1H, m), 8.03 (1H, d, J=2.6 Hz), 10.63-10.76 (1H, m), 11.13 (1H, s).

Example 66

(1R)-6-ethoxy-N-(7-fluoro-1,1-dimethyl-2,3-dihydro-1H-inden-5-yl)-2-((3-hydroxy-1,2-oxazol-5-yl)acetyl)-1,2,3,4-tetrahydroisoquinoline-1-carboxamide 6-Ethoxy-N-(7-fluoro-1,1-dimethyl-2,3-dihydro-1H-inden-5-yl)-2-((3-hydroxy-1,2-oxazol-5-yl)acetyl)-1,2,3,4-tetrahydroisoquinoline-1-carboxamide (213.5 mg) was resolved by chiral column chromatography. The fraction having a shorter retention time was concentrated to give (1R)-6-ethoxy-N-(7-fluoro-1,1-dimethyl-2,3-dihydro-1H-inden-5-yl)-2-((3-hydroxy-1,2-oxazol-5-yl)acetyl)-1,2,3,4-tetrahydroisoquinoline-1-carboxamide (108.5 mg, >99.9% ee) as a white solid.

MS(API): Calculated 507.6. Found 508.2 (M+H).

purification condition by chiral column chromatography
    column: CHIRALPAK IA (QK001) 50 mmID×500 mmL
    solvent: hexane/EtOH/acetic acid=500/500/1
    flow rate: 80 mL/min
    temperature: 30° C.
    detection method: UV 220 nm
    $[α]_D^{25}$+7.2 (c 0.2500, MeOH)

Example 67

(1R)-N-(4-tert-butyl-3-fluorophenyl)-6-ethoxy-2-((3-hydroxy-1,2-oxazol-5-yl)acetyl)-1,2,3,4-tetrahydroisoquinoline-1-carboxamide N-(4-tert-Butyl-3-fluorophenyl)-6-ethoxy-2-((3-hydroxy-1,2-oxazol-5-yl)acetyl)-1,2,3,4-tetrahydroisoquinoline-1-carboxamide (434.5 mg) was resolved by chiral column chromatography. The fraction having a shorter retention time was concentrated to give (1R)-N-(4-tert-butyl-3-fluorophenyl)-6-ethoxy-2-((3-hydroxy-1,2-oxazol-5-yl)acetyl)-1,2,3,4-tetrahydroisoquinoline-1-carboxamide (194.8 mg, >99.9% ee) as a white solid.

MS(API): Calculated 495.5. Found 496.1 (M+H).

purification condition by chiral column chromatography
    column: CHIRALPAK IA (QK001) 50 mmID×500 mmL
    solvent: hexane/EtOH/acetic acid=500/500/1
    flow rate: 80 mL/min
    temperature: 30° C.
    detection method: UV 220 nm
    $[α]_D^{25}$+1.6 (c 0.2500, MeOH)

Example 68

(1R)-N-(7-fluoro-1,1-dimethyl-2,3-dihydro-1H-inden-5-yl)-2-((3-hydroxy-1,2-oxazol-5-yl)carbonyl)-6-methoxy-1,2,3,4-tetrahydroisoquinoline-1-carboxamide To a solution of (R)-N-(7-fluoro-1,1-dimethyl-2,3-dihydro-1H-inden-5-yl)-6-methoxy-1,2,3,4-tetrahydroisoquinoline-1-carboxamide (500 mg, 1.36 mmol), DIEA (0.464 mL, 2.71 mmol) and 3-hydroxy-1,2-oxazole-5-carboxylic acid (193 mg, 1.49 mmol) in DMF (10 mL) was added COMU (697 mg, 1.63 mmol) at 0° C., and the mixture was stirred at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; 50% ethyl acetate/hexane), and then silica gel column chromatography (Diol, solvent; 50% ethyl acetate/hexane) to give the title compound (423.0 mg, 0.882 mmol, 65.0%) as a white solid.

MS(API): Calculated 479.5. Found 480.1 (M+H).

$^1$H NMR (300 MHz, DMSO-$d_6$): δ 1.28 (6H, d, J=1.5 Hz), 1.87 (2H, t, J=7.4 Hz), 2.86 (3H, t, J=7.2 Hz), 3.06-3.25 (1H, m), 3.67-3.80 (4H, m), 4.10-4.22 (1H, m), 5.54-5.72 (1H, m), 6.35-6.61 (1H, m), 6.79-6.90 (2H, m), 7.09-7.27 (2H, m), 7.48-7.57 (1H, m), 10.22-10.61 (1H, m), 11.78 (1H, brs).

$[α]_D^{25}$ −10.1 (c 0.2500, MeOH)

Example 69

(1R)-N-(3-fluoro-4-(1-methoxy-2-methylpropan-2-yl)phenyl)-2-((3-hydroxy-1,2-oxazol-5-yl)carbonyl)-6-methoxy-1,2,3,4-tetrahydroisoquinoline-1-carboxamide (Step 1)

A solution of conc. sulfuric acid (1 mL, 18.76 mmol) and 2-(2-fluoro-4-nitrophenyl)acetic acid (10 g, 50.22 mmol) in MeOH (200 mL) was heated under reflux for 4 hr. To the reaction mixture was added aqueous sodium hydrogen carbonate solution until the mixture became neutral, and the mixture was concentrated under reduced pressure. To the residue were added ethyl acetate and water, and the organic layer was washed with brine, and dried over magnesium sulfate, and the solvent was evaporated under reduced pressure to give methyl 2-(2-fluoro-4-nitrophenyl)acetate (10.70 g, 50.2 mmol, 100%) as a pale yellow solid.

$^1$H NMR (300 MHz, DMSO-$d_6$): δ 3.65 (3H, s), 3.93 (2H, d, J=1.1 Hz), 7.59-7.78 (1H, m), 8.02-8.21 (2H, m).

(Step 2)

To a solution of methyl 2-(2-fluoro-4-nitrophenyl)acetate (10.7 g, 50.20 mmol) and iodomethane (12.55 mL, 200.79 mmol) in DMF (100 mL) was added sodium hydride (60% oil, 5.02 g, 125.49 mmol) at 0° C., and the mixture was stirred at 0° C. for 4 hr. To the reaction mixture was added aqueous ammonium chloride solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→20% ethyl acetate/hexane) to give methyl 2-(2-fluoro-4-nitrophenyl)-2-methylpropanoate (12.10 g, 50.2 mmol, 100%) as a yellow solid.

$^1$H NMR (300 MHz, DMSO-$d_6$): δ 1.54 (6H, s), 3.61 (3H, s), 7.65-7.82 (1H, m), 8.04-8.15 (2H, m).

(Step 3)

1.5M DIBAL-H/toluene solution (83 mL, 124.37 mmol) was added to a solution of methyl 2-(2-fluoro-4-nitrophenyl)-2-methylpropanoate (10 g, 41.46 mmol) in THF (100 mL) at 0° C., and the mixture was stirred at room temperature for 4 hr. To the reaction mixture was slowly added saturated potassium sodium tartrate aqueous solution at 0° C., and the mixture was extracted with ethyl acetate. The organic layer was washed with brine, and dried over magnesium sulfate, and the solvent was evaporated under reduced pressure. The obtained residue was purified by silica gel column chromatography (solvent gradient; 10→80% ethyl acetate/hexane) to give 2-(2-fluoro-4-nitrophenyl)-2-methylpropan-1-ol (8.31 g, 39.0 mmol, 94%) as a brown oil.

$^1$H NMR (300 MHz, DMSO-$d_6$): δ 1.31 (6H, d, J=1.1 Hz), 3.52-3.66 (2H, m), 4.87 (1H, t, J=5.5 Hz), 7.51-7.72 (1H, m), 7.93-8.09 (2H, m).

(Step 4)

Sodium hydride (60% oil, 0.703 g, 17.59 mmol) was slowly added to a solution of iodomethane (1.466 mL, 23.45 mmol) and 2-(2-fluoro-4-nitrophenyl)-2-methylpropan-1-ol (2.5 g, 11.73 mmol) in THF (10 mL) at −10° C., and the mixture was stirred at room temperature for 2 hr. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→20% ethyl acetate/hexane) to give 2-fluoro-1-(1-methoxy-2-methylpropan-2-yl)-4-nitrobenzene (2.280 g, 10.03 mmol, 86%) as a pale yellow oil.

$^1$H NMR (300 MHz, DMSO-$d_6$): δ 1.34 (6H, d, J=1.1 Hz), 3.22 (3H, s), 3.53 (2H, d, J=1.1 Hz), 7.61 (1H, t, J=8.5 Hz), 7.96-8.05 (2H, m).

(Step 5)

A solution of 2-fluoro-1-(1-methoxy-2-methylpropan-2-yl)-4-nitrobenzene (2.6 g, 11.44 mmol) and 10% palladium-carbon (260 mg, 0.12 mmol, 50% wet) in MeOH (100 mL) was stirred overnight under hydrogen atmosphere (1 atm) at room temperature. The catalyst was removed by filtration, and the filtrate was concentrated under reduced pressure to give 3-fluoro-4-(1-methoxy-2-methylpropan-2-yl)aniline (2170 mg, 11.00 mmol, 96%) as a pale yellow solid.

$^1$H NMR (300 MHz, DMSO-$d_6$): δ 1.21 (6H, s), 3.20 (3H, s), 3.36 (2H, d, J=0.8 Hz), 5.16 (2H, s), 6.17-6.35 (2H, m), 6.89 (1H, dd, J=9.6,8.5 Hz).

(Step 6)

T3P (50% ethyl acetate solution) (4.52 mL, 7.60 mmol) was added to a solution of 2-(tert-butoxycarbonyl)-6-methoxy-1,2,3,4-tetrahydroisoquinoline-1-carboxylic acid (1.730 g, 3.56 mmol, 70.1%), 3-fluoro-4-(1-methoxy-2-methylpropan-2-yl)aniline (1 g, 5.07 mmol), DIEA (4.43 mL, 25.35 mmol) and DMAP (0.681 g, 5.58 mmol) in ethyl acetate (100 mL) at room temperature, and the mixture was stirred at 70° C. for 15 hr. To the reaction mixture was added water, and the mixture was extracted twice with ethyl acetate. The organic layer was washed with aqueous sodium hydrogen carbonate solution and brine, and dried over magnesium sulfate, and the solvent was evaporated under reduced pressure. The obtained residue was purified by silica gel column chromatography (solvent gradient; 10→70% ethyl acetate/hexane) to give tert-butyl 1-((3-fluoro-4-(1-methoxy-2-methylpropan-2-yl)phenyl)carbamoyl)-6-methoxy-3,4-dihydroisoquinoline-2(1H)-carboxylate (1.730 g, 3.56 mmol, 70.1%) as white crystals.

$^1$H NMR (300 MHz, DMSO-$d_6$): δ 1.26 (6H, s), 1.31-1.49 (9H, m), 2.74 (1H, dt, J=15.5, 4.7 Hz), 2.95-3.11 (1H, m), 3.20 (3H, s), 3.27-3.37 (1H, m), 3.43 (2H, s), 3.72 (3H, s), 3.85-3.98 (1H, m), 5.23-5.53 (1H, m), 6.72-6.93 (2H, m), 7.12-7.30 (2H, m), 7.35-7.58 (2H, m), 10.30-10.60 (1H, m).

(Step 7)

tert-Butyl 1-((3-fluoro-4-(1-methoxy-2-methylpropan-2-yl)phenyl) carbamoyl)-6-methoxy-3,4-dihydroisoquinoline-2 (1H)-carboxylate (0.44 g) was resolved by chiral column chromatography. The fraction having a shorter retention time was concentrated to give tert-butyl (R)-1-((3-fluoro-4-(1-methoxy-2-methylpropan-2-yl)phenyl)carbamoyl)-6-methoxy-3,4-dihydroisoquinoline-2(1H)-carboxylate (0.20 g, >99.9% ee) as a white solid.

purification condition by chiral column chromatography
   column: CHIRALCEL OD (NF001) 50 mmID×500 mmL
   solvent: hexane/EtOH=900/100
   flow rate: 80 mL/min
   temperature: 30° C.
   detection method: UV 220 nm
(Step 8)

To tert-Butyl (R)-1-((3-fluoro-4-(1-methoxy-2-methylpropan-2-yl)phenyl)carbamoyl)-6-methoxy-3,4-dihydroisoquinoline-2(1H)-carboxylate (730 mg, 1.50 mmol) was added 4M hydrogen chloride/ethyl acetate (5 mL, 20.00 mmol), and the mixture was stirred at room temperature for 2 hr. The reaction mixture was concentrated under reduced pressure, and the residue was crystallized from ethyl acetate/hexane to give (R)-N-(3-fluoro-4-(1-methoxy-2-methylpropan-2-yl)phenyl)-6-methoxy-1,2,3,4-tetrahydroisoquinoline-1-carboxamide hydrochloride (577 mg, 1.364 mmol, 91%) as a white solid.

$^1$H NMR (300 MHz, DMSO-$d_6$): δ 1.29 (6H, s), 2.84-3.03 (1H, m), 3.05-3.18 (1H, m), 3.22 (3H, s), 3.35-3.49 (3H, m), 3.61-3.72 (1H, m), 3.74 (3H, s), 5.18 (1H, s), 6.82-6.92 (2H, m), 7.25-7.40 (3H, m), 7.46-7.57 (1H, m), 8.88-10.32 (2H, m), 11.32 (1H, s).
(Step 9)

HATU (108 mg, 0.28 mmol) was added to a solution of DIEA (0.124 mL, 0.71 mmol), 3-hydroxy-1,2-oxazole-5-carboxylic acid (33.6 mg, 0.26 mmol) and (R)-N-(3-fluoro-4-(1-methoxy-2-methylpropan-2-yl)phenyl)-6-methoxy-1,2,3,4-tetrahydroisoquinoline-1-carboxamide hydrochloride (100 mg, 0.24 mmol) in DMF (2 mL) at room temperature, and the mixture was stirred overnight at room temperature. To the reaction mixture was added water, and the mixture was extracted three times with a mixed solvent of ethyl acetate/THF. The organic layer was washed with brine, and dried over magnesium sulfate, and the solvent was evaporated under reduced pressure. The obtained residue was purified by silica gel column chromatography (solvent gradient; 50→100% ethyl acetate/hexane) to give the title compound (37.0 mg, 0.074 mmol, 31.5%) as a white solid.
MS(API): Calculated 497.5. Found 498.0 (M+H).
$^1$H NMR (300 MHz, DMSO-$d_6$): δ 1.26 (6H, s), 2.87 (1H, d, J=15.5 Hz), 3.14 (1H, d, J=8.7 Hz), 3.19 (3H, s), 3.43 (2H, s), 3.74 (4H, s), 4.02-4.24 (1H, m), 5.69 (1H, s), 6.55 (1H, s), 6.78-6.91 (2H, m), 7.15-7.28 (2H, m, J=5.3 Hz), 7.39-7.56 (2H, m), 10.66 (1H, s), 11.86 (1H, brs).

Example 70

(1R)-N-(3-fluoro-4-(1-methoxy-2-methylpropan-2-yl)phenyl)-2-((3-hydroxy-1,2-oxazol-5-yl)acetyl)-6-methoxy-1,2,3,4-tetrahydroisoquinoline-1-carboxamide HATU (108 mg, 0.28 mmol) was added to a solution of DIEA (0.124 mL, 0.71 mmol), 2-(3-hydroxy-1,2-oxazol-5-yl)acetic acid (37.2 mg, 0.26 mmol) and (R)-N-(3-fluoro-4-(1-methoxy-2-methylpropan-2-yl)phenyl)-6-methoxy-1,2,3,4-tetrahydroisoquinoline-1-carboxamide hydrochloride (100 mg, 0.24 mmol) in DMF (2 mL) at room temperature, and the mixture was stirred overnight. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane) to give the title compound (12.00 mg, 0.023 mmol, 9.92%) as a white solid.
MS(API): Calculated 511.5. Found 512.1 (M+H).
$^1$H NMR (300 MHz, DMSO-$d_6$): δ 1.26 (6H, s), 2.85 (1H, brs), 3.13 (1H, s), 3.19 (3H, s), 3.42 (2H, s), 3.63 (1H, s), 3.73 (3H, s), 3.86-4.14 (3H, m), 5.67 (1H, s), 5.90 (1H, s), 6.74-6.88 (2H, m), 7.11-7.27 (2H, m), 7.37-7.54 (2H, m), 10.54 (1H, s), 11.12 (1H, brs).

Example 71

N-(4-(2,2-dimethylpropyl)-3-fluorophenyl)-2-((3-hydroxy-1,2-oxazol-5-yl)acetyl)-6-methoxy-1,2,3,4-tetrahydroisoquinoline-1-carboxamide The title compound was synthesized using 3-fluoro-4-neo-pentylaniline, by the reaction and purification in the same manner as in Example 65.

Example 72

(1R)-N-(3-cyano-4-(trimethylsilyl)phenyl)-2-((3-hydroxy-1,2-oxazol-5-yl)acetyl)-6-methoxy-1,2,3,4-tetrahydroisoquinoline-1-carboxamide (Step 1)
A solution of 2-chloro-5-nitrobenzonitrile (19.5 g, 106.81 mmol), HMDS (43.7 mL, 213.62 mmol), Pd$_2$(dba)$_3$ (2.93 g, 3.20 mmol), 2'-(di-tert-butylphosphino)-N,N-dimethyl-[1,1'-biphenyl]-2-amine (3.28 g, 9.61 mmol), water (3.85 g, 213.62 mmol) and lithium acetate (35.2 g, 534.06 mmol) in DMF (400 mL) was stirred under argon gas atmosphere at 100° C. for 5 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→5% ethyl acetate/hexane) to give 5-nitro-2-(trimethylsilyl)benzonitrile (13.2 g, 59.9 mmol, 56.1%) as a white solid.
(Step 2)
A solution of 5-nitro-2-(trimethylsilyl)benzonitrile and 10% palladium-carbon (1.32 g, 0.62 mmol, 50% wet) in MeOH (260 mL) was stirred under hydrogen atmosphere (1 atm) at room temperature for 5 hr. The catalyst was removed by filtration, and the filtrate was concentrated under reduced pressure. The obtained residue was purified by silica gel column chromatography (solvent gradient; 10→20% ethyl acetate/hexane) to give 5-amino-2-(trimethylsilyl)benzonitrile (9.56 g, 50.2 mmol, 84%) as a white solid.
(Step 3)
To a solution of 2-(tert-butoxycarbonyl)-6-methoxy-1,2,3,4-tetrahydroisoquinoline-1-carboxylic acid (1.776 g, 5.78 mmol), DMAP (0.706 g, 5.78 mmol) and DIEA (4.59 mL, 26.27 mmol) in ethyl acetate (30 mL) was added T3P (6.18 mL, 10.51 mmol) at room temperature, and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→20% ethyl acetate/hexane), and crystallized from diethyl ether/hexane to give tert-butyl 1-((3-cyano-4-(trimethylsilyl)phenyl)carbamoyl)-6-methoxy-3,4-dihydroisoquinoline-2(1H)-carboxylate (758 mg, 1.580 mmol, 30.1%) as white crystals.

$^1$H NMR (300 MHz, CDCl$_3$): δ 0.38 (9H, s), 1.53 (9H, s), 2.81-2.99 (2H, m), 3.50-3.75 (2H, m), 3.80 (3H, s), 5.57-5.69 (1H, m), 6.74 (1H, d, J=2.3 Hz), 6.81 (1H, dd, J=8.5,2.3 Hz), 7.19 (1H, brs), 7.48 (1H, d, J=7.9 Hz), 7.62 (1H, dd, J=8.1,2.1 Hz), 7.90 (1H, d, J=2.1 Hz), 8.82-9.44 (1H, m).

(Step 4)

tert-Butyl 1-((3-cyano-4-(trimethylsilyl)phenyl)carbamoyl)-6-methoxy-3,4-dihydroisoquinoline-2(1H)-carboxylate (758 mg) was resolved by chiral column chromatography. The fraction having a shorter retention time was concentrated to give tert-butyl (R)-1-((3-cyano-4-(trimethylsilyl) phenyl)carbamoyl)-6-methoxy-3,4-dihydroisoquinoline-2 (1H)-carboxylate (310 mg, >99.5% ee) as a white solid.

purification condition by chiral column chromatography column: CHIRALCEL OD (NL001) 50 mmID×500 mmL solvent: hexane/EtOH=900/100 flow rate: 80 mL/min temperature: 30° C.

detection method: UV 220 nm (Step 5)

Cooled TFA (3.0 mL) was added to tert-butyl (R)-1-((3-cyano-4-(trimethylsilyl)phenyl)carbamoyl)-6-methoxy-3,4-dihydroisoquinoline-2(1H)-carboxylate (310 mg, 0.65 mmol) at room temperature, and the mixture was stirred at room temperature for 2 min. The reaction mixture was added to ice and aqueous sodium hydrogen carbonate solution, and aqueous sodium hydrogen carbonate solution was added thereto until the pH of the mixture became 8. Then, the mixture was extracted with ethyl acetate. The organic layer was washed with brine, and dried over magnesium sulfate, and the solvent was evaporated under reduced pressure to give (R)-N-(3-cyano-4-(trimethylsilyl)phenyl)-6-methoxy-1,2,3,4-tetrahydroisoquinoline-1-carboxamide (228.6 mg, 0.602 mmol, 93%) as a white solid.

(Step 6)

To a solution of (R)-N-(3-cyano-4-(trimethylsilyl)phenyl)-6-methoxy-1,2,3,4-tetrahydroisoquinoline-1-carboxamide (100 mg, 0.26 mmol), DIEA (0.090 mL, 0.53 mmol) and 2-(3-hydroxy-1,2-oxazol-5-yl)acetic acid (45.2 mg, 0.32 mmol) in DMF (2.0 mL) was added HATU (120 mg, 0.32 mmol) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (46.6 mg, 0.092 mmol, 35.0%) as white crystals.

MS(API): Calculated 504.6. Found 505.1 (M+H).

$^1$H NMR (300 MHz, DMSO-d$_6$): δ 0.34 (9H, s), 2.76-2.92 (1H, m), 3.05-3.20 (1H, m), 3.50-3.65 (1H, m), 3.73 (3H, s), 3.90-4.18 (3H, m), 5.74 (1H, s), 5.79-5.94 (1H, m), 6.74-6.92 (2H, m), 7.50 (1H, d, J=8.7 Hz), 7.60 (1H, d, J=8.3 Hz), 7.76 (1H, dd, J=8.3,2.3 Hz), 8.06 (1H, d, J=1.9 Hz), 10.77 (1H, s), 11.14 (1H, brs).

Example 73

(1R)-N-(3-fluoro-4-(trimethylsilyl)phenyl)-2-((3-hydroxy-1,2-oxazol-5-yl)acetyl)-6-methoxy-1,2,3,4-tetrahydroisoquinoline-1-carboxamide (Step 1)

To a solution of 3-fluoro-4-(trimethylsilyl)aniline (1.2 g, 6.55 mmol), 2-(tert-butoxycarbonyl)-6-methoxy-1,2,3,4-tetrahydroisoquinoline-1-carboxylic acid (2.213 g, 7.20 mmol), DMAP (0.880 g, 7.20 mmol) and DIEA (5.72 mL, 32.73 mmol) in ethyl acetate (30 mL) was added T3P (11.55 mL, 19.64 mmol) at room temperature, and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→20% ethyl acetate/hexane), and crystallized from diethyl ether/hexane to give tert-butyl 1-((3-fluoro-4-(trimethylsilyl)phenyl)carbamoyl)-6-methoxy-3,4-dihydroisoquinoline-2(1H)-carboxylate (1.75 g, 3.70 mmol, 56.6%) as white crystals.

$^1$H NMR (300 MHz, CDCl$_3$): δ 0.27 (9H, s), 1.52 (9H, s), 2.75-2.97 (2H, m), 3.46-3.76 (2H, m), 3.80 (3H, s), 5.60 (1H, brs), 6.72 (1H, d, J=2.3 Hz), 6.81 (1H, dd, J=8.3,2.3 Hz), 7.10 (1H, d, J=7.6 Hz), 7.26-7.33 (2H, m), 7.39 (1H, dd, J=10.6,1.5 Hz), 8.95 (1H, brs).

(Step 2)

Cooled TFA (3.0 mL) was added to tert-butyl 1-((3-fluoro-4-(trimethylsilyl)phenyl)carbamoyl)-6-methoxy-3,4-dihydroisoquinoline-2(1H)-carboxylate (794 mg, 1.68 mmol) at room temperature, and the mixture was stirred at room temperature for 2 min. The pH of the reaction mixture was adjusted to 8 with ice and aqueous sodium hydrogen carbonate solution. Then, the mixture was extracted with ethyl acetate. The organic layer was washed with brine, and dried over magnesium sulfate, and the solvent was evaporated under reduced pressure to give N-(3-fluoro-4-(trimethylsilyl)phenyl)-6-methoxy-1,2,3,4-tetrahydroisoquinoline-1-carboxamide (642.6 mg, 1.725 mmol, 103%) as a white solid.

$^1$H NMR (300 MHz, CDCl$_3$): δ 0.27 (9H, d, J=0.8 Hz), 2.68-2.98 (2H, m), 3.08-3.26 (2H, m), 3.78 (3H, s), 4.74 (1H, s), 6.64 (1H, d, J=2.6 Hz), 6.78 (1H, dd, J=8.5,2.6 Hz), 7.11-7.20 (1H, m), 7.23-7.30 (1H, m), 7.37-7.52 (2H, m), 9.49 (1H, brs) (The exchangeable 1H was not observed).

(Step 3)

To a solution of N-(3-fluoro-4-(trimethylsilyl)phenyl)-6-methoxy-1,2,3,4-tetrahydroisoquinoline-1-carboxamide (100 mg, 0.27 mmol), DIEA (0.092 mL, 0.54 mmol) and 2-(3-hydroxy-1,2-oxazol-5-yl)acetic acid (46.1 mg, 0.32 mmol) in DMF (2.0 mL) was added HATU (122 mg, 0.32 mmol) at 0° C., and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give N-(3-fluoro-4-(trimethylsilyl)phenyl)-2-(2-(3-hydroxy-1,2-oxazol-5-yl)acetyl)-6-methoxy-1,2,3,4-tetrahydroisoquinoline-1-carboxamide (35.3 mg, 0.071 mmol, 26.4%) as white crystals.

$^1$H NMR (300 MHz, DMSO-d$_6$): δ 0.21-0.28 (9H, m), 2.72-2.90 (1H, m), 3.03-3.21 (1H, m), 3.49-3.66 (1H, m), 3.69-3.76 (3H, m), 3.87-4.14 (3H, m), 5.64-5.73 (1H, m), 5.82-5.95 (1H, m), 6.78-6.87 (2H, m), 7.25-7.38 (2H, m), 7.41-7.53 (2H, m), 10.64 (1H, s), 11.12 (1H, brs).
(Step 4)
N-(3-Fluoro-4-(trimethylsilyl)phenyl)-2-(2-(3-hydroxy-1,2-oxazol-5-yl)acetyl)-6-methoxy-1,2,3,4-tetrahydroisoquinoline-1-carboxamide (380 mg) was resolved by chiral column chromatography. The fraction having a shorter retention time was concentrated to give the title compound (160 mg, >98.8% ee) as a white solid.
MS(API): Calculated 497.6. Found 498.1 (M+H).
purification condition by chiral column chromatography
  column: CHIRALPAK IC (1F001) 50 mmID×500 mmL
  solvent: hexane/EtOH/acetic acid=500/500/1
  flow rate: 80 mL/min
  temperature: 30° C.
  detection method: UV 220 nm
$[\alpha]_D^{25}$ +8.0 (c 0.2550, MeOH)

Example 74

(1R)-N-(4-fluoro-3,3-dimethyl-2,3-dihydro-1-benzofuran-6-yl)-2-((3-hydroxy-1,2-oxazol-5-yl)acetyl)-6-methoxy-1,2,3,4-tetrahydroisoquinoline-1-carboxamide The title compound was synthesized using 4-fluoro-3,3-dimethyl-2,3-dihydrobenzofuran-6-amine, by the reaction and purification in the same manner as in Example 65.

Example 75

(1R)-N-(4-(1-(2,2-difluoroethoxy)-2-methylpropan-2-yl)-3-fluorophenyl)-2-((3-hydroxy-1,2-oxazol-5-yl)carbonyl)-6-methoxy-1,2,3,4-tetrahydroisoquinoline-1-carboxamide (Step 1)
Sodium hydride (60% oil, 0.563 g, 14.07 mmol) was slowly added to a solution of 2,2-difluoroethyl trifluoromethanesulfonate (3.01 g, 14.07 mmol) and 2-(2-fluoro-4-nitrophenyl)-2-methylpropan-1-ol (2.5 g, 11.73 mmol) in THF (100 mL) at −10° C., and the mixture was stirred at room temperature for 2 hr. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→20% ethyl acetate/hexane) to give 1-(1-(2,2-difluoroethoxy)-2-methylpropan-2-yl)-2-fluoro-4-nitrobenzene (2.88 g, 10.39 mmol, 89%) as a pale yellow oil.
$^1$H NMR (300 MHz, DMSO-d$_6$): δ 1.36 (6H, d, J=0.8 Hz), 3.67 (2H, td, J=15.3,3.8 Hz), 3.74 (2H, s), 5.83-6.33 (1H, m), 7.57-7.69 (1H, m), 7.98-8.09 (2H, m).
(Step 2)
A solution of 1-(1-(2,2-difluoroethoxy)-2-methylpropan-2-yl)-2-fluoro-4-nitrobenzene (2.88 g, 10.39 mmol) and 10% palladium-carbon (300 mg, 0.014 mmol, 50% wet) in MeOH (100 mL) was stirred overnight under hydrogen atmosphere (1 atm) at room temperature. The catalyst was removed by filtration, and the filtrate was concentrated under reduced pressure to give 4-(1-(2,2-difluoroethoxy)-2-methylpropan-2-yl)-3-fluoroaniline (2440 mg, 9.87 mmol, 95%) as a brown oil.
$^1$H NMR (300 MHz, DMSO-d$_6$): δ 1.23 (6H, s), 3.56 (2H, s), 3.57-3.70 (2H, m), 5.19 (2H, s), 5.86-6.27 (1H, m), 6.21-6.34 (2H, m), 6.82-7.01 (1H, m).
(Step 3)
T3P (3.61 mL, 6.07 mmol) was added to a solution of 4-(1-(2,2-difluoroethoxy)-2-methylpropan-2-yl)-3-fluoroaniline (1 g, 4.04 mmol), 2-(tert-butoxycarbonyl)-6-methoxy-1,2,3,4-tetrahydroisoquinoline-1-carboxylic acid (1.243 g, 4.04 mmol), DIEA (3.53 mL, 20.22 mmol) and DMAP (0.544 g, 4.45 mmol) in ethyl acetate (100 mL) at room temperature, and the mixture was stirred at 70° C. for 15 hr. To the reaction mixture was added water, and the mixture was extracted twice with ethyl acetate. The organic layer was washed with aqueous sodium hydrogen carbonate solution and brine, and dried over magnesium sulfate, and the solvent was evaporated under reduced pressure. The obtained residue was purified by silica gel column chromatography (solvent gradient; 10→70% ethyl acetate/hexane) to give tert-butyl 1-((4-(1-(2,2-difluoroethoxy)-2-methylpropan-2-yl)-3-fluorophenyl)carbamoyl)-6-methoxy-3,4-dihydroisoquinoline-2(1H)-carboxylate (0.508 g, 0.947 mmol, 23.41%) as white crystals.
$^1$H NMR (300 MHz, DMSO-d$_6$): δ 1.22-1.46 (15H, m), 2.74 (1H, d, J=15.5 Hz), 3.05 (1H, brs), 3.33-3.50 (1H, m), 3.54-3.69 (4H, m), 3.72 (3H, s), 3.86-4.03 (1H, m), 5.24-5.48 (1H, m), 5.82-6.34 (1H, m), 6.71-6.89 (2H, m), 7.13-7.31 (2H, m), 7.37-7.54 (2H, m), 10.30-10.61 (1H, m).
(Step 4)
tert-Butyl 1-((4-(1-(2,2-difluoroethoxy)-2-methylpropan-2-yl)-3-fluorophenyl)carbamoyl)-6-methoxy-3,4-dihydroisoquinoline-2(1H)-carboxylate (0.508 g) was resolved by chiral column chromatography. The fraction having a shorter retention time was concentrated to give tert-butyl (R)-1-((4-(1-(2,2-difluoroethoxy)-2-methylpropan-2-yl)-3-fluorophenyl)carbamoyl)-6-methoxy-3,4-dihydroisoquinoline-2(1H)-carboxylate (230 mg, >99.8% ee) as a white solid.
purification condition by chiral column chromatography
  column: CHIRALCEL OD (NL001) 50 mmID×500 mmL
  solvent: hexane/EtOH=900/100
  flow rate: 80 mL/min
  temperature: 30° C.
  detection method: UV 220 nm
(Step 5)
To tert-butyl (R)-1-((4-(1-(2,2-difluoroethoxy)-2-methylpropan-2-yl)-3-fluorophenyl)carbamoyl)-6-methoxy-3,4-dihydroisoquinoline-2(1H)-carboxylate (230 mg, 0.43 mmol) was added 4M hydrogen chloride/ethyl acetate (5 mL, 20.00 mmol) at room temperature, and the mixture was stirred at room temperature for 2 hr. The reaction mixture was concentrated under reduced pressure, and the residue was crystallized from ethyl acetate/hexane to give (R)-N-(4-(1-(2,2-difluoroethoxy)-2-methylpropan-2-yl)-3-fluorophenyl)-6-methoxy-1,2,3,4-tetrahydroisoquinoline-1-carboxamide hydrochloride (207 mg, 0.438 mmol, 102%) as white crystals.
$^1$H NMR (300 MHz, DMSO-d$_6$): δ 1.31 (6H, s), 2.87-3.03 (1H, m), 3.06-3.15 (1H, m), 3.40 (1H, d, J=12.8 Hz), 3.59-3.73 (5H, m), 3.74 (3H, s), 5.20 (1H, s), 5.85-6.31 (1H, m), 6.81-6.95 (2H, m), 7.27-7.40 (3H, m), 7.46-7.59 (1H, m), 9.36 (1H, brs), 9.95 (1H, brs), 11.36 (1H, s).
(Step 6)
HATU (105 mg, 0.27 mmol) was added to a solution of DIEA (0.111 mL, 0.63 mmol), 3-hydroxy-1,2-oxazole-5-carboxylic acid (32.8 mg, 0.25 mmol) and (R)-N-(4-(1-(2,2-difluoroethoxy)-2-methylpropan-2-yl)-3-fluorophenyl)-6-methoxy-1,2,3,4-tetrahydroisoquinoline-1-carboxamide hydrochloride (100 mg, 0.21 mmol) in DMF (2 mL) at room temperature, and the mixture was stirred overnight. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane) to give the title compound (28.0 mg, 0.051 mmol, 24.19%) as a white solid.

MS(API): Calculated 547.5. Found 546.0 (M−H).

$^1$H NMR (300 MHz, DMSO-$d_6$): δ 1.22-1.33 (6H, m), 2.87 (1H, d, J=17.0 Hz), 3.08-3.22 (1H, m), 3.54-3.69 (4H, m), 3.74 (4H, s), 4.08-4.23 (1H, m), 5.69 (1H, s), 5.83-6.28 (1H, m), 6.55 (1H, s), 6.79-6.90 (2H, m), 7.17-7.30 (2H, m), 7.42-7.58 (2H, m), 10.67 (1H, s), 11.67-12.08 (1H, m)

Example 77

(5R)-N-(4-tert-butyl-3-fluorophenyl)-6-((3-hydroxy-1,2-oxazol-5-yl)carbonyl)-2-methoxy-5,6,7,8-tetrahydro-1,6-naphthyridine-5-carboxamide (Step 1)

tert-Butyl 5-((4-(tert-butyl)-3-fluorophenyl)carbamoyl)-2-methoxy-7,8-dihydro-1,6-naphthyridine-6 (5H)-carboxylate (3.47 g) was resolved by chiral column chromatography. The fraction having a shorter retention time was concentrated to give tert-butyl (R)-5-((4-(tert-butyl)-3-fluorophenyl) carbamoyl)-2-methoxy-7,8-dihydro-1, 6-naphthyridine-6(5H)-carboxylate (1.47 g, >99.9% ee) as a white solid.

MS(API): Calculated 468.5. Found 469.1 (M+H).

purification condition by chiral column chromatography
column: CHIRALPAK IA (QK001) 50 mmID×500 mmL
solvent: hexane/EtOH=600/400
flow rate: 80 mL/min
temperature: 30° C.
detection method: UV 220 nm (Step 2)

Cooled TFA (20 mL) was added to tert-butyl (R)-5-((4-(tert-butyl)-3-fluorophenyl)carbamoyl)-2-methoxy-7,8-dihydro-1,6-naphthyridine-6(5H)-carboxylate (1.47 g, 3.21 mmol) at room temperature, and the mixture was stirred at room temperature for 15 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(4-(tert-butyl)-3-fluorophenyl)-2-methoxy-5,6,7,8-tetrahydro-1,6-naphthyridine-5-carboxamide (1.05 g, 2.94 mmol, 91%) as a white solid.

$^1$H NMR (300 MHz, CDCl$_3$): δ 1.34 (9H, d, J=0.8 Hz), 1.75 (1H, brs), 2.74-2.85 (1H, m), 2.87-2.99 (1H, m), 3.13-3.29 (2H, m), 3.90 (3H, s), 4.58 (1H, s), 6.60 (1H, d, J=8.7 Hz), 7.11 (1H, dd), 7.20 (1H, t), 7.43 (1H, dd, J=14.4,2.3 Hz), 7.83 (1H, d, J=8.7 Hz), 9.44 (1H, s).

(Step 3)

HATU (249 mg, 0.65 mmol) was added to a solution of (R)-N-(4-(tert-butyl)-3-fluorophenyl)-2-methoxy-5,6,7,8-tetrahydro-1, 6-naphthyridine-5-carboxamide (180 mg, 0.50 mmol), 3-hydroxy-1,2-oxazole-5-carboxylic acid (78 mg, 0.60 mmol) and DIEA (175 μL, 1.00 mmol) in DMF (2.5 mL) at room temperature, and the mixture was stirred for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 30→100% ethyl acetate/hexane) to give the title compound (110.6 mg, 0.236 mmol, 46.9%) as a white solid.

$^1$H NMR (300 MHz, CDCl$_3$): δ 1.34 (9H, s), 2.83 (1H, s), 3.00-3.10 (1H, m), 3.15-3.29 (1H, m), 3.78-3.89 (1H, m), 3.93 (3H, s), 4.32-4.42 (1H, m), 5.97 (1H, s), 6.58 (1H, s), 6.68 (1H, d, J=8.7 Hz), 7.11 (1H, dd), 7.21 (1H, t), 7.36-7.44 (2H, m), 8.96 (1H, s).

Example 78

(5R)-N-(4-tert-butyl-3-fluorophenyl)-6-((3-hydroxy-1,2-oxazol-5-yl)acetyl)-2-methoxy-5,6,7,8-tetrahydro-1,6-naphthyridine-5-carboxamide HATU (249 mg, 0.65 mmol) was added to a solution of (R)-N-(4-(tert-butyl)-3-fluorophenyl)-2-methoxy-5,6,7,8-tetrahydro-1, 6-naphthyridine-5-carboxamide (180 mg, 0.50 mmol), 2-(3-hydroxy-1,2-oxazol-5-yl)acetic acid (86 mg, 0.60 mmol) and DIEA (175 μL, 1.00 mmol) in DMF (2.5 mL) at room temperature, and the mixture was stirred for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane), and crystallized from diisopropyl ether/hexane to give the title compound (95.0 mg, 0.197 mmol, 39.1%) as white crystals.

MS(API): Calculated 482.5. Found 483.1 (M+H).

$^1$H NMR (300 MHz, CDCl$_3$): δ 1.30 (9H, s), 2.88-3.01 (1H, m), 3.08-3.18 (1H, m), 3.89 (3H, s), 3.91-4.00 (4H, m), 5.96 (1H, s), 5.98 (1H, s), 6.64 (1H, d, J=8.3 Hz), 6.94 (1H, dd, J=8.5,2.1 Hz), 7.10 (1H, t), 7.24-7.31 (2H, m), 7.44 (1H, d, J=8.7 Hz), 9.07 (1H, s).

Example 79

(5R)-N-(3-fluoro-4-(trimethylsilyl)phenyl)-6-((3-hydroxy-1,2-oxazol-5-yl)carbonyl)-2-methoxy-5,6,7,8-tetrahydro-1,6-naphthyridine-5-carboxamide (Step 1)

T3P (8.45 mL, 14.21 mmol) was added to a solution of 6-(tert-butoxycarbonyl)-2-methoxy-5,6,7,8-tetrahydro-1,6-naphthyridine-5-carboxylic acid (2.92 g, 9.47 mmol), 3-fluoro-4-(trimethylsilyl)aniline (1.736 g, 9.47 mmol), DIEA (8.25 mL, 47.35 mmol) and DMAP (1.273 g, 10.42 mmol) in ethyl acetate (70 mL) at room temperature, and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with cooled hexane to give tert-butyl 5-((3-fluoro-4-(trimethylsilyl)phenyl)carbamoyl)-2-methoxy-7,8-dihydro-1,6-naphthyridine-6(5H)-carboxylate (3.66 g, 7.73 mmol, 82%) as white crystals.

$^1$H NMR (300 MHz, CDCl$_3$): δ 0.28 (9H, s), 1.53 (9H, s), 2.84-3.03 (2H, m), 3.46 (1H, brs), 3.92 (3H, s), 4.01-4.12 (1H, m), 5.59 (1H, brs), 6.64 (1H, d, J=8.3 Hz), 7.11 (1H, dd, J=8.1,1.3 Hz), 7.29 (1H, dd, J=7.9, 6.4 Hz), 7.39 (1H, dd, J=10.6,1.9 Hz), 7.47 (1H, brs), 8.94 (1H, brs).
(Step 2)
tert-Butyl 5-((3-fluoro-4-(trimethylsilyl)phenyl)carbamoyl)-2-methoxy-7,8-dihydro-1,6-naphthyridine-6(5H)-carboxylate (3.66 g) was resolved by chiral column chromatography. The fraction having a shorter retention time was concentrated to give tert-butyl (R)-5-((3-fluoro-4-(trimethylsilyl)phenyl)carbamoyl)-2-methoxy-7,8-dihydro-1,6-naphthyridine-6(5H)-carboxylate (1.76 g, >99.9% ee) as a white solid.
purification condition by chiral column chromatography
   column: CHIRALPAK IA (QK001) 50 mmID×500 mmL
   solvent: hexane/EtOH=600/400
   flow rate: 80 mL/min
   temperature: 30° C.
   detection method: UV 220 nm
(Step 3)
Cooled TFA (24 mL) was added to tert-butyl (R)-5-((3-fluoro-4-(trimethylsilyl)phenyl)carbamoyl)-2-methoxy-7,8-dihydro-1,6-naphthyridine-6(5H)-carboxylate (1.76 g, 3.72 mmol) at room temperature, and the mixture was stirred at room temperature for 2 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(3-fluoro-4-(trimethylsilyl)phenyl)-2-methoxy-5,6,7,8-tetrahydro-1,6-naphthyridine-5-carboxamide (1.37 g, 3.67 mmol, 99%) as a white solid.
$^1$H NMR (300 MHz, CDCl$_3$): δ 0.28 (9H, s), 2.00 (1H, brs), 2.75-2.86 (1H, m), 2.87-2.99 (1H, m), 3.14-3.30 (2H, m), 3.90 (3H, s), 4.60 (1H, s), 6.60 (1H, d, J=8.7 Hz), 7.17 (1H, dd), 7.25-7.32 (1H, m), 7.44 (1H, dd, J=10.6,1.5 Hz), 7.83 (1H, d, J=8.7 Hz), 9.55 (1H, brs).
(Step 4)
HATU (249 mg, 0.65 mmol) was added to a solution of (R)-N-(3-fluoro-4-(trimethylsilyl)phenyl)-2-methoxy-5,6,7,8-tetrahydro-1, 6-naphthyridine-5-carboxamide (188 mg, 0.50 mmol), 3-hydroxy-1,2-oxazole-5-carboxylic acid (78 mg, 0.60 mmol) and DIEA (175 µL, 1.00 mmol) in DMF (2.5 mL) at room temperature, and the mixture was stirred for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 20→90% ethyl acetate/hexane) to give the title compound (94.5 mg, 0.195 mmol, 38.7%) as a white solid.
MS(API): Calculated 484.6. Found 485.2 (M+H).
$^1$H NMR (300 MHz, CDCl$_3$): δ 0.28 (9H, s), 2.83 (1H, s), 3.01-3.10 (1H, m), 3.16-3.29 (1H, m), 3.78-3.89 (1H, m), 3.93 (3H, s), 4.32-4.42 (1H, m), 5.97 (1H, s), 6.58 (1H, s), 6.68 (1H, d, J=8.7 Hz), 7.16 (1H, dd, J=7.9,1.5 Hz), 7.30 (1H, dd), 7.36-7.44 (2H, m), 9.07 (1H, s).
$[α]_D^{25}$+91.9 (c 0.2500, MeOH)

Example 80

(5R)-N-(3-fluoro-4-(trimethylsilyl)phenyl)-6-((3-hydroxy-1,2-oxazol-5-yl)acetyl)-2-methoxy-5,6,7,8-tetrahydro-1,6-naphthyridine-5-carboxamide HATU (249 mg, 0.65 mmol) was added to a solution of (R)-N-(3-fluoro-4-(trimethylsilyl)phenyl)-2-methoxy-5,6,7, 8-tetrahydro-1, 6-naphthyridine-5-carboxamide (188 mg, 0.50 mmol), 2-(3-hydroxy-1,2-oxazol-5-yl)acetic acid (86 mg, 0.60 mmol) and DIEA (175 µL, 1.00 mmol) in DMF (2.5 mL) at room temperature, and the mixture was stirred for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 20→90% ethyl acetate/hexane), and crystallized from diisopropyl ether/hexane to give the title compound (97.8 mg, 0.196 mmol, 39.0%) as white crystals.
MS(API): Calculated 498.6. Found 499.1 (M+H).
$^1$H NMR (300 MHz, CDCl$_3$): δ 0.25 (9H, s), 2.88-3.02 (1H, m), 3.08-3.18 (1H, m), 3.89 (3H, s), 3.91-3.99 (4H, m), 5.96 (1H, s), 5.99 (1H, s), 6.65 (1H, d, J=8.7 Hz), 7.00 (1H, dd, J=7.9,1.9 Hz), 7.20 (1H, dd, J=7.9,6.4 Hz), 7.25-7.30 (2H, m), 7.44 (1H, d, J=8.3 Hz), 9.12 (1H, s).
$[α]_D^{25}$+105.8 (c 0.2500, MeOH)

Example 81

(1R)-N-(4-fluoro-3,3-dimethyl-2,3-dihydro-1-benzofuran-6-yl)-2-((3-hydroxy-1,2-oxazol-5-yl)carbonyl)-6-methoxy-1,2,3,4-tetrahydroisoquinoline-1-carboxamide The title compound was synthesized using 4-fluoro-3,3-dimethyl-2,3-dihydrobenzofuran-6-amine, by the reaction, purification and resolution in the same manner as in Example 3.

Example 82

5-((1R)-1-((3,5-difluoro-4-(trimethylsilyl)phenyl)carbamoyl)-6-methoxy-3,4-dihydroisoquinolin-2(1H)-yl)-5-oxopentanoic acid (Step 1)
To a solution of 3,5-difluoro-4-(trimethylsilyl)aniline (700 mg, 3.48 mmol), 2-(tert-butoxycarbonyl)-6-methoxy-1,2,3,4-tetrahydroisoquinoline-1-carboxylic acid (1176 mg, 3.83 mmol), DMAP (467 mg, 3.83 mmol) and DIEA (3.04 mL, 17.39 mmol) in ethyl acetate (6.0 mL) was added T3P (6.14 mL, 10.43 mmol) at room temperature, and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The precipitate was washed with diethyl ether/hexane to give tert-butyl 1-((3,5-difluoro-4-(trimethylsilyl)phenyl)carbamoyl)-6-methoxy-3,4-dihydroisoquinoline-2(1H)-carboxylate (994.1 mg, 2.026 mmol, 58.3%) as white crystals. 1H NMR (300 MHz, CDCl$_3$): δ 0.32 (9H, s), 1.52 (9H, s), 2.76-2.98 (2H, m), 3.51-3.75 (2H, m), 3.80 (3H, s), 5.58 (1H, brs), 6.73 (1H, d, J=2.3 Hz), 6.81 (1H, dd, J=8.3,2.3 Hz), 6.97-7.07 (2H, m), 7.19 (1H, brs), 9.11 (1H, brs).
(Step 2)
tert-Butyl 1-((3,5-difluoro-4-(trimethylsilyl)phenyl)carbamoyl)-6-methoxy-3,4-dihydroisoquinoline-2(1H)-carboxylate (900 mg) was resolved by chiral column chromatography. The fraction having a shorter retention time was concentrated to give tert-butyl (R)-1-((3,5-difluoro-4-(trimethylsilyl)phenyl)carbamoyl)-6-methoxy-3,4-dihydroisoquinoline-2(1H)-carboxylate (410 mg, >99.6% ee) as a white solid.

purification condition by chiral column chromatography
    column: CHIRALPAK AD (NF001) 50 mmID×500 mmL
    solvent: hexane/EtOH=850/150
    flow rate: 80 mL/min
    temperature: 30° C.
    detection method: UV 220 nm (Step 3)

Cooled TFA (4.5 mL) was added to tert-butyl (R)-1-((3,5-difluoro-4-(trimethylsilyl)phenyl)carbamoyl)-6-methoxy-3,4-dihydroisoquinoline-2(1H)-carboxylate (439 mg, 0.89 mmol) at room temperature, and the mixture was stirred at room temperature for 2 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The precipitate was washed with IPE/hexane to give (R)-N-(3,5-difluoro-4-(trimethylsilyl)phenyl)-6-methoxy-1,2,3,4-tetrahydroisoquinoline-1-carboxamide (246 mg, 0.630 mmol, 70.4%) as white crystals.

$^1$H NMR (300 MHz, CDCl$_3$): δ 0.27 (9H, d, J=1.1 Hz), 2.23 (1H, brs), 2.69-2.80 (1H, m), 2.84-2.94 (1H, m), 3.14 (2H, t, J=5.9 Hz), 3.78 (3H, s), 4.63 (1H, s), 6.64 (1H, d, J=2.6 Hz), 6.78 (1H, dd, J=8.7,2.6 Hz), 7.17 (1H, dd), 7.24-7.30 (1H, m), 7.45 (1H, dd, J=10.6,1.9 Hz), 7.53 (1H, d, J=8.7 Hz), 9.45 (1H, s)

(Step 4)

A solution of (R)-N-(3,5-difluoro-4-(trimethylsilyl)phenyl)-6-methoxy-1,2,3,4-tetrahydroisoquinoline-1-carboxamide (80 mg, 0.20 mmol), dihydro-2H-pyran-2,6(3H)-dione (28.1 mg, 0.25 mmol) and TEA (0.034 mL, 0.25 mmol) in THF (2.0 mL) was stirred overnight at room temperature. The reaction mixture was concentrated under reduced pressure. The obtained residue was purified by silica gel column chromatography (Diol, solvent gradient; 10→50% ethyl acetate/hexane) to give the title compound (42.2 mg, 0.084 mmol, 40.8%) as a white solid.

MS(API): Calculated 504.6. Found 503.0 (M−H).

$^1$H NMR (300 MHz, DMSO-d$_6$): δ 0.29 (9H, s), 1.63-1.82 (2H, m), 2.18-2.32 (3H, m), 2.36-2.49 (1H, m), 2.52-2.61 (1H, m), 2.72-2.88 (1H, m), 3.05-3.19 (1H, m), 3.43-3.56 (1H, m), 3.73 (3H, s), 5.56-5.67 (1H, m), 6.77-6.86 (2H, m), 7.15-7.25 (2H, m), 7.46 (1H, d, J=9.1 Hz), 10.76 (1H, s), 12.01 (1H, brs).

$[α]_D^{25}$ −6.6 (c 0.2500, MeOH)

Example 83

4-((1R)-1-((3,5-difluoro-4-(trimethylsilyl)phenyl)carbamoyl)-6-methoxy-3,4-dihydroisoquinolin-2(1H)-yl)-4-oxobutanoic acid The title compound was synthesized using dihydrofuran-2,5-dione, by the reaction and purification in the same manner as in Example 82.

Example 84

(1R)-N-(4-tert-butyl-3,5-difluorophenyl)-2-(cyanoacetyl)-6-methoxy-1,2,3,4-tetrahydroisoquinoline-1-carboxamide HATU (222 mg, 0.58 mmol) was added to a solution of DIEA (0.255 mL, 1.46 mmol), 2-cyanoacetic acid (45.5 mg, 0.54 mmol) and (R)-N-(4-(tert-butyl)-3,5-difluorophenyl)-6-methoxy-1,2,3,4-tetrahydroisoquinoinoline-1-carboxamide hydrochloride (200 mg, 0.49 mmol) in DMF (5 mL), and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 30→100% ethyl acetate/hexane) to give the title compound (154 mg, 0.349 mmol, 71.7%) as a white solid.

MS(API): Calculated 441.5. Found 440.0 (M−H).

$^1$H NMR (300 MHz, DMSO-d$_6$): δ 1.38 (9H, t, J=1.9 Hz), 2.79-2.94 (1H, m), 3.01-3.21 (1H, m), 3.40-3.52 (1H, m), 3.73 (3H, s), 3.86-4.02 (1H, m), 4.08-4.39 (2H, m), 5.62 (1H, s), 6.84 (2H, dd, J=4.3,1.7 Hz), 7.06-7.30 (2H, m), 7.41-7.52 (1H, m), 10.69 (1H, s).

Example 85

(1R)-N-(3,5-difluoro-4-(trimethylsilyl)phenyl)-2-((3-hydroxy-1,2-oxazol-5-yl)acetyl)-6-methoxy-1,2,3,4-tetrahydroisoquinoline-1-carboxamide To a solution of (R)-N-(3,5-difluoro-4-(trimethylsilyl)phenyl)-6-methoxy-1,2,3,4-tetrahydroisoquinoline-1-carboxamide (70 mg, 0.18 mmol), DIEA (0.061 mL, 0.36 mmol) and 2-(3-hydroxy-1,2-oxazol-5-yl)acetic acid (30.8 mg, 0.22 mmol) in DMF (2.0 mL) was added HATU (82 mg, 0.22 mmol) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (39.0 mg, 0.076 mmol, 42.2%) as white crystals.

MS(API): Calculated 515.6. Found 516.1 (M+H).

$^1$H NMR (300 MHz, DMSO-d$_6$): δ 0.29 (9H, s), 2.71-2.90 (1H, m), 3.05-3.21 (1H, m), 3.49-3.64 (1H, m), 3.73 (3H, s), 3.90-4.14 (3H, m), 5.59-5.72 (1H, m), 5.82-5.93 (1H, m), 6.79-6.88 (2H, m), 7.13-7.25 (2H, m), 7.47 (1H, d, J=9.4 Hz), 10.72-10.83 (1H, m), 11.12 (1H, s).

Example 86

5-((1R)-1-((4-(ethyl(dimethyl)silyl)-3,5-difluorophenyl)carbamoyl)-6-methoxy-3,4-dihydroisoquinolin-2(1H)-yl)-5-oxopentanoic acid (Step 1)

To a solution of 1,3-difluoro-5-nitrobenzene (3 g, 18.86 mmol) and chloro(ethyl)dimethylsilane (3.47 g, 28.29 mmol) in THF (45 mL) was added 1.9M NaHMDS/THF solution (12.90 mL, 24.51 mmol) under argon gas atmosphere at −78° C., and the mixture was stirred at −78° C. for 1 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; hexane) to give (2,6-difluoro-4-nitrophenyl)(ethyl)dimethylsilane (2.93 g, 11.94 mmol, 63.3%) as a pale yellow oil.

¹H NMR (300 MHz, CDCl₃): δ 0.36-0.42 (6H, m), 0.83-0.92 (2H, m), 0.93-1.03 (3H, m), 7.61-7.70 (2H, m).
(Step 2)
A solution of (2,6-difluoro-4-nitrophenyl) (ethyl)dimethylsilane (2.9 g, 11.82 mmol) and 10% palladium-carbon (300 mg, 0.14 mmol, 50% wet) in MeOH (50 mL) was stirred under hydrogen atmosphere (1 atm) at room temperature for 5 hr. The catalyst was removed by filtration, and the filtrate was concentrated under reduced pressure. The obtained residue was purified by silica gel column chromatography (solvent gradient; 10→20% MeOH/ethyl acetate) to give 4-(ethyldimethylsilyl)-3,5-difluoroaniline (2.32 g, 10.77 mmol, 91%) as a colorless oil. 1H NMR (300 MHz, CDCl₃): δ 0.24-0.32 (6H, m), 0.70-0.83 (2H, m), 0.89-1.00 (3H, m), 3.89 (2H, brs), 6.05-6.14 (2H, m).
(Step 3)
To a solution of 4-(ethyldimethylsilyl)-3,5-difluoroaniline (700 mg, 3.25 mmol), 2-(tert-butoxycarbonyl)-6-methoxy-1,2,3,4-tetrahydroisoquinoline-1-carboxylic acid (1099 mg, 3.58 mmol), DMAP (437 mg, 3.58 mmol) and DIEA (2.84 mL, 16.26 mmol) in ethyl acetate (20 mL) was added T3P (5.74 mL, 9.75 mmol) at room temperature, and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→10% ethyl acetate/hexane), and crystallized from diethyl ether/hexane to give tert-butyl 1-((4-(ethyldimethylsilyl)-3,5-difluorophenyl)carbamoyl)-6-methoxy-3,4-dihydroisoquinoline-2(1H)-carboxylate (983.2 mg, 1.948 mmol, 59.9%) as white crystals.
¹H NMR (300 MHz, CDCl₃): δ 0.26-0.34 (6H, m), 0.72-0.86 (2H, m), 0.92 (3H, q, J=7.4 Hz), 1.52 (9H, s), 2.74-2.98 (2H, m), 3.46-3.75 (2H, m), 3.80 (3H, s), 5.58 (1H, brs), 6.73 (1H, d, J=2.3 Hz), 6.81 (1H, dd, J=8.7,2.3 Hz), 6.96-7.07 (2H, m), 7.19 (1H, brs), 9.11 (1H, brs).
(Step 4)
tert-Butyl 1-((4-(ethyldimethylsilyl)-3,5-difluorophenyl)carbamoyl)-6-methoxy-3,4-dihydroisoquinoline-2(1H)-carboxylate (1.0 g) was resolved by chiral column chromatography. The fraction having a shorter retention time was concentrated to give tert-butyl (R)-1-((4-(ethyldimethylsilyl)-3,5-difluorophenyl) carbamoyl)-6-methoxy-3,4-dihydroisoquinoline-2(1H)-carboxylate (0.48 g, >99.8% ee) as a white solid.
purification condition by chiral column chromatography
  column: CHIRALPAK AD (NF001) 50 mmID×500 mmL
  solvent: hexane/EtOH=850/150
  flow rate: 80 mL/min
  temperature: 30° C.
  detection method: UV 220 nm
(Step 5)
Cooled TFA (4.5 mL) was added to tert-butyl (R)-1-((4-(ethyldimethylsilyl)-3,5-difluorophenyl)carbamoyl)-6-methoxy-3,4-dihydroisoquinoline-2(1H)-carboxylate (475 mg, 0.94 mmol) at room temperature, and the mixture was stirred at room temperature for 2 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The precipitate was washed with diethyl ether/IPE to give (R)-N-(4-(ethyldimethylsilyl)-3,5-difluorophenyl)-6-methoxy-1,2,3,4-tetrahydroisoquinoline-1-carboxamide (853.8 mg, 2.111 mmol, 224%) as white crystals.
(Step 6)
A solution of (R)-N-(4-(ethyldimethylsilyl)-3,5-difluorophenyl)-6-methoxy-1,2,3,4-tetrahydroisoquinoline-1-carboxamide (160 mg, 0.40 mmol), dihydro-2H-pyran-2,6 (3H)-dione (54.2 mg, 0.47 mmol) and TEA (0.066 mL, 0.47 mmol) in THF (4.0 mL) was stirred overnight at room temperature. The reaction mixture was concentrated under reduced pressure. The obtained residue was purified by silica gel column chromatography (Diol, solvent gradient; 10→50% ethyl acetate/hexane) to give the title compound (85.7 mg, 0.165 mmol, 41.8%) as white crystals.
MS(API): Calculated 518.6. Found 519.1 (M+H).
¹H NMR (300 MHz, DMSO-d₆): δ 0.28 (6H, s), 0.66-0.80 (2H, m), 0.83-0.94 (3H, m), 1.64-1.82 (2H, m), 2.17-2.32 (3H, m), 2.35-2.61 (1H, m), 2.70-2.88 (1H, m), 3.00-3.20 (1H, m), 3.42-3.57 (1H, m), 3.73 (3H, s), 3.95-4.09 (1H, m), 5.56-5.65 (1H, m), 6.77-6.87 (2H, m), 7.14-7.26 (2H, m), 7.46 (1H, d, J=9.4 Hz), 10.76 (1H, s), 12.01 (1H, s).
[α]D₂₅ −7.6 (c 0.2500, MeOH)

Example 87

4-((1R)-1-((4-(ethyl (dimethyl) silyl)-3,5-difluorophenyl)carbamoyl)-6-methoxy-3,4-dihydroisoquinolin-2 (1H)-yl)-4-oxobutanoic acid The title compound was synthesized using dihydrofuran-2,5-dione, by the reaction and purification in the same manner as in Example 86.

Example 88

(1R)-N-(4-(ethyl (dimethyl) silyl)-3,5-difluorophenyl)-2-((3-hydroxy-1,2-oxazol-5-yl)acetyl)-6-methoxy-1,2,3,4-tetrahydroisoquinoline-1-carboxamide To a solution of (R)-N-(4-(ethyldimethylsilyl)-3,5-difluorophenyl)-6-methoxy-1,2,3,4-tetrahydroisoquinoline-1-carboxamide (80 mg, 0.20 mmol), DIEA (0.068 mL, 0.40 mmol) and 2-(3-hydroxy-1,2-oxazol-5-yl)acetic acid (34.0 mg, 0.24 mmol) in DMF (2.0 mL) was added HATU (90 mg, 0.24 mmol) at room temperature, and the mixture was stirred overnight. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (24.9 mg, 0.047 mmol, 23.77%) as white crystals.
MS(API): Calculated 529.6. Found 530.1 (M+H).
¹H NMR (300 MHz, DMSO-d₆): δ 0.28 (6H, s), 0.67-0.79 (2H, m), 0.83-0.93 (3H, m), 2.75-2.90 (1H, m), 3.05-3.22 ((H, m)), 3.48-3.63 (1H, m), 3.73 (3H, s), 3.90-4.15 (3H, m), 5.58-5.73 (1H, m), 5.82-5.95 (1H, m), 6.76-6.90 (2H, m), 7.13-7.27 (2H, m), 7.40-7.53 (1H, m), 10.72-10.86 (1H, m), 11.11 (1H, brs).

Example 89

(1R)-N-(3,5-difluoro-4-(2-methyl-1-oxo-1-(pyrrolidin-1-yl)propan-2-yl)phenyl)-2-((3-hydroxy-1,2-oxazol-5-yl)carbonyl)-6-methoxy-1,2,3,4-tetrahydroisoquinoline-1-carboxamide The title compound was synthesized using 2-(4-amino-2,6-difluorophenyl)-2-methyl-1-(pyrrolidin-1-yl) propan-1-one, by the reaction and purification in the same manner as in Example 3.

Example 90

(1R)-N-(3,5-difluoro-4-(2-methyl-1-oxo-1-(pyrrolidin-1-yl)propan-2-yl)phenyl)-2-((3-hydroxy-1,2-oxazol-5-yl)acetyl)-6-methoxy-1,2,3,4-tetrahydroisoquinoline-1-carboxamide The title compound was synthesized using 2-(4-amino-2,6-difluorophenyl)-2-methyl-1-(pyrrolidin-1-yl)propan-1-one, by the reaction and purification in the same manner as in Example 65.

Example 91

((1R)-1-((4-tert-butyl-3,5-difluorophenyl)carbamoyl)-6-methoxy-3,4-dihydroisoquinolin-2 (1H)-yl)(oxo)acetic acid The title compound was synthesized using 2-(tert-butoxy)-2-oxoacetic acid, by the reaction and purification in the same manner as in Example 12.

Example 92

6-((1R)-1-((3,5-difluoro-4-(trimethylsilyl)phenyl)carbamoyl)-6-methoxy-3,4-dihydroisoquinolin-2 (1H)-yl)-6-oxohexanoic acid A solution of (R)-N-(3,5-difluoro-4-(trimethylsilyl)phenyl)-6-methoxy-1,2,3,4-tetrahydroisoquinoline-1-carboxamide (70 mg, 0.18 mmol), oxepane-2,7-dione (27.6 mg, 0.22 mmol) and TEA (0.030 mL, 0.22 mmol) in THF (2.0 mL) was stirred at room temperature for 5 hr, and the reaction mixture was concentrated under reduced pressure. The obtained residue was purified by silica gel column chromatography (Diol, solvent gradient; 10→50% ethyl acetate/hexane) to give the title compound (9.9 mg, 0.019 mmol, 10.65%) as a white solid.

MS(API): Calculated 518.6. Found 519.2 (M+H).

$^1$H NMR (300 MHz, DMSO-$d_6$): δ 0.29 (9H, s), 1.41-1.67 (4H, m), 2.12-2.31 (1H, m), 2.36-2.61 (3H, m), 2.66-2.89 (1H, m), 3.00-3.19 (1H, m), 3.43-3.60 (1H, m), 3.72 (3H, s), 3.95-4.11 (1H, m), 5.61 (1H, s), 6.82 (2H, d, J=9.8 Hz), 7.19 (2H, d, J=9.8 Hz), 7.45 (1H, d, J=8.3 Hz), 10.74 (1H, s), 11.97 (1H, s).

Example 93

(2-((1R)-1-((3,5-difluoro-4-(trimethylsilyl)phenyl)carbamoyl)-6-methoxy-3,4-dihydroisoquinolin-2 (1H)-yl)-2-oxoethoxy)acetic acid The title compound was synthesized using 1,4-dioxane-2,6-dione, by the reaction and purification in the same manner as in Example 92.

Example 94

5-((1R)-1-((3,5-difluoro-4-(trimethylsilyl)phenyl)carbamoyl)-6-methoxy-3,4-dihydroisoquinolin-2 (1H)-yl)-3-methyl-5-oxopentanoic acid A solution of (R)-N-(3,5-difluoro-4-(trimethylsilyl)phenyl)-6-methoxy-1,2,3,4-tetrahydroisoquinoline-1-carboxamide (70 mg, 0.18 mmol), 4-methyldihydro-2H-pyran-2,6 (3H)-dione (27.6 mg, 0.22 mmol) and TEA (0.030 mL, 0.22 mmol) in THF (2.0 mL) was stirred at room temperature for 3 hr, and the reaction mixture was concentrated under reduced pressure. The obtained residue was purified by silica gel column chromatography (Diol, solvent gradient; 10→50% ethyl acetate/hexane) to give the title compound (42.8 mg, 0.083 mmol, 46.0%) as a white solid.

MS(API): Calculated 518.6. Found 517.1 (M–H).

$^1$H NMR (300 MHz, DMSO-$d_6$): δ 0.30 (9H, s), 0.82-0.99 (3H, m), 2.04-2.20 (1H, m), 2.21-2.41 (3H, m), 2.42-2.61 (1H, m), 2.75-2.89 (1H, m), 3.03-3.21 (1H, m), 3.45-3.59 (1H, m), 3.73 (3H, s), 3.97-4.10 (1H, m), 5.62 (1H, s), 6.78-6.85 (2H, m), 7.14-7.25 (2H, m), 7.46 (1H, d, J=9.4 Hz), 10.77 (1H, s), 12.04 (1H, brs).

Example 95

5-((1R)-1-((3,5-difluoro-4-(trimethylsilyl)phenyl)carbamoyl)-6-methoxy-3,4-dihydroisoquinolin-2 (1H)-yl)-3,3-dimethyl-5-oxopentanoic acid A solution of (R)-N-(3,5-difluoro-4-(trimethylsilyl)phenyl)-6-methoxy-1,2,3,4-tetrahydroisoquinoline-1-carboxamide (70 mg, 0.18 mmol), 4,4-dimethyldihydro-2H-pyran-2,6(3H)-dione (30.6 mg, 0.22 mmol) and TEA (0.030 mL, 0.22 mmol) in THF (2.0 mL) was stirred at room temperature for 3 hr, and the reaction mixture was concentrated under reduced pressure. The obtained residue was purified by silica gel column chromatography (Diol, solvent gradient; 10→50% ethyl acetate/hexane) to give the title compound (46.8 mg, 0.088 mmol, 49.0%) as a white solid.

MS(API): Calculated 532.7. Found 531.0 (M–H).

$^1$H NMR (300 MHz, DMSO-$d_6$): δ 0.29 (9H, s), 1.09 (6H, d, J=1.1 Hz), 2.25-2.44 (2H, m), 2.56-2.86 (2H, m), 3.04-3.19 (1H, m), 3.45-3.61 (1H, m), 3.73 (3H, s), 3.96-4.15 (2H, m), 5.57-5.70 (1H, m), 6.76-6.89 (2H, m), 7.14-7.25 (2H, m), 7.45 (1H, d, J=9.1 Hz), 10.77 (1H, s), 11.93 (1H, brs).

Example 96

(1R)-2-(amino(oxo)acetyl)-N-(4-tert-butyl-3,5-difluorophenyl)-6-methoxy-1,2,3,4-tetrahydroisoquinoline-1-carboxamide The title compound was synthesized by subjecting the compound of Example 91 to amidation.

Example 97

(1R)-N-(3,5-difluoro-4-(1-methoxy-2-methylpropan-2-yl)phenyl)-2-((3-hydroxy-1,2-oxazol-5-yl)carbonyl)-6-methoxy-1,2,3,4-tetrahydroisoquinoline-1-carboxamide (Step 1)

Diethyl malonate (44.8 g, 280 mmol) was added to a suspension of sodium hydride (60% oil, 28.0 g, 700 mmol)

in THF (280 mL) at 0° C., and the mixture was stirred at room temperature for 1 hr. Then, 1,2,3-trifluoro-5-nitrobenzene (24.79 g, 140 mmol) was added thereto at 0° C., and the mixture was stirred at room temperature for 2 hr. To the reaction mixture was added aqueous ammonium chloride solution, and the mixture was extracted twice with ethyl acetate. The organic layer was washed with brine, and dried over magnesium sulfate, and the solvent was evaporated under reduced pressure to give diethyl 2,6-difluoro-4-nitrophenylmalonate (42 g) as a colorless oil.

A solution of thus-obtained diethyl 2,6-difluoro-4-nitrophenylmalonate (42 g) in a mixed solvent of acetic acid (200 mL), water (150 mL) and conc. sulfuric acid (50 mL) was heated under reflux for 18 hr, and the reaction mixture was concentrated under reduced pressure. To the residue was added water, and the mixture was extracted twice with ethyl acetate. The organic layer was back extracted with 10% aqueous sodium carbonate solution, and the aqueous layer was acidified with 2N hydrochloric acid. The precipitate was collected by filtration to give 2-(2,6-difluoro-4-nitrophenyl) acetic acid (27.90 g, 128 mmol, 92.0%) as white crystals.

$^1$H NMR (300 MHz, DMSO-d$_6$): δ 3.79 (2H, s), 7.81-8.24 (2H, m), 12.93 (1H, brs).

(Step 2)

A solution of 2-(2,6-difluoro-4-nitrophenyl)acetic acid (27.90 g, 128.5 mmol) and conc. sulfuric acid (1.0 mL) in MeOH (260 mL) was heated under reflux for 18 hr. The reaction mixture was neutralized with aqueous sodium hydrogen carbonate solution, and ethyl acetate and water were added thereto. The organic layer was dried over magnesium sulfate, and the solvent was evaporated under reduced pressure. The obtained residue was purified by silica gel column chromatography (solvent gradient; 0→100% ethyl acetate/hexane) to give methyl 2-(2,6-difluoro-4-nitrophenyl)acetate (28.71 g, 128.5 mmol, 97.0%) as a yellow solid.

$^1$H NMR (300 MHz, CDCl$_3$): δ 3.75 (3H, s), 3.80 (2H, s), 7.80-7.85 (2H, m).

(Step 3)

To a solution of methyl 2-(2,6-difluoro-4-nitrophenyl) acetate (10.7 g, 50.20 mmol) and iodomethane (12.55 mL, 200.79 mmol) in DMF (100 mL) was added sodium hydride (60% oil, 5.02 g, 125.49 mmol) at 0° C., and the mixture was stirred at 0° C. for 4 hr. To the reaction mixture was added aqueous ammonium chloride solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→20% ethyl acetate/hexane) to give methyl 2-(2,6-difluoro-4-nitrophenyl)-2-methylpropanoate (12.10 g, 50.2 mmol, 100%) as yellow crystals.

(Step 4)

A solution of methyl 2-(2,6-difluoro-4-nitrophenyl)-2-methylpropanoate (3.2 g, 12.35 mmol) and 10% palladium-carbon (1.314 g, 0.617 mmol, 50% wet) in MeOH (30 mL) was stirred overnight under hydrogen atmosphere (1 atm) at room temperature. The catalyst was removed by filtration, and the filtrate was concentrated under reduced pressure. The obtained residue was purified by silica gel column chromatography (solvent gradient; 3→50% ethyl acetate/hexane) to give methyl 2-(4-amino-2,6-difluorophenyl)-2-methylpropanoate (2.87 g, 12.52 mmol, 101%) as a colorless oil. 1H NMR (300 MHz, CDCl$_3$): δ 1.59 (6H, t, J=1.7 Hz), 3.69 (3H, s), 3.77 (2H, brs), 6.00-6.25 (2H, m).

(Step 5)

To a solution of methyl 2-(4-amino-2,6-difluorophenyl)-2-methylpropanoate (2.8 g, 12.22 mmol) and α-chloro-4-methoxytoluene (3.48 mL, 25.65 mmol) in DMF (50 mL) was added sodium hydride (60% oil, 1.075 g, 26.87 mmol) at 0° C., and the mixture was stirred at 0° C. for 4 hr. To the reaction mixture was added aqueous ammonium chloride solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give methyl 2-(4-(bis(4-methoxybenzyl)amino)-2,6-difluorophenyl)-2-methylpropanoate (2.470 g, 5.26 mmol, 43.1%) as an orange oil.

(Step 6)

To a solution of methyl 2-(4-(bis(4-methoxybenzyl) amino)-2,6-difluorophenyl)-2-methylpropanoate (2.17 g, 4.62 mmol) in THF (30 mL) was added 1M DIBAL-H/THF solution (13.87 mL, 13.87 mmol) at 0° C., and the mixture was stirred at 0° C. for 5 hr. 1M DIBAL-H/THF solution (1.0 mL, 1.0 mmol) was again added thereto at 0° C., and the mixture was stirred at 0° C. for 1.5 hr. To the reaction mixture were added 1N hydrochloric acid and water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane), and then silica gel column chromatography (NH, solvent gradient; 3→50% ethyl acetate/hexane) to give 2-(4-(bis(4-methoxybenzyl)amino)-2,6-difluorophenyl)-2-methylpropan-1-ol (1.310 g, 2.97 mmol, 64.2%) as a colorless oil.

(Step 7)

To a solution of 2-(4-(bis(4-methoxybenzyl)amino)-2,6-difluorophenyl)-2-methylpropan-1-ol (1.31 g, 2.97 mmol) and iodomethane (0.278 mL, 4.45 mmol) in DMF (10 mL) was added sodium hydride (60% oil, 0.154 g, 3.86 mmol) at 0° C., and the mixture was stirred at 0° C. for 4 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→40% ethyl acetate/hexane) to give 3,5-difluoro-4-(1-methoxy-2-methylpropan-2-yl)-N,N-bis(4-methoxybenzyl)aniline (1.000 g, 2.195 mmol, 74.0%) as a yellow oil.

$^1$H NMR (300 MHz, CDCl$_3$): δ 1.37-1.42 (6H, m), 3.33 (3H, s), 3.50 (2H, s), 3.80 (6H, s), 4.46 (4H, s), 6.08-6.24 (2H, m), 6.86 (4H, d, J=8.3 Hz), 7.11 (4H, d, J=8.7 Hz).

(Step 8)

A solution of 3,5-difluoro-4-(1-methoxy-2-methylpropan-2-yl)-N,N-bis(4-methoxybenzyl)aniline (1 g, 2.20 mmol) in TFA (10 mL) was stirred at room temperature for 1 hr. The reaction mixture was concentrated under reduced pressure, and to the obtained residue was added ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give 3,5-difluoro-4-(1-methoxy-2-methylpropan-2-yl)aniline (0.470 g, 2.184 mmol, 99%) as a pale yellow oil.

$^1$H NMR (300 MHz, CDCl$_3$): δ 1.40 (6H, t, J=2.5 Hz), 3.32 (3H, s), 3.50 (2H, s), 3.69 (2H, brs), 6.07-6.16 (2H, m).

(Step 9)

To a solution of 2-(tert-butoxycarbonyl)-6-methoxy-1,2,3,4-tetrahydroisoquinoline-1-carboxylic acid (671 mg, 2.18 mmol), 3,5-difluoro-4-(1-methoxy-2-methylpropan-2-yl)aniline (470 mg, 2.18 mmol), DIEA (1.907 mL, 10.92 mmol) and DMAP (267 mg, 2.18 mmol) in ethyl acetate (30 mL) was added T3P (3.85 mL, 6.55 mmol) at room temperature, and the mixture was stirred overnight at 60° C. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→60% ethyl acetate/hexane), and then silica gel column chromatography (NH, solvent gradient; 5-60% ethyl acetate/hexane), and the precipitate was washed with ethyl acetate/hexane to give tert-butyl 1-((3,5-difluoro-4-(1-methoxy-2-methylpropan-2-yl)phenyl)carbamoyl)-6-methoxy-3,4-dihydroisoquinoline-2(1H)-carboxylate (440 mg, 0.872 mmol, 39.9%) as white crystals.

$^1$H NMR (300 MHz, CDCl$_3$): δ 1.42 (6H, t, J=2.3 Hz), 1.51 (9H, s), 2.72-2.99 (2H, m), 3.30 (3H, s), 3.46-3.75 (4H, m), 3.80 (3H, s), 5.57 (1H, brs), 6.73 (1H, s), 6.81 (1H, dd, J=8.5,2.8 Hz), 6.94-7.11 (2H, m), 7.10-7.20 (1H, m), 8.93 (1H, brs).

(Step 10)

tert-Butyl 1-((3,5-difluoro-4-(1-methoxy-2-methylpropan-2-yl)phenyl)carbamoyl)-6-methoxy-3,4-dihydroisoquinoline-2(1H)-carboxylate (440 mg) was resolved by chiral column chromatography. The fraction having a shorter retention time was concentrated to give tert-butyl (R)-1-((3,5-difluoro-4-(1-methoxy-2-methylpropan-2-yl)phenyl)carbamoyl)-6-methoxy-3,4-dihydroisoquinoline-2(1H)-carboxylate (200 mg, >99.9% ee) as a white solid.

purification condition by chiral column chromatography
    column: CHIRALCEL OD (NF001) 50 mmID×500 mmL
    solvent: hexane/EtOH=900/100
    flow rate: 80 mL/min
    temperature: 30° C.
    detection method: UV 220 nm (Step 11)

To a solution of tert-butyl (R)-1-((3,5-difluoro-4-(1-methoxy-2-methylpropan-2-yl)phenyl)carbamoyl)-6-methoxy-3,4-dihydroisoquinoline-2(1H)-carboxylate (200 mg, 0.40 mmol) in ethyl acetate (3 mL) was added 4M hydrogen chloride/ethyl acetate (4 mL) at room temperature, and the mixture was stirred overnight. The reaction mixture was concentrated under reduced pressure to give (R)-N-(3,5-difluoro-4-(1-methoxy-2-methylpropan-2-yl)phenyl)-6-methoxy-1,2,3,4-tetrahydroisoquinoline-1-carboxamide hydrochloride (175 mg, 0.397 mmol, 100%) as white crystals.

(Step 12)

A solution of (R)-N-(3,5-difluoro-4-(1-methoxy-2-methylpropan-2-yl)phenyl)-6-methoxy-1,2,3,4-tetrahydroisoquinoline-1-carboxamide hydrochloride (50 mg, 0.11 mmol), DIEA (0.048 mL, 0.27 mmol), 3-hydroxy-1,2-oxazole-5-carboxylic acid (17.56 mg, 0.14 mmol) and COMU (58.3 mg, 0.14 mmol) in DMF (2 mL) was stirred at 0° C. for 1 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane, 0→20% MeOH/ethyl acetate) to give the title compound (37.0 mg, 0.072 mmol, 63.3%) as brown crystals.

MS(API): Calculated 515.5. Found 514.0 (M−H).

$^1$H NMR (300 MHz, DMSO-d$_6$): δ 1.36 (6H, s), 2.79-2.95 (1H, m), 3.07-3.23 (4H, m), 3.45 (2H, s), 3.64-3.82 (4H, m), 3.93-4.25 (1H, m), 5.54-5.70 (1H, m), 6.58 (1H, s), 6.76-6.94 (2H, m), 7.19 (2H, d, J=13.2 Hz), 7.44-7.58 (1H, m), 10.80 (1H, s), 11.81 (1H, brs).

$[α]_D^{25}$ −19.4 (c 0.2520, MeOH

Example 98

(1R)-N-(3,5-difluoro-4-(1-methoxy-2-methylpropan-2-yl)phenyl)-2-((3-hydroxy-1,2-oxazol-5-yl)acetyl)-6-methoxy-1,2,3,4-tetrahydroisoquinoline-1-carboxamide A solution of (R)-N-(3,5-difluoro-4-(1-methoxy-2-methylpropan-2-yl)phenyl)-6-methoxy-1,2,3,4-tetrahydroisoquinoline-1-carboxamide hydrochloride (48 mg, 0.11 mmol), DIEA (0.046 mL, 0.26 mmol), 2-(3-hydroxy-1,2-oxazol-5-yl)acetic acid (18.69 mg, 0.13 mmol) and HATU (49.7 mg, 0.13 mmol) in DMF (2 mL) was stirred at 0° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane, 0→90% MeOH/ethyl acetate), and crystallized from ethyl acetate/hexane to give the title compound (31.0 mg, 0.059 mmol, 53.8%) as white crystals.

MS(API): Calculated 529.5. Found 530.1 (M+H).

$^1$H NMR (300 MHz, DMSO-d$_6$): δ 1.35 (6H, s), 2.75-2.90 (1H, m), 3.04-3.16 (1H, m), 3.19 (3H, s), 3.44 (2H, s), 3.51-3.63 (1H, m), 3.73 (3H, s), 3.88-4.17 (3H, m), 5.62 (1H, s), 5.91 (1H, s), 6.75-6.91 (2H, m), 7.17 (2H, d, J=13.2 Hz), 7.47 (1H, d, J=9.4 Hz), 10.68 (1H, s), 11.11 (1H, brs).

Example 99

(1R)-N-(3-fluoro-4-(2-methyl-1-oxo-1-(pyrrolidin-1-yl)propan-2-yl)phenyl)-2-((3-hydroxy-1,2-oxazol-5-yl)carbonyl)-6-methoxy-1,2,3,4-tetrahydroisoquinoline-1-carboxamide The title compound was synthesized using 2-(4-amino-2-fluorophenyl)-2-methyl-1-(pyrrolidin-1-yl)propan-1-one, by the reaction and purification in the same manner as in Example 3.

Example 100

(1R)-N-(6-(1-(2,2-difluoroethoxy)-2-methylpropan-2-yl)-5-fluoropyridin-3-yl)-6-methoxy-2-(3,3,3-trifluoropropanoyl)-1,2,3,4-tetrahydroisoquinoline-1-carboxamide The title compound was synthesized using 6-(1-(2,2-difluoroethoxy)-2-methylpropan-2-yl)-5-fluoropyridin-3-amine and 3,3,3-trifluoro-propionic acid, by the reaction and purification in the same manner as in Example 65.

Example 101

(1R)-N-(3-fluoro-4-(trimethylsilyl)phenyl)-2-((3-hydroxy-1,2-oxazol-5-yl)acetyl)-6-(methoxymethyl)-1,2,3,4-tetrahydroisoquinoline-1-carboxamide (Step 1)

To a solution of 1-ethyl 2-tert-butyl 6-hydroxy-3,4-dihydroisoquinoline-1,2(1H)-dicarboxylate (5 g, 15.56 mmol), DIEA (5.43 mL, 31.12 mmol) and DMAP (0.190 g, 1.56 mmol) in THF (30 mL) was added 1,1,1-trifluoro-N-phenyl-N-(trifluoromethyl)sulfonylmethanesulfonamide (8.34 g, 23.34 mmol) at room temperature, and the mixture was stirred at room temperature for 3 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane), and then silica gel column chromatography (NH, solvent gradient; 3→50% ethyl acetate/hexane) to give 1-ethyl 2-tert-butyl 6-(((trifluoromethyl)sulfonyl)oxy)-3,4-dihydroisoquinoline-1,2(1H)-dicarboxylate (7.44 g, 16.41 mmol, 105%) as a colorless oil.

$^1$H NMR (300 MHz, CDCl$_3$): δ 1.21-1.31 (3H, m), 1.45-1.53 (9H, m), 2.82-2.99 (2H, m), 3.60-3.77 (1H, m), 3.80-3.99 (1H, m), 4.18 (2H, q, J=7.2 Hz), 5.28-5.69 (1H, m), 7.01-7.19 (2H, m), 7.60 (1H, dd, J=8.7,3.8 Hz).

Step 2

A solution of 1-ethyl 2-tert-butyl 6-(((trifluoromethyl)sulfonyl)oxy)-3,4-dihydroisoquinoline-1,2(1H)-dicarboxylate (7.44 g, 16.41 mmol), Pd(PPh$_3$)$_4$(0.948 g, 0.82 mmol) and zinc cyanide (2.119 g, 18.05 mmol) in DMF (100 mL) was stirred overnight at 100° C. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 30→60% ethyl acetate/hexane) to give 1-ethyl 2-tert-butyl 6-cyano-3,4-dihydroisoquinoline-1,2(1H)-dicarboxylate (4.92 g, 14.89 mmol, 91%) as a colorless oil.

$^1$H NMR (300 MHz, CDCl$_3$): δ 1.18-1.33 (3H, m), 1.42-1.53 (9H, m), 2.78-3.03 (2H, m), 3.62-3.78 (1H, m), 3.80-3.99 (1H, m), 4.18 (2H, q, J=7.1 Hz), 5.38-5.71 (1H, m), 7.40-7.55 (2H, m), 7.58-7.69 (1H, m).

(Step 3)

To a mixture of Raney-nickel catalyst (NDHT-90) (0.5 g) and 1-ethyl 2-tert-butyl 6-cyano-3,4-dihydroisoquinoline-1,2(1H)-dicarboxylate (0.5 g, 1.51 mmol) in a mixed solvent of acetic acid (5.00 mL), pyridine (10 mL) and water (5 mL) was added sodium hypophosphite monohydrate (2.5 g, 23.59 mmol) at room temperature under argon gas atmosphere, and the mixture was stirred at 60° C. for 3 hr, and then overnight at 100° C. The catalyst was removed by filtration with ethyl acetate, and the filtrate was washed with aqueous ammonium chloride solution, aqueous sodium hydrogen carbonate solution and brine, and dried over magnesium sulfate, and the solvent was evaporated under reduced pressure. The obtained residue was purified by silica gel column chromatography (solvent gradient; 5→70% ethyl acetate/hexane) to give 1-ethyl 2-tert-butyl 6-formyl-3,4-dihydroisoquinoline-1,2(1H)-dicarboxylate (0.430 g, 1.290 mmol, 85%) as a colorless oil.

$^1$H NMR (300 MHz, CDCl$_3$): δ 1.26 (3H, t, J=7.2 Hz), 1.45-1.53 (9H, m), 2.80-3.13 (2H, m), 3.63-3.97 (2H, m), 4.18 (2H, q, J=7.2 Hz), 5.44-5.72 (1H, m), 7.61-7.80 (3H, m), 9.99 (1H, s).

(Step 4)

To a solution of 1-ethyl 2-tert-butyl 6-formyl-3,4-dihydroisoquinoline-1,2(1H)-dicarboxylate (430 mg, 1.29 mmol) in MeOH (10 mL) was added sodium borohydride (24.40 mg, 0.64 mmol) at 0° C., and the mixture was stirred at room temperature for 20 min. To the reaction mixture was added aqueous ammonium chloride solution, and the mixture was extracted with ethyl acetate. The organic layer was washed with brine, and dried over magnesium sulfate, and the solvent was evaporated under reduced pressure to give 1-ethyl 2-tert-butyl 6-(hydroxymethyl)-3,4-dihydroisoquinoline-1,2(1H)-dicarboxylate (390 mg, 1.163 mmol, 90%) as a colorless oil.

$^1$H NMR (300 MHz, CDCl$_3$): δ 1.23-1.30 (3H, m), 1.37-1.51 (9H, m), 1.67 (1H, brs), 2.70-3.05 (2H, m), 3.66-3.84 (2H, m), 4.11-4.21 (2H, m), 4.67 (2H, s), 5.28-5.64 (1H, m), 7.13-7.25 (2H, m), 7.44-7.54 (1H, m).

(Step 5)

To a solution of 1-ethyl 2-tert-butyl 6-(hydroxymethyl)-3,4-dihydroisoquinoline-1,2(1H)-dicarboxylate (390 mg, 1.16 mmol) and methanesulfonyl chloride (0.135 mL, 1.74 mmol) in THF (10 mL) was added TEA (0.243 mL, 1.74 mmol) at 0° C., and the mixture was stirred at room temperature for 1 hr. To the reaction mixture was added water, and the mixture was extracted with ethyl acetate. The organic layer was washed with brine, and dried over magnesium sulfate, and the solvent was evaporated under reduced pressure to give 1-ethyl 2-tert-butyl 6-(((methylsulfonyl)oxy)methyl)-3,4-dihydroisoquinoline-1,2(1H)-dicarboxylate (500 mg, 1.209 mmol, 104%) as a colorless oil.

$^1$H NMR (300 MHz, CDCl$_3$): δ 1.20-1.30 (3H, m), 1.44-1.51 (9H, m), 2.78-3.05 (5H, m), 3.70-3.92 (2H, m), 4.16 (2H, q, J=7.2 Hz), 5.20 (2H, s), 5.37-5.65 (1H, m), 7.20-7.30 (2H, m), 7.49-7.59 (1H, m).

(Step 6)

To a solution of 1-ethyl 2-tert-butyl 6-(((methylsulfonyl)oxy)methyl)-3,4-dihydroisoquinoline-1,2 (1H)-dicarboxylate (500 mg, 1.21 mmol) in MeOH (5 mL) was added TEA (0.337 mL, 2.42 mmol) at room temperature, and the mixture was stirred at 70° C. for 2 hr. The reaction mixture was concentrated under reduced pressure, and the obtained residue was purified by silica gel column chromatography (solvent gradient; 3→60% ethyl acetate/hexane) to give 1-ethyl 2-tert-butyl 6-(methoxymethyl)-3,4-dihydroisoquinoline-1,2(1H)-dicarboxylate (169 mg, 0.484 mmol, 40.0%) as a colorless oil.

$^1$H NMR (300 MHz, CDCl$_3$): δ 1.20-1.30 (3H, m), 1.43-1.53 (9H, m), 2.73-3.06 (2H, m), 3.40 (3H, s), 3.67-3.84 (2H, m), 4.14 (2H, q, J=7.2 Hz), 4.42 (2H, s), 5.22-5.64 (1H, m), 7.05-7.22 (2H, m), 7.42-7.56 (1H, m).

(Step 7)

To a solution of 1-ethyl 2-tert-butyl 6-(methoxymethyl)-3,4-dihydroisoquinoline-1,2(1H)-dicarboxylate (160 mg, 0.46 mmol) in a mixed solvent of MeOH (5 mL), THF (5.00 mL) and water (5.00 mL) was added lithium hydroxide (65.8 mg, 2.75 mmol) at room temperature, and the mixture was stirred at 60° C. for 1 hr. The reaction mixture was concentrated under reduced pressure. To the obtained residue was added ethyl acetate. The organic layer was washed with brine, and dried over magnesium sulfate, and the solvent was evaporated under reduced pressure to give 2-(tert-butoxycarbonyl)-6-(methoxymethyl)-1,2,3,4-tetrahydroiso-quinoline-1-carboxylic acid (148 mg, 0.461 mmol, 101%) as a white solid.

¹H NMR (300 MHz, CDCl₃): δ 1.35-1.57 (9H, m), 2.77-3.02 (2H, m), 3.39 (3H, s), 3.60-3.90 (2H, m), 4.42 (2H, s), 5.23-5.66 (1H, m), 7.07-7.22 (2H, m), 7.45 (1H, d, J=7.6 Hz) (The exchangeable 1H was not observed).

(Step 8)

To a solution of 2-(tert-butoxycarbonyl)-6-(methoxymethyl)-1,2,3,4-tetrahydroisoquinoline-1-carboxylic acid (148 mg, 0.46 mmol), 3-fluoro-4-(trimethylsilyl)aniline (84 mg, 0.46 mmol), DIEA (0.402 mL, 2.30 mmol) and DMAP (56.3 mg, 0.46 mmol) in ethyl acetate (5 mL) was added T3P (0.813 mL, 1.38 mmol) at room temperature, and the mixture was stirred at 60° C. for 48 hr. To the reaction mixture was added water, and the mixture was extracted with ethyl acetate. The organic layer was washed with brine, and dried over magnesium sulfate, and the solvent was evaporated under reduced pressure. The residue was purified by silica gel column chromatography (solvent gradient; 2→40% ethyl acetate/hexane) to give tert-butyl 1-((3-fluoro-4-(trimethylsilyl)phenyl)carbamoyl)-6-(methoxymethyl)-3,4-dihydroisoquinoline-2(1H)-carboxylate (178 mg, 0.366 mmol, 79%) as a white solid. 1H NMR (300 MHz, CDCl₃): δ 0.27 (9H, s), 1.52 (9H, s), 2.80-3.01 (2H, m), 3.39 (3H, s), 3.49-3.85 (2H, m), 4.44 (2H, s), 5.64 (1H, brs), 7.10 (1H, d, J=7.6 Hz), 7.21 (2H, d, J=10.6 Hz), 7.26-7.32 (2H, m), 7.38 (1H, dd, J=10.6,1.9 Hz), 8.95 (1H, brs).

(Step 9)

Cooled TFA (2 mL) was added to tert-butyl 1-((3-fluoro-4-(trimethylsilyl)phenyl)carbamoyl)-6-(methoxymethyl)-3,4-dihydroisoquinoline-2(1H)-carboxylate (178 mg, 0.37 mmol) at 0° C., and the mixture was stirred at room temperature for 2 min. The reaction mixture was added to ice and aqueous sodium hydrogen carbonate solution. Then, the mixture was extracted with ethyl acetate. The organic layer was washed with brine, and dried over sodium sulfate, and the solvent was evaporated under reduced pressure. To the obtained residue was added cooled TFA (2 mL) at 0° C., and the mixture was stirred at room temperature for 7 min. The reaction mixture was added to ice and aqueous sodium hydrogen carbonate solution. Then, the mixture was extracted with ethyl acetate. The organic layer was washed with brine, and dried over sodium sulfate, and the solvent was evaporated under reduced pressure to give N-(3-fluoro-4-(trimethylsilyl)phenyl)-6-(methoxymethyl)-1,2,3,4-tetrahydroisoquinoline-1-carboxamide (141 mg) as a crude product. The total amount thereof was used for the next step.

(Step 10)

A solution of N-(3-fluoro-4-(trimethylsilyl)phenyl)-6-(methoxymethyl)-1,2,3,4-tetrahydroisoquinoline-1-carboxamide (141 mg) obtained in Step 9, DIEA (0.076 mL, 0.44 mmol), 2-(3-hydroxy-1,2-oxazol-5-yl)acetic acid (62.6 mg, 0.44 mmol) and HATU (166 mg, 0.44 mmol) in DMF (4 mL) was stirred at 0° C. for 1 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane, 0→10% MeOH/ethyl acetate), and crystallized from ethyl acetate/hexane to give N-(3-fluoro-4-(trimethylsilyl)phenyl)-2-(2-(3-hydroxy-1,2-oxazol-5-yl)acetyl)-6-(methoxymethyl)-1,2,3,4-tetrahydroisoquinoline-1-carboxamide (96 mg, 0.188 mmol, 51.4%) as white crystals.

¹H NMR (300 MHz, DMSO-d₆): δ 0.18-0.29 (9H, m), 2.87 (1H, d, J=15.1 Hz), 3.13 (1H, d, J=4.5 Hz), 3.27 (3H, s), 3.64 (1H, t, J=8.1 Hz), 3.89-4.16 (3H, m), 4.36 (2H, s), 5.75 (1H, s), 5.91 (1H, s), 7.13-7.23 (2H, m), 7.24-7.38 (2H, m), 7.45 (1H, d, J=11.3 Hz), 7.55 (1H, d, J=7.6 Hz), 10.70 (1H, s), 11.11 (1H, s).

(Step 11)

N-(3-Fluoro-4-(trimethylsilyl)phenyl)-2-(2-(3-hydroxy-1,2-oxazol-5-yl)acetyl)-6-(methoxymethyl)-1,2,3,4-tetrahydroisoquinoline-1-carboxamide (96 mg) was resolved by chiral column chromatography. The fraction having a shorter retention time was concentrated to give the title compound (45 mg, >99.8% ee) as a white solid.

MS(API): Calculated 511.6. Found 512.1 (M+H).

purification condition by chiral column chromatography
column: CHIRALPAK IA (QK001) 50 mmID×500 mmL
solvent: hexane/EtOH/acetic acid=500/500/1
flow rate: 80 mL/min
temperature: 30° C.
detection method: UV 220 nm
$[\alpha]_D^{25}$+16.8 (c 0.2505, MeOH)

The compounds described in Examples 1 to 101 are as follows (Table 1-1-Table 1-11).

TABLE 1-1

| EXAMPLE | IUPACNAME | Structure | ADDITIVE | MS |
|---|---|---|---|---|
| 1 | 2-((3-hydroxy-1,2-oxazol-5-yl)carbonyl)-6-methoxy-N-(4-(trimethylsilyl)phenyl)-1,2,3,4-tetrahydroisoquinoline-1-carboxamide | 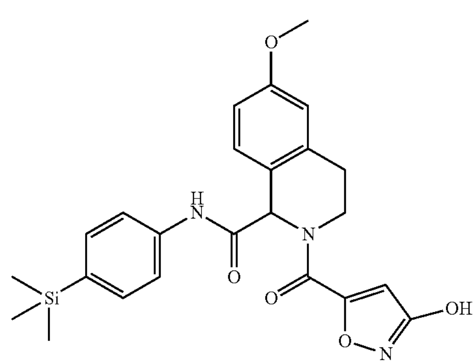 [SMILES: COc1ccc2c(c1)CCN(C(=O)c1cc(O)no1)C2C(=O)Nc1ccc([Si](C)(C)C)cc1] | | 466.1 (M + H) |

TABLE 1-1-continued

| EXAMPLE | IUPAC NAME | Structure | ADDITIVE | MS |
|---|---|---|---|---|
| 2 | 6-methoxy-2-((6-oxo-1,6-dihydropyridin-3-yl)carbonyl)-N-(4-(trimethylsilyl)phenyl)-1,2,3,4-tetrahydroisoquinoline-1-carboxamide | 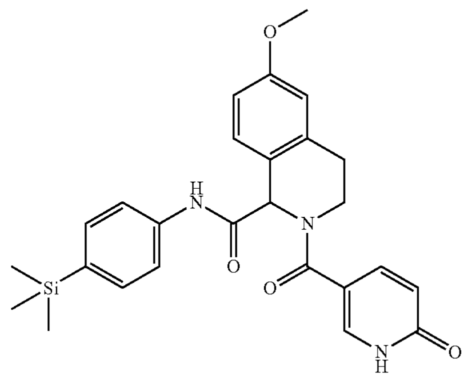 [SMILES: COc1ccc2c(c1)CCN(C(=O)c1ccc(=O)[nH]c1)C2C(=O)Nc1ccc([Si](C)(C)C)cc1] | | 474.2 (M − H) |
| 3 | N-(3-fluoro-4-(trimethylsilyl)phenyl)-2-((3-hydroxy-1,2-oxazol-5-yl)carbonyl)-6-methoxy-1,2,3,4-tetrahydroisoquinoline-1-carboxamide | 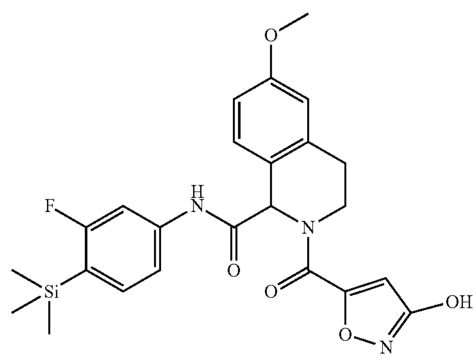 [SMILES: COc1ccc2c(c1)CCN(C(=O)c1cc(O)no1)C2C(=O)Nc1ccc([Si](C)(C)C)c(F)c1] | | 484.2 (M + H) |
| 4 | N-(3-fluoro-4-(trimethylsilyl)phenyl)-6-methoxy-2-((6-oxo-1,6-dihydropyridin-3-yl)carbonyl)-1,2,3,4-tetrahydroisoquinoline-1-carboxamide | 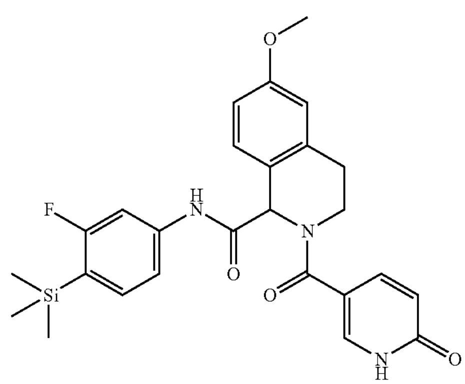 [SMILES: COc1ccc2c(c1)CCN(C(=O)c1ccc(=O)[nH]c1)C2C(=O)Nc1ccc([Si](C)(C)C)c(F)c1] | | 492.2 (M − H) |
| 5 | 4-((3-hydroxy-1,2-oxazol-5-yl)carbonyl)-8-methoxy-N-(4-(trimethylsilyl)phenyl)-2,3,4,5-tetrahydro-1,4-benzoxazepine-5-carboxamide | 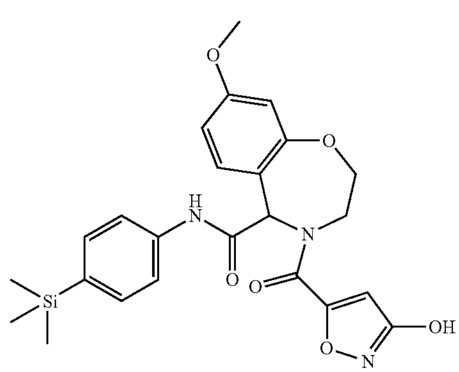 [SMILES: COc1ccc2c(c1)OCCN(C(=O)c1cc(O)no1)C2C(=O)Nc1ccc([Si](C)(C)C)cc1] | | 482.1 (M + H) |

TABLE 1-1-continued

| EXAMPLE | IUPACNAME | Structure | ADDITIVE | MS |
|---|---|---|---|---|
| 6 | 8-methoxy-4-((6-oxo-1,6-dihydropyridin-3-yl)carbonyl)-N-(4-(trimethylsilyl)phenyl)-2,3,4,5-tetrahydro-1,4-benzoxazepine-5-carboxamide | 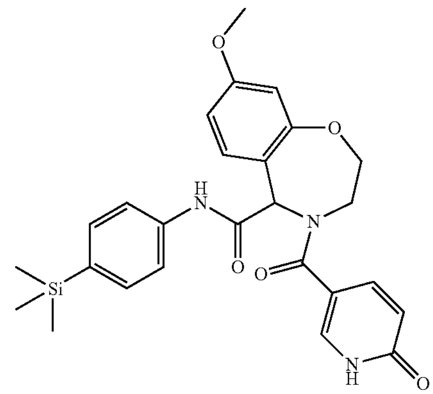 [SMILES: COc1ccc2c(c1)OCCN(C(=O)c1ccc(=O)[nH]c1)C2C(=O)Nc1ccc([Si](C)(C)C)cc1] | | 490.2 (M − H) |
| 7 | (1R)-N-(3-fluoro-4-(trimethylsilyl)phenyl)-2-((3-hydroxy-1,2-oxazol-5-yl)carbonyl)-6-methoxy-1,2,3,4-tetrahydroisoquinoline-1-carboxamide | 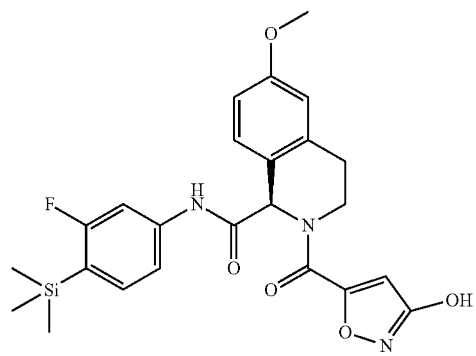 [SMILES: COc1ccc2c(c1)CCN(C(=O)c1cc(O)no1)[C@H]2C(=O)Nc1ccc([Si](C)(C)C)c(F)c1] | | 484.2 (M + H) |
| 8 | (1R)-N-(3-fluoro-4-(trimethylsilyl)phenyl)-6-methoxy-2-((6-oxo-1,6-dihydropyridin-3-yl)carbonyl)-1,2,3,4-tetrahydroisoquinoline-1-carboxamide | 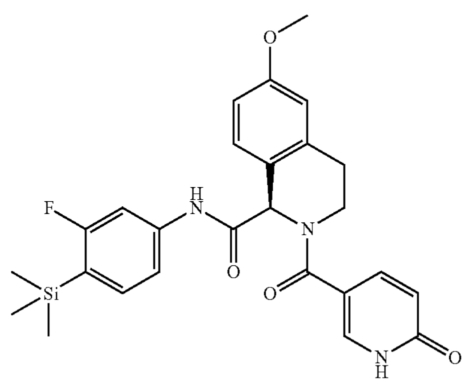 [SMILES: COc1ccc2c(c1)CCN(C(=O)c1ccc(=O)[nH]c1)[C@H]2C(=O)Nc1ccc([Si](C)(C)C)c(F)c1] | | 492.2 (M − H) |
| 9 | N-(4-tert-butyl-3-fluorophenyl)-2-((3-hydroxy-1,2-oxazol-5-yl)carbonyl)-6-methoxy-1,2,3,4-tetrahydroisoquinoline-1-carboxamide | 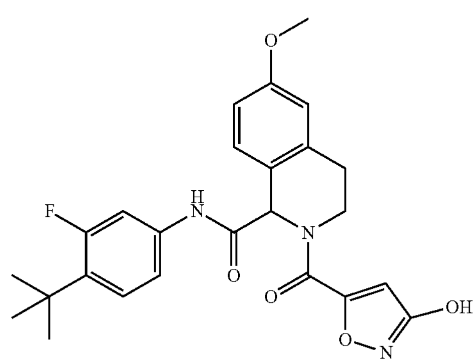 [SMILES: COc1ccc2c(c1)CCN(C(=O)c1cc(O)no1)C2C(=O)Nc1ccc(C(C)(C)C)c(F)c1] | | 468.2 (M + H) |

TABLE 1-1-continued

| EXAMPLE | IUPACNAME | Structure | ADDITIVE | MS |
|---|---|---|---|---|
| 10 | N-(4-tert-butyl-3-chlorophenyl)-2-((3-hydroxy-1,2-oxazol-5-yl)carbonyl)-6-methoxy-1,2,3,4-tetrahydroisoquinoline-1-carboxamide | 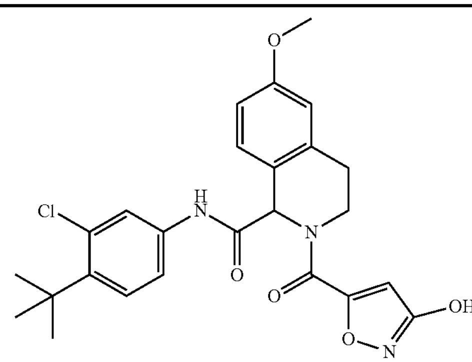 | | 482.0 (M − H) |

TABLE 1-2

| EXAMPLE | IUPACNAME | Structure | ADDITIVE | MS |
|---|---|---|---|---|
| 11 | N-(7-fluoro-1,1-dimethyl-2,3-dihydro-1H-inden-5-yl)-2-((3-hydroxy-1,2-oxazol-5-yl)carbonyl)-6-methoxy-1,2,3,4-tetrahydroisoquinoline-1-carboxamide | 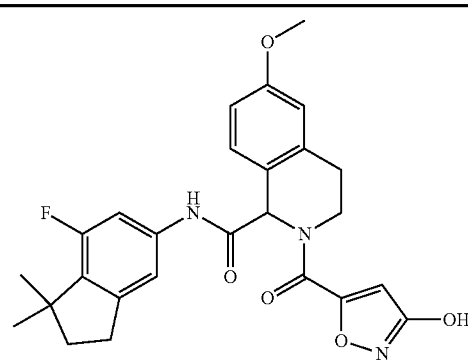 | | 480.1 (M + H) |
| 12 | N-(4-tert-butyl-3,5-difluorophenyl)-2-((3-hydroxy-1,2-oxazol-5-yl)carbonyl)-6-methoxy-1,2,3,4-tetrahydroisoquinoline-1-carboxamide | 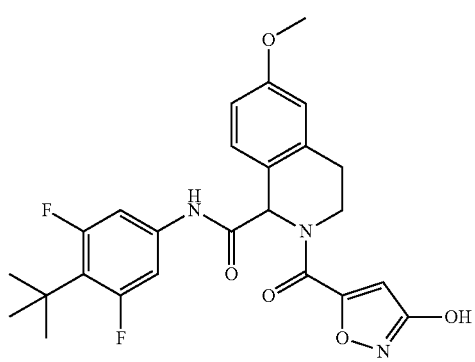 [SMILES: COc1ccc2c(c1)CCN(C(=O)c1cc(O)no1)C2C(=O)Nc1cc(F)c(C(C)(C)C)c(F)c1] | | 486.1 (M + H) |
| 13 | (1R)-N-(4-tert-butyl-3-fluorophenyl)-2-((3-hydroxy-1,2-oxazol-5-yl)carbonyl)-6-methoxy-1,2,3,4-tetrahydroisoquinoline-1-carboxamide | 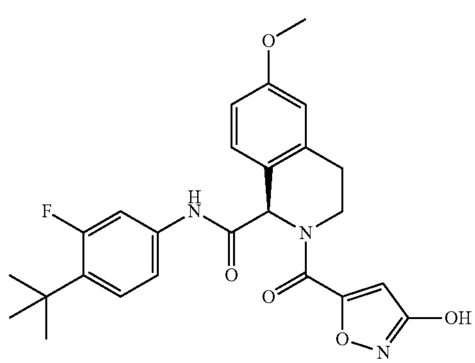 [SMILES: COc1ccc2c(c1)CCN(C(=O)c1cc(O)no1)[C@H]2C(=O)Nc1ccc(C(C)(C)C)c(F)c1] | | 468.2 (M + H) |

TABLE 1-2-continued

| EXAMPLE | IUPACNAME | Structure | ADDITIVE | MS |
|---|---|---|---|---|
| 14 | (1S)-N-(4-tert-butyl-3-fluorophenyl)-2-((3-hydroxy-1,2-oxazol-5-yl)carbonyl)-6-methoxy-1,2,3,4-tetrahydroisoquinoline-1-carboxamide | 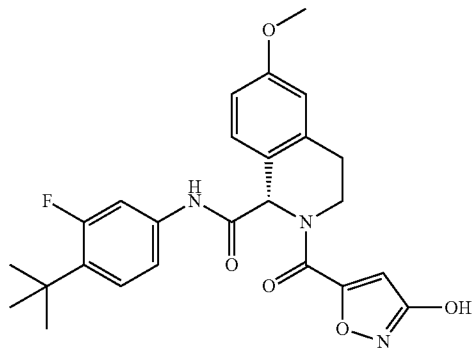 [SMILES: COc1ccc2c(c1)CCN(C(=O)c1cc(O)no1)[C@@H]2C(=O)Nc1ccc(C(C)(C)C)c(F)c1] | | 468.1 (M + H) |
| 15 | (1R)-N-(4-tert-butyl-3-fluorophenyl)-2-((2,4-dioxo-1,3-thiazolidin-5-yl)acetyl)-6-methoxy-1,2,3,4-tetrahydroisoquinoline-1-carboxamide | 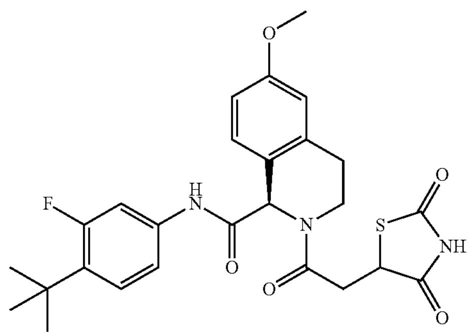 [SMILES: COc1ccc2c(c1)CCN(C(=O)CC1SC(=O)NC1=O)[C@H]2C(=O)Nc1ccc(C(C)(C)C)c(F)c1] | | 512.0 (M − H) |
| 16 | (1R)-N-(4-tert-butyl-3-fluorophenyl)-2-((2,6-dioxopiperidin-4-yl)acetyl)-6-methoxy-1,2,3,4-tetrahydroisoquinoline-1-carboxamide | 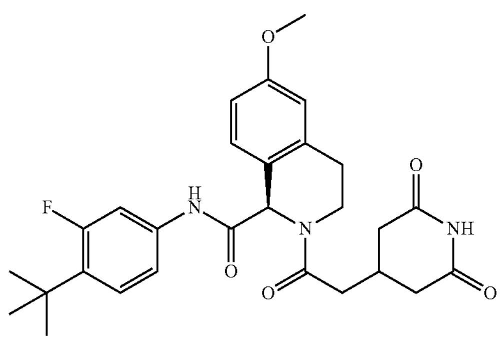 [SMILES: COc1ccc2c(c1)CCN(C(=O)CC1CC(=O)NC(=O)C1)[C@H]2C(=O)Nc1ccc(C(C)(C)C)c(F)c1] | | 508.2 (M − H) |
| 17 | (1R)-N$^1$-(4-tert-butyl-3-fluorophenyl)-6-methoxy-N$^2$-(pyridazin-3-yl)-3,4-dihydroisoquinoline-1,2(1H)-dicarboxamide | 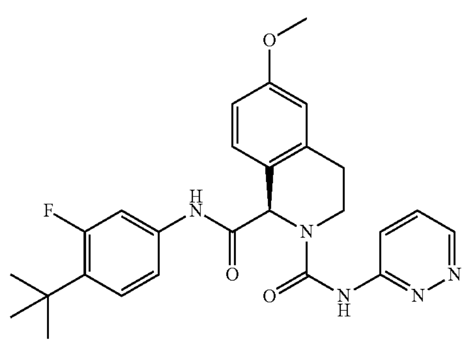 [SMILES: COc1ccc2c(c1)CCN(C(=O)Nc1cccnn1)[C@H]2C(=O)Nc1ccc(C(C)(C)C)c(F)c1] | | 478.1 (M + H) |

TABLE 1-2-continued

| EXAMPLE | IUPACNAME | Structure | ADDITIVE | MS |
|---|---|---|---|---|
| 18 | (1R)-N-(4-tert-butyl-3-fluorophenyl)-2-((2,5-dioxoimidazolidin-4-yl)acetyl)-6-methoxy-1,2,3,4-tetrahydroisoquinoline-1-carboxamide | 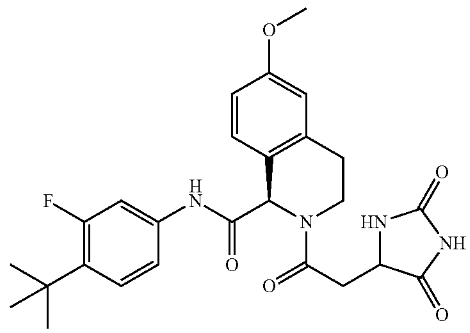 [SMILES: COc1ccc2c(c1)CCN(C(=O)CC1NC(=O)NC1=O)[C@H]2C(=O)Nc1ccc(C(C)(C)C)c(F)c1] | | 495.0 (M − H) |
| 19 | (1R)-N-(4-tert-butyl-3-fluorophenyl)-2-((2,4-dioxoimidazolidin-1-yl)acetyl)-6-methoxy-1,2,3,4-tetrahydroisoquinoline-1-carboxamide | 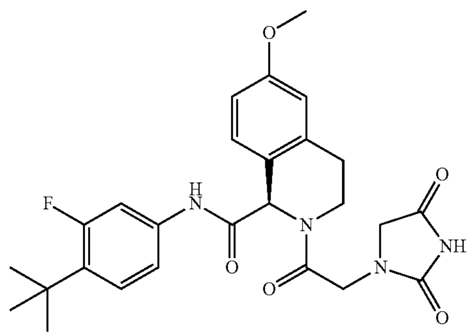 [SMILES: COc1ccc2c(c1)CCN(C(=O)CN1CC(=O)NC1=O)[C@H]2C(=O)Nc1ccc(C(C)(C)C)c(F)c1] | | 497.2 (M + H) |
| 20 | (1R)-N-(4-tert-butyl-3-fluorophenyl)-6-methoxy-2-((5-oxopyrrolidin-3-yl)acetyl)-1,2,3,4-tetrahydroisoquinoline-1-carboxamide | 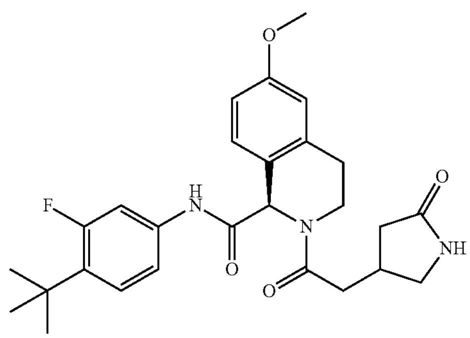 [SMILES: COc1ccc2c(c1)CCN(C(=O)CC1CNC(=O)C1)[C@H]2C(=O)Nc1ccc(C(C)(C)C)c(F)c1] | | 482.2 (M + H) |

TABLE 1-3

| EXAMPLE | IUPACNAME | Structure | ADDITIVE | MS |
|---|---|---|---|---|
| 21 | (1R)-N[1]-(4-tert-butyl-3-fluorophenyl)-6-methoxy-N[2]-(1-methyl-1H-pyrazol-3-yl)-3,4-dihydroisoquinoline-1,2(1H)-dicarboxamide | 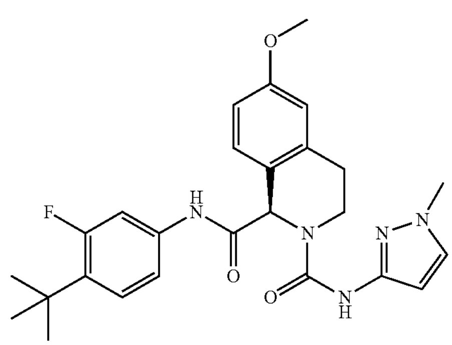 [SMILES: COc1ccc2c(c1)CCN(C(=O)Nc1ccn(C)n1)[C@H]2C(=O)Nc1ccc(C(C)(C)C)c(F)c1] | | 480.2 (M + H) |

TABLE 1-3-continued

| EXAMPLE | IUPACNAME | Structure | ADDITIVE | MS |
|---------|-----------|-----------|----------|-----|
| 22 | (1R)-N-(4-tert-butyl-3-fluorophenyl)-2-((5,5-dimethyl-2,4-dioxo-1,3-oxazolidin-3-yl)acetyl)-6-methoxy-1,2,3,4-tetrahydroisoquinoline-1-carboxamide | 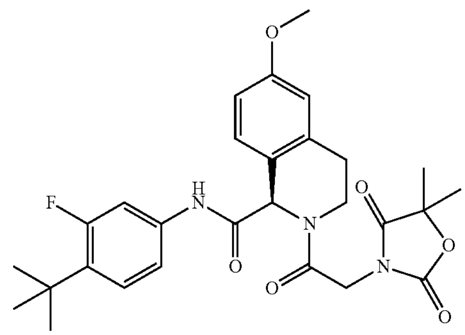 [SMILES: COc1ccc2c(c1)CCN(C(=O)CN1C(=O)OC(C)(C)C1=O)[C@H]2C(=O)Nc1ccc(C(C)(C)C)c(F)c1] | | 524.1 (M − H) |
| 23 | (1R)-N-(4-tert-butyl-3-fluorophenyl)-6-methoxy-2-((2-oxoimidazolidin-1-yl)acetyl)-1,2,3,4-tetrahydroisoquinoline-1-carboxamide | 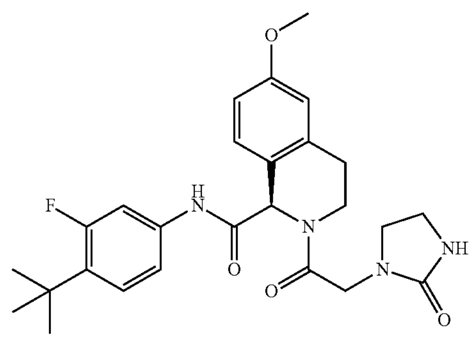 [SMILES: COc1ccc2c(c1)CCN(C(=O)CN1CCNC1=O)[C@H]2C(=O)Nc1ccc(C(C)(C)C)c(F)c1] | | 483.1 (M + H) |
| 24 | (1R)-N-(4-tert-butyl-3-fluorophenyl)-2-((2,4-dioxo-3,4-dihydropyrimidin-1(2H)-yl)acetyl)-6-methoxy-1,2,3,4-tetrahydroisoquinoline-1-carboxamide | 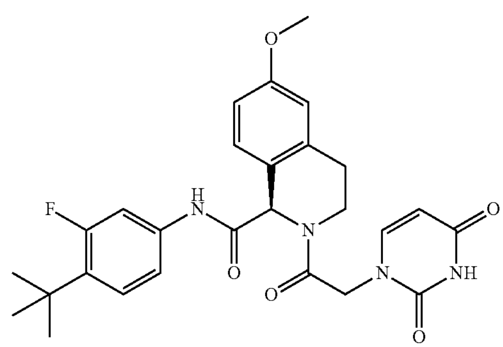 [SMILES: COc1ccc2c(c1)CCN(C(=O)Cn1ccc(=O)[nH]c1=O)[C@H]2C(=O)Nc1ccc(C(C)(C)C)c(F)c1] | | 507.1 (M − H) |
| 25 | (1R)-N-(4-tert-butyl-3-fluorophenyl)-6-methoxy-2-(((3S)-5-oxopyrrolidin-3-yl)carbonyl)-1,2,3,4-tetrahydroisoquinoline-1-carboxamide | 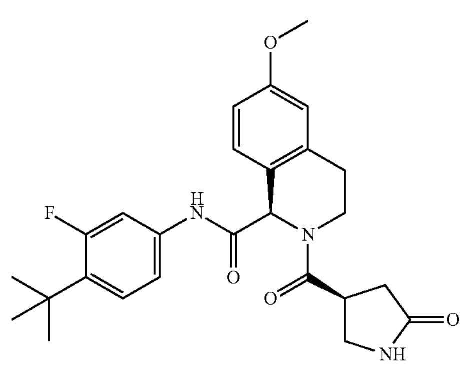 [SMILES: COc1ccc2c(c1)CCN(C(=O)[C@@H]1CNC(=O)C1)[C@H]2C(=O)Nc1ccc(C(C)(C)C)c(F)c1] | | 466.0 (M − H) |

TABLE 1-3-continued

| EXAMPLE | IUPACNAME | Structure | ADDITIVE | MS |
|---|---|---|---|---|
| 26 | (1R)-N-(4-tert-butyl-3-fluorophenyl)-6-methoxy-2-(((3R)-5-oxopyrrolidin-3-yl)carbonyl)-1,2,3,4-tetrahydroisoquinoline-1-carboxamide | 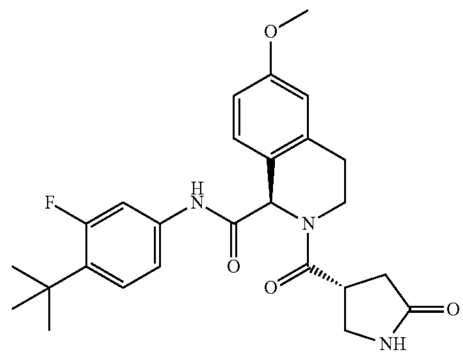 [SMILES: COc1ccc2c(c1)CCN(C(=O)[C@H]1CNC(=O)C1)[C@H]2C(=O)Nc1ccc(C(C)(C)C)c(F)c1] | | 466.0 (M − H) |
| 27 | (1R)-N-(4-tert-butyl-3-fluorophenyl)-2-((3-hydroxy-1,2-oxazol-5-yl)acetyl)-6-methoxy-1,2,3,4-tetrahydroisoquinoline-1-carboxamide | 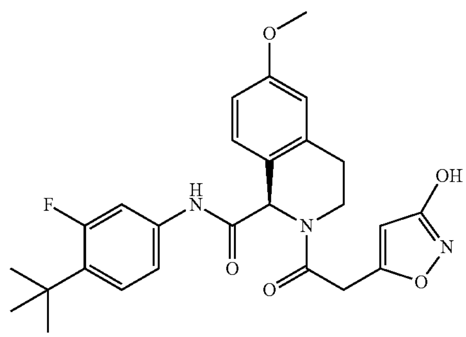 [SMILES: COc1ccc2c(c1)CCN(C(=O)Cc1cc(O)no1)[C@H]2C(=O)Nc1ccc(C(C)(C)C)c(F)c1] | | 480.0 (M − H) |
| 28 | (1R)-N-(4-tert-butyl-3-fluorophenyl)-6-methoxy-2-((5-methyl-1,3,4-oxadiazol-2-yl)acetyl)-1,2,3,4-tetrahydroisoquinoline-1-carboxamide | 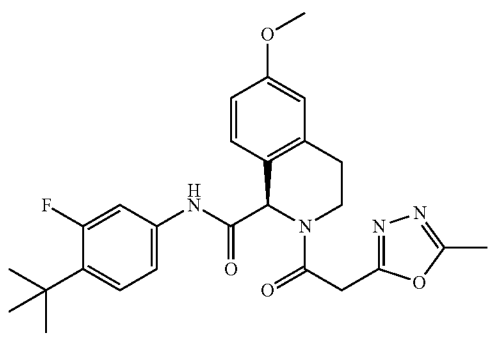 [SMILES: COc1ccc2c(c1)CCN(C(=O)Cc1nnc(C)o1)[C@H]2C(=O)Nc1ccc(C(C)(C)C)c(F)c1] | | 481.1 (M + H) |
| 29 | (1R)-N-(4-tert-butyl-3-fluorophenyl)-6-methoxy-2-((6-oxopyrimidin-1(6H)-yl)acetyl)-1,2,3,4-tetrahydroisoquinoline-1-carboxamide | 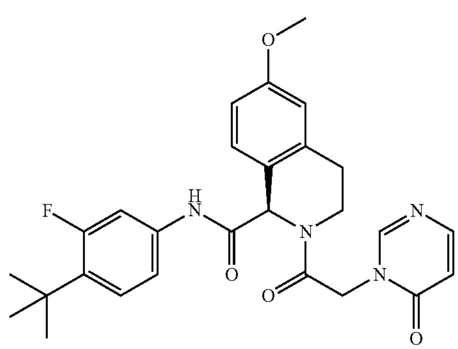 [SMILES: COc1ccc2c(c1)CCN(C(=O)Cn1cnccc1=O)[C@H]2C(=O)Nc1ccc(C(C)(C)C)c(F)c1] | | 491.1 (M − H) |

TABLE 1-3-continued

| EXAMPLE | IUPACNAME | Structure | ADDITIVE | MS |
|---|---|---|---|---|
| 30 | (1R)-N-(4-tert-butyl-3-fluorophenyl)-2-(3-hydroxypropanoyl)-6-methoxy-1,2,3,4-tetrahydroisoquinoline-1-carboxamide | 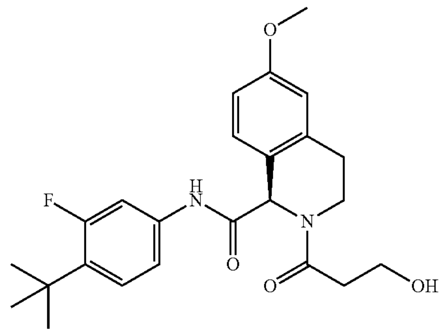 [SMILES: COc1ccc2c(c1)CCN(C(=O)CCO)[C@H]2C(=O)Nc1ccc(C(C)(C)C)c(F)c1] | | 427.1 (M − H) |

TABLE 1-4

| EXAMPLE | IUPACNAME | Structure | ADDITIVE | MS |
|---|---|---|---|---|
| 31 | (1R)-N-(4-tert-butyl-3-fluorophenyl)-6-methoxy-2-(3-(methylsulfonyl)propanoyl)-1,2,3,4-tetrahydroisoquinoline-1-carboxamide | 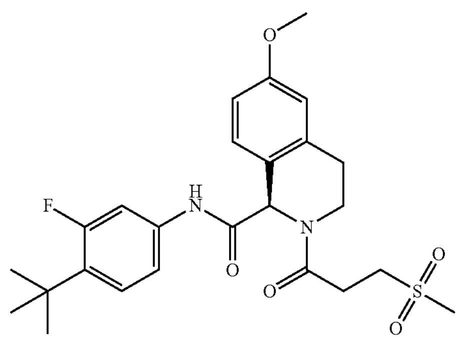 [SMILES: COc1ccc2c(c1)CCN(C(=O)CCS(C)(=O)=O)[C@H]2C(=O)Nc1ccc(C(C)(C)C)c(F)c1] | | 491.1 (M + H) |
| 32 | (1R)-N-(4-tert-butyl-3-fluorophenyl)-6-methoxy-2-((6-methoxypyridin-3-yl)acetyl)-1,2,3,4-tetrahydroisoquinoline-1-carboxamide | 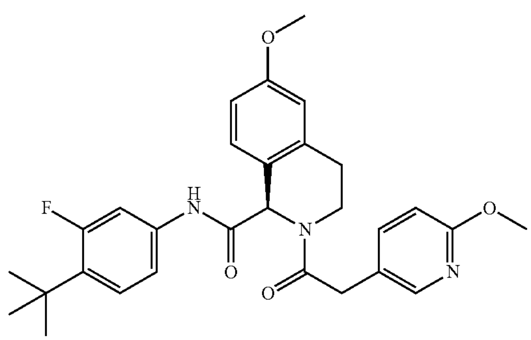 [SMILES: COc1ccc2c(c1)CCN(C(=O)Cc1ccc(OC)nc1)[C@H]2C(=O)Nc1ccc(C(C)(C)C)c(F)c1] | | 506.2 (M + H) |
| 33 | (1R)-N-(4-tert-butyl-3-fluorophenyl)-6-methoxy-2-((6-oxo-1,6-dihydropyridin-3-yl)acetyl)-1,2,3,4-tetrahydroisoquinoline-1-carboxamide | 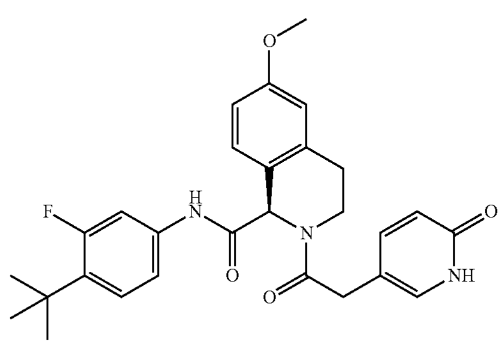 [SMILES: COc1ccc2c(c1)CCN(C(=O)Cc1ccc(=O)[nH]c1)[C@H]2C(=O)Nc1ccc(C(C)(C)C)c(F)c1] | | 492.2 (M + H) |

TABLE 1-4-continued

| EXAMPLE | IUPACNAME | Structure | ADDITIVE | MS |
|---|---|---|---|---|
| 34 | 4-((1R)-1-((4-tert-butyl-3-fluorophenyl)carbamoyl)-6-methoxy-3,4-dihydroisoquinolin-2(1H)-yl)-4-oxobutanoic acid | 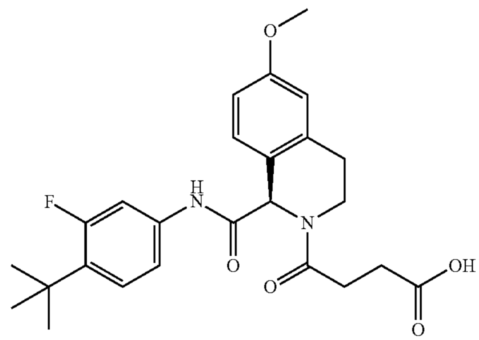 [SMILES: COc1ccc2c(c1)CCN(C(=O)CCC(=O)O)[C@H]2C(=O)Nc1ccc(C(C)(C)C)c(F)c1] | | 455.1 (M − H) |
| 35 | N-(4-tert-butyl-3-fluorophenyl)-4-((3-hydroxy-1,2-oxazol-5-yl)carbonyl)-8-methoxy-2,3,4,5-tetrahydro-1,4-benzoxazepine-5-carboxamide | 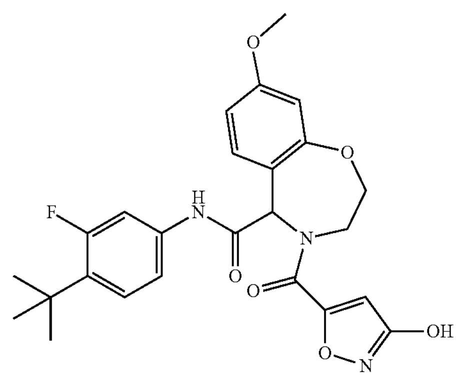 [SMILES: COc1ccc2c(c1)OCCN(C(=O)c1cc(O)no1)C2C(=O)Nc1ccc(C(C)(C)C)c(F)c1] | | 484.1 (M + H) |
| 36 | N-(3,5-difluoro-4-(trimethylsilyl)phenyl)-4-((3-hydroxy-1,2-oxazol-5-yl)carbonyl)-8-methoxy-2,3,4,5-tetrahydro-1,4-benzoxazepine-5-carboxamide | 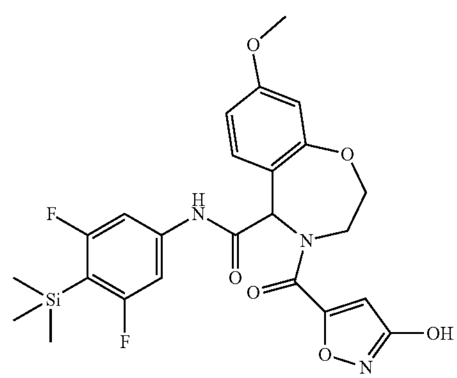 [SMILES: COc1ccc2c(c1)OCCN(C(=O)c1cc(O)no1)C2C(=O)Nc1cc(F)c([Si](C)(C)C)c(F)c1] | | 518.1 (M + H) |
| 37 | ethyl 2-(2-fluoro-4-(((2-((3-hydroxy-1,2-oxazol-5-yl)carbonyl)-6-methoxy-1,2,3,4-tetrahydroisoquinolin-1-yl)carbonyl)amino)phenyl)-2-methylpropanoate | 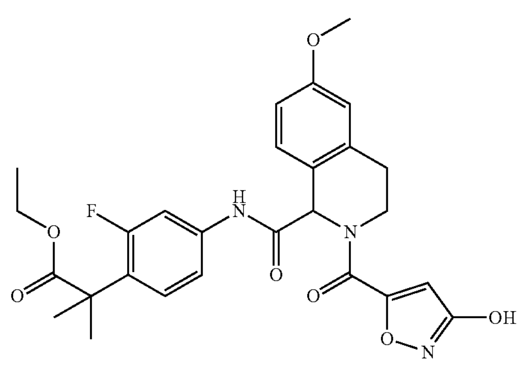 [SMILES: CCOC(=O)C(C)(C)c1ccc(NC(=O)C2c3ccc(OC)cc3CCN2C(=O)c2cc(O)no2)cc1F] | | 524.1 (M − H) |

TABLE 1-4-continued

| EXAMPLE | IUPACNAME | Structure | ADDITIVE | MS |
|---|---|---|---|---|
| 38 | N-(4-tert-butyl-3-fluorophenyl)-6-(1H-indazol-1-ylacetyl)-1-methyl-2-oxo-1,2,5,6,7,8-hexahydro-1,6-naphthyridine-5-carboxamide | 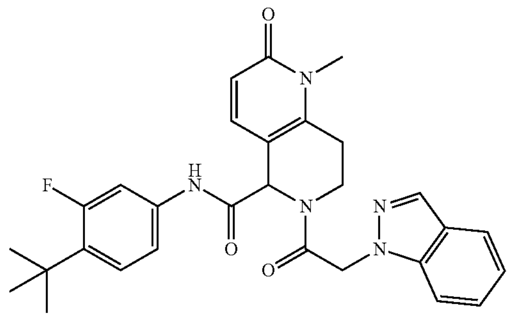 [SMILES: Cn1c2c(ccc1=O)C(C(=O)Nc1ccc(C(C)(C)C)c(F)c1)N(C(=O)Cn1ncc3ccccc31)CC2] | | 516.3 (M + H) |
| 39 | N-(3,5-difluoro-4-(trimethylsilyl)phenyl)-6-(1H-indazol-1-ylacetyl)-1-methyl-2-oxo-1,2,5,6,7,8-hexahydro-1,6-naphthyridine-5-carboxamide | 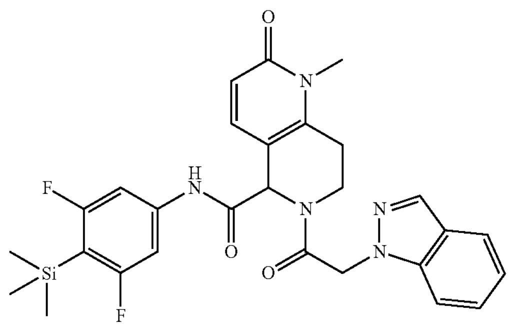 [SMILES: Cn1c2c(ccc1=O)C(C(=O)Nc1cc(F)c([Si](C)(C)C)c(F)c1)N(C(=O)Cn1ncc3ccccc31)CC2] | | 550.2 (M + H) |
| 40 | (1R)-N-(4-tert-butyl-3-fluorophenyl)-6-methoxy-2-(2H-tetrazol-5-ylacetyl)-1,2,3,4-tetrahydroisoquinoline-1-carboxamide | 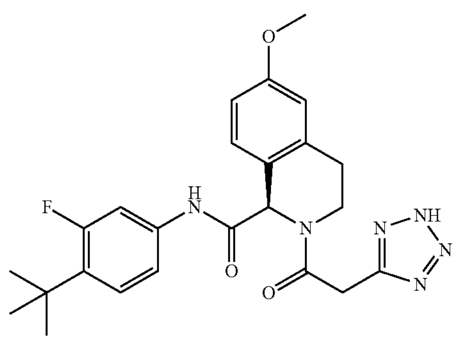 [SMILES: COc1ccc2c(c1)CCN(C(=O)Cc1nn[nH]n1)[C@H]2C(=O)Nc1ccc(C(C)(C)C)c(F)c1] | | 465.0 (M − H) |

TABLE 1-5

| EXAMPLE | IUPACNAME | Structure | ADDITIVE | MS |
|---|---|---|---|---|
| 41 | N-(4-tert-butyl-3-fluorophenyl)-6-((3-hydroxy-1,2-oxazol-5-yl)acetyl)-2-methoxy-5,6,7,8-tetrahydro-1,6-naphthyridine-5-carboxamide | 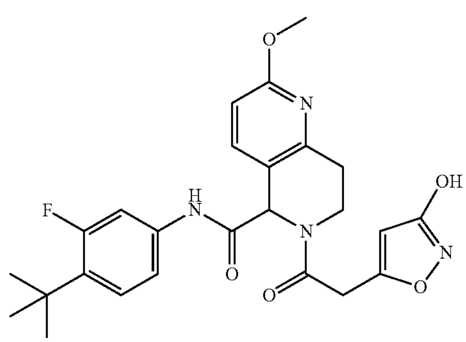 [SMILES: COc1ccc2c(n1)CCN(C(=O)Cc1cc(O)no1)C2C(=O)Nc1ccc(C(C)(C)C)c(F)c1] | | 483.1 (M + H) |

TABLE 1-5-continued

| EXAMPLE | IUPACNAME | Structure | ADDITIVE | MS |
|---|---|---|---|---|
| 42 | N-(4-(1-(ethylamino)-2-methyl-1-oxopropan-2-yl)-3-fluorophenyl)-6-methoxy-2-propionyl-1,2,3,4-tetrahydroisoquinoline-1-carboxamide | 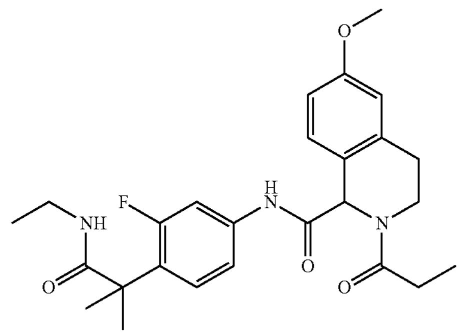 [SMILES: CCNC(=O)C(C)(C)c1ccc(NC(=O)C2c3ccc(OC)cc3CCN2C(=O)CC)cc1F] | | 468.2 (M − H) |
| 43 | (1R)-N-(4-tert-butyl-3,5-difluorophenyl)-2-((3-hydroxy-1,2-oxazol-5-yl)acetyl)-6-methoxy-1,2,3,4-tetrahydroisoquinoline-1-carboxamide | 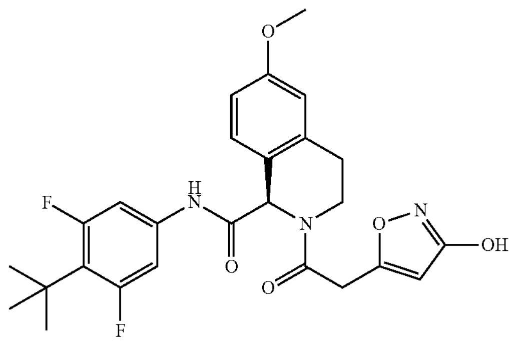 [SMILES: COc1ccc2c(c1)CCN(C(=O)Cc1cc(O)no1)[C@H]2C(=O)Nc1cc(F)c(C(C)(C)C)c(F)c1] | | 497.8 (M − H) |
| 44 | (1R)-N-(4-tert-butyl-3-fluorophenyl)-2-((1,1-dioxidotetrahydro-2H-thiopyran-4-yl)acetyl)-6-methoxy-1,2,3,4-tetrahydroisoquinoline-1-carboxamide | 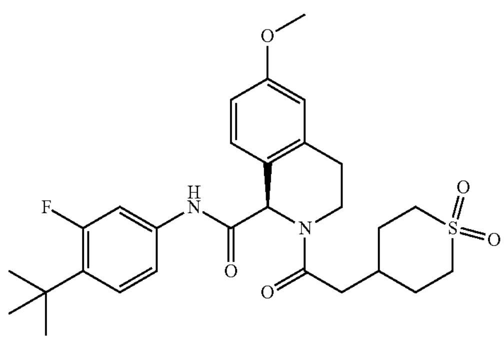 [SMILES: COc1ccc2c(c1)CCN(C(=O)CC1CCS(=O)(=O)CC1)[C@H]2C(=O)Nc1ccc(C(C)(C)C)c(F)c1] | | 529.0 (M − H) |
| 45 | (1R)-N-(7-fluoro-1,1-dimethyl-2,3-dihydro-1H-inden-5-yl)-2-((3-hydroxy-1,2-oxazol-5-yl)acetyl)-6-methoxy-1,2,3,4-tetrahydroisoquinoline-1-carboxamide | 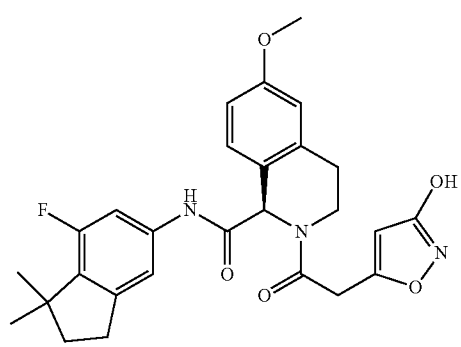 [SMILES: COc1ccc2c(c1)CCN(C(=O)Cc1cc(O)no1)[C@H]2C(=O)Nc1cc(F)c2c(c1)CCC2(C)C] | | 492.1 (M − H) |

TABLE 1-5-continued

| EXAMPLE | IUPACNAME | Structure | ADDITIVE | MS |
|---|---|---|---|---|
| 46 | N-(3-fluoro-4-(2-(5-methyl-1,3,4-oxadiazol-2-yl)propan-2-yl)phenyl)-6-methoxy-2-propionyl-1,2,3,4-tetrahydroisoquinoline-1-carboxamide | 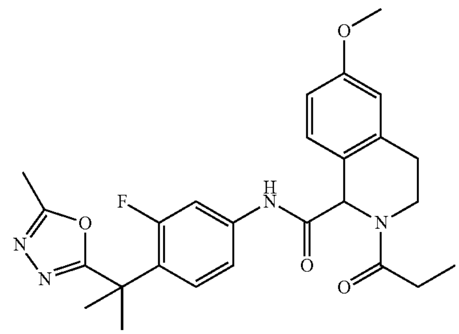 [SMILES: CCC(=O)N1CCc2cc(OC)ccc2C1C(=O)Nc1ccc(C(C)(C)c2nnc(C)o2)c(F)c1] | | 481.1 (M + H) |
| 47 | (1R)-N-(4-tert-butyl-3-fluorophenyl)-6-methoxy-2-propionyl-1,2,3,4-tetrahydroisoquinoline-1-carboxamide | 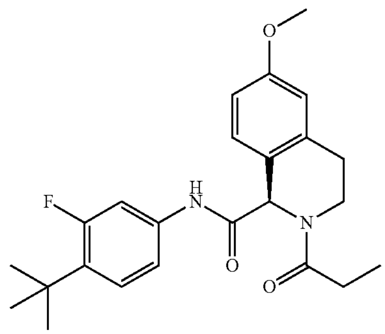 [SMILES: CCC(=O)N1CCc2cc(OC)ccc2[C@@H]1C(=O)Nc1ccc(C(C)(C)C)c(F)c1] | | 411.1 (M − H) |
| 48 | (1R)-N-(4-tert-butyl-3-fluorophenyl)-6-methoxy-2-(3,3,3-trifluoropropanoyl)-1,2,3,4-tetrahydroisoquinoline-1-carboxamide | 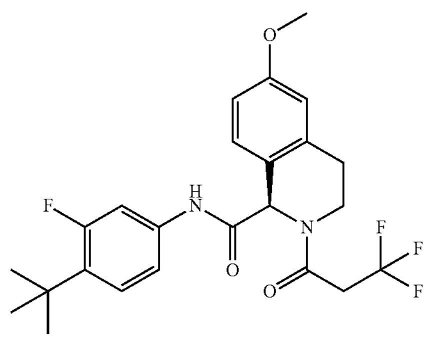 [SMILES: COc1ccc2c(c1)CCN(C(=O)CC(F)(F)F)[C@H]2C(=O)Nc1ccc(C(C)(C)C)c(F)c1] | | 467.1 (M + H) |
| 49 | N-(4-tert-butyl-3-fluorophenyl)-4-((3-hydroxy-1,2-oxazol-5-yl)acetyl)-8-methoxy-2,3,4,5-tetrahydro-1,4-benzoxazepine-5-carboxamide | 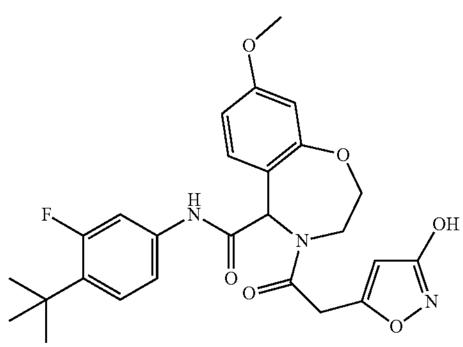 [SMILES: COc1ccc2c(c1)OCCN(C(=O)Cc1cc(O)no1)C2C(=O)Nc1ccc(C(C)(C)C)c(F)c1] | | 498.1 (M + H) |

TABLE 1-5-continued

| EXAMPLE | IUPACNAME | Structure | ADDITIVE | MS |
|---|---|---|---|---|
| 50 | N-(3,5-difluoro-4-(trimethylsilyl)phenyl)-4-((3-hydroxy-1,2-oxazol-5-yl)acetyl)-8-methoxy-2,3,4,5-tetrahydro-1,4-benzoxazepine-5-carboxamide | 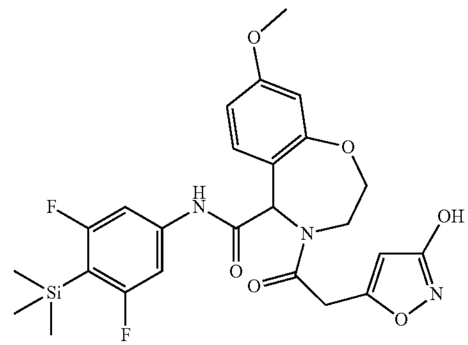 [SMILES: COc1ccc2c(c1)OCCN(C(=O)Cc1cc(O)no1)C2C(=O)Nc1cc(F)c([Si](C)(C)C)c(F)c1] | | 530.0 (M − H) |

TABLE 1-6

| EXAMPLE | IUPACNAME | Structure | ADDITIVE | MS |
|---|---|---|---|---|
| 51 | N-(4-tert-butyl-3-(difluoromethoxy)phenyl)-2-((3-hydroxy-1,2-oxazol-5-yl)acetyl)-6-methoxy-1,2,3,4-tetrahydroisoquinoline-1-carboxamide | 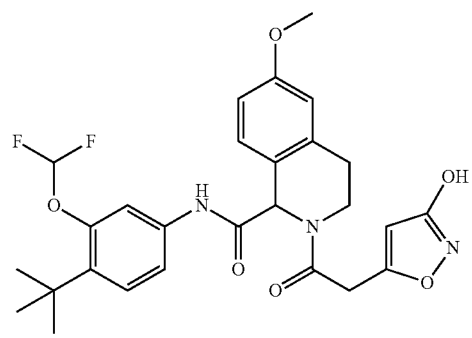 [SMILES: COc1ccc2c(c1)CCN(C(=O)Cc1cc(O)no1)C2C(=O)Nc1ccc(C(C)(C)C)c(OC(F)F)c1] | | 528.0 (M − H) |
| 52 | N-(4-tert-butyl-3-(2,2-difluoroethoxy)phenyl)-2-((3-hydroxy-1,2-oxazol-5-yl)acetyl)-6-methoxy-1,2,3,4-tetrahydroisoquinoline-1-carboxamide | 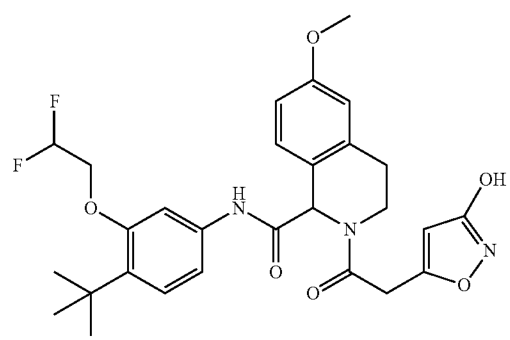 [SMILES: COc1ccc2c(c1)CCN(C(=O)Cc1cc(O)no1)C2C(=O)Nc1ccc(C(C)(C)C)c(OCC(F)F)c1] | | 542.1 (M − H) |
| 53 | N-(4-tert-butyl-3-cyanophenyl)-2-((3-hydroxy-1,2-oxazol-5-yl)acetyl)-6-methoxy-1,2,3,4-tetrahydroisoquinoline-1-carboxamide | 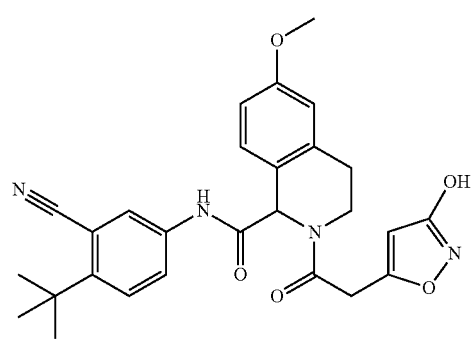 [SMILES: COc1ccc2c(c1)CCN(C(=O)Cc1cc(O)no1)C2C(=O)Nc1ccc(C(C)(C)C)c(C#N)c1] | | 487.1 (M − H) |

TABLE 1-6-continued

| EXAMPLE | IUPACNAME | Structure | ADDITIVE | MS |
|---|---|---|---|---|
| 54 | N-(4-tert-butyl-3-fluorophenyl)-6-ethoxy-2-((3-hydroxy-1,2-oxazol-5-yl)acetyl)-1,2,3,4-tetrahydroisoquinoline-1-carboxamide | 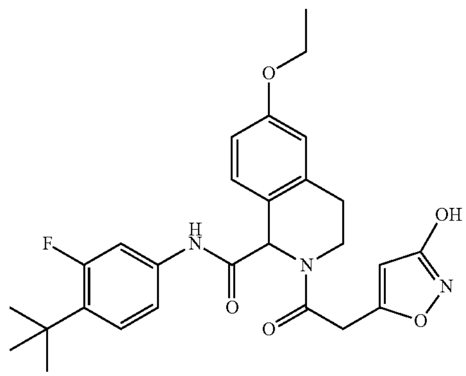 [SMILES: CCOc1ccc2c(c1)CCN(C(=O)Cc1cc(O)no1)C2C(=O)Nc1ccc(C(C)(C)C)c(F)c1] | | 494.1 (M − H) |
| 55 | 6-ethoxy-N-(7-fluoro-1,1-dimethyl-2,3-dihydro-1H-inden-5-yl)-2-((3-hydroxy-1,2-oxazol-5-yl)acetyl)-1,2,3,4-tetrahydroisoquinoline-1-carboxamide | 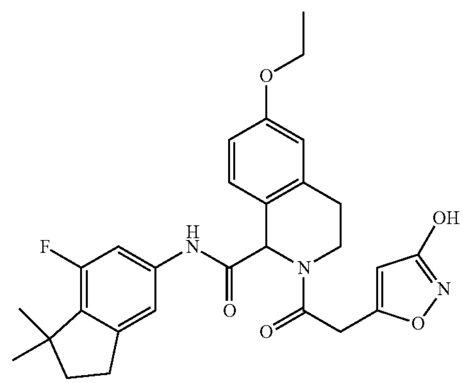 [SMILES: CCOc1ccc2c(c1)CCN(C(=O)Cc1cc(O)no1)C2C(=O)Nc1cc(F)c2c(c1)CCC2(C)C] | | 506.1 (M − H) |
| 56 | (5R)-N-(3,5-difluoro-4-(trimethylsilyl)phenyl)-4-((3-hydroxy-1,2-oxazol-5-yl)acetyl)-8-methoxy-2,3,4,5-tetrahydro-1,4-benzoxazepine-5-carboxamide | 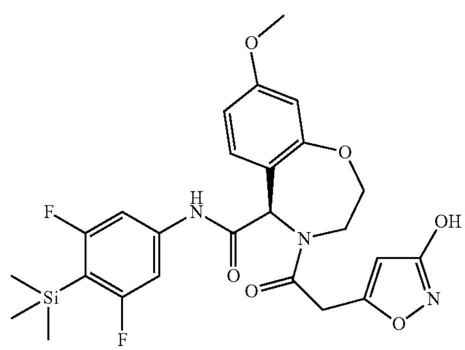 [SMILES: COc1ccc2c(c1)OCCN(C(=O)Cc1cc(O)no1)[C@H]2C(=O)Nc1cc(F)c([Si](C)(C)C)c(F)c1] | | 532.1 (M + H) |
| 57 | (5S)-N-(3,5-difluoro-4-(trimethylsilyl)phenyl)-4-((3-hydroxy-1,2-oxazol-5-yl)acetyl)-8-methoxy-2,3,4,5-tetrahydro-1,4-benzoxazepine-5-carboxamide | 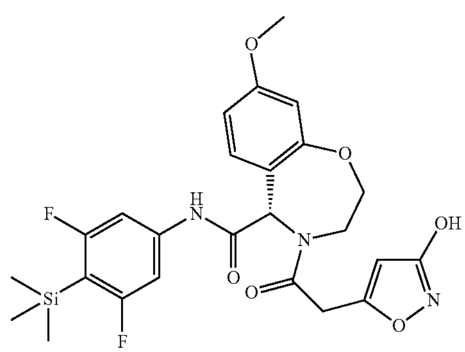 [SMILES: COc1ccc2c(c1)OCCN(C(=O)Cc1cc(O)no1)[C@@H]2C(=O)Nc1cc(F)c([Si](C)(C)C)c(F)c1] | | 532.1 (M + H) |

TABLE 1-6-continued

| EXAMPLE | IUPACNAME | Structure | ADDITIVE | MS |
|---|---|---|---|---|
| 58 | (5R)-N-(4-tert-butyl-3,5-difluorophenyl)-4-((3-hydroxy-1,2-oxazol-5-yl)carbonyl)-8-methoxy-2,3,4,5-tetrahydro-1,4-benzoxazepine-5-carboxamide | 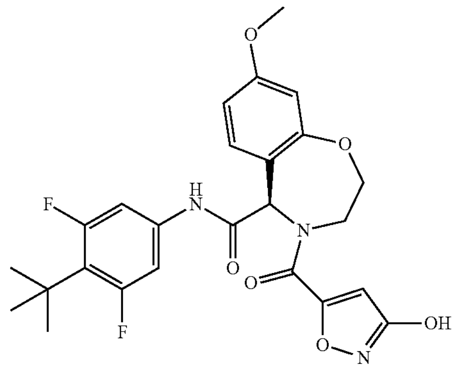 [SMILES: COc1ccc2c(c1)OCCN(C(=O)c1cc(O)no1)[C@H]2C(=O)Nc1cc(F)c(C(C)(C)C)c(F)c1] | | 502.1 (M + H) |
| 59 | (5S)-N-(4-tert-butyl-3,5-difluorophenyl)-4-((3-hydroxy-1,2-oxazol-5-yl)carbonyl)-8-methoxy-2,3,4,5-tetrahydro-1,4-benzoxazepine-5-carboxamide | 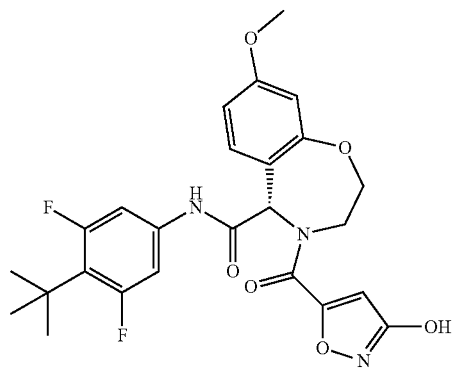 [SMILES: COc1ccc2c(c1)OCCN(C(=O)c1cc(O)no1)[C@@H]2C(=O)Nc1cc(F)c(C(C)(C)C)c(F)c1] | | 502.1 (M + H) |
| 60 | (5R)-N-(4-tert-butyl-3,5-difluorophenyl)-4-((3-hydroxy-1,2-oxazol-5-yl)acetyl)-8-methoxy-2,3,4,5-tetrahydro-1,4-benzoxazepine-5-carboxamide | 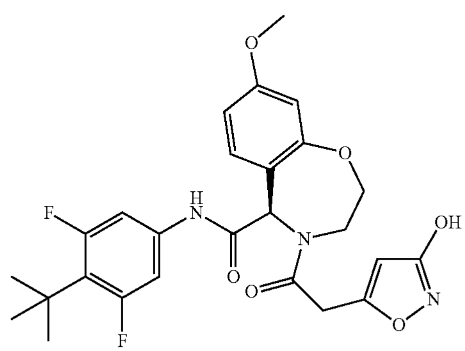 [SMILES: COc1ccc2c(c1)OCCN(C(=O)Cc1cc(O)no1)[C@H]2C(=O)Nc1cc(F)c(C(C)(C)C)c(F)c1] | | 516.2 (M + H) |

TABLE 1-7

| EXAMPLE | IUPACNAME | Structure | ADDITIVE | MS |
|---|---|---|---|---|
| 61 | N-(4-(1-(cyclopropylamino)-2-methyl-1-oxopropan-2-yl)-3-fluorophenyl)-6-methoxy-2-(3,3,3-trifluoropropanoyl)-1,2,3,4-tetrahydroisoquinoline-1-carboxamide | 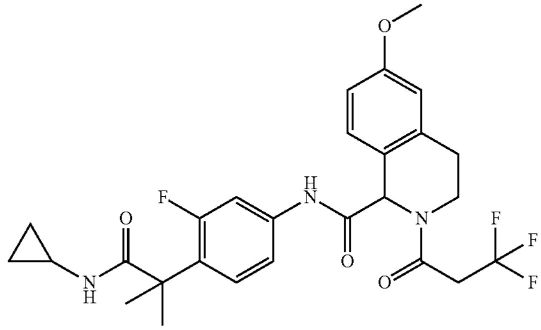 [SMILES: COc1ccc2c(c1)CCN(C(=O)CC(F)(F)F)C2C(=O)Nc1ccc(C(C)(C)C(=O)NC2CC2)c(F)c1] | | 536.2 (M + H) |

TABLE 1-7-continued

| EXAMPLE | IUPACNAME | Structure | ADDITIVE | MS |
|---|---|---|---|---|
| 62 | N-(3-fluoro-4-(2-methyl-1-oxo-1-(pyrrolidin-1-yl)propan-2-yl)phenyl)-6-methoxy-2-(3,3,3-trifluoropropanoyl)-1,2,3,4-tetrahydroisoquinoline-1-carboxamide | 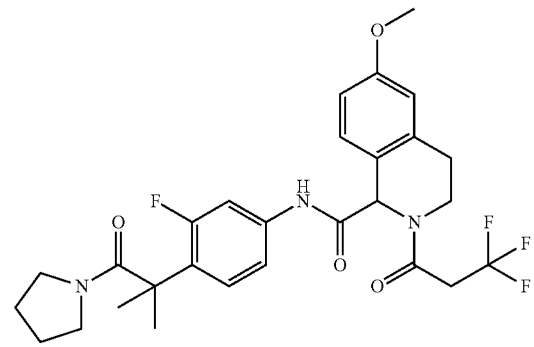 [SMILES: COc1ccc2c(c1)CCN(C(=O)CC(F)(F)F)C2C(=O)Nc1ccc(C(C)(C)C(=O)N2CCCC2)c(F)c1] | | 550.2 (M + H) |
| 63 | (1R)-N-(7-fluoro-1,1-dimethyl-2,3-dihydro-1H-inden-5-yl)-2-(3-(3-hydroxy-1,2-oxazol-5-yl)propanoyl)-6-methoxy-1,2,3,4-tetrahydroisoquinoline-1-carboxamide | 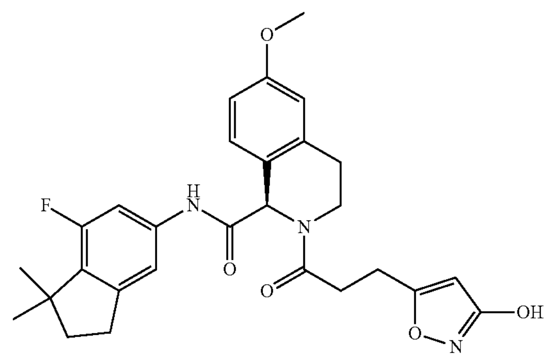 [SMILES: COc1ccc2c(c1)CCN(C(=O)CCc1cc(O)no1)[C@H]2C(=O)Nc1cc(F)c2c(c1)CCC2(C)C] | | 508.2 (M + H) |
| 65 | (1R)-N-(4-tert-butyl-3-cyanophenyl)-2-((3-hydroxy-1,2-oxazol-5-yl)acetyl)-6-methoxy-1,2,3,4-tetrahydroisoquinoline-1-carboxamide | 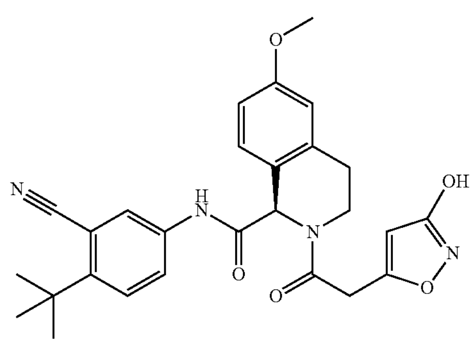 [SMILES: COc1ccc2c(c1)CCN(C(=O)Cc1cc(O)no1)[C@H]2C(=O)Nc1ccc(C(C)(C)C)c(C#N)c1] | | 487.0 (M − H) |
| 66 | (1R)-6-ethoxy-N-(7-fluoro-1,1-dimethyl-2,3-dihydro-1H-inden-5-yl)-2-((3-hydroxy-1,2-oxazol-5-yl)acetyl)-1,2,3,4-tetrahydroisoquinoline-1-carboxamide | 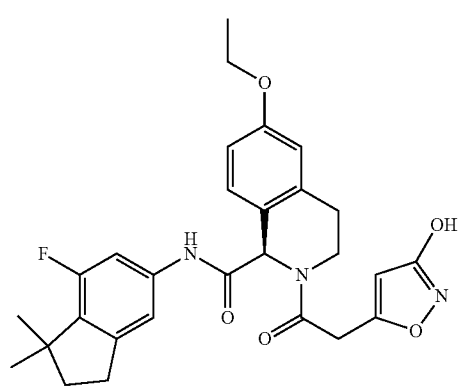 [SMILES: CCOc1ccc2c(c1)CCN(C(=O)Cc1cc(O)no1)[C@H]2C(=O)Nc1cc(F)c2c(c1)CCC2(C)C] | | 508.2 (M + H) |

TABLE 1-7-continued

| EXAMPLE | IUPACNAME | Structure | ADDITIVE | MS |
|---|---|---|---|---|
| 67 | (1R)-N-(4-tert-butyl-3-fluorophenyl)-6-ethoxy-2-((3-hydroxy-1,2-oxazol-5-yl)acetyl)-1,2,3,4-tetrahydroisoquinoline-1-carboxamide | 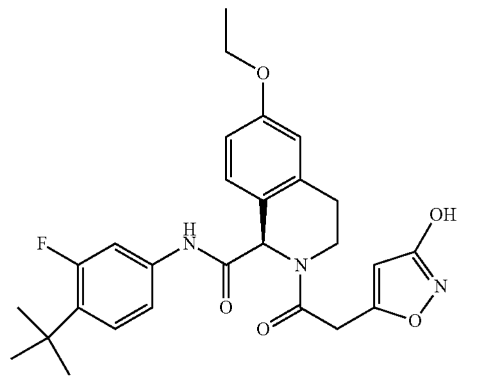 [SMILES: CCOc1ccc2c(c1)CCN(C(=O)Cc1cc(O)no1)[C@H]2C(=O)Nc1ccc(C(C)(C)C)c(F)c1] | | 496.1 (M + H) |
| 68 | (1R)-N-(7-fluoro-1,1-dimethyl-2,3-dihydro-1H-inden-5-yl)-2-((3-hydroxy-1,2-oxazol-5-yl)carbonyl)-6-methoxy-1,2,3,4-tetrahydroisoquinoline-1-carboxamide | 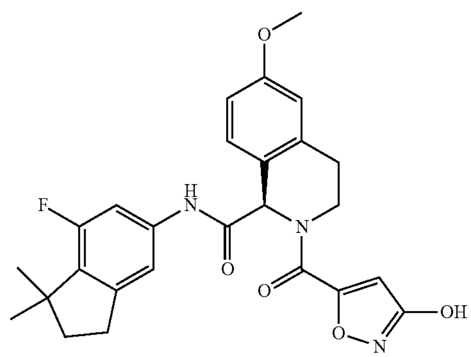 [SMILES: COc1ccc2c(c1)CCN(C(=O)c1cc(O)no1)[C@H]2C(=O)Nc1cc(F)c2c(c1)CCC2(C)C] | | 480.1 (M + H) |
| 69 | (1R)-N-(3-fluoro-4-(1-methoxy-2-methylpropan-2-yl)phenyl)-2-((3-hydroxy-1,2-oxazol-5-yl)carbonyl)-6-methoxy-1,2,3,4-tetrahydroisoquinoline-1-carboxamide | 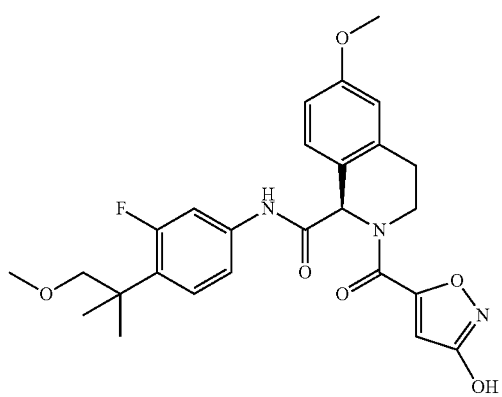 [SMILES: COCC(C)(C)c1ccc(NC(=O)[C@H]2c3ccc(OC)cc3CCN2C(=O)c2cc(O)no2)cc1F] | | 498.0 (M + H) |
| 70 | (1R)-N-(3-fluoro-4-(1-methoxy-2-methylpropan-2-yl)phenyl)-2-((3-hydroxy-1,2-oxazol-5-yl)acetyl)-6-methoxy-1,2,3,4-tetrahydroisoquinoline-1-carboxamide | 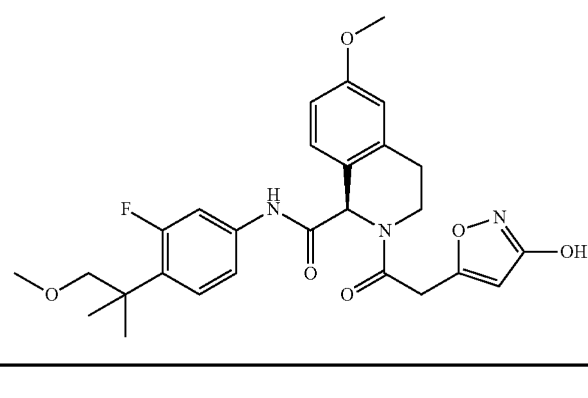 | | 512.1 (M + H) |

TABLE 1-8

| EXAMPLE | IUPACNAME | Structure | ADDITIVE | MS |
|---|---|---|---|---|
| 71 | N-(4-(2,2-dimethylpropyl)-3-fluorophenyl)-2-((3-hydroxy-1,2-oxazol-5-yl)acetyl)-6-methoxy-1,2,3,4-tetrahydroisoquinoline-1-carboxamide | 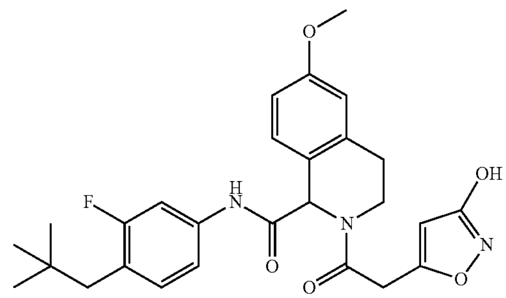 [SMILES: COc1ccc2c(c1)CCN(C(=O)Cc1cc(O)no1)C2C(=O)Nc1ccc(CC(C)(C)C)c(F)c1] | | 496.2 (M + H) |
| 72 | (1R)-N-(3-cyano-4-(trimethylsilyl)phenyl)-2-((3-hydroxy-1,2-oxazol-5-yl)acetyl)-6-methoxy-1,2,3,4-tetrahydroisoquinoline-1-carboxamide | 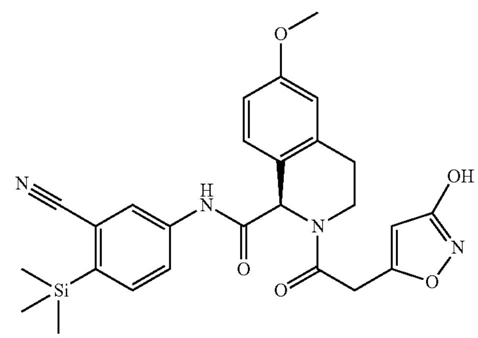 [SMILES: COc1ccc2c(c1)CCN(C(=O)Cc1cc(O)no1)[C@H]2C(=O)Nc1ccc([Si](C)(C)C)c(C#N)c1] | | 505.1 (M + H) |
| 73 | (1R)-N-(3-fluoro-4-(trimethylsilyl)phenyl)-2-((3-hydroxy-1,2-oxazol-5-yl)acetyl)-6-methoxy-1,2,3,4-tetrahydroisoquinoline-1-carboxamide | 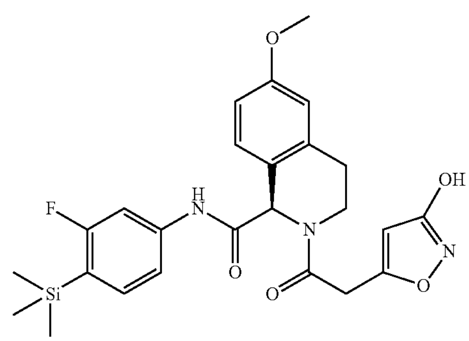 [SMILES: COc1ccc2c(c1)CCN(C(=O)Cc1cc(O)no1)[C@H]2C(=O)Nc1ccc([Si](C)(C)C)c(F)c1] | | 498.1 (M + H) |
| 74 | (1R)-N-(4-fluoro-3,3-dimethyl-2,3-dihydro-1-benzofuran-6-yl)-2-((3-hydroxy-1,2-oxazol-5-yl)acetyl)-6-methoxy-1,2,3,4-tetrahydroisoquinoline-1-carboxamide | 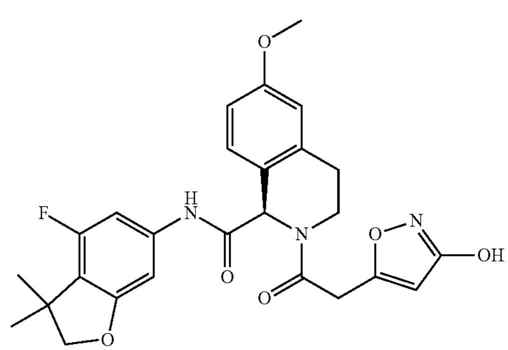 [SMILES: COc1ccc2c(c1)CCN(C(=O)Cc1cc(O)no1)[C@H]2C(=O)Nc1cc(F)c2c(c1)OCC2(C)C] | | 496.1 (M + H) |

| EXAMPLE | IUPACNAME | Structure | ADDITIVE | MS |
|---|---|---|---|---|
| 75 | (1R)-N-(4-(1-(2,2-difluoroethoxy)-2-methylpropan-2-yl)-3-fluorophenyl)-2-((3-hydroxy-1,2-oxazol-5-yl)carbonyl)-6-methoxy-1,2,3,4-tetrahydroisoquinoline-1-carboxamide | 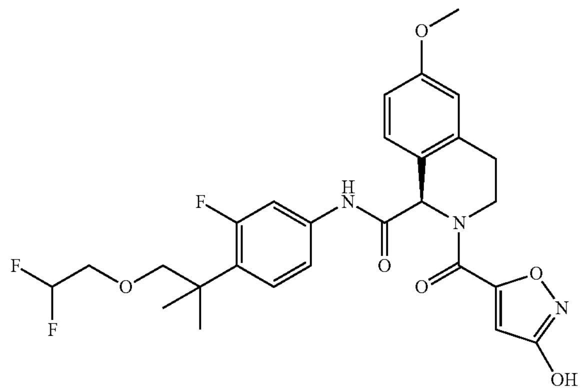 [SMILES: COc1ccc2c(c1)CCN(C(=O)c1cc(O)no1)[C@H]2C(=O)Nc1ccc(C(C)(C)COCC(F)F)c(F)c1] | | 546.0 (M + H) |
| 77 | (5R)-N-(4-tert-butyl-3-fluorophenyl)-6-((3-hydroxy-1,2-oxazol-5-yl)carbonyl)-2-methoxy-5,6,7,8-tetrahydro-1,6-naphthyridine-5-carboxamide | 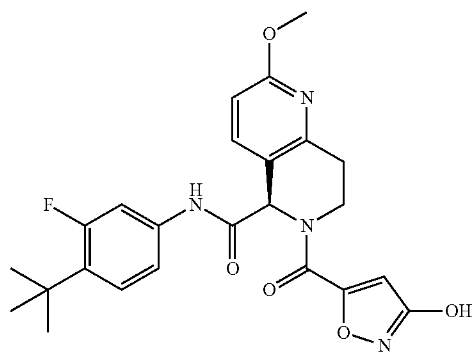 [SMILES: COc1ccc2c(n1)CCN(C(=O)c1cc(O)no1)[C@H]2C(=O)Nc1ccc(C(C)(C)C)c(F)c1] | | 469.1 (M + H) |
| 78 | (5R)-N-(4-tert-butyl-3-fluorophenyl)-6-((3-hydroxy-1,2-oxazol-5-yl)acetyl)-2-methoxy-5,6,7,8-tetrahydro-1,6-naphthyridine-5-carboxamide | 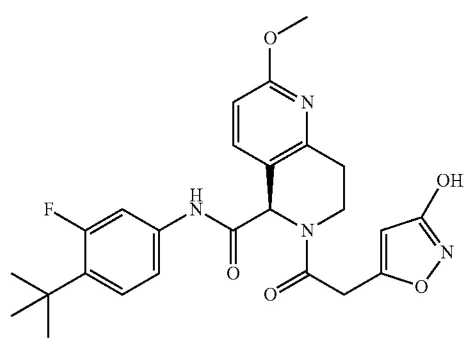 [SMILES: COc1ccc2c(n1)CCN(C(=O)Cc1cc(O)no1)[C@H]2C(=O)Nc1ccc(C(C)(C)C)c(F)c1] | | 483.1 (M + H) |
| 79 | (5R)-N-(3-fluoro-4-(trimethylsilyl)phenyl)-6-((3-hydroxy-1,2-oxazol-5-yl)carbonyl)-2-methoxy-5,6,7,8-tetrahydro-1,6-naphthyridine-5-carboxamide | 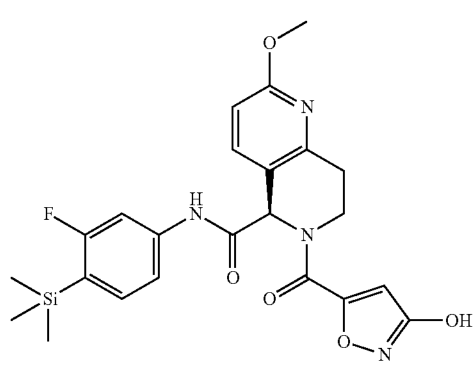 [SMILES: COc1ccc2c(n1)CCN(C(=O)c1cc(O)no1)[C@H]2C(=O)Nc1ccc([Si](C)(C)C)c(F)c1] | | 485.2 (M + H) |

TABLE 1-8-continued

| EXAMPLE | IUPACNAME | Structure | ADDITIVE | MS |
|---|---|---|---|---|
| 80 | (5R)-N-(3-fluoro-4-(trimethylsilyl)phenyl)-6-((3-hydroxy-1,2-oxazol-5-yl)acetyl)-2-methoxy-5,6,7,8-tetrahydro-1,6-naphthyridine-5-carboxamide | 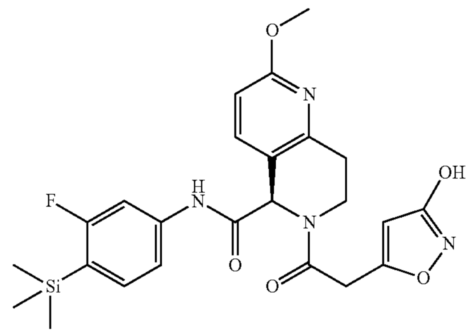 [SMILES: COc1ccc2c(n1)CCN(C(=O)Cc1cc(O)no1)[C@H]2C(=O)Nc1ccc([Si](C)(C)C)c(F)c1] | | 499.1 (M + H) |

TABLE 1-9

| EXAMPLE | IUPACNAME | Structure | ADDITIVE | MS |
|---|---|---|---|---|
| 81 | (1R)-N-(4-fluoro-3,3-dimethyl-2,3-dihydro-1-benzofuran-6-yl)-2-((3-hydroxy-1,2-oxazol-5-yl)carbonyl)-6-methoxy-1,2,3,4-tetrahydroisoquinoline-1-carboxamide | 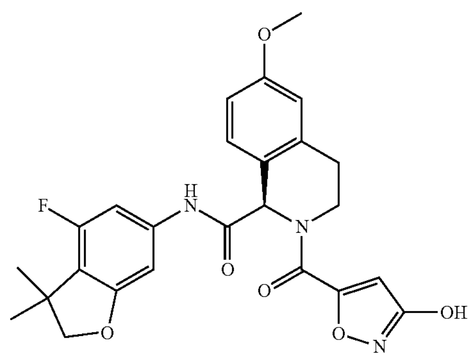 [SMILES: COc1ccc2c(c1)CCN(C(=O)c1cc(O)no1)[C@H]2C(=O)Nc1cc(F)c2c(c1)OCC2(C)C] | | 480.0 (M − H) |
| 82 | 5-((1R)-1-((3,5-difluoro-4-(trimethylsilyl)phenyl)carbamoyl)-6-methoxy-3,4-dihydroisoquinolin-2(1H)-yl)-5-oxopentanoic acid | 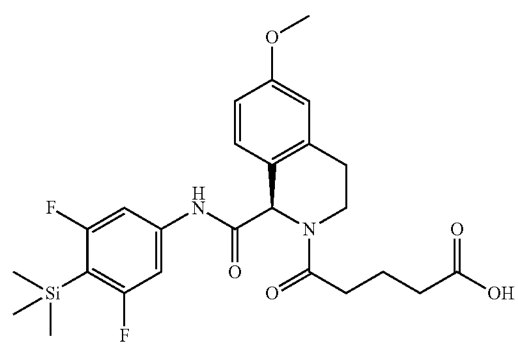 [SMILES: COc1ccc2c(c1)CCN(C(=O)CCCC(=O)O)[C@H]2C(=O)Nc1cc(F)c([Si](C)(C)C)c(F)c1] | | 503.0 (M − H) |
| 83 | 4-((1R)-1-((3,5-difluoro-4-(trimethylsilyl)phenyl)carbamoyl)-6-methoxy-3,4-dihydroisoquinolin-2(1H)-yl)-4-oxobutanoic acid | 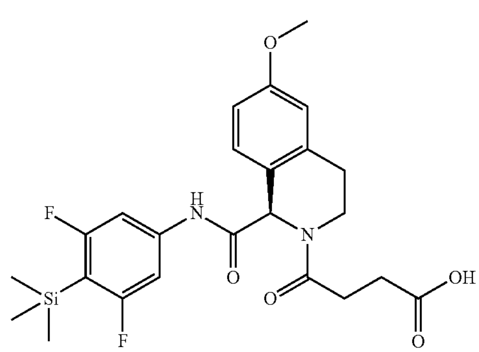 [SMILES: COc1ccc2c(c1)CCN(C(=O)CCC(=O)O)[C@H]2C(=O)Nc1cc(F)c([Si](C)(C)C)c(F)c1] | | 489.1 (M − H) |

TABLE 1-9-continued

| EXAMPLE | IUPACNAME | Structure | ADDITIVE | MS |
|---|---|---|---|---|
| 84 | (1R)-N-(4-tert-butyl-3,5-difluorophenyl)-2-(cyanoacetyl)-6-methoxy-1,2,3,4-tetrahydroisoquinoline-1-carboxamide | 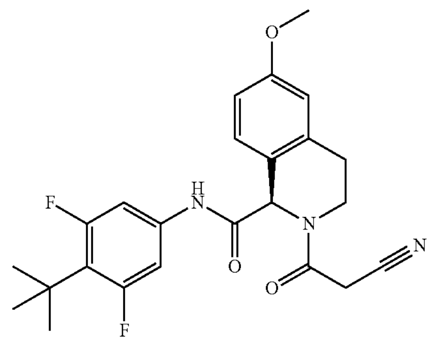 [SMILES: COc1ccc2c(c1)CCN(C(=O)CC#N)[C@H]2C(=O)Nc1cc(F)c(C(C)(C)C)c(F)c1] | | 440.0 (M − H) |
| 85 | (1R)-N-(3,5-difluoro-4-(trimethylsilyl)phenyl)-2-((3-hydroxy-1,2-oxazol-5-yl)acetyl)-6-methoxy-1,2,3,4-tetrahydroisoquinoline-1-carboxamide | 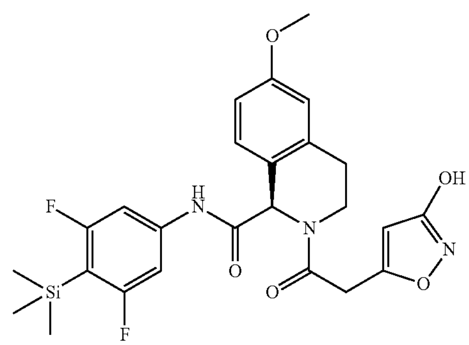 [SMILES: COc1ccc2c(c1)CCN(C(=O)Cc1cc(O)no1)[C@H]2C(=O)Nc1cc(F)c([Si](C)(C)C)c(F)c1] | | 516.1 (M + H) |
| 86 | 5-((1R)-1-((4-(ethyl(dimethyl)silyl)-3,5-difluorophenyl)carbamoyl)-6-methoxy-3,4-dihydroisoquinolin-2(1H)-yl)-5-oxopentanoic acid | 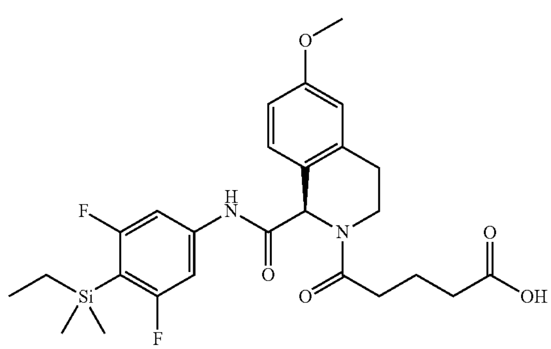 [SMILES: CC[Si](C)(C)c1c(F)cc(NC(=O)[C@H]2c3ccc(OC)cc3CCN2C(=O)CCCC(=O)O)cc1F] | | 519.1 (M + H) |
| 87 | 4-((1R)-1-((4-(ethyl(dimethyl)silyl)-3,5-difluorophenyl)carbamoyl)-6-methoxy-3,4-dihydroisoquinolin-2(1H)-yl)-4-oxobutanoic acid | 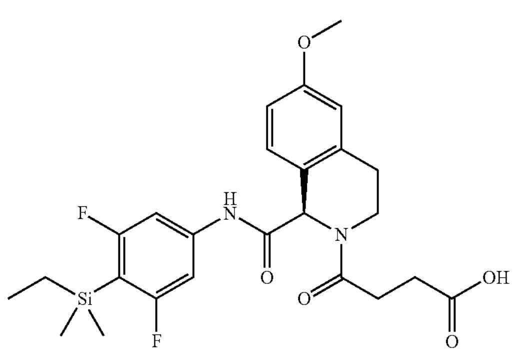 [SMILES: CC[Si](C)(C)c1c(F)cc(NC(=O)[C@H]2c3ccc(OC)cc3CCN2C(=O)CCC(=O)O)cc1F] | | 503.0 (M − H) |

TABLE 1-9-continued

| EXAMPLE | IUPACNAME | Structure | ADDITIVE | MS |
|---|---|---|---|---|
| 88 | (1R)-N-(4-(ethyl(dimethyl)silyl)-3,5-difluorophenyl)-2-((3-hydroxy-1,2-oxazol-5-yl)acetyl)-6-methoxy-1,2,3,4-tetrahydroisoquinoline-1-carboxamide | 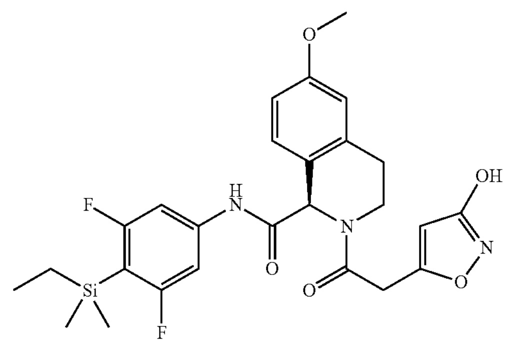 [SMILES: CC[Si](C)(C)c1c(F)cc(NC(=O)[C@H]2c3ccc(OC)cc3CCN2C(=O)Cc2cc(O)no2)cc1F] | | 530.1 (M + H) |
| 89 | (1R)-N-(3,5-difluoro-4-(2-methyl-1-oxo-1-(pyrrolidin-1-yl)propan-2-yl)phenyl)-2-((3-hydroxy-1,2-oxazol-5-yl)carbonyl)-6-methoxy-1,2,3,4-tetrahydroisoquinoline-1-carboxamide | 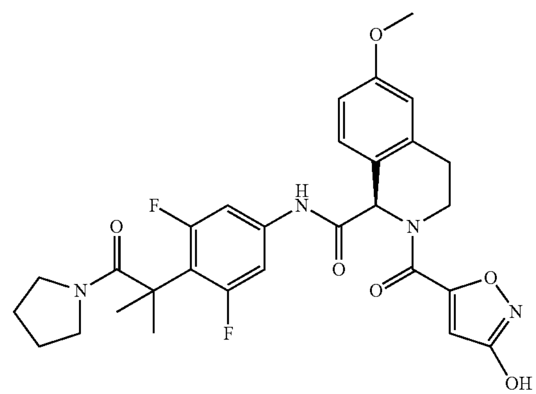 [SMILES: COc1ccc2c(c1)CCN(C(=O)c1cc(O)no1)[C@H]2C(=O)Nc1cc(F)c(C(C)(C)C(=O)N2CCCC2)c(F)c1] | | 569.1 (M + H) |
| 90 | (1R)-N-(3,5-difluoro-4-(2-methyl-1-oxo-1-(pyrrolidin-1-yl)propan-2-yl)phenyl)-2-((3-hydroxy-1,2-oxazol-5-yl)acetyl)-6-methoxy-1,2,3,4-tetrahydroisoquinoline-1-carboxamide | 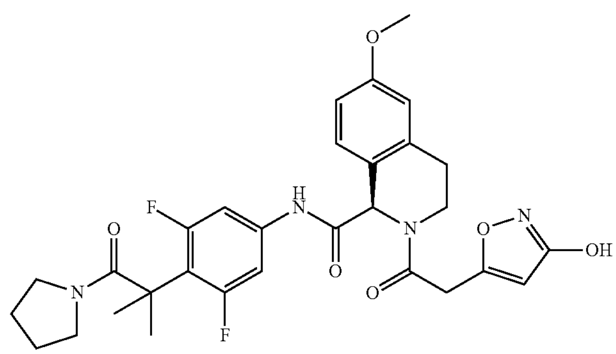 [SMILES: COc1ccc2c(c1)CCN(C(=O)Cc1cc(O)no1)[C@H]2C(=O)Nc1cc(F)c(C(C)(C)C(=O)N2CCCC2)c(F)c1] | | 583.2 (M + H) |

TABLE 1-10

| EXAMPLE | IUPACNAME | Structure | ADDITIVE | MS |
|---|---|---|---|---|
| 91 | ((1R)-1-((4-tert-butyl-3,5-difluorophenyl)carbamoyl)-6-methoxy-3,4-dihydroisoquinolin-2(1H)-yl)(oxo)acetic acid | 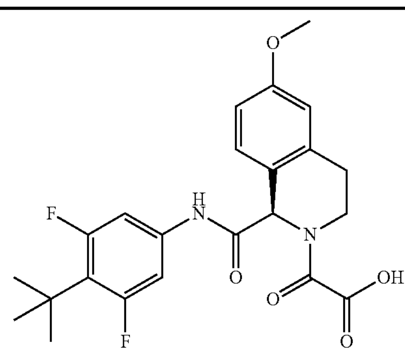 | | 445.1 (M − H) |

TABLE 1-10-continued

| EXAMPLE | IUPACNAME | Structure | ADDITIVE | MS |
|---|---|---|---|---|
| 92 | 6-((1R)-1-((3,5-difluoro-4-(trimethylsilyl)phenyl)carbamoyl)-6-methoxy-3,4-dihydroisoquinolin-2(1H)-yl)-6-oxohexanoic acid | 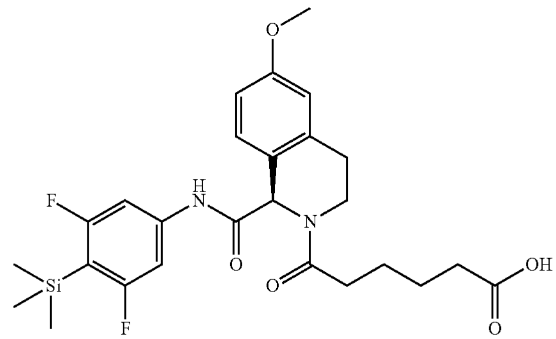 [SMILES: COc1ccc2c(c1)CCN(C(=O)CCCCC(=O)O)[C@H]2C(=O)Nc1cc(F)c([Si](C)(C)C)c(F)c1] | | 519.2 (M + H) |
| 93 | (2-((1R)-1-((3,5-difluoro-4-(trimethylsilyl)phenyl)carbamoyl)-6-methoxy-3,4-dihydroisoquinolin-2(1H)-yl)-2-oxoethoxy)acetic acid | 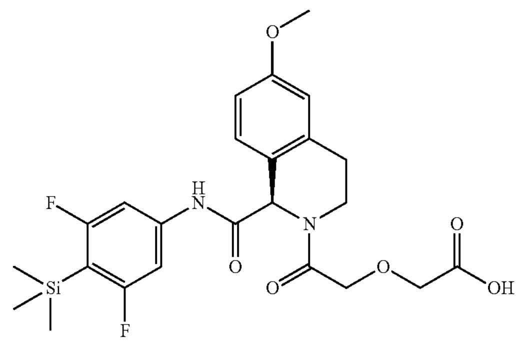 [SMILES: COc1ccc2c(c1)CCN(C(=O)COCC(=O)O)[C@H]2C(=O)Nc1cc(F)c([Si](C)(C)C)c(F)c1] | | 505.0 (M − H) |
| 94 | 5-((1R)-1-((3,5-difluoro-4-(trimethylsilyl)phenyl)carbamoyl)-6-methoxy-3,4-dihydroisoquinolin-2(1H)-yl)-3-methyl-5-oxopentanoic acid | 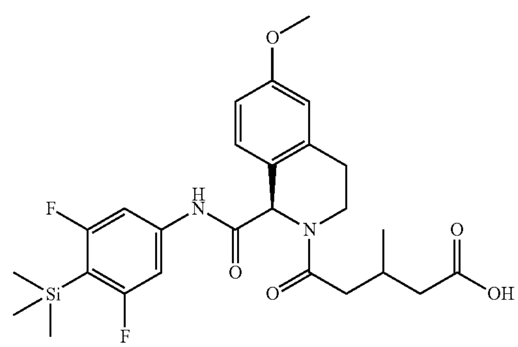 [SMILES: COc1ccc2c(c1)CCN(C(=O)CC(C)CC(=O)O)[C@H]2C(=O)Nc1cc(F)c([Si](C)(C)C)c(F)c1] | | 517.1 (M − H) |
| 95 | 5-((1R)-1-((3,5-difluoro-4-(trimethylsilyl)phenyl)carbamoyl)-6-methoxy-3,4-dihydroisoquinolin-2(1H)-yl)-3,3-dimethyl-5-oxopentanoic acid | 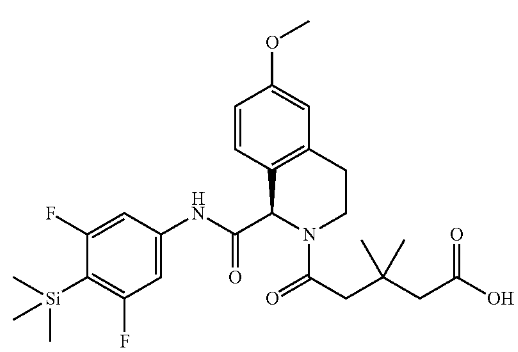 [SMILES: COc1ccc2c(c1)CCN(C(=O)CC(C)(C)CC(=O)O)[C@H]2C(=O)Nc1cc(F)c([Si](C)(C)C)c(F)c1] | | 531.0 (M − H) |

TABLE 1-10-continued

| EXAMPLE | IUPACNAME | Structure | ADDITIVE | MS |
|---|---|---|---|---|
| 96 | (1R)-2-(amino(oxo)acetyl)-N-(4-tert-butyl-3,5-difluorophenyl)-6-methoxy-1,2,3,4-tetrahydroisoquinoline-1-carboxamide | 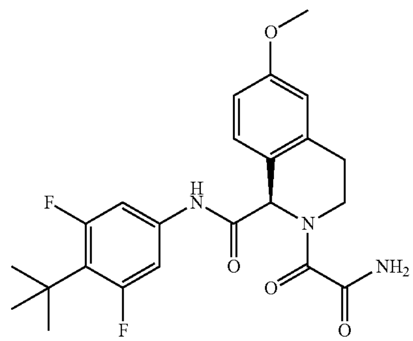 [SMILES: COc1ccc2c(c1)CCN(C(=O)C(N)=O)[C@H]2C(=O)Nc1cc(F)c(C(C)(C)C)c(F)c1] | | 446.0 (M + H) |
| 97 | (1R)-N-(3,5-difluoro-4-(1-methoxy-2-methylpropan-2-yl)phenyl)-2-((3-hydroxy-1,2-oxazol-5-yl)carbonyl)-6-methoxy-1,2,3,4-tetrahydroisoquinoline-1-carboxamide | 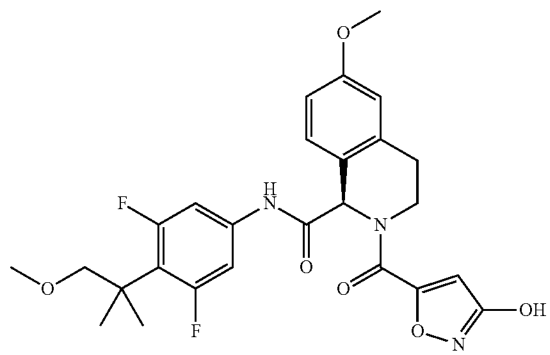 [SMILES: COCC(C)(C)c1c(F)cc(NC(=O)[C@H]2c3ccc(OC)cc3CCN2C(=O)c2cc(O)no2)cc1F] | | 514.0 (M − H) |
| 98 | (1R)-N-(3,5-difluoro-4-(1-methoxy-2-methylpropan-2-yl)phenyl)-2-((3-hydroxy-1,2-oxazol-5-yl)acetyl)-6-methoxy-1,2,3,4-tetrahydroisoquinoline-1-carboxamide | 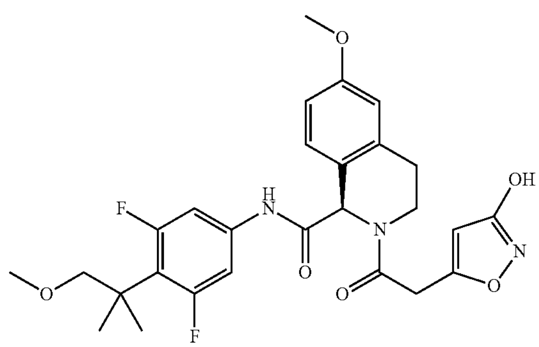 [SMILES: COCC(C)(C)c1c(F)cc(NC(=O)[C@H]2c3ccc(OC)cc3CCN2C(=O)Cc2cc(O)no2)cc1F] | | 530.1 (M + H) |
| 99 | N-(3-fluoro-4-(2-methyl-1-oxo-1-(pyrrolidin-1-yl)propan-2-yl)phenyl)-2-((3-hydroxy-1,2-oxazol-5-yl)carbonyl)-6-methoxy-1,2,3,4-tetrahydroisoquinoline-1-carboxamide | 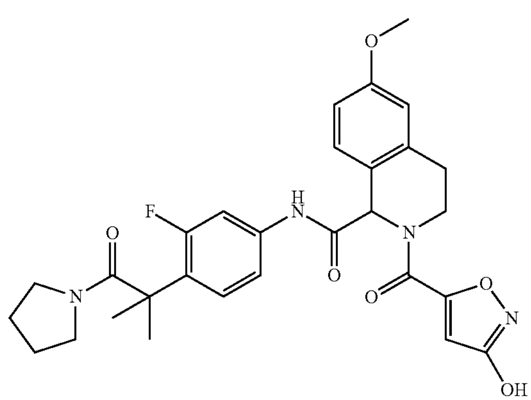 [SMILES: COc1ccc2c(c1)CCN(C(=O)c1cc(O)no1)C2C(=O)Nc1ccc(C(C)(C)C(=O)N2CCCC2)c(F)c1] | | 551.2 (M + H) |

TABLE 1-10-continued

| EXAMPLE | IUPACNAME | Structure | ADDITIVE | MS |
|---|---|---|---|---|
| 100 | (1R)-N-(6-(1-(2,2-difluoroethoxy)-2-methylpropan-2-yl)-5-fluoropyridin-3-yl)-6-methoxy-2-(3,3,3-trifluoropropanoyl)-1,2,3,4-tetrahydroisoquinoline-1-carboxamide | 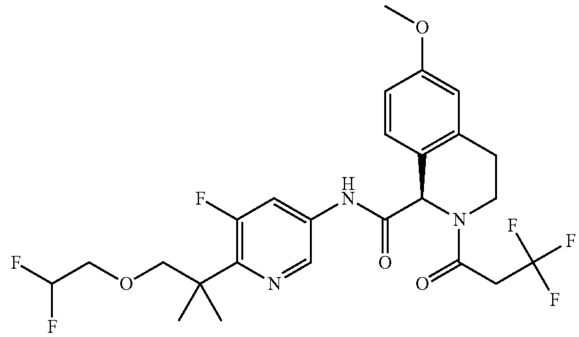 [SMILES: COc1ccc2c(c1)CCN(C(=O)CC(F)(F)F)[C@H]2C(=O)Nc1cnc(C(C)(C)COCC(F)F)c(F)c1] | | 548.1 (M + H) |

TABLE 1-11

| EXAMPLE | IUPACNAME | Structure | ADDITIVE | MS |
|---|---|---|---|---|
| 110 | (1R)-N-(3-fluoro-4-(trimethylsilyl)phenyl)-2-((3-hydroxy-1,2-oxazol-5-yl)acetyl)-6-(methoxymethyl)-1,2,3,4-tetrahydroisoquinoline-1-carboxamide | 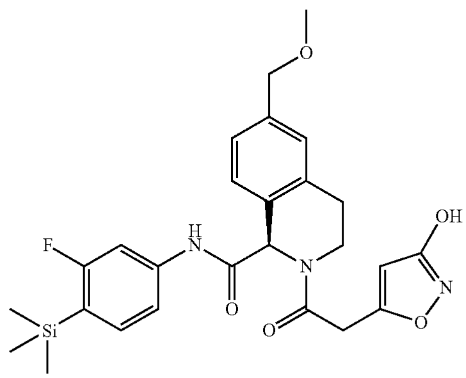 [SMILES: COCc1ccc2c(c1)CCN(C(=O)Cc1cc(O)no1)[C@H]2C(=O)Nc1ccc([Si](C)(C)C)c(F)c1] | | 512.1 (M + H) |

Example 102

(1R)-N-(6-(1-(2,2-difluoroethoxy)-2-methylpropan-2-yl)-5-fluoropyridin-3-yl)-2-((3-hydroxy-1,2-oxazol-5-yl)acetyl)-6-methoxy-1,2,3,4-tetrahydroisoquinoline-1-carboxamide The title compound was synthesized using 6-(1-(2,2-difluoroethoxy)-2-methylpropan-2-yl)-5-fluoropyridin-3-amine and 2-(3-hydroxyisoxazol-5-yl)acetic acid, by the reaction and purification in the same manner as in Example 65.

$^1$H NMR (300 MHz, DMSO-d$_6$): δ 1.30 (6H, s), 2.84 (1H, d, J=17.0 Hz), 3.10 (1H, brs), 3.62 (3H, td, J=15.1,3.8 Hz), 3.73 (5H, s), 3.86-4.15 (3H, m), 5.68 (1H, s), 5.79-6.28 (1H, m), 5.91 (1H, s), 6.78-6.88 (2H, m), 7.49 (1H, d, J=9.8 Hz), 7.87 (1H, d, J=14.7 Hz), 8.45 (1H, s), 10.84 (1H, s), 11.10 (1H, s).

Example 103

(1R)-2-(cyanoacetyl)-N-(3,5-difluoro-4-(2-methyl-1-oxo-1-(pyrrolidin-1-yl)propan-2-yl)phenyl)-6-methoxy-1,2,3,4-tetrahydroisoquinoline-1-carboxamide (Step 1)

8M aqueous sodium hydroxide solution (10 mL, 80.00 mmol) was added to a mixture of methyl 2-(2,6-difluoro-4-nitrophenyl)-2-methylpropanoate (2 g, 7.72 mmol) in ethanol (30 mL) at room temperature, and the mixture was stirred for 3 hr. The pH of the mixture was adjusted to 4 with 1N hydrochloric acid at room temperature, ethyl acetate was added thereto, and the organic layer was separated. The organic layer was washed with brine, and dried over magnesium sulfate, and the solvent was evaporated under reduced pressure to give 2-(2,6-difluoro-4-nitrophenyl)-2-methylpropanoic acid (1.650 g, 6.73 mmol, 87%) as a pale yellow solid.

$^1$H NMR (300 MHz, DMSO-d$_6$): δ 1.58 (6H, t, J=1.9 Hz), 7.88-8.17 (2H, m), 12.80 (1H, brs) (The peak derived from COOH was not observed)

(Step 2)

HATU (3.07 g, 8.08 mmol) was added to a solution of DIEA (2.351 mL, 13.46 mmol), pyrrolidine (0.674 mL, 8.08 mmol) and 2-(2,6-difluoro-4-nitrophenyl)-2-methylpropanoic acid (1.65 g, 6.73 mmol) in DMF (10 mL) at room temperature, and the mixture was stirred at room temperature. To the reaction mixture was added saturated aqueous sodium hydrogen carbonate, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→70% ethyl acetate/hexane) to give 2-(2,6-difluoro-4-nitrophenyl)-2-methyl-1-(pyrrolidin-1-yl)propan-1-one (1.940 g, 6.50 mmol, 97%) as a yellow oil.

¹H NMR (300 MHz, DMSO-d₆): δ 1.56 (6H, t, J=2.1 Hz), 1.61-1.74 (4H, m), 2.76 (2H, brs), 3.33 (2H, brs), 7.78-8.25 (2H, m).

(Step 3)

A solution of 2-(2,6-difluoro-4-nitrophenyl)-2-methyl-1-(pyrrolidin-1-yl)propan-1-one (1.94 g, 6.50 mmol) and 10% palladium-carbon (200 mg, 1.88 mmol, 50% wet) in MeOH (30 mL) was stirred overnight under hydrogen atmosphere (1 atm) at room temperature. The catalyst was removed by filtration, and the filtrate was concentrated under reduced pressure to give 2-(4-amino-2,6-difluorophenyl)-2-methyl-1-(pyrrolidin-1-yl)propan-1-one (1650 mg, 6.15 mmol, 95%) as a yellow oil.

¹H NMR (300 MHz, DMSO-d₆): δ 1.42 (6H, s), 1.65 (4H, brs), 2.86 (2H, brs), 3.29 (2H, brs), 5.61 (2H, s), 6.03-6.22 (2H, m)

(Step 4)

T3P (5.49 mL, 9.22 mmol) was added to a solution of 2-(tert-butoxycarbonyl)-6-methoxy-1,2,3,4-tetrahydroisoquinoline-1-carboxylic acid (1.89 g, 6.15 mmol), 2-(4-amino-2,6-difluorophenyl)-2-methyl-1-(pyrrolidin-1-yl)propan-1-one (1.65 g, 6.15 mmol), DIEA (5.37 mL, 30.75 mmol) and DMAP (0.826 g, 6.76 mmol) in ethyl acetate (100 mL) at room temperature, and the mixture was stirred at 70° C. for 15 hr. To the reaction mixture was added water (350 mL), and the mixture was extracted twice with ethyl acetate. The organic layer was washed with aqueous sodium hydrogen carbonate solution and brine, and dried over magnesium sulfate, and the solvent was evaporated under reduced pressure. The obtained residue was purified by silica gel column chromatography (solvent gradient; 50→100% ethyl acetate/hexane) to give crude tert-butyl 1-((3,5-difluoro-4-(2-methyl-1-oxo-1-(pyrrolidin-1-yl)propan-2-yl)phenyl)carbamoyl)-6-methoxy-3,4-dihydroisoquinoline-2(1H)-carboxylate (3.16 g, 5.67 mmol, 92%) as a yellow oil.

¹H NMR (300 MHz, DMSO-d₆): δ 1.21-1.70 (19H, m), 2.75 (3H, dd, J=10.8,4.3 Hz), 3.08 (1H, d, J=10.6 Hz), 3.22-3.50 (3H, m), 3.73 (3H, s), 3.97 (1H, brs), 5.21-5.45 (1H, m), 6.75-6.90 (2H, m), 7.27 (2H, d, J=12.1 Hz), 7.45 (1H, d, J=7.9 Hz), 10.33-10.88 (1H, m).

(Step 5)

The crude tert-butyl 1-((3,5-difluoro-4-(2-methyl-1-oxo-1-(pyrrolidin-1-yl)propan-2-yl)phenyl)carbamoyl)-6-methoxy-3,4-dihydroisoquinoline-2(1H)-carboxylate (0.98 g) was resolved by chiral column chromatography. The fraction having a shorter retention time was concentrated to give tert-butyl (R)-1-((3,5-difluoro-4-(2-methyl-1-oxo-1-(pyrrolidin-1-yl)propan-2-yl)phenyl)carbamoyl)-6-methoxy-3,4-dihydroisoquinoline-2(1H)-carboxylate (450 mg, >99% ee), and the fraction having a longer retention time was concentrated to give tert-butyl (S)-1-((3,5-difluoro-4-(2-methyl-1-oxo-1-(pyrrolidin-1-yl)propan-2-yl)phenyl)carbamoyl)-6-methoxy-3,4-dihydroisoquinoline-2(1H)-carboxylate (460 mg, >99% ee).

purification condition by chiral column chromatography
    column: CHIRALCEL OD (NL001) 50 mmID×500 mmL
    solvent: hexane/EtOH=850/150
    flow rate: 80 mL/min
    temperature: 30° C.
    detection method: UV 220 nm (Step 6)

4N Hydrogen chloride/ethyl acetate (5 mL, 20.00 mmol) was added to tert-butyl (R)-1-((3,5-difluoro-4-(2-methyl-1-oxo-1-(pyrrolidin-1-yl)propan-2-yl)phenyl) carbamoyl)-6-methoxy-3,4-dihydroisoquinoline-2(1H)-carboxylate (450 mg, 0.81 mmol), and the mixture was stirred at room temperature for 3 hr. The reaction mixture was concentrated under reduced pressure to give (R)-N-(3,5-difluoro-4-(2-methyl-1-oxo-1-(pyrrolidin-1-yl)propan-2-yl)phenyl)-6-methoxy-1,2,3,4-tetrahydroisoquinoline-1-carboxamide hydrochloride (380 mg, 0.769 mmol, 95%) as a white solid.

MS(API): Calculated 493.7. Found 456.2 (M−HCl-H.)

(Step 7)

HATU (41.6 mg, 0.11 mmol) was added to a solution of DIEA (0.048 mL, 0.27 mmol), 2-cyanoacetic acid (9.30 mg, 0.11 mmol) and (R)-N-(3,5-difluoro-4-(2-methyl-1-oxo-1-(pyrrolidin-1-yl)propan-2-yl)phenyl)-6-methoxy-1,2,3,4-tetrahydroisoquinoline-1-carboxamide hydrochloride (45 mg, 0.09 mmol) in DMF (2 mL) at room temperature, and the mixture was stirred overnight at room temperature. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→20% MeOH/ethyl acetate) to give the title compound (19.00 mg, 0.036 mmol, 39.8%) as a white solid.

¹H NMR (300 MHz, DMSO-d₆): δ 1.47 (6H, s), 1.64 (4H, brs), 2.69-2.92 (3H, m), 3.02-3.18 (1H, m), 3.37-3.50 (3H, m), 3.73 (3H, s), 3.89-4.03 (1H, m), 4.08-4.42 (2H, m), 5.61 (1H, s), 6.77-6.91 (2H, m), 7.25 (2H, d, J=12.1 Hz), 7.40-7.54 (1H, m), 10.77 (1H, s).

Example 104

(1R)-N-(3,5-difluoro-4-(2-methyl-1-oxo-1-(pyrrolidin-1-yl)propan-2-yl)phenyl)-6-methoxy-2-(3,3,3-trifluoropropanoyl)-1,2,3,4-tetrahydroisoquinoline-1-carboxamide HATU (41.6 mg, 0.11 mmol) was added to a solution of DIEA (0.048 mL, 0.27 mmol), 3,3,3-trifluoropropanoic acid (14.00 mg, 0.11 mmol) and (R)-N-(3,5-difluoro-4-(2-methyl-1-oxo-1-(pyrrolidin-1-yl)propan-2-yl)phenyl)-6-methoxy-1,2,3,4-tetrahydroisoquinoline-1-carboxamide hydrochloride (45 mg, 0.09 mmol) in DMF (2 mL) at room temperature, and the mixture was stirred overnight at room temperature. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→80% ethyl acetate/hexane) to give the title compound (30.0 mg, 0.053 mmol, 58.0%) as a white solid.

¹H NMR (300 MHz, DMSO-d₆): δ 1.47 (6H, s), 1.64 (4H, brs), 2.67-2.94 (3H, m), 3.05-3.20 (1H, m), 3.23-3.30 (2H, m), 3.39-3.56 (1H, m), 3.73 (3H, s), 3.76-3.86 (1H, m), 3.87-3.98 (1H, m), 3.98-4.14 (1H, m), 5.62 (1H, s), 6.80-6.80-6.89 (2H, m), 7.25 (2H, d, J=12.1 Hz), 7.48 (1H, d, J=9.1 Hz), 10.78 (1H, s).

Example 105

(1R)-N-(3,5-difluoro-4-(2-methyl-1-oxo-1-(pyrrolidin-1-yl)propan-2-yl)phenyl)-6-methoxy-2-(pyridin-3-ylacetyl)-1,2,3,4-tetrahydroisoquinoline-1-carboxamide HATU (41.6 mg, 0.11 mmol) was added to a solution of DIEA (0.048 mL, 0.27 mmol), 2-(pyridin-3-yl)acetic acid hydrochloride (18.98 mg, 0.11 mmol) and (R)-N-(3,5-difluoro-4-(2-methyl-1-oxo-1-(pyrrolidin-1-yl)propan-2-yl) phenyl)-6-methoxy-1,2,3,4-tetrahydroisoquinoline-1-carboxamide hydrochloride (45 mg, 0.09 mmol) in DMF (2 mL) at room temperature, and the mixture was stirred overnight at room temperature. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→25% MeOH/ethyl acetate) to give the title compound (33.0 mg, 0.057 mmol, 62.8%) as a white solid.

$^1$H NMR (300 MHz, DMSO-$d_6$): δ 1.46 (6H, s), 1.63 (4H, brs), 2.67-2.90 (3H, m), 3.15 (1H, s), 3.22-3.30 (2H, m), 3.59 (1H, brs), 3.73 (3H, s), 3.80-4.03 (2H, m), 4.08-4.21 (1H, m), 5.62 (1H, s), 6.79-6.88 (2H, m), 7.24 (2H, d, J=12.1 Hz), 7.33 (1H, dd, J=7.9,4.9 Hz), 7.47 (1H, d, J=9.1 Hz), 7.63 (1H, d, J=7.6 Hz), 8.33-8.54 (2H, m), 10.73 (1H, s).

Example 106

(1R)-N-(3,5-difluoro-4-(2-methyl-1-oxo-1-(pyrrolidin-1-yl)propan-2-yl)phenyl)-6-methoxy-2-((5-methyl-1,3,4-oxadiazol-2-yl)acetyl)-1,2,3,4-tetrahydroisoquinoline-1-carboxamide HATU (41.6 mg, 0.11 mmol) was added to a solution of DIEA (0.048 mL, 0.27 mmol), lithium 2-(5-methyl-1,3,4-oxadiazol-2-yl)acetate (16.18 mg, 0.11 mmol) and (R)-N-(3,5-difluoro-4-(2-methyl-1-oxo-1-(pyrrolidin-1-yl)propan-2-yl)phenyl)-6-methoxy-1,2,3,4-tetrahydroisoquinoline-1-carboxamide hydrochloride (45 mg, 0.09 mmol) in DMF (2 mL) at room temperature, and the mixture was stirred overnight at room temperature. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→15% MeOH/ethyl acetate) to give the title compound (28.0 mg, 0.048 mmol, 52.8%) as a white solid.

$^1$H NMR (300 MHz, DMSO-$d_6$): δ 1.47 (6H, s), 1.63 (4H, brs), 2.47 (3H, s), 2.70-2.95 (3H, m), 3.07-3.23 (1H, m), 3.24-3.30 (2H, m), 3.46-3.65 (1H, m), 3.74 (3H, s), 4.05-4.19 (1H, m), 4.22-4.48 (2H, m), 5.58 (1H, s), 6.79-6.92 (2H, m), 7.24 (2H, d, J=12.1 Hz), 7.48 (1H, d, J=8.3 Hz), 10.71 (1H, s).

Example 107

(1R)-N-(3-fluoro-4-(trimethylsilyl)phenyl)-2-((3-hydroxy-1,2-oxazol-5-yl)carbonyl)-6-(methoxymethyl)-1,2,3,4-tetrahydroisoquinoline-1-carboxamide (Step 1)
To a solution of 2-(tert-butoxycarbonyl)-6-(methoxymethyl)-1,2,3,4-tetrahydroisoquinoline-1-carboxylic acid (1.54 g, 4.79 mmol), 3-fluoro-4-(trimethylsilyl)aniline (0.878 g, 4.79 mmol), DIEA (4.18 mL, 23.96 mmol) and DMAP (0.644 g, 5.27 mmol) in ethyl acetate (40 mL) was added T3P (8.46 mL, 14.38 mmol) at room temperature, and the mixture was stirred at 60° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 2→40% ethyl acetate/hexane) to give tert-butyl 1-((3-fluoro-4-(trimethylsilyl)phenyl)carbamoyl)-6-(methoxymethyl)-3,4-dihydroisoquinoline-2(1H)-carboxylate (1.830 g, 3.76 mmol, 78%) as white crystals.

MS(API): Calculated 486.7. Found 387.3 (M+H-Boc).
(Step 2)
tert-Butyl 1-((3-fluoro-4-(trimethylsilyl)phenyl)carbamoyl)-6-(methoxymethyl)-3,4-dihydroisoquinoline-2(1H)-carboxylate (1.80 g) was resolved by chiral column chromatography. The fraction having a shorter retention time was concentrated to give tert-butyl (R)-1-((3-fluoro-4-(trimethylsilyl)phenyl)carbamoyl)-6-(methoxymethyl)-3,4-dihydroisoquinoline-2(1H)-carboxylate (0.81 g, >99% ee), and the fraction having a longer retention time was concentrated to give tert-butyl (S)-1-((3-fluoro-4-(trimethylsilyl)phenyl) carbamoyl)-6-(methoxymethyl)-3,4-dihydroisoquinoline-2 (1H)-carboxylate (0.83 g, >99% ee), each as a white solid.
purification condition by chiral column chromatography
column: CHIRALPAK AD (NF001) 50 mmID×500 mmL
solvent: hexane/EtOH=900/100
flow rate: 80 mL/min
temperature: 30° C.
detection method: UV 220 nm
(Step 3)
Cooled TFA (12 mL) was added to a solution of tert-butyl (R)-1-((3-fluoro-4-(trimethylsilyl)phenyl) carbamoyl)-6-(methoxymethyl)-3,4-dihydroisoquinoline-2(1H)-carboxylate (0.83 g, 1.71 mmol) at 0° C., and the mixture was stirred at 0° C. for 3 min. The reaction mixture was added to ice and aqueous sodium hydrogen carbonate solution, and potassium carbonate was added thereto until the pH of the mixture became 8. Then, the mixture was extracted with ethyl acetate to give (R)-N-(3-fluoro-4-(trimethylsilyl)phenyl)-6-(methoxymethyl)-1,2,3,4-tetrahydroisoquinoline-1-carboxamide (0.600 g, 1.552 mmol, 91%) as a colorless oil.
MS(API): Calculated 386.5. Found 387.3(M+H).
(Step 4)
To a solution of (R)-N-(3-fluoro-4-(trimethylsilyl)phenyl)-6-(methoxymethyl)-1,2,3,4-tetrahydroisoquinoline-1-carboxamide (40 mg, 0.10 mmol), DIEA (0.022 mL, 0.12 mmol) and 3-hydroxyisoxazole-5-carboxylic acid (16.03 mg, 0.12 mmol) in DMF (2 mL) was added COMU (53.2 mg, 0.12 mmol) at 0° C., and the mixture was stirred at 0° C. for 1 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 80→100% ethyl acetate/hexane, 0→10% MeOH/ethyl acetate) to give the title compound (44.0 mg, 0.088 mmol, 85%) as a colorless solid.
$^1$H NMR (300 MHz, DMSO-$d_6$): δ 0.25 (9H, s), 2.84-2.98 (1H, m), 3.08-3.23 (1H, m), 3.28 (3H, s), 3.79 (1H, ddd, J=12.5,8.5,4.0 Hz), 4.11-4.26 (1H, m), 4.38 (2H, s), 5.78 (1H, s), 6.58 (1H, s), 7.19-7.25 (2H, m), 7.27-7.40 (2H, m), 7.41-7.51 (1H, m), 7.59 (1H, d, J=8.7 Hz), 10.83 (1H, s), 11.84 (1H, brs).
$[α]_D^{25}$ −5.9 (c 0.2500, MeOH)

Example 108

((2-((1R)-1-((3,5-difluoro-4-(trimethylsilyl)phenyl) carbamoyl)-6-methoxy-3,4-dihydroisoquinolin-2 (1H)-yl)-2-oxoethyl) (methyl)amino)acetic acid A solution of (R)-N-(3,5-difluoro-4-(trimethylsilyl)phenyl)-6-methoxy-1,2,3,4-tetrahydroisoquinoline-1-carboxamide (50 mg, 0.13 mmol), 4-methylmorpholine-2,6-dione (19.84 mg, 0.15 mmol) and TEA (0.021 mL, 0.15 mmol) in THF (2.0 mL) was stirred overnight at room temperature.

267

The reaction mixture was concentrated under reduced pressure, and the obtained residue was purified by silica gel column chromatography (solvent; ethyl acetate) to give the title compound (51.2 mg, 0.099 mmol, 77%) as a white powder.

$^1$H NMR (300 MHz, DMSO-$d_6$): δ 0.30 (9H, s), 2.38 (3H, s), 2.72-2.89 (1H, m), 2.89-3.00 (1H, m), 3.01-3.20 (2H, m), 3.35-3.49 (1H, m), 3.51-3.66 (3H, m), 3.73 (3H, s), 4.06-4.22 (1H, m), 5.60 (1H, s), 6.72-6.86 (2H, m), 7.13-7.26 (2H, m), 7.39-7.50 (1H, m), 10.81 (1H, s).

Example 109

5-((1R)-1-((4-tert-butyl-3,5-difluorophenyl) carbamoyl)-6-methoxy-3,4-dihydroisoquinolin-2(1H)-yl)-5-oxopentanoic acid A solution of (R)-N-(4-(tert-butyl)-3,5-difluorophenyl)-6-methoxy-1,2,3,4-tetrahydroisoquinoline-1-carboxamide (100 mg, 0.27 mmol), dihydro-2H-pyran-2,6(3H)-dione (45.7 mg, 0.40 mmol) and TEA (0.093 mL, 0.67 mmol) in THF (2.0 mL) was stirred at room temperature for 3 hr. The reaction mixture was concentrated under reduced pressure, and the obtained residue was purified by silica gel column chromatography (solvent gradient; 50→100% ethyl acetate/hexane) to give the title compound (52.8 mg, 0.108 mmol, 40.5%) as a white powder.

$^1$H NMR (300 MHz, DMSO-$d_6$): δ 0.30 (9H, s), 1.63-1.82 (2H, m), 2.16-2.32 (3H, m), 2.35-2.48 (1H, m), 2.51-2.63 (1H, m), 2.70-2.88 (1H, m), 3.04-3.20 (1H, m), 3.42-3.58 (1H, m), 3.73 (3H, s), 5.58-5.65 (1H, m), 6.76-6.87 (2H, m), 7.13-7.26 (2H, m), 7.46 (1H, d, J=9.4 Hz), 10.76 (1H, s), 12.03 (1H, brs).

$[α]_D^{25}$ −5.7 (c 0.252, MeOH)

Example 110

5-((1R)-1-((3-fluoro-4-(trimethylsilyl)phenyl)carbamoyl)-6-(methoxymethyl)-3,4-dihydroisoquinolin-2 (1H)-yl)-5-oxopentanoic acid A solution of (R)-N-(3-fluoro-4-(trimethylsilyl)phenyl)-6-(methoxymethyl)-1,2,3, 4-tetrahydroisoquinoline-1-carboxamide (208 mg, 0.54 mmol), TEA (0.076 mL, 0.54 mmol) and dihydro-2H-pyran-2,6(3H)-dione (61.4 mg, 0.54 mmol) in THF (4 mL) was stirred at 60° C. for 4 hr, and the reaction mixture was concentrated under reduced pressure. The obtained residue was purified by silica gel column chromatography (solvent gradient; 10→100% ethyl acetate/hexane) to give the title compound (223 mg, 0.445 mmol, 83%) as a white powder.

$^1$H NMR (300 MHz, DMSO-$d_6$): δ 0.19-0.29 (9H, m), 1.64-1.83 (1H, m), 2.22-2.33 (2H, m), 2.42 (3H, s), 2.46-2.62 (2H, m), 2.75-2.93 (1H, m), 3.03-3.20 (1H, m), 3.26 (2H, s), 3.48-3.64 (1H, m), 4.03 (1H, q, J=6.9 Hz), 4.36 (2H, s), 5.74 (1H, s), 7.11-7.22 (2H, m), 7.27-7.38 (2H, m), 7.45 (1H, d, J=11.0 Hz), 7.53 (1H, d, J=7.6 Hz), 10.66 (1H, s).

$[α]_D^{25}$ +2.2 (c 0.2500, MeOH)

268

Example 111

(5R)-N-(4-(ethyl (dimethyl) silyl)-3,5-difluorophenyl)-6-((3-hydroxy-1,2-oxazol-5-yl)carbonyl)-2-methoxy-5,6,7,8-tetrahydro-1, 6-naphthyridine-5-carboxamide (Step 1)

To a solution of 6-(tert-butoxycarbonyl)-2-methoxy-5,6, 7,8-tetrahydro-1,6-naphthyridine-5-carboxylic acid (1.141 g, 3.7 mmol), 4-(ethyldimethylsilyl)-3,5-difluoroaniline (0.797 g, 3.70 mmol), DIEA (3.22 mL, 18.50 mmol) and DMAP (0.497 g, 4.07 mmol) in ethyl acetate (27 mL) was added T3P (3.30 mL, 5.55 mmol) at room temperature, and the mixture was stirred at 65° C. for 15 hr. To the reaction mixture was added water, and the mixture was extracted three times with ethyl acetate. The organic layer was washed with 10% aqueous citric acid solution, sodium hydrogen carbonate solution, water and brine, and dried over magnesium sulfate, and the solvent was evaporated under reduced pressure. The precipitate was collected by filtration with cooled hexane to give tert-butyl 5-((4-(ethyldimethylsilyl)-3,5-difluorophenyl)carbamoyl)-2-methoxy-7,8-dihydro-1, 6-naphthyridine-6(5H)-carboxylate (1.42 g, 2.81 mmol, 76%) as white crystals.

$^1$H NMR (300 MHz, CDCl$_3$): δ 0.31 (6H, t, J=1.5 Hz), 0.77-0.98 (5H, m), 1.53 (9H, s), 2.82-3.03 (2H, m), 3.44 (1H, brs), 3.92 (3H, s), 4.00-4.10 (1H, m), 5.58 (1H, brs), 6.65 (1H, d, J=8.3 Hz), 6.99-7.07 (2H, m), 7.46 (1H, brs), 9.03 (1H, brs).

(Step 2)

tert-Butyl 5-((4-(ethyldimethylsilyl)-3,5-difluorophenyl)carbamoyl)-2-methoxy-7,8-dihydro-1,6-naphthyridine-6 (5H)-carboxylate (1.41 g) was resolved by chiral column chromatography. The fraction having a shorter retention time was concentrated to give tert-butyl (R)-5-((4-(ethyldimethylsilyl)-3,5-difluorophenyl)carbamoyl)-2-methoxy-7,8-dihydro-1,6-naphthyridine-6(5H)-carboxylate (620 mg, >99% ee), and the fraction having a longer retention was concentrated to give tert-butyl (S)-5-((4-(ethyldimethylsilyl)-3,5-difluorophenyl)carbamoyl)-2-methoxy-7,8-dihydro-1,6-naphthyridine-6(5H)-carboxylate (635 mg, >99% ee), each as white crystals.

purification condition by chiral column chromatography
    column: CHIRALPAK IA (QK001) 50 mmID×500 mmL
    solvent: hexane/EtOH=900/100
    flow rate: 80 mL/min
    temperature: 30° C.
    detection method: UV 220 nm (Step 3)

Cooled TFA (8.5 mL) was added to tert-butyl (R)-5-((4-(ethyldimethylsilyl)-3,5-difluorophenyl)carbamoyl)-2-methoxy-7,8-dihydro-1,6-naphthyridine-6(5H)-carboxylate (617 mg, 1.22 mmol) at room temperature, and the mixture was stirred at room temperature for 3 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The precipitate was washed with IPE/hexane to give (R)-N-(4-(ethyldimethylsilyl)-3,5-difluorophenyl)-2-methoxy-5,6,7,8-tetrahydro-1,6-naphthyridine-5-carboxamide (478 mg, 1.179 mmol, 97%) as a colorless oil.

$^1$H NMR (300 MHz, CDCl$_3$): δ 0.31 (6H, t, J=1.5 Hz), 0.74-0.84 (2H, m), 0.93 (3H, t), 1.66 (1H, brs), 2.74-2.98

(2H, m), 3.11-3.30 (2H, m), 3.90 (3H, s), 4.58 (1H, s), 6.61 (1H, d, J=8.3 Hz), 7.05-7.13 (2H, m), 7.81 (1H, d, J=8.7 Hz), 9.59 (1H, s).

(Step 4)

HATU (215 mg, 0.56 mmol) was added to a solution of (R)-N-(4-(ethyldimethylsilyl)-3,5-difluorophenyl)-2-methoxy-5,6,7,8-tetrahydro-1,6-naphthyridine-5-carboxamide (176 mg, 0.43 mmol), 3-hydroxyisoxazole-5-carboxylic acid (67.2 mg, 0.52 mmol) and DIEA (151 μL, 0.87 mmol) in DMF (2.2 mL), and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 15→85% ethyl acetate/hexane) to give the title compound (175.7 mg, 0.340 mmol, 78%) as a white solid.

$^1$H NMR (300 MHz, CDCl$_3$): δ 0.31 (6H, s), 0.74-0.84 (2H, m), 0.93 (3H, t), 2.84 (1H, s), 3.02-3.11 (1H, m), 3.16-3.29 (1H, m), 3.78-3.89 (1H, m), 3.94 (3H, s), 4.32-4.42 (1H, m), 5.95 (1H, s), 6.60 (1H, s), 6.68 (1H, d, J=8.7 Hz), 7.01-7.10 (2H, m), 7.41 (1H, d, J=8.7 Hz), 9.19 (1H, s).

Example 112

(5S)—N-(4-(ethyl (dimethyl) silyl)-3,5-difluorophenyl)-6-((3-hydroxy-1,2-oxazol-5-yl)carbonyl)-2-methoxy-5,6,7,8-tetrahydro-1, 6-naphthyridine-5-carboxamide The title compound was synthesized using tert-butyl (S)-5-((4-(ethyldimethylsilyl)-3,5-difluorophenyl)carbamoyl)-2-methoxy-7,8-dihydro-1, 6-naphthyridine-6 (5H)-carboxylate, by the reaction and purification in the same manner as in Example 111.

$^1$H NMR (300 MHz, CDCl$_3$): δ 0.31 (6H, s), 0.74-0.84 (2H, m), 0.93 (3H, t), 2.84 (1H, s), 3.02-3.11 (1H, m), 3.16-3.29 (1H, m), 3.78-3.90 (1H, m), 3.94 (3H, s), 4.32-4.42 (1H, m), 5.95 (1H, s), 6.60 (1H, s), 6.69 (1H, d, J=8.7 Hz), 7.06 (2H, d, J=8.7 Hz), 7.41 (1H, d, J=8.7 Hz), 9.17 (1H, s).

Example 113

(5R)-N-(4-(ethyl (dimethyl) silyl)-3,5-difluorophenyl)-6-((3-hydroxy-1,2-oxazol-5-yl)acetyl)-2-methoxy-5,6,7,8-tetrahydro-1,6-naphthyridine-5-carboxamide HATU (216 mg, 0.57 mmol) was added to a solution of (R)-N-(4-(ethyldimethylsilyl)-3,5-difluorophenyl)-2-methoxy-5,6,7,8-tetrahydro-1,6-naphthyridine-5-carboxamide (177 mg, 0.44 mmol), 2-(3-hydroxyisoxazol-5-yl)acetic acid (75.0 mg, 0.52 mmol) and DIEA (152 μL, 0.87 mmol) in DMF (2.2 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 15→85% ethyl acetate/hexane), and the precipitate was washed with IPE/hexane to give the title compound (87.5 mg, 0.165 mmol, 37.8%) as white crystals.

$^1$H NMR (300 MHz, CDCl$_3$): δ 0.27 (6H, s), 0.70-0.81 (2H, m), 0.91 (3H, t), 2.91-3.02 (2H, m), 3.18 (1H, dt, J=16.6,4.9 Hz), 3.88 (3H, s), 3.90-4.07 (4H, m), 5.95 (1H, s), 5.97 (1H, s), 6.64 (1H, d, J=8.7 Hz), 6.84-6.92 (2H, m), 7.44 (1H, d, J=8.3 Hz), 9.38 (1H, s).

Example 114

5-((5R)-5-((4-(ethyl(dimethyl)silyl)-3,5-difluorophenyl)carbamoyl)-2-methoxy-7,8-dihydro-1,6-naphthyridin-6(5H)-yl)-5-oxopentanoic acid Dihydro-2H-pyran-2,6(3H)-dione (35.2 mg, 0.31 mmol) was added to a solution of (R)-N-(4-(ethyldimethylsilyl)-3, 5-difluorophenyl)-2-methoxy-5,6,7,8-tetrahydro-1, 6-naphthyridine-5-carboxamide (119 mg, 0.29 mmol) and TEA (45 μL, 0.32 mmol) in THF (2.5 mL) at room temperature, and the mixture was stirred at room temperature for 4 hr. To the reaction mixture was added water, and 2N hydrochloric acid was added thereto until the pH of the mixture became 4. Then, the mixture was extracted three times with a mixed solvent of ethyl acetate/THF (3:1). The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane) to give the title compound (64.6 mg, 0.124 mmol, 42.4%) as white crystals.

$^1$H NMR (300 MHz, CDCl$_3$): δ 0.26 (6H, d, J=1.5 Hz), 0.69-0.79 (2H, m), 0.90 (3H, t), 1.58 (1H, brs), 2.05-2.19 (2H, m), 2.44 (2H, t, J=6.2 Hz), 2.56 (1H, ddd, J=14.7,8.7, 5.7 Hz), 2.88-3.10 (2H, m), 3.25 (1H, dt, J=16.1,5.5 Hz), 3.92 (3H, s), 3.94-4.00 (1H, m), 4.06 (1H, td, J=8.4,4.0 Hz), 5.85 (1H, s), 6.63 (1H, d, J=8.7 Hz), 6.77-6.85 (2H, m), 7.70 (1H, d, J=8.3 Hz), 9.84 (1H, s).

Example 115

(5R)-N-(7-fluoro-1,1-dimethyl-2,3-dihydro-1H-inden-5-yl)-6-((3-hydroxy-1,2-oxazol-5-yl)carbonyl)-2-methoxy-5,6,7,8-tetrahydro-1,6-naphthyridine-5-carboxamide (Step 1)

T3P (4.89 mL, 8.22 mmol) was added to a solution of 6-(tert-butoxycarbonyl)-2-methoxy-5,6,7,8-tetrahydro-1,6-naphthyridine-5-carboxylic acid (1.69 g, 5.48 mmol), 7-fluoro-1,1-dimethyl-2,3-dihydro-1H-inden-5-amine (0.982 g, 5.48 mmol), DIEA (4.77 mL, 27.41 mmol) and DMAP (0.737 g, 6.03 mmol) in ethyl acetate (40 mL), and the mixture was stirred at 65° C. for 15 hr. The reaction mixture was washed with 10% aqueous citric acid solution, aqueous sodium hydrogen carbonate solution and brine, and dried over magnesium sulfate, and the solvent was evaporated under reduced pressure. The obtained precipitate was washed with hexane to give tert-butyl 5-((7-fluoro-1,1-dimethyl-2,3-dihydro-1H-inden-5-yl)carbamoyl)-2-methoxy-7,8-dihydro-1,6-naphthyridine-6(5H)-carboxylate (2.09 g, 4.45 mmol, 81%) as grayish white crystals.

$^1$H NMR (300 MHz, CDCl$_3$): δ 1.34 (6H, s), 1.53 (9H, s), 1.91 (2H, t, J=7.4 Hz), 2.83-3.01 (4H, m), 3.45 (1H, brs), 3.91 (3H, s), 4.06 (1H, dt, J=13.2,4.9 Hz), 5.56 (1H, brs), 6.64 (1H, d, J=8.3 Hz), 7.05-7.12 (2H, m), 7.48 (1H, brs), 8.70 (1H, brs).

(Step 2)

tert-Butyl 5-((7-fluoro-1,1-dimethyl-2,3-dihydro-1H-inden-5-yl)carbamoyl)-2-methoxy-7,8-dihydro-1,6-naphthyridine-6(5H)-carboxylate (2.09 g) was resolved by chiral column chromatography. The fraction having a shorter retention time was concentrated to give tert-butyl (R)-5-((7-fluoro-1,1-dimethyl-2,3-dihydro-1H-inden-5-yl)carbamoyl)-2-methoxy-7,8-dihydro-1,6-naphthyridine-6(5H)-carboxylate (960 mg, >99% ee), and the fraction having a longer retention time was concentrated to give tert-butyl (S)-5-((7-fluoro-1,1-dimethyl-2,3-dihydro-1H-inden-5-yl)carbamoyl)-2-methoxy-7,8-dihydro-1,6-naphthyridine-6 (5H)-carboxylate (920 mg, >99% ee), each as a grayish white solid.

purification condition by chiral column chromatography
   column: CHIRALPAK IA (QK001) 50 mmID×500 mmL
   solvent: hexane/EtOH=900/100
   flow rate: 80 mL/min
   temperature: 30° C.
   detection method: UV 220 nm
(Step 3)

Cooled TFA (13 mL) was added to tert-butyl (R)-5-((7-fluoro-1,1-dimethyl-2,3-dihydro-1H-inden-5-yl)carbamoyl)-2-methoxy-7,8-dihydro-1,6-naphthyridine-6(5H)-carboxylate (957 mg, 2.04 mmol) at room temperature, and the mixture was stirred at room temperature for 20 min. The reaction mixture was added to ice and aqueous sodium hydrogen carbonate solution, and aqueous sodium hydrogen carbonate solution was added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(7-fluoro-1,1-dimethyl-2,3-dihydro-1H-inden-5-yl)-2-methoxy-5,6,7,8-tetrahydro-1, 6-naphthyridine-5-carboxamide (732 mg, 1.981 mmol, 97%) as a grayish white solid.

$^1$H NMR (300 MHz, CDCl$_3$): δ 1.34 (6H, s), 1.69 (1H, brs), 1.91 (2H, t, J=7.4 Hz), 2.73-2.98 (4H, m), 3.12-3.28 (2H, m), 3.90 (3H, s), 4.57 (1H, s), 6.60 (1H, d, J=8.7 Hz), 7.11-7.17 (2H, m), 7.84 (1H, d, J=8.7 Hz), 9.41 (1H, s).

(Step 4)

HATU (214 mg, 0.56 mmol) was added to a solution of (R)-N-(7-fluoro-1,1-dimethyl-2,3-dihydro-1H-inden-5-yl)-2-methoxy-5,6,7,8-tetrahydro-1,6-naphthyridine-5-carboxamide (160 mg, 0.43 mmol), 3-hydroxyisoxazole-5-carboxylic acid (67.1 mg, 0.52 mmol) and DIEA (151 μL, 0.87 mmol) in DMF (2.2 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 20→90% ethyl acetate/hexane) to give the title compound (142.9 mg, 0.297 mmol, 68.7%) as white crystals.

$^1$H NMR (300 MHz, CDCl$_3$): δ 1.34 (6H, s), 1.91 (2H, t, J=7.4 Hz), 2.83 (1H, s), 2.87 (2H, t, J=7.4 Hz), 2.99-3.09 (1H, m), 3.15-3.29 (1H, m), 3.76-3.88 (1H, m), 3.93 (3H, s), 4.31-4.41 (1H, m), 5.95 (1H, s), 6.57 (1H, s), 6.68 (1H, d, J=8.3 Hz), 7.08 (1H, s), 7.15 (1H, d, J=11.3 Hz), 7.41 (1H, d, J=8.7 Hz), 8.90 (1H, s).

$[α]_D^{25}$+89.6 (c 0.2525, MeOH)

Example 116

(5S)—N-(7-fluoro-1,1-dimethyl-2,3-dihydro-1H-inden-5-yl)-6-((3-hydroxy-1,2-oxazol-5-yl)carbonyl)-2-methoxy-5,6,7,8-tetrahydro-1, 6-naphthyridine-5-carboxamide The title compound was synthesized using tert-butyl (S)-5-((7-fluoro-1,1-dimethyl-2,3-dihydro-1H-inden-5-yl) carbamoyl)-2-methoxy-7,8-dihydro-1,6-naphthyridine-6 (5H)-carboxylate, by the reaction and purification in the same manner as in Steps 3 to 4 of Example 115.

$^1$H NMR (300 MHz, CDCl$_3$): δ 1.33 (6H, s), 1.91 (2H, t, J=7.4 Hz), 2.83-2.92 (3H, m), 3.00-3.09 (1H, m), 3.15-3.28 (1H, m), 3.79-3.90 (1H, m), 3.93 (3H, s), 4.30-4.39 (1H, m), 5.95 (1H, s), 6.57 (1H, s), 6.67 (1H, d, J=8.7 Hz), 7.08 (1H, s), 7.14 (1H, d, J=11.7 Hz), 7.42 (1H, d, J=8.7 Hz), 8.94 (1H, s)

Example 117

(5R)-N-(7-fluoro-1,1-dimethyl-2,3-dihydro-1H-inden-5-yl)-6-((3-hydroxy-1,2-oxazol-5-yl)acetyl)-2-methoxy-5,6,7,8-tetrahydro-1, 6-naphthyridine-5-carboxamide HATU (214 mg, 0.56 mmol) was added to a solution of (R)-N-(7-fluoro-1,1-dimethyl-2,3-dihydro-1H-inden-5-yl)-2-methoxy-5,6,7,8-tetrahydro-1,6-naphthyridine-5-carboxamide (160 mg, 0.43 mmol), 2-(3-hydroxyisoxazol-5-yl) acetic acid (74.4 mg, 0.52 mmol) and DIEA (151 μL, 0.87 mmol) in DMF (2.2 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 15→85% ethyl acetate/hexane), and the precipitate was washed with IPE/hexane to give the title compound (97.6 mg, 0.197 mmol, 45.6%) as white crystals.

$^1$H NMR (300 MHz, CDCl$_3$): δ 1.30 (6H, s), 1.87 (2H, t, J=7.4 Hz), 2.81 (2H, t, J=7.4 Hz), 2.88-3.01 (2H, m), 3.11 (1H, dt), 3.89 (3H, s), 3.91-3.98 (4H, m), 5.96 (2H, s), 6.64 (1H, d, J=8.3 Hz), 6.92 (1H, s), 7.05 (1H, d, J=11.7 Hz), 7.44 (1H, d, J=8.3 Hz), 9.00 (1H, s).

$[α]_D^{25}$+113.5 (c 0.2505, MeOH)

Example 118

5-((5R)-5-((7-fluoro-1,1-dimethyl-2,3-dihydro-1H-inden-5-yl) carbamoyl)-2-methoxy-7,8-dihydro-1, 6-naphthyridin-6(5H)-yl)-5-oxopentanoic acid Dihydro-2H-pyran-2,6(3H)-dione (51.9 mg, 0.45 mmol) was added to a solution of (R)-N-(7-fluoro-1,1-dimethyl-2, 3-dihydro-1H-inden-5-yl)-2-methoxy-5,6,7,8-tetrahydro-1, 6-naphthyridine-5-carboxamide (160 mg, 0.43 mmol) and TEA (66 μL, 0.47 mmol) in THF (3.8 mL) at room temperature, and the mixture was stirred at room temperature for 4 hr. The reaction mixture was poured into water, and 2N hydrochloric acid was added thereto until the pH of the mixture became 4. The mixture was extracted three times with a mixed solvent of ethyl acetate/THF (3:1). The organic layer was washed with water and brine, and dried over magnesium sulfate, and the solvent was evaporated under reduced pressure. The obtained residue was purified by silica gel column chromatography (Diol, solvent gradient; 20→100% ethyl acetate/hexane) to give the title compound (80.1 mg, 0.166 mmol, 38%) as a white solid.

$^1$H NMR (300 MHz, CDCl$_3$): δ 1.28 (6H, d, J=1.9 Hz), 1.85 (2H, t, J=7.4 Hz), 2.02-2.16 (3H, m), 2.45 (2H, t, J=6.4 Hz), 2.57 (1H, dt, J=15.0,7.4 Hz), 2.73-2.91 (3H, m), 2.96-3.20 (2H, m), 3.91 (3H, s), 3.94-4.00 (2H, m), 5.95

(1H, s), 6.63 (1H, d, J=8.3 Hz), 6.90 (1H, s), 7.03 (1H, d, J=12.1 Hz), 7.61 (1H, d, J=8.7 Hz), 9.41 (1H, s).

[α]$_D^{25}$+102.5 (c 0.2525, MeOH)

Example 119

5-((1R)-1-((3,5-difluoro-4-(1-methoxy-2-methylpropan-2-yl)phenyl)carbamoyl)-6-methoxy-3,4-dihydroisoquinolin-2 (1H)-yl)-5-oxopentanoic acid The title compound was synthesized using (R)-N-(3,5-difluoro-4-(1-methoxy-2-methylpropan-2-yl)phenyl)-6-methoxy-1,2,3,4-tetrahydroisoquinoline-1-carboxamide hydrochloride and dihydro-2H-pyran-2,6(3H)-dione, by the reaction and purification in the same manner as in Example 109.

$^1$H NMR (300 MHz, DMSO-d$_6$): δ 1.35 (6H, s), 1.63-1.83 (1H, m), 2.16-2.34 (3H, m), 2.35-2.62 (2H, m), 2.69-2.89 (1H, m), 3.04-3.17 (1H, m), 3.31 (3H, s), 3.39-3.57 (3H, m), 3.73 (3H, s), 3.92-4.09 (1H, m), 5.53-5.65 (1H, m), 6.72-6.89 (2H, m), 7.07-7.26 (2H, m), 7.45 (1H, d, J=9.4 Hz), 10.63 (1H, s), 12.04 (1H, brs).

Example 120

(2S)-5-((1R)-1-((4-tert-butyl-3,5-difluorophenyl) carbamoyl)-6-methoxy-3,4-dihydroisoquinolin-2 (1H)-yl)-2-hydroxy-5-oxopentanoic acid The title compound was synthesized using (R)-N-(4-(tert-butyl)-3,5-difluorophenyl)-6-methoxy-1,2,3,4-tetrahydroisoquinoline-1-carboxamide hydrochloride and (S)-5-(tert-butoxy)-4-hydroxy-5-oxopentanoic acid, by the reaction and purification in the same manner as in Step 8 of Example 1 and Step 7 of Example 1.

$^1$H NMR (300 MHz, CDCl$_3$): δ 1.38 (9H, s), 2.09-2.41 (2H, m), 2.60-2.94 (4H, m), 3.06-3.21 (2H, m, J=2.0 Hz), 3.53-3.69 (1H, m), 3.80 (3H, s), 3.84-3.97 (1H, m), 4.23-4.37 (1H, m), 5.89 (1H, s), 6.70-6.86 (2H, m), 6.89-7.04 (2H, m), 7.22 (1H, d, J=8.7 Hz), 8.69 (1H, brs).

Example 121

(1R)-N-(3,5-difluoro-4-(trimethylsilyl)phenyl)-2-((3-hydroxy-1,2-oxazol-5-yl)acetyl)-6-(methoxymethyl)-1,2,3,4-tetrahydroisoquinoline-1-carboxamide (Step 1)
T3P (10.38 mL, 17.64 mmol) was added to a solution of 2-(tert-butoxycarbonyl)-6-(methoxymethyl)-1,2,3,4-tetrahydroisoquinoline-1-carboxylic acid (1.89 g, 5.88 mmol), 3,5-difluoro-4-(trimethylsilyl)aniline (1.184 g, 5.88 mmol), DIEA (5.14 mL, 29.41 mmol) and DMAP (0.718 g, 5.88 mmol) in ethyl acetate (5 mL), and the mixture was stirred at 60° C. overnight. To the reaction mixture was added water, and the mixture was extracted with ethyl acetate. The organic layer was washed with water and brine, and dried over magnesium sulfate, and the solvent was evaporated under reduced pressure. The obtained residue was crystallized from ethyl acetate/hexane, and collected by filtration to give tert-butyl 1-((3,5-difluoro-4-(trimethylsilyl)phenyl)carbamoyl)-6-(methoxymethyl)-3,4-dihydroisoquinoline-2 (1H)-carboxylate. The filtrate was concentrated under reduced pressure, and the residue was purified by silica gel column chromatography (solvent gradient; 3→40% ethyl acetate/hexane) to give tert-butyl 1-((3,5-difluoro-4-(trimethylsilyl)phenyl)carbamoyl)-6-(methoxymethyl)-3,4-dihydroisoquinoline-2(1H)-carboxylate. The both are combined to give a white solid (1.89 g, 63.7%).

$^1$H NMR (300 MHz, CDCl$_3$): δ 0.32 (9H, t, J=1.3 Hz), 1.52 (9H, s), 2.71-2.99 (2H, m), 3.39 (3H, s), 3.50-3.81 (2H, m), 4.45 (2H, s), 5.61 (1H, brs), 6.96-7.07 (2H, m), 7.17-7.25 (3H, m), 9.05 (1H, s).

(Step 2)
tert-Butyl 1-((3,5-difluoro-4-(trimethylsilyl)phenyl)carbamoyl)-6-(methoxymethyl)-3,4-dihydroisoquinoline-2 (1H)-carboxylate (1.80 g) was resolved by chiral column chromatography. The fraction having a shorter retention time was concentrated to give tert-butyl (R)-1-((3,5-difluoro-4-(trimethylsilyl)phenyl)carbamoyl)-6-(methoxymethyl)-3,4-dihydroisoquinoline-2(1H)-carboxylate (0.81 g, >99% ee), and the fraction having a longer retention time was concentrated to give tert-butyl (S)-1-((3,5-difluoro-4-(trimethylsilyl)phenyl)carbamoyl)-6-(methoxymethyl)-3,4-dihydroisoquinoline-2(1H)-carboxylate (0.83 g, >99% ee), each as a white solid.

purification condition by chiral column chromatography column: CHIRALPAK AD (NF001) 50 mmID×500 mmL solvent: hexane/EtOH=900/100 flow rate: 80 mL/min temperature: 30° C.

detection method: UV 220 nm (Step 3)
Cooled TFA (5 mL) was added to tert-butyl (R)-1-((3,5-difluoro-4-(trimethylsilyl)phenyl)carbamoyl)-6-(methoxymethyl)-3,4-dihydroisoquinoline-2(1H)-carboxylate (767 mg, 1.52 mmol), and the mixture was stirred under ice-cooling for 1 hr. The reaction mixture was added to ice and aqueous sodium hydrogen carbonate solution, and the mixture was extracted with ethyl acetate. The organic layer was washed with brine, and dried over sodium sulfate, and the solvent was evaporated under reduced pressure to give (R)-N-(3,5-difluoro-4-(trimethylsilyl)phenyl)-6-(methoxymethyl)-1,2,3,4-tetrahydroisoquinoline-1-carboxamide (228.6 mg, 0.602 mmol, 93%) as a pale yellow solid.

MS(API): Calculated 404.5. Found 403.2 (M−H).

(Step 4)
HATU (82 mg, 0.22 mmol) was added to a solution of (R)-N-(3,5-difluoro-4-(trimethylsilyl)phenyl)-6-(methoxymethyl)-1,2,3,4-tetrahydroisoquinoline-1-carboxamide (73 mg, 0.18 mmol), DIEA (0.038 mL, 0.22 mmol) and 2-(3-hydroxyisoxazol-5-yl)acetic acid (31.0 mg, 0.22 mmol) in DMF (4 mL) at 0° C., and the mixture was stirred at 0° C. for 1 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 5→100% ethyl acetate/hexane), and precipitated from ethyl acetate/hexane to give the title compound (48.0 mg, 0.091 mmol, 50.2%) as white crystals.

$^1$H NMR (300 MHz, DMSO-d$_6$): δ 0.29 (9H, s), 2.76-2.95 (1H, m), 3.07-3.21 (1H, m), 3.27 (3H, s), 3.54-3.70 (1H, m), 3.88-4.18 (3H, m), 4.37 (2H, s), 5.70 (1H, s), 5.91 (1H, s), 7.08-7.26 (4H, m), 7.53 (1H, d, J=7.6 Hz), 10.87 (1H, s), 11.11 (1H, s).

Example 122

(5R)-N-(3,5-difluoro-4-(trimethylsilyl)phenyl)-6-((3-hydroxy-1,2-oxazol-5-yl)carbonyl)-2-methoxy-5,6,7,8-tetrahydro-1,6-naphthyridine-5-carboxamide (Step 1)

T3P (3.84 mL, 6.45 mmol) was added to a solution of 6-(tert-butoxycarbonyl)-2-methoxy-5,6,7,8-tetrahydro-1,6-naphthyridine-5-carboxylic acid (1.326 g, 4.3 mmol), 3,5-difluoro-4-(trimethylsilyl)aniline (0.866 g, 4.30 mmol), DIEA (3.74 mL, 21.50 mmol) and DMAP (0.578 g, 4.73 mmol) in ethyl acetate (31 mL) at room temperature, and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with cooled hexane to give tert-butyl 5-((3,5-difluoro-4-(trimethylsilyl)phenyl)carbamoyl)-2-methoxy-7,8-dihydro-1,6-naphthyridine-6(5H)-carboxylate (1.69 g, 3.44 mmol, 80%) as white crystals.

$^1$H NMR (300 MHz, CDCl$_3$): δ 0.33 (9H, t, J=1.3 Hz), 1.54 (9H, s), 2.83-3.02 (2H, m), 3.47 (1H, brs), 3.92 (3H, s), 3.98-4.09 (1H, m), 5.58 (1H, brs), 6.64 (1H, d, J=8.3 Hz), 6.98-7.06 (2H, m), 7.46 (1H, brs), 9.06 (1H, brs).

(Step 2)

tert-Butyl 5-((3,5-difluoro-4-(trimethylsilyl)phenyl)carbamoyl)-2-methoxy-7,8-dihydro-1,6-naphthyridine-6(5H)-carboxylate (1.69 g) was resolved by chiral column chromatography. The fraction having a shorter retention time was concentrated to give tert-butyl (R)-5-((3,5-difluoro-4-(trimethylsilyl)phenyl)carbamoyl)-2-methoxy-7,8-dihydro-1,6-naphthyridine-6(5H)-carboxylate (750 mg, >99% ee), and the fraction having a longer retention time was concentrated to give tert-butyl (S)-5-((3,5-difluoro-4-(trimethylsilyl)phenyl)carbamoyl)-2-methoxy-7,8-dihydro-1,6-naphthyridine-6(5H)-carboxylate (750 mg, >99% ee), each as a white solid.

purification condition by chiral column chromatography
  column: CHIRALPAK AD (NF001) 50 mmID×500 mmL
  solvent: hexane/EtOH=900/100
  flow rate: 80 mL/min
  temperature: 30° C.
  detection method: UV 220 nm (Step 3)

Cooled TFA (10.5 mL) was added to tert-butyl (R)-5-((3,5-difluoro-4-(trimethylsilyl)phenyl)carbamoyl)-2-methoxy-7,8-dihydro-1,6-naphthyridine-6(5H)-carboxylate (747 mg, 1.52 mmol) at room temperature, and the mixture was stirred at room temperature for 3 min. The reaction mixture was added to ice and aqueous sodium hydrogen carbonate solution, and aqueous sodium hydrogen carbonate solution was added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(3,5-difluoro-4-(trimethylsilyl)phenyl)-2-methoxy-5,6,7,8-tetrahydro-1,6-naphthyridine-5-carboxamide (567 mg, 1.448 mmol, 95%) as a white solid.

$^1$H NMR (300 MHz, CDCl$_3$): δ 0.32 (9H, t, J=1.3 Hz), 1.66 (1H, brs), 2.74-2.97 (2H, m), 3.11-3.29 (2H, m), 3.90 (3H, s), 4.58 (1H, s), 6.61 (1H, d, J=8.3 Hz), 7.05-7.13 (2H, m), 7.80 (1H, d, J=8.3 Hz), 9.60 (1H, s).

(Step 4)

HATU (128 mg, 0.34 mmol) was added to a solution of (R)-N-(3,5-difluoro-4-(trimethylsilyl)phenyl)-2-methoxy-5,6,7,8-tetrahydro-1,6-naphthyridine-5-carboxamide (101 mg, 0.26 mmol), 3-hydroxyisoxazole-5-carboxylic acid (40.0 mg, 0.31 mmol) and DIEA (90 μL, 0.52 mmol) in DMF (1.3 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 15→85% ethyl acetate/hexane) to give the title compound (89.9 mg, 0.179 mmol, 69.3%) as a white solid.

$^1$H NMR (300 MHz, CDCl$_3$): δ 0.33 (9H, s), 2.83 (1H, s), 3.01-3.11 (1H, m), 3.16-3.29 (1H, m), 3.76-3.87 (1H, m), 3.94 (3H, s), 4.32-4.42 (1H, m), 5.95 (1H, s), 6.60 (1H, s), 6.69 (1H, d, J=8.3 Hz), 7.06 (2H, d, J=8.7 Hz), 7.40 (1H, d, J=8.7 Hz), 9.13 (1H, s).

Example 123

(5S)—N-(3,5-difluoro-4-(trimethylsilyl)phenyl)-6-((3-hydroxy-1,2-oxazol-5-yl)carbonyl)-2-methoxy-5,6,7,8-tetrahydro-1,6-naphthyridine-5-carboxamide The title compound was obtained using tert-butyl (S)-5-((3,5-difluoro-4-(trimethylsilyl)phenyl)carbamoyl)-2-methoxy-7,8-dihydro-1,6-naphthyridine-6(5H)-carboxylate, by the reaction and purification in the same manner as in Steps 3 to 4 of Example 122.

$^1$H NMR (300 MHz, CDCl$_3$): δ 0.33 (9H, s), 2.83 (1H, s), 3.01-3.10 (1H, m), 3.17-3.30 (1H, m), 3.75-3.86 (1H, m), 3.94 (3H, s), 4.33-4.42 (1H, m), 5.95 (1H, s), 6.60 (1H, s), 6.69 (1H, d, J=8.7 Hz), 7.06 (2H, d, J=8.7 Hz), 7.40 (1H, d, J=8.7 Hz), 9.12 (1H, s).

Example 124

(5R)-N-(3,5-difluoro-4-(trimethylsilyl)phenyl)-6-((3-hydroxy-1,2-oxazol-5-yl)acetyl)-2-methoxy-5,6,7,8-tetrahydro-1,6-naphthyridine-5-carboxamide HATU (129 mg, 0.34 mmol) was added to a solution of (R)-N-(3,5-difluoro-4-(trimethylsilyl)phenyl)-2-methoxy-5,6,7,8-tetrahydro-1,6-naphthyridine-5-carboxamide (102 mg, 0.26 mmol), 2-(3-hydroxyisoxazol-5-yl)acetic acid (44.7 mg, 0.31 mmol) and DIEA (91 μL, 0.52 mmol) in DMF (1.3 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 15→85% ethyl acetate/hexane), and crystallized from IPE/hexane to give the title compound (45.3 mg, 0.088 mmol, 33.7%) as a white solid.

$^1$H NMR (300 MHz, CDCl$_3$): δ 0.29 (9H, s), 2.88-3.01 (2H, m), 3.17 (1H, dt, J=16.5, 4.8 Hz), 3.88 (3H, s), 3.90-4.04 (4H, m), 5.95 (1H, s), 5.97 (1H, s), 6.65 (1H, d, J=8.3 Hz), 6.88 (2H, d, J=8.7 Hz), 7.43 (1H, d, J=8.7 Hz), 9.31 (1H, s).

Example 125

5-((5R)-5-((3,5-difluoro-4-(trimethylsilyl)phenyl)carbamoyl)-2-methoxy-7,8-dihydro-1,6-naphthyridin-6(5H)-yl)-5-oxopentanoic acid Dihydro-2H-pyran-2,6(3H)-dione (34.6 mg, 0.30 mmol) was added to a solution of (R)-N-(3,5-difluoro-4-(trimethylsilyl)phenyl)-2-methoxy-5,6,7,8-tetrahydro-1,6-naphthyridine-5-carboxamide (113 mg, 0.29 mmol) and TEA (44 µL, 0.32 mmol) in THF (2.5 mL) at room temperature, and the mixture was stirred at room temperature for 15 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane) to give the title compound (66.5 mg, 0.132 mmol, 45.6%) as a white solid.

$^1$H NMR (300 MHz, CDCl$_3$): δ 0.27 (9H, s), 2.06-2.20 (2H, m), 2.43 (2H, t), 2.55 (1H, ddd, J=14.5, 9.1, 5.5 Hz), 2.93-3.10 (2H, m), 3.22-3.34 (1H, m), 3.92 (3H, s), 3.94-4.00 (1H, m), 4.07-4.17 (1H, m), 5.83 (1H, s), 6.63 (1H, d, J=8.3 Hz), 6.73-6.81 (2H, m), 7.74 (1H, d, J=8.7 Hz), 9.94 (1H, s).

$[\alpha]_D^{25}$+93.2 (c 0.2525, MeOH)

Example 126

(5R)-N-(3,5-difluoro-4-(trimethylsilyl)phenyl)-2-ethoxy-6-((3-hydroxy-1,2-oxazol-5-yl)carbonyl)-5,6,7,8-tetrahydro-1,6-naphthyridine-5-carboxamide (Step 1)

Iodoethane (6.82 mL, 84.88 mmol) was added to a solution of 5-ethyl 6-tert-butyl 2-hydroxy-7,8-dihydro-1,6-naphthyridine-5,6(5H)-dicarboxylate (4.56 g, 14.15 mmol) and silver(I) carbonate (5.07 g, 18.39 mmol) in THF (90 mL) at room temperature, and the mixture was stirred at room temperature for 15 hr, and then at 50° C. for 4 hr. The insoluble substance was removed by filtration with ethyl acetate. The filtrate was concentrated under reduced pressure, and the obtained residue was purified by silica gel column chromatography (solvent gradient; 5-25% ethyl acetate/hexane) to give 5-ethyl 6-tert-butyl 2-ethoxy-7,8-dihydro-1,6-naphthyridine-5,6(5H)-dicarboxylate (4.45 g, 12.70 mmol, 90%) as a colorless oil.

$^1$H NMR (300 MHz, CDCl$_3$): δ 1.22-1.30 (3H, m), 1.37 (3H, t, J=7.0 Hz), 1.45-1.52 (9H, m), 2.84-2.94 (2H, m), 3.55-3.70 (1H, m), 4.00-4.22 (3H, m), 4.33 (2H, q, J=6.9 Hz), 5.33-5.53 (1H, m), 6.58 (1H, d, J=8.7 Hz), 7.64-7.73 (1H, m).

(Step 2)

2N Aqueous lithium hydroxide solution (38.0 mL, 76.03 mmol) was added to a solution of 5-ethyl 6-tert-butyl 2-ethoxy-7,8-dihydro-1,6-naphthyridine-5,6(5H)-dicarboxylate (4.44 g, 12.67 mmol) in a mixed solvent of EtOH (20 mL) and THF (20 mL), and the mixture was stirred at room temperature for 1.5 hr. To the reaction mixture was added ice water, and 2N hydrochloric acid was added thereto until the pH of the mixture became 4. Then, the mixture was extracted three times with a mixed solvent of ethyl acetate/THF (3:1). The organic layer was washed with brine, and dried over magnesium sulfate, and the solvent was evaporated under reduced pressure to give 6-(tert-butoxycarbonyl)-2-ethoxy-5,6,7,8-tetrahydro-1,6-naphthyridine-5-carboxylic acid (4.03 g, 12.50 mmol, 99%) as a white solid.

$^1$H NMR (300 MHz, CDCl$_3$): δ 1.37 (3H, t, J=7.2 Hz), 1.42-1.53 (9H, m), 2.89 (2H, brs), 3.63 (1H, dt, J=13.3, 6.8 Hz), 3.95-4.08 (1H, m), 4.32 (2H, q, J=6.9 Hz), 5.35-5.57 (1H, m), 6.59 (1H, d, J=8.3 Hz), 7.68 (1H, d, J=8.7 Hz)

(Step 3)

T3P (3.84 mL, 6.45 mmol) was added to a solution of 6-(tert-butoxycarbonyl)-2-ethoxy-5,6,7,8-tetrahydro-1,6-naphthyridine-5-carboxylic acid (1.386 g, 4.3 mmol), 3,5-difluoro-4-(trimethylsilyl)aniline (0.866 g, 4.30 mmol), DIEA (3.74 mL, 21.50 mmol) and DMAP (0.578 g, 4.73 mmol) in ethyl acetate (31 mL) at room temperature, and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with cooled hexane to give tert-butyl 5-((3,5-difluoro-4-(trimethylsilyl)phenyl)carbamoyl)-2-ethoxy-7,8-dihydro-1,6-naphthyridine-6(5H)-carboxylate (1.82 g, 3.60 mmol, 84%) as a white solid.

$^1$H NMR (300 MHz, CDCl$_3$): δ 0.32 (9H, t, J=1.3 Hz), 1.38 (3H, t, J=7.2 Hz), 1.53 (9H, s), 2.81-3.01 (2H, m), 3.46 (1H, brs), 3.99-4.09 (1H, m), 4.29-4.38 (2H, m), 5.57 (1H, brs), 6.62 (1H, d, J=8.7 Hz), 6.98-7.06 (2H, m), 7.46 (1H, brs), 9.07 (1H, brs).

(Step 4)

tert-Butyl 5-((3,5-difluoro-4-(trimethylsilyl)phenyl)carbamoyl)-2-ethoxy-7,8-dihydro-1,6-naphthyridine-6(5H)-carboxylate (1.80 g) was resolved by chiral column chromatography. The fraction having a shorter retention time was concentrated to give tert-butyl (R)-5-((3,5-difluoro-4-(trimethylsilyl)phenyl)carbamoyl)-2-ethoxy-7,8-dihydro-1,6-naphthyridine-6(5H)-carboxylate (760 mg, >99% ee), and the fraction having a longer retention time was concentrated to give tert-butyl (S)-5-((3,5-difluoro-4-(trimethylsilyl)phenyl)carbamoyl)-2-ethoxy-7,8-dihydro-1,6-naphthyridine-6(5H)-carboxylate (780 mg, >99% ee), each as a white solid.

purification condition by chiral column chromatography
  column: CHIRALPAK AD (NF001) 50 mmID×500 mmL
  solvent: hexane/EtOH=900/100
  flow rate: 80 mL/min
  temperature: 30° C.
  detection method: UV 220 nm (Step 5)

Cooled TFA (10.5 mL) was added to tert-butyl (R)-5-((3,5-difluoro-4-(trimethylsilyl)phenyl)carbamoyl)-2-ethoxy-7,8-dihydro-1,6-naphthyridine-6(5H)-carboxylate (757 mg, 1.50 mmol), and the mixture was stirred at room temperature for 3 min. The reaction mixture was added to ice and aqueous sodium hydrogen carbonate solution, and 8N aqueous sodium hydroxide solution and potassium carbonate were added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(3,5-difluoro-4-(trimethylsilyl)phenyl)-2-ethoxy-5,6,7,8-tetrahydro-1,6-naphthyridine-5-carboxamide (589 mg, 1.452 mmol, 97%) as a white solid.

$^1$H NMR (300 MHz, CDCl$_3$): δ 0.32 (9H, s), 1.37 (3H, t, J=7.0 Hz), 1.73 (1H, brs), 2.72-2.96 (2H, m), 3.10-3.29 (2H, m), 4.31 (2H, q, J=7.2 Hz), 4.57 (1H, s), 6.59 (1H, d, J=8.7 Hz), 7.05-7.13 (2H, m), 7.80 (1H, d, J=8.7 Hz), 9.59 (1H, s).

(Step 6)

HATU (126 mg, 0.33 mmol) was added to a solution of (R)-N-(3,5-difluoro-4-(trimethylsilyl)phenyl)-2-ethoxy-5,6,7,8-tetrahydro-1, 6-naphthyridine-5-carboxamide (103 mg, 0.25 mmol), 3-hydroxyisoxazole-5-carboxylic acid (39.3 mg, 0.30 mmol) and DIEA (88 μL, 0.51 mmol) in DMF (1.3 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 15→85% ethyl acetate/hexane) to give the title compound (94.2 mg, 0.182 mmol, 71.8%) as a white solid.

$^1$H NMR (300 MHz, CDCl$_3$): δ 0.33 (9H, s), 1.39 (3H, t, J=7.0 Hz), 2.83 (1H, s), 2.98-3.09 (1H, m), 3.14-3.28 (1H, m), 3.75-3.88 (1H, m), 4.30-4.41 (3H, m), 5.94 (1H, s), 6.60 (1H, s), 6.66 (1H, d, J=8.7 Hz), 7.06 (2H, d, J=8.7 Hz), 7.39 (1H, d, J=8.3 Hz), 9.13 (1H, s).

Example 127

(5S)—N-(3,5-difluoro-4-(trimethylsilyl)phenyl)-2-ethoxy-6-((3-hydroxy-1,2-oxazol-5-yl)carbonyl)-5,6,7,8-tetrahydro-1,6-naphthyridine-5-carboxamide The title compound was synthesized using tert-butyl (S)-5-((3,5-difluoro-4-(trimethylsilyl)phenyl)carbamoyl)-2-ethoxy-7,8-dihydro-1,6-naphthyridine-6(5H)-carboxylate, by the reaction and purification in the same manner as in Steps 5 to 6 of Example 126.

$^1$H NMR (300 MHz, CDCl$_3$): δ 0.33 (9H, s), 1.39 (3H, t, J=7.0 Hz), 2.83 (1H, s), 2.97-3.09 (1H, m), 3.13-3.28 (1H, m), 3.76-3.89 (1H, m), 4.30-4.40 (3H, m), 5.94 (1H, s), 6.60 (1H, s), 6.66 (1H, d, J=8.3 Hz), 7.01-7.09 (2H, m), 7.40 (1H, d, J=8.7 Hz), 9.16 (1H, s).

Example 128

(5R)-N-(3,5-difluoro-4-(trimethylsilyl)phenyl)-2-ethoxy-6-((3-hydroxy-1,2-oxazol-5-yl)acetyl)-5,6,7,8-tetrahydro-1,6-naphthyridine-5-carboxamide HATU (127 mg, 0.33 mmol) was added to a solution of (R)-N-(3,5-difluoro-4-(trimethylsilyl)phenyl)-2-ethoxy-5,6,7,8-tetrahydro-1, 6-naphthyridine-5-carboxamide (104 mg, 0.26 mmol), 2-(3-hydroxyisoxazol-5-yl)acetic acid (44.0 mg, 0.31 mmol) and DIEA (89 μL, 0.51 mmol) in DMF (1.3 mL) at room temperature, and the mixture was stirred for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 15→80% MeOH/ethyl acetate), and crystallized from IPE/hexane to give the title compound (58.2 mg, 0.110 mmol, 42.8%) as a white solid.

$^1$H NMR (300 MHz, CDCl$_3$): δ 0.30 (9H, s), 1.35 (3H, t, J=7.0 Hz), 2.88-3.00 (2H, m), 3.14 (1H, dt), 3.88-4.02 (4H, m), 4.30 (2H, qd, J=7.0, 2.1 Hz), 5.94 (1H, s), 5.97 (1H, s), 6.63 (1H, s), d, J=8.7 Hz), 6.90 (2H, d, J=8.7 Hz), 7.43 (1H, d, J=8.7 Hz), 9.27 (1H, s).

Example 129

5-((5R)-5-((3,5-difluoro-4-(trimethylsilyl)phenyl)carbamoyl)-2-ethoxy-7,8-dihydro-1,6-naphthyridin-6(5H)-yl)-5-oxopentanoic acid Dihydro-2H-pyran-2,6(3H)-dione (39.0 mg, 0.34 mmol) was added to a solution of (R)-N-(3,5-difluoro-4-(trimethylsilyl)phenyl)-2-ethoxy-5,6,7,8-tetrahydro-1,6-naphthyridine-5-carboxamide (132 mg, 0.33 mmol) and TEA (50 μL, 0.36 mmol) in THF (2.8 mL) at room temperature, and the mixture was stirred at room temperature for 15 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane) to give the title compound (63.3 mg, 0.122 mmol, 37.4%)) as a white solid.

$^1$H NMR (300 MHz, CDCl$_3$): δ 0.27 (9H, s), 1.37 (3H, t, J=7.0 Hz), 2.08-2.19 (2H, m), 2.43 (2H, t), 2.55 (1H, ddd, J=14.6, 9.0, 5.5 Hz), 2.91-3.08 (2H, m), 3.20-3.31 (1H, m), 3.89-3.99 (1H, m), 4.06-4.17 (1H, m), 4.33 (2H, q, J=7.2 Hz), 5.83 (1H, s), 6.60 (1H, d, J=8.7 Hz), 6.74-6.82 (2H, m), 7.72 (1H, d, J=8.7 Hz), 9.92 (1H, s).

Example 130

5-((1R)-1-((3,5-difluoro-4-(trimethylsilyl)phenyl)carbamoyl)-6-(methoxymethyl)-3,4-dihydroisoquinolin-2(1H)-yl)-5-oxopentanoic acid Dihydro-2H-pyran-2,6(3H)-dione (58.9 mg, 0.52 mmol) was added to a solution of (R)-N-(3,5-difluoro-4-(trimethylsilyl)phenyl)-6-(methoxymethyl)-1,2,3,4-tetrahydroisoquinoline-1-carboxamide (209 mg, 0.52 mmol) and TEA (0.073 mL, 0.52 mmol) in THF (2 mL) at room temperature, and the mixture was stirred at 60° C. for 4 hr. The reaction mixture was concentrated under reduced pressure, and the obtained residue was purified by silica gel column chromatography (solvent gradient; 10→100% ethyl acetate/hexane) to give the title compound (170 mg, 0.328 mmol, 63.4%) as a white solid.

$^1$H NMR (300 MHz, DMSO-d$_6$): δ 0.30 (9H, s), 1.75 (2H, quin, J=7.3 Hz), 2.18-2.33 (2H, m), 2.37-2.62 (2H, m), 2.78-2.92 (1H, m), 3.04-3.20 (1H, m), 3.27 (3H, s), 3.47-3.64 (1H, m), 3.96-4.12 (1H, m), 4.36 (2H, s), 5.69 (1H, s), 7.10-7.31 (4H, m), 7.51 (1H, d, J=7.6 Hz), 10.82 (1H, s), 12.04 (1H, brs).

$[α]_D^{25}$ −3.8 (c 0.2275, MeOH)

Example 131

(1R)-N-(3,5-difluoro-4-(trimethylsilyl)phenyl)-2-((3-hydroxy-1,2-oxazol-5-yl)carbonyl)-6-(methoxymethyl)-1,2,3,4-tetrahydroisoquinoline-1-carboxamide A solution of (R)-N-(3,5-difluoro-4-(trimethylsilyl)phenyl)-6-(methoxymethyl)-1,2,3,4-tetrahydroisoquinoline-1-carboxamide (67 mg, 0.15 mmol), DIEA (0.032 mL, 0.18 mmol), 3-hydroxyisoxazole-5-carboxylic acid (23.53 mg, 0.18 mmol) and COMU (71.6 mg, 0.17 mmol) in DMF (2 mL) was stirred at 0° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified twice by silica gel column chromatography (Diol, solvent gradient; 5→90% ethyl acetate/hexane) to give the title compound (36.0 mg, 0.070 mmol, 46.0%) as a white solid.

$^1$H NMR (300 MHz, CDCl$_3$): δ 0.30 (9H, s), 2.92 (1H, dt, J=16.0, 4.3 Hz), 3.08-3.23 (1H, m), 3.28 (3H, s), 3.68-3.89 (H, m), 4.10-4.26 (1H, m), 4.38 (2H, s), 5.73 (1H, s), 6.60 (1H, s), 7.08-7.32 (4H, m), 7.58 (1H, d, J=8.3 Hz), 10.99 (1H, s), 11.77 (1H, s).

Example 132

(1R)-N-(4-tert-butyl-3-fluorophenyl)-2-((3-hydroxy-1,2-oxazol-5-yl)acetyl)-6-(methoxymethyl)-1,2,3,4-tetrahydroisoquinoline-1-carboxamide (Step 1)

T3P (2.75 mL, 4.67 mmol) was added to a solution of 2-(tert-butoxycarbonyl)-6-(methoxymethyl)-1,2,3,4-tetrahydroisoquinoline-1-carboxylic acid (500 mg, 1.56 mmol), 4-(tert-butyl)-3-fluoroaniline (260 mg, 1.56 mmol), DIEA (1.359 mL, 7.78 mmol) and DMAP (190 mg, 1.56 mmol) in ethyl acetate (5 mL), and the mixture was stirred at 60° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 32→40% ethyl acetate/hexane) to give tert-butyl 1-((4-(tert-butyl)-3-fluorophenyl) carbamoyl)-6-(methoxymethyl)-3,4-dihydroisoquinoline-2 (1H)-carboxylate (500 mg, 1.063 mmol, 68.3%) as a white solid.

$^1$H NMR (300 MHz, CDCl$_3$): δ 1.33 (9H, s), 1.52 (9H, s), 2.83-2.99 (1H, m), 3.39 (3H, s), 3.48-3.84 (2H, m), 4.44 (2H, s), 5.64 (1H, brs), 7.04 (1H, d, J=8.3 Hz), 7.13-7.26 (4H, m), 7.33-7.43 (1H, m), 8.83 (1H, s).
(Step 2)

tert-Butyl 1-((4-(tert-butyl)-3-fluorophenyl)carbamoyl)-6-(methoxymethyl)-3,4-dihydroisoquinoline-2 (1H)-carboxylate (1.83 g) was resolved by chiral column chromatography. The fraction having a shorter retention time was concentrated to give tert-butyl (R)-1-((4-(tert-butyl)-3-fluorophenyl)carbamoyl)-6-(methoxymethyl)-3,4-dihydroisoquinoline-2(1H)-carboxylate (0.83 g, >99% ee), and the fraction having a longer retention time was concentrated to give tert-butyl (S)-1-((4-(tert-butyl)-3-fluorophenyl)carbamoyl)-6-(methoxymethyl)-3,4-dihydroisoquinoline-2 (1H)-carboxylate (0.83 g, >99% ee), each as a white solid.
purification condition by chiral column chromatography
  column: CHIRALPAK IA (QK001) 50 mmID×500 mmL
  solvent: hexane/EtOH=900/100
  flow rate: 80 mL/min
  temperature: 30° C.
  detection method: UV 220 nm
(Step 3)

4N Hydrogen chloride/ethyl acetate (2 mL) was added to a solution of tert-butyl (R)-1-((4-(tert-butyl)-3-fluorophenyl)carbamoyl)-6-(methoxymethyl)-3,4-dihydroisoquinoline-2(1H)-carboxylate (0.24 g, 0.51 mmol) in ethyl acetate (2 mL) at room temperature, and the mixture was stirred overnight at room temperature. The reaction mixture was concentrated under reduced pressure, and the precipitate was collected by filtration ethyl acetate/hexane to give (R)-N-(4-(tert-butyl)-3-fluorophenyl)-6-(methoxymethyl)-1,2,3,4-tetrahydroisoquinoline-1-carboxamide hydrochloride (0.208 g, 0.511 mmol, 100%) as a white solid.

MS(API): Calculated 406.92. Found 369.2 (M−HCl−H.)
(Step 4)

HATU (233 mg, 0.61 mmol) was added to a solution of (R)-N-(4-(tert-butyl)-3-fluorophenyl)-6-(methoxymethyl)-1,2,3,4-tetrahydroisoquinoline-1-carboxamide hydrochloride (208 mg, 0.51 mmol), 2-(3-hydroxyisoxazol-5-yl)acetic acid (88 mg, 0.61 mmol) and DIEA (0.214 mL, 1.23 mmol) in DMF (3 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 5→90% ethyl acetate/hexane) to give the title compound (157 mg, 0.317 mmol, 62.0%) as a white solid.

$^1$H NMR (300 MHz, DMSO-d$_6$): δ 1.29 (9H, s), 2.78-2.93 (1H, m), 3.06-3.20 (1H, m), 3.27 (3H, s), 3.58-3.74 (1H, m), 3.87-4.16 (3H, m), 4.36 (2H, s), 5.74 (1H, s), 5.91 (1H, s), 7.15-7.31 (4H, m), 7.40-7.50 (1H, m), 7.55 (1H, d, J=7.6 Hz), 10.60 (1H, s), 11.10 (1H, s).

Example 133

(1R)-N-(7-fluoro-1,1-dimethyl-2,3-dihydro-1H-inden-5-yl)-2-((3-hydroxy-1,2-oxazol-5-yl)carbonyl)-6-(methoxymethyl)-1,2,3,4-tetrahydroisoquinoline-1-carboxamide (Step 1)

T3P (8.24 mL, 14.00 mmol) was added to a solution of 2-(tert-butoxycarbonyl)-6-(methoxymethyl)-1,2,3,4-tetrahydroisoquinoline-1-carboxylic acid (1.5 g, 4.67 mmol), 7-fluoro-1,1-dimethyl-2,3-dihydro-1H-inden-5-amine (0.837 g, 4.67 mmol), DIEA (4.08 mL, 23.34 mmol) and DMAP (0.570 g, 4.67 mmol) in ethyl acetate (5 mL), and the mixture was stirred at 60° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 32-40% ethyl acetate/hexane) to give tert-butyl 1-((7-fluoro-1,1-dimethyl-2,3-dihydro-1H-inden-5-yl)carbamoyl)-6-(methoxymethyl)-3,4-dihydroisoquinoline-2(1H)-carboxylate (1.600 g, 3.32 mmol, 71.0%) as a white solid.

MS(API): Calculated 482.6. Found 481.3 (M−H).
(Step 2)

tert-Butyl 1-((7-fluoro-1,1-dimethyl-2,3-dihydro-1H-inden-5-yl)carbamoyl)-6-(methoxymethyl)-3,4-dihydroisoquinoline-2(1H)-carboxylate (1.60 g) was resolved by chiral column chromatography. The fraction having a shorter retention time was concentrated to give tert-butyl (R)-1-((7-fluoro-1,1-dimethyl-2,3-dihydro-1H-inden-5-yl)carbamoyl)-6-(methoxymethyl)-3,4-dihydroisoquinoline-2 (1H)-carboxylate (0.77 g, >99% ee), and the fraction having a longer retention time was concentrated to give tert-butyl (S)-1-((7-fluoro-1,1-dimethyl-2,3-dihydro-1H-inden-5-yl) carbamoyl)-6-(methoxymethyl)-3,4-dihydroisoquinoline-2 (1H)-carboxylate (0.73 g, >99% ee), each as a white solid.
purification condition by chiral column chromatography
  column: CHIRALCEL OD (NL001) 50 mmID×500 mmL
  solvent: hexane/EtOH=900/100
  flow rate: 80 mL/min
  temperature: 30° C.
  detection method: UV 220 nm (Step 3)

4N Hydrogen chloride/ethyl acetate (4 mL) was added to a solution of tert-butyl (R)-1-((7-fluoro-1,1-dimethyl-2,3-dihydro-1H-inden-5-yl)carbamoyl)-6-(methoxymethyl)-3,4-dihydroisoquinoline-2(1H)-carboxylate (0.77 g, 1.60 mmol) in ethyl acetate (2 mL), and the mixture was stirred overnight at room temperature. The precipitate was collected by filtration ethyl acetate/hexane to give (R)-N-(7-fluoro-1,1-dimethyl-2,3-dihydro-1H-inden-5-yl)-6-(methoxymethyl)-1,2,3,4-tetrahydroisoquinoline-1-carboxamide hydrochloride (0.730 g, 1.743 mmol, 109%) as a white solid.

MS(API): Calculated 418.9. Found 381.2 (M−HCl−H.)

(Step 4)

A solution of (R)-N-(7-fluoro-1,1-dimethyl-2,3-dihydro-1H-inden-5-yl)-6-(methoxymethyl)-1,2,3,4-tetrahydroisoquinoline-1-carboxamide hydrochloride (250 mg, 0.60 mmol), DIEA (0.250 mL, 1.43 mmol), 3-hydroxyisoxazole-5-carboxylic acid (92 mg, 0.72 mmol) and COMU (281 mg, 0.66 mmol) in DMF (2 mL) was stirred at 0° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane, 0-10% MeOH/ethyl acetate), and crystallized from ethyl acetate/hexane to give the title compound (204 mg, 0.413 mmol, 69.3%) as a white solid.

$^1$H NMR (300 MHz, DMSO-d$_6$): δ 1.28 (6H, s), 1.87 (2H, t, J=7.4 Hz), 2.79-2.99 (3H, m), 3.07-3.21 (1H, m), 3.28 (3H, s), 3.79 (1H, ddd, J=12.4, 8.2, 4.0 Hz), 4.10-4.24 (1H, m), 4.38 (2H, s), 5.49-5.84 (1H, m), 6.29-6.68 (1H, m), 7.07-7.30 (4H, m), 7.49-7.64 (1H, m), 10.25-10.75 (1H, m), 11.78 (1H, brs).

$[α]_D^{25}$ +0.9 (c 0.2525, MeOH)

Example 134

5-((1R)-1-((7-fluoro-1,1-dimethyl-2,3-dihydro-1H-inden-5-yl)carbamoyl)-6-(methoxymethyl)-3,4-dihydroisoquinolin-2(1H)-yl)-5-oxopentanoic acid The title compound was synthesized using (R)-N-(7-fluoro-1,1-dimethyl-2,3-dihydro-1H-inden-5-yl)-6-(methoxymethyl)-1,2,3,4-tetrahydroisoquinoline-1-carboxamide hydrochloride, by the reaction and purification in the same manner as in Example 109.

$^1$H NMR (300 MHz, DMSO-d$_6$): δ 1.28 (6H, s), 1.74 (2H, dq, J=14.9, 7.4 Hz), 1.86 (2H, t, J=7.4 Hz), 2.17-2.33 (4H, m), 2.77-2.91 (3H, m), 3.06-3.19 (1H, m), 3.27 (3H, s), 3.48-3.67 (1H, m), 3.91-4.13 (1H, m), 4.36 (2H, s), 5.54-5.80 (1H, m), 7.07-7.29 (4H, m), 7.52 (1H, d, J=7.9 Hz), 10.33-10.55 (1H, m), 11.96 (1H, brs)

Example 135

5-((1R)-1-((3-fluoro-4-(trimethylsilyl)phenyl)carbamoyl)-6-methoxy-3,4-dihydroisoquinolin-2(1H)-yl)-5-oxopentanoic acid (Step 1)

tert-Butyl 1-((3-fluoro-4-(trimethylsilyl)phenyl)carbamoyl)-6-methoxy-3,4-dihydroisoquinoline-2(1H)-carboxylate (1.10 g) was resolved by chiral column chromatography. The fraction having a shorter retention time was concentrated to give tert-butyl (R)-1-((3-fluoro-4-(trimethylsilyl)phenyl)carbamoyl)-6-methoxy-3,4-dihydroisoquinoline-2(1H)-carboxylate (0.53 g, >99% ee), and the fraction having a longer retention time was concentrated to give tert-butyl (S)-1-((3-fluoro-4-(trimethylsilyl)phenyl)carbamoyl)-6-methoxy-3,4-dihydroisoquinoline-2(1H)-carboxylate (0.51 g, 96.7% ee), each as a white solid.
purification condition by chiral column chromatography
    column: CHIRALCEL OD (NL001) 50 mmID×500 mmL
    solvent: hexane/EtOH=900/100
    flow rate: 80 mL/min
    temperature: 30° C.
    detection method: UV 220 nm (Step 2)

Cooled TFA (5.0 mL) was added to tert-butyl (R)-1-((3-fluoro-4-(trimethylsilyl)phenyl)carbamoyl)-6-methoxy-3,4-dihydroisoquinoline-2(1H)-carboxylate (526 mg, 1.11 mmol), and the mixture was stirred at room temperature for 2 min. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by NH-silica gel column chromatography (solvent gradient; 20→50% ethyl acetate/hexane) to give (R)-N-(3-fluoro-4-(trimethylsilyl)phenyl)-6-methoxy-1,2,3,4-tetrahydroisoquinoline-1-carboxamide (350.3 mg, 0.940 mmol, 84%) as a white solid.

$^1$H NMR (300 MHz, CDCl$_3$): δ 0.28 (9H, d, J=0.8 Hz), 2.68-2.82 (1H, m), 2.83-2.97 (1H, m), 3.10-3.19 (2H, m), 3.79 (3H, s), 4.64 (1H, s), 6.65 (1H, d, J=2.6 Hz), 6.79 (1H, dd, J=8.5, 2.6 Hz), 7.18 (1H, dd, J=7.9, 1.9 Hz), 7.27 (1H, s), 7.46 (1H, dd, J=10.6, 1.9 Hz), 7.53 (1H, d, J=8.6 Hz), 9.46 (1H, s)

(Step 3)

Dihydro-2H-pyran-2,6(3H)-dione (36.8 mg, 0.32 mmol) was added to a solution of (R)-N-(3-fluoro-4-(trimethylsilyl)phenyl)-6-methoxy-1,2,3,4-tetrahydroisoquinoline-1-carboxamide (80 mg, 0.21 mmol) and TEA (0.060 mL, 0.43 mmol) in THF (2.0 mL) at room temperature, and the mixture was stirred at room temperature for 3 hr. The reaction mixture was concentrated under reduced pressure. The obtained residue was purified by silica gel column chromatography (solvent gradient; 50→100% ethyl acetate/hexane) to give the title compound (27.9 mg, 0.057 mmol, 26.7%) as a white solid.

$^1$H NMR (300 MHz, DMSO-d$_6$): δ 0.25 (9H, s), 1.65-1.85 (2H, m), 2.22-2.32 (2H, m), 2.36-2.60 (2H, m), 2.72-2.88 (1H, m), 3.05-3.19 (1H, m), 3.46-3.58 (1H, m), 3.72 (3H, s), 3.95-4.08 (1H, m), 5.57-5.71 (1H, m), 6.76-6.87 (2H, m), 7.25-7.38 (2H, m), 7.41-7.52 (2H, m), 10.53-10.66 (1H, m), 11.95 (1H, brs).

$[α]_D^{25}$ −7.7 (c 0.2525, MeOH)

Example 136

(5R)-N-(3,5-difluoro-4-(trimethylsilyl)phenyl)-6-((3-hydroxy-1,2-oxazol-5-yl)carbonyl)-2-(methoxymethyl)-5,6,7,8-tetrahydro-1,6-naphthyridine-5-carboxamide (Step 1)

Trifluoromethanesulfonic anhydride (16.35 mL, 96.79 mmol) was added to a solution of 5-ethyl 6-tert-butyl 2-hydroxy-7,8-dihydro-1,6-naphthyridine-5,6(5H)-dicarboxylate (15.6 g, 48.39 mmol) in pyridine (150 mL) at 0° C., and the mixture was stirred at room temperature for 1 hr. The reaction mixture was concentrated under reduced pressure, and to the obtained residue were added water and ethyl acetate. The organic layer was washed with 10% aqueous citric acid solution, and dried over magnesium sulfate, and the solvent was evaporated under reduced pressure. The obtained residue was purified by silica gel column chromatography (solvent; ethyl acetate/hexane) to give 5-ethyl 6-tert-butyl 2-(((trifluoromethyl)sulfonyl)oxy)-7,8-dihydro-1,6-naphthyridine-5,6(5H)-dicarboxylate (18.0 g, 39.6 mmol, 82%) as a colorless oil.

$^1$H NMR (300 MHz, CDCl$_3$): δ 1.23-1.33 (3H, m), 1.49 (9H, d, J=8.3 Hz), 2.89-3.11 (2H, m), 3.42-3.65 (1H, m), 4.14-4.36 (3H, m), 5.46-5.74 (1H, m), 7.05 (1H, d, J=8.3 Hz), 8.06 (1H, d, J=8.3 Hz).

(Step 2)

A solution of 5-ethyl 6-tert-butyl 2-(((trifluoromethyl)sulfonyl)oxy)-7,8-dihydro-1, 6-naphthyridine-5,6(5H)-dicarboxylate (18.0 g, 39.61 mmol), Pd(PPh$_3$)$_4$(2.289 g, 1.98 mmol) and zinc cyanide (5.12 g, 43.57 mmol) in DMF (270 mL) was stirred at 100° C. for 5 hr. To the reaction mixture was added ethyl acetate, and the insoluble substance was removed by filtration. The filtrate was washed with water and brine, and dried over magnesium sulfate, and the solvent was evaporated under reduced pressure. The obtained residue was purified by silica gel column chromatography (solvent; ethyl acetate/hexane) to give 5-ethyl 6-tert-butyl 2-cyano-7,8-dihydro-1,6-naphthyridine-5,6(5H)-dicarboxylate (12.4 g, 37.4 mmol, 94%) as a colorless oil.

$^1$H NMR (300 MHz, CDCl$_3$): δ 1.24-1.33 (3H, m), 1.50 (9H, d, J=8.7 Hz), 3.01-3.16 (2H, m), 3.48-3.69 (1H, m), 4.14-4.32 (3H, m), 5.51-5.77 (1H, m), 7.58 (1H, d, J=7.9 Hz), 8.01 (1H, d, J=7.9 Hz).

(Step 3)

2N Aqueous sodium hydroxide solution (56.1 mL, 112.26 mmol) was added to a solution of 5-ethyl 6-tert-butyl 2-cyano-7,8-dihydro-1,6-naphthyridine-5,6(5H)-dicarboxylate (12.4 g, 37.42 mmol) in a mixed solvent of EtOH (100 mL) and THF (100 mL) at room temperature, and the mixture was stirred at room temperature for 5 hr. 2N Hydrochloric acid was added thereto until the pH of the reaction mixture became 4, and the mixture was extracted with ethyl acetate. The organic layer was washed with brine, and dried over magnesium sulfate, and the solvent was evaporated under reduced pressure to give crude 6-(tert-butoxycarbonyl)-2-(ethoxycarbonyl)-5,6,7,8-tetrahydro-1, 6-naphthyridine-5-carboxylic acid (11.8 g, 33.7 mmol, 90%) as a white solid.

(Step 4)

T3P (25.4 mL, 43.22 mmol) was added to a solution of the crude 6-(tert-butoxycarbonyl)-2-(ethoxycarbonyl)-5,6,7,8-tetrahydro-1,6-naphthyridine-5-carboxylic acid (5.55 g, 15.85 mmol), 3,5-difluoro-4-(trimethylsilyl)aniline (2.9 g, 14.41 mmol), DMAP (1.936 g, 15.85 mmol) and DIEA (12.58 mL, 72.04 mmol) in ethyl acetate (100 mL) at room temperature, and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give 2-ethyl 6-tert-butyl 5-((3,5-difluoro-4-(trimethylsilyl)phenyl)carbamoyl)-7,8-dihydro-1,6-naphthyridine-2,6(5H)-dicarboxylate (3.44 g, 6.45 mmol, 44.7%) as a white solid.

MS(API): Calculated 533.6. Found 532.3 (M−H).

(Step 5)

Sodium borohydride (0.723 g, 19.11 mmol) was added to a mixture of 2-ethyl 6-tert-butyl 5-((3,5-difluoro-4-(trimethylsilyl)phenyl)carbamoyl)-7,8-dihydro-1,6-naphthyridine-2,6(5H)-dicarboxylate (3.4 g, 6.37 mmol) and calcium chloride (1.061 g, 9.56 mmol) in a mixed solvent of EtOH (35 mL) and THF (35 mL) at 0° C., and the mixture was stirred at room temperature for 5 hr. The reaction mixture was neutralized with 1N hydrochloric acid, and the mixture was extracted with ethyl acetate. The organic layer was washed with water and brine, and dried over magnesium sulfate, and the solvent was evaporated under reduced pressure. The obtained residue was purified by silica gel column chromatography (solvent; ethyl acetate/hexane) to give tert-butyl 5-((3,5-difluoro-4-(trimethylsilyl)phenyl)carbamoyl)-2-(hydroxymethyl)-7,8-dihydro-1,6-naphthyridine-6(5H)-carboxylate (2.09 g, 4.25 mmol, 66.7%) as a colorless oil.

$^1$H NMR (300 MHz, CDCl$_3$): δ 0.33 (9H, t, J=1.3 Hz), 1.55 (9H, s), 2.98-3.11 (2H, m), 3.51 (1H, brs), 3.72 (1H, t, J=4.9 Hz), 4.02-4.12 (1H, m), 4.75 (2H, d, J=4.5 Hz), 5.69 (1H, brs), 6.95-7.07 (2H, m), 7.16 (1H, d, J=7.9 Hz), 7.61 (1H, brs), 9.12 (1H, brs).

(Step 6)

Methanesulfonyl chloride (0.655 mL, 8.46 mmol) was added to a solution of tert-butyl 5-((3,5-difluoro-4-(trimethylsilyl)phenyl)carbamoyl)-2-(hydroxymethyl)-7,8-dihydro-1,6-naphthyridine-6(5H)-carboxylate (2.08 g, 4.23 mmol) and TEA (1.179 mL, 8.46 mmol) in THF (40 mL) at 0° C., and the mixture was stirred at the same temperature for 1 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give tert-butyl 5-((3,5-difluoro-4-(trimethylsilyl)phenyl)carbamoyl)-2-(((methylsulfonyl)oxy)methyl)-7,8-dihydro-1,6-naphthyridine-6(5H)-carboxylate (1.97 g, 3.46 mmol, 82%) as a colorless oil.

$^1$H NMR (300 MHz, CDCl$_3$): δ 0.33 (9H, t, J=1.3 Hz), 1.55 (9H, s), 2.97-3.08 (2H, m), 3.09 (3H, s), 3.50 (1H, brs), 4.06-4.16 (1H, m), 5.31 (2H, s), 5.72 (1H, brs), 6.95-7.06 (2H, m), 7.39 (1H, d, J=8.3 Hz), 7.66 (1H, brs), 9.11 (1H, brs).

(Step 7)

A solution of tert-butyl 5-((3,5-difluoro-4-(trimethylsilyl)phenyl)carbamoyl)-2-(((methylsulfonyl)oxy)methyl)-7,8-dihydro-1,6-naphthyridine-6(5H)-carboxylate (1.80 g, 3.16 mmol) in MeOH (40 mL) was stirred overnight at 60° C. The reaction mixture was neutralized with aqueous sodium hydrogen carbonate solution, and the mixture was extracted twice with ethyl acetate. The organic layer was washed with brine, and dried over magnesium sulfate, and the solvent was evaporated under reduced pressure. The obtained residue was purified by silica gel column chromatography (solvent gradient; 5→100% ethyl acetate/hexane; 0→10% MeOH/ethyl acetate) to give tert-butyl 5-((3,5-difluoro-4-(trimethylsilyl)phenyl)carbamoyl)-2-(methoxymethyl)-7,8-dihydro-1,6-naphthyridine-6(5H)-carboxylate (760 mg, 1.503 mmol) and N-(3,5-difluoro-4-(trimethylsilyl)phenyl)-2-(methoxymethyl)-5, 6,7,8-tetrahydro-1,6-naphthyridine-5-carboxamide (350 mg, 0.863 mmol), each as a white solid.

NMR spectrum of tert-butyl 5-((3,5-difluoro-4-(trimethylsilyl)phenyl)carbamoyl)-2-(methoxymethyl)-7,8-dihydro-1,6-naphthyridine-6(5H)-carboxylate $^1$H NMR (300 MHz, CDCl$_3$): δ 0.33 (9H, s), 1.54 (9H, s), 3.04 (2H, brs), 3.47 (5H, s), 4.56 (2H, s), 5.57-5.76 (1H, m), 7.02 (2H, d, J=8.7 Hz), 7.34 (1H, d, J=7.9 Hz), 7.48-7.74 (1H, m), 8.83-9.30 (1H, m).

NMR spectrum of N-(3,5-difluoro-4-(trimethylsilyl)phenyl)-2-(methoxymethyl)-5,6,7,8-tetrahydro-1,6-naphthyridine-5-carboxamide $^1$H NMR (300 MHz, CDCl$_3$): δ 0.26-0.40 (9H, m), 2.85-3.11 (2H, m), 3.12-3.36 (2H, m), 3.46 (3H, s), 4.53 (2H, d, J=1.9 Hz), 4.66 (1H, s), 7.09 (2H, d, J=9.1 Hz), 7.29 (1H, d, J=8.3 Hz), 7.96 (1H, d, J=7.9 Hz), 9.55-9.67 (1H, m).
(Step 8)

Boc$_2$O (0.240 mL, 1.04 mmol) was added to a solution of N-(3,5-difluoro-4-(trimethylsilyl)phenyl)-2-(methoxymethyl)-5,6,7,8-tetrahydro-1,6-naphthyridine-5-carboxamide (350 mg, 0.86 mmol) and TEA (0.144 mL, 1.04 mmol) in THF (7.0 mL) at room temperature, and the mixture was stirred at room temperature for 3 hr. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give tert-butyl 5-((3,5-difluoro-4-(trimethylsilyl)phenyl)carbamoyl)-2-(methoxymethyl)-7,8-dihydro-1,6-naphthyridine-6(5H)-carboxylate (429.8 mg, 0.850 mmol, 98%) as a white solid.

MS(API): Calculated 505.6. Found 504.2 (M−H).
(Step 9)

tert-Butyl 5-((3,5-difluoro-4-(trimethylsilyl)phenyl)carbamoyl)-2-(methoxymethyl)-7,8-dihydro-1,6-naphthyridine-6(5H)-carboxylate (1.53 g) was resolved by chiral column chromatography. The fraction having a shorter retention time was concentrated to give tert-butyl (R)-5-((3,5-difluoro-4-(trimethylsilyl)phenyl)carbamoyl)-2-(methoxymethyl)-7,8-dihydro-1,6-naphthyridine-6(5H)-carboxylate (0.54 g, >99% ee), and the fraction having a longer retention time was concentrated to give tert-butyl (S)-5-((3,5-difluoro-4-(trimethylsilyl)phenyl)carbamoyl)-2-(methoxymethyl)-7,8-dihydro-1,6-naphthyridine-6(5H)-carboxylate (0.50 g, >99% ee), each as a white solid.
purification condition by chiral column chromatography
    column: CHIRALCEL OD (NL001) 50 mmID×500 mmL
    solvent: hexane/EtOH=900/100
    flow rate: 80 mL/min
    temperature: 30° C.
    detection method: UV 220 nm
(Step 10)

Cooled TFA (3.0 mL) was added to tert-butyl (R)-5-((3,5-difluoro-4-(trimethylsilyl)phenyl)carbamoyl)-2-(methoxymethyl)-7,8-dihydro-1,6-naphthyridine-6(5H)-carboxylate (540 mg, 1.07 mmol) at room temperature, and the mixture was stirred at room temperature for 5 min. The reaction mixture was added to ice and aqueous sodium hydrogen carbonate solution, and the mixture was extracted with ethyl acetate. The organic layer was dried over magnesium sulfate, and the solvent was evaporated under reduced pressure to give (R)-N-(3,5-difluoro-4-(trimethylsilyl)phenyl)-2-(methoxymethyl)-5,6,7,8-tetrahydro-1,6-naphthyridine-5-carboxamide (415.3 mg, 1.024 mmol, 96%) as a white solid.

$^1$H NMR (300 MHz, CDCl$_3$): δ 0.29-0.37 (9H, m), 2.86-3.13 (2H, m), 3.14-3.35 (2H, m), 3.41-3.50 (3H, m), 4.46-4.60 (2H, m), 4.66 (1H, s), 5.05 (1H, brs), 7.03-7.16 (2H, m), 7.29 (1H, d, J=8.3 Hz), 7.96 (1H, d, J=7.9 Hz), 9.62 (1H, s).
(Step 11)

HATU (56.3 mg, 0.15 mmol) was added to a solution of (R)-N-(3,5-difluoro-4-(trimethylsilyl)phenyl)-2-(methoxymethyl)-5,6,7,8-tetrahydro-1,6-naphthyridine-5-carboxamide (50 mg, 0.12 mmol), 3-hydroxyisoxazole-5-carboxylic acid (19.10 mg, 0.15 mmol) and DIEA (0.042 mL, 0.25 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (35.3 mg, 0.068 mmol, 55.4%) as a white solid.

$^1$H NMR (300 MHz, DMSO-d$_6$): δ 0.31 (9H, s), 2.96-3.11 (1H, m), 3.13-3.26 (1H, m), 3.35 (3H, s), 3.92-4.08 (1H, m), 4.12-4.29 (1H, m), 4.47 (2H, s), 5.72-5.86 (1H, m), 6.40-6.68 (1H, m), 7.23 (2H, d, J=9.4 Hz), 7.36 (1H, d, J=7.9 Hz), 7.96 (1H, d, J=7.9 Hz), 10.68-11.10 (1H, m), 11.79 (1H, brs).

Example 137

(1R)-N-(3,5-difluoro-4-(1-methoxy-2-methylpropan-2-yl)phenyl)-2-((3-hydroxy-1,2-oxazol-5-yl)carbonyl)-6-(methoxymethyl)-1,2,3,4-tetrahydroisoquinoline-1-carboxamide (Step 1)

T3P (3.24 mL, 5.51 mmol) was added to a solution of 2-(tert-butoxycarbonyl)-6-(methoxymethyl)-1,2,3,4-tetrahydroisoquinoline-1-carboxylic acid (0.59 g, 1.84 mmol), 3,5-difluoro-4-(1-methoxy-2-methylpropan-2-yl)aniline (0.395 g, 1.84 mmol), DIEA (1.603 mL, 9.18 mmol) and DMAP (0.224 g, 1.84 mmol) in ethyl acetate (5 mL), and the mixture was stirred at 60° C. for 2 days. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5-60% ethyl acetate/hexane) to give tert-butyl 1-((3,5-difluoro-4-(1-methoxy-2-methylpropan-2-yl)phenyl)carbamoyl)-6-(methoxymethyl)-3,4-dihydroisoquinoline-2(1H)-carboxylate (0.690 g, 1.331 mmol, 72.5%) as a white solid.

$^1$H NMR (300 MHz, CDCl$_3$): δ 1.42 (6H, t, J=2.3 Hz), 1.52 (9H, s), 2.90 (2H, t, J=6.4 Hz), 3.30 (3H, s), 3.39 (3H, s), 3.51 (2H, s), 3.55-3.82 (2H, m), 4.44 (2H, s), 5.61 (1H, brs), 6.95-7.11 (2H, m), 7.15-7.24 (3H, m), 8.94 (1H, brs).
(Step 2)

tert-Butyl 1-((3,5-difluoro-4-(1-methoxy-2-methylpropan-2-yl)phenyl)carbamoyl)-6-(methoxymethyl)-3,4-dihydroisoquinoline-2(1H)-carboxylate (0.76 g) was resolved by chiral column chromatography. The fraction having a shorter retention time was concentrated to give tert-butyl (R)-1-((3,5-difluoro-4-(1-methoxy-2-methylpropan-2-yl)phenyl) carbamoyl)-6-(methoxymethyl)-3,4-dihydroisoquinoline-2(1H)-carboxylate (0.35 g, >99% ee), and the fraction having a longer retention time was concentrated to give tert-butyl (S)-1-((3,5-difluoro-4-(1-methoxy-2-methylpropan-2-yl)phenyl)carbamoyl)-6-(methoxymethyl)-3,4-dihydroisoquinoline-2(1H)-carboxylate (0.36 g, >99% ee), each as a white solid.
purification condition by chiral column chromatography
    column: CHIRALCEL OD (NL001) 50 mmID×500 mmL
    solvent: hexane/EtOH=900/100
    flow rate: 80 mL/min
    temperature: 30° C.
    detection method: UV 220 nm (Step 3)

4N Hydrogen chloride/ethyl acetate (4 mL) was added to tert-butyl (R)-1-((3,5-difluoro-4-(1-methoxy-2-methylpropan-2-yl)phenyl) carbamoyl)-6-(methoxymethyl)-3,4-dihydroisoquinoline-2(1H)-carboxylate (350 mg, 0.67 mmol) at room temperature, and the mixture was stirred overnight at room temperature. The reaction mixture was concentrated under reduced pressure to give (R)-N-(3,5-difluoro-4-(1-methoxy-2-methylpropan-2-yl)phenyl)-6-(methoxymethyl)-1,2,3,4-tetrahydroisoquinoline-1-carboxamide hydrochloride (307 mg, 0.675 mmol, 100%) as a white solid.

MS(API): Calculated 454.9. Found 417.2 (M−HCl−H.)

(Step 4)

A solution of (R)-N-(3,5-difluoro-4-(1-methoxy-2-methylpropan-2-yl)phenyl)-6-(methoxymethyl)-1,2,3,4-tetrahydroisoquinoline-1-carboxamide hydrochloride (307 mg, 0.73 mmol), DIEA (0.308 mL, 1.76 mmol), 3-hydroxyisoxazole-5-carboxylic acid (114 mg, 0.88 mmol) and COMU (346 mg, 0.81 mmol) in DMF (4 mL) was stirred at 0° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane), and then silica gel column chromatography (solvent gradient; 20-100% ethyl acetate/hexane), and crystallized from ethyl acetate/hexane to give the title compound (164 mg, 0.310 mmol, 42.2%) as a white solid.

$^1$H NMR (300 MHz, DMSO-d$_6$): δ 1.36 (6H, s), 2.84-2.99 (1H, m), 3.07-3.22 (4H, m), 3.28 (3H, s), 3.44 (2H, s), 3.66-3.83 (1H, m), 4.08-4.24 (1H, m), 4.38 (2H, s), 5.52-5.81 (1H, m), 6.41-6.68 (1H, m), 7.19 (4H, d, J=13.2 Hz), 7.57 (1H, d, J=8.3 Hz), 10.88 (1H, s), 11.76 (1H, s).

$[α]_D^{25}$ −7.9 (c 0.2505, MeOH)

Example 138

(5R)-N-(3,5-difluoro-4-(trimethylsilyl)phenyl)-6-((3-hydroxy-1,2-oxazol-5-yl)acetyl)-2-(methoxymethyl)-5,6,7,8-tetrahydro-1,6-naphthyridine-5-carboxamide HATU (56.3 mg, 0.15 mmol) was added to a solution of (R)-N-(3,5-difluoro-4-(trimethylsilyl)phenyl)-2-(methoxymethyl)-5,6,7,8-tetrahydro-1,6-naphthyridine-5-carboxamide (50 mg, 0.12 mmol), 2-(3-hydroxyisoxazol-5-yl)acetic acid and DIEA (0.042 mL, 0.25 mmol) in DMF (2.0 mL) at room temperature, and the mixture was stirred at room temperature for 2 hr. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and recrystallized from ethyl acetate/hexane to give the title compound (20.0 mg, 0.038 mmol, 30.6%) as white crystals.

$^1$H NMR (300 MHz, DMSO-d$_6$): δ 0.30 (9H, s), 2.89-3.05 (1H, m), 3.08-3.22 (1H, m), 3.34 (3H, s), 3.79-3.96 (1H, m), 3.96-4.19 (3H, m), 4.38-4.53 (2H, m), 5.75-5.97 (2H, m), 7.21 (2H, d, J=9.4 Hz), 7.33 (1H, d, J=7.9 Hz), 7.83-7.96 (1H, m), 10.76-10.99 (1H, m), 11.13 (1H, brs).

Example 139

5-((5R)-5-((3,5-difluoro-4-(trimethylsilyl)phenyl) carbamoyl)-2-(methoxymethyl)-7,8-dihydro-1, 6-naphthyridin-6(5H)-yl)-5-oxopentanoic acid The title compound was synthesized using (R)-N-(3,5-difluoro-4-(trimethylsilyl)phenyl)-2-(methoxymethyl)-5,6,7,8-tetrahydro-1,6-naphthyridine-5-carboxamide, by the reaction and purification in the same manner as in Example 109.

$^1$H NMR (300 MHz, DMSO-d$_6$): δ 0.30 (9H, s), 1.63-1.84 (2H, m), 2.15-2.40 (2H, m), 2.54-2.66 (1H, m), 2.87-3.04 (1H, m), 3.06-3.23 (1H, m), 3.34 (3H, s), 3.59 (1H, s), 3.71-3.90 (1H, m), 3.98-4.14 (1H, m), 4.45 (2H, s), 5.79 (1H, s), 7.15-7.36 (3H, m), 7.90 (1H, d, J=7.9 Hz), 10.78-10.95 (1H, m), 12.06 (1H, brs)

Example 140

5-((5R)-5-((3-fluoro-4-(trimethylsilyl)phenyl)carbamoyl)-2-methoxy-7,8-dihydro-1,6-naphthyridin-6 (5H)-yl)-5-oxopentanoic acid (Step 1)

T3P (8.45 mL, 14.21 mmol) was added to a solution of 6-(tert-butoxycarbonyl)-2-methoxy-5,6,7,8-tetrahydro-1,6-naphthyridine-5-carboxylic acid (2.92 g, 9.47 mmol), 3-fluoro-4-(trimethylsilyl)aniline (1.736 g, 9.47 mmol), DIEA (8.25 mL, 47.35 mmol) and DMAP (1.273 g, 10.42 mmol) in ethyl acetate (70 mL), and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure to give tert-butyl 5-((3-fluoro-4-(trimethylsilyl)phenyl)carbamoyl)-2-methoxy-7,8-dihydro-1,6-naphthyridine-6(5H)-carboxylate (3.66 g, 7.73 mmol, 82%) as a white solid.

$^1$H NMR (300 MHz, CDCl$_3$): δ 0.28 (9H, s), 1.53 (9H, s), 2.84-3.03 (2H, m), 3.46 (1H, brs), 3.92 (3H, s), 4.01-4.12 (1H, m), 5.59 (1H, brs), 6.64 (1H, d, J=8.3 Hz), 7.11 (1H, dd, J=8.1, 1.3 Hz), 7.29 (1H, dd, J=7.9, 6.4 Hz), 7.39 (1H, dd, J=10.6, 1.9 Hz), 7.47 (1H, brs), 8.94 (1H, brs).

(Step 2)

tert-Butyl 5-((3-fluoro-4-(trimethylsilyl)phenyl)carbamoyl)-2-methoxy-7,8-dihydro-1,6-naphthyridine-6(5H)-carboxylate (1.30 g) was resolved by chiral column chromatography. The fraction having a shorter retention time was concentrated to give tert-butyl (R)-5-((3-fluoro-4-(trimethylsilyl)phenyl)carbamoyl)-2-methoxy-7,8-dihydro-1,6-naphthyridine-6(5H)-carboxylate (0.62 g, >99% ee), and the fraction having a longer retention time was concentrated to give tert-butyl (S)-5-((3-fluoro-4-(trimethylsilyl)phenyl)carbamoyl)-2-methoxy-7,8-dihydro-1,6-naphthyridine-6(5H)-carboxylate (0.61 g, % ee was not measured), each as a white solid.

purification condition by chiral column chromatography
    column: CHIRALCEL OD (NL001) 50 mmID×500 mmL
    solvent: hexane/EtOH=900/100
    flow rate: 80 mL/min
    temperature: 30° C.
    detection method: UV 220 nm (Step 3)

Cooled TFA (8.5 mL) was added to tert-butyl (R)-5-((3-fluoro-4-(trimethylsilyl)phenyl)carbamoyl)-2-methoxy-7,8-dihydro-1,6-naphthyridine-6(5H)-carboxylate (622 mg, 1.31 mmol) at room temperature, and the mixture was stirred at room temperature for 3 min. The reaction mixture was added to ice and aqueous sodium hydrogen carbonate solution, and aqueous sodium hydrogen carbonate solution was added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(3-fluoro-4-(trimethylsilyl)phenyl)-2-methoxy-5,6,7,8-tetrahydro-1,6-naphthyridine-5-carboxamide (472 mg, 1.264 mmol, 96%) as a white solid.

MS(API): Calculated 373.5. Found 374.3 (M+H).

(Step 4)

Dihydro-2H-pyran-2,6(3H)-dione (159 mg, 1.39 mmol) was added to a solution of (R)-N-(3-fluoro-4-(trimethylsilyl)phenyl)-2-methoxy-5,6,7,8-tetrahydro-1,6-naphthyridine-5-carboxamide (472 mg, 1.26 mmol) and TEA (211 µL, 1.51 mmol) in THF (12 mL) at room temperature, and the mixture was stirred at room temperature for 15 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane) to give the title compound (411.3 mg, 0.844 mmol, 66.7%) as a white solid.

$^1$H NMR (300 MHz, CDCl$_3$): δ 0.23 (9H, s), 1.99-2.20 (2H, m), 2.41-2.62 (3H, m), 2.89 (1H, dt, J=14.8, 5.8 Hz), 2.98-3.10 (1H, m), 3.17-3.27 (1H, m), 3.92 (3H, s), 3.94-4.08 (2H, m), 5.93 (1H, s), 6.63 (1H, d, J=8.3 Hz), 6.91 (1H, dd, J=8.1, 1.7 Hz), 7.08-7.19 (2H, m), 7.69 (1H, d, J=8.7 Hz), 9.73 (1H, s).

$[α]_D^{25}$+97.8 (c 0.2525, MeOH)

Example 141

5-((1R)-1-((3,5-difluoro-4-(1-(2-methoxyethoxy)-2-methylpropan-2-yl)phenyl)carbamoyl)-6-ethoxy-3,4-dihydroisoquinolin-2(1H)-yl)-5-oxopentanoic acid The title compound was synthesized using (R)-N-(3,5-difluoro-4-(1-(2-methoxyethoxy)-2-methylpropan-2-yl)phenyl)-6-ethoxy-1,2,3,4-tetrahydroisoquinoline-1-carboxamide, by the reaction and purification in the same manner as in Example 109.

$^1$H NMR (300 MHz, DMSO-d$_6$): δ 1.30 (3H, t, J=7.0 Hz), 1.35 (6H, s), 1.62-1.84 (2H, m), 2.19-2.34 (2H, m), 2.38-2.61 (2H, m), 2.68-2.85 (1H, m), 3.04-3.21 (4H, m), 3.33-3.38 (2H, m), 3.40-3.48 (2H, m), 3.49-3.58 (3H, m), 3.88-4.08 (3H, m), 5.50-5.66 (1H, m), 6.67-6.89 (2H, m), 7.08-7.23 (2H, m), 7.43 (1H, d, J=9.4 Hz), 10.64 (1H, s), 11.98 (1H, brs).

Example 142

(1R)-N-(3,5-difluoro-4-(1-(2-methoxyethoxy)-2-methylpropan-2-yl)phenyl)-6-ethoxy-2-((3-hydroxy-1,2-oxazol-5-yl)carbonyl)-1,2,3,4-tetrahydroisoquinoline-1-carboxamide The title compound was synthesized using (R)-N-(3,5-difluoro-4-(1-(2-methoxyethoxy)-2-methylpropan-2-yl) phenyl)-6-ethoxy-1,2,3,4-tetrahydroisoquinoline-1-carboxamide, by the reaction and purification in the same manner as in Example 131.

$^1$H NMR (300 MHz, DMSO-d$_6$): δ 1.30 (3H, t, J=7.0 Hz), 1.36 (6H, s), 2.78-2.94 (1H, m), 3.07-3.23 (4H, m), 3.34-3.39 (2H, m), 3.42-3.48 (2H, m), 3.54 (2H, s), 3.65-3.81 (1H, m), 4.01 (2H, q, J=6.8 Hz), 4.10-4.22 (1H, m), 5.53-5.68 (1H, m), 6.58 (1H, s), 6.72-6.91 (2H, m), 7.09-7.30 (2H, m), 7.37-7.60 (1H, m), 10.81 (1H, s), 11.76 (1H, s).

Example 143

(1R)-N-(3,5-difluoro-4-(1-(2-methoxyethoxy)-2-methylpropan-2-yl)phenyl)-6-ethoxy-2-((3-hydroxy-1,2-oxazol-5-yl)acetyl)-1,2,3,4-tetrahydroisoquinoline-1-carboxamide (Step 1)

Sodium hydride (60% oil, 0.679 g, 16.99 mmol) was added to a solution of 2-(4-(bis(4-methoxybenzyl)amino)-2,6-difluorophenyl)-2-methylpropan-1-ol (3.0 g, 6.79 mmol), 1-bromo-2-methoxyethane (1.595 mL, 16.99 mmol) and sodium iodide (7.64 g, 50.96 mmol) in DMF (9 mL) at 5° C., and the mixture was stirred at 5° C. for 4 hr. DMF (3 mL) was added again thereto, and the mixture was stirred at room temperature for 14 hr. To the reaction mixture was added aqueous ammonium chloride solution, and the mixture was extracted twice with ethyl acetate. The organic layer was washed with brine, and dried over magnesium sulfate, and the solvent was evaporated under reduced pressure. The obtained residue was purified by silica gel column chromatography (solvent gradient; 5→20% ethyl acetate/hexane) to give 3,5-difluoro-N,N-bis(4-methoxybenzyl)-4-(1-(2-methoxyethoxy)-2-methylpropan-2-yl)aniline (2.65 g, 5.30 mmol, 78%) as a colorless oil.

$^1$H NMR (300 MHz, CDCl$_3$): δ 1.40 (6H, t, J=2.3 Hz), 3.33 (3H, s), 3.47-3.52 (2H, m), 3.53-3.58 (2H, m), 3.59 (2H, s), 3.79 (6H, s), 4.46 (4H, s), 6.17 (2H, d, J=14.4 Hz), 6.82-6.90 (4H, m), 7.10 (4H, d, J=8.7 Hz).

(Step 2)

A solution of 3,5-difluoro-N,N-bis(4-methoxybenzyl)-4-(1-(2-methoxyethoxy)-2-methylpropan-2-yl)aniline (2.65 g, 5.30 mmol), 1N hydrochloric acid (10.61 mL, 10.61 mmol) and 10% palladium-carbon (0.564 g, 0.27 mmol, 50% wet) in MeOH (100 mL) was stirred under hydrogen atmosphere (1 atm) at room temperature for 1.5 hr. The catalyst was filtered off, and the filtrate was concentrated under reduced pressure. The obtained residue was dissolved in ethyl acetate, the solution was washed with 1N aqueous sodium hydroxide solution and brine, and dried over magnesium sulfate, and the solvent was evaporated under reduced pressure. The obtained residue was purified by silica gel column chromatography (solvent gradient; 5→20% ethyl acetate/hexane) to give 3,5-difluoro-4-(1-(2-methoxyethoxy)-2-methylpropan-2-yl)aniline (1.090 g, 4.20 mmol, 79%) as a colorless oil.

$^1$H NMR (300 MHz, CDCl$_3$): δ 1.41 (6H, t, J=2.3 Hz), 3.34 (3H, s), 3.46-3.52 (2H, m), 3.53-3.58 (2H, m), 3.60 (2H, t, J=1.1 Hz), 3.67-3.86 (2H, m), 6.04-6.21 (2H, m).

(Step 3)

T3P (6.81 mL, 11.57 mmol) was added to a solution of 2-(tert-butoxycarbonyl)-6-ethoxy-1,2,3,4-tetrahydroisoquinoline-1-carboxylic acid (1.239 g, 3.86 mmol), 3,5-difluoro-4-(1-(2-methoxyethoxy)-2-methylpropan-2-yl)aniline (1 g, 3.86 mmol), DIEA (3.37 mL, 19.28 mmol) and DMAP (0.471 g, 3.86 mmol) in ethyl acetate (5 mL), and the mixture was stirred at 60° C. for 15 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5-60% ethyl acetate/hexane) to give tert-butyl 1-((3,5-difluoro-4-(1-(2-methoxyethoxy)-2-methylpropan-2-yl)phenyl)carbamoyl)-6-ethoxy-3,4-dihydroisoquinoline-2(1H)-carboxylate (1.690 g, 3.00 mmol, 78%) as a white solid.

$^{1}$H NMR (300 MHz, CDCl$_{3}$): δ 1.36-1.45 (9H, m), 1.52 (9H, s), 2.72-2.98 (2H, m), 3.32 (3H, s), 3.38-3.80 (8H, m), 4.03 (2H, q, J=7.2 Hz), 5.55 (1H, brs), 6.71 (1H, d, J=2.3 Hz), 6.79 (1H, dd, J=8.3, 2.6 Hz), 6.96-7.09 (2H, m), 7.17 (H, m), 7.17 (1H, brs), 8.95 (1H, brs).

(Step 4)

tert-Butyl 1-((3,5-difluoro-4-(1-(2-methoxyethoxy)-2-methylpropan-2-yl)phenyl)carbamoyl)-6-ethoxy-3,4-dihydroisoquinoline-2(1H)-carboxylate (1.70 g) was resolved by chiral column chromatography. The fraction having a shorter retention time was concentrated to give tert-butyl (R)-1-((3,5-difluoro-4-(1-(2-methoxyethoxy)-2-methylpropan-2-yl)phenyl)carbamoyl)-6-ethoxy-3,4-dihydroisoquinoline-2(1H)-carboxylate (0.75 g, >99% ee), and the fraction having a longer retention time was concentrated to give tert-butyl (S)-1-((3,5-difluoro-4-(1-(2-methoxyethoxy)-2-methylpropan-2-yl)phenyl)carbamoyl)-6-ethoxy-3,4-dihydroisoquinoline-2 (1H)-carboxylate (0.75 g, >99% ee), each as a white solid.

purification condition by chiral column chromatography
    column: CHIRALCEL OD (NL001) 50 mmID×500 mmL
    solvent: hexane/EtOH=900/100
    flow rate: 80 mL/min
    temperature: 30° C.
    detection method: UV 220 nm (Step 5)

Cooled TFA (6 mL) was added to tert-butyl (R)-1-((3,5-difluoro-4-(1-(2-methoxyethoxy)-2-methylpropan-2-yl)phenyl)carbamoyl)-6-ethoxy-3,4-dihydroisoquinoline-2 (1H)-carboxylate (0.75 g, 1.33 mmol) at 0° C., and the mixture was stirred at 0° C. for 1 hr. The reaction mixture was added to aqueous sodium hydrogen carbonate solution, and the mixture was extracted with ethyl acetate. The organic layer was dried over magnesium sulfate, and the solvent was evaporated under reduced pressure to give (R)-N-(3,5-difluoro-4-(1-(2-methoxyethoxy)-2-methylpropan-2-yl)phenyl)-6-ethoxy-1,2,3,4-tetrahydroisoquinoline-1-carboxamide (0.740 g, 1.600 mmol, 120%) as a white solid.

MS(API): Calculated 462.5. Found 461.2 (M−H).

(Step 6)

HATU (46.4 mg, 0.12 mmol) was added to a solution of (R)-N-(3,5-difluoro-4-(1-(2-methoxyethoxy)-2-methylpropan-2-yl)phenyl)-6-ethoxy-1,2,3,4-tetrahydroisoquinoline-1-carboxamide (47 mg, 0.10 mmol), DIEA (0.021 mL, 0.12 mmol) and 2-(3-hydroxyisoxazol-5-yl)acetic acid (17.45 mg, 0.12 mmol) in DMF (4 mL) at room temperature, and the mixture was stirred at room temperature for 1 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 5→90% ethyl acetate/hexane), and crystallized from ethyl acetate/hexane to give the title compound (28.0 mg, 0.048 mmol, 46.9%) as a white solid.

$^{1}$H NMR (300 MHz, DMSO-d$_{6}$): δ 1.30 (3H, t, J=7.0 Hz), 1.35 (6H, s), 2.75-2.88 (1H, m), 3.04-3.20 (4H, m), 3.33-3.39 (2H, m), 3.41-3.48 (2H, m), 3.49-3.66 (3H, m), 3.87-4.14 (5H, m), 5.61 (1H, s), 5.90 (1H, s), 6.71-6.90 (2H, m), 7.07-7.25 (2H, m), 7.45 (1H, d, J=9.1 Hz), 10.68 (1H, s), 11.11 (1H, brs).

Example 144

5-((1R)-1-((4-tert-butyl-3,5-difluorophenyl)carbamoyl)-6-(methoxymethyl)-3,4-dihydroisoquinolin-2 (1H)-yl)-5-oxopentanoic acid (Step 1)

T3P (4.34 mL, 7.37 mmol) was added to a solution of 2-(tert-butoxycarbonyl)-6-(methoxymethyl)-1,2,3,4-tetrahydroisoquinoline-1-carboxylic acid (790 mg, 2.46 mmol), 4-(tert-butyl)-3,5-difluoroaniline (455 mg, 2.46 mmol), DIEA (2.147 mL, 12.29 mmol) and DMAP (300 mg, 2.46 mmol) in ethyl acetate (5 mL), and the mixture was stirred at 65° C. for 8 hr. To the reaction mixture was added ethyl acetate. The organic layer was washed with water and brine, and dried over magnesium sulfate, and the solvent was evaporated under reduced pressure. The obtained residue was purified by silica gel column chromatography (solvent gradient; 5→60% ethyl acetate/hexane) to give tert-butyl 1-((4-(tert-butyl)-3,5-difluorophenyl) carbamoyl)-6-(methoxymethyl)-3,4-dihydroisoquinoline-2(1H)-carboxylate (1140 mg, 2.333 mmol, 95%) as white crystals.

$^{1}$H NMR (300 MHz, CDCl$_{3}$): δ 1.41 (9H, t, J=2.3 Hz), 1.52 (9H, s), 2.80-3.01 (2H, m), 3.39 (3H, s), 3.45-3.83 (2H, m), 4.44 (2H, s), 5.61 (1H, brs), 6.93-7.09 (2H, m), 7.14-7.24 (3H, m), 8.96 (1H, s).

(Step 2)

tert-Butyl 1-((4-(tert-butyl)-3,5-difluorophenyl) carbamoyl)-6-(methoxymethyl)-3,4-dihydroisoquinoline-2(1H)-carboxylate (1.05 g) was resolved by chiral column chromatography. The fraction having a shorter retention time was concentrated to give tert-butyl (R)-1-((4-(tert-butyl)-3,5-difluorophenyl)carbamoyl)-6-(methoxymethyl)-3,4-dihydroisoquinoioline-2(1H)-carboxylate (0.46 g, >99% ee), and the fraction having a longer retention time was concentrated to give tert-butyl (S)-1-((4-(tert-butyl)-3,5-difluorophenyl) carbamoyl)-6-(methoxymethyl)-3,4-dihydroisoquinoline-2 (1H)-carboxylate (0.49 g, >99% ee), each as a white solid.

purification condition by chiral column chromatography
    column: CHIRALCEL OD (NL001) 50 mmID×500 mmL
    solvent: hexane/EtOH=900/100
    flow rate: 80 mL/min
    temperature: 30° C.
    detection method: UV 220 nm (Step 3)

4N Hydrogen chloride/ethyl acetate (4 mL) was added to a solution of tert-butyl (R)-1-((4-(tert-butyl)-3,5-difluorophenyl)carbamoyl)-6-(methoxymethyl)-3,4-dihydroisoquinoline-2(1H)-carboxylate (0.459 g, 0.94 mmol) in ethyl acetate (2 mL) at room temperature, and the mixture was stirred overnight at room temperature. The reaction mixture was concentrated under reduced pressure, and the residue was crystallized from ethyl acetate/hexane to give (R)-N-(4-(tert-butyl)-3,5-difluorophenyl)-6-(methoxymethyl)-1,2,3,4-tetrahydroisoquinoline-1-carboxamide hydrochloride (0.403 g, 0.948 mmol, 101%) as white crystals.

MS(API): Calculated 424.9. Found 389.3 (M−HCl+H).

(Step 4)

Dihydro-2H-pyran-2,6(3H)-dione (13.43 mg, 0.12 mmol) was added to a solution of (R)-N-(4-(tert-butyl)-3,5-difluorophenyl)-6-(methoxymethyl)-1,2,3,4-tetrahydroisoquinoline-1-carboxamide hydrochloride (50 mg, 0.12 mmol) and TEA (0.017 mL, 0.12 mmol) in THF (4 mL) at room temperature, and the mixture was stirred at 60° C. for 3 hr. The reaction mixture was concentrated under reduced pressure, and the obtained residue was purified by silica gel column chromatography (solvent gradient; 5→100% ethyl acetate/hexane, 0→10% MeOH/ethyl acetate) to give the title compound (51.0 mg, 0.101 mmol, 86%) as a white solid.

$^1$H NMR (300 MHz, DMSO-$d_6$): δ 1.38 (9H, t, J=1.9 Hz), 1.73 (2H, dq, J=14.4, 7.4 Hz), 2.26 (4H, dt, J=11.5, 7.3 Hz), 2.78-2.92 (1H, m), 3.04-3.19 (1H, m), 3.27 (3H, s), 3.48-3.64 (1H, m), 3.93-4.09 (1H, m), 4.36 (2H, s), 5.68 (1H, s), 7.09-7.27 (4H, m), 7.51 (1H, d, J=7.9 Hz), 10.70 (1H, s), 12.03 (1H, brs).

$[α]_D^{25}$+0.9 (c 0.2505, MeOH)

Example 145

(5R)-2-ethoxy-N-(7-fluoro-1,1-dimethyl-2,3-dihydro-1H-inden-5-yl)-6-((3-hydroxy-1,2-oxazol-5-yl)carbonyl)-5,6,7,8-tetrahydro-1, 6-naphthyridine-5-carboxamide (Step 1)
T3P (3.60 mL, 6.05 mmol) was added to a solution of 6-(tert-butoxycarbonyl)-2-ethoxy-5,6,7,8-tetrahydro-1,6-naphthyridine-5-carboxylic acid (1.30 g, 4.03 mmol), 7-fluoro-1,1-dimethyl-2,3-dihydro-1H-inden-5-amine (0.723 g, 4.03 mmol), DIEA (3.51 mL, 20.16 mmol) and DMAP (0.542 g, 4.44 mmol) in ethyl acetate (30 mL), and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with hexane to give tert-butyl 2-ethoxy-5-((7-fluoro-1,1-dimethyl-2,3-dihydro-1H-inden-5-yl)carbamoyl)-7,8-dihydro-1,6-naphthyridine-6(5H)-carboxylate (1.51 g, 3.12 mmol, 77%) as white crystals.

$^1$H NMR (300 MHz, CDCl$_3$): δ 1.34 (6H, s), 1.38 (3H, t, J=7.0 Hz), 1.53 (9H, s), 1.91 (2H, t, J=7.4 Hz), 2.81-3.01 (4H, m), 3.45 (1H, brs), 4.01-4.14 (1H, m), 4.28-4.37 (2H, m), 5.56 (1H, brs), 6.61 (1H, d, J=8.3 Hz), 7.05-7.12 (2H, m), 7.49 (1H, brs), 8.77 (1H, brs).

(Step 2)
tert-Butyl 2-ethoxy-5-((7-fluoro-1,1-dimethyl-2,3-dihydro-1H-inden-5-yl) carbamoyl)-7,8-dihydro-1, 6-naphthyridine-6(5H)-carboxylate (1.50 g) was resolved by chiral column chromatography. The fraction having a shorter retention time was concentrated to give tert-butyl (R)-2-ethoxy-5-((7-fluoro-1,1-dimethyl-2,3-dihydro-1H-inden-5-yl) carbamoyl)-7,8-dihydro-1, 6-naphthyridine-6 (5H)-carboxylate (0.69 g, >99% ee), and the fraction having a longer retention time was concentrated to give tert-butyl (S)-2-ethoxy-5-((7-fluoro-1,1-dimethyl-2,3-dihydro-1H-inden-5-yl)carbamoyl)-7,8-dihydro-1,6-naphthyridine-6(5H)-carboxylate (0.68 g, >99% ee), each as a white solid.

purification condition by chiral column chromatography
    column: CHIRALCEL OD (NL001) 50 mmID×500 mmL
    solvent: hexane/EtOH=900/100
    flow rate: 80 mL/min
    temperature: 30° C.
    detection method: UV 220 nm (Step 3)
Cooled TFA (9.5 mL) was added to tert-butyl (R)-2-ethoxy-5-((7-fluoro-1,1-dimethyl-2,3-dihydro-1H-inden-5-yl) carbamoyl)-7,8-dihydro-1, 6-naphthyridine-6 (5H)-carboxylate (688 mg, 1.42 mmol) at room temperature, and the mixture was stirred at room temperature for 15 min. The reaction mixture was added to ice and aqueous sodium hydrogen carbonate solution, and 8N aqueous sodium hydroxide solution and potassium carbonate were added thereto until the pH of the mixture became 8. Then, the mixture was extracted three times with ethyl acetate. The organic layer was washed with brine, and dried over magnesium sulfate, and the solvent was evaporated under reduced pressure to give (R)-2-ethoxy-N-(7-fluoro-1,1-dimethyl-2,3-dihydro-1H-inden-5-yl)-5,6,7,8-tetrahydro-1, 6-naphthyridine-5-carboxamide (532 mg, 1.387 mmol, 98%) as a white solid.

MS(API): Calculated 383.5. Found 384.3 (M+H).

(Step 4)
HATU (106 mg, 0.28 mmol) was added to a solution of (R)-2-ethoxy-N-(7-fluoro-1,1-dimethyl-2,3-dihydro-1H-inden-5-yl)-5,6,7,8-tetrahydro-1,6-naphthyridine-5-carboxamide (82 mg, 0.21 mmol), 3-hydroxyisoxazole-5-carboxylic acid (33.1 mg, 0.26 mmol) and DIEA (74 μL, 0.42 mmol) in DMF (1.1 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 15→85% ethyl acetate/hexane) to give the title compound (66.4 mg, 0.134 mmol, 62.8%) as a white solid.

$^1$H NMR (300 MHz, CDCl$_3$): δ 1.34 (6H, s), 1.39 (3H, t, J=7.0 Hz), 1.91 (2H, t, J=7.4 Hz), 2.82-2.92 (3H, m), 2.97-3.06 (1H, m), 3.13-3.27 (1H, m), 3.76-3.88 (1H, m), 4.30-4.40 (3H, m), 5.94 (1H, s), 6.57 (1H, s), 6.65 (1H, d, J=8.7 Hz), 7.08 (1H, s), 7.15 (1H, d, J=11.7 Hz), 7.40 (1H, d, J=8.7 Hz), 8.88 (1H, s).

Example 146

(5S)-2-ethoxy-N-(7-fluoro-1,1-dimethyl-2,3-dihydro-1H-inden-5-yl)-6-((3-hydroxy-1,2-oxazol-5-yl)carbonyl)-5,6,7,8-tetrahydro-1, 6-naphthyridine-5-carboxamide The title compound was synthesized using tert-butyl (S)-2-ethoxy-5-((7-fluoro-1,1-dimethyl-2,3-dihydro-1H-inden-5-yl)carbamoyl)-7,8-dihydro-1,6-naphthyridine-6(5H)-carboxylate, by the reaction and purification in the same manner as in Steps 3 to 4 of Example 145.

$^1$H NMR (300 MHz, CDCl$_3$): δ 1.34 (6H, s), 1.39 (3H, t, J=7.0 Hz), 1.91 (2H, t, J=7.4 Hz), 2.83-2.92 (3H, m), 2.97-3.07 (1H, m), 3.13-3.26 (1H, m), 3.76-3.88 (1H, m), 4.30-4.39 (3H, m), 5.94 (1H, s), 6.57 (1H, s), 6.65 (1H, d, J=8.3 Hz), 7.08 (1H, s), 7.15 (1H, d, J=11.7 Hz), 7.40 (1H, d, J=8.7 Hz), 8.90 (1H, s).

Example 147

(5R)-2-ethoxy-N-(7-fluoro-1,1-dimethyl-2,3-dihydro-1H-inden-5-yl)-6-((3-hydroxy-1,2-oxazol-5-yl)acetyl)-5,6,7,8-tetrahydro-1,6-naphthyridine-5-carboxamide HATU (110 mg, 0.29 mmol) was added to a solution of (R)-2-ethoxy-N-(7-fluoro-1,1-dimethyl-2,3-dihydro-1H-inden-5-yl)-5,6,7,8-tetrahydro-1,6-naphthyridine-5-carboxamide (85 mg, 0.22 mmol), 2-(3-hydroxyisoxazol-5-yl)acetic acid (38.1 mg, 0.27 mmol) and DIEA (77 μL, 0.44 mmol) in DMF (1.1 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 10→80% ethyl acetate/hexane), and the precipitate was collected by filtration and washed with IPE/hexane to give the title compound (52.4 mg, 0.103 mmol, 46.5%) as white crystals.

$^1$H NMR (300 MHz, CDCl$_3$): δ 1.30 (6H, s), 1.36 (3H, t, J=7.0 Hz), 1.87 (2H, t, J=7.4 Hz), 2.78-3.00 (4H, m), 3.02-3.13 (1H, m), 3.89-3.97 (4H, m), 4.25-4.37 (2H, m), 5.96 (2H, s), 6.62 (1H, d, J=8.7 Hz), 6.94 (1H, s), 7.07 (1H, d, J=11.7 Hz), 7.43 (1H, d, J=8.3 Hz), 8.95 (1H, s)

Example 148

5-((5R)-2-ethoxy-5-((7-fluoro-1,1-dimethyl-2,3-dihydro-1H-inden-5-yl) carbamoyl)-7,8-dihydro-1,6-naphthyridin-6(5H)-yl)-5-oxopentanoic acid The title compound was synthesized using (R)-2-ethoxy-N-(7-fluoro-1,1-dimethyl-2,3-dihydro-1H-inden-5-yl)-5,6,7,8-tetrahydro-1,6-naphthyridine-5-carboxamide, by the reaction and purification in the same manner as in Example 109.

$^1$H NMR (300 MHz, CDCl$_3$): δ 1.29 (6H, d, J=1.5 Hz), 1.38 (3H, t, J=7.0 Hz), 1.85 (2H, t, J=7.4 Hz), 2.02-2.15 (2H, m), 2.45 (2H, t), 2.57 (1H, dt, J=15.2, 7.3 Hz), 2.71-2.88 (3H, m), 2.94-3.17 (2H, m), 3.91-3.98 (2H, m), 4.33 (2H, qd), 5.94 (1H, s), 6.60 (1H, d, J=8.7 Hz), 6.91 (1H, s), 7.04 (1H, d, J=12.1 Hz), 7.59 (1H, d, J=8.7 Hz), 9.37 (1H, s).

Example 149

(5R)-2-ethoxy-N-(3-fluoro-4-(trimethylsilyl)phenyl)-6-((3-hydroxy-1,2-oxazol-5-yl)carbonyl)-5,6,7,8-tetrahydro-1,6-naphthyridine-5-carboxamide (Step 1)
T3P (3.46 mL, 5.82 mmol) was added to a solution of 6-(tert-butoxycarbonyl)-2-ethoxy-5,6,7,8-tetrahydro-1,6-naphthyridine-5-carboxylic acid (1.25 g, 3.88 mmol), 3-fluoro-4-(trimethylsilyl)aniline (0.711 g, 3.88 mmol), DIEA (3.38 mL, 19.39 mmol) and DMAP (0.521 g, 4.27 mmol) in ethyl acetate (29 mL), and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was collected by filtration and washed with cooled hexane to give tert-butyl 2-ethoxy-5-((3-fluoro-4-(trimethylsilyl)phenyl)carbamoyl)-7,8-dihydro-1,6-naphthyridine-6(5H)-carboxylate (1.50 g, 3.08 mmol, 79%) as white crystals.

$^1$H NMR (300 MHz, CDCl$_3$): δ 0.28 (9H, d, J=0.8 Hz), 1.38 (3H, t, J=7.0 Hz), 1.53 (9H, s), 2.82-3.01 (2H, m), 3.46 (1H, brs), 4.01-4.14 (1H, m), 4.29-4.37 (2H, m), 5.58 (1H, brs), 6.62 (1H, d, J=8.7 Hz), 7.11 (1H, dd, J=7.9, 1.5 Hz), 7.29 (1H, dd), 7.39 (1H, dd, J=10.4, 1.7 Hz), 7.47 (1H, brs), 8.92 (1H, brs).

(Step 2)
tert-Butyl 2-ethoxy-5-((3-fluoro-4-(trimethylsilyl)phenyl)carbamoyl)-7,8-dihydro-1,6-naphthyridine-6(5H)-carboxylate (1.50 g) was resolved by chiral column chromatography. The fraction having a shorter retention time was concentrated to give tert-butyl (R)-2-ethoxy-5-((3-fluoro-4-(trimethylsilyl)phenyl)carbamoyl)-7,8-dihydro-1,6-naphthyridine-6(5H)-carboxylate (0.68 g, >99% ee), and the fraction having a longer retention time was concentrated to give tert-butyl (S)-2-ethoxy-5-((3-fluoro-4-(trimethylsilyl)phenyl)carbamoyl)-7,8-dihydro-1,6-naphthyridine-6(5H)-carboxylate (0.68 g, >99% ee), each as a white solid.

purification condition by chiral column chromatography
   column: CHIRALCEL OD (NL001) 50 mmID×500 mmL
   solvent: hexane/EtOH=900/100
   flow rate: 80 mL/min
   temperature: 30° C.
   detection method: UV 220 nm (Step 3)
Cooled TFA (9.5 mL) was added to tert-butyl (R)-2-ethoxy-5-((3-fluoro-4-(trimethylsilyl)phenyl)carbamoyl)-7,8-dihydro-1,6-naphthyridine-6(5H)-carboxylate (680 mg, 1.39 mmol), and the mixture was stirred at room temperature for 3 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The residue was crystallized from cooled hexane to give (R)-2-ethoxy-N-(3-fluoro-4-(trimethylsilyl)phenyl)-5,6,7,8-tetrahydro-1,6-naphthyridine-5-carboxamide (525 mg, 1.355 mmol, 97%) as white crystals.

MS(API): Calculated 387.5. Found 388.3 (M+H).

(Step 4)
HATU (98 mg, 0.26 mmol) was added to a solution of (R)-2-ethoxy-N-(3-fluoro-4-(trimethylsilyl)phenyl)-5,6,7,8-tetrahydro-1,6-naphthyridine-5-carboxamide (77 mg, 0.20 mmol), 3-hydroxyisoxazole-5-carboxylic acid (30.8 mg, 0.24 mmol) and DIEA (69 μL, 0.40 mmol) in DMF (1 mL) at room temperature, and the mixture was stirred at room temperature for 15 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 15→85% ethyl acetate/hexane) to give the title compound (71.6 mg, 0.144 mmol, 72.3%) as a white solid.

$^1$H NMR (300 MHz, CDCl$_3$): δ 0.28 (9H, d, J=0.8 Hz), 1.39 (3H, t, J=7.0 Hz), 2.83 (1H, s), 2.97-3.07 (1H, m), 3.14-3.28 (1H, m), 3.76-3.87 (1H, m), 4.31-4.40 (3H, m), 5.96 (1H, s), 6.58 (1H, s), 6.66 (1H, d, J=8.7 Hz), 7.17 (1H, dd, J=7.9, 1.5 Hz), 7.30 (1H, dd, J=7.7, 6.2 Hz), 7.37-7.43 (2H, m), 9.02 (1H, s).

Example 150

(5S)-2-ethoxy-N-(3-fluoro-4-(trimethylsilyl)phenyl)-6-((3-hydroxy-1,2-oxazol-5-yl)carbonyl)-5,6,7,8-tetrahydro-1,6-naphthyridine-5-carboxamide The title compound was synthesized using tert-butyl (S)-2-ethoxy-5-((3-fluoro-4-(trimethylsilyl)phenyl)carbamoyl)-7,8-dihydro-1,6-naphthyridine-6(5H)-carboxylate, by the reaction and purification in the same manner as in Steps 3 to 4 of Example 149.

¹H NMR (300 MHz, CDCl₃): δ 0.28 (9H, s), 1.39 (3H, t, J=7.0 Hz), 2.91 (1H, s), 2.98-3.08 (1H, m), 3.14-3.27 (1H, m), 3.77-3.89 (1H, m), 4.31-4.40 (3H, m), 5.96 (1H, s), 6.58 (1H, s), 6.66 (1H, d, J=8.7 Hz), 7.16 (1H, dd, J=7.9, 1.9 Hz), 7.30 (1H, dd, J=7.9, 6.4 Hz), 7.37-7.44 (2H, m), 9.04 (1H, s).

Example 151

(5R)-2-ethoxy-N-(3-fluoro-4-(trimethylsilyl)phenyl)-6-((3-hydroxy-1,2-oxazol-5-yl)acetyl)-5,6,7,8-tetrahydro-1,6-naphthyridine-5-carboxamide HATU (102 mg, 0.27 mmol) was added to a solution of (R)-2-ethoxy-N-(3-fluoro-4-(trimethylsilyl)phenyl)-5,6,7,8-tetrahydro-1,6-naphthyridine-5-carboxamide (80 mg, 0.21 mmol), 2-(3-hydroxyisoxazol-5-yl)acetic acid (35.4 mg, 0.25 mmol) and DIEA (72 μL, 0.41 mmol) in DMF (1 mL) at room temperature, and the mixture was stirred at room temperature for 15 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 10→80% ethyl acetate/hexane), and the obtained precipitate was collected by filtration and washed with IPE/hexane to give the title compound (49.7 mg, 0.097 mmol, 47.0%) as a white solid.

¹H NMR (300 MHz, CDCl₃): δ 0.25 (9H, s), 1.36 (3H, t, J=7.0 Hz), 2.88-3.00 (2H, m), 3.10 (1H, dt), 3.89-3.99 (4H, m), 4.31 (2H, qd, J=7.1, 2.3 Hz), 5.96 (1H, s), 5.98 (1H, s), 6.63 (1H, d, J=8.7 Hz), 7.01 (1H, dd, J=7.9, 1.9 Hz), 7.22 (1H, dd, J=7.9, 6.4 Hz), 7.25-7.31 (1H, m), 7.43 (1H, d, J=8.7 Hz), 9.08 (1H, s).

Example 152

5-((5R)-2-ethoxy-5-((3-fluoro-4-(trimethylsilyl)phenyl)carbamoyl)-7,8-dihydro-1,6-naphthyridin-6(5H)-yl)-5-oxopentanoic acid Dihydro-2H-pyran-2,6(3H)-dione (26.6 mg, 0.23 mmol) was added to a solution of (R)-2-ethoxy-N-(3-fluoro-4-(trimethylsilyl)phenyl)-5,6,7,8-tetrahydro-1,6-naphthyridine-5-carboxamide (82 mg, 0.21 mmol) and TEA (35 μL, 0.25 mmol) in THF (2 mL) at room temperature, and the mixture was stirred at room temperature for 7.5 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane) to give the title compound (53.1 mg, 0.106 mmol, 50.0%) as a white solid.

¹H NMR (300 MHz, CDCl₃): δ 0.23 (9H, s), 1.37 (3H, t, J=7.0 Hz), 2.04-2.17 (2H, m), 2.44 (2H, t, J=6.2 Hz), 2.50-2.62 (1H, m), 2.88 (1H, dt, J=15.0, 5.9 Hz), 2.96-3.08 (1H, m), 3.19 (1H, dt), 3.93-4.07 (2H, m), 4.29-4.37 (2H, m), 5.92 (1H, s), 6.60 (1H, d, J=8.7 Hz), 6.92 (1H, dd, J=7.9, 1.9 Hz), 7.08-7.19 (2H, m), 7.67 (1H, d, J=8.7 Hz), 9.72 (1H, s).

Example 153

5-((1R)-1-((4-(1-(2,2-difluoroethoxy)-2-methylpropan-2-yl)-3,5-difluorophenyl)carbamoyl)-6-ethoxy-3,4-dihydroisoquinolin-2 (1H)-yl)-5-oxopentanoic acid (Step 1)
Sodium hydride (60% oil, 0.408 g, 10.19 mmol) was added to a solution of 2-(4-(bis(4-methoxybenzyl)amino)-2,6-difluorophenyl)-2-methylpropan-1-ol (3.0 g, 6.79 mmol) and 2,2-difluoroethyl trifluoromethanesulfonate (1.381 mL, 10.19 mmol) in THF (15 mL) at 5° C., and the mixture was stirred at 5° C. for 4 hr. To the reaction mixture was added aqueous ammonium chloride solution, and the mixture was extracted twice with ethyl acetate. The organic layer was washed with brine, and dried over magnesium sulfate, and the solvent was evaporated under reduced pressure. The obtained residue was purified by silica gel column chromatography (solvent gradient; 5-20% ethyl acetate/hexane) to give 4-(1-(2,2-difluoroethoxy)-2-methylpropan-2-yl)-3,5-difluoro-N,N-bis(4-methoxybenzyl)aniline (3.52 g, 6.96 mmol, 102%) as a colorless oil.

¹H NMR (300 MHz, CDCl₃): δ 1.36-1.45 (6H, m), 3.56-3.69 (4H, m), 3.78-3.82 (6H, m), 4.47 (4H, s), 5.56-6.03 (1H, m), 6.18 (2H, d, J=14.7 Hz), 6.79-6.93 (4H, m), 7.02-7.33 (4H, m).

(Step 2)
A solution of 4-(1-(2,2-difluoroethoxy)-2-methylpropan-2-yl)-3,5-difluoro-N,N-bis(4-methoxybenzyl)aniline (3.52 g, 6.96 mmol), 10% palladium-carbon (0.741 g, 0.35 mmol, 50% wet) and 1N hydrochloric acid (13.93 mL, 13.93 mmol) in MeOH (150 mL) was stirred under hydrogen atmosphere (4 atm) at room temperature for 1.5 hr. The catalyst was removed by filtration, and the filtrate was concentrated under reduced pressure. The obtained residue was dissolved in ethyl acetate, and the organic layer was washed with 1N aqueous sodium hydroxide solution and brine, and dried over magnesium sulfate, and the solvent was evaporated under reduced pressure. The obtained residue was purified by silica gel column chromatography (solvent gradient; 5→20% ethyl acetate/hexane) to give 4-(1-(2,2-difluoroethoxy)-2-methylpropan-2-yl)-3,5-difluoroaniline (1.720 g, 6.48 mmol, 93%) as a colorless oil.

¹H NMR (300 MHz, CDCl₃): δ 1.41 (6H, t, J=2.3 Hz), 3.51-3.85 (6H, m), 5.79 (1H, s), 6.07-6.20 (2H, m).

(Step 3)
T3P (5.66 mL, 9.61 mmol) was added to a mixture of 2-(tert-butoxycarbonyl)-6-ethoxy-1,2,3,4-tetrahydroisoquinoline-1-carboxylic acid (1030 mg, 3.20 mmol), 4-(1-(2,2-difluoroethoxy)-2-methylpropan-2-yl)-3,5-difluoroaniline (850 mg, 3.20 mmol), DIEA (2.80 mL, 16.02 mmol) and DMAP (391 mg, 3.20 mmol) in ethyl acetate (30 mL), and the mixture was stirred overnight at 60° C. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→40% ethyl acetate/hexane), and crystallized from ethyl acetate/hexane to give tert-butyl 1-((4-(1-(2,2-difluoroethoxy)-2-methylpropan-2-yl)-3,5-difluorophenyl)carbamoyl)-6-ethoxy-3,4-dihydroisoquinoline-2(1H)-carboxylate (1190 mg, 2.093 mmol, 65.3%) as a white solid.

1H NMR (300 MHz, CDCl3)d 1.35-1.46 (9H, m), 1.51 (9H, s), 2.71-2.98 (2H, m), 3.50-3.78 (6H, m), 4.03 (2H, q,

J=7.2 Hz), 5.41-6.03 (2H, m), 6.72 (1H, s), 6.80 (1H, dd, J=8.5, 2.5 Hz), 6.97-7.10 (2H, m), 7.15 (1H, brs), 8.94 (1H, brs).

(Step 4)

tert-Butyl 1-((4-(1-(2,2-difluoroethoxy)-2-methylpropan-2-yl)-3,5-difluorophenyl)carbamoyl)-6-ethoxy-3,4-dihydroisoquinoline-2(1H)-carboxylate (1.05 g) was resolved by chiral column chromatography. The fraction having a shorter retention time was concentrated to give tert-butyl (R)-1-((4-(1-(2,2-difluoroethoxy)-2-methylpropan-2-yl)-3,5-difluorophenyl)carbamoyl)-6-ethoxy-3,4-dihydroisoquinoline-2(1H)-carboxylate (0.49 g, >99% ee), and the fraction having a longer retention time was concentrated to give tert-butyl (S)-1-((4-(1-(2,2-difluoroethoxy)-2-methylpropan-2-yl)-3,5-difluorophenyl)carbamoyl)-6-ethoxy-3,4-dihydroisoquinoline-2(1H)-carboxylate (0.48 g, 97.9% ee), each as a white solid.

purification condition by chiral column chromatography
  column: CHIRALCEL OD (NL001) 50 mmID×500 mmL
  solvent: hexane/EtOH=900/100
  flow rate: 80 mL/min
  temperature: 30° C.
  detection method: UV 220 nm (Step 5)

4N Hydrogen chloride/ethyl acetate (4 mL) was added to a solution of tert-butyl (R)-1-((4-(1-(2,2-difluoroethoxy)-2-methylpropan-2-yl)-3,5-difluorophenyl)carbamoyl)-6-ethoxy-3,4-dihydroisoquinoline-2(1H)-carboxylate (0.49 g, 0.86 mmol) in ethyl acetate (2 mL), and the mixture was stirred overnight at room temperature. The precipitate was collected by filtration with ethyl acetate/hexane to give (R)-N-(4-(1-(2,2-difluoroethoxy)-2-methylpropan-2-yl)-3,5-difluorophenyl)-6-ethoxy-1,2,3,4-tetrahydroisoquinoline-1-carboxamide hydrochloride (0.392 g, 0.776 mmol, 90%) as a white solid.

MS(API): Calculated 504.9. Found 469.4 (M−HCl+H).

(Step 6)

Dihydro-2H-pyran-2,6(3H)-dione (9.72 mg, 0.09 mmol) was added to a solution of (R)-N-(4-(1-(2,2-difluoroethoxy)-2-methylpropan-2-yl)-3,5-difluorophenyl)-6-ethoxy-1,2,3,4-tetrahydroisoquinoline-1-carboxamide hydrochloride (43 mg, 0.09 mmol) and TEA (0.024 mL, 0.17 mmol) in THF (4 mL) at room temperature, and the mixture was stirred at 60° C. for 3 hr. The reaction mixture was concentrated under reduced pressure, and the obtained residue was purified by silica gel column chromatography (solvent gradient; 5→100% ethyl acetate/hexane) to give the title compound (35.0 mg, 0.060 mmol, 70.5%) as a white solid.

$^1$H NMR (300 MHz, DMSO-d$_6$): δ 1.30 (3H, t, J=7.0 Hz), 1.36 (6H, s), 1.66-1.81 (2H, m), 2.17-2.31 (4H, m), 2.71-2.86 (1H, m), 3.11 (1H, dt, J=15.6, 4.7 Hz), 3.45-3.55 (1H, m), 3.55-3.71 (4H, m), 4.00 (3H, q, J=7.2 Hz), 5.51-5.63 (1H, m), 5.80-6.31 (1H, m), 6.76-6.84 (2H, m), 7.11-7.26 (2H, m), 7.43 (1H, d, J=9.1 Hz), 10.65 (1H, s), 12.04 (1H, brs).

Example 154

(1R)-N-(4-(1-(2,2-difluoroethoxy)-2-methylpropan-2-yl)-3,5-difluorophenyl)-6-ethoxy-2-((3-hydroxy-1,2-oxazol-5-yl) carbonyl)-1,2,3,4-tetrahydroisoquinoline-1-carboxamide HATU (45.2 mg, 0.12 mmol) was added to a solution of (R)-N-(4-(1-(2,2-difluoroethoxy)-2-methylpropan-2-yl)-3,5-difluorophenyl)-6-ethoxy-1,2,3,4-tetrahydroisoquinoline-1-carboxamide hydrochloride (50 mg, 0.10 mmol), DIEA (0.042 mL, 0.24 mmol) and 3-hydroxyisoxazole-5-carboxylic acid (15.34 mg, 0.12 mmol) in DMF (4 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→90% ethyl acetate/hexane), and then silica gel column chromatography (Diol, solvent gradient; 0→10% MeOH/ethyl acetate) to give the title compound (50.0 mg, 0.086 mmol, 87%) as a white solid.

$^1$H NMR (300 MHz, DMSO-d$_6$): δ 1.30 (3H, t, J=7.0 Hz), 1.37 (6H, s), 2.76-2.93 (1H, m), 3.04-3.21 (1H, m), 3.51-3.80 (5H, m), 4.01 (2H, q, J=7.1 Hz), 4.09-4.23 (1H, m), 5.53-5.69 (1H, m), 5.83-6.29 (1H, m), 6.58 (1H, s), 6.73-6.89 (2H, m), 7.08-7.26 (2H, m), 7.42-7.56 (1H, m), 10.45-10.93 (1H, m), 11.76 (1H, brs).

Example 155

(1R)-N-(4-(1-(2,2-difluoroethoxy)-2-methylpropan-2-yl)-3,5-difluorophenyl)-6-ethoxy-2-((3-hydroxy-1,2-oxazol-5-yl)acetyl)-1,2,3,4-tetrahydroisoquinoline-1-carboxamide HATU (38.0 mg, 0.10 mmol) was added to a solution of (R)-N-(4-(1-(2,2-difluoroethoxy)-2-methylpropan-2-yl)-3,5-difluorophenyl)-6-ethoxy-1,2,3,4-tetrahydroisoquinoline-1-carboxamide hydrochloride (42 mg, 0.08 mmol), DIEA (0.035 mL, 0.20 mmol) and 2-(3-hydroxyisoxazol-5-yl) acetic acid (14.28 mg, 0.10 mmol) in DMF (2 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 5→90% ethyl acetate/hexane), and crystallized from ethyl acetate/hexane to give the title compound (28.0 mg, 0.047 mmol, 56.7%) as a white solid.

$^1$H NMR (300 MHz, DMSO-d$_6$): δ 1.30 (3H, t, J=7.0 Hz), 1.36 (6H, s), 2.71-2.88 (1H, m), 3.03-3.19 (1H, m), 3.50-3.72 (5H, m), 3.88-4.12 (5H, m), 5.61 (1H, s), 5.80-6.27 (2H, m), 6.75-6.87 (2H, m), 7.09-7.25 (2H, m, J=13.2 Hz), 7.45 (1H, d, J=9.4 Hz), 10.69 (1H, s), 11.10 (1H, s).

Example 156

5-((1R)-1-((3,5-difluoro-4-(trimethylsilyl)phenyl) carbamoyl)-6-methoxy-3,4-dihydroisoquinolin-2 (1H)-yl)-3-hydroxy-3-methyl-5-oxopentanoic acid 4-Hydroxy-4-methyldihydro-2H-pyran-2,6(3H)-dione (55.4 mg, 0.38 mmol) was added to a solution of (R)-N-(3,5-difluoro-4-(trimethylsilyl)phenyl)-6-methoxy-1,2,3,4-tetrahydroisoquinoline-1-carboxamide (100 mg, 0.26 mmol) and TEA (0.071 mL, 0.51 mmol) in THF (2.0 mL) at room temperature, and the mixture was stirred at room temperature for 3 hr. The reaction mixture was concentrated under reduced pressure, and the obtained residue was purified by silica gel column chromatography (solvent gradient; 50→100% ethyl acetate/hexane) to give the title compound (47.0 mg, 0.088 mmol, 34.3%) as a pale yellow solid.

Example 157

(1R)-N-(4-(1-(cyclopropylmethoxy)-2-methylpropan-2-yl)-3,5-difluorophenyl)-2-((3-hydroxy-1,2-oxazol-5-yl)acetyl)-6-methoxy-1,2,3,4-tetrahydroisoquinoline-1-carboxamide (Step 1)
Sodium hydride (60% oil, 7.64 g, 50.96 mmol) was added to a solution of 2-(4-(bis(4-methoxybenzyl)amino)-2,6-difluorophenyl)-2-methylpropan-1-ol (3.0 g, 6.79 mmol), (bromomethyl)cyclopropane (1.647 mL, 16.99 mmol) and sodium iodide (7.64 g, 50.96 mmol) in DMF (9 mL) at 5° C., and the mixture was stirred at 5° C. for 4 hr. DMF (3 mL) was added again thereto, and the mixture was stirred at room temperature for 14 hr. To the reaction mixture was added aqueous ammonium chloride solution, and the mixture was extracted twice with ethyl acetate. The organic layer was washed with brine, and dried over magnesium sulfate, and the solvent was evaporated under reduced pressure. The obtained residue was purified by silica gel column chromatography (solvent gradient; 5→20% ethyl acetate/hexane) to give 4-(1-(cyclopropylmethoxy)-2-methylpropan-2-yl)-3,5-difluoro-N,N-bis(4-methoxybenzyl)aniline (3.38 g, 6.82 mmol, 100%) as a colorless oil.
$^1$H NMR (300 MHz, CDCl$_3$): δ 0.01 (2H, dd, J=4.9, 1.1 Hz), 0.32 (2H, dd, J=8.3, 1.5 Hz), 0.80-0.94 (1H, m), 1.28 (6H, t, J=2.1 Hz), 3.13 (2H, d, J=6.8 Hz), 3.44 (2H, s), 3.67 (6H, s), 4.34 (4H, s), 6.04 (2H, d, J=14.4 Hz), 6.69-6.79 (4H, m), 6.98 (4H, d, J=8.7 Hz).
(Step 2)
A solution of 4-(1-(cyclopropylmethoxy)-2-methylpropan-2-yl)-3,5-difluoro-N,N-bis(4-methoxybenzyl)aniline (1.03 g, 2.62 mmol), 1N hydrochloric acid (5.25 mL) and 10% palladium-carbon (0.558 g, 0.26 mmol, 50% wet) in MeOH (50 mL) was stirred under hydrogen atmosphere (4 atm) at room temperature for 1.5 hr. Separately, a solution of 4-(1-(cyclopropylmethoxy)-2-methylpropan-2-yl)-3,5-difluoro-N,N-bis(4-methoxybenzyl)aniline (2.03 g, 4.10 mmol), 1N hydrochloric acid (8.19 mL) and 10% palladium-carbon (0.872 g, 0.41 mmol, 50% wet) in MeOH (100 mL) was stirred under hydrogen atmosphere (4 atm) at room temperature for 1.5 hr. The catalyst contained in each solution was removed by filtration, and the filtrates were concentrated under reduced pressure. The obtained residue was dissolved in ethyl acetate, the solution was washed with 1N aqueous sodium hydroxide solution and brine, and dried over magnesium sulfate, and the solvent was evaporated under reduced pressure. The obtained residue was purified by silica gel column chromatography (solvent gradient; 5→20% ethyl acetate/hexane) to give 4-(1-(cyclopropylmethoxy)-2-methylpropan-2-yl)-3,5-difluoroaniline (1.810 g, 7.09 mmol, 105%) as a colorless oil.
1H NMR (300 MHz, CDCl3)d −0.04-0.06 (2H, m), 0.26-0.38 (2H, m), 0.76-0.94 (1H, m), 1.28 (6H, t, J=2.3 Hz), 3.12 (2H, d, J=6.8 Hz), 3.44 (2H, s), 3.47-3.70 (2H, m), 5.90-6.06 (2H, m).
(Step 3)
T3P (6.22 mL, 10.58 mmol) was added to a solution of 4-(1-(cyclopropylmethoxy)-2-methylpropan-2-yl)-3,5-difluoroaniline (900 mg, 3.53 mmol), 2-(tert-butoxycarbonyl)-6-methoxy-1,2,3,4-tetrahydroisoquinoline-1-carboxylic acid (1192 mg, 3.88 mmol), DMAP (474 mg, 3.88 mmol) and DIEA (3.08 mL, 17.63 mmol) in ethyl acetate (30 mL), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give tert-butyl 1-((4-(1-(cyclopropylmethoxy)-2-methylpropan-2-yl)-3,5-difluorophenyl)carbamoyl)-6-methoxy-3,4-dihydroisoquinoline-2(1H)-carboxylate (994.1 mg, 1.825 mmol, 51.8%) as a white solid.
$^1$H NMR (300 MHz, CDCl$_3$): δ 0.07-0.16 (2H, m), 0.37-0.49 (2H, m), 0.85-1.05 (1H, m), 1.42 (6H, t, J=2.3 Hz), 1.52 (9H, s), 2.75-2.99 (2H, m), 3.23 (2H, d, J=6.4 Hz), 3.51-3.74 (4H, m), 3.80 (3H, s), 5.57 (1H, brs), 6.72 (1H, d, J=2.3 Hz), 6.80 (1H, dd, J=8.3, 2.3 Hz), 6.94-7.09 (2H, m), 7.19 (1H, brs), 9.01 (1H, brs).
(Step 4)
tert-Butyl 1-((4-(1-(cyclopropylmethoxy)-2-methylpropan-2-yl)-3,5-difluorophenyl)carbamoyl)-6-methoxy-3,4-dihydroisoquinoline-2(1H)-carboxylate (0.70 g) was resolved by chiral column chromatography. The fraction having a shorter retention time was concentrated to give tert-butyl (R)-1-((4-(1-(cyclopropylmethoxy)-2-methylpropan-2-yl)-3,5-difluorophenyl)carbamoyl)-6-methoxy-3,4-dihydroisoquinoline-2(1H)-carboxylate (0.29 g, >99% ee), and the fraction having a longer retention time was concentrated to give tert-butyl (S)-1-((4-(1-(cyclopropylmethoxy)-2-methylpropan-2-yl)-3,5-difluorophenyl)carbamoyl)-6-methoxy-3,4-dihydroisoquinoline-2(1H)-carboxylate (0.30 g, >99% ee), each as a white solid.
purification condition by chiral column chromatography
   column: CHIRALCEL OD (NL001) 50 mmID×500 mmL
   solvent: hexane/EtOH=900/100
   flow rate: 80 mL/min
   temperature: 30° C.
   detection method: UV 220 nm
(Step 5)
Cooled TFA (3.0 mL) was added to tert-butyl (R)-1-((4-(1-(cyclopropylmethoxy)-2-methylpropan-2-yl)-3,5-difluorophenyl)carbamoyl)-6-methoxy-3,4-dihydroisoquinoline-2(1H)-carboxylate (294 mg, 0.54 mmol), and the mixture was stirred at room temperature for 2 min. The reaction mixture was added to ice and aqueous sodium hydrogen carbonate solution, and the mixture was extracted three times with ethyl acetate. The organic layer was washed with brine, and dried over magnesium sulfate, and the solvent was evaporated under reduced pressure to give (R)-N-(4-(1-(cyclopropylmethoxy)-2-methylpropan-2-yl)-3,5-difluorophenyl)-6-methoxy-1,2,3,4-tetrahydroisoquinoline-1-carboxamide (239.2 mg, 0.538 mmol, 100%) as a white solid.
MS(API): Calculated 444.5. Found 443.2 (M−H).
(Step 6)
HATU (82 mg, 0.22 mmol) was added to a solution of (R)-N-(4-(1-(cyclopropylmethoxy)-2-methylpropan-2-yl)-3,5-difluorophenyl)-6-methoxy-1,2,3,4-tetrahydroisoquinoline-1-carboxamide (80 mg, 0.18 mmol), DIEA (0.062 mL, 0.36 mmol) and 2-(3-hydroxyisoxazol-5-yl)acetic acid (30.9 mg, 0.22 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (33.3 mg, 0.058 mmol, 32.5%) as white crystals.
$^1$H NMR (300 MHz, DMSO-d$_6$): δ 0.03-0.11 (2H, m), 0.31-0.44 (2H, m), 0.81-0.96 (1H, m), 1.36 (6H, s), 2.76-2.90 (H, m), 3.03-3.22 (3H, m), 3.43-3.65 (3H, m), 3.73 (3H, s), 3.88-4.17 (3H, m), 5.56-5.73 (1H, m), 5.82-5.95 (1H, m), 6.77-6.91 (2H, m), 7.09-7.24 (2H, m), 7.47 (1H, d, J=9.1 Hz), 10.61-10.74 (1H, m), 11.13 (1H, brs)

Example 158

(1R)-N-(4-(1-(cyclopropylmethoxy)-2-methylpropan-2-yl)-3,5-difluorophenyl)-2-((3-hydroxy-1,2-oxazol-5-yl)carbonyl)-6-methoxy-1,2,3,4-tetrahydroisoquinoline-1-carboxamide HATU (82 mg, 0.22 mmol) was added to a solution of (R)-N-(4-(1-(cyclopropylmethoxy)-2-methylpropan-2-yl)-3,5-difluorophenyl)-6-methoxy-1,2,3,4-tetrahydroisoquinoline-1-carboxamide (80 mg, 0.18 mmol), DIEA (0.062 mL, 0.36 mmol) and 3-hydroxyisoxazole-5-carboxylic acid (27.9 mg, 0.22 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (39.2 mg, 0.071 mmol, 39.2%) as a white solid.

$^1$H NMR (300 MHz, DMSO-$d_6$): δ 0.04-0.14 (2H, m), 0.32-0.44 (2H, m), 0.78-0.97 (1H, m), 1.37 (6H, s), 2.81-2.94 (1H, m), 3.02-3.24 (3H, m), 3.52 (2H, s), 3.63-3.84 (4H, m), 4.09-4.24 (1H, m), 5.51-5.73 (1H, m), 6.35-6.64 (1H, m), 6.76-6.92 (2H, m), 7.07-7.28 (2H, m), 7.45-7.58 (1H, m), 10.39-10.89 (1H, m), 11.80 (1H, brs).

Example 159

(1R)-N-(4-(1-(2,2-difluoroethoxy)-2-methylpropan-2-yl)-3,5-difluorophenyl)-2-((3-hydroxy-1,2-oxazol-5-yl)acetyl)-6-methoxy-1,2,3,4-tetrahydroisoquinoline-1-carboxamide (Step 1)
T3P (5.66 mL, 9.61 mmol) was added to a solution of 4-(1-(2,2-difluoroethoxy)-2-methylpropan-2-yl)-3,5-difluoroaniline (850 mg, 3.20 mmol), 2-(tert-butoxycarbonyl)-6-methoxy-1,2,3,4-tetrahydroisoquinoline-1-carboxylic acid (1083 mg, 3.53 mmol), DMAP (431 mg, 3.53 mmol) and DIEA (2.80 mL, 16.02 mmol) in ethyl acetate (30 mL), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give tert-butyl 1-((4-(1-(2,2-difluoroethoxy)-2-methylpropan-2-yl)-3,5-difluorophenyl)carbamoyl)-6-methoxy-3,4-dihydroisoquinoline-2(1H)-carboxylate (757.3 mg, 1.366 mmol, 42.6%) as a white solid.

$^1$H NMR (300 MHz, CDCl$_3$): δ 1.42 (6H, t, J=2.1 Hz), 1.52 (9H, s), 2.76-2.98 (2H, m), 3.51-3.75 (6H, m), 3.80 (3H, s), 5.35-5.99 (2H, m), 6.73 (1H, d, J=2.3 Hz), 6.81 (1H, dd, J=8.3, 2.3 Hz), 6.97-7.10 (2H, m), 7.18 (1H, brs), 9.03 (1H, brs).

(Step 2)
tert-Butyl 1-((4-(1-(2,2-difluoroethoxy)-2-methylpropan-2-yl)-3,5-difluorophenyl)carbamoyl)-6-methoxy-3,4-dihydroisoquinoline-2(1H)-carboxylate (0.80 g) was resolved by chiral column chromatography. The fraction having a shorter retention time was concentrated to give tert-butyl (R)-1-((4-(1-(2,2-difluoroethoxy)-2-methylpropan-2-yl)-3,5-difluorophenyl)carbamoyl)-6-methoxy-3,4-dihydroisoquinoline-2(1H)-carboxylate (0.34 g, >99% ee), and the fraction having a longer retention time was concentrated to give tert-butyl (S)-1-((4-(1-(2,2-difluoroethoxy)-2-methylpropan-2-yl)-3,5-difluorophenyl)carbamoyl)-6-methoxy-3,4-dihydroisoquinoline-2(1H)-carboxylate (0.34 g, >99% ee), each as a white solid.

purification condition by chiral column chromatography
column: CHIRALCEL OD (NL001) 50 mmID×500 mmL
solvent: hexane/EtOH=900/100
flow rate: 80 mL/min
temperature: 30° C.
detection method: UV 220 nm (Step 3)
Cooled TFA (3.0 mL) was added to tert-butyl (R)-1-((4-(1-(2,2-difluoroethoxy)-2-methylpropan-2-yl)-3,5-difluorophenyl)carbamoyl)-6-methoxy-3,4-dihydroisoquinoline-2(1H)-carboxylate (337 mg, 0.61 mmol), and the mixture was stirred at room temperature for 2 min. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure. The precipitate was washed with hexane to give (R)-N-(4-(1-(2,2-difluoroethoxy)-2-methylpropan-2-yl)-3,5-difluorophenyl)-6-methoxy-1,2,3,4-tetrahydroisoquinoline-1-carboxamide (264.6 mg, 0.582 mmol, 96%) as white crystals.

MS(API): Calculated 454.5. Found 455.3 (M+H).

(Step 4)
HATU (80 mg, 0.21 mmol) was added to a solution of (R)-N-(4-(1-(2,2-difluoroethoxy)-2-methylpropan-2-yl)-3,5-difluorophenyl)-6-methoxy-1,2,3,4-tetrahydroisoquinoline-1-carboxamide (80 mg, 0.18 mmol), DIEA (0.060 mL, 0.35 mmol) and 2-(3-hydroxyisoxazol-5-yl)acetic acid (30.2 mg, 0.21 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (22.8 mg, 0.039 mmol, 22.35%) as white crystals.

$^1$H NMR (300 MHz, DMSO-$d_6$): δ 1.36 (6H, s), 2.70-2.90 (1H, m), 3.02-3.20 (1H, m), 3.53-3.70 (5H, m), 3.73 (3H, s), 3.90-4.14 (3H, m), 5.55-5.70 (1H, m), 5.82-6.27 (2H, m), 6.78-6.88 (2H, m), 7.12-7.24 (2H, m), 7.47 (1H, d, J=9.4 Hz), 10.63-10.72 (1H, m), 11.12 (1H, brs)

Example 160

(1R)-N-(4-(1-(2,2-difluoroethoxy)-2-methylpropan-2-yl)-3,5-difluorophenyl)-2-((3-hydroxy-1,2-oxazol-5-yl) carbonyl)-6-methoxy-1,2,3,4-tetrahydroisoquinoline-1-carboxamide HATU (80 mg, 0.21 mmol) was added to a solution of (R)-N-(4-(1-(2,2-difluoroethoxy)-2-methylpropan-2-yl)-3,5-difluorophenyl)-6-methoxy-1,2,3,4-tetrahydroisoquinoline-1-carboxamide (80 mg, 0.18 mmol), DIEA (0.060 mL, 0.35 mmol) and 3-hydroxyisoxazole-5-carboxylic acid (27.3 mg, 0.21 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (31.3 mg, 0.055 mmol, 31.4%) as a white solid.

$^1$H NMR (300 MHz, DMSO-$d_6$): δ 1.37 (6H, s), 2.81-2.95 (2H, m), 3.04-3.22 (1H, m), 3.56-3.70 (4H, m), 3.74 (3H, s), 4.09-4.24 (1H, m), 5.54-5.70 (1H, m), 5.82-6.29 (1H, m), 6.37-6.64 (1H, m), 6.80-6.93 (2H, m), 7.11-7.28 (2H, m), 7.47-7.57 (1H, m), 10.42-10.88 (1H, m), 11.67-11.83 (1H, m).

Example 161

5-((1R)-1-((4-(1-(cyclopropylmethoxy)-2-methylpropan-2-yl)-3,5-difluorophenyl)carbamoyl)-6-methoxy-3,4-dihydroisoquinolin-2 (1H)-yl)-5-oxopentanoic acid Dihydro-2H-pyran-2,6(3H)-dione (30.8 mg, 0.27 mmol) was added to a solution of (R)-N-(4-(1-(cyclopropylmethoxy)-2-methylpropan-2-yl)-3,5-difluorophenyl)-6-methoxy-1,2,3,4-tetrahydroisoquinoline-1-carboxamide (80 mg, 0.18 mmol) and TEA (0.050 mL, 0.36 mmol) in THF (2.0 mL) at room temperature, and the mixture was stirred at room temperature for 3 hr. The reaction mixture was concentrated under reduced pressure, and the obtained residue was purified by silica gel column chromatography (solvent gradient; 50→100% ethyl acetate/hexane) to give the title compound (43.3 mg, 0.078 mmol, 43.1%) as a colorless oil.

$^1$H NMR (300 MHz, DMSO-$d_6$): δ 0.03-0.15 (2H, m), 0.30-0.48 (2H, m), 0.77-1.00 (1H, m), 1.36 (6H, brs), 1.63-1.84 (2H, m), 2.16-2.35 (3H, m), 2.38-2.62 (1H, m), 2.71-2.89 (1H, m), 3.18 (3H, d, J=6.4 Hz), 3.43-3.57 (3H, m), 3.73 (3H, s), 3.94-4.11 (1H, m), 5.51-5.65 (1H, m), 6.76-6.88 (2H, m), 7.07-7.26 (2H, m), 7.46 (1H, d, J=9.4 Hz), 10.55-10.71 (1H, m).

Example 162

5-((1R)-1-((4-(1-(2,2-difluoroethoxy)-2-methylpropan-2-yl)-3,5-difluorophenyl)carbamoyl)-6-methoxy-3,4-dihydroisoquinolin-2(1H)-yl)-5-oxopentanoic acid Dihydro-2H-pyran-2,6(3H)-dione (30.1 mg, 0.26 mmol) was added to a solution of (R)-N-(4-(1-(2,2-difluoroethoxy)-2-methylpropan-2-yl)-3,5-difluorophenyl)-6-methoxy-1,2,3,4-tetrahydroisoquinoline-1-carboxamide (80 mg, 0.18 mmol) and TEA (0.049 mL, 0.35 mmol) in THF (2.0 mL) at room temperature, and the mixture was stirred at room temperature for 3 hr. The reaction mixture was concentrated under reduced pressure, and the obtained residue was purified by silica gel column chromatography (solvent gradient; 50→100% ethyl acetate/hexane) to give the title compound (62.9 mg, 0.111 mmol, 62.8%) as a colorless oil.

$^1$H NMR (300 MHz, DMSO-$d_6$): δ 1.36 (6H, brs), 1.64-1.84 (2H, m), 2.19-2.34 (2H, m), 2.37-2.64 (2H, m), 2.71-2.89 (1H, m), 3.10-3.20 (1H, m), 3.44-3.55 (3H, m), 3.56-3.69 (4H, m), 3.73 (3H, s), 3.96-4.10 (1H, m), 5.54-5.64 (1H, m), 5.82-6.28 (1H, m), 6.76-6.88 (2H, m), 7.12-7.26 (2H, m), 7.46 (1H, d, J=9.4 Hz), 10.57-10.72 (1H, m).

Example 163

(1R)-N-(3,5-difluoro-4-(1-methoxy-2-methylpropan-2-yl)phenyl)-6-ethoxy-2-((3-hydroxy-1,2-oxazol-5-yl)carbonyl)-1,2,3,4-tetrahydroisoquinoline-1-carboxamide (Step 1)

T3P (9.88 mL, 16.80 mmol) was added to a solution of 2-(tert-butoxycarbonyl)-6-ethoxy-1,2,3,4-tetrahydroisoquinoline-1-carboxylic acid (1.8 g, 5.60 mmol), 3,5-difluoro-4-(1-methoxy-2-methylpropan-2-yl)aniline (1.206 g, 5.60 mmol), DIEA (4.89 mL, 28.01 mmol) and DMAP (0.684 g, 5.60 mmol) in ethyl acetate (5 mL), and the mixture was stirred overnight at 60° C. To the reaction mixture was added water, and the mixture was extracted with ethyl acetate. The organic layer was washed with 10% aqueous citric acid solution, aqueous sodium hydrogen carbonate solution and brine, and dried over magnesium sulfate, and the solvent was evaporated under reduced pressure. The obtained residue was purified by silica gel column chromatography (solvent gradient; 3→50% ethyl acetate/hexane) to give tert-butyl 1-((3,5-difluoro-4-(1-methoxy-2-methylpropan-2-yl)phenyl)carbamoyl)-6-ethoxy-3,4-dihydroisoquinoline-2 (1H)-carboxylate (2.380 g, 4.59 mmol, 82%) as a white solid.

$^1$H NMR (300 MHz, CDCl$_3$): δ 1.38-1.44 (9H, m), 1.51 (9H, s), 2.71-2.99 (2H, m), 3.30 (3H, s), 3.51 (2H, s), 3.54-3.76 (2H, m), 4.03 (2H, q, J=6.8 Hz), 5.55 (1H, brs), 6.72 (1H, s), 6.80 (1H, dd, J=8.5, 2.5 Hz), 7.03 (2H, d, J=12.5 Hz), 7.14 (1H, brs), 8.89 (1H, s).

(Step 2)

tert-Butyl 1-((3,5-difluoro-4-(1-methoxy-2-methylpropan-2-yl)phenyl)carbamoyl)-6-ethoxy-3,4-dihydroisoquinoline-2 (1H)-carboxylate (2.20 g) was resolved by chiral column chromatography. The fraction having a shorter retention time was concentrated to give tert-butyl (R)-1-((3,5-difluoro-4-(1-methoxy-2-methylpropan-2-yl)phenyl) carbamoyl)-6-ethoxy-3, 4-dihydroisoquinoline-2(1H)-carboxylate (1.02 g, >99% ee), and the fraction having a longer retention time was concentrated to give tert-butyl (S)-1-((3,5-difluoro-4-(1-methoxy-2-methylpropan-2-yl)phenyl)carbamoyl)-6-ethoxy-3,4-dihydroisoquinoline-2(1H)-carboxylate (1.03 g, 98.7% ee), each as a white solid.

purification condition by chiral column chromatography
column: CHIRALCEL OD (NL001) 50 mmID×500 mmL
solvent: hexane/EtOH=900/100
flow rate: 80 mL/min
temperature: 30° C.
detection method: UV 220 nm (Step 3)

4N Hydrogen chloride/ethyl acetate (5 mL) was added to a solution of tert-butyl (R)-1-((3,5-difluoro-4-(1-methoxy-2-methylpropan-2-yl)phenyl)carbamoyl)-6-ethoxy-3,4-dihydroisoquinoline-2(1H)-carboxylate (1.02 g, 1.97 mmol) in ethyl acetate (2 mL), and the mixture was stirred overnight at room temperature. The reaction mixture was concentrated under reduced pressure, and the precipitate was collected by filtration with hexane to give (R)-N-(3,5-difluoro-4-(1-methoxy-2-methylpropan-2-yl)phenyl)-6-ethoxy-1,2,3,4-tetrahydroisoquinoline-1-carboxamide hydrochloride (0.917 g, 2.016 mmol, 102%) as a white solid.

MS(API): Calculated 454.9. Found 419.4 (M−HCl+H).

(Step 4)

HATU (47.1 mg, 0.12 mmol) was added to a solution of (R)-N-(3,5-difluoro-4-(1-methoxy-2-methylpropan-2-yl)phenyl)-6-ethoxy-1,2,3,4-tetrahydroisoquinoline-1-carboxamide hydrochloride (47 mg, 0.10 mmol), DIEA (0.043 mL, 0.25 mmol) and 3-hydroxyisoxazole-5-carboxylic acid (16.00 mg, 0.12 mmol) in DMF (4 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→90% ethyl acetate/hexane) to give the title compound (40.0 mg, 0.076 mmol, 73.1%) as a white solid.

$^1$H NMR (300 MHz, DMSO-d$_6$): δ 1.30 (3H, t, J=6.8 Hz), 1.36 (6H, s), 2.80-2.89 (1H, m), 3.12 (1H, d, J=9.4 Hz), 3.19 (3H, s), 3.45 (2H, s), 3.73 (1H, t, J=9.1 Hz), 4.01 (2H, q, J=6.9 Hz), 4.10-4.22 (1H, m), 5.64 (1H, s), 6.59 (1H, s), 6.78-6.90 (2H, m), 7.09-7.25 (2H, m), 7.49 (1H, d, J=9.4 Hz), 10.81 (1H, s), 11.75 (1H, s).

Example 164

5-((1R)-1-((3,5-difluoro-4-(1-methoxy-2-methylpropan-2-yl)phenyl)carbamoyl)-6-ethoxy-3,4-dihydroisoquinolin-2(1H)-yl)-5-oxopentanoic acid Dihydro-2H-pyran-2,6(3H)-dione (12.29 mg, 0.11 mmol) was added to a solution of (R)-N-(3,5-difluoro-4-(1-methoxy-2-methylpropan-2-yl)phenyl)-6-ethoxy-1,2,3,4-tetrahydroisoquinoline-1-carboxamide hydrochloride (49 mg, 0.11 mmol) and TEA (0.030 mL, 0.22 mmol) in THF (4 mL) at room temperature, and the mixture was stirred at 60° C. for 2 hr. The reaction mixture was concentrated under reduced pressure, and the obtained residue was purified by silica gel column chromatography (solvent gradient; 5→100% ethyl acetate/hexane) to give the title compound (25.00 mg, 0.047 mmol, 43.6%) as a white solid.

$^1$H NMR (300 MHz, DMSO-d$_6$): δ 1.30 (3H, t, J=7.0 Hz), 1.35 (6H, s), 1.63-1.82 (2H, m), 2.17-2.31 (2H, m), 2.38-2.60 (2H, m), 2.70-2.86 (1H, m), 3.03-3.16 (1H, m), 3.19 (3H, s), 3.40-3.57 (3H, m), 3.88-4.07 (3H, m), 5.60 (1H, s), 6.70-6.88 (2H, m), 7.05-7.25 (2H, m), 7.43 (1H, d, J=9.4 Hz), 10.64 (1H, s), 12.03 (1H, brs).

Example 165

(1R)-N-(3,5-difluoro-4-(1-methoxy-2-methylpropan-2-yl)phenyl)-6-ethoxy-2-((3-hydroxy-1,2-oxazol-5-yl)acetyl)-1,2,3,4-tetrahydroisoquinoline-1-carboxamide HATU (43.1 mg, 0.11 mmol) was added to a solution of (R)-N-(3,5-difluoro-4-(1-methoxy-2-methylpropan-2-yl)phenyl)-6-ethoxy-1,2,3,4-tetrahydroisoquinoline-1-carboxamide hydrochloride (43 mg, 0.09 mmol), DIEA (0.040 mL, 0.23 mmol) and 2-(3-hydroxyisoxazol-5-yl)acetic acid (16.23 mg, 0.11 mmol) in DMF (4 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane) to give the title compound (22.00 mg, 0.040 mmol, 42.8%) as a white solid.

$^1$H NMR (300 MHz, DMSO-d$_6$): δ 1.30 (3H, t, J=6.8 Hz), 1.35 (6H, s), 2.75-2.90 (1H, m), 3.05-3.24 (4H, m), 3.44 (2H, s), 3.52-3.66 (1H, m), 3.91-4.14 (5H, m), 5.61 (1H, s), 5.90 (1H, s), 6.75-6.89 (2H, m), 7.06-7.24 (2H, m, J=13.2 Hz), 7.45 (1H, d, J=9.1 Hz), 10.69 (1H, s), 11.10 (1H, s).

Example 166

5-((1R)-6-ethoxy-1-((4-(1-ethoxy-2-methylpropan-2-yl)-3,5-difluorophenyl)carbamoyl)-3,4-dihydroisoquinolin-2(1H)-yl)-5-oxopentanoic acid (Step 1)

Sodium hydride (60% oil, 1.726 g, 43.15 mmol) was added to a solution of 2-(4-(bis(4-methoxybenzyl)amino)-2,6-difluorophenyl)-2-methylpropan-1-ol (7.62 g, 17.26 mmol) and iodoethane (3.49 mL, 43.15 mmol) in DMF (30 mL) at 5° C., and the mixture was stirred at room temperature for 14 hr. To the reaction mixture was added aqueous ammonium chloride solution, and the mixture was extracted twice with ethyl acetate. The organic layer was washed with brine, and dried over magnesium sulfate, and the solvent was evaporated under reduced pressure. The obtained residue was purified by silica gel column chromatography (Diol, solvent gradient; 5→20% ethyl acetate/hexane) to give 4-(1-ethoxy-2-methylpropan-2-yl)-3,5-difluoro-N,N-bis(4-methoxybenzyl)aniline (8.51 g, 18.12 mmol, 105%) as a colorless oil.

$^1$H NMR (300 MHz, CDCl$_3$): δ 1.14 (3H, t, J=7.0 Hz), 1.39 (6H, t, J=2.1 Hz), 3.47 (2H, d, J=7.2 Hz), 3.53 (2H, s), 3.79 (6H, s), 4.46 (4H, s), 6.17 (2H, d, J=14.4 Hz), 6.79-6.91 (4H, m), 7.11 (4H, d, J=8.7 Hz).

(Step 2)

A solution of 4-(1-ethoxy-2-methylpropan-2-yl)-3,5-difluoro-N,N-bis(4-methoxybenzyl)aniline (8.51 g, 18.12 mmol), 1N hydrochloric acid (36.2 mL) and 10% palladium-carbon (1.929 g, 0.91 mmol, 50% wet) in MeOH (164 mL) was stirred under hydrogen atmosphere (4 atm) at room temperature for 1.5 hr. The catalyst was filtered off, and the filtrate was concentrated under reduced pressure. The obtained residue was dissolved in ethyl acetate, and the solvent was washed with 1N aqueous sodium hydroxide solution and brine, and dried over magnesium sulfate, and the solvent was evaporated under reduced pressure. The obtained residue was purified by silica gel column chromatography (solvent gradient; 5→20% ethyl acetate/hexane) to give 4-(1-ethoxy-2-methylpropan-2-yl)-3,5-difluoroaniline (3.87 g, 16.88 mmol, 93%) as a white solid.

$^1$H NMR (300 MHz, CDCl$_3$): δ 1.13 (3H, t, J=7.0 Hz), 1.40 (6H, t, J=2.5 Hz), 3.40-3.50 (2H, m, J=7.2, 7.2, 7.2 Hz), 3.53 (2H, s), 3.57-3.87 (2H, m), 6.09 (1H, s), 6.13 (1H, s).

(Step 3)

T3P (4.62 mL, 7.85 mmol) was added to a solution of 2-(tert-butoxycarbonyl)-6-ethoxy-1,2,3,4-tetrahydroisoquinoline-1-carboxylic acid (841 mg, 2.62 mmol), 4-(1-ethoxy-2-methylpropan-2-yl)-3,5-difluoroaniline (600 mg, 2.62 mmol), DIEA (2.285 mL, 13.09 mmol) and DMAP (320 mg, 2.62 mmol) in ethyl acetate (5 mL), and the mixture was stirred overnight at 60° C. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane), and crystallized from ethyl acetate/hexane to give tert-butyl 6-ethoxy-1-((4-(1-ethoxy-2-methylpropan-2-yl)-3,5-difluorophenyl)carbamoyl)-3,4-dihydroisoquinoline-2(1H)-carboxylate (700 mg, 1.314 mmol, 50.2%) as white crystals.

$^1$H NMR (300 MHz, CDCl$_3$): δ 1.10 (3H, t, J=7.0 Hz), 1.36-1.45 (9H, m), 1.51 (9H, s), 2.76-2.98 (2H, m), 3.44 (2H, q, J=6.8 Hz), 3.54 (3H, s), 3.62-3.78 (1H, m), 4.03 (2H, q, J=6.8 Hz), 5.55 (1H, brs), 6.71 (1H, d, J=2.3 Hz), 6.80 (1H, dd, J=8.3, 2.6 Hz), 6.95-7.08 (2H, m, J=12.5 Hz), 7.10-7.22 (1H, m), 8.92 (1H, s).

(Step 4)

tert-Butyl 6-ethoxy-1-((4-(1-ethoxy-2-methylpropan-2-yl)-3,5-difluorophenyl)carbamoyl)-3,4-dihydroisoquinoline-2 (1H)-carboxylate (0.70 g) was resolved by chiral column chromatography. The fraction having a shorter retention time was concentrated to give tert-butyl (R)-6-ethoxy-1-((4-(1-ethoxy-2-methylpropan-2-yl)-3,5-difluorophenyl) carbamoyl)-3,4-dihydroisoquinoline-2(1H)-carboxylate (0.32 g, >99% ee), and the fraction having a longer retention time was concentrated to give tert-butyl (S)-6-ethoxy-1-((4-(1-ethoxy-2-methylpropan-2-yl)-3,5-difluorophenyl)carbamoyl)-3,4-dihydroisoquinoline-2(1H)-carboxylate (0.32 g, 92.2% ee), each as a white solid.

purification condition by chiral column chromatography column: CHIRALPAK IA (QK001) 50 mmID×500 mmL solvent: hexane/EtOH=850/150 flow rate: 80 mL/min temperature: 30° C.

detection method: UV 220 nm (Step 5)

4N Hydrogen chloride/ethyl acetate (4 mL) was added to a solution of tert-butyl (R)-6-ethoxy-1-((4-(1-ethoxy-2-methylpropan-2-yl)-3,5-difluorophenyl)carbamoyl)-3,4-dihydroisoquinoline-2(1H)-carboxylate (320 mg, 0.60 mmol) in ethyl acetate (2 mL), and the mixture was stirred overnight at room temperature. The reaction mixture was concentrated under reduced pressure, and the precipitate was collected by filtration with hexane to give (R)-6-ethoxy-N-(4-(1-ethoxy-2-methylpropan-2-yl)-3,5-difluorophenyl)-1,2,3,4-tetrahydroisoquinoline-1-carboxamide hydrochloride (273 mg, 0.582 mmol, 97%) as a white solid.

MS(API): Calculated 468.96. Found 433.4 (M−HCl+H).

(Step 6)

Dihydro-2H-pyran-2,6(3H)-dione (83 mg, 0.73 mmol) was added to a solution of (R)-6-ethoxy-N-(4-(1-ethoxy-2-methylpropan-2-yl)-3,5-difluorophenyl)-1,2,3,4-tetrahydroisoquinoline-1-carboxamide hydrochloride (285 mg, 0.61 mmol) and TEA (0.102 mL, 0.73 mmol) in THF (5 mL) at room temperature, and the mixture was stirred at 60° C. for 1 hr. The reaction mixture was concentrated under reduced pressure, and the obtained residue was purified by silica gel column chromatography (solvent gradient; 10→100% ethyl acetate/hexane) to give the title compound (308 mg, 0.563 mmol, 93%) as a white solid.

$^1$H NMR (300 MHz, DMSO-d$_6$): δ 1.01 (3H, t, J=7.0 Hz), 1.30 (3H, t, J=7.0 Hz), 1.35 (6H, s), 1.58-1.83 (2H, m), 2.18-2.32 (2H, m), 2.35-2.60 (2H, m), 2.74-2.88 (1H, m), 3.04-3.18 (1H, m), 3.37 (2H, q, J=7.2 Hz), 3.44-3.58 (3H, m), 3.99 (3H, q, J=7.2 Hz), 5.60 (1H, s), 6.70-6.88 (2H, m), 7.09-7.26 (2H, m), 7.43 (1H, d, J=9.1 Hz), 10.64 (1H, s), 12.05 (1H, brs).

[α]$_D^{25}$ −10.4 (c 0.251, MeOH)

Example 167

(1R)-6-ethoxy-N-(4-(1-ethoxy-2-methylpropan-2-yl)-3,5-difluorophenyl)-2-((3-hydroxy-1,2-oxazol-5-yl)carbonyl)-1,2,3,4-tetrahydroisoquinoline-1-carboxamide HATU (38.9 mg, 0.10 mmol) was added to a solution of (R)-6-ethoxy-N-(4-(1-ethoxy-2-methylpropan-2-yl)-3,5-difluorophenyl)-1,2,3, 4-tetrahydroisoquinoline-1-carboxamide hydrochloride (40 mg, 0.09 mmol), DIEA (0.036 mL, 0.20 mmol) and 3-hydroxyisoxazole-5-carboxylic acid (13.21 mg, 0.10 mmol) in DMF (4 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→90% ethyl acetate/hexane) to give the title compound (30.0 mg, 0.055 mmol, 64.7%) as a white solid.

$^1$H NMR (300 MHz, DMSO-d$_6$): δ 1.02 (3H, t, J=7.0 Hz), 1.30 (3H, t, J=7.0 Hz), 1.36 (6H, s), 2.78-2.94 (H, m), 3.05-3.22 (H, m), 3.35-3.42 (2H, m), 3.49 (2H, s), 3.62-3.80 (1H, m, J=8.7 Hz), 4.01 (2H, q, J=6.9 Hz), 4.10-4.22 (1H, m), 5.64 (1H, s), 6.58 (1H, s), 6.78-6.90 (2H, m), 7.11-7.24 (2H, m), 7.49 (1H, d, J=9.1 Hz), 10.80 (1H, s), 11.75 (1H, s).

Example 168

(1R)-6-ethoxy-N-(4-(1-ethoxy-2-methylpropan-2-yl)-3,5-difluorophenyl)-2-((3-hydroxy-1,2-oxazol-5-yl)acetyl)-1,2,3,4-tetrahydroisoquinoline-1-carboxamide HATU (38.9 mg, 0.10 mmol) was added to a solution of (R)-6-ethoxy-N-(4-(1-ethoxy-2-methylpropan-2-yl)-3,5-difluorophenyl)-1,2,3,4-tetrahydroisoquinoline-1-carboxamide hydrochloride (40 mg, 0.09 mmol), DIEA (0.036 mL, 0.20 mmol) and 2-(3-hydroxyisoxazol-5-yl)acetic acid (14.65 mg, 0.10 mmol) in DMF (4 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→100% ethyl acetate/hexane), and solidified with ethyl acetate/hexane to give title compound (15.00 mg, 0.027 mmol, 31.5%) as a white solid.

$^1$H NMR (300 MHz, DMSO-d$_6$): δ 1.01 (3H, t, J=7.0 Hz), 1.30 (3H, t, J=7.0 Hz), 1.35 (6H, brs), 2.76-2.88 (1H, m), 3.05-3.19 (1H, m), 3.33-3.41 (2H, m), 3.48 (2H, s), 3.52-3.64 (1H, m), 3.86-4.15 (5H, m), 5.61 (1H, s), 5.91 (1H, s), 6.76-6.88 (2H, m), 7.17 (2H, d, J=12.8 Hz), 7.45 (1H, d, J=9.1 Hz), 10.68 (1H, s), 11.10 (1H, s).

Example 169

(1R)-N-(7-fluoro-1,1-dimethyl-2,3-dihydro-1H-inden-5-yl)-2-((3-hydroxy-1,2-oxazol-5-yl)acetyl)-6-(methoxymethyl)-1,2,3,4-tetrahydroisoquinoline-1-carboxamide HATU (273 mg, 0.72 mmol) was added to a solution of (R)-N-(7-fluoro-1,1-dimethyl-2,3-dihydro-1H-inden-5-yl)-

6-(methoxymethyl)-1,2,3,4-tetrahydroisoquinoline-1-carboxamide hydrochloride (251 mg, 0.60 mmol), DIEA (0.251 mL, 1.44 mmol) and 2-(3-hydroxyisoxazol-5-yl)acetic acid (103 mg, 0.72 mmol) in DMF (4 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→90% ethyl acetate/hexane) to give the title compound (208 mg, 0.410 mmol, 68.4%) as a white solid.

$^1$H NMR (300 MHz, DMSO-d$_6$): δ 1.28 (6H, s), 1.86 (2H, t, J=7.4 Hz), 2.79-2.92 (3H, m), 3.05-3.19 (1H, m), 3.31 (3H, s), 3.65 (1H, ddd, J=12.3, 8.3, 4.3 Hz), 3.86-4.17 (3H, m), 4.36 (2H, s), 5.74 (1H, s), 5.84-5.96 (1H, m), 7.07-7.30 (4H, m), 7.54 (1H, d, J=7.9 Hz), 10.51 (1H, s), 11.11 (1H, s).

$[α]_D^{25}$+22.7 (c 0.2510, MeOH)

Example 170

(1R)-N-(4-(1-ethoxy-2-methylpropan-2-yl)-3,5-difluorophenyl)-2-((3-hydroxy-1,2-oxazol-5-yl)acetyl)-6-methoxy-1,2,3,4-tetrahydroisoquinoline-1-carboxamide (Step 1)
T3P (4.62 mL, 7.85 mmol) was added to a solution of 4-(1-ethoxy-2-methylpropan-2-yl)-3,5-difluoroaniline (600 mg, 2.62 mmol), 2-(tert-butoxycarbonyl)-6-methoxy-1,2,3,4-tetrahydroisoquinoline-1-carboxylic acid (885 mg, 2.88 mmol), DMAP (352 mg, 2.88 mmol) and DIEA (2.285 mL, 13.09 mmol) in ethyl acetate (30 mL), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane), and then preparative HPLC (C18, mobile phase: water/acetonitrile (containing 0.1% TFA)) to give tert-butyl 1-((4-(1-ethoxy-2-methylpropan-2-yl)-3,5-difluorophenyl)carbamoyl)-6-methoxy-3,4-dihydroisoquinoline-2(1H)-carboxylate (644 mg, 1.242 mmol, 47.5%).

$^1$H NMR (300 MHz, CDCl$_3$): δ 1.10 (3H, t, J=7.2 Hz), 1.39-1.44 (6H, m), 1.52 (9H, s), 2.78-2.97 (2H, m), 3.44 (2H, q, J=7.2 Hz), 3.51-3.74 (4H, m), 3.80 (3H, s), 5.56 (1H, brs), 6.69-6.76 (1H, m), 6.81 (1H, dd, J=8.3, 2.6 Hz), 6.96-7.09 (2H, m), 7.18 (1H, brs), 8.96 (1H, brs).

(Step 2)
tert-Butyl 1-((4-(1-ethoxy-2-methylpropan-2-yl)-3,5-difluorophenyl)carbamoyl)-6-methoxy-3,4-dihydroisoquinoline-2(1H)-carboxylate (0.45 g) was resolved by chiral column chromatography. The fraction having a shorter retention time was concentrated to give tert-butyl (R)-1-((4-(1-ethoxy-2-methylpropan-2-yl)-3,5-difluorophenyl)carbamoyl)-6-methoxy-3,4-dihydroisoquinoioline-2(1H)-carboxylate (0.19 g, >99% ee), and the fraction having a longer retention time was concentrated to give tert-butyl (S)-1-((4-(1-ethoxy-2-methylpropan-2-yl)-3,5-difluorophenyl)carbamoyl)-6-methoxy-3,4-dihydroisoquinoline-2(1H)-carboxylate (0.20 g, >99% ee), each as a white solid.
purification condition by chiral column chromatography
  column: CHIRALPAK IA (QK001) 50 mmID×500 mmL
  solvent: hexane/EtOH=850/150
  flow rate: 80 mL/min
  temperature: 30° C.
  detection method: UV 220 nm (Step 3)
Cooled TFA (2.0 mL) was added to tert-butyl (R)-1-((4-(1-ethoxy-2-methylpropan-2-yl)-3,5-difluorophenyl)carbamoyl)-6-methoxy-3,4-dihydroisoquinoline-2(1H)-carboxylate (194 mg, 0.37 mmol), and the mixture was stirred at room temperature for 2 min. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure to give crude (R)-N-(4-(1-ethoxy-2-methylpropan-2-yl)-3,5-difluorophenyl)-6-methoxy-1,2,3,4-tetrahydroisoquinoline-1-carboxamide (157 mg, 0.375 mmol, 100%) as a white solid.

MS(API): Calculated 418.5. Found 417.2 (M–H).

(Step 4)
HATU (54.5 mg, 0.14 mmol) was added to a solution of the crude (R)-N-(4-(1-ethoxy-2-methylpropan-2-yl)-3,5-difluorophenyl)-6-methoxy-1,2,3,4-tetrahydroisoquinoline-1-carboxamide (50 mg, 0.12 mmol), DIEA (0.041 mL, 0.24 mmol) and 2-(3-hydroxyisoxazol-5-yl)acetic acid (20.52 mg, 0.14 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane), and recrystallized from ethyl acetate/hexane to give the title compound (21.1 mg, 0.039 mmol, 32.5%) as white crystals.

$^1$H NMR (300 MHz, DMSO-d$_6$): δ 1.01 (3H, t, J=7.0 Hz), 1.35 (6H, s), 2.76-2.89 (1H, m), 3.05-3.20 (1H, m), 3.36 (2H, q, J=7.1 Hz), 3.48 (2H, s), 3.52-3.64 (1H, m), 3.73 (3H, s), 3.90-4.15 (3H, m), 5.56-5.70 (1H, m), 5.83-5.96 (1H, m), 6.76-6.88 (2H, m), 7.17 (2H, d, J=13.2 Hz), 7.47 (1H, d, J=9.4 Hz), 10.68 (1H, s), 11.10 (1H, s).

Example 171

(1R)-N-(4-(1-ethoxy-2-methylpropan-2-yl)-3,5-difluorophenyl)-2-((3-hydroxy-1,2-oxazol-5-yl)carbonyl)-6-methoxy-1,2,3,4-tetrahydroisoquinoline-1-carboxamide HATU (54.5 mg, 0.14 mmol) was added to a solution of (R)-N-(4-(1-ethoxy-2-methylpropan-2-yl)-3,5-difluorophenyl)-6-methoxy-1,2,3,4-tetrahydroisoquinoline-1-carboxamide (50 mg, 0.12 mmol), DIEA (0.041 mL, 0.24 mmol) and 3-hydroxyisoxazole-5-carboxylic acid (18.51 mg, 0.14 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane, 0→10% MeOH/ethyl acetate), and solidified with ethyl acetate/hexane to give the title compound (46.3 mg, 0.087 mmol, 73.2%) as a white solid.

$^1$H NMR (300 MHz, DMSO-d$_6$): δ 1.02 (3H, t, J=7.0 Hz), 1.36 (6H, s), 2.83-2.92 (1H, m), 3.06-3.22 (1H, m), 3.37

(2H, q, J=7.0 Hz), 3.49 (2H, s), 3.67-3.80 (4H, m), 4.11-4.22 (1H, m), 5.55-5.68 (1H, m), 6.41-6.62 (1H, m), 6.81-6.91 (2H, m), 7.10-7.25 (2H, m), 7.48-7.58 (1H, m), 10.43-10.85 (1H, m), 11.76 (1H, brs).

Example 172

5-((1R)-1-((4-(1-ethoxy-2-methylpropan-2-yl)-3,5-difluorophenyl)carbamoyl)-6-methoxy-3,4-dihydroisoquinolin-2(1H)-yl)-5-oxopentanoic acid Dihydro-2H-pyran-2,6(3H)-dione (297 mg, 2.60 mmol) was added to a solution of (R)-N-(4-(1-ethoxy-2-methylpropan-2-yl)-3,5-difluorophenyl)-6-methoxy-1,2,3,4-tetrahydroisoquinoline-1-carboxamide (790 mg, 1.74 mmol) and TEA (0.726 mL, 5.21 mmol) in THF (15 mL) at room temperature, and the mixture was stirred at room temperature for 3 hr. The reaction mixture was concentrated under reduced pressure, and the obtained residue was purified by silica gel column chromatography (solvent gradient; 50→100% ethyl acetate/hexane), and crystallized from ethyl acetate/hexane to give the title compound (568.1 mg, 1.067 mmol, 61.4%) as white crystals.
$[\alpha]_D^{25}$ −3.3 (c 0.2530, MeOH)

Example 173

(5R)-N-(4-(ethyl (dimethyl) silyl)-3,5-difluorophenyl)-6-((3-hydroxy-1,2-oxazol-5-yl)acetyl)-2-(methoxymethyl)-5,6,7,8-tetrahydro-1,6-naphthyridine-5-carboxamide (Step 1)
T3P (32.8 mL, 55.73 mmol) was added to a solution of 6-(tert-butoxycarbonyl)-2-(ethoxycarbonyl)-5,6,7,8-tetrahydro-1,6-naphthyridine-5-carboxylic acid (7.16 g, 20.44 mmol), 4-(ethyldimethylsilyl)-3,5-difluoroaniline (4.0 g, 18.58 mmol), DMAP (2.497 g, 20.44 mmol) and DIEA (16.22 mL, 92.89 mmol) in ethyl acetate (120 mL), and the mixture was stirred at 80° C. for 2 hr. To the reaction mixture was added water, and the mixture was extracted with ethyl acetate. The organic layer was washed with water and brine, and dried over magnesium sulfate, and the solvent was evaporated under reduced pressure. The obtained residue was purified by silica gel column chromatography (solvent; ethyl acetate/hexane) to give 2-ethyl 6-tert-butyl 5-((4-(ethyldimethylsilyl)-3,5-difluorophenyl)carbamoyl)-7,8-dihydro-1,6-naphthyridine-2,6(5H)-dicarboxylate (4.61 g, 8.42 mmol, 45.3%) as a grayish white solid.
$^1$H NMR (300 MHz, CDCl$_3$): δ 0.31 (6H, t, J=1.5 Hz), 0.74-0.85 (2H, m), 0.89-0.98 (3H, m), 1.43 (3H, t, J=7.0 Hz), 1.55 (9H, s), 3.11-3.22 (2H, m), 3.42-3.63 (1H, m), 4.05-4.14 (1H, m), 4.43-4.54 (2H, m), 5.76 (1H, brs), 6.97-7.06 (2H, m), 7.74 (1H, brs), 8.03 (1H, d, J=7.9 Hz), 9.11 (1H, brs).
(Step 2)
Sodium borohydride (0.953 g, 25.20 mmol) was added to a solution of 2-ethyl 6-tert-butyl 5-((4-(ethyldimethylsilyl)-3,5-difluorophenyl)carbamoyl)-7,8-dihydro-1,6-naphthyridine-2,6(5H)-dicarboxylate (4.6 g, 8.40 mmol) and calcium chloride (1.398 g, 12.60 mmol) in a mixed solvent of EtOH (45 mL) and THF (45 mL) at 0° C., and the mixture was stirred at room temperature for 5 hr. To the reaction mixture was added 1N hydrochloric acid, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give tert-butyl 5-((4-(ethyldimethylsilyl)-3,5-difluorophenyl) carbamoyl)-2-(hydroxymethyl)-7,8-dihydro-1, 6-naphthyridine-6(5H)-carboxylate (1.45 g, 2.87 mmol, 34.1%) as a colorless oil.
$^1$H NMR (300 MHz, CDCl$_3$): δ 0.25-0.35 (6H, m), 0.71-0.85 (2H, m), 0.89-0.99 (3H, m), 1.55 (9H, s), 2.99-3.10 (2H, m), 3.52 (1H, brs), 3.75 (1H, brs), 4.03-4.14 (1H, m), 4.74 (2H, s), 5.69 (1H, brs), 6.97-7.06 (2H, m), 7.12-7.19 (1H, m), 7.61 (1H, brs), 9.13 (1H, brs).
(Step 3)
Methanesulfonyl chloride (0.444 mL, 5.74 mmol) was added to a solution of tert-butyl 5-((4-(ethyldimethylsilyl)-3,5-difluorophenyl)carbamoyl)-2-(hydroxymethyl)-7,8-dihydro-1,6-naphthyridine-6(5H)-carboxylate (1.45 g, 2.87 mmol) and TEA (0.799 mL, 5.74 mmol) in THF (30 mL) at 0° C., and the mixture was stirred at room temperature for 1 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give tert-butyl 5-((4-(ethyldimethylsilyl)-3,5-difluorophenyl)carbamoyl)-2-(((methylsulfonyl)oxy)methyl)-7,8-dihydro-1,6-naphthyridine-6(5H)-carboxylate (1.97 g, 3.37 mmol, 118%) as a colorless oil.
$^1$H NMR (300 MHz, CDCl$_3$): δ 0.25-0.36 (6H, m), 0.72-0.85 (2H, m), 0.88-1.00 (3H, m), 1.55 (9H, s), 2.92-3.16 (5H, m), 3.49 (1H, brs), 4.02-4.16 (1H, m), 5.31 (2H, s), 5.72 (1H, brs), 6.96-7.07 (2H, m), 7.39 (1H, d, J=7.9 Hz), 7.66 (1H, brs), 9.09 (1H, brs).
(Step 4)
A solution of tert-butyl 5-((4-(ethyldimethylsilyl)-3,5-difluorophenyl)carbamoyl)-2-(((methylsulfonyl)oxy)methyl)-7,8-dihydro-1,6-naphthyridine-6(5H)-carboxylate (1.80 g, 3.08 mmol) in MeOH (40 mL) was stirred overnight at 60° C., and the reaction mixture was concentrated under reduced pressure. To a solution of the obtained residue in THF (40.0 mL) were added TEA (0.516 mL, 3.70 mmol) and Boc$_2$O (0.859 mL, 3.70 mmol) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane), and then preparative HPLC (C18, mobile phase: water/acetonitrile (containing 0.1% TFA)) to give tert-butyl 5-((4-(ethyldimethylsilyl)-3,5-difluorophenyl)carbamoyl)-2-(methoxymethyl)-7,8-dihydro-1,6-naphthyridine-6(5H)-carboxylate (970 mg, 1.867 mmol, 60.5%) as a white solid.
$^1$H NMR (300 MHz, CDCl$_3$): δ 0.31 (6H, t, J=1.5 Hz), 0.71-0.85 (2H, m), 0.89-0.99 (3H, m), 1.54 (9H, s), 2.97-3.12 (2H, m), 3.43-3.62 (4H, m), 4.00-4.15 (1H, m), 4.51-4.60 (2H, m), 5.68 (1H, brs), 6.95-7.07 (2H, m), 7.33 (1H, d, J=7.9 Hz), 7.61 (1H, brs), 9.08 (1H, brs).
(Step 5)
tert-Butyl 5-((4-(ethyldimethylsilyl)-3,5-difluorophenyl) carbamoyl)-2-(methoxymethyl)-7,8-dihydro-1,6-naphthyridine-6(5H)-carboxylate (0.72 g) was resolved by chiral column chromatography. The fraction having a shorter retention time was concentrated to give tert-butyl (R)-5-((4-(ethyldimethylsilyl)-3,5-difluorophenyl)carbamoyl)-2-(methoxymethyl)-7,8-dihydro-1,6-naphthyridine-6(5H)-carboxylate (0.33 g, >99% ee), and the fraction having a longer retention time was concentrated to give tert-butyl (S)-5-((4-(ethyldimethylsilyl)-3,5-difluorophenyl) carbamoyl)-2-(methoxymethyl)-7,8-dihydro-1,6-naphthyridine-6 (5H)-carboxylate (0.33 g, >99% ee), each as a white solid. purification condition by chiral column chromatography
    column: CHIRALPAK IA (QK001) 50 mmID×500 mmL
    solvent: hexane/EtOH=850/150
    flow rate: 80 mL/min
    temperature: 30° C.
    detection method: UV 220 nm
(Step 6)

Cooled TFA (3.0 mL) was added to tert-butyl (R)-5-((4-(ethyldimethylsilyl)-3,5-difluorophenyl)carbamoyl)-2-(methoxymethyl)-7,8-dihydro-1,6-naphthyridine-6(5H)-carboxylate (333 mg, 0.64 mmol), and the mixture was stirred at room temperature for 2 min. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure to give crude (R)-N-(4-(ethyldimethylsilyl)-3,5-difluorophenyl)-2-(methoxymethyl)-5,6,7,8-tetrahydro-1,6-naphthyridine-5-carboxamide (266.4 mg, 0.635 mmol, 99%) as a white solid.

$^1$H NMR (300 MHz, CDCl$_3$): δ 0.22-0.38 (6H, m), 0.73-0.86 (2H, m), 0.86-1.00 (3H, m), 2.84-3.11 (2H, m), 3.14-3.35 (2H, m), 3.46 (3H, s), 4.47-4.60 (2H, m), 4.67 (1H, s), 7.02-7.14 (2H, m), 7.30 (1H, d, J=8.3 Hz), 7.97 (1H, d, J=8.3 Hz), 9.63 (1H, brs).

(Step 7)

HATU (32.6 mg, 0.09 mmol) was added to a solution of (R)-N-(4-(ethyldimethylsilyl)-3,5-difluorophenyl)-2-(methoxymethyl)-5,6,7,8-tetrahydro-1,6-naphthyridine-5-carboxamide (30 mg, 0.07 mmol), DIEA (0.024 mL, 0.14 mmol) and 2-(3-hydroxyisoxazol-5-yl)acetic acid (12.28 mg, 0.09 mmol) in DMF (2.0 mL) at room temperature, and the mixture was stirred at room temperature for 4 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and recrystallized from ethyl acetate/hexane to give (7.8 mg, 0.014 mmol, 20.03%) as white crystals.

$^1$H NMR (300 MHz, DMSO-d$_6$): δ 0.28 (6H, s), 0.68-0.80 (2H, m), 0.84-0.94 (3H, m), 2.90-3.05 (1H, m), 3.08-3.22 (1H, m), 3.34 (3H, s), 3.81-3.95 (1H, m), 3.96-4.20 (3H, m), 4.46 (2H, s), 5.80 (1H, s), 5.91 (1H, s), 7.21 (2H, d, J=9.8 Hz), 7.28-7.38 (1H, m), 7.85-7.95(1H, m), 10.80-10.99 (1H, m), 11.12 (1H, brs)

Example 174

(5R)-N-(4-(ethyl (dimethyl)silyl)-3,5-difluorophenyl)-6-((3-hydroxy-1,2-oxazol-5-yl)carbonyl)-2-(methoxymethyl)-5,6,7,8-tetrahydro-1,6-naphthyridine-5-carboxamide HATU (32.6 mg, 0.09 mmol) was added to a solution of (R)-N-(4-(ethyldimethylsilyl)-3,5-difluorophenyl)-2-(methoxymethyl)-5,6,7,8-tetrahydro-1,6-naphthyridine-5-carboxamide (30 mg, 0.07 mmol), DIEA (0.024 mL, 0.14 mmol) and 3-hydroxyisoxazole-5-carboxylic acid (11.08 mg, 0.09 mmol) in DMF (2.0 mL) at room temperature, and the mixture was stirred at room temperature for 4 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane) to give the title compound (13.6 mg, 0.026 mmol, 35.8%) as a white solid.

$^1$H NMR (300 MHz, DMSO-d$_6$): δ 0.29 (6H, s), 0.67-0.80 (2H, m), 0.84-0.95 (3H, m), 2.92-3.12 (1H, m), 3.13-3.26 (1H, m), 3.35 (3H, s), 3.94-4.07 (1H, m), 4.15-4.28 (1H, m), 4.47 (2H, s), 5.82 (1H, s), 6.61 (1H, s), 7.23 (2H, d, J=9.4 Hz), 7.36 (1H, d, J=7.9 Hz), 7.96 (1H, d, J=7.9 Hz), 10.63-11.20 (1H, m), 11.81 (1H, brs).

Example 175

5-((5R)-5-((4-(ethyl(dimethyl)silyl)-3,5-difluorophenyl)carbamoyl)-2-(methoxymethyl)-7,8-dihydro-1,6-naphthyridin-6(5H)-yl)-5-oxopentanoic acid Dihydro-2H-pyran-2,6(3H)-dione (12.24 mg, 0.11 mmol) was added to a solution of (R)-N-(4-(ethyldimethylsilyl)-3,5-difluorophenyl)-2-(methoxymethyl)-5,6,7,8-tetrahydro-1,6-naphthyridine-5-carboxamide (30 mg, 0.07 mmol) and TEA (0.020 mL, 0.14 mmol) in THF (8.0 mL) at room temperature, and the mixture was stirred at room temperature for 3 hr. The reaction mixture was concentrated under reduced pressure, and the obtained residue was purified by silica gel column chromatography (solvent gradient; 50→100% ethyl acetate/hexane) to give the title compound (19.8 mg, 0.037 mmol, 51.9%) as a colorless oil.

$^1$H NMR (300 MHz, DMSO-d$_6$): δ 0.29 (6H, d, J=1.5 Hz), 0.68-0.80 (2H, m), 0.84-0.95 (3H, m), 1.64-1.82 (2H, m), 2.18-2.37 (2H, m), 2.41-2.66 (2H, m), 2.87-3.21 (2H, m), 3.34 (3H, d, J=1.5 Hz), 3.74-3.88 (1H, m), 3.97-4.12 (1H, m), 4.45 (2H, s), 5.79 (1H, s), 7.22 (2H, d, J=9.8 Hz), 7.31 (1H, d, J=7.9 Hz), 7.90 (1H, d, J=7.9 Hz), 10.89 (1H, s), 11.49 (1H, brs).

Example 176

5-((1R)-1-((7-fluoro-1,1-dimethyl-2,3-dihydro-1H-inden-5-yl) carbamoyl)-6-methoxy-3,4-dihydroisoquinolin-2 (1H)-yl)-5-oxopentanoic acid Dihydro-2H-pyran-2,6(3H)-dione (220 mg, 1.93 mmol) was added to a solution of (R)-N-(7-fluoro-1,1-dimethyl-2,3-dihydro-1H-inden-5-yl)-6-methoxy-1,2,3,4-tetrahydroisoquinoline-1-carboxamide hydrochloride (520 mg, 1.28 mmol) (which can be synthesized in the same manner as above) and TEA (0.537 mL, 3.85 mmol) in THF (10 mL) at room temperature, and the mixture was stirred at room temperature for 3 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane), and crystallized from ethyl acetate/hexane to give the title compound (531.3 mg, 1.101 mmol, 86%) as white crystals.

$^1$H NMR (300 MHz, DMSO-d$_6$): δ 1.28 (6H, d, J=1.5 Hz), 1.63-1.81 (2H, m), 1.86 (2H, t, J=7.4 Hz), 2.20-2.32 (2H, m), 2.35-2.62 (2H, m), 2.69-2.90 (3H, m), 3.04-3.19 (1H, m), 3.45-3.60 (1H, m), 3.72 (3H, s), 3.92-4.08 (1H, m), 5.53-5.69 (1H, m), 6.75-6.86 (2H, m), 7.12-7.27 (2H, m), 7.41-7.52 (1H, m), 10.35-10.48 (1H, m), 12.05 (1H, brs).

$[α]_D^{25}$+2.7 (c 0.2535, MeOH)

Example 177

4-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)-4-oxobutanoic acid Succinic anhydride (58.8 mg, 0.59 mmol) was added to a solution of (R)-N-(7-fluoro-1,1-dimethyl-2,3-dihydro-1H-inden-5-yl)-2-methoxy-5,6,7,8-tetrahydro-1,6-naphthyridine-5-carboxamide (167 mg, 0.45 mmol) and TEA (95 µL, 0.68 mmol) in THF (3.9 mL) at room temperature, and the mixture was stirred at room temperature for 15 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 30→100% ethyl acetate/hexane) to give the title compound (162.0 mg, 0.345 mmol, 76%) as a white solid.

$^1$H NMR (300 MHz, CDCl$_3$): δ 1.31 (6H, s), 1.87 (2H, t, J=7.4 Hz), 2.69-2.93 (7H, m), 2.97-3.06 (2H, m), 3.72-3.83 (1H, m), 3.91 (3H, s), 3.98 (1H, dt), 5.99 (1H, s), 6.63 (1H, d, J=8.7 Hz), 7.01-7.09 (2H, m), 7.45 (1H, d, J=8.7 Hz), 8.81 (1H, s)

Example 178

4-((5R)-5-((3,5-difluoro-4-(trimethylsilyl)phenyl)carbamoyl)-2-methoxy-7,8-dihydro-1,6-naphthyridin-6(5H)-yl)-4-oxobutanoic acid Succinic anhydride (30.7 mg, 0.31 mmol) was added to a solution of (R)-N-(3,5-difluoro-4-(trimethylsilyl)phenyl)-2-methoxy-5,6,7,8-tetrahydro-1,6-naphthyridine-5-carboxamide (100 mg, 0.26 mmol) and TEA (0.071 mL, 0.51 mmol) in THF (2.0 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 50→100% ethyl acetate/hexane) to give the title compound (91.6 mg, 0.186 mmol, 73.0%) as a white solid.

$^1$H NMR (300 MHz, DMSO-d$_6$): δ 0.30 (9H, s), 2.43-2.54 (2H, m), 2.65-2.79 (2H, m), 2.83-2.97 (1H, m), 3.00-3.13 (1H, m), 3.75-3.90 (4H, m), 3.97-4.12 (1H, m), 5.66-5.76 (1H, m), 6.73 (1H, d, J=8.7 Hz), 7.15-7.29 (2H, m), 7.70-7.81 (1H, m), 10.76 (1H, s), 12.08 (1H, brs).

Example 179

5-((1R)-1-((3,5-difluoro-4-(trimethylsilyl)phenyl)carbamoyl)-6-ethoxy-3,4-dihydroisoquinolin-2(1H)-yl)-5-oxopentanoic acid (Step 1)
T3P (4.39 mL, 7.47 mmol) was added to a solution of 2-(tert-butoxycarbonyl)-6-ethoxy-1,2,3,4-tetrahydroisoquinoline-1-carboxylic acid (0.8 g, 2.49 mmol), 3,5-difluoro-4-(trimethylsilyl)aniline (0.501 g, 2.49 mmol), DIEA (2.174 mL, 12.45 mmol) and DMAP (0.304 g, 2.49 mmol) in ethyl acetate (25 mL) and the mixture was stirred at 70° C. for 20 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 2→40% ethyl acetate/hexane) to give tert-butyl 1-((3,5-difluoro-4-(trimethylsilyl)phenyl)carbamoyl)-6-ethoxy-3,4-dihydroisoquinoline-2 (1H)-carboxylate (1.110 g, 2.200 mmol, 88%) as a white solid.

$^1$H NMR (300 MHz, CDCl$_3$): δ 0.26-0.36 (9H, m), 1.41 (3H, t, J=7.0 Hz), 1.52 (9H, s), 2.66-2.95 (2H, m), 3.35-3.77 (2H, m), 4.03 (2H, q, J=7.2 Hz), 5.56 (1H, brs), 6.72 (1H, s), 6.80 (1H, dd, J=8.3, 2.6 Hz), 7.02 (2H, d, J=9.1 Hz), 7.09-7.22 (1H, m, J=8.3 Hz), 9.09 (1H, brs).

(Step 2)
tert-Butyl 1-((3,5-difluoro-4-(trimethylsilyl)phenyl)carbamoyl)-6-ethoxy-3,4-dihydroisoquinoline-2(1H)-carboxylate (1.09 g) was resolved by chiral column chromatography. The fraction having a shorter retention time was concentrated to give tert-butyl (R)-1-((3,5-difluoro-4-(trimethylsilyl)phenyl)carbamoyl)-6-ethoxy-3,4-dihydroisoquinoline-2 (1H)-carboxylate (0.436 g, >99% ee), and the fraction having a longer retention time was concentrated to give tert-butyl (S)-1-((3,5-difluoro-4-(trimethylsilyl)phenyl)carbamoyl)-6-ethoxy-3,4-dihydroisoquinoline-2(1H)-carboxylate (0.441 g, >99% ee), each as a white solid.
purification condition by chiral column chromatography
    column CHIRALPAK IA 50 mmID×500 mmL
    solvent: hexane/EtOH=950/50
    flow rate: 80 mL/min
    temperature: 30° C.
    detection method: UV 220 nm (Step 3)
Cooled TFA (6 mL) was added to tert-butyl (R)-1-((3,5-difluoro-4-(trimethylsilyl)phenyl)carbamoyl)-6-ethoxy-3,4-dihydroisoquinoline-2(1H)-carboxylate (436 mg, 0.86 mmol), and the mixture was stirred for 30 min under ice water. The reaction mixture was added to aqueous sodium hydrogen carbonate solution, and the mixture was extracted with ethyl acetate. The organic layer was dried over magnesium sulfate, and the solvent was evaporated under reduced pressure to give (R)-N-(3,5-difluoro-4-(trimethylsilyl)phenyl)-6-ethoxy-1,2,3,4-tetrahydroisoquinoline-1-carboxamide (350 mg, 0.865 mmol, 100%) as a white gum-like substance.

MS(API): Calculated 404.5. Found 405.1 (M+H).

(Step 4)
Dihydro-2H-pyran-2,6(3H)-dione (26.7 mg, 0.23 mmol) was added to a solution of (R)-N-(3,5-difluoro-4-(trimethylsilyl)phenyl)-6-ethoxy-1,2,3,4-tetrahydroisoquinoline-1-carboxamide (63 mg, 0.16 mmol) and TEA (0.033 mL, 0.23 mmol) in THF (2 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 10→90% ethyl acetate/hexane), and crystallized from ethyl acetate/hexane to give the title compound (25.00 mg, 0.048 mmol, 31.0%) as white crystals.

$^1$H NMR (300 MHz, DMSO-d$_6$): δ 0.29 (9H, s), 1.30 (3H, t, J=7.0 Hz), 1.59-1.83 (2H, m), 2.17-2.32 (3H, m), 2.38-2.61 (1H, m), 2.70-2.86 (1H, m), 3.04-3.18 (1H, m), 3.50 (1H, t, J=8.3 Hz), 3.91-4.07 (3H, m), 5.61 (1H, s), 6.73-6.85 (2H, m), 7.20 (2H, d, J=9.8 Hz), 7.44 (1H, d, J=9.1 Hz), 10.76 (1H, s), 12.06 (1H, brs).

$[α]_D^{25}$ −11.1 (c 0.2500, MeOH)

Example 180

4-((1R)-1-((3,5-difluoro-4-(trimethylsilyl)phenyl) carbamoyl)-6-ethoxy-3,4-dihydroisoquinolin-2(1H)-yl)-4-oxobutanoic acid Succinic anhydride (30.4 mg, 0.30 mmol) was added to a solution of (R)-N-(3,5-difluoro-4-(trimethylsilyl)phenyl)-6-ethoxy-1,2,3,4-tetrahydroisoquinoline-1-carboxamide (82 mg, 0.20 mmol) and TEA (0.042 mL, 0.30 mmol) in THF (6 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane) to give the title compound (1.0 mg, 0.121 mmol, 59.6%) as a white solid.

$^1$H NMR (300 MHz, DMSO-$d_6$): δ 0.29 (9H, s), 1.30 (3H, t, J=7.0 Hz), 2.40-2.48 (2H, m), 2.63-2.89 (3H, m), 3.05-3.22 (1H, m), 3.43-3.60 (1H, m), 3.94-4.09 (3H, m), 5.55-5.67 (1H, m), 6.72-6.88 (2H, m), 7.12-7.26 (2H, m), 7.42 (1H, d, J=8.3 Hz), 10.72 (1H, s), 12.05 (1H, brs).

Example 181

5-((1R)-6-((difluoromethoxy)methyl)-1-((3,5-difluoro-4-(trimethylsilyl)phenyl)carbamoyl)-3,4-dihydroisoquinolin-2 (1H)-yl)-5-oxopentanoic acid Dihydro-2H-pyran-2,6(3H)-dione (22.15 mg, 0.19 mmol) was added to a solution of (R)-N-(3,5-difluoro-4-(trimethylsilyl)phenyl)-6-((difluoromethoxy)methyl)-1,2,3,4-tetrahydroisoquinoline-1-carboxamide (57 mg, 0.13 mmol) (which can be synthesized in the same manner as above) and TEA (0.027 mL, 0.19 mmol) in THF (6 mL) at room temperature, and the mixture was stirred overnight at room temperature. The reaction mixture was concentrated under reduced pressure. To the obtained residue was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 10→90% ethyl acetate/hexane) to give the title compound (31.0 mg, 0.056 mmol, 43.2%) as a white solid.

$^1$H NMR (300 MHz, DMSO-$d_6$): δ 0.30 (9H, s), 1.73 (2H, dq, J=15.0, 7.3 Hz), 2.18-2.35 (3H, m), 2.38-2.61 (1H, m), 2.80-2.94 (1H, m), 3.04-3.22 (1H, m), 3.57 (1H, ddd, J=12.4, 8.4, 4.2 Hz), 3.96-4.10 (1H, m), 4.86 (2H, s), 5.71 (1H, s), 6.77 (1H, t, J=75.5 Hz), 7.15-7.31 (4H, m), 7.56 (1H, d, J=7.9 Hz), 10.83 (1H, s), 12.05 (1H, brs).

Example 182

5-((1R)-6-ethoxy-1-((7-fluoro-1,1-dimethyl-2,3-dihydro-1H-inden-5-yl)carbamoyl)-3,4-dihydroisoquinolin-2(1H)-yl)-5-oxopentanoic acid (Step 1)

tert-Butyl 6-ethoxy-1-((7-fluoro-1,1-dimethyl-2,3-dihydro-1H-inden-5-yl) carbamoyl)-3,4-dihydroisoquinoline-2(1H)-carboxylate (0.786 g) was resolved by chiral column chromatography. The fraction having a shorter retention time was concentrated to give tert-butyl (R)-6-ethoxy-1-((7-fluoro-1,1-dimethyl-2,3-dihydro-1H-inden-5-yl)carbamoyl)-3,4-dihydroisoquinoline-2(1H)-carboxylate (0.367 g, >99% ee), and the fraction having a longer retention time was concentrated to give tert-butyl (S)-6-ethoxy-1-((7-fluoro-1,1-dimethyl-2,3-dihydro-1H-inden-5-yl)carbamoyl)-3,4-dihydroisoquinoline-2(1H)-carboxylate (0.358 g, 97.9% ee), each as a white solid.

purification condition by chiral column chromatography
column: CHIRALPAK IA 50 mmID×500 mmL
solvent: hexane/EtOH=950/50
flow rate: 80 mL/min
temperature: 30° C.
detection method: UV 220 nm (Step 2)

Cooled TFA (4.0 mL) was added to tert-butyl (R)-6-ethoxy-1-((7-fluoro-1,1-dimethyl-2,3-dihydro-1H-inden-5-yl)carbamoyl)-3,4-dihydroisoquinoline-2(1H)-carboxylate (367 mg, 0.76 mmol), and the mixture was stirred at room temperature for 2 min. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure. The precipitate was washed with hexane to give (R)-6-ethoxy-N-(7-fluoro-1,1-dimethyl-2,3-dihydro-1H-inden-5-yl)-1,2,3,4-tetrahydroisoquinoline-1-carboxamide (272.3 mg, 0.712 mmol, 94%) as a white solid.

MS(API): Calculated 382.5. Found 383.3 (M+H).

(Step 3)

Dihydro-2H-pyran-2,6(3H)-dione (67.1 mg, 0.59 mmol) was added to a solution of (R)-6-ethoxy-N-(7-fluoro-1,1-dimethyl-2,3-dihydro-1H-inden-5-yl)-1,2,3,4-tetrahydroisoquinoline-1-carboxamide (150 mg, 0.39 mmol) and TEA (0.082 mL, 0.59 mmol) in THF (3.0 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→90% ethyl acetate/hexane), and crystallized from ethyl acetate/hexane to give the title compound (130.7 mg, 0.263 mmol, 67.1%) as white crystals.

$^1$H NMR (300 MHz, DMSO-$d_6$): δ 1.22-1.35 (9H, m), 1.66-1.80 (2H, m), 1.82-1.91 (2H, m), 2.20-2.32 (2H, m), 2.35-2.61 (2H, m), 2.69-2.90 (3H, m), 3.03-3.18 (1H, m), 3.46-3.59 (1H, m), 3.93-4.07 (3H, m), 5.57-5.68 (1H, m), 6.75-6.83 (2H, m), 7.12-7.27 (2H, m), 7.40-7.48 (1H, m), 10.33-10.55 (1H, m), 12.05 (1H, brs).

Example 183

5-((1R)-6-ethoxy-1-((3-fluoro-4-(trimethylsilyl)phenyl)carbamoyl)-3,4-dihydroisoquinolin-2 (1H)-yl)-5-oxopentanoic acid (Step 1)

T3P (5.78 mL, 9.82 mmol) was added to a solution of 2-(tert-butoxycarbonyl)-6-ethoxy-1,2,3,4-tetrahydroisoquinoline-1-carboxylic acid (1157 mg, 3.60 mmol), 3-fluoro-4-(trimethylsilyl)aniline (600 mg, 3.27 mmol), DMAP (440 mg, 3.60 mmol) and DIEA (2.86 mL, 16.37 mmol) in ethyl acetate (20 mL), and the mixture was stirred at 80° C. for 2 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The residue was solidified with Et$_2$O to give tert-butyl 6-ethoxy-1-((3-fluoro-4-(trimethylsilyl)phenyl)carbamoyl)-3,4-dihydroisoquinoline-2(1H)-carboxylate (601.8 mg, 1.237 mmol, 37.8%) as a white solid.

MS(API): Calculated 486.7. Found 485.3 (M−H).

(Step 2)

tert-Butyl 6-ethoxy-1-((3-fluoro-4-(trimethylsilyl)phenyl)carbamoyl)-3,4-dihydroisoquinoline-2(1H)-carboxylate (0.602 g) was resolved by chiral column chromatography. The fraction having a shorter retention time was concentrated to give tert-butyl (R)-6-ethoxy-1-((3-fluoro-4-(trimethylsilyl)phenyl)carbamoyl)-3,4-dihydroisoquinoline-2(1H)-carboxylate (0.267 g, >99% ee), and the fraction having a longer retention time was concentrated to give tert-butyl (S)-6-ethoxy-1-((3-fluoro-4-(trimethylsilyl)phenyl)carbamoyl)-3,4-dihydroisoquinoline-2(1H)-carboxylate (0.270 g, >99% ee), each as a white solid.

column: CHIRALPAK IA
solvent: hexane/EtOH=950/50
flow rate: 80 mL/min
temperature: 30° C.
detection method: UV 220 nm (Step 3)

Cooled TFA (3.0 mL) was added to tert-butyl (R)-6-ethoxy-1-((3-fluoro-4-(trimethylsilyl)phenyl)carbamoyl)-3,4-dihydroisoquinoline-2(1H)-carboxylate (267 mg, 0.55 mmol), and the mixture was stirred at room temperature for 2 min. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure to give (R)-6-ethoxy-N-(3-fluoro-4-(trimethylsilyl)phenyl)-1,2,3,4-tetrahydroisoquinoline-1-carboxamide (211.9 mg, 0.548 mmol, 100%) as a white solid.

MS(API): Calculated 386.5. Found 387.3 (M+H).

(Step 4)

Dihydro-2H-pyran-2,6(3H)-dione (66.4 mg, 0.58 mmol) was added to a solution of (R)-6-ethoxy-N-(3-fluoro-4-(trimethylsilyl)phenyl)-1,2,3,4-tetrahydroisoquinoline-1-carboxamide (150 mg, 0.39 mmol) and TEA (0.081 mL, 0.58 mmol) in THF (3.0 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (Diol, solvent gradient; 20→90% ethyl acetate/hexane), and crystallized from ethyl acetate/hexane to give the title compound (93.8 mg, 0.187 mmol, 48.3%) as white crystals.

$^1$H NMR (300 MHz, DMSO-d$_6$): δ 0.25 (9H, s), 1.29 (3H, t, J=7.0 Hz), 1.74 (2H, quin, J=7.2 Hz), 2.18-2.32 (2H, m), 2.35-2.61 (2H, m), 2.70-2.87 (1H, m), 3.04-3.04-3.20 (1H, m), 3.44-3.58 (1H, m), 3.93-4.07 (3H, m), 5.59-5.69 (1H, m), 6.75-6.84 (2H, m), 7.24-7.37 (2H, m), 7.41-7.50 (2H, m), 10.53-10.71 (1H, m), 12.04 (1H, brs).

Example 184

5-((1R)-1-((2,5-difluoro-4-(trimethylsilyl)phenyl)carbamoyl)-6-ethoxy-3,4-dihydroisoquinolin-2(1H)-yl)-5-oxopentanoic acid (Step 1)

Nitric acid (d 1.42) (26.2 g, 286.81 mmol) was slowly added dropwise to conc. sulfuric acid (102 g, 1042.96 mmol) over 1 hr under ice water, while the mixture was maintained at 10° C. or below. Then, 2-bromo-1,4-difluorobenzene (50.32 g, 260.74 mmol) was slowly added thereto over 3 hr while the mixture was maintained at 10° C. or below. The reaction mixture was stirred at 5° C. for 30 min, and then at room temperature for 1 hr. The reaction mixture was poured into ice (about 600 g), and the mixture was extracted three times with a mixed solvent of Et$_2$O/THF (3:1). The organic layer was washed with brine, and dried over magnesium sulfate, and the solvent was evaporated under reduced pressure. The obtained residue was purified by silica gel column chromatography (solvent; 20% ethyl acetate/hexane) to give 1-bromo-2,5-difluoro-4-nitrobenzene (49.64 g, 209 mmol, 80%) as a pale yellow solid.

$^1$H NMR (300 MHz, CDCl$_3$): δ 7.59 (1H, dd, J=9.4, 5.3 Hz), 7.89 (1H, dd, J=7.2, 6.4 Hz).

(Step 2)

Hexamethyldisilane (34.4 mL, 167.91 mmol) was added to a solution of 1-bromo-2,5-difluoro-4-nitrobenzene (10.8 g, 45.38 mmol) and Pd(Ph$_3$P)$_4$ (1.311 g, 1.13 mmol) in xylene (15 mL), and the mixture was stirred at 140° C. for 2 days under argon gas atmosphere. The reaction mixture was cooled. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give (2,5-difluoro-4-nitrophenyl)trimethylsilane (2.44 g, 10.55 mmol, 23.25%) as a yellow oil.

(Step 3)

A solution of (2,5-difluoro-4-nitrophenyl)trimethylsilane (2.44 g, 10.55 mmol) and 10% palladium-carbon (650 mg, 6.11 mmol, 50% wet) in MeOH (50 mL) was stirred under hydrogen atmosphere (1 atm) at room temperature for 5 hr. The catalyst was filtered off, and the filtrate was concentrated under reduced pressure. The obtained residue was purified by silica gel column chromatography (NH, solvent; ethyl acetate/hexane) to give 2,5-difluoro-4-(trimethylsilyl)aniline (1.11 g, 5.51 mmol, 52.3%) as a yellow oil.

$^1$H NMR (300 MHz, CDCl$_3$): δ 0.26 (9H, d, J=1.1 Hz), 3.84 (2H, brs), 6.40 (1H, dd, J=9.1, 6.8 Hz), 6.86-6.95 (1H, m).

(Step 4)

T3P (3.51 mL, 5.96 mmol) was added to a solution of 2-(tert-butoxycarbonyl)-6-ethoxy-1,2,3,4-tetrahydroisoquinoline-1-carboxylic acid (702 mg, 2.19 mmol), 2,5-difluoro-4-(trimethylsilyl)aniline (400 mg, 1.99 mmol), DMAP (267 mg, 2.19 mmol) and DIEA (1.735 mL, 9.94 mmol) in ethyl acetate (10 mL), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→10% ethyl acetate/hexane), and solidified with Et$_2$O/hexane to give tert-butyl 1-((2,5-difluoro-4-(trimethylsilyl)phenyl)carbamoyl)-6-ethoxy-3,4-dihydroisoquinoline-2(1H)-carboxylate (239.3 mg, 0.474 mmol, 23.86%) as a white solid.

MS(API): Calculated 504.6. Found 503.3 (M+H).

(Step 5)

tert-Butyl 1-((2,5-difluoro-4-(trimethylsilyl)phenyl)carbamoyl)-6-ethoxy-3,4-dihydroisoquinoline-2(1H)-carboxylate (0.239 g) was resolved by chiral column chromatography. The fraction having a shorter retention time was concentrated to give tert-butyl (R)-1-((2,5-difluoro-4-(trimethylsilyl)phenyl)carbamoyl)-6-ethoxy-3,4-dihydroisoquinoline-2(1H)-carboxylate (0.088 g, >99% ee), and the fraction having a longer retention time was concentrated to give tert-butyl (S)-1-((2,5-difluoro-4-(trimethylsilyl)phenyl)carbamoyl)-6-ethoxy-3,4-dihydroisoquinoline-2(1H)-carboxylate (0.112 g, >99% ee), each as a white solid.

purification condition by chiral column chromatography
    column: CHIRALPAK IA 50 mmID×500 mmL
    solvent: hexane/EtOH=950/50
    flow rate: 80 mL/min
    temperature: 30° C.
    detection method: UV 220 nm (Step 6)

Cooled TFA (2.0 mL) was added to tert-butyl (R)-1-((2,5-difluoro-4-(trimethylsilyl)phenyl)carbamoyl)-6-ethoxy-3,4-dihydroisoquinoline-2(1H)-carboxylate (80 mg, 0.16 mmol), and the mixture was stirred at room temperature for 2 min. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure to give (R)-N-(2,5-difluoro-4-(trimethylsilyl)phenyl)-6-ethoxy-1,2,3,4-tetrahydroisoquinoline-1-carboxamide (62.1 mg, 0.154 mmol, 97%) as a white solid.

$^1$H NMR (300 MHz, CDCl$_3$): δ 0.27 (9H, d, J=0.8 Hz), 1.39 (3H, t, J=7.0 Hz), 2.68-2.95 (2H, m), 3.12-3.12-3.21 (2H, m), 4.01 (2H, q, J=7.0 Hz), 4.72 (1H, s), 5.13 (1H, brs), 6.64 (1H, d, J=2.6 Hz), 6.79 (1H, dd, J=8.7, 2.6 Hz), 7.01 (1H, dd, J=10.6, 4.5 Hz), 7.49 (1H, d, J=8.7 Hz), 8.10 (1H, dd, J=9.8, 6.0 Hz), 9.76 (1H, brs).

(Step 7)

Dihydro-2H-pyran-2,6(3H)-dione (27.1 mg, 0.24 mmol) was added to a solution of (R)-N-(2,5-difluoro-4-(trimethylsilyl)phenyl)-6-ethoxy-1,2,3,4-tetrahydroisoquinoline-1-carboxamide (64 mg, 0.16 mmol) and TEA (0.033 mL, 0.24 mmol) in THF (2.0 mL) at room temperature, and the mixture was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (Diol, solvent gradient; 20→90% ethyl acetate/hexane), and crystallized from ethyl acetate/hexane to give the title compound (45.7 mg, 0.088 mmol, 55.7%) as white crystals.

$^1$H NMR (300 MHz, DMSO-d$_6$): δ 0.26 (9H, s), 1.30 (3H, t, J=7.0 Hz), 1.63-1.81 (2H, m), 2.17-2.33 (2H, m), 2.35-2.61 (2H, m), 2.68-2.86 (1H, m), 2.99-3.17 (1H, m), 3.43-3.59 (1H, m), 3.89-4.07 (3H, m), 5.93 (1H, s), 6.72-6.85 (2H, m), 7.21 (1H, dd, J=10.4, 4.7 Hz), 7.44-7.56 (1H, m), 7.69 (1H, dd, J=10.4, 5.7 Hz), 10.30 (1H, s), 12.07 (1H, brs).

[α]$_D^{25}$ −3.7 (c 0.2515, MeOH)

Example 185

5-((1-((3,5-difluoro-4-(trimethylsilyl)phenyl)carbamoyl)-6-methoxy-3,4-dihydroisoquinolin-2(1H)-yl)carbonyl)-1-methyl-1H-pyrazole-3-carboxylic acid (Step 1)

HATU (117 mg, 0.31 mmol) was added to a solution of N-(3,5-difluoro-4-(trimethylsilyl)phenyl)-6-methoxy-1,2,3,4-tetrahydroisoquinoline-1-carboxamide (100 mg, 0.26 mmol) (which can be synthesized in the same manner as above), DIEA (0.088 mL, 0.51 mmol) and 3-(ethoxycarbonyl)-1-methyl-1H-pyrazole-5-carboxylic acid (60.9 mg, 0.31 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give ethyl 5-(1-((3,5-difluoro-4-(trimethylsilyl)phenyl)carbamoyl)-6-methoxy-1,2,3,4-tetrahydroisoquinoline-2-carbonyl)-1-methyl-1H-pyrazole-3-carboxylate (90.8 mg, 0.159 mmol, 62.1%) as a white solid.

$^1$H NMR (300 MHz, CDCl$_3$): δ 0.32 (9H, s), 1.37-1.45 (3H, m), 2.93-3.14 (2H, m), 3.82 (3H, s), 3.83-3.89 (1H, m), 3.90-4.01 (1H, m), 4.07-4.17 (4H, m), 4.36-4.48 (2H, m), 5.98 (1H, s), 6.72-6.92 (2H, m), 6.95-7.08 (2H, m), 7.19 (1H, d, J=8.3 Hz), 9.01 (1H, s).

(Step 2)

1N Aqueous sodium hydroxide solution (0.308 mL, 0.31 mmol) was added to a solution of ethyl 5-(1-((3,5-difluoro-4-(trimethylsilyl)phenyl)carbamoyl)-6-methoxy-1,2,3,4-tetrahydroisoquinoline-2-carbonyl)-1-methyl-1H-pyrazole-3-carboxylate (88 mg, 0.15 mmol) in a mixed solvent of EtOH (1.0 mL) and THF (1.0 mL) at room temperature, and the mixture was stirred overnight at room temperature. The reaction mixture was concentrated under reduced pressure, 1N hydrochloric acid was added thereto until the pH of the mixture became 2 to 3, and the mixture was extracted with ethyl acetate. The organic layer was dried over magnesium sulfate, and the solvent was evaporated under reduced pressure. The obtained residue was purified by silica gel column chromatography (Diol, solvent gradient; 20→90% ethyl acetate/hexane), and then preparative HPLC (C18, mobile phase: water/acetonitrile (containing 0.1% TFA)) to give the title compound (6.2 mg, 0.011 mmol, 7.41%) as a white solid.

$^1$H NMR (300 MHz, DMSO-d$_6$): δ 0.30 (9H, s), 2.76-2.94 (1H, m), 3.04-3.17 (1H, m), 3.58-3.70 (1H, m), 3.74 (3H, s), 3.74-3.82 (1H, m), 3.90 (3H, s), 3.96-4.09 (1H, m), 5.68 (1H, s), 6.75-6.92 (2H, m), 7.02 (1H, s), 7.23 (2H, d, J=9.4 Hz), 7.55 (1H, d, J=7.9 Hz), 10.89 (1H, s).

Example 186 ethyl N-((1-((3,5-difluoro-4-(trimethylsilyl)phenyl)carbamoyl)-6-methoxy-3,4-dihydroisoquinolin-2(1H)-yl) carbonyl)-beta-alaninate TEA (0.056 mL, 0.40 mmol) was added to a solution of ethyl 3-isocyanatopropionate (0.053 mL, 0.40 mmol) and N-(3,5-difluoro-4-(trimethylsilyl)phenyl)-6-methoxy-1,2,3,4-tetrahydroisoquinoline-1-carboxamide (130 mg, 0.33 mmol) in THF (2.0 mL), and the mixture was stirred at room temperature for 4 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 10→50% ethyl acetate/hexane) to give ethyl 3-(1-((3,5-difluoro-4-(trimethylsilyl)phenyl)carbamoyl)-6-methoxy-1,2,3,4-tetrahydroisoquinoline-2-carboxamide)propanoate (145.3 mg, 0.272 mmol, 82%) as a white solid.

¹H NMR (300 MHz, DMSO-d₆): δ 0.29 (9H, s), 1.12-1.19 (3H, m), 2.37-2.55 (2H, m), 2.67-2.84 (1H, m), 3.00-3.17 (1H, m), 3.22-3.41 (3H, m), 3.72 (3H, s), 3.75-3.85 (1H, m), 3.99-4.08 (2H, m), 5.52 (1H, s), 6.71 (1H, t, J=5.5 Hz), 6.76-6.84 (2H, m), 7.15-7.26 (2H, m), 7.39-7.46 (1H, m), 10.64 (1H, s).

Example 187

(1R)-N-(3,5-difluoro-4-(trimethylsilyl)phenyl)-2-((2,4-dioxo-1,3-thiazolidin-5-yl)acetyl)-6-methoxy-1,2,3,4-tetrahydroisoquinoline-1-carboxamide HATU (58.4 mg, 0.15 mmol) was added to a solution of (R)-N-(3,5-difluoro-4-(trimethylsilyl)phenyl)-6-methoxy-1,2,3,4-tetrahydroisoquinoline-1-carboxamide (50 mg, 0.13 mmol), DIEA (0.044 mL, 0.26 mmol) and 2-(2,4-dioxothiazolidin-5-yl)acetic acid (26.9 mg, 0.15 mmol) in DMF (2.0 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 10→50% ethyl acetate/hexane, 0-10% MeOH/ethyl acetate), and recrystallized from ethyl acetate/hexane to give the title compound (36.3 mg, 0.066 mmol, 51.8%) as white crystals.

¹H NMR (300 MHz, DMSO-d₆): δ 0.29 (9H, s), 2.76-2.90 (1H, m), 3.08-3.22 (1H, m), 3.24-3.38 (2H, m), 3.39-3.58 (1H, m), 3.73 (3H, s), 3.94-4.09 (1H, m), 4.54-4.70 (1H, m), 5.61 (1H, s), 6.77-6.90 (2H, m), 7.12-7.27 (2H, m), 7.44 (1H, t, J=8.3 Hz), 10.77 (1H, d, J=11.7 Hz), 11.96 (1H, brs).

Example 188

N-(((1R)-1-(((3,5-difluoro-4-(trimethylsilyl)phenyl)carbamoyl)-6-methoxy-3,4-dihydroisoquinolin-2(1H)-yl)carbonyl)-beta-alanine (Step 1)
HATU (44.2 mg, 0.12 mmol) was added to a solution of (R)-N-(3,5-difluoro-4-(trimethylsilyl)phenyl)-6-methoxy-1,2,3,4-tetrahydroisoquinoline-1-carboxamide (50 mg, 0.13 mmol), benzyl 3-(((4-nitrophenoxy)carbonyl)amino)propanoate (52.9 mg, 0.15 mmol) and DIEA (0.045 mL, 0.26 mmol) in DMF (2.0 mL) at room temperature, and the mixture was stirred at room temperature for 3 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→20% ethyl acetate/hexane) to give crude benzyl (R)-3-(1-(((3,5-difluoro-4-(trimethylsilyl)phenyl)carbamoyl)-6-methoxy-1,2,3,4-tetrahydroisoquinoline-2-carboxamide)propanoate (39.2 mg, 0.066 mmol, 51.4%) as a colorless oil.

MS(API): Calculated 595.7. Found 594.3 (M−H).
(Step 2)
A solution of benzyl (R)-3-(1-(((3,5-difluoro-4-(trimethylsilyl)phenyl)carbamoyl)-6-methoxy-1,2,3,4-tetrahydroisoquinoline-2-carboxamide)propanoate (39 mg, 0.07 mmol) and 10% palladium-carbon (10 mg, 0.09 mmol, 50% wet) in MeOH (2.0 mL) was stirred under hydrogen atmosphere (1 atm) at room temperature for 2 hr. The catalyst was removed by filtration, and the filtrate was concentrated under reduced pressure. The obtained residue was purified by silica gel column chromatography (solvent gradient; 20→90% ethyl acetate/hexane) to give the title compound (12.0 mg, 0.024 mmol, 25.3%) as a white solid.

¹H NMR (300 MHz, DMSO-d₆): δ 0.29 (9H, s), 2.32-2.47 (3H, m), 2.70-2.84 (1H, m), 3.03-3.15 (1H, m), 3.19-3.41 (2H, m), 3.72 (3H, s), 3.75-3.85 (1H, m), 5.52 (1H, s), 6.66-6.84 (3H, m), 7.22 (2H, d, J=9.8 Hz), 7.38-7.47 (1H, m), 10.66 (1H, s), 12.26 (1H, s).

Example 189

5-(2-(((1R)-1-(((4-tert-butyl-3,5-difluorophenyl)carbamoyl)-6-methoxy-3,4-dihydroisoquinolin-2(1H)-yl)-2-oxoethyl)-1,2-oxazole-3-carboxylic acid (Step 1)
HATU (44.2 mg, 0.12 mmol) was added to a solution of (R)-N-(4-(tert-butyl)-3,5-difluorophenyl)-6-methoxy-1,2,3,4-tetrahydroisoquinoline-1-carboxamide hydrochloride (39.8 mg, 0.10 mmol), DIEA (0.041 mL, 0.23 mmol) and 2-(3-(tert-butoxycarbonyl)isoxazol-5-yl)acetic acid (22 mg, 0.10 mmol) in DMF (4 mL)) at 0° C., and the mixture was stirred at 0° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→90% ethyl acetate/hexane) to give crude tert-butyl (R)-5-(2-(1-((4-(tert-butyl)-3,5-difluorophenyl)carbamoyl)-6-methoxy-3,4-dihydroisoquinolin-2 (1H)-yl)-2-oxoethyl)isoxazole-3-carboxylate as a pale yellow oil. The total amount thereof was used for the next step.

MS(API): Calculated 583.6. Found 582.3 (M−H).
(Step 2)
Cooled TFA (4 mL) was added to the crude tert-butyl (R)-5-(2-(1-((4-(tert-butyl)-3,5-difluorophenyl)carbamoyl)-6-methoxy-3,4-dihydroisoquinolin-2(1H)-yl)-2-oxoethyl)isoxazole-3-carboxylate at 0° C., and the mixture was stirred at 0° C. for 2 hr. The reaction mixture was concentrated under reduced pressure. The obtained residue was purified by silica gel column chromatography (Diol, solvent gradient; 10→90% ethyl acetate/hexane, 0→20% MeOH/ethyl acetate) to give the title compound (5.00 mg, 9.48 μmol) as a solid.

Example 190

5-((1R)-1-(((3,5-difluoro-4-(trimethylsilyl)phenyl)carbamoyl)-6-(oxetan-3-yloxy)-3,4-dihydroisoquinolin-2(1H)-yl)-5-oxopentanoic acid Dihydro-2H-pyran-2,6(3H)-dione (45.3 mg, 0.40 mmol) was added to a solution of (R)-N-(3,5-difluoro-4-(trimethylsilyl)phenyl)-6-(oxetan-3-yloxy)-1,2,3,4-tetrahydroisoquinoline-1-carboxamide (132 mg, 0.31 mmol) (which can be synthesized in the same manner as above) and TEA (0.055 mL, 0.40 mmol) in THF (2 mL) at room temperature, and the mixture was stirred overnight at room temperature. The reaction mixture was concentrated under reduced pressure, and the obtained residue was crystallized from THF and water. The crystals were collected by filtration with water and hexane to give the title compound (127 mg, 0.232 mmol, 76%) as white crystals.

¹H NMR (300 MHz, DMSO-d₆): δ 0.29 (9H, s), 1.69-1.81 (2H, m), 2.20-2.31 (2H, m), 2.35-2.60 (2H, m), 2.76-2.87 (1H, m), 3.04-3.19 (1H, m), 3.42-3.56 (1H, m), 3.93-4.10 (1H, m), 4.44-4.58 (2H, m), 4.90 (2H, t, J=6.6 Hz), 5.17-5.33 (1H, m), 5.62 (1H, s), 6.58-6.77 (2H, m), 7.09-7.26 (2H, m), 7.46 (1H, d, J=9.4 Hz), 10.78 (1H, s), 12.04 (1H, brs).

Example 191

5-((1R)-6-(3,3-difluoroazetidin-1-yl)-1-((7-fluoro-1,1-dimethyl-2,3-dihydro-1H-inden-5-yl)carbamoyl)-3,4-dihydroisoquinolin-2(1H)-yl)-5-oxopentanoic acid Dihydro-2H-pyran-2,6(3H)-dione (40.8 mg, 0.36 mmol) was added to a solution of (R)-6-(3,3-difluoroazetidin-1-yl)-N-(7-fluoro-1,1-dimethyl-2,3-dihydro-1H-inden-5-yl)-1,2,3,4-tetrahydroisoquinoline-1-carboxamide (118 mg, 0.27 mmol) (which can be synthesized in the same manner as above) and TEA (0.050 mL, 0.36 mmol) in THF (2 mL) at room temperature, and the mixture was stirred overnight at room temperature. To the reaction mixture was added brine, and the mixture was extracted with ethyl acetate. The organic layer was washed with water, and dried over magnesium sulfate, and the solvent was evaporated under reduced pressure. The obtained residue was purified by silica gel column chromatography (solvent gradient; 30→100% ethyl acetate/hexane) to give the title compound (51.0 mg, 0.094 mmol, 34.1%) as a white solid.
¹H NMR (300 MHz, DMSO-d₆): δ 1.28 (6H, d, J=1.5 Hz), 1.74 (2H, quin, J=7.3 Hz), 1.86 (2H, t, J=7.4 Hz), 2.20-2.32 (2H, m), 2.35-2.60 (2H, m), 2.70-2.91 (3H, m), 3.04-3.18 (1H, m), 3.43-3.56 (1H, m), 3.96-4.08 (1H, m), 4.22 (4H, t, J=12.3 Hz), 5.61 (1H, s), 6.35-6.54 (2H, m), 7.15 (1H, s), 7.22 (1H, d, J=14.0 Hz), 7.42 (1H, d, J=9.1 Hz), 10.35 (1H, s), 12.06 (1H, brs).

Example 192

(1R)-2-(5-amino-5-oxopentanoyl)-N-(3,5-difluoro-4-(trimethylsilyl)phenyl)-6-methoxy-1,2,3,4-tetrahydroisoquinoline-1-carboxamide HATU (181 mg, 0.48 mmol) was added to a solution of 5-((1R)-1-((3,5-difluoro-4-(trimethylsilyl)phenyl)carbamoyl)-6-methoxy-3,4-dihydroisoquinolin-2(1H)-yl)-5-oxopentanoic acid (200 mg, 0.40 mmol), ammonium chloride (25.4 mg, 0.48 mmol) and DIEA (0.203 mL, 1.19 mmol) in DMF (4.0 mL) at room temperature, and the mixture was stirred at room temperature for 3 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→50% ethyl acetate/hexane), and recrystallized from ethyl acetate/hexane to give the title compound (114.1 mg, 0.227 mmol, 57.2%) as white crystals.
¹H NMR (300 MHz, DMSO-d₆): δ 0.29 (9H, s), 1.73 (2H, quin, J=7.1 Hz), 2.05-2.16 (2H, m), 2.32-2.57 (2H, m), 2.70-2.88 (1H, m), 3.04-3.18 (1H, m), 3.43-3.58 (1H, m), 3.73 (3H, s), 3.94-4.08 (1H, m), 5.62 (1H, s), 6.71 (1H, brs), 6.77-6.87 (2H, m), 7.14-7.29 (3H, m), 7.46 (1H, d, J=9.4 Hz), 10.76 (1H, s).

Example 193

4-((1R)-6-(difluoromethoxy)-1-((3-fluoro-4-(trimethylsilyl)phenyl)carbamoyl)-3,4-dihydroisoquinolin-2 (1H)-yl)-4-oxobutanoic acid Succinic anhydride (42.0 mg, 0.42 mmol) was added to a solution of (R)-6-(difluoromethoxy)-N-(3-fluoro-4-(trimethylsilyl)phenyl)-1,2,3,4-tetrahydroisoquinoline-1-carboxamide (132 mg, 0.32 mmol) and TEA (68 μL, 0.49 mmol) in THF (3.1 mL) at room temperature, and the mixture was stirred at room temperature for 15 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 30→100% ethyl acetate/hexane) to give the title compound (120.5 mg, 0.237 mmol, 73.3%) as a white solid.
¹H NMR (300 MHz, CDCl₃): δ 0.24 (9H, s), 2.68-2.96 (5H, m), 3.10-3.21 (1H, m), 3.72 (1H, ddd, J=12.4, 7.5, 4.7 Hz), 3.86-3.95 (1H, m), 6.04 (1H, s), 6.48 (1H, t), 6.97 (1H, s), 6.98-7.07 (2H, m), 7.16-7.25 (2H, m), 7.35 (1H, d, J=8.7 Hz), 9.17 (1H, s).

Example 194

5-((1R)-6-(difluoromethoxy)-1-((3-fluoro-4-(trimethylsilyl)phenyl)carbamoyl)-3,4-dihydroisoquinolin-2(1H)-yl)-5-oxopentanoic acid (Step 1)
Sodium 2-chloro-2,2-difluoroacetate (4.36 g, 28.57 mmol) was added to a solution of 1-ethyl 2-tert-butyl 6-hydroxy-3,4-dihydroisoquinoline-1,2(1H)-dicarboxylate (4.59 g, 14.28 mmol) and cesium carbonate (6.98 g, 21.42 mmol) in DMF (70 mL) at room temperature, and the mixture was stirred at 95° C. for 3 hr. To the reaction mixture was added water, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 4→20% ethyl acetate/hexane) to give 1-ethyl 2-tert-butyl 6-(difluoromethoxy)-3,4-dihydroisoquinoline-1,2(1H)-dicarboxylate (2.76 g, 7.43 mmol, 52.0%) as a colorless oil.
¹H NMR (300 MHz, CDCl₃): δ 1.21-1.29 (3H, m), 1.46-1.51 (9H, m), 2.79-2.99 (2H, m), 3.67-3.89 (2H, m), 4.12-4.21 (2H, m), 5.38-5.57 (1H, m), 6.49 (1H, t), 6.92 (1H, s), 6.98 (1H, d, J=8.7 Hz), 7.46-7.53 (1H, m).
(Step 2)
2N Aqueous lithium hydroxide solution (22.21 mL, 44.43 mmol) was added to a solution of 1-ethyl 2-tert-butyl 6-(difluoromethoxy)-3,4-dihydroisoquinoline-1,2(1H)-dicarboxylate (2.75 g, 7.40 mmol) in a mixed solvent of EtOH (11 mL) and THF (11 mL) at room temperature, and the mixture was stirred at room temperature for 2 hr. To the reaction mixture was added water, and 2N hydrochloric acid was added thereto until the pH of the mixture became 3. Then, the mixture was extracted three times with ethyl acetate. The organic layer was washed with brine, and dried over magnesium sulfate, and the solvent was evaporated under reduced pressure to give 2-(tert-butoxycarbonyl)-6-

(difluoromethoxy)-1,2,3,4-tetrahydroisoquinoline-1-carboxylic acid (2.48 g, 7.22 mmol, 98%) as a white solid.

$^1$H NMR (300 MHz, CDCl$_3$): δ 1.40-1.53 (9H, m), 2.77-3.00 (2H, m), 3.67-3.79 (2H, m), 5.39-5.60 (1H, m), 6.49 (1H, t), 6.93 (1H, d, J=2.3 Hz), 6.99 (1H, dd, J=8.3, 2.3 Hz), 7.48 (1H, d, J=8.7 Hz).

(Step 3)

T3P (1.949 mL, 3.28 mmol) was added to a solution of 2-(tert-butoxycarbonyl)-6-(difluoromethoxy)-1,2,3,4-tetrahydroisoquinoline-1-carboxylic acid (750 mg, 2.18 mmol), 3-fluoro-4-(trimethylsilyl)aniline (400 mg, 2.18 mmol), DIEA (1.903 mL, 10.92 mmol) and DMAP (294 mg, 2.40 mmol) in ethyl acetate (16 mL), and the mixture was stirred at 65° C. for 16 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with cooled hexane to give tert-butyl 6-(difluoromethoxy)-1-((3-fluoro-4-(trimethylsilyl)phenyl)carbamoyl)-3,4-dihydroisoquinoline-2(1H)-carboxylate (933 mg, 1.834 mmol, 84%) as grayish white crystals.

$^1$H NMR (300 MHz, CDCl$_3$): δ 0.28 (9H, d, J=0.8 Hz), 1.53 (9H, s), 2.90 (2H, t, J=5.7 Hz), 3.57 (1H, brs), 3.79 (1H, dt, J=12.6, 6.0 Hz), 5.65 (1H, brs), 6.50 (1H, t), 6.97 (1H, s), 7.02 (1H, dd), 7.10 (1H, dd, J=7.9, 1.5 Hz), 7.25-7.31 (2H, m), 7.38 (1H, dd, J=10.4, 1.7 Hz), 9.03 (1H, brs)

(Step 4)

tert-Butyl 6-(difluoromethoxy)-1-((3-fluoro-4-(trimethylsilyl)phenyl)carbamoyl)-3,4-dihydroisoquinoline-2(1H)-carboxylate (0.931 g) was resolved by chiral column chromatography. The fraction having a shorter retention time was concentrated to give tert-butyl (R)-6-(difluoromethoxy)-1-((3-fluoro-4-(trimethylsilyl)phenyl) carbamoyl)-3, 4-dihydroisoquinoline-2(1H)-carboxylate (0.434 g, >99% ee), and the fraction having a longer retention time was concentrated to give tert-butyl (S)-6-(difluoromethoxy)-1-((3-fluoro-4-(trimethylsilyl)phenyl)carbamoyl)-3,4-dihydroisoquinoline-2(1H)-carboxylate (0.429 g, >99% ee), each as a white solid.

purification condition by chiral column chromatography
    column: CHIRALPAK IA 50 mmID×500 mmL
    solvent: hexane/EtOH=950/50
    flow rate: 80 mL/min
    temperature: 30° C.
    detection method: UV 220 nm (Step 5)

Cooled TFA (5.5 mL) was added to tert-butyl (R)-6-(difluoromethoxy)-1-((3-fluoro-4-(trimethylsilyl)phenyl)carbamoyl)-3,4-dihydroisoquinoline-2(1H)-carboxylate (429 mg, 0.84 mmol), and the mixture was stirred at room temperature for 3 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure. The precipitate was washed with hexane to give (R)-6-(difluoromethoxy)-N-(3-fluoro-4-(trimethylsilyl)phenyl)-1,2,3,4-tetrahydroisoquinoline-1-carboxamide (341 mg, 0.835 mmol, 99%) as a colorless oil.

MS(API): Calculated 408.5. Found 409.2 (M+H).

(Step 6)

Dihydro-2H-pyran-2,6(3H)-dione (73.3 mg, 0.64 mmol) was added to a solution of (R)-6-(difluoromethoxy)-N-(3-fluoro-4-(trimethylsilyl)phenyl)-1,2,3,4-tetrahydroisoquinoline-1-carboxamide (202 mg, 0.49 mmol) and TEA (103 μL, 0.74 mmol) in THF (4.7 mL) at room temperature, and the mixture was stirred at room temperature for 4 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 30→100% ethyl acetate/hexane) to give the title compound (190.5 mg, 0.365 mmol, 73.7%) as a white solid.

$^1$H NMR (300 MHz, CDCl$_3$): δ 0.21 (9H, d, J=0.8 Hz), 2.10-2.20 (2H, m), 2.37-2.63 (3H, m), 2.88-3.00 (2H, m), 3.30-3.41 (1H, m), 3.77 (1H, ddd, J=12.3, 8.5, 4.2 Hz), 4.06-4.16 (1H, m), 5.95 (1H, s), 6.48 (1H, t), 6.84 (1H, dd, J=8.1, 1.7 Hz), 6.95-7.02 (2H, m), 7.04-7.12 (2H, m), 7.61 (1H, d, J=8.3 Hz), 9.88 (1H, s), 11.26 (1H, brs).

Example 195

4-((1R)-6-(difluoromethoxy)-1-((3,5-difluoro-4-(trimethylsilyl)phenyl)carbamoyl)-3,4-dihydroisoquinolin-2 (1H)-yl)-4-oxobutanoic acid (Step 1)

T3P (1.949 mL, 3.28 mmol) was added to a solution of 2-(tert-butoxycarbonyl)-6-(difluoromethoxy)-1,2,3,4-tetrahydroisoquinoline-1-carboxylic acid (750 mg, 2.18 mmol), 3,5-difluoro-4-(trimethylsilyl)aniline (440 mg, 2.18 mmol), DIEA (1.903 mL, 10.92 mmol) and DMAP (294 mg, 2.40 mmol) in ethyl acetate (16 mL), and the mixture was stirred at 65° C. for 16 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with cooled hexane to give tert-butyl 1-((3,5-difluoro-4-(trimethylsilyl)phenyl)carbamoyl)-6-(difluoromethoxy)-3,4-dihydroisoquinoline-2(1H)-carboxylate (769 mg, 1.460 mmol, 66.8%) as grayish white crystals.

$^1$H NMR (300 MHz, CDCl$_3$): δ 0.32 (9H, t, J=1.3 Hz), 1.53 (9H, s), 2.83-2.97 (2H, m), 3.59 (1H, brs), 3.72-3.81 (1H, m), 5.64 (1H, brs), 6.50 (1H, t), 6.96-7.05 (4H, m), 7.26 (1H, s), 9.16 (1H, brs).

(Step 2)

tert-Butyl 1-((3,5-difluoro-4-(trimethylsilyl)phenyl)carbamoyl)-6-(difluoromethoxy)-3,4-dihydroisoquinoline-2 (1H)-carboxylate (0.75 g) was resolved by chiral column chromatography. The fraction having a shorter retention time was concentrated to give tert-butyl (R)-1-((3,5-difluoro-4-(trimethylsilyl)phenyl)carbamoyl)-6-(difluoromethoxy)-3,4-dihydroisoquinoline-2(1H)-carboxylate (0.363 g, >99% ee), and the fraction having a longer retention time was concentrated to give tert-butyl (S)-1-((3, 5-difluoro-4-(trimethylsilyl)phenyl)carbamoyl)-6-(difluoromethoxy)-3,4-dihydroisoquinoline-2(1H)-carboxylate (0.352 g, >99% ee), each as a white solid.

purification condition by chiral column chromatography
    column: CHIRALPAK IA 50 mmID×500 mmL
    solvent: hexane/EtOH=950/50
    flow rate: 80 mL/min
    temperature: 30° C.
    detection method: UV 220 nm (Step 3)

Cooled TFA (4.5 mL) was added to tert-butyl (R)-1-((3,5-difluoro-4-(trimethylsilyl)phenyl)carbamoyl)-6-(difluoromethoxy)-3,4-dihydroisoquinoline-2(1H)-carboxylate (351 mg, 0.67 mmol), and the mixture was stirred at room temperature for 3 min. The reaction mixture was added to ice and aqueous sodium hydrogen carbonate solution, and potassium carbonate was added thereto until the pH of the mixture became 8.. Then, the mixture was extracted three times with ethyl acetate. The organic layer was washed with brine, and dried over magnesium sulfate, and the solvent was evaporated under reduced pressure. The precipitate was washed with hexane to give (R)-N-(3,5-difluoro-4-(trimethylsilyl)phenyl)-6-(difluoromethoxy)-1,2,3,4-tetrahydroisoquinoline-1-carboxamide (294 mg, 0.689 mmol, quant.) as a colorless oil.

MS(API): Calculated 426.3, Found 427.31 (M+H).

(Step 4)

Succinic anhydride (42.1 mg, 0.42 mmol) was added to a solution of (R)-N-(3,5-difluoro-4-(trimethylsilyl)phenyl)-6-(difluoromethoxy)-1,2,3,4-tetrahydroisoquinoline-1-carboxamide (138 mg, 0.32 mmol) and TEA (68 μL, 0.49 mmol) in THF (3.2 mL) at room temperature, and the mixture was stirred at room temperature for 15 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 30→100% ethyl acetate/hexane) to give the title compound (134.3 mg, 0.255 mmol, 79%) as a white solid.

$^1$H NMR (300 MHz, CDCl$_3$): δ 0.29 (9H, t), 2.67-2.76 (1H, m), 2.78-2.85 (2H, m), 2.87-2.96 (2H, m), 3.11-3.22 (1H, m), 3.73 (1H, ddd, J=12.2, 7.5, 4.9 Hz), 3.88-3.97 (1H, m), 6.03 (1H, s), 6.49 (1H, t), 6.89-6.96 (2H, m), 6.96-7.03 (2H, m), 7.34 (1H, d, J=8.7 Hz), 9.26 (1H, s).

Example 196

5-((1R)-6-(difluoromethoxy)-1-((3,5-difluoro-4-(trimethylsilyl)phenyl)carbamoyl)-3,4-dihydroisoquinolin-2 (1H)-yl)-5-oxopentanoic acid Dihydro-2H-pyran-2,6 (3H)-dione (52.5 mg, 0.46 mmol) was added to a solution of (R)-N-(3,5-difluoro-4-(trimethylsilyl)phenyl)-6-(difluoromethoxy)-1,2,3,4-tetrahydroisoquinoline-1-carboxamide (151 mg, 0.35 mmol) and TEA (74 μL, 0.53 mmol) in THF (3.5 mL) at room temperature, and the mixture was stirred at room temperature for 4 hr. To the reaction mixture was added water, and 2N hydrochloric acid was added thereto until the pH of the mixture became 4.Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 30→100% ethyl acetate/hexane) to give the title compound (141.7 mg, 0.262 mmol, 74.0%) as a white solid.

$^1$H NMR (300 MHz, CDCl$_3$): δ 0.26 (9H, s), 2.11-2.25 (2H, m), 2.37-2.63 (3H, m), 2.89-3.05 (2H, m), 3.34-3.45 (1H, m), 3.76 (1H, ddd, J=12.2, 9.0, 3.8 Hz), 4.10-4.20 (1H, m), 5.86 (1H, s), 6.23-6.76 (3H, m), 6.97 (1H, s), 7.00 (1H, dd), 7.64 (1H, d, J=8.7 Hz), 10.01 (1H, s), 11.47 (1H, brs).

The compounds described in Examples 197 to 208 were synthesized by the reaction and purification in the same manner as in the above-mentioned Examples.

Example 197

4-((1R)-6-(2,2-difluoroethoxy)-1-((3-fluoro-4-(trimethylsilyl)phenyl)carbamoyl)-3,4-dihydroisoquinolin-2 (1H)-yl)-4-oxobutanoic acid $^1$H NMR (300 MHz, CDCl$_3$): δ 0.24 (9H, d, J=0.8 Hz), 2.64-2.93 (5H, m), 3.13 (1H, ddd, J=15.7, 7.6, 4.7 Hz), 3.69 (1H, ddd, J=12.2, 7.6, 4.7 Hz), 3.83-3.93 (1H, m), 4.11-4.22 (2H, m), 5.86-6.28 (2H, m), 6.76 (1H, d, J=2.3 Hz), 6.81 (1H, dd, J=8.7, 2.6 Hz), 7.06 (1H, dd, J=8.1, 1.7 Hz), 7.20 (1H, dd, J=7.9, 6.4 Hz), 7.23-7.29 (2H, m), 9.09 (1H, s).

Example 198

5-((1R)-6-(2,2-difluoroethoxy)-1-((3-fluoro-4-(trimethylsilyl)phenyl)carbamoyl)-3,4-dihydroisoquinolin-2 (1H)-yl)-5-oxopentanoic acid $^1$H NMR (300 MHz, CDCl$_3$): δ 0.21 (9H, d, J=0.8 Hz), 2.09-2.19 (2H, m), 2.38-2.63 (3H, m), 2.81-2.95 (2H, m), 3.25-3.36 (1H, m), 3.73 (1H, ddd, J=12.2, 8.6, 4.2 Hz), 4.01-4.22 (3H, m), 5.86-6.27 (2H, m), 6.74 (1H, d, J=2.3 Hz), 6.80 (1H, dd, J=8.3, 2.6 Hz), 6.88 (1H, dd, J=7.9, 1.9 Hz), 7.05-7.16 (2H, m), 7.50 (1H, d, J=8.7 Hz), 9.77 (1H, s), 11.03 (1H, brs).

Example 199

4-((1R)-6-(2,2-difluoroethoxy)-1-((3,5-difluoro-4-(trimethylsilyl)phenyl)carbamoyl)-3,4-dihydroisoquinolin-2 (1H)-yl)-4-oxobutanoic acid $^1$H NMR (300 MHz, CDCl$_3$): δ 0.28 (9H, s), 2.67-2.96 (5H, m), 3.10-3.21 (1H, m), 3.68 (1H, ddd, J=12.2, 7.8, 4.5 Hz), 3.88-3.97 (1H, m), 4.10-4.22 (2H, m), 5.86-6.27 (2H, m), 6.76 (1H, d, J=2.3 Hz), 6.81 (1H, dd, J=8.3, 2.6 Hz), 6.88-6.96 (2H, m), 7.29 (1H, d, J=8.7 Hz), 9.28 (1H, s).

Example 200

5-((1R)-6-(2,2-difluoroethoxy)-1-((3,5-difluoro-4-(trimethylsilyl)phenyl)carbamoyl)-3,4-dihydroisoquinolin-2 (1H)-yl)-5-oxopentanoic acid $^1$H NMR (300 MHz, CDCl$_3$): δ 0.26 (9H, s), 2.10-2.20 (2H, m), 2.39-2.63 (3H, m), 2.84-3.00 (2H, m), 3.30-3.42 (1H, m), 3.67-3.77 (1H, m), 4.07-4.22 (3H, m), 5.83 (1H, s), 6.07 (1H, tt), 6.71-6.78 (3H, m), 6.81 (1H, dd, J=8.3, 2.6 Hz), 7.54 (1H, d, J=8.7 Hz), 9.94 (1H, s), 11.27 (1H, brs). $[α]_D^{25}$ −3.2 (c 0.2525, MeOH)

Example 201

4-((1R)-1-((3-fluoro-4-(trimethylsilyl)phenyl)carbamoyl)-6-(2,2,2-trifluoroethoxy)-3,4-dihydroisoquinolin-2(1H)-yl)-4-oxobutanoic acid $^1$H NMR (300 MHz, CDCl$_3$): δ 0.24 (9H, s), 2.67-2.93 (5H, m), 3.09-3.20 (1H, m), 3.69 (1H, ddd, J=12.3, 7.6, 4.7 Hz), 3.85-3.94 (1H, m), 4.32 (2H, q, J=8.3 Hz), 6.01 (1H, s), 6.79 (1H, d, J=2.3 Hz), 6.83 (1H, dd, J=8.7, 2.6 Hz), 7.05

(1H, dd, J=8.1, 1.7 Hz), 7.19 (1H, dd, J=7.9, 6.4 Hz), 7.22-7.27 (1H, m), 7.30 (1H, d, J=8.7 Hz), 9.14 (1H, s).

Example 202

5-((1R)-1-((3-fluoro-4-(trimethylsilyl)phenyl)carbamoyl)-6-(2,2,2-trifluoroethoxy)-3,4-dihydroisoquinolin-2(1H)-yl)-5-oxopentanoic acid $^1$H NMR (300 MHz, CDCl$_3$): δ 0.21 (9H, s), 2.10-2.18 (2H, m), 2.38-2.63 (3H, m), 2.82-2.96 (2H, m), 3.25-3.37 (1H, m), 3.74 (1H, ddd, J=12.2, 8.4, 4.0 Hz), 4.02-4.12 (1H, m), 4.33 (2H, q, J=7.9 Hz), 5.93 (1H, s), 6.78 (1H, d, J=2.6 Hz), 6.83 (1H, dd, J=8.7, 2.6 Hz), 6.87 (1H, dd, J=7.9, 1.9 Hz), 7.05-7.15 (2H, m), 7.52 (1H, d, J=8.7 Hz), 9.78 (1H, s), 11.08 (1H, brs).

Example 203

4-((1R)-1-((3,5-difluoro-4-(trimethylsilyl)phenyl)carbamoyl)-6-(2,2,2-trifluoroethoxy)-3,4-dihydroisoquinolin-2 (1H)-yl)-4-oxobutanoic acid $^1$H NMR (300 MHz, CDCl$_3$): δ 0.29 (9H, s), 2.65-2.96 (5H, m), 3.08-3.19 (1H, m), 3.70 (1H, ddd, J=12.3, 7.7, 4.9 Hz), 3.85-3.94 (1H, m), 4.33 (2H, q, J=8.3 Hz), 6.00 (1H, s), 6.80 (1H, d, J=2.3 Hz), 6.84 (1H, dd), 6.90-6.98 (2H, m), 7.28 (1H, d), 9.20 (1H, s).

Example 204

5-((1R)-1-((3,5-difluoro-4-(trimethylsilyl)phenyl)carbamoyl)-6-(2,2,2-trifluoroethoxy)-3,4-dihydroisoquinolin-2(1H)-yl)-5-oxopentanoic acid $^1$H NMR (300 MHz, CDCl$_3$): δ 0.26 (9H, t, J=1.3 Hz), 2.10-2.24 (2H, m), 2.37-2.63 (3H, m), 2.85-3.01 (2H, m), 3.30-3.43 (1H, m), 3.68-3.78 (1H, m), 4.07-4.16 (1H, m), 4.33 (2H, q, J=8.3 Hz), 5.84 (1H, s), 6.71-6.79 (3H, m), 6.83 (1H, dd, J=8.7, 2.6 Hz), 7.56 (1H, d, J=8.7 Hz), 9.95 (1H, s), 11.32 (1H, brs).

Example 205

4-((1R)-6-(difluoromethoxy)-1-((7-fluoro-1,1-dimethyl-2,3-dihydro-1H-inden-5-yl)carbamoyl)-3,4-dihydroisoquinolin-2 (1H)-yl)-4-oxobutanoic acid $^1$H NMR (300 MHz, CDCl$_3$): δ 1.30 (6H, s), 1.87 (2H, t, J=7.4 Hz), 2.66-2.97 (7H, m), 3.06-3.17 (1H, m), 3.69-3.79 (1H, m), 3.81-3.91 (1H, m), 6.02 (1H, s), 6.49 (1H, t), 6.96-7.06 (4H, m), 7.28 (1H, d, J=8.3 Hz), 8.88 (1H, s).

Example 206

5-((1R)-6-(difluoromethoxy)-1-((7-fluoro-1,1-dimethyl-2,3-dihydro-1H-inden-5-yl)carbamoyl)-3,4-dihydroisoquinolin-2 (1H)-yl)-5-oxopentanoic acid $^1$H NMR (300 MHz, CDCl$_3$): δ 1.27 (6H, d, J=3.0 Hz), 1.83 (2H, t, J=7.4 Hz), 2.07-2.16 (2H, m), 2.46 (2H, t), 2.58 (1H, dt, J=15.2, 7.3 Hz), 2.68-2.85 (3H, m), 2.88-3.00 (1H, m), 3.19-3.31 (1H, m), 3.77 (1H, ddd, J=12.2, 7.6, 4.3 Hz), 4.01 (1H, ddd, J=12.1, 7.2, 4.5 Hz), 5.98 (1H, s), 6.48 (1H, t), 6.86 (1H, s), 6.94-7.03 (3H, m), 7.50 (1H, d, J=8.3 Hz), 9.53 (1H, s), 10.99 (1H, brs).
[α]$_D^{25}$+22.7 (c 0.2540, MeOH)

Example 207

4-((1R)-6-(2,2-difluoroethoxy)-1-((7-fluoro-1,1-dimethyl-2,3-dihydro-1H-inden-5-yl)carbamoyl)-3,4-dihydroisoquinolin-2 (1H)-yl)-4-oxobutanoic acid $^1$H NMR (300 MHz, CDCl$_3$): δ 1.30 (6H, s), 1.86 (2H, t, J=7.2 Hz), 2.65-2.93 (7H, m), 3.06-3.17 (1H, m), 3.70 (1H, ddd, J=12.4, 7.5, 4.7 Hz), 3.81-3.91 (1H, m), 4.10-4.22 (2H, m), 5.87-6.28 (2H, m), 6.75 (1H, d, J=2.3 Hz), 6.81 (1H, dd, J=8.3, 2.6 Hz), 6.99-7.06 (2H, m), 7.23 (1H, d, J=8.7 Hz), 8.88 (1H, s).

Example 208

5-((1R)-6-(2,2-difluoroethoxy)-1-((7-fluoro-1,1-dimethyl-2,3-dihydro-1H-inden-5-yl)carbamoyl)-3,4-dihydroisoquinolin-2 (1H)-yl)-5-oxopentanoic acid $^1$H NMR (300 MHz, CDCl$_3$): δ 1.27 (6H, d, J=2.3 Hz), 1.83 (2H, t, J=7.4 Hz), 2.06-2.15 (2H, m), 2.47 (2H, t), 2.53-2.73 (2H, m), 2.78 (2H, t, J=7.6 Hz), 2.83-2.94 (1H, m), 3.16-3.27 (1H, m), 3.72 (1H, ddd, J=12.2, 7.8, 4.5 Hz), 3.97 (1H, ddd, J=12.2, 7.1, 4.5 Hz), 4.11-4.22 (2H, m), 5.86-6.27 (2H, m), 6.74 (1H, d, J=2.6 Hz), 6.80 (1H, dd, J=8.7, 2.6 Hz), 6.89 (1H, s), 7.02 (1H, dd, J=12.1, 1.5 Hz), 7.40 (1H, d, J=8.3 Hz), 9.43 (1H, s), 10.88 (1H, brs).

Example 209

(4R)-5-((1R)-1-((3,5-difluoro-4-(trimethylsilyl)phenyl)carbamoyl)-6-ethoxy-3,4-dihydroisoquinolin-2 (1H)-yl)-4-hydroxy-5-oxopentanoic acid (Step 1)
A solution of sodium nitrite (539 mg, 7.81 mmol) in water (3 mL) was added to a solution of (R)-2-amino-5-(benzyloxy)-5-oxopentanoic acid (309 mg, 1.30 mmol) in conc. sulfuric acid (2 mL, 1.30 mmol) at 0° C., and the mixture was stirred at 0° C. overnight. The reaction mixture was saturated with sodium chloride, and the mixture was extracted with ethyl acetate. The organic layer was dried over sodium sulfate, and the solvent was evaporated under reduced pressure. The residue was crystallized from ethyl acetate to give (R)-2-hydroxy-5-(benzyloxy)-5-oxopentanoic acid.
MS(API): Calculated 238.2, Found 237.2 (M+H).
(Step 2)
HATU (43.4 mg, 0.11 mmol) was added to a solution of (R)-N-(3,5-difluoro-4-(trimethylsilyl)phenyl)-6-ethoxy-1,2,3,4-tetrahydroisoquinoline-1-carboxamide (42 mg, 0.10 mmol), (R)-2-hydroxy-5-(benzyloxy)-5-oxopentanoic acid (49.5 mg, 0.21 mmol) and DIEA (0.020 mL, 0.11 mmol) in DMF (4 mL) at 0° C., and the mixture was stirred at 0° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→90% ethyl acetate/hexane) to give benzyl (4R)-5-((1R)-1-((3,5-difluoro-4-(trimethylsilyl)phenyl)carbamoyl)-6-ethoxy-3,4-dihydroisoquinolin-2 (1H)-yl)-4-hydroxy-5-oxopentanoate as a white solid.
MS(API): Calculated 624.8, Found 625.5 (M+H).

(Step 3)

A solution of benzyl (4R)-5-((1R)-1-((3,5-difluoro-4-(trimethylsilyl)phenyl)carbamoyl)-6-ethoxy-3,4-dihydroisoquinolin-2(1H)-yl)-4-hydroxy-5-oxopentanoate and 10% palladium-carbon in MeOH (4 mL) was stirred under hydrogen atmosphere (1 atm) at room temperature for 3 hr. The catalyst was filtered off, and the filtrate was concentrated under reduced pressure. The obtained residue was purified by silica gel column chromatography (solvent gradient; 10→100% ethyl acetate/hexane) to give the title compound (7.00 mg, 0.013 mmol) as a white solid.

$^1$H NMR (300 MHz, DMSO-d$_6$): δ 0.30 (9H, s), 1.30 (3H, t, J=7.0 Hz), 1.57-1.74 (1H, m), 1.81-1.97 (1H, m), 2.30-2.42 (2H, m), 2.74-2.88 (1H, m), 2.97-3.15 (1H, m), 3.67 (1H, ddd, J=12.3, 8.1, 3.8 Hz), 3.90-4.15 (3H, m), 4.43 (1H, dd, J=8.3, 3.8 Hz), 5.62 (1H, s), 6.74-6.87 (2H, m), 7.20 (2H, d, J=9.8 Hz), 7.39-7.49 (1H, m), 10.85 (1H, s).

Example 210

6-((1R)-6-ethoxy-1-((7-fluoro-1,1-dimethyl-2,3-dihydro-1H-inden-5-yl)carbamoyl)-3,4-dihydroisoquinolin-2(1H)-yl)-6-oxohexanoic acid Oxepane-2,7-dione (50.1 mg, 0.39 mmol) was added to a solution of (R)-6-ethoxy-N-(7-fluoro-1,1-dimethyl-2,3-dihydro-1H-inden-5-yl)-1,2,3,4-tetrahydroisoquinoline-1-carboxamide (115 mg, 0.30 mmol) and TEA (0.054 mL, 0.39 mmol) in THF (2.0 mL) at room temperature, and the mixture was stirred at room temperature for 5 hr. To the reaction mixture was added water, and the mixture was extracted with ethyl acetate. The organic layer was dried over magnesium sulfate, and the solvent was evaporated under reduced pressure. The obtained residue was purified by silica gel column chromatography (Diol, solvent gradient; 20→90% ethyl acetate/hexane) to give the title compound (35.0 mg, 0.069 mmol, 22.80%) as a white solid.

$^1$H NMR (300 MHz, DMSO-d$_6$): δ 1.22-1.33 (9H, m), 1.42-1.65 (4H, m), 1.79-1.92 (2H, m), 2.10-2.30 (2H, m), 2.37-2.58 (2H, m), 2.69-2.90 (3H, m), 2.99-3.18 (1H, m), 3.45-3.62 (1H, m), 3.91-4.10 (3H, m), 5.64 (1H, s), 6.72-6.84 (2H, m), 7.10-7.28 (2H, m), 7.38-7.50 (1H, m), 10.40 (1H, s), 12.06 (1H, brs).

Example 211

6-((1R)-6-ethoxy-1-((3-fluoro-4-(trimethylsilyl)phenyl)carbamoyl)-3,4-dihydroisoquinolin-2 (1H)-yl)-6-oxohexanoic acid Oxepane-2,7-dione (27.6 mg, 0.22 mmol) was added to a solution of (R)-6-ethoxy-N-(3-fluoro-4-(trimethylsilyl)phenyl)-1,2,3,4-tetrahydroisoquinoline-1-carboxamide (64 mg, 0.17 mmol) and TEA (0.030 mL, 0.22 mmol) in THF (2.0 mL) at room temperature, and the mixture was stirred at room temperature for 5 hr. To the reaction mixture was added water, and the mixture was extracted with ethyl acetate. The organic layer was dried over magnesium sulfate, and the solvent was evaporated under reduced pressure. The obtained residue was purified by silica gel column chromatography (Diol, solvent gradient; 20→90% ethyl acetate/hexane) to give the title compound (23.7 mg, 0.046 mmol, 27.8%) as a white solid.

$^1$H NMR (300 MHz, DMSO-d$_6$): δ 0.24 (9H, s), 1.29 (3H, t, J=7.0 Hz), 1.43-1.64 (4H, m), 2.09-2.30 (2H, m), 2.37-2.58 (2H, m), 2.68-2.87 (1H, m), 3.01-3.19 (1H, m), 3.45-3.59 (1H, m), 3.90-4.09 (3H, m), 5.60-5.69 (1H, m), 6.72-6.84 (2H, m), 7.25-7.37 (2H, m), 7.45 (2H, d, J=11.0 Hz), 10.60 (1H, s), 12.04 (1H, brs).

The compound described in Example 212 was synthesized by the reaction and purification in the same manner as in the above-mentioned Examples.

Example 212

5-((5R)-2-(difluoromethoxy)-5-((7-fluoro-1,1-dimethyl-2,3-dihydro-1H-inden-5-yl)carbamoyl)-7,8-dihydro-1,6-naphthyridin-6(5H)-yl)-5-oxopentanoic acid $^1$H NMR (300 MHz, CDCl$_3$): δ 1.27 (6H, d, J=3.0 Hz), 1.83 (2H, t, J=7.4 Hz), 2.01-2.20 (2H, m), 2.33-2.61 (3H, m), 2.68-2.95 (3H, m), 3.02-3.13 (1H, m), 3.21 (1H, dt), 3.95-4.10 (2H, m), 5.99 (1H, s), 6.76-6.82 (2H, m), 6.97 (1H, dd, J=11.7, 1.5 Hz), 7.47 (1H, t), 7.87 (1H, d, J=8.3 Hz), 9.61 (1H, s), 10.98 (1H, brs).

Example 213

(1R)-N-(3,5-difluoro-4-(trimethylsilyl)phenyl)-2-((1,1-dioxido-4-oxo-1,2,5-thiadiazolysin-2-yl)acetyl)-6-ethoxy-1,2,3,4-tetrahydroisoquinoline-1-carboxamide (Step 1)

Chlorosulfonyl isocyanate (1.230 mL, 14.13 mmol) was added to a solution of t-butyl alcohol (1.047 g, 14.13 mmol) in acetonitrile (20 mL) at 0° C., and the mixture was stirred at 0° C. for 1 hr. Then, pyridine (4 mL) was added thereto at 0° C., and the mixture was stirred at 0° C. for 40 min (Reaction Mixture A). To a mixture of ethyl 2-aminoacetate hydrochloride in acetonitrile (10 mL) was added TEA (4.92 mL, 35.33 mmol) at 0° C., and the mixture was stirred at 0° C. for 20 min. The reaction mixture was filtered through Celite to remove the triethylamine hydrochloride, the filtrate was added to Reaction Mixture A at 0° C., and the mixture was stirred overnight at room temperature. The reaction mixture was concentrated under reduced pressure, and the pH of the residue was adjusted to 4 with 2N hydrochloric acid. Then, the residue was extracted with ethyl acetate. The organic layer was dried over magnesium sulfate, and the solvent was evaporated under reduced pressure. The obtained residue was crystallized from ethyl acetate/hexane to give ethyl 2-((N-(tert-butoxycarbonyl) sulfamoyl)amino) acetate (3.58 g, 12.68 mmol, 90%) as white crystals.

$^1$H NMR (300 MHz, DMSO-d$_6$): δ 1.20 (3H, t, J=7.0 Hz), 1.42 (9H, s), 3.79 (2H, d, J=6.0 Hz), 4.10 (2H, q, J=7.2 Hz), 8.06 (1H, brs), 10.89 (1H, s).

(Step 2)

DEAD (5.92 mL, 12.68 mmol) was added to a solution of ethyl 2-((N-(tert-butoxycarbonyl)sulfamoyl)amino)acetate (3.58 g, 12.68 mmol), PPh$_3$ (3.33 g, 12.68 mmol) and benzyl alcohol (1.319 mL, 12.68 mmol) in THF (20 mL) at 0° C., and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give ethyl 2-((N-benzyl-N-(tert-butoxycarbonyl)sulfamoyl) amino)acetate (4.75 g, 12.75 mmol, 101%) as a colorless oil.

¹H NMR (300 MHz, CDCl₃): δ 1.26 (3H, t, J=7.2 Hz), 1.52 (9H, s), 3.58 (2H, d, J=4.9 Hz), 4.16 (2H, q, J=7.2 Hz), 4.83 (2H, s), 5.73 (1H, t, J=4.7 Hz), 7.28-7.41 (5H, m).
(Step 3)

4N Hydrogen chloride/ethyl acetate (15 mL) was added to a solution of ethyl 2-((N-benzyl-N-(tert-butoxycarbonyl)sulfamoyl)amino)acetate (4.75 g, 12.75 mmol) in ethyl acetate (20 mL) at room temperature, and the mixture was stirred at room temperature for 2 days. The reaction mixture was concentrated under reduced pressure, and the obtained residue was purified by silica gel column chromatography (solvent gradient; 10-60% ethyl acetate/hexane) to give ethyl 2-((N-benzyl sulfamoyl)amino)acetate (3.10 g, 11.38 mmol, 89%) as white crystals.

¹H NMR (300 MHz, DMSO-d₆): δ 1.19 (3H, t, J=7.0 Hz), 3.65 (2H, s), 4.04 (2H, brs), 4.10 (2H, q, J=7.2 Hz), 7.21-7.35 (5H, m), 7.39 (1H, brs), 7.47 (1H, brs).
(Step 4)

Sodium methanolate (1.845 g, 34.15 mmol) was added to a solution of ethyl 2-((N-benzyl sulfamoyl)amino)acetate (3.1 g, 11.38 mmol) in MeOH (70 mL) at room temperature, and the mixture was stirred at room temperature for 20 hr. The reaction mixture was concentrated under reduced pressure, and to the obtained residue was added water. The precipitate was collected by filtration with water to give 2-benzyl-1,2,5-thiadiazolysin-3-one 1,1-dioxide (1.370 g, 6.06 mmol, 53.2%) as a white solid.

¹H NMR (300 MHz, DMSO-d₆): δ 4.14 (2H, s), 4.68 (2H, s), 7.21-7.43 (5H, m), 8.57 (1H, brs).
(Step 5)

Sodium hydride (60% oil, 72.2 mg, 1.80 mmol) was added to a solution of 2-benzyl-1,2,5-thiadiazolysin-3-one 1,1-dioxide (314 mg, 1.39 mmol) in acetonitrile (6 mL) at 0° C., and the mixture was stirred at the same temperature for 30 min. tert-Butyl bromoacetate (0.291 mL, 1.80 mmol) was added thereto, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give tert-butyl 2-(5-benzyl-1,1-dioxido-4-oxo-1,2,5-thiadiazolysin-2-yl)acetate (421 mg, 1.237 mmol, 89%) as white crystals.

¹H NMR (300 MHz, CDCl₃): δ 1.43 (s, 9H) 3.91 (s, 2H) 4.20 (s, 2H) 4.77 (s, 2H) 7.28-7.39 (m, 3H) 7.40-7.48 (m, 2H)
(Step 6)

Cooled TFA (5 mL) was added to tert-butyl 2-(5-benzyl-1,1-dioxido-4-oxo-1,2,5-thiadiazolysin-2-yl)acetate (421 mg, 1.24 mmol) at 0° C., and the mixture was stirred at 0° C. for 50 min. The reaction mixture was concentrated under reduced pressure, and the obtained precipitate was collected by filtration with ethyl acetate/heptane to give 2-(5-benzyl-1,1-dioxido-4-oxo-1,2,5-thiadiazolysin-2-yl)acetic acid (327 mg, 1.150 mmol, 93%) as a grayish white solid.

¹H NMR (300 MHz, DMSO-d₆): δ 4.11 (s, 2H) 4.38 (s, 2H) 4.73 (s, 2H) 7.14-7.49 (m, 5H) 13.16 (brs, 1H)
(Step 7)

HATU (108 mg, 0.28 mmol) was added to a solution of (R)-N-(3,5-difluoro-4-(trimethylsilyl)phenyl)-6-ethoxy-1,2,3,4-tetrahydroisoquinoline-1-carboxamide (104 mg, 0.26 mmol), DIEA (0.049 mL, 0.28 mmol) and 2-(5-benzyl-1,1-dioxido-4-oxo-1,2,5-thiadiazolysin-2-yl)acetic acid (80 mg, 0.28 mmol) in DMF (2 mL) at room temperature, and the mixture was stirred at room temperature for 2 hr. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→70% ethyl acetate/hexane) to give (R)-2-(2-(5-benzyl-1,1-dioxido-4-oxo-1,2,5-thiadiazolysin-2-yl)acetyl)-N-(3,5-difluoro-4-(trimethylsilyl)phenyl)-6-ethoxy-1,2,3,4-tetrahydroisoquinoline-1-carboxamide (110 mg, 0.164 mmol, 63.8%) as a white solid.

MS(API): Calculated 670.8, Found 669.3 (M–H).
(Step 8)

A solution of (R)-2-(2-(5-benzyl-1,1-dioxido-4-oxo-1,2,5-thiadiazolysin-2-yl)acetyl)-N-(3,5-difluoro-4-(trimethylsilyl)phenyl)-6-ethoxy-1,2,3,4-tetrahydroisoquinoline-1-carboxamide (100 mg, 0.15 mmol) and 10% palladium-carbon (15.86 mg, 0.15 mmol) in MeOH (2 mL) was stirred under hydrogen atmosphere (1 atm) at room temperature for 2 hr. The catalyst was removed by filtration, and the filtrate was concentrated under reduced pressure. The obtained residue was purified by silica gel column chromatography (solvent gradient; 10→100% ethyl acetate/hexane) to give the title compound (19.00 mg, 0.033 mmol, 21.95%) as a white solid.

¹H NMR (300 MHz, DMSO-d₆): δ 0.30 (9H, s), 1.30 (3H, t, J=6.8 Hz), 2.83 (1H, d, J=15.1 Hz), 3.02-3.21 (1H, m), 3.43-3.55 (1H, m), 3.76-3.94 (2H, m), 3.94-4.11 (4H, m), 4.22 (1H, d, J=16.2 Hz), 5.60 (1H, s), 6.75-6.87 (2H, m), 7.20 (2H, d, J=9.8 Hz), 7.43 (1H, d, J=9.1 Hz), 10.77 (1H, s).

The compounds described in Examples 214 to 219 were synthesized by the reaction and purification in the same manner as in the above-mentioned Examples.

Example 214

(5R)-6-((1,1-dioxido-4-oxo-1,2,5-thiadiazolysin-2-yl)acetyl)-N-(7-fluoro-1,1-dimethyl-2,3-dihydro-1H-inden-5-yl)-2-methoxy-5,6,7,8-tetrahydro-1,6-naphthyridine-5-carboxamide ¹H NMR (300 MHz, DMSO-d₆): δ 1.29 (6H, s), 1.81-1.93 (2H, m), 2.80-3.08 (4H, m), 3.73-4.34 (10H, m), 5.73 (1H, s), 6.73 (1H, d, J=8.7 Hz), 7.11-7.27 (2H, m), 7.77 (1H, d, J=8.3 Hz), 10.46 (1H, s).

Example 215

5-((1R)-1-((7-fluoro-1,1-dimethyl-2,3-dihydro-1H-inden-5-yl) carbamoyl)-6-(2,2,2-trifluoroethoxy)-3,4-dihydroisoquinolin-2(1H)-yl)-5-oxopentanoic acid ¹H NMR (300 MHz, CDCl₃): δ 1.27 (6H, d, J=2.3 Hz), 1.83 (2H, t, J=7.4 Hz), 2.06-2.16 (2H, m), 2.47 (2H, t), 2.52-2.64 (1H, m), 2.67-2.82 (3H, m), 2.84-2.95 (1H, m), 3.16-3.28 (1H, m), 3.73 (1H, ddd, J=12.2, 7.6, 4.3 Hz), 3.98 (1H, ddd, J=12.1, 7.2, 4.5 Hz), 4.33 (2H, q, J=7.9 Hz), 5.96 (1H, s), 6.78 (1H, d, J=2.3 Hz), 6.82 (1H, dd, J=8.3, 2.6 Hz), 6.88 (1H, s), 7.02 (1H, dd, J=11.7, 1.5 Hz), 7.42 (1H, d, J=8.3 Hz), 9.44 (1H, s), 10.85 (1H, brs).

Example 216

(4R)-4-amino-5-((1R)-1-((3,5-difluoro-4-(trimethylsilyl)phenyl)carbamoyl)-6-ethoxy-3,4-dihydroisoquinolin-2(1H)-yl)-5-oxopentanoic acid $^1$H NMR (300 MHz, DMSO-$d_6$): δ 0.30 (9H, s), 1.26-1.35 (3H, m), 1.39-1.58 (1H, m, J=14.7, 8.7 Hz), 1.69-1.87 (1H, m), 2.41 (2H, t, J=6.8 Hz), 2.75-2.90 (1H, m, J=16.2 Hz), 3.00-3.13 (1H, m), 3.58-3.70 (1H, m), 3.85 (1H, dd, J=9.1, 3.0 Hz), 3.94-4.14 (3H, m), 5.65 (1H, s), 6.73-6.86 (2H, m), 7.14-7.33 (2H, m), 7.45 (1H, d, J=9.4 Hz), 10.86 (1H, s).

Example 217

5-((1R)-1-((7-fluoro-1,1-dimethyl-2,3-dihydro-1H-inden-5-yl)carbamoyl)-6-isopropoxy-3,4-dihydroisoquinolin-2(1H)-yl)-5-oxopentanoic acid $^1$H NMR (300 MHz, DMSO-$d_6$): δ 1.23 (6H, d, J=6.0 Hz), 1.28 (6H, d, J=1.5 Hz), 1.74 (2H, quin, J=7.2 Hz), 1.81-1.93 (2H, m), 2.16-2.32 (2H, m), 2.35-2.62 (2H, m), 2.67-2.67-2.92 (3H, m), 3.01-3.18 (1H, m), 3.45-3.60 (1H, m), 3.93-4.07 (1H, m), 4.49-4.66 (1H, m), 5.64 (1H, s), 6.71-6.83 (2H, m), 7.13-7.29 (2H, m), 7.37-7.49 (1H, m), 10.42 (1H, s), 12.08 (1H, brs).

Example 218

5-((1R)-6-(cyclopropylmethoxy)-1-((7-fluoro-1,1-dimethyl-2,3-dihydro-1H-inden-5-yl) carbamoyl)-3,4-dihydroisoquinolin-2 (1H)-yl)-5-oxopentanoic acid $^1$H NMR (300 MHz, DMSO-$d_6$): δ 0.21-0.35 (2H, m), 0.47-0.61 (2H, m), 1.18-1.24 (1H, m), 1.28 (6H, d, J=1.5 Hz), 1.63-1.79 (2H, m), 1.82-1.91 (2H, m), 2.17-2.34 (2H, m), 2.35-2.61 (2H, m), 2.70-2.92 (3H, m), 2.99-3.18 (1H, m), 3.45-3.58 (1H, m), 3.73-3.87 (2H, m), 3.96-4.07 (1H, m), 5.55-5.67 (1H, m), 6.73-6.84 (2H, m), 7.12-7.27 (2H, m), 7.40-7.48 (1H, m), 10.35-10.52 (1H, m), 12.10 (1H, brs).

Example 219

5-((1R)-1-((7-fluoro-1,1-dimethyl-2,3-dihydro-1H-inden-5-yl)carbamoyl)-6-propoxy-3,4-dihydroisoquinolin-2(1H)-yl)-5-oxopentanoic acid $^1$H NMR (300 MHz, DMSO-$d_6$): δ 0.95 (3H, t, J=7.4 Hz), 1.28 (6H, d, J=1.5 Hz), 1.62-1.79 (3H, m), 1.80-1.92 (2H, m), 2.16-2.32 (3H, m), 2.34-2.62 (2H, m), 2.67-2.91 (3H, m), 3.03-3.18 (1H, m), 3.46-3.60 (1H, m), 3.83-3.94 (2H, m), 3.96-4.08 (1H, m), 5.53-5.70 (1H, m), 6.74-6.86 (2H, m), 7.12-7.27 (2H, m), 7.40-7.49 (1H, m), 10.36-10.52 (1H, m), 12.11 (1H, brs).

Example 220

(3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)azetidin-1-yl)acetic acid Cooled TFA (4 mL) was added to tert-butyl (R)-2-(3-(5-((7-fluoro-1,1-dimethyl-2,3-dihydro-1H-inden-5-yl)carbamoyl)-2-methoxy-5,6,7,8-tetrahydro-1,6-naphthyridine-6-carbonyl)azetidin-1-yl)acetate (321 mg, 0.57 mmol) (which can be synthesized in the same manner as in Example 230), and the mixture was stirred at room temperature for 45 min. The reaction mixture was added to ice and aqueous sodium hydrogen carbonate solution, and potassium carbonate was added thereto until the pH of the mixture became 7Then, the mixture was subjected to salt precipitation with sodium chloride, and the mixture was extracted three times with a mixed solvent of ethyl acetate/THF (3:1). The organic layer was washed with brine, and dried over magnesium sulfate, and the solvent was evaporated under reduced pressure. The obtained residue was solidified with IPE/hexane to give the title compound (135.1 mg, 0.265 mmol, 46.7%) as a white solid.

$^1$H NMR (300 MHz, DMSO-$d_6$): δ 1.29 (6H, s), 1.87 (2H, t, J=7.4 Hz), 2.82-2.94 (3H, m), 3.02 (1H, dt), 3.36 (1H, brs), 3.57-3.67 (1H, m), 3.83 (3H, s), 3.95 (1H, ddd, J=12.9, 8.2, 4.9 Hz), 4.08-4.25 (4H, m), 4.30-4.42 (3H, m), 5.78 (1H, s), 6.75 (1H, d, J=8.3 Hz), 7.20 (1H, s), 7.25 (1H, d, J=12.5 Hz), 7.88 (1H, d, J=8.7 Hz), 10.67 (1H, s)

Example 221

5-((1R)-1-((3-cyano-4-(trimethylsilyl)phenyl)carbamoyl)-6-ethoxy-3,4-dihydroisoquinolin-2(1H)-yl)-5-oxopentanoic acid (Step 1)
T3P (3.61 mL, 6.14 mmol) was added to a solution of 2-(tert-butoxycarbonyl)-6-ethoxy-1,2,3,4-tetrahydroisoquinoline-1-carboxylic acid (658 mg, 2.05 mmol), 5-amino-2-(trimethylsilyl)benzonitrile (429 mg, 2.25 mmol), DIEA (1.838 mL, 10.24 mmol) and DMAP (275 mg, 2.25 mmol) in ethyl acetate (5 mL), and the mixture was stirred overnight at 70° C. To the reaction mixture was added water, and the mixture was extracted with ethyl acetate. The organic layer was washed with water, and dried over magnesium sulfate, and the solvent was evaporated under reduced pressure. The obtained residue was purified by silica gel column chromatography (solvent gradient; 3→50% ethyl acetate/hexane) to give tert-butyl 1-((3-cyano-4-(trimethylsilyl)phenyl)carbamoyl)-6-ethoxy-3,4-dihydroisoquinoline-2(1H)-carboxylate (310 mg, 0.628 mmol, 30.7%) as a pale yellow solid.

MS(API): Calculated 493.7, Found 492.3 (M–H).
(Step 2)
tert-Butyl 1-((3-cyano-4-(trimethylsilyl)phenyl)carbamoyl)-6-ethoxy-3,4-dihydroisoquinoline-2(1H)-carboxylate (0.31 g) was resolved by chiral column chromatography. The fraction having a shorter retention time was concentrated to give tert-butyl (R)-1-((3-cyano-4-(trimethylsilyl)phenyl)carbamoyl)-6-ethoxy-3,4-dihydroisoquinoline-2 (1H)-carboxylate (0.073 g, >99% ee), and the fraction having a longer retention time was concentrated to give tert-butyl (S)-1-((3-cyano-4-(trimethylsilyl)phenyl)carbamoyl)-6-ethoxy-3,4-dihydroisoquinoline-2(1H)-carboxylate (0.063 g, >99% ee), each as a white solid.
purification condition by chiral column chromatography
column: CHIRALCEL OD (NL001) 50 mmID×500 mmL
solvent: hexane/EtOH=950/50
flow rate: 80 mL/min
temperature: 30° C.
(Step 3)
Cooled TFA (5 mL) was added to tert-butyl (R)-1-((3-cyano-4-(trimethylsilyl)phenyl)carbamoyl)-6-ethoxy-3,4-dihydroisoquinoline-2(1H)-carboxylate (75 mg, 0.15 mmol)

at 0° C., and the mixture was stirred at 0° C. for 1 hr. The reaction mixture was added to cooled aqueous sodium hydrogen carbonate solution, and the mixture was extracted twice with ethyl acetate. The organic layer was dried over magnesium sulfate, and the solvent was evaporated under reduced pressure to give (R)-N-(3-cyano-4-(trimethylsilyl)phenyl)-6-ethoxy-1,2,3,4-tetrahydroisoquinoline-1-carboxamide (59.8 mg, 0.152 mmol, 100%).

MS(API): Calculated 393.6, Found 394.3 (M+H).

(Step 4)

Dihydro-2H-pyran-2,6(3H)-dione (34.7 mg, 0.30 mmol) was added to a solution of (R)-N-(3-cyano-4-(trimethylsilyl)phenyl)-6-ethoxy-1,2,3,4-tetrahydroisoquinoline-1-carboxamide (59.8 mg, 0.15 mmol) and TEA (0.042 mL, 0.30 mmol) in THF (2 mL) at room temperature, and the mixture was stirred overnight at room temperature. To the reaction mixture was added brine, and the mixture was extracted with ethyl acetate. The organic layer was dried over magnesium sulfate, and the solvent was evaporated under reduced pressure. The obtained residue was purified by silica gel column chromatography (solvent gradient; 10→100% ethyl acetate/hexane), and crystallized with ethyl acetate/heptane to give the title compound (28.0 mg, 0.055 mmol, 36.3%) as white crystals.

$^1$H NMR (300 MHz, DMSO-d$_6$): δ 0.28-0.38 (9H, m), 1.26-1.33 (3H, m), 1.67-1.83 (2H, m), 2.21-2.30 (2H, m), 2.37-2.61 (2H, m), 2.68-2.90 (1H, m), 3.03-3.19 (1H, m), 3.44-3.58 (1H, m), 3.93-4.09 (3H, m), 5.65 (1H, s), 6.72-6.86 (2H, m), 7.46 (1H, d, J=8.3 Hz), 7.60 (1H, d, J=8.3 Hz), 7.77 (1H, dd, J=8.3, 1.9 Hz), 8.07 (1H, d, J=1.9 Hz), 10.76 (1H, s), 12.07 (1H, brs).

Example 222

(2E)-4-((1R)-1-((3, 5-difluoro-4-(trimethylsilyl)phenyl)carbamoyl)-6-methoxy-3,4-dihydroisoquinolin-2(1H)-yl)-4-oxobut-2-enoic acid HATU (82 mg, 0.22 mmol) was added to a solution of (R)-N-(3,5-difluoro-4-(trimethylsilyl)phenyl)-6-methoxy-1,2,3,4-tetrahydroisoquinoline-1-carboxamide (70 mg, 0.18 mmol), DIEA (0.061 mL, 0.36 mmol) and trans-2-butenedioic acid (208 mg, 1.79 mmol) in DMF (2.0 mL) at room temperature, and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→900% ethyl acetate/hexane), and then preparative HPLC (C18, mobile phase: water/acetonitrile (containing 0.1% TFA)) to give the title compound (15.4 mg, 0.032 mmol, 17.58%) as a white solid.

$^1$H NMR (300 MHz, DMSO-d$_6$): δ 0.30 (9H, s), 2.78-2.93 (1H, m), 3.06-3.21 (1H, m), 3.60-3.71 (1H, m), 3.73 (3H, s), 4.08-4.21 (1H, m), 5.63-5.79 (1H, m), 6.51-6.62 (1H, m), 6.77-6.90 (2H, m), 7.13-7.25 (2H, m), 7.39-7.57 (2H, m), 10.84 (1H, s), 13.07 (1H, brs).

The compounds described in Examples 223 to 224 were synthesized by the reaction and purification in the same manner as in the above-mentioned Examples.

Example 223

(1R)-N-(3,5-difluoro-4-(trimethylsilyl)phenyl)-2-(((3S)-1,1-dioxido-4-oxo-1,2,5-thiadiazolysin-3-yl)acetyl)-6-ethoxy-1,2,3,4-tetrahydroisoquinoline-1-carboxamide $^1$H NMR (300 MHz, DMSO-d$_6$): δ 0.29 (9H, s), 1.30 (3H, t, J=7.0 Hz), 2.77-2.99 (3H, m), 3.06-3.19 (1H, m, J=9.4 Hz), 3.43-3.55 (1H, m), 3.95-4.11 (3H, m), 4.34-4.44 (1H, m), 5.66 (1H, s), 6.71-6.89 (2H, m), 7.20 (2H, d, J=9.8 Hz), 7.44 (1H, d, J=8.3 Hz), 7.87 (1H, brs), 10.82 (1H, s).

Example 224

(1R)-2-(((3S)-1,1-dioxido-4-oxo-1,2,5-thiadiazolysin-3-yl)acetyl)-6-ethoxy-N-(7-fluoro-1,1-dimethyl-2,3-dihydro-1H-inden-5-yl)-1,2,3,4-tetrahydroisoquinoline-1-carboxamide $^1$H NMR (300 MHz, DMSO-d$_6$): δ 1.24-1.34 (9H, m), 1.80-1.90 (2H, m), 2.77-2.92 (3H, m), 2.93-3.21 (3H, m), 3.42-3.59 (1H, m), 3.94-4.10 (3H, m), 4.44 (1H, dd, J=6.6, 3.6 Hz), 5.58-5.74 (1H, m), 6.75-6.85 (2H, m), 7.13-7.18 (1H, m), 7.22 (1H, d, J=12.5 Hz), 7.36-7.51 (1H, m), 8.09 (1H, brs), 10.37-10.51 (1H, m).

Example 225

3-((((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)oxy)propanoic acid (Step 1)

A solution of bis(trichloromethyl) carbonate (147 mg, 0.50 mmol) in THF (2 mL) was added to a solution of tert-butyl 3-hydroxypropanoate (0.133 mL, 0.90 mmol) and pyridine (0.120 mL, 1.49 mmol) in THF (2 mL) at 0° C., and the mixture was stirred at room temperature for 30 min. The reaction mixture was concentrated under reduced pressure, the obtained residue was dissolved in DMF (2 mL), and the solution was cooled to 0° C. A solution of (R)-N-(7-fluoro-1,1-dimethyl-2,3-dihydro-1H-inden-5-yl)-2-methoxy-5,6,7,8-tetrahydro-1,6-naphthyridine-5-carboxamide (100 mg, 0.27 mmol) and DIEA (0.236 mL, 1.35 mmol) in DMF (2 mL) was added thereto, and the mixture was stirred at room temperature for 1 hr. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 10→50% ethyl acetate/hexane, 0→10% MeOH/ethyl acetate) to give 3-(tert-butoxy)-3-oxopropyl (R)-5-((7-fluoro-1,1-dimethyl-2,3-dihydro-1H-inden-5-yl)carbamoyl)-2-methoxy-7,8-dihydro-1,6-naphthyridine-6(5H)-carboxylate (120.2 mg, 0.222 mmol, 82%) as a white solid.

$^1$H NMR (300 MHz, CDCl$_3$): δ 1.34 (6H, s), 1.45 (9H, s), 1.91 (2H, t, J=7.4 Hz), 2.57-2.67 (2H, m), 2.81-3.05 (4H, m), 3.48 (1H, brs), 3.91 (3H, s), 4.29-4.62 (3H, m), 5.36-5.78 (1H, m), 6.63 (1H, d, J=8.7 Hz), 7.04-7.23 (2H, m), 7.48 (1H, d, J=8.7 Hz), 8.60 (1H, brs).

(Step 2)

Cooled TFA (2.0 mL) was added to 3-(tert-butoxy)-3-oxopropyl (R)-5-((7-fluoro-1,1-dimethyl-2,3-dihydro-1H-inden-5-yl) carbamoyl)-2-methoxy-7,8-dihydro-1, 6-naphthyridine-6 (5H)-carboxylate (120 mg, 0.22 mmol), and the mixture was stirred at room temperature for 1 hr. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20-90% ethyl acetate/hexane) to give the title compound (72.3 mg, 0.149 mmol, 67.2%) as a white solid.

$^1$H NMR (300 MHz, DMSO-d$_6$): δ 1.29 (6H, s), 1.80-1.93 (2H, m), 2.52-2.67 (2H, m), 2.72-3.05 (4H, m), 3.73-4.00 (5H, m), 4.15-4.31 (2H, m), 5.40-5.56 (1H, m), 6.72 (1H, d, J=8.3 Hz), 7.12-7.33 (2H, m), 7.78 (1H, d, J=8.3 Hz), 10.40-10.61 (1H, m), 12.30 (1H, brs).

The compound described in Example 226 was synthesized by the reaction and purification in the same manner as in the above-mentioned Examples.

Example 226

4-(((((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)oxy)butanoic acid $^1$H NMR (300 MHz, DMSO-d$_6$): δ 1.29 (6H, s), 1.70-1.92 (3H, m), 2.19-2.38 (3H, m), 2.79-2.91 (3H, m), 2.93-3.07 (1H, m), 3.83 (3H, s), 3.86-4.12 (4H, m), 5.49 (1H, d, J=10.6 Hz), 6.72 (1H, d, J=8.3 Hz), 7.10-7.29 (2H, m), 7.79 (1H, d, J=8.3 Hz), 10.52 (1H, d, J=5.7 Hz), 12.14 (1H, brs)

Example 227

N-(((1R)-1-((3,5-difluoro-4-(trimethylsilyl)phenyl)carbamoyl)-6-ethoxy-3,4-dihydroisoquinolin-2(1H)-yl)carbonyl)-beta-alanine (Step 1)

A solution of benzyl 3-aminopropanoate 4-methylbenzenesulfonate (5.0 g, 14.23 mmol) and 4-nitrophenyl chloroformate (5.74 g, 28.46 mmol) in THF (300 mL) was heated under reflux overnight. The reaction mixture was poured into water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give benzyl 3-(((4-nitrophenoxy)carbonyl)amino)propanoate (1.45 g, 4.21 mmol, 29.6%) as a white solid.

$^1$H NMR (300 MHz, CDCl$_3$): δ 2.69 (2H, t, J=5.9 Hz), 3.49-3.66 (2H, m), 5.18 (2H, s), 5.73 (1H, brs), 7.27-7.33 (2H, m), 7.34-7.44 (5H, m), 8.18-8.29 (2H, m).

(Step 2)

To a solution of (R)-N-(3,5-difluoro-4-(trimethylsilyl)phenyl)-6-ethoxy-1,2,3,4-tetrahydroisoquinoline-1-carboxamide (100 mg, 0.25 mmol) and benzyl 3-(((4-nitrophenoxy)carbonyl)amino)propanoate (102 mg, 0.30 mmol) in DMF (2.0 mL) was added DIEA (0.086 mL, 0.49 mmol) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give benzyl (R)-3-(1-((3,5-difluoro-4-(trimethylsilyl)phe-nyl)carbamoyl)-6-ethoxy-1,2,3,4-tetrahydroisoquinoline-2-carboxamide)propanoate (46.5 mg, 0.076 mmol, 30.9%) as a colorless oil.

$^1$H NMR (300 MHz, CDCl$_3$): δ 0.31 (9H, s), 1.41 (3H, t, J=7.0 Hz), 2.65 (2H, t, J=5.7 Hz), 2.70-2.81 (1H, m), 2.96-3.09 (1H, m), 3.10-3.22 (1H, m), 3.49 (1H, dt, J=9.7, 4.8 Hz), 3.61 (2H, q, J=5.8 Hz), 4.04 (2H, q, J=7.0 Hz), 5.13 (2H, s), 5.38 (1H, t, J=5.9 Hz), 5.72 (1H, s), 6.74-6.83 (2H, m), 6.99-7.09 (2H, m), 7.13 (1H, d, J=8.3 Hz), 7.30-7.39 (5H, m), 9.76 (1H, s).

(Step 3)

A solution of benzyl (R)-3-(1-((3,5-difluoro-4-(trimethylsilyl)phenyl)carbamoyl)-6-ethoxy-1,2,3,4-tetrahydroisoquinoline-2-carboxamide)propanoate (45 mg, 0.07 mmol) and 10% palladium-carbon (10 mg, 0.09 mmol, 50% wet) in MeOH (2.0 mL) was stirred under hydrogen atmosphere (1 atm) at room temperature for 5 hr. The catalyst was removed by filtration, and the filtrate was concentrated under reduced pressure. The obtained residue was purified by silica gel column chromatography (solvent gradient; 20→90% ethyl acetate/hexane) to give the title compound (14.0 mg, 0.027 mmol, 36.5%) as a white solid.

$^1$H NMR (300 MHz, DMSO-d$_6$): δ 0.29 (9H, s), 1.29 (3H, t, J=6.8 Hz), 2.40 (2H, t, J=7.2 Hz), 2.70-2.83 (1H, m), 3.00-3.15 (1H, m), 3.19-3.36 (3H, m), 3.73-3.86 (1H, m), 3.99 (2H, q, J=6.8 Hz), 5.51 (1H, s), 6.65-6.82 (3H, m), 7.22 (2H, d, J=9.8 Hz), 7.41 (1H, d, J=9.8 Hz), 10.68 (1H, s), 12.15 (1H, brs).

Example 228

1-(((1R)-1-((3,5-difluoro-4-(trimethylsilyl)phenyl)carbamoyl)-6-ethoxy-3,4-dihydroisoquinolin-2(1H)-yl)carbonyl)pyrrolidine-3-carboxylic acid The title compound was synthesized using (R)-N-(3,5-difluoro-4-(trimethylsilyl)phenyl)-6-ethoxy-1,2,3,4-tetrahydroisoquinoline-1-carboxamide and benzyl pyrrolidine-3-carboxylate, by the reaction and purification in the same manner as in Step 1 of Example 225 and Step 3 of Example 227.

Example 229

5-((1R)-1-((3,5-difluoro-4-(trimethylsilyl)phenyl)carbamoyl)-6-ethoxy-3,4-dihydroisoquinolin-2(1H)-yl)-4,5-dioxopentanoic acid The title compound was synthesized using (R)-N-(3,5-difluoro-4-(trimethylsilyl)phenyl)-6-ethoxy-1,2,3,4-tetrahydroisoquinoline-1-carboxamide and 2-oxopentanedioic acid, by the reaction and purification in the same manner as in Example 1.

Example 230 benzyl (1-(((1R)-1-((3,5-difluoro-4-(trimethylsilyl)phenyl)carbamoyl)-6-ethoxy-3,4-dihydroisoquinolin-2(1H)-yl)carbonyl)azetidin-3-yl)acetate A solution of benzyl 2-(azetidin-3-yl)acetate (50.7 mg, 0.25 mmol) and pyridine (0.055 mL, 0.68 mmol) in THF (1 mL) was added to a solution of bis(trichloromethyl) carbonate (135 mg, 0.45 mmol) in THF (1 mL) at 5° C., and the mixture was stirred at room temperature for 30 min. The reaction mixture was concentrated under reduced pressure, the obtained residue was dissolved in DMF (1 mL), and the solution was cooled to 5° C. A solution of (R)-N-(3,5-difluoro-4-(trimethylsilyl)phenyl)-6-ethoxy-1,2,3,4-tetrahydroisoquinoline-1-carboxamide and DIEA (0.135 mL, 0.76 mmol) in DMF (1 mL) was added thereto at room temperature, and the mixture was stirred at room temperature for 1 hr. To the reaction mixture was added water, and 2N hydrochloric acid was added thereto until the pH of the mixture became 4. Then, the mixture was extracted with ethyl acetate. The organic layer was aqueous ammonium chloride solution and washed with brine, and dried over magnesium sulfate, and the solvent was evaporated under reduced pressure. The obtained residue was purified by silica gel column chromatography (solvent gradient; 3→33% ethyl acetate/hexane) to give the title compound (58 mg, 0.091 mmol, 60.2%) as a white solid.

$^1$H NMR (300 MHz, CDCl$_3$): δ 0.27-0.34 (9H, m), 1.40 (3H, t, J=7.0 Hz), 2.68-2.76 (2H, m), 2.83-3.13 (3H, m), 3.41-3.56 (2H, m), 3.61-3.73 (1H, m), 3.87-3.95 (1H, m), 3.97-4.07 (2H, m), 4.08-4.17 (1H, m), 4.30-4.42 (1H, m), 5.12 (2H, s), 5.58 (1H, s), 6.69-6.83 (2H, m), 7.04 (3H, d, J=9.4 Hz), 7.34 (5H, d, J=1.5 Hz), 10.02-10.12 (1H, m)

Example 231

(1-(((1R)-1-((3,5-difluoro-4-(trimethylsilyl)phenyl) carbamoyl)-6-ethoxy-3,4-dihydroisoquinolin-2(1H)-yl)carbonyl)azetidin-3-yl)acetic acid A solution of benzyl (1-(((1R)-1-((3,5-difluoro-4-(trimethylsilyl)phenyl)carbamoyl)-6-ethoxy-3,4-dihydroisoquinolin-2(1H)-yl)carbonyl)azetidin-3-yl)acetate (45 mg, 0.07 mmol) and 10% palladium-carbon (30 mg, 0.01 mmol, 50% wet) in MeOH (3 mL) was stirred under hydrogen atmosphere (1 atm) at room temperature for 1 hr. The catalyst was removed by filtration, and the filtrate was concentrated under reduced pressure. The obtained residue was purified by silica gel column chromatography (Diol, solvent gradient; 20→80% ethyl acetate/hexane/) to give the title compound (34 mg, 0.062 mmol, 88%) as a white solid.

$^1$H NMR (300 MHz, CDCl$_3$): δ 0.31 (9H, brs), 1.40 (3H, t, J=7.0 Hz), 2.67-2.75 (2H, m), 2.83-3.09 (3H, m), 3.42-3.60 (2H, m), 3.66-3.75 (1H, m), 3.90-3.97 (1H, m), 3.98-4.21 (3H, m), 4.32-4.43 (1H, m), 5.58 (1H, s), 6.68-6.73 (1H, m), 6.76-6.84 (1H, m), 7.00-7.14 (3H, m), 9.91-10.01 (1H, m).

$[α]_D^{25}$ −14.2 (c 0.2510, MeOH)

Example 232 benzyl (1-(((1R)-6-ethoxy-1-((7-fluoro-1,1-dimethyl-2,3-dihydro-1H-inden-5-yl)carbamoyl)-3,4-dihydroisoquinolin-2 (1H)-yl)carbonyl)azetidin-3-yl)acetate The title compound was synthesized using (R)-6-ethoxy-N-(7-fluoro-1,1-dimethyl-2,3-dihydro-1H-inden-5-yl)-1,2,3,4-tetrahydroisoquinoline-1-carboxamide hydrochloride, by the reaction and purification in the same manner as in Example 230.

$^1$H NMR (300 MHz, CDCl$_3$): δ 1.32 (6H, s), 1.40 (3H, t, J=7.0 Hz), 1.88 (2H, t, J=7.4 Hz), 2.71 (2H, dd, J=7.7, 2.1 Hz), 2.78-2.89 (3H, m), 2.91-3.08 (1H, m), 3.50 (2H, d, J=5.3 Hz), 3.67 (1H, s), 3.90 (1H, m, s), 3.97-4.07 (2H, m), 4.07-4.17 (2H, m), 4.35 (1H, s), 5.12 (2H, s), 5.58 (1H, s), 6.69 (1H, d, J=2.6 Hz), 6.75-6.82 (1H, m), 7.05-7.21 (3H, m), 7.29-7.40 (5H, m), 9.70 (1H, s).

Example 233

(1-(((1R)-6-ethoxy-1-((7-fluoro-1,1-dimethyl-2,3-dihydro-1H-inden-5-yl)carbamoyl)-3,4-dihydroisoquinolin-2 (1H)-yl)carbonyl)azetidin-3-yl)acetic acid The title compound was synthesized using benzyl (1-(((1R)-6-ethoxy-1-((7-fluoro-1,1-dimethyl-2,3-dihydro-1H-inden-5-yl)carbamoyl)-3,4-dihydroisoquinolin-2 (1H)-yl)carbonyl)azetidin-3-yl)acetate, by the reaction and purification in the same manner as in Example 231.

$^1$H NMR (300 MHz, CDCl$_3$): δ 1.29-1.35 (6H, m), 1.40 (3H, t, J=6.8 Hz), 1.89 (2H, t, J=7.4 Hz), 2.70 (2H, d, J=8.3 Hz), 2.78-3.05 (5H, m), 3.47-3.60 (2H, m), 3.70 (1H, d, J=2.6 Hz), 3.91 (1H, d, J=2.6 Hz), 3.96-4.07 (2H, m), 4.07-4.20 (2H, m), 4.36 (1H, s), 5.58 (1H, s), 6.69 (1H, d, J=2.3 Hz), 6.75-6.82 (1H, m), 7.05-7.20 (3H, m), 9.56 (1H, s).

Example 234

(2Z)-4-((1R)-1-((3,5-difluoro-4-(trimethylsilyl)phenyl)carbamoyl)-6-methoxy-3,4-dihydroisoquinolin-2 (1H)-yl)-4-oxobut-2-enoic acid The title compound was synthesized using maleic acid and (R)-N-(3,5-difluoro-4-(trimethylsilyl)phenyl)-6-methoxy-1,2,3,4-tetrahydroisoquinoline-1-carboxamide, by the reaction and purification in the same manner as in Example 1.

$^1$H NMR (300 MHz, DMSO-d$_6$): δ 0.30 (9H, s), 2.68-2.89 (1H, m), 2.92-3.08 (1H, m), 3.40-3.52 (1H, m), 3.73 (3H, s), 3.85-4.05 (1H, m), 5.70 (1H, s), 6.07 (1H, d, J=12.1 Hz), 6.75-6.87 (3H, m), 7.20-7.31 (2H, m), 7.43 (1H, d, J=8.3 Hz), 10.65-10.81 (1H, m), 12.82 (1H, brs).

Example 235

5-((1R)-1-((3,5-difluoro-4-(trimethylsilyl)phenyl)carbamoyl)-6-(methylsulfonyl)-3,4-dihydroisoquinolin-2(1H)-yl)-5-oxopentanoic acid (Step 1)
Lithium hydroxide monohydrate (4.00 g, 95.40 mmol) was added to a mixture of 1-ethyl 2-tert-butyl 6-hydroxy-3,4-dihydroisoquinoline-1,2(1H)-dicarboxylate (5.11 g, 15.90 mmol) in a mixed solvent of THF (20 mL), EtOH (20 mL) and water (20 mL) at room temperature, and the mixture was stirred overnight at room temperature. The reaction mixture was concentrated under reduced pressure, and to the residue was added 6N hydrochloric acid. The mixture was extracted with ethyl acetate. The organic layer was washed with brine, and dried over magnesium sulfate, and the solvent was evaporated under reduced pressure to give 2-(tert-butoxycarbonyl)-6-hydroxy-1,2,3,4-tetrahydroisoquinoline-1-carboxylic acid (4.8 g, 16.36 mmol, 103%) as a white solid.

$^1$H NMR (300 MHz, DMSO-d$_6$): δ 1.33-1.52 (9H, m), 2.61-2.87 (2H, m), 3.41-3.68 (2H, m), 5.05-5.28 (1H, m), 6.45-6.75 (2H, m), 7.24 (1H, d, J=8.3 Hz), 9.41 (1H, d, J=4.2 Hz), 12.67 (1H, brs).

(Step 2)
A mixture of 2-(tert-butoxycarbonyl)-6-hydroxy-1,2,3,4-tetrahydroisoquinoline-1-carboxylic acid (3.35 g, 11.42 mmol), benzyl bromide (6.79 mL, 57.11 mmol) and sodium hydrogen carbonate (1.919 g, 22.84 mmol) in DMF (50 mL)

was stirred at room temperature for 2 days. The reaction mixture was extracted with ethyl acetate. The organic layer was washed with brine, and dried over magnesium sulfate, and the solvent was evaporated under reduced pressure. The obtained residue was purified by silica gel column chromatography (solvent gradient; 2→50% ethyl acetate/hexane) to give 2-tert-butyl 1-benzyl 6-hydroxy-3,4-dihydroisoquinoline-1,2(1H)-dicarboxylate (3.91 g, 10.20 mmol, 89%) as a white solid.

$^1$H NMR (300 MHz, CDCl$_3$): δ 1.32-1.54 (9H, m), 2.57-3.03 (2H, m), 3.50-3.84 (2H, m), 4.94-5.22 (3H, m), 5.30-5.65 (1H, m), 6.54-6.77 (2H, m), 7.18-7.47 (6H, m).

(Step 3)

1,1,1-Trifluoro-N-phenyl-N-(trifluoromethyl)sulfonyl-methanesulfonamide (5.46 g, 15.30 mmol) was added to a solution of 2-tert-butyl 1-benzyl 6-hydroxy-3,4-dihydroisoquinoline-1,2(1H)-dicarboxylate (3.91 g, 10.20 mmol), DIEA (3.56 mL, 20.39 mmol) and DMAP (0.374 g, 3.06 mmol) in THF (30 mL) at room temperature, and the mixture was stirred at room temperature for 3 hr. The reaction mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane), and then silica gel column chromatography (NH, solvent gradient; 3-50% ethyl acetate/hexane) to give 2-tert-butyl 1-benzyl 6-(((trifluoromethyl)sulfonyl)oxy)-3,4-dihydroisoquinoline-1,2(1H)-dicarboxylate (4.35 g, 8.44 mmol, 83%) as a colorless oil.

$^1$H NMR (300 MHz, CDCl$_3$): δ 1.35-1.52 (9H, m), 2.71-3.06 (2H, m), 3.63-3.76 (1H, m), 3.77-3.98 (1H, m), 5.04-5.29 (2H, m), 5.44-5.75 (1H, m), 7.01-7.15 (2H, m), 7.19-7.40 (5H, m), 7.57 (1H, d, J=8.3 Hz)

(Step 4)

A solution of 2-tert-butyl 1-benzyl 6-(((trifluoromethyl)sulfonyl)oxy)-3,4-dihydroisoquinoline-1,2(1H)-dicarboxylate (1.75 g, 3.39 mmol), bis(pinacolato)diboron (1.293 g, 5.09 mmol), PdCl$_2$(dppf) (0.248 g, 0.34 mmol) and potassium acetate (1.000 g, 10.18 mmol) in DME (3 mL) was stirred under nitrogen gas atmosphere at 80° C. for 3 hr. To the reaction mixture was added ethyl acetate. The organic layer was washed with brine, and dried over magnesium sulfate, and the solvent was evaporated under reduced pressure. The obtained residue was purified by silica gel column chromatography (solvent gradient; 3-50% ethyl acetate/hexane) to give 2-tert-butyl 1-benzyl 6-(4,4,5,5-tetramethyl-1,3,2-dioxaborolan-2-yl)-3,4-dihydroisoquinoline-1,2(1H)-dicarboxylate (1.810 g, 3.67 mmol, 108%) as a colorless oil.

$^1$H NMR (300 MHz, CDCl$_3$): δ 1.34 (12H, s), 1.36-1.50 (9H, m), 2.76-3.04 (2H, m), 3.64-3.86 (2H, m), 5.01-5.21 (2H, m), 5.42-5.70 (1H, m), 7.26-7.36 (5H, m), 7.45-7.53 (1H, m), 7.57-7.68 (2H, m).

(Step 5)

Sodium periodate (2.354 g, 11.01 mmol) was added to a mixture of 2-tert-butyl 1-benzyl 6-(4,4,5,5-tetramethyl-1,3,2-dioxaborolan-2-yl)-3,4-dihydroisoquinoline-1,2(1H)-dicarboxylate (1.81 g, 3.67 mmol) in a mixed solvent of water (2.500 mL) and acetone (10 mL) at room temperature, and the mixture was stirred at room temperature for 1 hr. To the reaction mixture was added 2N hydrochloric acid (3.67 mL) at room temperature, and the mixture was stirred at room temperature for additional 4 hr. To the reaction mixture was added water, and the precipitate was collected by filtration with water to give (1-((benzyloxy)carbonyl)-2-(tert-butoxycarbonyl)-1,2,3,4-tetrahydroisoquinolin-6-yl)boronic acid (1.100 g, 2.67 mmol, 72.9%) as a white solid.

MS(API): Calculated 411.3, Found 312.1(M-Boc+H).

(Step 6)

(1-((Benzyloxy)carbonyl)-2-(tert-butoxycarbonyl)-1,2,3,4-tetrahydroisoquinolin-6-yl)boronic acid (1 g, 2.43 mmol), copper(II) acetate (0.022 g, 0.12 mmol), sodium methanesulfinate (0.248 g, 2.43 mmol) and 1-butyl-3-methylimidazolium trifluoromethylsulfonate (1.5 mL, 6.74 mmol) were stirred overnight at room temperature, and then overnight at 60° C. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 5→70% ethyl acetate/hexane) to give crude 2-tert-butyl 1-benzyl 6-(methylsulfonyl)-3,4-dihydroisoquinoline-1,2(1H)-dicarboxylate (0.317 g, 0.712 mmol, 29.3%) as a colorless oil.

(Step 7)

A solution of 2-tert-butyl 1-benzyl 6-(methylsulfonyl)-3,4-dihydroisoquinoline-1,2(1H)-dicarboxylate (317 mg, 0.71 mmol) and 10% palladium-carbon (76 mg, 0.71 mmol, 50% wet) in MeOH (5 mL) was stirred under hydrogen atmosphere (1 atm) at room temperature for 2 days. The catalyst was removed by filtration, and the filtrate was concentrated under reduced pressure to give 2-(tert-butoxycarbonyl)-6-(methylsulfonyl)-1,2,3,4-tetrahydroisoquinoline-1-carboxylic acid (253 mg, 0.712 mmol, 100%) as a colorless oil.

MS(API): Calculated 355.4, Found 709.3 (2M–H).

(Step 8)

T3P (1.256 mL, 2.14 mmol) was added to a solution of 2-(tert-butoxycarbonyl)-6-(methylsulfonyl)-1,2,3,4-tetrahydroisoquinoline-1-carboxylic acid (253 mg, 0.71 mmol), 3,5-difluoro-4-(trimethylsilyl)aniline (143 mg, 0.71 mmol), DIEA (0.622 mL, 3.56 mmol) and DMAP (87 mg, 0.71 mmol) in ethyl acetate (10 mL), and the mixture was stirred at 70° C. for 24 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 2→40% ethyl acetate/hexane) and then silica gel column chromatography (NH, solvent gradient; 5→40% ethyl acetate/hexane) to give tert-butyl 1-((3,5-difluoro-4-(trimethylsilyl)phenyl)carbamoyl)-6-(methylsulfonyl)-3,4-dihydroisoquinoline-2 (1H)-carboxylate (140 mg, 0.260 mmol, 36.5%) as a white solid.

MS(API): Calculated 538.7, Found 537.3 (M–H).

(Step 9)

tert-Butyl 1-((3,5-difluoro-4-(trimethylsilyl)phenyl)carbamoyl)-6-(methylsulfonyl)-3,4-dihydroisoquinoline-2 (1H)-carboxylate (140 mg) was resolved by chiral column chromatography. The fraction having a shorter retention time was concentrated to give tert-butyl (R)-1-((3,5-difluoro-4-(trimethylsilyl)phenyl)carbamoyl)-6-(methylsulfonyl)-3,4-dihydroisoquinoline-2(1H)-carboxylate (43.4 mg, >99% ee), and the fraction having a longer retention time was concentrated to give tert-butyl (S)-1-((3,5-difluoro-4-(trimethylsilyl)phenyl)carbamoyl)-6-(methylsulfonyl)-3,4-dihydroisoquinoline-2(1H)-carboxylate (45.2 mg, >99% ee).

purification condition by chiral column chromatography
　　column: CHIRALCEL OD (NL001) 50 mmID×500 mmL
　　solvent: hexane/EtOH=800/200
　　flow rate: 80 mL/min
　　temperature: 30° C.
　　detection method: UV 220 nm (Step 10)

Cooled TFA (5 mL) was added to tert-butyl (R)-1-((3,5-difluoro-4-(trimethylsilyl)phenyl)carbamoyl)-6-(methylsulfonyl)-3,4-dihydroisoquinoline-2(1H)-carboxylate (43 mg, 0.08 mmol) under ice water, and the mixture was stirred under ice water for 1 hr. The reaction mixture was added to ice and aqueous sodium hydrogen carbonate solution, and the mixture was extracted twice with ethyl acetate. The organic layer was washed with brine, and dried over sodium sulfate, and the solvent was evaporated under reduced pressure to give (R)-N-(3,5-difluoro-4-(trimethylsilyl)phenyl)-6-(methylsulfonyl)-1,2,3,4-tetrahydroisoquinoline-1-carboxamide (35.0 mg, 0.080 mmol, 100%).

MS(API): Calculated 438.6, Found 439.3 (M+H).

(Step 11)

Dihydro-2H-pyran-2,6(3H)-dione (11.84 mg, 0.10 mmol) was added to a solution of (R)-N-(3,5-difluoro-4-(trimethylsilyl)phenyl)-6-(methylsulfonyl)-1,2,3,4-tetrahydroisoquinoline-1-carboxamide (35 mg, 0.08 mmol) and DIEA (18 µL, 0.10 mmol) in THF (2 mL) at room temperature, and the mixture was stirred overnight at room temperature. The reaction mixture was concentrated under reduced pressure, and the obtained residue was purified by silica gel column chromatography (solvent gradient; 10→90% ethyl acetate/hexane), crystallized from ethyl acetate/heptane to give the title compound (10.00 mg, 0.018 mmol, 22.67%) as white crystals.

$^1$H NMR (300 MHz, DMSO-d$_6$): δ 0.30 (9H, s), 1.67-1.84 (2H, m), 2.22-2.32 (2H, m), 2.38-2.63 (2H, m), 2.93-3.08 (1H, m), 3.12-3.28 (4H, m), 3.54-3.70 (1H, m), 3.96-4.15 (1H, m), 5.72-5.91 (1H, m), 7.21 (2H, d, J=9.4 Hz), 7.71-7.91 (3H, m), 10.95 (1H, s), 12.06 (1H, brs).

Example 236

5-(((1R)-6-ethoxy-1-((7-fluoro-1,1-dimethyl-2,3-dihydro-1H-inden-5-yl) carbamoyl)-3,4-dihydroisoquinolin-2 (1H)-yl)-3-hydroxy-3-methyl-5-oxopentanoic acid The title compound was synthesized using (R)-6-ethoxy-N-(7-fluoro-1,1-dimethyl-2,3-dihydro-1H-inden-5-yl)-1,2,3,4-tetrahydroisoquinoline-1-carboxamide hydrochloride and 3-methyl-3-hydroxyglutaric acid, by the reaction and purification in the same manner as in Example 1.

Example 237 tert-butyl (((1R)-1-((3,5-difluoro-4-(trimethylsilyl)phenyl)carbamoyl)-6-ethoxy-3,4-dihydroisoquinolin-2(1H)-yl)sulfonyl)carbamate The title compound was synthesized using (R)-N-(3,5-difluoro-4-(trimethylsilyl)phenyl)-6-ethoxy-1,2,3,4-tetrahydroisoquinoline-1-carboxamide, by the reaction and purification in the same manner as in Step 1 of Example 213.

$^1$H NMR (300 MHz, CDCl$_3$): δ 0.25-0.37 (9H, m), 1.40 (3H, t, J=7.0 Hz), 1.50 (9H, s), 2.77 (1H, dt, J=16.4, 4.6 Hz), 3.09-3.26 (1H, m), 3.41-3.57 (1H, m), 3.75-3.88 (1H, m), 4.02 (2H, q, J=7.2 Hz), 5.59 (1H, s), 6.67 (1H, d, J=2.3 Hz), 6.84 (1H, dd, J=8.7, 2.6 Hz), 7.22 (2H, d, J=9.4 Hz), 7.28 (1H, s), 9.43 (1H, s) (The peak derived from NH was not observed).

Example 238

4-((((1R)-1-((3,5-difluoro-4-(trimethylsilyl)phenyl)carbamoyl)-6-ethoxy-3,4-dihydroisoquinolin-2(1H)-yl)carbonyl)amino)butanoic acid (Step 1)

A solution of benzyl 4-aminobutanoate 4-methylbenzenesulfonate (3.0 g, 8.21 mmol) and 4-nitrophenyl chloroformate (3.31 g, 16.42 mmol) in THF (150 mL) was heated under reflux overnight. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give benzyl 4-(((4-nitrophenoxy)carbonyl)amino)butanoate (1.59 g, 4.44 mmol, 54.0%) as a white solid.

$^1$H NMR (300 MHz, CDCl$_3$): δ 1.96 (2H, quin, J=7.0 Hz), 2.49 (2H, t, J=7.0 Hz), 3.35 (2H, q, J=7.0 Hz), 5.14 (2H, s), 5.35 (1H, brs), 7.27-7.32 (2H, m), 7.33-7.40 (5H, m), 8.19-8.27 (2H, m).

(Step 2)

DIEA (0.086 mL, 0.49 mmol) was added to a solution of (R)-N-(3,5-difluoro-4-(trimethylsilyl)phenyl)-6-ethoxy-1,2,3,4-tetrahydroisoquinoline-1-carboxamide (100 mg, 0.25 mmol) and benzyl 4-(((4-nitrophenoxy)carbonyl)amino)butanoate (97 mg, 0.27 mmol) in DMF (2.0 mL) at room temperature, and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give benzyl (R)-4-(1-((3,5-difluoro-4-(trimethylsilyl)phenyl)carbamoyl)-6-ethoxy-1,2,3,4-tetrahydroisoquinoline-2-carboxamide)butanoate (41.3 mg, 0.066 mmol, 26.8%) as a colorless oil.

MS(API): Calculated 623.8, Found 622.3 (M−H).

(Step 3)

A solution of benzyl (R)-4-(1-((3,5-difluoro-4-(trimethylsilyl)phenyl)carbamoyl)-6-ethoxy-1,2,3,4-tetrahydroisoquinoline-2-carboxamide)butanoate (40 mg, 0.06 mmol) and 10% palladium-carbon (10 mg, 0.09 mmol, 50% wet) in MeOH (2.0 mL) was stirred under hydrogen atmosphere (1 atm) at room temperature for 2 hr. The catalyst was removed by filtration, and the filtrate was concentrated under reduced pressure. The obtained residue was purified by silica gel column chromatography (solvent gradient; 20→90% ethyl acetate/hexane) to give the title compound (22.3 mg, 0.042 mmol, 65.2%) as a white solid.

$^1$H NMR (300 MHz, CDCl$_3$): δ 0.29 (9H, s), 1.33-1.44 (3H, m), 1.77-1.99 (2H, m), 2.37-2.49 (2H, m), 2.70-2.85 (1H, m), 3.06-3.49 (5H, m), 3.60-3.72 (1H, m), 4.01 (2H, q, J=7.1 Hz), 5.18 (1H, brs), 5.75 (1H, s), 6.68-6.81 (2H, m), 7.01 (2H, d, J=9.1 Hz), 7.18-7.31 (1H, m), 9.70 (1H, brs).

Example 239

4-(((1R)-1-((3,5-difluoro-4-(trimethylsilyl)phenyl)carbamoyl)-6-ethoxy-3,4-dihydroisoquinolin-2(1H)-yl)carbonyl)morpholine-2-carboxylic acid The title compound was synthesized using benzyl morpholine-2-carboxylate hydrochloride and (R)-N-(3,5-difluoro-4-(trimethylsilyl)phenyl)-6-ethoxy-1,2,3,4-tetrahydroisoquinoline-1-carboxamide, by the reaction and purification in the same manner as in Step 1 of Example 225 and Step 3 of Example 227.

$^1$H NMR (300 MHz, CDCl$_3$): δ 0.31 (9H, d, J=5.3 Hz), 1.37-1.45 (3H, m), 2.80-3.28 (3H, m), 3.30-4.35 (10H, m), 5.29-5.51 (1H, m), 6.64-6.85 (2H, m), 6.90-7.19 (3H, m), 9.74-10.08 (1H, m).

Example 240

5-((1R)-1-((3,5-difluoro-4-(trimethylsilyl)phenyl) carbamoyl)-6-ethoxy-3,4-dihydroisoquinolin-2(1H)-yl)-3-hydroxy-3-methyl-5-oxopentanoic acid HATU (113 mg, 0.30 mmol) was added to a solution of (R)-N-(3,5-difluoro-4-(trimethylsilyl)phenyl)-6-ethoxy-1,2,3,4-tetrahydroisoquinoline-1-carboxamide (100 mg, 0.25 mmol), DIEA (0.127 mL, 0.74 mmol) and 3-methyl-3-hydroxyglutaric acid (200 mg, 1.24 mmol) in DMF (2.0 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane) to give the title compound (62.3 mg, 0.114 mmol, 45.9%) as a white solid.

$^1$H NMR (300 MHz, DMSO-d$_6$): δ 0.29 (9H, s), 1.23-1.37 (6H, m), 2.64-2.87 (3H, m), 2.89-3.01 (2H, m), 3.02-3.21 (1H, m), 3.48-3.63 (1H, m), 3.93-4.16 (3H, m), 5.50 (1H, s), 5.65 (1H, s), 6.74-6.86 (2H, m), 7.13-7.26 (2H, m), 7.38-7.50 (1H, m), 10.71 (1H, s), 12.07 (1H, brs).

Example 241

5-((1R)-6-ethoxy-1-((7-fluoro-1,1-dimethyl-2,3-dihydro-1H-inden-5-yl)carbamoyl)-3,4-dihydroisoquinolin-2(1H)-yl)-2,2-dimethyl-5-oxopentanoic acid The title compound was synthesized using (R)-6-ethoxy-N-(7-fluoro-1,1-dimethyl-2,3-dihydro-1H-inden-5-yl)-1,2,3,4-tetrahydroisoquinoline-1-carboxamide hydrochloride and 2,2-dimethylglutaric anhydride, by the reaction and purification in the same manner as in Example 109.

$^1$H NMR (300 MHz, CDCl$_3$): δ 1.18-1.29 (12H, m), 1.39 (3H, t, J=7.0 Hz), 1.82 (2H, t, J=7.4 Hz), 1.98-2.05 (2H, m), 2.55 (1H, dt, J=15.0, 7.4 Hz), 2.65-2.94 (4H, m), 3.18-3.18-3.32 (1H, m), 3.65-3.79 (1H, m), 3.94-4.07 (3H, m), 5.89 (1H, s), 6.66-6.77 (2H, m), 6.82 (1H, s), 6.90-7.03 (1H, m), 7.41 (1H, d, J=8.3 Hz), 9.52 (1H, s).

Example 242

4-((((1R)-1-((3,5-difluoro-4-(trimethylsilyl)phenyl) carbamoyl)-6-methoxy-3,4-dihydroisoquinolin-2 (1H)-yl)carbonyl)amino)butanoic acid (Step 1)
DIEA (0.107 mL, 0.61 mmol) was added to a solution of (R)-N-(3,5-difluoro-4-(trimethylsilyl)phenyl)-6-methoxy-1,2,3,4-tetrahydroisoquinoline-1-carboxamide (120 mg, 0.31 mmol) and benzyl 4-((((4-nitrophenoxy)carbonyl)amino)butanoate (121 mg, 0.34 mmol) in DMF (3.0 mL) at room temperature, and the mixture was stirred at room temperature for 3 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give benzyl (R)-4-(1-((3,5-difluoro-4-(trimethylsilyl)phenyl)carbamoyl)-6-methoxy-1,2,3,4-tetrahydroisoquinoline-2-carboxamide)butanoate (105.2 mg, 0.173 mmol, 56.1%) as a colorless oil.

MS(API): Calculated 609.7, Found 608.3 (M−H).
(Step 2)
A solution of benzyl (R)-4-(1-((3,5-difluoro-4-(trimethylsilyl)phenyl)carbamoyl)-6-methoxy-1,2,3,4-tetrahydroisoquinoline-2-carboxamide)butanoate (100 mg, 0.16 mmol) and 10% palladium-carbon (20 mg, 0.19 mmol, 50% wet) in MeOH (2.0 mL) was stirred under hydrogen atmosphere (1 atm) at room temperature for 3 hr. The catalyst was removed by filtration, and the filtrate was concentrated under reduced pressure. The obtained residue was purified by silica gel column chromatography (solvent gradient; 20→90% ethyl acetate/hexane) to give the title compound (50.0 mg, 0.096 mmol, 58.7%) as a white solid.

$^1$H NMR (300 MHz, DMSO-d$_6$): δ 0.29 (9H, s), 1.56-1.74 (2H, m), 2.16-2.28 (2H, m), 2.70-2.85 (1H, m), 2.99-3.16 (3H, m), 3.34-3.44 (1H, m), 3.72 (3H, s), 3.77-3.88 (1H, m), 5.51 (1H, s), 6.67 (1H, t, J=5.3 Hz), 6.76-6.83 (2H, m), 7.22 (2H, d, J=9.8 Hz), 7.43 (1H, d, J=9.8 Hz), 10.64 (1H, s), 12.02 (1H, brs).

Example 243

4-((((1R)-1-((3,5-difluoro-4-(trimethylsilyl)phenyl) carbamoyl)-6-ethoxy-3,4-dihydroisoquinolin-2(1H)-yl)sulfonyl)amino)butanoic acid (Step 1)
DEAD (0.080 mL, 0.17 mmol) was added to a solution of tert-butyl((((1R)-1-((3,5-difluoro-4-(trimethylsilyl)phenyl) carbamoyl)-6-ethoxy-3,4-dihydroisoquinolin-2(1H)-yl)sulfonyl)carbamate (50 mg, 0.09 mmol) and PPh$_3$ (44.9 mg, 0.17 mmol) in THF (20 mL) at 0° C., and the mixture was stirred overnight at room temperature. The reaction mixture was concentrated under reduced pressure, and the obtained residue was purified by silica gel column chromatography (solvent gradient; 10-60% ethyl acetate/hexane) to give tert-butyl (R)-4-(N-(tert-butoxycarbonyl)-1-((3,5-difluoro-4-(trimethylsilyl)phenyl)carbamoyl)-6-ethoxy-1,2,3,4-tetrahydroisoquinoline-2-sulfonamido)butanoate (63.0 mg, 0.087 mmol, 101%) as a colorless oil.

MS(API): Calculated 725.9, Found 724.4 (M−H).
(Step 2)
Cooled TFA (2 mL) was added to tert-butyl (R)-4-(N-(tert-butoxycarbonyl)-1-((3,5-difluoro-4-(trimethylsilyl) phenyl)carbamoyl)-6-ethoxy-1,2,3,4-tetrahydroisoquinoline-2-sulfonamido)butanoate (63 mg, 0.09 mmol) under ice water, and the mixture was stirred at the same temperature for 1 hr. Cooled TFA (2 mL) was added again thereto, and the mixture was stirred at the same temperature for 1 hr. The reaction mixture was added to ice and aqueous sodium hydrogen carbonate solution, and the mixture was extracted with ethyl acetate. The organic layer was washed with brine, and dried over magnesium sulfate, and the solvent was evaporated under reduced pressure. The obtained residue was purified twice by silica gel column chromatography (solvent; 5% ethyl acetate/hexane) to give the title compound (2.0 mg, 3.51 μmol, 4.05%) as a colorless oil.

MS(API): Calculated 569.7, Found 570.4 (M+H).

Example 244

N-(((1R)-1-((3,5-difluoro-4-(trimethylsilyl)phenyl)carbamoyl)-6-methoxy-3,4-dihydroisoquinolin-2(1H)-yl)carbonyl)-2-methylalanine The title compound was synthesized using benzyl 2-amino-2-methylpropanoate and (R)-N-(3,5-difluoro-4-(trimethylsilyl)phenyl)-6-methoxy-1,2,3,4-tetrahydroisoquinoline-1-carboxamide, by the reaction and purification in the same manner as in Step 1 of Example 225 and Step 3 of Example 227.

$^1$H NMR (300 MHz, CDCl$_3$): δ 0.30 (9H, t, J=1.3 Hz), 1.60 (6H, d, J=14.0 Hz), 2.82-2.97 (1H, m), 2.97-3.13 (1H, m), 3.40-3.56 (1H, m), 3.81 (4H, s), 5.22-5.36 (1H, m), 5.59-5.74 (1H, m), 6.75 (1H, d, J=2.3 Hz), 6.78-6.85 (1H, m), 7.12 (2H, d, J=9.5 Hz), 7.20 (1H, s), 9.07-9.29 (1H, m).

Example 245 benzyl N-(((1R)-1-((3,5-difluoro-4-(trimethylsilyl)phenyl)carbamoyl)-6-methoxy-3,4-dihydroisoquinolin-2(1H)-yl)carbonyl)-D-alaninate The title compound was synthesized using benzyl (R)-2-aminopropanoate and (R)-N-(3,5-difluoro-4-(trimethylsilyl)phenyl)-6-methoxy-1,2,3,4-tetrahydroisoquinoline-1-carboxamide, by the reaction and purification in the same manner as in Step 1 of Example 225.

$^1$H NMR (300 MHz, CDCl$_3$): δ 0.29 (9H, t, J=1.3 Hz), 1.50 (3H, d, J=7.2 Hz), 2.77-2.90 (1H, m), 3.11-3.28 (1H, m), 3.34-3.49 (1H, m), 3.78 (4H, s), 4.63 (1H, s), 5.10-5.29 (2H, m), 5.33-5.41 (1H, m), 5.70 (1H, s), 6.72-6.82 (2H, m), 6.96 (2H, d, J=9.1 Hz), 7.21 (1H, d, J=8.3 Hz), 7.32 (5H, s), 9.65-9.90 (1H, m).

Example 246

N-(((1R)-1-((3,5-difluoro-4-(trimethylsilyl)phenyl)carbamoyl)-6-methoxy-3,4-dihydroisoquinolin-2(1H)-yl)carbonyl)-D-alanine The title compound was synthesized using benzyl N-(((1R)-1-((3,5-difluoro-4-(trimethylsilyl)phenyl)carbamoyl)-6-methoxy-3,4-dihydroisoquinolin-2(1H)-yl)carbonyl)-D-alaninate, by the reaction and purification in the same manner as in Step 3 of Example 227.

$^1$H NMR (300 MHz, CDCl$_3$): δ 0.28 (9H, s), 1.48 (3H, d, J=7.2 Hz), 2.72-2.90 (1H, m), 3.30 (2H, s), 3.78 (4H, s), 4.46-4.62 (1H, m), 5.21-5.38 (1H, m), 5.68 (1H, s), 6.72 (2H, d, J=2.3 Hz), 6.91 (2H, d, J=9.1 Hz), 7.28 (1H, d, J=8.7 Hz), 9.41-9.58 (1H, m).

Example 247

5-((1R)-6-cyano-1-((3,5-difluoro-4-(trimethylsilyl)phenyl)carbamoyl)-3,4-dihydroisoquinolin-2(1H)-yl)-5-oxopentanoic acid (Step 1)

A solution of 1-ethyl 2-tert-butyl 6-(((trifluoromethyl)sulfonyl)oxy)-3,4-dihydroisoquinoline-1,2(1H)-dicarboxylate (2.5 g, 5.51 mmol), Pd(PPh$_3$)$_4$ (0.191 g, 0.17 mmol) and zinc cyanide (0.712 g, 6.06 mmol) in DMF (14 mL) was stirred overnight at 100° C. To the reaction mixture was added ethyl acetate. The mixture was washed with water and brine, and dried over magnesium sulfate, and the solvent was evaporated under reduced pressure. The obtained residue was purified by silica gel column chromatography (solvent gradient; 3→60% ethyl acetate/hexane) to give 1-ethyl 2-tert-butyl 6-cyano-3,4-dihydroisoquinoline-1,2(1H)-dicarboxylate (0.400 g, 1.211 mmol, 21.96%) as a colorless oil.

MS(API): Calculated 330.4, Found 329.1 (M–H).

(Step 2)

Lithium hydroxide monohydrate (152 mg, 3.63 mmol) was added to a mixture of 1-ethyl 2-tert-butyl 6-cyano-3,4-dihydroisoquinoline-1,2(1H)-dicarboxylate (400 mg, 1.21 mmol) in a mixed solvent of EtOH (10 mL) and water (10 mL) at room temperature, and the mixture was stirred overnight at room temperature. To the reaction mixture was added 2N hydrochloric acid, and the mixture was extracted with ethyl acetate. The organic layer was dried over magnesium sulfate, and the solvent was evaporated under reduced pressure to give 2-(tert-butoxycarbonyl)-6-cyano-1,2,3,4-tetrahydroisoquinoline-1-carboxylic acid (400 mg, 1.323 mmol, 109%) as a colorless oil.

MS(API): Calculated 302.3, Found 603 (2M–H).

(Step 3)

T3P (2.335 mL, 3.97 mmol) was added to a solution of 2-(tert-butoxycarbonyl)-6-cyano-1,2,3,4-tetrahydroisoquinoline-1-carboxylic acid (400 mg, 1.32 mmol), 3,5-difluoro-4-(trimethylsilyl)aniline (266 mg, 1.32 mmol), DIEA (1.155 mL, 6.62 mmol) and DMAP (162 mg, 1.32 mmol) in ethyl acetate (10 mL), and the mixture was stirred at 70° C. for 24 hr. To the reaction mixture was added ethyl acetate. The mixture was washed with water and brine, and dried over magnesium sulfate, and the solvent was evaporated under reduced pressure. The obtained residue was purified by silica gel column chromatography (solvent gradient; 2-40% ethyl acetate/hexane), and then silica gel column chromatography (NH, solvent gradient; 5→40% ethyl acetate/hexane) to give tert-butyl 6-cyano-1-((3,5-difluoro-4-(trimethylsilyl)phenyl)carbamoyl)-3,4-dihydroisoquinoline-2(1H)-carboxylate (290 mg, 0.597 mmol, 45.1%) as a white solid.

MS(API): Calculated 485.6, Found 484.2 (M–H).

(Step 4)

tert-Butyl 6-cyano-1-((3,5-difluoro-4-(trimethylsilyl)phenyl)carbamoyl)-3,4-dihydroisoquinoline-2(1H)-carboxylate (290 mg) was resolved by chiral column chromatography. The fraction having a shorter retention time was concentrated to give tert-butyl (R)-6-cyano-1-((3,5-difluoro-4-(trimethylsilyl)phenyl)carbamoyl)-3,4-dihydroisoquinoline-2(1H)-carboxylate (126 mg, >99% ee), and the fraction having a longer retention time was concentrated to give tert-butyl (S)-6-cyano-1-((3,5-difluoro-4-(trimethylsilyl)phenyl)carbamoyl)-3,4-dihydroisoquinoline-2(1H)-carboxylate (135 mg, >99% ee).

purification condition by chiral column chromatography
column: CHIRALPAK AD (NF001) 50 mmID×500 mmL
solvent: hexane/EtOH=800/200
flow rate: 80 mL/min
temperature: 30° C.
detection method: UV 220 nm (Step 5)

Cooled TFA (5 mL) was added to tert-butyl (R)-6-cyano-1-((3,5-difluoro-4-(trimethylsilyl)phenyl)carbamoyl)-3,4-dihydroisoquinoline-2(1H)-carboxylate (125 mg, 0.26 mmol), and the mixture was stirred under ice water for 1.5 hr. The reaction mixture was added to ice and aqueous sodium hydrogen carbonate solution, and the mixture was extracted twice with ethyl acetate. The organic layer was washed with brine, and dried over sodium sulfate, and the solvent was evaporated under reduced pressure to give (R)-6-cyano-N-(3,5-difluoro-4-(trimethylsilyl)phenyl)-1,2,3,4-tetrahydroisoquinoline-1-carboxamide (99 mg, 0.257 mmol, 100%) as a white solid.

MS(API): Calculated 385.5, Found 386.2 (M+H).
(Step 6)
The title compound was synthesized using (R)-6-cyano-N-(3,5-difluoro-4-(trimethylsilyl)phenyl)-1,2,3,4-tetrahydroisoquinoline-1-carboxamide, by the reaction and purification in the same manner as in Example 82.

$^1$H NMR (300 MHz, DMSO-$d_6$): δ 0.30 (9H, s), 1.64-1.83 (2H, m), 2.19-2.30 (2H, m), 2.38-2.61 (2H, m), 2.85-3.01 (1H, m), 3.07-3.22 (1H, m), 3.51-3.70 (1H, m), 3.98-4.10 (1H, m), 5.80 (1H, s), 7.20 (2H, d, J=9.8 Hz), 7.68-7.76 (2H, m), 7.79 (1H, s), 10.94 (1H, s), 12.06 (1H, brs).

Example 248

(4S)-5-((1R)-1-((3,5-difluoro-4-(trimethylsilyl)phenyl)carbamoyl)-6-methoxy-3,4-dihydroisoquinolin-2(1H)-yl)-4-hydroxy-5-oxopentanoic acid (Step 1)
A solution of potassium (S)-5-(tert-butoxy)-4-hydroxy-5-oxopentanoate (390 mg, 1.61 mmol) and benzyl bromide (0.249 mL, 2.09 mmol) in DMF (8 mL) was stirred at room temperature for 4 hr. To the reaction mixture was added water, and the mixture was extracted with ethyl acetate. The organic layer was washed with water, and dried over magnesium sulfate, and the solvent was evaporated under reduced pressure. The obtained residue was purified by silica gel column chromatography (solvent gradient; 3→45% ethyl acetate/hexane) to give 1-tert-butyl (S)-5-benzyl 2-hydroxypentanedioate (347 mg, 1.179 mmol, 73.2%) as a colorless oil.

$^1$H NMR (300 MHz, CDCl$_3$): δ 1.48 (9H, s), 1.81-1.99 (1H, m), 2.16 (1H, dddd, J=14.0, 8.9, 7.0, 4.2 Hz), 2.37-2.63 (2H, m), 2.86 (1H, d, J=5.3 Hz), 4.00-4.14 (1H, m), 5.13 (2H, s), 7.28-7.42 (5H, m).
(Step 2)
Cooled TFA (5 mL) was added to 1-tert-butyl (S)-5-benzyl 2-hydroxypentanedioate (347 mg, 1.18 mmol), and the mixture was stirred at 0° C. for 2 hr. The reaction mixture was concentrated under reduced pressure, and the obtained residue was subjected twice to azeotropy with toluene to give crude (S)-5-(benzyloxy)-2-hydroxy-5-oxopentanoic acid as a colorless oil.

$^1$H NMR (300 MHz, CDCl$_3$): δ 1.90-2.15 (1H, m), 2.34-2.46 (1H, m), 2.55-2.67 (2H, m), 4.33 (1H, dd, J=7.7, 4.0 Hz), 5.15 (2H, s), 7.34-7.38 (5H, m)
(Step 3)
HATU (86 mg, 0.23 mmol) was added to a solution of (R)-N-(3,5-difluoro-4-(trimethylsilyl)phenyl)-6-methoxy-1,2,3,4-tetrahydroisoquinoline-1-carboxamide (80 mg, 0.20 mmol), DIEA (0.039 mL, 0.23 mmol) and (S)-5-(benzyloxy)-2-hydroxy-5-oxopentanoic acid (53.7 mg, 0.23 mmol) in DMF (2 mL) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→80% ethyl acetate/hexane) to give benzyl (S)-5-((R)-1-((3,5-difluoro-4-(trimethylsilyl)phenyl)carbamoyl)-6-methoxy-3,4-dihydroisoquinolin-2(1H)-yl)-4-hydroxy-5-oxopentanoate (40.0 mg, 0.065 mmol, 32.0%) as a colorless oil.

MS(API): Calculated 610.7, Found 611.4 (M+H).
(Step 4)
A solution of benzyl (S)-5-((R)-1-((3,5-difluoro-4-(trimethylsilyl)phenyl)carbamoyl)-6-methoxy-3,4-dihydroisoquinolin-2(1H)-yl)-4-hydroxy-5-oxopentanoate (40 mg, 0.07 mmol) and 10% palladium-carbon (6.97 mg, 0.07 mmol, 50% wet) in MeOH (2 mL) was stirred under hydrogen atmosphere (1 atm) at room temperature for 3 hr. The catalyst was removed by filtration, and the filtrate was concentrated under reduced pressure. The obtained residue was purified by silica gel column chromatography (solvent gradient; 10→30% MeOH/ethyl acetate) to give the title compound (14.00 mg, 0.027 mmol, 41.1%) as a white solid.

$^1$H NMR (300 MHz, DMSO-$d_6$): δ 0.30 (9H, s), 1.25-1.33 (1H, m), 1.61-1.75 (1H, m), 1.79-1.93 (1H, m), 2.21-2.21-2.35 (2H, m), 2.76-2.90 (1H, m), 3.03-3.17 (1H, m), 3.57-3.70 (1H, m), 3.73 (3H, s), 4.09-4.23 (1H, m), 4.46 (1H, dd, J=8.3, 4.2 Hz), 5.57 (1H, s), 6.70-6.95 (2H, m), 7.21 (2H, d, J=9.8 Hz), 7.44 (1H, d, J=9.1 Hz), 10.86 (1H, s), 12.06 (1H, s).

Example 249

N-(((1R)-1-((3,5-difluoro-4-(trimethylsilyl)phenyl)carbamoyl)-6-methoxy-3,4-dihydroisoquinolin-2(1H)-yl)carbonyl)-L-alanine The title compound was synthesized using (R)-N-(3,5-difluoro-4-(trimethylsilyl)phenyl)-6-methoxy-1,2,3,4-tetrahydroisoquinoline-1-carboxamide and benzyl (S)-2-aminopropanoate, by the reaction and purification in the same manner as in Step 1 of Example 225 and Step 3 of Example 227.

Example 250

5-((5R)-5-((3,5-difluoro-4-(trimethylsilyl)phenyl)carbamoyl)-2-isopropyl-7,8-dihydro-1,6-naphthyridin-6(5H)-yl)-5-oxopentanoic acid The title compound was synthesized using (R)-N-(3,5-difluoro-4-(trimethylsilyl)phenyl)-2-isopropyl-5,6,7,8-tetrahydro-1,6-naphthyridine-5-carboxamide, by the reaction and purification in the same manner as in Example 82.

$^1$H NMR (300 MHz, DMSO-$d_6$): δ 0.30 (9H, s), 1.20 (6H, d, J=6.8 Hz), 1.73 (2H, dq, J=15.3, 7.5 Hz), 2.15-2.32 (2H, m), 2.37-2.66 (2H, m), 2.85-3.03 (2H, m), 3.04-3.22 (1H, m), 3.71-3.87 (1H, m), 4.06 (1H, ddd, J=12.6, 7.5, 4.5 Hz), 5.74 (1H, s), 7.13-7.29 (3H, m), 7.80 (1H, d, J=8.3 Hz), 10.87 (1H, s), 12.08 (1H, brs).

Example 251

5-((5R)-5-((3,5-difluoro-4-(trimethylsilyl)phenyl)carbamoyl)-2-propyl-7,8-dihydro-1,6-naphthyridin-6(5H)-yl)-5-oxopentanoic acid The title compound was synthesized using (R)-N-(3,5-difluoro-4-(trimethylsilyl)phenyl)-2-propyl-5, 6,7,8-tetrahydro-1, 6-naphthyridine-5-carboxamide, by the reaction and purification in the same manner as in Example 82.

$^1$H NMR (300 MHz, DMSO-$d_6$): δ 0.30 (9H, s), 0.86-0.96 (3H, m), 1.52-1.86 (4H, m), 2.15-2.33 (3H, m), 2.39-2.58 (1H, m), 2.65 (2H, t, J=7.7 Hz), 2.83-3.01 (1H, m), 3.03-

3.22 (1H, m), 3.69-3.89 (1H, m), 4.05 (1H, ddd, J=12.7, 7.6, 4.7 Hz), 5.74 (1H, s), 7.05-7.28 (3H, m), 7.78 (1H, d, J=8.3 Hz), 10.87 (1H, s), 12.12 (1H, brs).

Example 252

5-((5R)-5-((3,5-difluoro-4-(trimethylsilyl)phenyl)carbamoyl)-2,3,7,8-tetrahydrofuro[2,3-g]isoquinolin-6(5H)-yl)-5-oxopentanoic acid (Step 1)

Potassium tert-butoxide (22.85 g, 203.61 mmol) was added to a mixture of 1,4-dibromo-2-fluorobenzene (14.77 g, 58.17 mmol) in a mixed solvent of ethylene glycol (75 mL, 0.00 mmol) and NMP (7.5 mL) with cooling at room temperature, and the mixture was stirred at 100° C. for 15 hr. The reaction mixture was poured into ice water (600 mL), ethyl acetate (about 200 mL) was added thereto, and the insoluble substance was removed by filtration. The organic layer of the filtrate was washed with brine, and dried over magnesium sulfate, and the solvent was evaporated under reduced pressure. The precipitate was washed with hexane to give 2-(2,5-dibromophenoxy)ethanol (13.22 g, 44.7 mmol, 77%) as a grayish white solid.

$^1$H NMR (300 MHz, CDCl$_3$): δ 2.15 (1H, t, J=6.6 Hz), 3.97-4.04 (2H, m), 4.13 (2H, t), 7.01 (1H, dd), 7.05 (1H, d, J=1.9 Hz), 7.40 (1H, d, J=8.3 Hz).

(Step 2)

Phosphorus tribromide (2.81 mL, 29.91 mmol) was added to a solution of 2-(2,5-dibromophenoxy)ethanol (13.21 g, 44.64 mmol) in toluene (100 mL) at room temperature, and the mixture was stirred at 90° C. for 2.5 hr. The reaction mixture was poured into ice water (350 mL), and the mixture was extracted three times with a mixed solvent of ethyl acetate/hexane (3:1) The organic layer was washed with brine, and dried over magnesium sulfate, and the solvent was evaporated under reduced pressure. The insoluble substance was removed by filtration, and washed with a mixed solvent of ethyl acetate/hexane (1:2), and the filtrate was concentrated under reduced pressure. The obtained residue was purified by silica gel column chromatography (solvent gradient; 2→8% ethyl acetate/hexane) to give 1,4-dibromo-2-(2-bromoethoxy)benzene (10.45 g, 29.1 mmol, 65.2%) as a white solid.

$^1$H NMR (300 MHz, CDCl$_3$): δ 3.68 (2H, t, J=6.4 Hz), 4.33 (2H, t, J=6.4 Hz), 6.99-7.04 (2H, m), 7.38-7.43 (1H, m).

(Step 3)

1.6 M n-Butyllithium/hexane solution (21.84 mL, 34.94 mmol) was slowly added to a solution of 1,4-dibromo-2-(2-bromoethoxy)benzene (10.45 g, 29.12 mmol) in THF (200 mL) at −78° C. under argon gas atmosphere. The reaction mixture was stirred at −78° C. for 30 min, and then at 0° C. for 2 hr. The reaction mixture was added to ice water, and 2N hydrochloric acid was added thereto until the pH of the mixture became 3. Then, the mixture was extracted three times with a mixed solvent of ethyl acetate/hexane (3:1). The organic layer was washed with brine, and dried over magnesium sulfate, and the solvent was evaporated under reduced pressure. The obtained residue was purified by silica gel column chromatography (solvent gradient; 2→8% ethyl acetate/hexane) to give 6-bromo-2,3-dihydrobenzofuran (4.57 g, 22.96 mmol, 79%) as a white solid.

$^1$H NMR (300 MHz, CDCl$_3$): δ 3.15 (2H, t, J=8.9 Hz), 4.58 (2H, t, J=8.9 Hz), 6.92-6.98 (2H, m), 7.04 (1H, d).

(Step 4)

Magnesium powder (0.668 g, 27.49 mmol) and iodine (7 mg, 0.03 mmol) were added to a solution of 6-bromo-2,3-dihydrobenzofuran (4.56 g, 22.91 mmol) in THF (40 mL) under argon gas atmosphere at room temperature. The mixture was stirred at 70° C. for 1 hr, 1.2M ethylene oxide/THF solution (25.0 mL, 30.00 mmol) was slowly added thereto at room temperature, and the mixture was stirred at room temperature for 2 hr. The reaction mixture was poured into 1N hydrochloric acid (200 mL) and ice, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 2→30% ethyl acetate/hexane) to give 2-(2,3-dihydrobenzofuran-6-yl)ethanol (2.42 g, 14.74 mmol, 64.3%) as a colorless oil.

$^1$H NMR (300 MHz, CDCl$_3$): δ 1.41 (1H, t, J=5.1 Hz), 2.82 (2H, t, J=6.4 Hz), 3.18 (2H, t, J=8.5 Hz), 3.83 (2H, q, J=6.0 Hz), 4.56 (2H, t, J=8.7 Hz), 6.67 (1H, s), 6.71 (1H, d, J=7.6 Hz), 7.13 (1H, d, J=7.6 Hz).

(Step 5)

2.2M DEAD/toluene solution (8.67 mL, 19.08 mmol) was added to a solution of 2-(2,3-dihydrobenzofuran-6-yl)ethanol (2.41 g, 14.68 mmol) and phthalimide (2.375 g, 16.14 mmol) in THF (32 mL) under argon gas atmosphere at 0° C., and the mixture was stirred at room temperature for 15 hr. The reaction mixture was poured into water (120 mL), and the mixture was extracted three times with ethyl acetate. The organic layer was washed with brine, and dried over magnesium sulfate, and the solvent was evaporated under reduced pressure. The precipitate was collected by filtration with diethyl ether to give 2-(2-(2,3-dihydrobenzofuran-6-yl)ethyl) isoindoline-1,3-dione (3.04 g, 10.36 mmol, 70.6%) as a pale yellow solid.

$^1$H NMR (300 MHz, CDCl$_3$): δ 2.93 (2H, t), 3.16 (2H, t, J=8.7 Hz), 3.85-3.93 (2H, m), 4.54 (2H, t, J=8.7 Hz), 6.69 (1H, s), 6.74 (1H, dd, J=7.6, 1.5 Hz), 7.09 (1H, d, J=7.6 Hz), 7.67-7.74 (2H, m), 7.80-7.87 (2H, m).

(Step 6)

Hydrazine monohydrate (2.505 mL, 51.65 mmol) was added to a solution of 2-(2-(2,3-dihydrobenzofuran-6-yl)ethyl)isoindoline-1,3-dione (3.03 g, 10.33 mmol) in EtOH (30 mL) at room temperature, and the mixture was heated under reflux for 1 hr. The reaction mixture was cooled, and the insoluble substance was removed by filtration with diethyl ether. The filtrate was concentrated under reduced pressure, and the obtained residue was subjected to azeotropy with toluene (about 80 mL). The obtained residue was purified by silica gel column chromatography (solvent gradient; 10→100% ethyl acetate/hexane) to give 2-(2,3-dihydrobenzofuran-6-yl)ethanamine (1.66 g, 10.17 mmol, 98%) as a pale yellow oil.

$^1$H NMR (300 MHz, CDCl$_3$): δ 1.17 (2H, brs), 2.69 (2H, t), 2.94 (2H, t), 3.17 (2H, t, J=8.7 Hz), 4.56 (2H, t, J=8.7 Hz), 6.65 (1H, s), 6.68 (1H, dd), 7.11 (1H, d, J=7.6 Hz).

(Step 7)

6-(tert-Butoxycarbonyl)-2,3,5,6,7,8-hexahydrofuro[2,3-g]isoquinoline-5-carboxylic acid was synthesized using 2-(2,3-dihydrobenzofuran-6-yl)ethanamine, by the reaction and purification in the same manner as in Steps 3 to 7 of Example 254 to give.

$^1$H NMR (300 MHz, CDCl$_3$): δ 1.41-1.52 (9H, m), 2.68-2.80 (1H, m), 2.84-2.97 (1H, m), 3.17 (2H, t, J=8.7 Hz), 3.54 (1H, ddd, J=12.5, 8.1, 4.7 Hz), 3.72-3.89 (1H, m), 4.55 (2H, t, J=9.1 Hz), 5.30-5.50 (1H, m), 6.57 (1H, s), 7.26 (1H, s).

(Step 8)

(R)-N-(3,5-Difluoro-4-(trimethylsilyl)phenyl)-2,3,5,6,7,8-hexahydrofuro[2,3-g]isoquinoline-5-carboxamide was synthesized using 6-(tert-butoxycarbonyl)-2,3,5,6,7,8-hexahydrofuro[2,3-g]isoquinoline-5-carboxylic acid, by the reaction and purification in the same manner as in Steps 8 to 10 of Example 254.

$^1$H NMR (300 MHz, CDCl$_3$): δ 0.32 (9H, t, J=1.3 Hz), 2.26 (1H, brs), 2.67-2.78 (1H, m), 2.80-2.91 (1H, m), 3.07-3.07-3.23 (4H, m), 4.49-4.57 (2H, m), 4.68 (1H, s), 6.52 (1H, s), 7.06-7.14 (2H, m), 7.40 (1H, s), 9.68 (1H, s).

(Step 9)

The title compound was synthesized using (R)-N-(3,5-difluoro-4-(trimethylsilyl)phenyl)-2,3,5,6,7,8-hexahydrofuro[2,3-g]isoquinoline-5-carboxamide, by the reaction and purification in the same manner as in Example 82.

$^1$H NMR (300 MHz, CDCl$_3$): δ 0.27 (9H, s), 2.10-2.20 (2H, m), 2.44-2.51 (2H, m), 2.53-2.64 (1H, m), 2.78-2.90 (2H, m), 3.08-3.36 (3H, m), 3.60-3.70 (1H, m), 3.98-4.08 (1H, m), 4.48-4.62 (2H, m), 5.83 (1H, s), 6.61 (1H, s), 6.77-6.86 (2H, m), 7.37 (1H, s), 9.82 (1H, s), 11.23 (1H, brs).

Example 253

5-((1R)-1-((3,5-difluoro-4-(trimethylsilyl)phenyl)carbamoyl)-6-methoxy-5-methyl-3,4-dihydroisoquinolin-2 (1H)-yl)-5-oxopentanoic acid The title compound was synthesized using (R)-N-(3,5-difluoro-4-(trimethylsilyl)phenyl)-6-methoxy-5-methyl-1,2,3,4-tetrahydroisoquinoline-1-carboxamide, by the reaction and purification in the same manner as in Example 82.

$^1$H NMR (300 MHz, CDCl$_3$): δ 0.27 (9H, s), 2.10-2.18 (5H, m), 2.46-2.65 (3H, m), 2.84 (1H, dt, J=15.1, 6.2 Hz), 2.96 (1H, dt, J=15.7, 5.0 Hz), 3.10-3.21 (1H, m), 3.62-3.74 (1H, m), 3.81 (3H, s), 3.98-4.07 (1H, m), 5.86 (1H, s), 6.76 (1H, d, J=8.7 Hz), 6.79-6.86 (2H, m), 7.34 (1H, d, J=8.7 Hz), 9.73 (1H, s), 11.06 (1H, brs).

Example 254

5-((6R)-6-((3,5-difluoro-4-(trimethylsilyl)phenyl)carbamoyl)-8,9-dihydro[1,3]dioxolo[4,5-f]isoquinolin-7(6H)-yl)-5-oxopentanoic acid (Step 1)

Benzo[d][1,3]dioxole-4-carbaldehyde (6.13 g, 40.83 mmol), nitromethane (85 mL, 1569.38 mmol) and ammonium acetate (4.72 g, 61.25 mmol) were heated under reflux for 1 hr. The reaction mixture was cooled, water was added thereto, and the mixture was extracted three times with ethyl acetate. The organic layer was washed with water and brine, and dried over magnesium sulfate, and the solvent was evaporated under reduced pressure. The precipitate was washed with ethyl acetate/IPE to give (E)-4-(2-nitrovinyl)benzo[d][1,3]dioxole (6.26 g, 32.4 mmol, 79%) as yellow crystals.

$^1$H NMR (300 MHz, CDCl$_3$): δ 6.13 (2H, s), 6.86-6.98 (3H, m), 7.83 (1H, d), 7.92 (1H, d).

(Step 2)

Lithium aluminium hydride (4.91 g, 129.43 mmol) was slowly added to a solution of (E)-4-(2-nitrovinyl)benzo[d][1,3]dioxole (6.25 g, 32.36 mmol) in THF (250 mL) at 0° C., and the mixture was stirred at 0° C. 5 min, and then at 70° C. for 4 hr. The reaction mixture was cooled to −78° C., 8N aqueous sodium hydroxide solution (130 mL) was slowly added thereto, and the mixture was stirred at room temperature for 30 min. The insoluble substance was removed by filtration, and washed with a mixed solvent of Et$_2$O/THF (1:1). The filtrate and washing were combined, and the aqueous layer was extracted twice with a mixed solvent of Et$_2$O/THF (1:1). The organic layer was washed with brine, and dried over magnesium sulfate, and the solvent was evaporated under reduced pressure. The obtained residue was purified by silica gel column chromatography (NH, solvent gradient; 10→100% ethyl acetate/hexane) to give 2-(benzo[d][1,3]dioxol-4-yl)ethanamine (1.96 g, 11.87 mmol, 36.7%) as a pale yellow oil.

$^1$H NMR (300 MHz, CDCl$_3$): δ 1.26 (2H, brs), 2.73 (2H, t), 2.97 (2H, t), 5.93 (2H, s), 6.65-6.81 (3H, m).

(Step 3)

Ethyl 2-chloro-2-oxoacetate (1.458 mL, 13.05 mmol) was added to a solution of 2-(benzo[d][1,3]dioxol-4-yl)ethanamine (1.96 g, 11.87 mmol) and TEA (1.819 mL, 13.05 mmol) in THF (30 mL) at 0° C., and the mixture was stirred at room temperature for 1 hr. To the reaction mixture was added aqueous sodium hydrogen carbonate solution, and the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 33→55% ethyl acetate/hexane) to give ethyl 2-((2-(benzo[d][1,3]dioxol-4-yl)ethyl)amino)-2-oxoacetate (2.37 g, 8.93 mmol, 75%) as a pale yellow oil.

$^1$H NMR (300 MHz, CDCl$_3$): δ 1.37 (3H, t, J=7.2 Hz), 2.87 (2H, t, J=6.8 Hz), 3.61 (2H, q, J=6.8 Hz), 4.33 (2H, q, J=7.1 Hz), 5.95 (2H, s), 6.66 (1H, dd), 6.74 (1H, dd), 6.79 (1H, t), 7.32 (1H, brs).

(Step 4)

Zinc(II) chloride (0.606 g, 4.45 mmol) was added to a solution of ethyl 2-((2-(benzo[d][1,3]dioxol-4-yl)ethyl)amino)-2-oxoacetate (2.36 g, 8.90 mmol) and phosphoryl chloride (4.15 mL, 44.48 mmol) in acetonitrile (12 mL) at room temperature, and the mixture was heated under reflux for 2 hr. To the reaction mixture were added ice and aqueous sodium hydrogen carbonate solution. 8N Aqueous sodium hydroxide solution and potassium carbonate were added thereto until the mixture became neutral. Then, the mixture was extracted three times with ethyl acetate. The organic layer was washed with brine, and dried over magnesium sulfate, and the solvent was evaporated under reduced pressure. The obtained residue was purified by silica gel column chromatography (solvent gradient; 8→50% ethyl acetate/hexane) to give ethyl 8,9-dihydro-[1,3]dioxolo[4,5-f]isoquinoline-6-carboxylate (1.99 g, 8.05 mmol, 90%) as a yellow oil.

$^1$H NMR (300 MHz, CDCl$_3$): δ 1.41 (3H, t, J=7.0 Hz), 2.72 (2H, dd, J=8.3, 6.8 Hz), 3.83-3.89 (2H, m), 4.41 (2H, q, J=7.2 Hz), 6.03 (2H, s), 6.74 (1H, d, J=8.3 Hz), 7.29 (1H, d, J=8.0 Hz).

(Step 5)

A solution of ethyl 8,9-dihydro-[1,3]dioxolo[4,5-f]isoquinoline-6-carboxylate (1.98 g, 8.01 mmol) and 20% palladium hydroxide-carbon (0.67 g, 2.20 mmol, 50% wet) in EtOH (40 mL) was stirred under hydrogen atmosphere (1 atm) at room temperature for 4 hr. The catalyst was removed by filtration, and the filtrate was concentrated under reduced pressure. The obtained residue was purified by silica gel column chromatography (solvent gradient; 10-100% ethyl acetate/hexane) to give ethyl 6,7,8,9-tetrahydro-[1,3]dioxolo[4,5-f]isoquinoline-6-carboxylate (1.82 g, 7.30 mmol, 91%) as a yellow oil.

¹H NMR (300 MHz, CDCl₃): δ 1.30 (3H, t, J=7.2 Hz), 1.97 (1H, brs), 2.66-2.73 (2H, m), 3.06 (1H, dt, J=12.8, 5.7 Hz), 3.23-3.33 (1H, m), 4.22 (2H, qd, J=7.2, 1.9 Hz), 4.66 (1H, s), 5.95 (2H, dd, J=7.6, 1.5 Hz), 6.68 (1H, d, J=7.9 Hz), 6.84 (1H, d, J=7.9 Hz).
(Step 6)
Boc₂O (1.664 g, 7.62 mmol) was added to a solution of ethyl 6,7,8,9-tetrahydro-[1,3]dioxolo[4,5-f]isoquinoline-6-carboxylate (1.81 g, 7.26 mmol) in THF (25 mL) at room temperature, and the mixture was stirred at room temperature for 4 hr. The reaction mixture was concentrated under reduced pressure, and the obtained residue was purified by silica gel column chromatography (solvent gradient; 2→20% ethyl acetate/hexane) to give 6-ethyl 7-tert-butyl 8,9-dihydro-[1,3]dioxolo[4,5-f]isoquinoline-6,7(6H)-dicarboxylate (2.45 g, 7.01 mmol, 97%) as a colorless oil.
¹H NMR (300 MHz, CDCl₃): δ 1.23-1.29 (3H, m), 1.45-1.51 (9H, m), 2.76-2.87 (2H, m), 3.67-3.88 (2H, m), 4.11-4.20 (2H, m), 5.35-5.56 (1H, m), 5.96 (2H, d, J=6.8 Hz), 6.71 (1H, d, J=7.9 Hz), 6.95-7.03 (1H, m).
(Step 7)
2N aqueous lithium hydroxide solution (22.41 mL, 44.82 mmol) was added to a solution of 6-ethyl 7-tert-butyl 8,9-dihydro-[1,3]dioxolo[4,5-f]isoquinoline-6,7(6H)-dicarboxylate (2.61 g, 7.47 mmol) in a mixed solvent of EtOH (11 mL) and THF (11 mL) at room temperature, and the mixture was stirred at room temperature for 2 hr. To the reaction mixture was added water, and 2N hydrochloric acid was added thereto until the pH of the mixture became 3. Then, the mixture was extracted three times with ethyl acetate. The organic layer was washed with brine, and dried over magnesium sulfate, and the solvent was evaporated under reduced pressure to give 7-(tert-butoxycarbonyl)-6,7,8,9-tetrahydro-[1,3]dioxolo[4,5-f]isoquinoline-6-carboxylic acid (2.14 g, 6.66 mmol, 89%) as a white solid.
¹H NMR (300 MHz, CDCl₃): δ 1.42-1.52 (9H, m), 2.81 (2H, brs), 3.65-3.81 (2H, m), 5.35-5.58 (1H, m), 5.96 (2H, dd, J=9.1, 1.5 Hz), 6.71 (1H, d, J=7.9 Hz), 6.97 (1H, d, J=7.9 Hz).
(Step 8)
T3P (2.97 mL, 4.99 mmol) was added to a solution of 7-(tert-butoxycarbonyl)-6,7,8,9-tetrahydro-[1,3]dioxolo[4,5-f]isoquinoline-6-carboxylic acid (1.07 g, 3.33 mmol), 3,5-difluoro-4-(trimethylsilyl)aniline (0.704 g, 3.50 mmol), DIEA (2.90 mL, 16.65 mmol) and DMAP (0.447 g, 3.66 mmol) in ethyl acetate (24 mL), and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with IPE/hexane to give tert-butyl 6-((3,5-difluoro-4-(trimethylsilyl)phenyl)carbamoyl)-8,9-dihydro-[1,3]dioxolo[4,5-f]isoquinoline-7(6H)-carboxylate (1.16 g, 2.299 mmol, 69.0%) as grayish white crystals.
¹H NMR (300 MHz, CDCl₃): δ 0.32 (9H, t, J=1.3 Hz), 1.53 (9H, s), 2.83 (2H, t, J=5.9 Hz), 3.58 (1H, brs), 3.71-3.81 (1H, m), 5.63 (1H, brs), 5.98 (2H, dd, J=11.3, 1.5 Hz), 6.71-6.81 (2H, m), 6.96-7.05 (2H, m), 9.06 (1H, brs).
(Step 9)
tert-Butyl 6-((3,5-difluoro-4-(trimethylsilyl)phenyl)carbamoyl)-8,9-dihydro-[1,3]dioxolo[4,5-f]isoquinoline-7(6H)-carboxylate (1.16 g) was resolved by chiral column chromatography. The fraction having a shorter retention time was concentrated to give tert-butyl (R)-6-((3,5-difluoro-4-(trimethylsilyl)phenyl)carbamoyl)-8,9-dihydro-[1,3]dioxolo[4,5-f]isoquinoline-7(6H)-carboxylate (0.58 g, >99% ee), and the fraction having a longer retention time was concentrated to give tert-butyl (S)-6-((3,5-difluoro-4-(trimethylsilyl)phenyl)carbamoyl)-8,9-dihydro-[1,3]dioxolo[4,5-f]isoquinoline-7(6H)-carboxylate (0.56 g, >99% ee), each as a white solid.
purification condition by chiral column chromatography
   column: CHIRALPAK AD (NF001) 50 mmID×500 mmL
   solvent: hexane/EtOH=900/100
   flow rate: 80 mL/min
   temperature: 30° C.
   detection method: UV 220 nm
(Step 10)
Cooled TFA (7.5 mL) was added to tert-butyl (R)-6-((3,5-difluoro-4-(trimethylsilyl)phenyl)carbamoyl)-8,9-dihydro-[1,3]dioxolo[4,5-f]isoquinoline-7(6H)-carboxylate (568 mg, 1.13 mmol), and the mixture was stirred at room temperature for 3 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(3,5-difluoro-4-(trimethylsilyl)phenyl)-6,7,8,9-tetrahydro-[1,3]dioxolo[4,5-f]isoquinoline-6-carboxamide (400 mg, 0.989 mmol, 88%) as a white solid.
¹H NMR (300 MHz, CDCl₃): δ 0.32 (9H, t, J=1.3 Hz), 2.09 (1H, brs), 2.65-2.83 (2H, m), 3.05-3.20 (2H, m), 4.62 (1H, s), 5.95 (2H, dd, J=9.1, 1.5 Hz), 6.72 (1H, d, J=8.3 Hz), 7.03-7.13 (3H, m), 9.42 (1H, s).
(Step 11)
Dihydro-2H-pyran-2,6(3H)-dione (48.9 mg, 0.43 mmol) was added to a solution of (R)-N-(3,5-difluoro-4-(trimethylsilyl)phenyl)-6,7,8,9-tetrahydro-[1,3]dioxolo[4,5-f]isoquinoline-6-carboxamide (133 mg, 0.33 mmol) and TEA (69 μL, 0.50 mmol) in THF (3.2 mL) at room temperature, and the mixture was stirred at room temperature for 4 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 30→100% ethyl acetate/hexane) to give the title compound (141.6 mg, 0.273 mmol, 83%) as a white solid.
¹H NMR (300 MHz, CDCl₃): δ 0.27 (9H, s), 2.08-2.19 (2H, m), 2.38-2.63 (3H, m), 2.85-3.01 (2H, m), 3.13-3.24 (1H, m), 3.72 (1H, ddd, J=12.3, 8.5, 4.2 Hz), 4.03-4.11 (1H, m), 5.85 (1H, s), 5.97 (2H, dd, J=12.7, 1.3 Hz), 6.71 (1H, d, J=7.9 Hz), 6.74-6.82 (2H, m), 7.07 (1H, d, J=8.3 Hz), 9.83 (1H, s), 11.30 (1H, brs).

Example 255

5-((5R)-5-((7-fluoro-1,1-dimethyl-2,3-dihydro-1H-inden-5-yl) carbamoyl)-2,3,7,8-tetrahydrofuro[2,3-g]isoquinolin-6(5H)-yl)-5-oxopentanoic acid (Step 1)
(R)-N-(7-Fluoro-1,1-dimethyl-2,3-dihydro-1H-inden-5-yl)-2,3,5,6,7,8-hexahydrofuro[2,3-g]isoquinoline-5-carboxamide was synthesized using 6-(tert-butoxycarbonyl)-2,3,5,6,7,8-hexahydrofuro[2,3-g]isoquinoline-5-carboxylic acid and 7-fluoro-1,1-dimethyl-2,3-dihydro-1H-inden-5-amine hydrochloride, by the reaction and purification in the same manner as in Step 8 of Example 252.

¹H NMR (300 MHz, CDCl₃): δ 1.33 (6H, s), 1.90 (2H, t, J=7.4 Hz), 2.65-2.92 (5H, m), 3.04-3.20 (4H, m), 4.53 (2H, t, J=9.1 Hz), 4.66 (1H, s), 6.52 (1H, s), 7.12-7.20 (2H, m), 7.43 (1H, s), 9.46 (1H, s).

(Step 2)

The title compound was synthesized using (R)-N-(7-fluoro-1,1-dimethyl-2,3-dihydro-1H-inden-5-yl)-2,3,5,6,7,8-hexahydrofuro[2,3-g]isoquinoline-5-carboxamide, by the reaction and purification in the same manner as in Step 9 of Example 252.

¹H NMR (300 MHz, CDCl₃): δ 1.29 (6H, s), 1.85 (2H, t, J=7.4 Hz), 2.05-2.14 (2H, m), 2.48 (2H, t, J=6.8 Hz), 2.61 (2H, td, J=7.0, 3.0 Hz), 2.76-2.89 (3H, m), 3.08-3.21 (3H, m), 3.65 (1H, ddd, J=12.2, 7.8, 4.5 Hz), 3.89 (1H, ddd, J=11.9, 6.8, 4.7 Hz), 4.49-4.59 (2H, m), 5.93 (1H, s), 6.61 (1H, s), 6.96 (1H, s), 7.07 (1H, dd, J=11.7, 1.5 Hz), 7.19 (1H, s), 9.26 (1H, s), 10.86 (1H, brs).

Example 256

5-((6R)-6-((7-fluoro-1,1-dimethyl-2,3-dihydro-1H-inden-5-yl) carbamoyl)-8,9-dihydro[1, 3]dioxolo[4, 5-f]isoquinolin-7 (6H)-yl)-5-oxopentanoic acid (Step 1)

T3P (2.94 mL, 4.95 mmol) was added to a solution of 7-(tert-butoxycarbonyl)-6,7,8,9-tetrahydro-[1,3]dioxolo[4,5-f]isoquinoline-6-carboxylic acid (1.06 g, 3.30 mmol), 7-fluoro-1,1-dimethyl-2,3-dihydro-1H-inden-5-amine hydrochloride (0.747 g, 3.46 mmol), DIEA (2.87 mL, 16.49 mmol) and DMAP (0.443 g, 3.63 mmol) in ethyl acetate (24 mL), and the mixture was stirred at 65° C. for 15 hr. To the reaction mixture was added water, and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The precipitate was washed with IPE/hexane to give tert-butyl 6-((7-fluoro-1,1-dimethyl-2,3-dihydro-1H-inden-5-yl)carbamoyl)-8,9-dihydro-[1,3]dioxolo[4,5-f]isoquinoline-7(6H)-carboxylate (1.44 g, 2.98 mmol, 90%) as a white solid.

¹H NMR (300 MHz, CDCl₃): δ 1.33 (6H, s), 1.52 (9H, s), 1.90 (2H, t, J=7.4 Hz), 2.78-2.89 (4H, m), 3.55 (1H, brs), 3.79 (1H, dt, J=12.4, 6.1 Hz), 5.63 (1H, brs), 5.97 (2H, dd, J=11.0, 1.5 Hz), 6.71-6.80 (2H, m), 7.04-7.11 (2H, m), 8.71 (1H, brs).

(Step 2)

tert-Butyl 6-((7-fluoro-1,1-dimethyl-2,3-dihydro-1H-inden-5-yl)carbamoyl)-8,9-dihydro-[1,3]dioxolo[4,5-f]isoquinoline-7(6H)-carboxylate (1.43 g) was resolved by chiral column chromatography. The fraction having a shorter retention time was concentrated to give tert-butyl (R)-6-((7-fluoro-1,1-dimethyl-2,3-dihydro-1H-inden-5-yl)carbamoyl)-8,9-dihydro-[1,3]dioxolo[4,5-f]isoquinoline-7(6H)-carboxylate (0.70 g, >99% ee), and the fraction having a longer retention time was concentrated to give tert-butyl (S)-6-((7-fluoro-1,1-dimethyl-2,3-dihydro-1H-inden-5-yl) carbamoyl)-8,9-dihydro-[1,3]dioxolo[4,5-f]isoquinoline-7 (6H)-carboxylate (0.68 g, >99% ee), each as a white solid. purification condition by chiral column chromatography column: CHIRALPAK AD (NF001) 50 mmID×500 mmL
    solvent: hexane/EtOH=800/200
    flow rate: 80 mL/min
    temperature: 30° C.
    detection method: UV 220 nm (Step 3)

Cooled TFA (9 mL) was added to tert-butyl (R)-6-((7-fluoro-1,1-dimethyl-2,3-dihydro-1H-inden-5-yl)carbamoyl)-8,9-dihydro-[1,3]dioxolo[4,5-f]isoquinoline-7(6H)-carboxylate (692 mg, 1.43 mmol), and the mixture was stirred at room temperature for 15 min. The reaction mixture was added to ice and aqueous sodium hydrogen carbonate solution, and potassium carbonate was added thereto until the pH of the mixture became 8. Then, the mixture was extracted three times with ethyl acetate. The organic layer was washed with brine, and dried over magnesium sulfate, and the solvent was evaporated under reduced pressure to give (R)-N-(7-fluoro-1,1-dimethyl-2,3-dihydro-1H-inden-5-yl)-6,7,8,9-tetrahydro-[1,3]dioxolo[4,5-f]isoquinoline-6-carboxamide (541 mg, 1.415 mmol, 99%) as a white solid.

¹H NMR (300 MHz, CDCl₃): δ 1.33 (6H, s), 1.90 (2H, t, J=7.4 Hz), 2.12 (1H, brs), 2.64-2.82 (2H, m), 2.87 (2H, t, J=7.4 Hz), 3.12 (2H, t, J=5.9 Hz), 4.61 (1H, s), 5.95 (2H, dd, J=7.9, 1.5 Hz), 6.71 (1H, d, J=8.3 Hz), 7.07 (1H, d, J=8.3 Hz), 7.11-7.17 (2H, m), 9.19 (1H, s).

(Step 4)

Dihydro-2H-pyran-2,6(3H)-dione (48.9 mg, 0.43 mmol) was added to a solution of (R)-N-(7-fluoro-1,1-dimethyl-2,3-dihydro-1H-inden-5-yl)-6,7,8,9-tetrahydro-[1,3]dioxolo [4,5-f]isoquinoline-6-carboxamide (126 mg, 0.33 mmol) and TEA (69 µL, 0.50 mmol) in THF (3.2 mL) at room temperature, and the mixture was stirred at room temperature for 4 hr. To the reaction mixture was added water, and 2N hydrochloric acid was added thereto until the pH of the mixture became 4. Then, the mixture was extracted three times with ethyl acetate. The organic layer was washed with brine, and dried over magnesium sulfate, and the solvent was evaporated under reduced pressure. The obtained residue was purified by silica gel column chromatography (Diol, solvent gradient; 30→100% ethyl acetate/hexane) to give the title compound (132.5 mg, 0.267 mmol, 81%) as a white solid.

¹H NMR (300 MHz, CDCl₃): δ 1.28 (6H, s), 1.85 (2H, t, J=7.4 Hz), 2.06-2.14 (2H, m), 2.48 (2H, t), 2.52-2.75 (2H, m), 2.80 (2H, t, J=7.4 Hz), 2.84-2.95 (1H, m), 3.01-3.12 (1H, m), 3.74 (1H, ddd, J=12.3, 7.2, 5.1 Hz), 3.86-3.97 (1H, m), 5.94-6.00 (3H, m), 6.72 (1H, d, J=7.9 Hz), 6.90 (1H, d, J=8.3 Hz), 6.92 (1H, d, J=0.8 Hz), 7.05 (1H, dd, J=11.7, 1.5 Hz), 9.21 (1H, s), 10.69 (1H, brs).

Example 257

N-(((1R)-1-((3,5-difluoro-4-(trimethylsilyl)phenyl) carbamoyl)-6-methoxy-3,4-dihydroisoquinolin-2 (1H)-yl) carbonyl)-N-methyl-beta-alanine The title compound was synthesized using benzyl 3-(methylamino)propanoate hydrochloride and (R)-N-(3,5-difluoro-4-(trimethylsilyl)phenyl)-6-methoxy-1,2,3,4-tetrahydroisoquinoline-1-carboxamide, by the reaction and purification in the same manner as in Step 1 of Example 225 and Step 3 of Example 227.

¹H NMR (300 MHz, DMSO-d₆): δ 0.30 (9H, s), 2.43-2.54 (2H, m), 2.80 (3H, s), 2.83-3.04 (2H, m), 3.26-3.40 (2H, m), 3.42-3.54 (1H, m), 3.72 (3H, s), 3.82-3.97 (1H, m), 5.13 (1H, s), 6.74-6.84 (2H, m), 7.23 (2H, d, J=9.8 Hz), 7.30-7.37 (1H, m), 10.70 (1H, s), 12.25 (1H, brs).

$[α]_D^{25}$+65.9 (c 0.2500, MeOH)

Example 258

1-(((1R)-1-((3,5-difluoro-4-(trimethylsilyl)phenyl)carbamoyl)-6-methoxy-3,4-dihydroisoquinolin-2(1H)-yl)carbonyl)azetidine-3-carboxylic acid The title compound was synthesized using benzyl azetidine-3-carboxylate and (R)-N-(3,5-difluoro-4-(trimethylsilyl)phenyl)-6-methoxy-1,2,3,4-tetrahydroisoquinoline-1-carboxamide, by the reaction and purification in the same manner as in Step 1 of Example 225 and Step 3 of Example 227.

$^1$H NMR (300 MHz, DMSO-$d_6$): δ 0.29 (9H, s), 2.69-2.84 (1H, m), 2.99-3.16 (1H, m), 3.29-3.45 (2H, m), 3.72 (3H, s), 3.75-3.85 (1H, m), 3.90 (1H, dd, J=8.1, 6.2 Hz), 3.95-4.14 (2H, m), 4.22 (1H, t, J=8.7 Hz), 5.31 (1H, s), 6.76-6.85 (2H, m), 7.15-7.25 (2H, m), 7.39-7.50 (1H, m), 10.67 (1H, s), 12.61 (1H, brs).

Example 259

1-(((1R)-1-((3,5-difluoro-4-(trimethylsilyl)phenyl)carbamoyl)-6-ethoxy-3,4-dihydroisoquinolin-2(1H)-yl)carbonyl)azetidine-3-carboxylic acid The title compound was synthesized using benzyl azetidine-3-carboxylate and (R)-N-(3,5-difluoro-4-(trimethylsilyl)phenyl)-6-ethoxy-1,2,3,4-tetrahydroisoquinoline-1-carboxamide, by the reaction and purification in the same manner as in Step 1 of Example 225 and Step 3 of Example 227.

$^1$H NMR (300 MHz, DMSO-$d_6$): δ 0.29 (9H, s), 1.29 (3H, t, J=6.8 Hz), 2.68-2.83 (1H, m), 2.99-3.13 (1H, m), 3.35-3.44 (2H, m), 3.73-3.85 (1H, m), 3.90 (1H, dd, J=7.9, 6.0 Hz), 3.95-4.05 (3H, m), 4.06-4.14 (1H, m), 4.21 (1H, t, J=8.7 Hz), 5.31 (1H, s), 6.75-6.83 (2H, m), 7.15-7.24 (2H, m), 7.39-7.46 (1H, m), 10.67 (1H, s), 12.59 (1H, brs).

Example 260

(1-(((1R)-1-((3, 5-difluoro-4-(trimethylsilyl)phenyl)carbamoyl)-6-methoxy-3,4-dihydroisoquinolin-2(1H)-yl)carbonyl)azetidin-3-yl)acetic acid (Step 1)
A solution of 2-(1-(tert-butoxycarbonyl)azetidin-3-yl)acetic acid (10.13 g, 47.06 mmol), benzyl bromide (6.72 mL, 56.47 mmol) and cesium carbonate (18.40 g, 56.47 mmol) in DMF (30 mL) was stirred at room temperature for 14 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→30% ethyl acetate/hexane) to give a colorless oil (14.86 g). Cooled TFA (50 mL) was added to a mixture of the colorless oil (14.86 g) in trifluoromethylbenzene (3.75 mL) at 5° C., and the mixture was stirred at room temperature for 10 min. The reaction mixture was added to a cooled mixture of potassium carbonate (90 g), water (500 mL) and ethyl acetate (100 mL). Saturated brine (50 mL) was added thereto, and the mixture was extracted three times with a mixed solvent of ethyl acetate/THF (3:1). The organic layer was washed with brine, and dried over magnesium sulfate, and the solvent was evaporated under reduced pressure to give a colorless oil (3.34 g). To the aqueous layer was added potassium carbonate (110 g), and the mixture was extracted twice with a mixed solvent of ethyl acetate/THF (3:1). The organic layer was washed with brine, and dried over magnesium sulfate, and the solvent was evaporated under reduced pressure to give a colorless oil (4.908 g). The obtained colorless oil (8.248 g) was dissolved in ethyl acetate, and the solution was dried over magnesium sulfate, and the solvent was evaporated under reduced pressure to give benzyl 2-(azetidin-3-yl)acetate (6.81 g, 33.2 mmol, 70.5%) as a pale brown solid.

$^1$H NMR (300 MHz, CDCl$_3$): δ 2.75 (s, 2H) 3.14-3.36 (m, 1H) 3.73-3.91 (m, 2H) 4.04-4.22 (m, 2H) 5.10 (s, 2H) 7.26-7.45 (m, 5H)

(Step 2)
A solution of bis(trichloromethyl) carbonate (228 mg, 0.77 mmol) in THF (2 mL) was added to a solution of benzyl 2-(azetidin-3-yl)acetate (158 mg, 0.77 mmol) and pyridine (0.124 mL, 1.54 mmol) in THF (2 mL) at 5° C., and the mixture was stirred at 5° C. for 30 min. The reaction mixture was concentrated under reduced pressure, the obtained residue was dissolved in DMF (2 mL), and the solution was cooled to 0° C. A solution of (R)-N-(3,5-difluoro-4-(trimethylsilyl)phenyl)-6-methoxy-1,2,3,4-tetrahydroisoquinoline-1-carboxamide (200 mg, 0.51 mmol) and DIEA (0.447 mL, 2.56 mmol) in DMF (2 mL) was added thereto, and the mixture was stirred at room temperature for 2 hr. To the reaction mixture was added aqueous sodium hydrogen carbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give benzyl (R)-2-(1-(1-((3,5-difluoro-4-(trimethylsilyl)phenyl)carbamoyl)-6-methoxy-1,2,3,4-tetrahydroisoquinoline-2-carbonyl)azetidin-3-yl)acetate (47.3 mg, 0.076 mmol, 14.85%) as a white solid.

$^1$H NMR (300 MHz, CDCl$_3$): δ 0.31 (9H, t, J=1.3 Hz), 2.66-2.77 (2H, m), 2.86 (2H, t, J=5.9 Hz), 2.92-3.09 (1H, m), 3.35-3.58 (2H, m), 3.67 (1H, dd, J=8.7, 5.7 Hz), 3.80 (3H, s), 3.91 (1H, dd, J=8.7, 5.7 Hz), 4.08-4.17 (1H, m), 4.37 (1H, t, J=8.7 Hz), 5.12 (2H, s), 5.58 (1H, s), 6.72 (1H, d, J=2.6 Hz), 6.82 (1H, dd, J=8.3, 2.6 Hz), 7.01-7.11 (3H, m), 7.28-7.42 (5H, m), 10.05 (1H, s).

(Step 3)
A solution of benzyl (R)-2-(1-(1-((3,5-difluoro-4-(trimethylsilyl)phenyl)carbamoyl)-6-methoxy-1,2,3,4-tetrahydroisoquinoline-2-carbonyl)azetidin-3-yl)acetate (45 mg, 0.07 mmol) and 10% palladium-carbon (10 mg, 0.09 mmol, 50% wet) in MeOH (2 mL) was stirred overnight under hydrogen atmosphere (1 atm) at room temperature. The catalyst was removed by filtration, and the filtrate was concentrated under reduced pressure. The obtained residue was purified by silica gel column chromatography (solvent gradient; 20→90% ethyl acetate/hexane) to give the title compound (26.6 mg, 0.050 mmol, 69.1%) as a white solid.

$^1$H NMR (300 MHz, DMSO-$d_6$): δ 0.29 (9H, s), 2.57 (2H, d, J=7.6 Hz), 2.68-2.85 (2H, m), 2.97-3.13 (1H, m), 3.35-3.42 (1H, m), 3.46-3.58 (1H, m), 3.67-3.86 (5H, m), 3.90-4.02 (1H, m), 4.15 (1H, t, J=8.1 Hz), 5.31 (1H, s), 6.76-6.85 (2H, m), 7.15-7.24 (2H, m), 7.38-7.47 (1H, m), 10.65 (1H, s), 12.21 (1H, brs).

$[α]_D^{25}$ −10.5 (c 0.2540, MeOH)

Example 261

5-((1R)-1-((7-fluoro-1,1-dimethyl-2,3-dihydro-1H-inden-5-yl)carbamoyl)-6-methoxy-5-methyl-3,4-dihydroisoquinolin-2 (1H)-yl)-5-oxopentanoic acid The title compound was synthesized using 2-(3-methoxy-2-methylphenyl)ethanamine, by the reaction and purification in the same manner as in Steps 3 to 11 of Example 254.

¹H NMR (300 MHz, CDCl₃): δ 1.29 (6H, s), 1.85 (2H, t, J=7.4 Hz), 2.02-2.11 (2H, m), 2.15 (3H, s), 2.49 (2H, t, J=6.8 Hz), 2.61 (2H, t), 2.80 (2H, t, J=7.4 Hz), 2.84-2.95 (1H, m), 2.97-3.08 (1H, m), 3.62-3.77 (1H, m), 3.81 (3H, s), 3.82-3.92 (1H, m), 5.97 (1H, s), 6.77 (1H, d, J=8.7 Hz), 6.97 (1H, s), 7.08 (1H, dd, J=11.9, 1.3 Hz), 7.17 (1H, d, J=8.3 Hz), 9.14 (1H, s), 10.82 (1H, brs).

Example 262

5-((1R)-1-((7-fluoro-1,1-dimethyl-2,3-dihydro-1H-inden-5-yl)carbamoyl)-6-propyl-3,4-dihydroisoquinolin-2(1H)-yl)-5-oxopentanoic acid The title compound was synthesized using 2-(3-propylphenyl)ethanamine, by the reaction and purification in the same manner as in Steps 3 to 11 of Example 254.

¹H NMR (300 MHz, CDCl₃): δ 0.93 (3H, t, J=7.4 Hz), 1.28 (6H, s), 1.62 (2H, sxt, J=7.5 Hz), 1.85 (2H, t, J=7.4 Hz), 2.05-2.14 (2H, m), 2.48 (2H, t, J=6.8 Hz), 2.54 (2H, t), 2.62 (2H, td, J=7.0, 3.8 Hz), 2.79 (2H, t, J=7.4 Hz), 2.84-2.93 (1H, m), 3.10-3.21 (1H, m), 3.72 (1H, ddd, J=12.2, 7.5, 4.5 Hz), 3.93 (1H, ddd, J=12.0, 7.3, 4.5 Hz), 5.98 (1H, s), 6.96 (1H, s), 7.00 (1H, s), 7.03-7.10 (2H, m), 7.29 (1H, d, J=7.9 Hz), 9.29 (1H, s), 10.90 (1H, brs).

Example 263 benzyl N-(((1R)-1-((3,5-difluoro-4-(trimethylsilyl)phenyl)carbamoyl)-6-methoxy-3,4-dihydroisoquinolin-2(1H)-yl)carbonyl)glycinate The title compound was synthesized using (R)-N-(3,5-difluoro-4-(trimethylsilyl)phenyl)-6-methoxy-1,2,3,4-tetrahydroisoquinoline-1-carboxamide and benzyl 2-(((4-nitrophenoxy)carbonyl)amino)acetate, by the reaction and purification in the same manner as in Step 1 of Example 242.

¹H NMR (300 MHz, CDCl₃): δ 0.30 (t, J=1.32 Hz, 9H), 2.84 (dt, J=15.30, 4.44 Hz, 1H), 3.17 (ddd, J=15.20, 10.10, 5.29 Hz, 1H), 3.41 (td, J=10.20, 4.53 Hz, 1H), 3.70-3.82 (m, 4H), 4.14-4.18 (m, 2H), 5.21 (d, J=2.64 Hz, 2H), 5.28-5.38 (m, 1H), 5.74-5.79 (m, 1H), 6.72-6.84 (m, 2H) 6.90-7.05 (m, 2H), 7.22 (d, J=8.31 Hz, 1H), 7.30-7.39 (m, 5H), 9.63 (s, 1H)

Example 264

N-((1R)-1-((3,5-difluoro-4-(trimethylsilyl)phenyl)carbamoyl)-6-methoxy-3,4-dihydroisoquinolin-2(1H)-yl)carbonyl)glycine The title compound was synthesized using benzyl (R)-2-(1-((3,5-difluoro-4-(trimethylsilyl)phenyl)carbamoyl)-6-methoxy-1,2,3,4-tetrahydroisoquinoline-2-carboxamide)acetate, by the reaction and purification in the same manner as in Step 2 of Example 242.

¹H NMR (300 MHz, CDCl₃): δ 0.29 (t, J=1.32 Hz, 9H), 2.77-2.93 (m, 1H), 3.04-3.24 (m, 1H) 3.34-3.50 (m, 1H), 3.80 (s, 4H), 4.08-4.12 (m, 2H), 5.37-5.49 (m, 1H), 5.74 (s, 1H), 6.72-6.86 (m, 2H), 6.94-7.07 (m, 2H), 7.21 (d, J=8.31 Hz, 1H), 9.27 (brs, 1H) (The exchangeable 1H was not observed)

Example 265

(4S)-5-((1R)-6-ethoxy-1-((7-fluoro-1,1-dimethyl-2,3-dihydro-1H-inden-5-yl)carbamoyl)-3,4-dihydroisoquinolin-2(1H)-yl)-4-methyl-5-oxopentanoic acid Example 266

(2S)-5-((1R)-6-ethoxy-1-((7-fluoro-1,1-dimethyl-2,3-dihydro-1H-inden-5-yl)carbamoyl)-3,4-dihydroisoquinolin-2(1H)-yl)-2-methyl-5-oxopentanoic acid The title compound was synthesized using (R)-6-ethoxy-N-(7-fluoro-1,1-dimethyl-2,3-dihydro-1H-inden-5-yl)-1,2,3,4-tetrahydroisoquinoline-1-carboxamide hydrochloride and (S)-(+)-2-methylglutaric acid, by the reaction and purification in the same manner as in Example 240.

The compound of Example 265

¹H NMR (300 MHz, DMSO-d₆): δ 1.04 (3H, d, J=6.8 Hz), 1.25-1.34 (9H, m), 1.46-1.64 (1H, m), 1.70-1.91 (3H, m), 2.09-2.20 (2H, m), 2.71-2.99 (4H, m), 3.03-3.17 (1H, m), 3.56-3.69 (1H, m), 3.92-4.15 (3H, m), 5.60-5.71 (1H, m), 6.74-6.83 (2H, m), 7.13-7.26 (2H, m), 7.41-7.49 (1H, m), 10.44 (1H, s), 12.08 (1H, brs).

The Compound of Example 266

¹H NMR (300 MHz, DMSO-d₆): δ 1.09 (3H, d, J=7.2 Hz), 1.24-1.34 (9H, m), 1.48-1.66 (1H, m), 1.73-1.91 (3H, m), 2.24-2.48 (3H, m), 2.69-2.90 (3H, m), 3.01-3.19 (1H, m), 3.44-3.59 (1H, m), 3.92-4.08 (3H, m), 5.64 (1H, s), 6.74-6.82 (2H, m), 7.12-7.26 (2H, m), 7.40-7.49 (1H, m), 10.41 (1H, s), 12.14 (1H, brs).

$[\alpha]_D^{25}$+10.4 (c 0.2520, MeOH)

Example 267

((1-(((1R)-1-((3,5-difluoro-4-(trimethylsilyl)phenyl)carbamoyl)-6-methoxy-3,4-dihydroisoquinolin-2(1H)-yl)carbonyl)azetidin-3-yl)oxy)acetic acid (Step 1)
Sodium hydride (60% oil, 163 mg, 4.06 mmol) was added to a solution of tert-butyl 3-hydroxyazetidine-1-carboxylate (640 mg, 3.69 mmol) and benzyl 2-bromoacetate (0.644 mL, 4.06 mmol) in DMF (10 mL) at 0° C., and the mixture was stirred overnight at 0° C. to room temperature. To the reaction mixture were added water and 2N hydrochloric acid, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→20% ethyl acetate/hexane) to give tert-butyl 3-(2-(benzyloxy)-2-oxoethoxy)azetidine-1-carboxylate (1 g, 3.11 mmol, 84%) as a pale yellow oil.

¹H NMR (300 MHz, CDCl₃): δ 1.38-1.47 (9H, m), 3.91 (2H, dd, J=10.2, 4.5 Hz), 4.01-4.14 (4H, m), 4.27-4.39 (1H, m), 5.19 (2H, s), 7.28-7.45 (5H, m).

(Step 2)
Cooled TFA (5 mL) was added to tert-butyl 3-(2-(benzyloxy)-2-oxoethoxy)azetidine-1-carboxylate (1 g, 3.11 mmol) at 0° C., and the mixture was stirred at 0° C. for 1 hr.

The reaction mixture was added to aqueous sodium hydrogen carbonate solution, and the mixture was extracted with ethyl acetate. The organic layer was washed with brine, and dried over sodium sulfate, and the solvent was evaporated under reduced pressure to give benzyl 2-(azetidin-3-yloxy) acetate (0.69 g, 3.12 mmol, 100%) as an orange oil.

MS(API): Calculated 221.3, Found 222.2 (M+H).

(Step 3)

The title compound was synthesized using (R)-N-(3,5-difluoro-4-(trimethylsilyl)phenyl)-6-methoxy-1,2,3,4-tetrahydroisoquinoline-1-carboxamide and benzyl 2-(azetidin-3-yloxy)acetate, by the reaction and purification in the same manner as in Example 240.

$^1$H NMR (300 MHz, DMSO-d$_6$): δ 0.29 (9H, s), 2.73-2.85 (1H, m), 2.96-3.16 (1H, m), 3.32-3.44 (1H, m), 3.68-3.84 (6H, m), 3.85-4.05 (4H, m), 4.11-4.27 (1H, m), 4.28-4.45 (1H, m), 5.32 (1H, s), 6.66-6.86 (2H, m), 7.21 (2H, d, J=9.8 Hz), 7.35-7.52 (1H, m), 10.69 (1H, s).

Example 268

(4R)-5-((1R)-6-ethoxy-1-((7-fluoro-1,1-dimethyl-2,3-dihydro-1H-inden-5-yl)carbamoyl)-3,4-dihydroisoquinolin-2(1H)-yl)-4-methyl-5-oxopentanoic acid Example 269

(2R)-5-((1R)-6-ethoxy-1-((7-fluoro-1,1-dimethyl-2,3-dihydro-1H-inden-5-yl)carbamoyl)-3,4-dihydroisoquinolin-2(1H)-yl)-2-methyl-5-oxopentanoic acid The title compound was synthesized using (R)-6-ethoxy-N-(7-fluoro-1,1-dimethyl-2,3-dihydro-1H-inden-5-yl)-1,2,3,4-tetrahydroisoquinoline-1-carboxamide hydrochloride and (R)-(−)-2-methylglutaric acid, by the reaction and purification in the same manner as in Example 240.

The Compound of Example 268

$^1$H NMR (300 MHz, CDCl$_3$): δ 1.21 (3H, d, J=6.4 Hz), 1.29 (6H, s), 1.40 (3H, t, J=7.0 Hz), 1.80-1.93 (3H, m), 2.08-2.23 (1H, m), 2.34-2.57 (2H, m), 2.79 (3H, s), 2.99-3.24 (2H, m), 3.64-3.80 (1H, m), 3.94-4.08 (3H, m), 6.01 (1H, s), 6.65-6.84 (2H, m), 6.99 (1H, s), 7.06 (1H, d, J=12.1 Hz), 7.33 (1H, d, J=8.7 Hz), 9.35 (1H, s)

The Compound of Example 269

$^1$H NMR (300 MHz, CDCl$_3$): δ 1.19 (3H, d, J=6.8 Hz), 1.24-1.31 (6H, m), 1.40 (3H, s), 1.84 (2H, s), 1.89-2.02 (1H, m), 2.10-2.28 (1H, m), 2.78 (6H, d, J=2.3 Hz), 3.16-3.31 (1H, m), 3.62-3.77 (1H, m), 4.02 (3H, d, J=7.2 Hz), 5.95 (1H, s), 6.68-6.81 (2H, m), 6.88 (1H, s), 6.97-7.06 (1H, m), 7.35 (1H, d, J=8.3 Hz), 9.33 (1H, s)

Example 270

5-((5R)-2-(difluoromethoxy)-5-((3,5-difluoro-4-(trimethylsilyl)phenyl)carbamoyl)-7,8-dihydro-1,6-naphthyridin-6(5H)-yl)-5-oxopentanoic acid (Step 1)

Using a light-resistant reaction container, silver(I) carbonate (12.83 g, 46.53 mmol) was added to 5-ethyl 6-tert-butyl 2-hydroxy-7,8-dihydro-1,6-naphthyridine-5,6(5H)-dicarboxylate (7.50 g, 23.27 mmol) and sodium 2-chloro-2,2-difluoroacetate (21.28 g, 139.60 mmol) in a mixed solvent of THF (160 mL) and DMF (160 mL), and the mixture was stirred at 90° C. for 15 hr. To the reaction mixture was added water, and the mixture was extracted three times with ethyl acetate. The insoluble substance was removed by filtration. The organic layer was washed with brine, and dried over magnesium sulfate, and the solvent was evaporated under reduced pressure. The obtained residue was purified by silica gel column chromatography (solvent gradient; 5→30% ethyl acetate/hexane) to give 5-ethyl 6-tert-butyl 2-(difluoromethoxy)-7,8-dihydro-1,6-naphthyridine-5,6(5H)-dicarboxylate (1.52 g, 4.08 mmol, 17.54%) as a pale yellow oil.

$^1$H NMR (300 MHz, CDCl$_3$): δ 1.22-1.31 (3H, m), 1.45-1.52 (9H, m), 2.86-2.98 (2H, m), 3.50-3.67 (1H, m), 4.06-4.24 (3H, m), 5.39-5.62 (1H, m), 6.77 (1H, d, J=8.3 Hz), 7.22-7.74 (1H, m), 7.87 (1H, dd, J=8.5, 5.5 Hz).

(Step 2)

6-(tert-Butoxycarbonyl)-2-(difluoromethoxy)-5,6,7,8-tetrahydro-1,6-naphthyridine-5-carboxylic acid was synthesized using 2-(difluoromethoxy)-7,8-dihydro-1,6-naphthyridine-5,6(5H)-dicarboxylate, by the reaction and purification in the same manner as in Step 7 of Example 254.

MS(API): Calculated 344.3, Found 345.2(M+H).

(Step 3)

The title compound was synthesized using 6-(tert-butoxycarbonyl)-2-(difluoromethoxy)-5,6,7,8-tetrahydro-1,6-naphthyridine-5-carboxylic acid, by the reaction and purification in the same manner as in Steps 8 to 11 of Example 254.

$^1$H NMR (300 MHz, CDCl$_3$): δ 0.27 (9H, s), 2.06-2.24 (2H, m), 2.34-2.46 (2H, m), 2.47-2.61 (1H, m), 3.01-3.15 (2H, m), 3.27-3.39 (1H, m), 3.93-4.04 (1H, m), 4.15-4.26 (1H, m), 5.88 (1H, s), 6.66-6.74 (2H, m), 6.79 (1H, d, J=8.7 Hz), 7.48 (1H, t), 7.96 (1H, d, J=8.7 Hz), 10.04 (1H, s), 11.54 (1H, brs).

Example 271

(1-(((6R)-6-((7-fluoro-1,1-dimethyl-2,3-dihydro-1H-inden-5-yl)carbamoyl)-8,9-dihydro[1,3]dioxolo[4,5-f]isoquinolin-7 (6H)-yl)carbonyl)azetidin-3-yl)acetic acid The title compound was synthesized using (R)-N-(7-fluoro-1,1-dimethyl-2,3-dihydro-1H-inden-5-yl)-6,7,8,9-tetrahydro-[1,3]dioxolo[4,5-f]isoquinoline-6-carboxamide, by the reaction and purification in the same manner as in Example 230 and Example 231.

Example 272

(1-(((6R)-6-((3,5-difluoro-4-(trimethylsilyl)phenyl)carbamoyl)-8,9-dihydro[1,3]dioxolo[4,5-f]isoquinolin-7(6H)-yl)carbonyl)azetidin-3-yl)acetic acid (Step 1)

A solution of pyridine (79 mg, 1.00 mmol) in THF (0.5 mL) was added to a solution of benzyl 2-(azetidin-3-yl) acetate (103 mg, 0.50 mmol) and bis(trichloromethyl) carbonate (149 mg, 0.50 mmol) in THF (1 mL) at 0° C., and the mixture was stirred at room temperature for 30 min. The reaction mixture was concentrated under reduced pressure, the obtained residue was dissolved in DMF (2 mL), and the solution was cooled to 0° C. A solution of (R)-N-(3,5-difluoro-4-(trimethylsilyl)phenyl)-6,7,8,9-tetrahydro-[1,3]dioxolo[4,5-f]isoquinoline-6-carboxamide (202 mg, 0.50 mmol) and DIEA (646 mg, 5.00 mmol) in DMF (1 mL) was added thereto at 0° C., and the mixture was stirred at 0° C. for 2 hr. The product (obtained in the same manner as above from a solution of pyridine (79 mg, 1.00 mmol) in THF (0.5 mL) and a solution of 2-(azetidin-3-yl)benzyl acetate (103 mg, 0.50 mmol) and bis(trichloromethyl) carbonate (149 mg, 0.50 mmol) in THF (1 mL)) was dissolved in DMF (2 mL), the solution was added to the reaction mixture at 0° C., and the mixture was stirred at 0° C. for 2 hr. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 0→100% ethyl acetate/hexane) to give benzyl (R)-2-(1-(6-((3,5-difluoro-4-(trimethylsilyl)phenyl)carbamoyl)-6,7,8,9-tetrahydro-[1,3]dioxolo[4,5-f]isoquinoline-7-carbonyl)azetidin-3-yl)acetate (280.0 mg, 88.0%) as a colorless oil.

MS(API): Calculated 635.7, Found 636.4 (M+H).

(Step 2)

A solution of benzyl (R)-2-(1-(6-((3,5-difluoro-4-(trimethylsilyl)phenyl)carbamoyl)-6,7,8,9-tetrahydro-[1,3]dioxolo[4,5-f]isoquinoline-7-carbonyl)azetidin-3-yl)acetate (280.0 mg, 0.44 mmol) and 10% palladium-carbon (280.0 mg, 50% wet) in MeOH (2 mL) was stirred under hydrogen atmosphere (1 atm) at room temperature for 0.5 hr. The catalyst was removed by filtration, and the filtrate was concentrated under reduced pressure. The obtained residue was purified by silica gel column chromatography (solvent gradient; 1→100% ethyl acetate/hexane) to give the title compound (180 mg, 0.33 mmol, 74.9%) as a white solid.

$^1$H NMR (300 MHz, DMSO-$d_6$): δ 0.30 (s, 9H), 2.57 (d, J=8.0 Hz, 2H), 2.69-2.82 (m, 1H), 2.89-2.94 (m, 1H), 3.37-3.46 (m, 1H), 3.54 (dd, J=6.0, 1.5 Hz, 1H), 3.72 (dd, J=6.0, 1.5 Hz, 1H), 3.76-3.82 (m, 1H), 3.96 (t, J=7.5 Hz, 1H), 4.15 (t, J=7.5 Hz, 1H), 5.34 (s, 1H), 6.02 (dd, J=8.3, 0.8 Hz, 2H), 6.82 (d, J=8.3 Hz, 1H), 7.03 (d, J=8.3 Hz, 1H), 7.21 (d, J=7.8 Hz, 2H), 10.67 (s, 1H), 12.21 (s, 1H)

$[α]_D^{25}$+30.7 (c 0.2515, MeOH)

Example 273

(1-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)azetidin-3-yl)acetic acid (Step 1)

Pyridine (194 μL, 2.40 mmol) was added to a solution of 2-(azetidin-3-yl)benzyl acetate (246 mg, 1.20 mmol) and bis(trichloromethyl) carbonate (355 mg, 1.20 mmol) in THF (6.5 mL) at 0° C., and the mixture was stirred at room temperature for 1 hr. The reaction mixture was concentrated under reduced pressure. To the obtained residue was added a solution of (R)-N-(7-fluoro-1,1-dimethyl-2,3-dihydro-1H-inden-5-yl)-2-methoxy-5,6,7,8-tetrahydro-1,6-naphthyridine-5-carboxamide (177 mg, 0.48 mmol) and DIEA (835 μL, 4.79 mmol) in DMF (6.5 mL) at 0° C., and the mixture was stirred at 0° C. for 2.5 hr. To the reaction mixture was added water, and 2N hydrochloric acid was added thereto until the pH of the mixture became 3. The mixture was extracted with ethyl acetate. The organic layer was washed with aqueous sodium hydrogen carbonate solution and brine, and dried over magnesium sulfate, and the solvent was evaporated under reduced pressure. The obtained residue was purified by silica gel column chromatography (solvent gradient; 37→58% ethyl acetate/hexane) to give benzyl (R)-2-(1-(5-((7-fluoro-1,1-dimethyl-2,3-dihydro-1H-inden-5-yl)carbamoyl)-2-methoxy-5,6,7,8-tetrahydro-1,6-naphthyridine-6-carbonyl)azetidin-3-yl)acetate (155 mg, 0.258 mmol, 53.9%) as a white solid.

$^1$H NMR (300 MHz, CDCl$_3$): δ 1.33 (6H, s), 1.90 (2H, t, J=7.4 Hz), 2.64-2.79 (2H, m), 2.80-3.09 (5H, m), 3.33-3.45 (1H, m), 3.69 (2H, dd, J=8.3, 5.7 Hz), 3.89-3.96 (4H, m), 4.14 (1H, t), 4.38 (1H, t, J=8.5 Hz), 5.12 (2H, s), 5.55 (1H, s), 6.64 (1H, d, J=8.3 Hz), 7.08 (1H, d, J=1.5 Hz), 7.17 (1H, dd, J=12.1, 1.5 Hz), 7.31-7.40 (6H, m), 9.77 (1H, s).

(Step 2)

A solution of benzyl (R)-2-(1-(5-((7-fluoro-1,1-dimethyl-2,3-dihydro-1H-inden-5-yl)carbamoyl)-2-methoxy-5,6,7,8-tetrahydro-1, 6-naphthyridine-6-carbonyl) azetidin-3-yl)acetate (151 mg, 0.25 mmol) and 10% palladium-carbon (50 mg, 0.42 mmol, 50% wet) in MeOH (5 mL) was stirred under hydrogen atmosphere (1 atm) at room temperature for 3 hr. The catalyst was removed by filtration, and the filtrate was concentrated under reduced pressure. The obtained residue was purified by silica gel column chromatography (Diol, solvent gradient; 30→100% ethyl acetate/hexane) to give the title compound (109.3 mg, 0.214 mmol, 85%) as a white solid.

$^1$H NMR (300 MHz, CDCl$_3$): δ 1.33 (6H, s), 1.90 (2H, t, J=7.4 Hz), 2.72 (2H, d, J=7.6 Hz), 2.86 (2H, t, J=7.2 Hz), 2.89-3.08 (3H, m), 3.40-3.53 (1H, m), 3.73 (2H, dd, J=8.5, 5.5 Hz), 3.88-3.98 (4H, m), 4.18 (1H, t), 4.40 (1H, t, J=8.3 Hz), 5.57 (1H, s), 6.64 (1H, d, J=8.7 Hz), 7.10 (1H, s), 7.15 (1H, d, J=11.7 Hz), 7.39 (1H, d, J=8.7 Hz), 9.70 (1H, s).

$[α]_D^{25}$+85.9 (c 0.2525, MeOH)

Example 274

(1-(((1R)-1-((3,5-difluoro-4-(trimethylsilyl)phenyl)carbamoyl)-6-methoxy-3,4-dihydroisoquinolin-2(1H)-yl)carbonyl)-3-hydroxyazetidin-3-yl)acetic acid (Step 1)

Benzyl acetate (2.78 mL, 19.28 mmol) was added to a solution of lithium hexamethyldisilazane (14.83 mL, 19.28 mmol, 1.6M) in THF (20 mL) at −78° C., and the mixture was stirred at −78° C. for 30 min. To the reaction mixture was added tert-butyl 3-oxoazetidine-1-carboxylate (3 g, 17.52 mmol), and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give tert-butyl 3-(2-(benzyloxy)-2-oxoethyl)-3-hydroxyazetidine-1-carboxylate (3.38 g, 10.52 mmol, 60.0%) as a pale yellow oil.

$^1$H NMR (300 MHz, CDCl$_3$): δ 1.43 (9H, s), 2.87 (2H, s), 3.74 (1H, brs), 3.77-3.85 (2H, m), 3.86-4.00 (2H, m), 5.18 (2H, s), 7.29-7.47 (5H, m).

(Step 2)

Sodium hydride (60% oil, 0.162 g, 4.05 mmol) was added to a solution of tert-butyl 3-(2-(benzyloxy)-2-oxoethyl)-3-hydroxyazetidine-1-carboxylate (1 g, 3.11 mmol) and benzyl bromide (0.389 mL, 3.27 mmol) in DMF (8 mL) at 0° C., and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→50% ethyl acetate/hexane) to give tert-butyl 3-(benzyloxy)-3-(2-(benzyloxy)-2-oxoethyl)azetidine-1-carboxylate (0.365 g, 0.887 mmol, 28.5%) as a colorless oil.

$^1$H NMR (300 MHz, CDCl$_3$): δ 1.44 (9H, s), 2.96 (2H, s), 3.93-4.18 (4H, m), 4.51 (2H, s), 5.14 (2H, s), 7.23-7.36 (10H, m).

(Step 3)

Cooled TFA (4 mL) was added to tert-butyl 3-(benzyloxy)-3-(2-(benzyloxy)-2-oxoethyl)azetidine-1-carboxylate (365 mg, 0.89 mmol) at 0° C., and the mixture was stirred at 0° C. for 20 min. The reaction mixture was added to aqueous sodium hydrogen carbonate solution, and the mixture was extracted with ethyl acetate. The organic layer was dried over sodium sulfate, and the solvent was evaporated under reduced pressure to give benzyl 2-(3-(benzyloxy)azetidin-3-yl)acetate (276 mg, 0.886 mmol, 100%) as a pale orange oil.

MS(API): Calculated 311.4, Found 312.3 (M+H).

(Step 4)

The title compound was synthesized using benzyl 2-(3-(benzyloxy)azetidin-3-yl)acetate and (R)-N-(3,5-difluoro-4-(trimethylsilyl)phenyl)-6-methoxy-1,2,3,4-tetrahydroisoquinoline-1-carboxamide, by the reaction and purification in the same manner as in Example 230 and Example 231.

$^1$H NMR (300 MHz, DMSO-d$_6$): δ 0.29 (9H, s), 2.62 (2H, s), 2.70-2.84 (1H, m), 3.00-3.18 (1H, m), 3.34-3.42 (1H, m), 3.69-3.75 (4H, m), 3.76-3.96 (3H, m), 4.14 (1H, d, J=8.3 Hz), 5.31 (1H, s), 5.71 (1H, brs), 6.70-6.87 (2H, m), 7.20 (2H, d, J=9.8 Hz), 7.35-7.53 (1H, m), 10.66 (1H, s), 12.15 (1H, brs).

Example 275

(1-(((1R)-1-((3,5-difluoro-4-(trimethylsilyl)phenyl)carbamoyl)-6-(methoxymethyl)-3,4-dihydroisoquinolin-2(1H)-yl)carbonyl)azetidin-3-yl)acetic acid (Step 1)

A solution of 1-benzhydrylazetidin-3-one (0.8 g, 3.37 mmol) and tert-butyl triphenylphosphoranylideneacetate (1.269 g, 3.37 mmol) in toluene (10 mL) was stirred at 90° C. for 18 hr. The reaction mixture was concentrated under reduced pressure, and the obtained residue was purified by silica gel column chromatography (solvent gradient; 5→50% ethyl acetate/hexane) to give tert-butyl 2-(1-benzhydrylazetidin-3-ylidene)acetate (0.880 g, 2.62 mmol, 78%) as a pale yellow solid.

$^1$H NMR (300 MHz, CDCl$_3$): δ 1.42 (9H, s), 3.81-3.92 (2H, m), 4.09-4.18 (2H, m), 4.52 (1H, s), 5.57 (1H, quin, J=2.3 Hz), 7.14-7.23 (2H, m), 7.23-7.31 (4H, m), 7.37-7.46 (4H, m).

(Step 2)

A solution of tert-butyl 2-(1-benzhydrylazetidin-3-ylidene)acetate (880 mg, 2.62 mmol) and 10% palladium-carbon (279 mg, 2.62 mmol, 50% wet) in MeOH (20 mL) was stirred overnight under hydrogen atmosphere (1 atm) at room temperature. The catalyst was removed by filtration, and the filtrate was concentrated under reduced pressure. The obtained residue was purified by silica gel column chromatography (solvent gradient; 5-50% ethyl acetate/hexane) to give tert-butyl 2-(1-benzhydrylazetidin-3-yl)acetate (830 mg, 2.460 mmol, 94%) as white crystals.

$^1$H NMR (300 MHz, CDCl$_3$): δ 1.35-1.42 (9H, m), 2.48 (2H, d, J=6.8 Hz), 2.65-2.89 (3H, m), 3.27-3.47 (2H, m), 4.31 (1H, s), 7.08-7.20 (2H, m), 7.21-7.31 (4H, m), 7.33-7.46 (4H, m).

(Step 3)

A solution of tert-butyl 2-(1-benzhydrylazetidin-3-yl)acetate (830 mg, 2.46 mmol) and 10% palladium hydroxide-carbon (200 mg, 1.88 mmol, 50% wet) in acetic acid (10 mL) was stirred under hydrogen atmosphere (1 atm) at room temperature for 2 days. The catalyst was removed by filtration, and the filtrate was concentrated under reduced pressure. The obtained residue was purified by silica gel column chromatography (NH, solvent gradient; 5→100% ethyl acetate/hexane) to give tert-butyl 2-(azetidin-3-yl)acetate (398 mg, 2.324 mmol, 94%) as a pale orange oil.

$^1$H NMR (300 MHz, CDCl$_3$): δ 1.43 (9H, s), 2.61 (2H, d, J=7.9 Hz), 3.16 (1H, spt, J=7.9 Hz), 3.71 (2H, dd, J=10.8, 7.4 Hz), 3.99-4.10 (2H, m), 5.20 (1H, brs).

(Step 4)

The title compound was synthesized using (R)-N-(3,5-difluoro-4-(trimethylsilyl)phenyl)-6-(methoxymethyl)-1,2,3,4-tetrahydroisoquinoline-1-carboxamide and tert-butyl 2-(azetidin-3-yl)acetate, by the reaction and purification in the same manner as in Example 230 and Example 225.

$^1$H NMR (300 MHz, DMSO-d$_6$): δ 0.29 (9H, s), 2.38-2.44 (2H, m), 2.82 (2H, brs), 3.04 (2H, d, J=7.9 Hz), 3.27 (3H, s), 3.52 (2H, d, J=10.6 Hz), 3.64-3.89 (2H, m), 4.12-4.20 (1H, m), 4.36 (3H, s), 5.38 (1H, s), 6.99-7.33 (4H, m), 7.50 (1H, d, J=8.3 Hz), 10.74 (1H, s).

Example 276

3-((((1R)-1-((3,5-difluoro-4-(trimethylsilyl)phenyl)carbamoyl)-6-methoxy-3,4-dihydroisoquinolin-2(1H)-yl)carbonyl)oxy)propanoic acid The title compound was synthesized using (R)-N-(3,5-difluoro-4-(trimethylsilyl)phenyl)-6-methoxy-1,2,3,4-tetrahydroisoquinoline-1-carboxamide and tert-butyl 3-hydroxypropanoate, by the reaction and purification in the same manner as in Example 230 and Example 225.

$^1$H NMR (300 MHz, DMSO-d$_6$): δ 0.30 (9H, s), 2.44-2.60 (2H, m), 2.66-2.83 (1H, m), 2.94-3.15 (1H, m), 3.39-3.50 (1H, m), 3.72 (3H, s), 3.79-4.00 (1H, m), 4.19 (2H, d, J=17.4 Hz), 5.44 (1H, s), 6.80 (2H, s), 7.14-7.32 (2H, m), 7.34-7.55 (1H, m), 10.70-10.91 (1H, m)

Example 277

3-((((1R)-1-((3,5-difluoro-4-(trimethylsilyl)phenyl)carbamoyl)-6-ethoxy-3,4-dihydroisoquinolin-2(1H)-yl)carbonyl)oxy)propanoic acid The title compound was synthesized using (R)-N-(3,5-difluoro-4-(trimethylsilyl)phenyl)-6-ethoxy-1,2,3,4-tetrahydroisoquinoline-1-carboxamide and tert-butyl 3-hydroxypropanoate, by the reaction and purification in the same manner as in Example 230 and Example 225.

$^1$H NMR (300 MHz, DMSO-d$_6$): δ 0.29 (9H, s), 1.29 (3H, t, J=7.0 Hz), 2.24-2.43 (1H, m), 2.60-2.82 (1H, m), 2.90-3.13 (1H, m), 3.28-3.51 (2H, m), 3.98 (3H, d, J=7.2 Hz), 4.08-4.29 (2H, m), 5.27-5.50 (1H, m), 6.77 (2H, brs), 7.14-7.34 (2H, m), 7.34-7.51 (1H, m), 10.86 (1H, s), 11.10-11.38 (1H, m)

Example 278

(1-(((5R)-2-(difluoromethoxy)-5-((3,5-difluoro-4-(trimethylsilyl)phenyl)carbamoyl)-7,8-dihydro-1,6-naphthyridin-6(5H)-yl)carbonyl)azetidin-3-yl)acetic acid (Step 1)
(R)-N-(3,5-Difluoro-4-(trimethylsilyl)phenyl)-2-(difluoromethoxy)-5,6,7,8-tetrahydro-1,6-naphthyridine-5-carboxamide was synthesized using 6-(tert-butoxycarbonyl)-2-(difluoromethoxy)-5,6,7,8-tetrahydro-1,6-naphthyridine-5-carboxylic acid, by the reaction and purification in the same manner as in Steps 8 to 10 of Example 254.
$^1$H NMR (300 MHz, CDCl$_3$): δ 0.33 (9H, t, J=1.5 Hz), 2.22 (1H, brs), 2.75-2.98 (2H, m), 3.08-3.20 (1H, m), 3.22-3.33 (1H, m), 4.60 (1H, s), 6.77 (1H, d, J=8.7 Hz), 7.05-7.13 (2H, m), 7.46 (1H, t), 7.98 (1H, d, J=8.7 Hz), 9.62 (1H, s).

(Step 2)
The title compound was synthesized using (R)-N-(3,5-difluoro-4-(trimethylsilyl)phenyl)-2-(difluoromethoxy)-5,6,7,8-tetrahydro-1,6-naphthyridine-5-carboxamide and benzyl 2-(azetidin-3-yl)acetate, by the reaction and purification in the same manner as in Example 230 and Example 231.
$^1$H NMR (300 MHz, CDCl$_3$): δ 0.32 (9H, s), 2.71-2.77 (2H, m), 2.86-3.09 (3H, m), 3.41-3.53 (1H, m), 3.74 (2H, dd, J=8.3, 5.7 Hz), 3.97 (1H, dd, J=8.5, 5.9 Hz), 4.19 (1H, t), 4.42 (1H, t, J=8.5 Hz), 5.63 (1H, s), 6.80 (1H, d, J=8.3 Hz), 7.00-7.08 (2H, m), 7.45 (1H, dd), 7.53 (1H, d, J=8.7 Hz), 10.06 (1H, s).

Example 279

(1-(((1R)-1-((3-fluoro-4-(trimethylsilyl)phenyl)carbamoyl)-6-methoxy-3,4-dihydroisoquinolin-2(1H)-yl)carbonyl)azetidin-3-yl)acetic acid (Step 1)
Pyridine (0.152 mL, 1.88 mmol) was slowly added to a solution of benzyl 2-(azetidin-3-yl)acetate (193 mg, 0.94 mmol) and bis(trichloromethyl) carbonate (279 mg, 0.94 mmol) in THF (5 mL) at 0° C., and the mixture was stirred at 0° C. for 1 hr. The reaction mixture was concentrated under reduced pressure. A solution of (R)-N-(3-fluoro-4-(trimethylsilyl)phenyl)-6-methoxy-1,2,3,4-tetrahydroisoquinoline-1-carboxamide (140 mg, 0.38 mmol) and DIEA (0.655 mL, 3.76 mmol) in DMF (5 mL) was added thereto at 0° C., and the mixture was stirred at room temperature for 2.5 hr. To the reaction mixture was added water, and the mixture was extracted with ethyl acetate. The organic layer was washed with 10% aqueous citric acid solution, and dried over magnesium sulfate, and the solvent was evaporated under reduced pressure. The obtained residue was purified by silica gel column chromatography (solvent gradient; 20→50% ethyl acetate/hexane) to give crude benzyl (R)-2-(1-(1-((3-fluoro-4-(trimethylsilyl)phenyl)carbamoyl)-6-methoxy-1,2,3,4-tetrahydroisoquinoline-2-carbonyl)azetidin-3-yl)acetate (160.7 mg, 0.266 mmol, 70.8%) as a white solid.

(Step 2)
A solution of benzyl (R)-2-(1-(1-((3-fluoro-4-(trimethylsilyl)phenyl)carbamoyl)-6-methoxy-1,2,3,4-tetrahydroisoquinoline-2-carbonyl)azetidin-3-yl)acetate (160.7 mg, 0.27 mmol) and 10% palladium-carbon (20 mg, 0.19 mmol, 50% wet) in MeOH (3.0 mL) was stirred under hydrogen atmosphere (1 atm) at room temperature for 2 hr. The catalyst was removed by filtration, and the filtrate was concentrated under reduced pressure. The obtained residue was purified by silica gel column chromatography (solvent gradient; 20→90% ethyl acetate/hexane) to give the title compound (94.3 mg, 0.184 mmol, 69.0%) as a white solid.
$^1$H NMR (300 MHz, DMSO-d$_6$): δ 0.24 (9H, s), 2.53-2.61 (2H, m), 2.69-2.85 (2H, m), 2.99-3.13 (1H, m), 3.34-3.43 (1H, m), 3.47-3.58 (1H, m), 3.66-3.75 (4H, m), 3.76-3.87 (1H, m), 3.90-3.99 (1H, m), 4.15 (1H, t, J=8.1 Hz), 5.34 (1H, s), 6.74-6.85 (2H, m), 7.23-7.37 (2H, m), 7.39-7.51 (2H, m), 10.49 (1H, s), 12.24 (1H, brs)
$[α]_D^{25}$ −7.9 (c 0.2525, MeOH)

Example 280

(1-(((1R)-6-ethoxy-1-((3-fluoro-4-(trimethylsilyl)phenyl)carbamoyl)-3,4-dihydroisoquinolin-2(1H)-yl)carbonyl)azetidin-3-yl)acetic acid The title compound was synthesized using (R)-6-ethoxy-N-(3-fluoro-4-(trimethylsilyl)phenyl)-1,2,3,4-tetrahydroisoquinoline-1-carboxamide and benzyl 2-(azetidin-3-yl)acetate, by the reaction and purification in the same manner as in Example 230 and Example 231.
$^1$H NMR (300 MHz, DMSO-d$_6$): δ 0.24 (9H, d, J=0.8 Hz), 1.29 (3H, t, J=7.0 Hz), 2.53-2.60 (2H, m), 2.68-2.85 (2H, m), 2.98-3.13 (1H, m), 3.35-3.43 (1H, m), 3.48-3.57 (1H, m), 3.67-3.75 (1H, m), 3.75-3.86 (1H, m), 3.91-4.03 (3H, m), 4.15 (1H, t, J=8.3 Hz), 5.33 (1H, s), 6.71-6.83 (2H, m), 7.24-7.37 (2H, m), 7.38-7.53 (2H, m), 10.49 (1H, s), 12.19 (1H, brs)
$[α]_D^{25}$ −11.6 (c 0.2515, MeOH)

Example 281

(1-(((5R)-5-((3,5-difluoro-4-(trimethylsilyl)phenyl)carbamoyl)-2-methoxy-7,8-dihydro-1,6-naphthyridin-6(5H)-yl)carbonyl)azetidin-3-yl)acetic acid (Step 1)
Pyridine (0.299 mL, 3.69 mmol) was slowly added to a solution of benzyl 2-(azetidin-3-yl)acetate (379 mg, 1.85 mmol) and bis(trichloromethyl) carbonate (548 mg, 1.85 mmol) in THF (10 mL) at 0° C., and the mixture was stirred at 0° C. for 1 hr. The reaction mixture was concentrated under reduced pressure. A solution of (R)-N-(3,5-difluoro-4-(trimethylsilyl)phenyl)-2-methoxy-5,6,7,8-tetrahydro-1,6-naphthyridine-5-carboxamide (289 mg, 0.74 mmol) and DIEA (1.286 mL, 7.38 mmol) in DMF (10 mL) was added thereto at 0° C., and the mixture was stirred at room temperature for 15 hr. To the reaction mixture was added water, and 2N hydrochloric acid was added thereto until the pH of the mixture became 3. The mixture was extracted three times with ethyl acetate. The organic layer was washed with aqueous sodium hydrogen carbonate solution and brine, and dried over magnesium sulfate, and the solvent was evaporated under reduced pressure. The obtained residue was purified by silica gel column chromatography (solvent gradient; 31→52% ethyl acetate/hexane), and then silica gel column chromatography (NH, solvent gradient; 20→45% ethyl acetate/hexane) to give benzyl (R)-2-(1-(5-((3,5-difluoro-4-(trimethylsilyl)phenyl)carbamoyl)-2-methoxy-5,6,7,8-tetrahydro-1,6-naphthyridine-6-carbonyl)azetidin-3-yl)acetate (131 mg, 0.210 mmol, 28.5%) as a white solid.
MS(API): Calculated 622.7, Found 623.2 (M+H).

¹H NMR (300 MHz, CDCl₃): δ 0.32 (9H, t), 2.72 (2H, dd, J=7.7, 2.1 Hz), 2.85-2.96 (2H, m), 2.97-3.08 (1H, m), 3.33-3.45 (1H, m), 3.64-3.73 (2H, m), 3.89-3.97 (4H, m), 4.10-4.19 (1H, m), 4.39 (1H, t, J=8.3 Hz), 5.13 (2H, s), 5.55 (1H, s), 6.64 (1H, d, J=8.7 Hz), 7.01-7.10 (2H, m), 7.29-7.40 (6H, m), 10.11 (1H, s).

(Step 2)

A solution of benzyl (R)-2-(1-(5-((3,5-difluoro-4-(trimethylsilyl)phenyl)carbamoyl)-2-methoxy-5, 6,7,8-tetrahydro-1, 6-naphthyridine-6-carbonyl)azetidin-3-yl)acetate (128 mg, 0.21 mmol) and 10% palladium-carbon (45 mg, 0.38 mmol, 50% wet) in MeOH (4 mL) was stirred under hydrogen atmosphere (1 atm) at room temperature for 1.5 hr. The catalyst was removed by filtration, and the filtrate was concentrated under reduced pressure. The obtained residue was purified by silica gel column chromatography (Diol, solvent gradient; 30→100% ethyl acetate/hexane) to give the title compound (79.2 mg, 0.149 mmol, 72.3%) as a white solid.

¹H NMR (300 MHz, CDCl₃): δ 0.32 (9H, s), 2.70-2.76 (2H, m), 2.86-3.09 (3H, m), 3.40-3.52 (1H, m), 3.74 (2H, dd, J=8.5, 5.9 Hz), 3.91 (3H, s), 3.96 (1H, dd, J=8.5, 5.9 Hz), 4.19 (1H, t), 4.42 (1H, t, J=8.5 Hz), 5.57 (1H, s), 6.65 (1H, d, J=8.3 Hz), 7.02-7.10 (2H, m), 7.37 (1H, d, J=8.7 Hz), 10.03 (1H, s).

$[\alpha]_D^{25}$+81.8 (c 0.2510, MeOH)

Example 282

5-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)-5-oxopentanoic acid monosulfate dihydrate (Step 1)

Morpholine (261 mg, 261 µL, 2.99 mmol) and acetic acid (200 mg, 191 µL, 3.32 mmol) were added to a solution of 2,2-dimethyl-1,3-dioxane-4,6-dione (24.0 g, 166.17 mmol) in acetone (120 g) under argon gas atmosphere at room temperature, and the mixture was stirred at room temperature for 18 hr. The reaction mixture was concentrated under reduced pressure. To the obtained residue was added saturated aqueous sodium hydrogen carbonate solution (200 mL), and the mixture was extracted with toluene (200 mL). The organic layer was washed with 10% brine (200 mL), and the solvent was evaporated under reduced pressure to give 5-isopropylidene-2,2-dimethyl-1,3-dioxane-4,6-dione as a white solid.

¹H NMR (500 MHz, CDCl₃): δ1.72 (6H, s), 2.52 (6H, s).

1M Isopropylmagnesium chloride THF solution (183 mL, 182.79 mmol) was added dropwise to a solution of 4-bromo-2-fluoro-1-iodobenzene (50.0 g, 166.17 mmol) in anhydrous THF (96 mL) over 20 min at −20° C. under argon gas atmosphere. The reaction mixture was stirred at −20° C. for 30 min, and added dropwise to a solution of 5-isopropylidene-2,2-dimethyl-1,3-dioxane-4,6-dione in anhydrous toluene (84 mL) at −20° C. over 20 min, and the container was washed with THF (24 mL). The reaction mixture was stirred at 0° C. for 3 hr, 10% aqueous citric acid solution (200 mL) was added thereto at 0° C., and the mixture was extracted with toluene (200 mL). The organic layer was concentrated under reduced pressure to give 5-(2-(4-bromo-2-fluorophenyl)propan-2-yl)-2,2-dimethyl-1,3-dioxane-4,6-dione as a pale yellow oil.

4M Hydrochloric acid (96 mL) was added to a solution of 5-(2-(4-bromo-2-fluorophenyl)propan-2-yl)-2,2-dimethyl-1,3-dioxane-4,6-dione in DMF (60 mL), and the mixture was stirred at 100° C. for 24 hr. The reaction mixture was concentrated under reduced pressure at 75° C., and the pH of the obtained residue was adjusted to 9.0 with 8M aqueous sodium hydroxide solution (50 mL). The mixture was stirred at 0° C. for 10 min, and filtered, and the insoluble substance was washed with water (100 mL). The pH of the filtrate was adjusted to 4.0 with 6M hydrochloric acid (20 mL) at 0° C., and the mixture was stirred at 0° C. for 1 hr. The precipitate was collected by filtration, washed with ice water, and dried at 50° C. to give 3-(4-bromo-2-fluorophenyl)-3-methylbutanoic acid (24.52 g, 85.49 mmol, 51%) as white crystals.

¹H NMR (500 MHz, CDCl₃): δ1.46 (6H, s), 2.80 (2H, s), 7.13-7.22 (3H, m) (The peak derived from COOH was not observed).

(Step 2)

A mixture of 3-(4-bromo-2-fluorophenyl)-3-methylbutanoic acid (20.0 g, 72.70 mmol) and PPA (200 g) was stirred at 100° C. for 4 hr. To the reaction mixture was added ice water (200 mL) at 0° C., and the mixture was extracted twice with ethyl acetate (200 mL). The organic layer was washed with saturated aqueous sodium hydrogen carbonate solution (200 mL), 8M aqueous sodium hydroxide solution (35 mL) and 10% brine, and concentrated under reduced pressure. To a mixture of the obtained residue in a mixed solvent of DMF (140 mL) and EtOH (140 mL) was added water (240 mL) at room temperature, and the mixture was stirred at 0° C. for 2 hr. The precipitate was collected by filtration, washed with water (100 mL), and dried at 50° C. to give 6-bromo-4-fluoro-3,3-dimethylindan-1-one (17.0 g, 66.12 mmol, 91%) as pale orange crystals.

¹H NMR (500 MHz, CDCl₃): δ1.52 (6H, s), 2.63 (2H, s), 7.41 (1H, dd, J=9.0, 1.7 Hz), 7.65 (1H, d, J=1.6 Hz).

(Step 3)

Triethylsilane (1.59 g, 2.17 mL, 13.63 mmol) was added to a solution of 6-bromo-4-fluoro-3,3-dimethylindan-1-one (1.5 g, 5.83 mmol) in TFA (30 mL) at room temperature, and the mixture was stirred at room temperature for 40 hr. To the reaction mixture was added ice water at 0° C., and the mixture was extracted twice with ethyl acetate. The organic layer was washed with aqueous sodium hydroxide solution (the pH of the aqueous layer was adjusted to 7.0) and 10% brine, and concentrated under reduced pressure to give crude 5-bromo-7-fluoro-1,1-dimethylindane as an orange oil.

¹H NMR (500 MHz, CDCl₃): δ1.35 (6H, s), 1.93 (2H, t, J=7.3 Hz), 2.90 (2H, t, J=7.4 Hz), 6.98 (1H, dt, J=9.5, 0.8 Hz), 7.06-7.13 (1H, m).

Pd₂(dba)₃ (267 mg, 0.29 mmol), BINAP (363 mg, 0.58 mmol), sodium tert-butoxide (841 mg, 8.75 mmol) and benzphenone imine (1.05 g, 0.98 mL, 5.83 mmol) were added to a solution of the crude 5-bromo-7-fluoro-1,1-dimethylindane in anhydrous toluene (30 mL) under argon gas atmosphere at room temperature, and the mixture was stirred at 80° C. for 1 hr. To the reaction mixture was added water, and the mixture was extracted twice with ethyl acetate. The organic layer was concentrated under reduced pressure to give crude N-(7-fluoro-1,1-dimethyl-2,3-dihydro-1H-inden-5-yl)-1,1-diphenylmethanimine as an orange oil.

To a solution of the crude N-(7-fluoro-1,1-dimethyl-2,3-dihydro-1H-inden-5-yl)-1,1-diphenylmethanimine in THF (30 mL) was added 1M hydrochloric acid (29 mL, 29.17 mmol) at room temperature, and the mixture was stirred at room temperature for 30 min. To the reaction mixture was added sodium hydroxide until the pH of the reaction mixture became >7, and the mixture was extracted twice with ethyl acetate. The organic layer was washed with 10% brine, and concentrated under reduced pressure to give crude 7-fluoro-1,1-dimethyl-2,3-dihydro-1H-inden-5-amine as an orange oil.

$^1$H NMR (500 MHz, CDCl$_3$): δ1.33 (6H, s), 1.88 (2H, t, J=7.4 Hz), 2.81 (2H, t, J=7.4 Hz), 3.60 (2H, s), 6.15-6.17 (1H, m), 6.28-6.29 (1H, m).

A solution of (+)-camphorsulfonic acid (1.49 g, 6.42 mmol) in ethyl acetate (37.5 mL) was added to the crude 7-fluoro-1,1-dimethyl-2,3-dihydro-1H-inden-5-amine in ethyl acetate (15 mL) at room temperature, and the container was washed with ethyl acetate (7.5 mL). The mixture was stirred at 0° C. for 2 hr. The precipitate was collected by filtration, washed with ethyl acetate, and dried at 40° C. to give 7-fluoro-1,1-dimethyl-2,3-dihydro-1H-inden-5-amine (+)-camphorsulfonate (1.38 g, 3.36 mmol, 58%) as pale yellow crystals.

$^1$H NMR (500 MHz, CDCl$_3$): δ0.74 (3H, s), 0.93 (3H, s), 1.22-1.30 (1H, m), 1.34 (6H, s), 1.52-1.60 (1H, m), 1.77-1.90 (2H, m), 1.93 (2H, t, J=7.4 Hz), 1.96-2.00 (1H, m), 2.23-2.30 (1H, m), 2.35-2.44 (1H, m), 2.74 (1H, d, J=14.8 Hz), 2.91 (2H, t, J=7.4 Hz), 3.31 (1H, d, J=14.5 Hz), 7.05-7.10 (1H, m), 7.15-7.20 (1H, m), 8.58-10.43 (2H, br) (The exchangeable 1H was not observed).

(Step 4)

1.6 M n-Butyllithium/hexane solution (282 mL, 451.96 mmol) was added dropwise to a solution of 2-methoxy-6-methylpyridine (50.60 g, 410.87 mmol) in THF (625 mL) over 1 hr under argon gas atmosphere at −78° C. The reaction mixture was stirred at −78° C. for 45 min, para-formaldehyde (49.3 g, 1643.49 mmol) was added thereto at −78° C., and the mixture was vigorously stirred at room temperature for 3.5 hr. The reaction mixture was poured into ice water (1000 mL), and the mixture was saturated with sodium chloride, and extracted three times with a mixed solvent of ethyl acetate/THF (3:1). The organic layer was washed with water and brine, and dried over magnesium sulfate, and the solvent was evaporated under reduced pressure. The obtained residue was purified by silica gel column chromatography (solvent gradient; 8→50% ethyl acetate/hexane) to give 2-(6-methoxypyridin-2-yl)ethanol (23.22 g, 152 mmol, 37%) as a colorless oil.

$^1$H NMR (300 MHz, CDCl$_3$): δ 2.94 (2H, t, J=5.5 Hz), 3.91 (3H, s), 4.00 (2H, q, J=4.5 Hz), 4.30 (1H, t, J=5.9 Hz), 6.62 (1H, d, J=8.3 Hz), 6.73 (1H, d, J=7.2 Hz), 7.51 (1H, dd, J=8.3, 7.2 Hz).

(Step 5)

ADDP (49.0 g, 194.09 mmol) was added to a mixture of 2-(6-methoxypyridin-2-yl)ethanol (22.87 g, 149.30 mmol), phthalimide (24.16 g, 164.23 mmol), tributylphosphine (48.5 mL, 194.09 mmol) and THF (340 mL) under argon gas atmosphere at 0° C., the obtain solution was stirred at room temperature for 16 hr. To the reaction mixture was added ethyl acetate (about 500 mL), and the mixture was stirred at 0° C. for 20 min. The insoluble substance was removed by filtration with ethyl acetate, and washed with ethyl acetate. The filtrate was added to water (1000 mL), and the mixture was extracted three times with ethyl acetate. The organic layer was washed with water and brine, and dried over magnesium sulfate, and the solvent was evaporated under reduced pressure. The obtained residue was purified by silica gel column chromatography (solvent gradient; 5→20% ethyl acetate/hexane), and the precipitate was collected by filtration with hexane to give 2-(2-(6-methoxypyridin-2-yl)ethyl)isoindoline-1,3-dione (29.03 g, 103 mmol, 69%) as a grayish white powder.

$^1$H NMR (300 MHz, CDCl$_3$): δ 3.08 (2H, t, J=7.2 Hz), 3.78 (3H, s), 4.11 (2H, t, J=7.2 Hz), 6.54 (1H, d, J=7.9 Hz), 6.72 (1H, d, J=7.2 Hz), 7.43 (1H, dd, J=8.3, 7.2 Hz), 7.70 (2H, dd, J=5.5, 3.2 Hz), 7.82 (2H, dd, J=6.3, 3.0 Hz).

(Step 6)

Hydrazine monohydrate (24.94 mL, 514.18 mmol) was added to a solution of 2-(2-(6-methoxypyridin-2-yl)ethyl)isoindoline-1,3-dione (29.03 g, 102.84 mmol) in EtOH (300 mL) at room temperature. The mixture was heated under reflux for 1 hr, and cooled to room temperature. The insoluble substance was removed by filtration, and washed with a mixed solvent of diethyl ether/IPE (1:1). The filtrate was concentrated under reduced pressure. To the obtained residue was added toluene (about 250 mL), and the mixture was concentrated under reduced pressure. The obtained residue was purified by silica gel column chromatography (NH, solvent gradient; 10→100% ethyl acetate/hexane) to give 2-(6-methoxypyridin-2-yl)ethanamine (14.43 g, 95 mmol, 92%) as a colorless oil.

$^1$H NMR (300 MHz, CDCl$_3$): δ 1.31 (2H, brs), 2.82 (2H, t, J=7.5 Hz), 3.11 (2H, t, J=6.0 Hz), 3.92 (3H, s), 6.57 (1H, d, J=7.9 Hz), 6.73 (1H, d, J=7.2 Hz), 7.48 (1H, dd, J=8.1, 7.4 Hz).

(Step 7)

1.6 M n-Butyllithium/hexane solution (300 mL, 479.43 mmol) was added to a solution of acetonitrile (21.87 g, 532.70 mmol) in THF (630 mL) under argon gas atmosphere at −78° C., and the mixture was stirred at −78° C. for 30 min. 2-Bromo-6-methoxypyridine (25.04 g, 133.18 mmol) was added dropwise thereto at −78° C. over 15 min, and the reaction mixture was stirred at room temperature for 4 hr. The reaction mixture was poured into ice water (900 mL), and the mixture was extracted three times with ethyl acetate. The organic layer was washed with water and brine, and dried over magnesium sulfate, and the solvent was evaporated under reduced pressure. The obtained residue was purified by silica gel column chromatography (solvent gradient; 2→20% ethyl acetate/hexane) to give 2-(6-methoxypyridin-2-yl)acetonitrile (11.37 g, 77 mmol, 58%) as a colorless oil.

$^1$H NMR (300 MHz, CDCl$_3$): δ 3.81 (2H, s), 3.93 (3H, s), 6.69 (1H, d, J=8.3 Hz), 6.93-6.98 (1H, m), 7.58 (1H, dd, J=8.3, 7.6 Hz).

(Step 8)

In the presence of Raney nickel (8 g, 136.30 mmol) [prepared by washing Kawaken NDHT-90 with 4N aqueous sodium hydroxide solution (40 m, 5 min), water (five times) and MeOH (three times)], a solution of 2-(6-methoxypyridin-2-yl)acetonitrile (5.00 g, 33.75 mmol) in 2M ammonia/MeOH (84 mL, 168.73 mmol) was stirred under hydrogen atmosphere (0.5 MPa) at room temperature for 22 hr. The catalyst was removed by decantation, and the reaction solution was concentrated under reduced pressure. To the obtained residue was added toluene (about 80 mL), and the mixture was concentrated under reduced pressure. The obtained residue was purified by silica gel column chromatography (NH, solvent gradient; 10→100% ethyl acetate/hexane) to give 2-(6-methoxypyridin-2-yl)ethanamine (4.30 g, 28.3 mmol, 84%) as a yellow oil.

(Step 9)

A solution of 2-(6-methoxypyridin-2-yl)ethanamine (14.43 g, 94.81 mmol), 4N hydrogen chloride/CPME (26.1 mL, 104.29 mmol) and 47% ethyl glyoxylate/toluene solution (polymer form) (30.0 mL, 142.22 mmol) in EtOH (175 mL) was heated under reflux for 8 hr. To the reaction mixture were added 4N hydrogen chloride/CPME (26.1 mL, 104.29 mmol) and 47% ethyl glyoxylate/toluene solution (polymer form) (30.0 mL, 142.22 mmol), and the mixture was heated under reflux for additional 16 hr. The reaction mixture was concentrated under reduced pressure to half volume, and to the residue was added diethyl ether (ca. 150 mL). The precipitate was collected by filtration, and washed with EtOH/diethyl ether to give crude ethyl 2-hydroxy-5,6,7,8-tetrahydro-1,6-naphthyridine-5-carboxylate hydrochloride (20.01 g, 77 mmol, 82%) as a grayish white powder.

$^1$H NMR (300 MHz, DMSO-d$_6$): δ 1.25 (3H, t, J=7.0 Hz), 2.71-2.93 (2H, m), 3.37-3.51 (2H, m), 4.19-4.31 (2H, m), 5.23 (1H, s), 6.30 (1H, d, J=9.4 Hz), 7.43 (1H, d, J=9.4 Hz), 8.12 (1H, brs), 9.65 (1H, brs), 10.56 (1H, brs).

(Step 10)

Boc$_2$O (17.72 g, 81.22 mmol) was added to a mixture of ethyl 2-hydroxy-5,6,7,8-tetrahydro-1,6-naphthyridine-5-carboxylate hydrochloride (20.01 g, 77.35 mmol), TEA (11.32 mL, 81.22 mmol), THF (205 mL) and water (75 mL) at room temperature, and the mixture was vigorously stirred at room temperature for 5.5 hr. The reaction mixture was poured into water (500 mL), and the mixture was saturated with sodium chloride, and extracted three times with a mixed solvent of ethyl acetate/THF (3:1). The organic layer was washed with water and brine, and dried over magnesium sulfate, and the solvent was evaporated under reduced pressure. The precipitate was collected by filtration, and washed with IPE/hexane to give 5-ethyl 6-tert-butyl 2-hydroxy-7,8-dihydro-1,6-naphthyridine-5,6(5H)-dicarboxylate (16.57 g, 51.4 mmol, 66%) as a white powder.

1H NMR (300 MHz, CDCl$_3$)d 1.24-1.32 (3H, m), 1.45-1.50 (9H, m), 2.66-2.92 (2H, m), 3.37-3.55 (1H, m), 4.10-4.29 (3H, m), 5.18-5.43 (1H, m), 6.46 (1H, d, J=9.4 Hz), 7.58-7.66 (1H, m), 12.94 (1H, brs).

(Step 11)

Iodomethane (8.69 mL, 139.60 mmol) was added to a mixture of 5-ethyl 6-tert-butyl 2-hydroxy-7,8-dihydro-1,6-naphthyridine-5,6(5H)-dicarboxylate (7.50 g, 23.27 mmol), silver(I) carbonate (8.34 g, 30.25 mmol) and THF (150 mL) at room temperature (the reaction container was light-blocked). The mixture was stirred at room temperature for 15 hr, and then at 50° C. for 5 hr. The insoluble substance was removed by filtration through Celite, and washed with ethyl acetate. The filtrate was concentrated under reduced pressure, and the obtained residue was purified by silica gel column chromatography (solvent gradient; 5→30% ethyl acetate/hexane) to give 5-ethyl 6-tert-butyl 2-methoxy-7,8-dihydro-1,6-naphthyridine-5,6(5H)-dicarboxylate (6.93 g, 20.60 mmol, 89%) as a pale yellow oil.

$^1$H NMR (300 MHz, CDCl$_3$): δ 1.21-1.30 (3H, m), 1.44-1.53 (9H, m), 2.84-2.96 (2H, m), 3.55-3.70 (1H, m), 3.91 (3H, s), 4.01-4.22 (3H, m), 5.33-5.54 (1H, m), 6.60 (1H, d, J=8.7 Hz), 7.69 (1H, t, J=7.5 Hz).

(Step 12)

Trimethyloxonium tetrafluoroborate (1.775 g, 12.00 mmol) was added to a mixture of 5-ethyl 6-tert-butyl 2-hydroxy-7,8-dihydro-1,6-naphthyridine-5,6(5H)-dicarboxylate (1.289 g, 4.00 mmol) and acetonitrile (18 mL) at 0° C. The mixture was stirred at 0° C. for 2 hr, the reaction mixture was poured into ice-cooled saturated aqueous sodium hydrogen carbonate solution (100 mL), and the mixture was extracted three times with ethyl acetate. The organic layer was washed with water and brine, and dried over magnesium sulfate, and the solvent was evaporated under reduced pressure. The obtained residue was purified by silica gel column chromatography (solvent gradient; 2→19% ethyl acetate/hexane) to give 5-ethyl 6-tert-butyl 2-methoxy-7,8-dihydro-1,6-naphthyridine-5,6(5H)-dicarboxylate (372 mg, 1.106 mmol, 28%) as a colorless oil.

(Step 13)

2N Lithium hydroxide (61.8 mL, 123.61 mmol) was added to a solution of 5-ethyl 6-tert-butyl 2-methoxy-7,8-dihydro-1,6-naphthyridine-5,6(5H)-dicarboxylate (6.93 g, 20.60 mmol) in a mixed solvent of EtOH (30 mL) and THF (30 mL) at room temperature, and the mixture was stirred at room temperature for 1.5 hr. The reaction mixture was poured into ice-cooled water, and 6N hydrochloric acid was added thereto until the pH of the mixture became 4. Then, the mixture was extracted three times with a mixed solvent of ethyl acetate/THF (3:1). The organic layer was washed with water and brine, and dried over magnesium sulfate, and the solvent was evaporated under reduced pressure to give 6-(tert-butoxycarbonyl)-2-methoxy-5,6,7,8-tetrahydro-1,6-naphthyridine-5-carboxylic acid (6.37 g, 20.66 mmol, 100%) as a colorless amorphous solid. 1H NMR (300 MHz, CDCl$_3$): δ 1.44-1.52 (9H, m), 2.85-2.95 (2H, m), 3.57-3.68 (1H, m), 3.90 (3H, s), 3.97-4.07 (1H, m), 5.36-5.57 (1H, m), 6.61 (1H, d, J=8.3 Hz), 7.68 (1H, d, J=8.7 Hz). (The exchangeable 1H was not observed)

(Step 14)

T3P (4.89 mL, 8.22 mmol) was added to a solution of 6-(tert-butoxycarbonyl)-2-methoxy-5,6,7,8-tetrahydro-1,6-naphthyridine-5-carboxylic acid (1.69 g, 5.48 mmol), 7-fluoro-1,1-dimethyl-2,3-dihydro-1H-inden-5-amine (0.982 g, 5.48 mmol), DIEA (4.77 mL, 27.41 mmol) and DMAP (0.737 g, 6.03 mmol) in ethyl acetate (40 mL) at room temperature. The mixture was stirred at 65° C. for 15 hr, the reaction mixture was poured into water (150 mL), and the mixture was extracted three times with ethyl acetate. The organic layer was washed with 10% aqueous citric acid solution, aqueous sodium hydrogen carbonate solution and brine, and dried over magnesium sulfate, and the solvent was evaporated under reduced pressure. The obtained precipitate was washed with hexane to give tert-butyl 5-((7-fluoro-1,1-dimethyl-2,3-dihydro-1H-inden-5-yl)carbamoyl)-2-methoxy-7,8-dihydro-1,6-naphthyridine-6(5H)-carboxylate (2.09 g, 4.45 mmol, 81%) as a grayish white powder.

$^1$H NMR (300 MHz, CDCl$_3$): δ 1.34 (6H, s), 1.53 (9H, s), 1.91 (2H, t, J=7.4 Hz), 2.83-3.01 (4H, m), 3.45 (1H, brs), 3.91 (3H, s), 4.06 (1H, dt, J=13.2, 4.9 Hz), 5.56 (1H, brs), 6.64 (1H, d, J=8.3 Hz), 7.05-7.12 (2H, m), 7.48 (1H, brs), 8.70 (1H, brs).

(Step 15)

tert-Butyl 5-((7-fluoro-1,1-dimethyl-2,3-dihydro-1H-inden-5-yl)carbamoyl)-2-methoxy-7,8-dihydro-1,6-naphthyridine-6(5H)-carboxylate (2.09 g) was resolved by chiral column chromatography. The fraction having a shorter retention time was concentrated to give tert-butyl (R)-5-((7-fluoro-1,1-dimethyl-2,3-dihydro-1H-inden-5-yl)carbamoyl)-2-methoxy-7,8-dihydro-1,6-naphthyridine-6(5H)-carboxylate (960 mg, >99% ee), and the fraction having a longer retention time was concentrated to give tert-butyl (S)-5-((7-fluoro-1,1-dimethyl-2,3-dihydro-1H-inden-5-yl)carbamoyl)-2-methoxy-7,8-dihydro-1,6-naphthyridine-6(5H)-carboxylate (920 mg, >99% ee), each as a grayish white amorphous solid.

purification condition by chiral column chromatography
    column: CHIRALPAK IA (QK001) 50 mmID×500 mmL
    solvent: hexane/EtOH=900/100
    flow rate: 80 mL/min
    temperature: 30° C.
    detection method: UV 220 nm (Step 16)

TFA (13 mL) was added to tert-butyl (R)-5-((7-fluoro-1,1-dimethyl-2,3-dihydro-1H-inden-5-yl)carbamoyl)-2-methoxy-7,8-dihydro-1,6-naphthyridine-6(5H)-carboxylate (957 mg, 2.04 mmol) at room temperature, and the mixture was stirred at room temperature for 20 min. The reaction mixture was added to ice-cooled saturated aqueous sodium hydrogen carbonate solution (110 mL), and potassium carbonate was added thereto until the pH of the mixture became 8. Then, the mixture was extracted three times with ethyl acetate. The organic layer was washed with water and brine, and dried over magnesium sulfate, and the solvent was evaporated under reduced pressure to give (R)-N-(7-fluoro-1,1-dimethyl-2,3-dihydro-1H-inden-5-yl)-2-methoxy-5,6,7,8-tetrahydro-1,6-naphthyridine-5-carboxamide (732 mg, 1.981 mmol, 97%) as a grayish white amorphous solid.

$^1$H NMR (300 MHz, CDCl$_3$): δ 1.34 (6H, s), 1.69 (1H, brs), 1.91 (2H, t, J=7.4 Hz), 2.73-2.98 (4H, m), 3.12-3.28 (2H, m), 3.90 (3H, s), 4.57 (1H, s), 6.60 (1H, d, J=8.7 Hz), 7.11-7.17 (2H, m), 7.84 (1H, d, J=8.7 Hz), 9.41 (1H, s).

(Step 17)

Dihydro-2H-pyran-2,6(3H)-dione (2.405 g, 21.08 mmol) was added to a solution of (R)-N-(7-fluoro-1,1-dimethyl-2,3-dihydro-1H-inden-5-yl)-2-methoxy-5,6,7,8-tetrahydro-1,6-naphthyridine-5-carboxamide (5.99 g, 16.21 mmol) and TEA (3.39 mL, 24.32 mmol) in THF (140 mL) at room temperature, and the mixture was stirred at room temperature for 15 hr. The reaction mixture was poured into water (600 mL), and 2N hydrochloric acid was added thereto until the pH of the mixture became 4. Then, the mixture was extracted three times with ethyl acetate. The organic layer was washed with water and brine, and dried over magnesium sulfate, and the solvent was evaporated under reduced pressure. The obtained residue was purified twice by silica gel column chromatography (Diol, solvent gradient; 30→100% ethyl acetate/hexane) to give 5-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)-5-oxopentanoic acid (7.77 g, 16.07 mmol, 99%) as a colorless amorphous solid. The obtained solid (4.50 g) was dissolved in ethyl acetate (16 mL) at 75° C., and heptane (25 mL) was added thereto. Seed crystals were added thereto, the mixture was treated with ultrasonic wave, and the precipitated crystals were washed with heptane to give colorless prism crystals (3.87 g).

Elemental Analysis: C$_{26}$H$_{30}$N$_3$O$_5$F
Calculated C, 64.58; H, 6.25; N, 8.69.
Found C, 64.74; H, 6.66; N, 8.27.

(Step 18)

0.126 M Sulfuric acid (6.89 mL, 0.87 mmol, THF solution) was added to a solution of 5-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)-5-oxopentanoic acid (400 mg, 0.83 mmol) in THF (10 mL) at room temperature, and the mixture was stirred at room temperature for 30 min. The reaction mixture was concentrated under reduced pressure to dryness, and to the obtained residue were added water (0.075 mL, 4.14 mmol) and toluene (17 mL). Seed crystals were added thereto, and the mixture was slowly cooled, and stirred at 0° C. for 6 days. The precipitated crystals were collected by filtration, and washed with diethyl ether to give the title compound (332.8 mg, 0.539 mmol, 65%) as white crystals.

$^1$H NMR (300 MHz, DMSO-d$_6$): δ 1.29 (6H, s), 1.75 (2H, quin, J=7.1 Hz), 1.87 (2H, t, J=7.4 Hz), 2.28 (2H, t, J=7.5 Hz), 2.41-2.48 (1H, m), 2.53-2.63 (1H, m), 2.82-2.95 (3H, m), 3.04 (1H, dt, J=18.0, 4.5 Hz), 3.79-3.89 (4H, m), 4.04 (1H, ddd, J=12.7, 8.0, 4.5 Hz), 5.74 (1H, s), 6.74 (1H, d, J=8.7 Hz), 7.18 (1H, s), 7.23 (1H, d, J=12.8 Hz), 7.80 (1H, d, J=8.7 Hz), 7.90 (3H, brs), 10.48 (1H, s). (4H derived from water was not observed)

Elemental Analysis: C$_{26}$H$_{30}$FN$_3$O$_5$.H$_2$SO$_4$.2H$_2$O
Calculated C, 50.56; H, 5.87; N, 6.80.
Found C, 50.33; H, 5.86; N, 6.69.
crystallinity: 61%
[α]$_{D25}$+81.1 (c 0.2510, MeOH)

Example 283

(1-(((1R)-6-(difluoromethoxy)-1-((3,5-difluoro-4-(trimethylsilyl)phenyl)carbamoyl)-3,4-dihydroisoquinolin-2(1H)-yl)carbonyl)azetidin-3-yl)acetic acid The title compound was synthesized using (R)-N-(3,5-difluoro-4-(trimethylsilyl)phenyl)-6-(difluoromethoxy)-1,2,3,4-tetrahydroisoquinoinoline-1-carboxamide and benzyl 2-(azetidin-3-yl)acetate, by the reaction and purification in the same manner as in Example 230 and Example 231.

$^1$H NMR (300 MHz, CDCl$_3$): δ0.31 (9H, s), 2.70-2.77 (2H, m), 2.85-3.08 (3H, m), 3.57 (2H, dd, J=7.0, 5.1 Hz), 3.73 (1H, dd, J=8.5, 5.9 Hz), 3.96 (1H, dd, J=8.5, 5.9 Hz), 4.19 (1H, t), 4.40 (1H, t, J=8.5 Hz), 5.66 (1H, s), 6.50 (1H, t), 6.95-7.07 (4H, m), 7.24 (1H, d), 10.06 (1H, s).
[α]$_D^{25}$+7.4 (c 0.2515, MeOH)

Example 284

5-((6R)-6-((7-fluoro-1,1-dimethyl-2,3-dihydro-1H-inden-5-yl)carbamoyl)-3,6,8,9-tetrahydrofuro[2,3-f]isoquinolin-7(2H)-yl)-5-oxopentanoic acid The title compound was synthesized using (R)-N-(7-fluoro-1,1-dimethyl-2,3-dihydro-1H-inden-5-yl)-2,3,6,7,8,9-hexahydrofuro[2,3-f]isoquinoline-6-carboxamide, by the reaction and purification in the same manner as in Step 9 of Example 252.

$^1$H NMR (300 MHz, CDCl$_3$): δ 1.30 (6H, s), 1.86 (2H, t, J=7.4 Hz), 2.06 (2H, quin, J=7.1 Hz), 2.48 (2H, t, J=6.8 Hz), 2.61 (2H, td, J=7.1, 2.5 Hz), 2.77-2.90 (3H, m), 2.97 (1H, dt), 3.20 (2H, t, J=8.7 Hz), 3.77-3.83 (2H, m), 4.59 (2H, t, J=8.9 Hz), 6.03 (1H, s), 6.82 (1H, d, J=7.6 Hz), 6.98 (1H, s), 7.05-7.14 (2H, m), 9.05 (1H, s).

Example 285

5-((7R)-7-((7-fluoro-1,1-dimethyl-2,3-dihydro-1H-inden-5-yl)carbamoyl)-2,3,9,10-tetrahydro[1,4]dioxino[2,3-f]isoquinolin-8(7H)-yl)-5-oxopentanoic acid (Step 1)

A solution of 2,3-dihydroxybenzaldehyde (10.00 g, 72.40 mmol), 1,2-dibromoethane (18.72 mL, 217.20 mmol) and potassium carbonate (30.0 g, 217.20 mmol) in DMF (200 mL) was stirred at 70° C. for 15 hr. The reaction mixture was cooled, water was added thereto, and the mixture was extracted three times with ethyl acetate. The organic layer was washed with brine, and dried over magnesium sulfate, and the solvent was evaporated under reduced pressure. The precipitate was collected by filtration with cooled hexane to give 2,3-dihydrobenzo[b][1,4]dioxin-5-carbaldehyde (10.86 g, 66.2 mmol, 91%) as pale yellow crystals.

$^1$H NMR (300 MHz, CDCl$_3$): δ 4.30-4.35 (2H, m), 4.37-4.42 (2H, m), 6.91 (1H, td), 7.10 (1H, dd, J=8.1, 1.7 Hz), 7.40 (1H, dd, J=7.7, 1.7 Hz), 10.37 (1H, s).

(Step 2)

8-(tert-Butoxycarbonyl)-2,3,7,8,9,10-hexahydro-[1,4]dioxino[2,3-f]isoquinoline-7-carboxylic acid was synthesized using 2,3-dihydrobenzo[b][1,4]dioxin-5-carbaldehyde, by the reaction and purification in the same manner as in Steps 1 to 7 of Example 254.

¹H NMR (300 MHz, CDCl₃): δ 1.47 (9H, d, J=11.3 Hz), 2.79 (2H, t), 3.61-3.80 (2H, m), 4.20-4.30 (4H, m), 5.33-5.54 (1H, m), 6.75 (1H, d, J=8.7 Hz), 6.97 (1H, d, J=8.7 Hz).
(Step 3)

(R)-N-(7-Fluoro-1,1-dimethyl-2,3-dihydro-1H-inden-5-yl)-2,3,7,8,9,10-hexahydro-[1,4]dioxino[2,3-f]isoquinoline-7-carboxamide was synthesized using 8-(tert-butoxycarbonyl)-2,3,7,8,9,10-hexahydro-[1,4]dioxino[2,3-f]isoquinoline-7-carboxylic acid and 7-fluoro-1,1-dimethyl-2,3-dihydro-1H-inden-5-amine hydrochloride, by the reaction and purification in the same manner as in Steps 8 to 10 of Example 254.

¹H NMR (300 MHz, CDCl₃): δ 1.33 (6H, s), 1.90 (2H, t, J=7.6 Hz), 2.05 (1H, brs), 2.69 (2H, t, J=5.9 Hz), 2.86 (2H, t, J=7.4 Hz), 3.10 (2H, t), 4.20-4.30 (4H, m), 4.58 (1H, s), 6.75 (1H, d, J=8.7 Hz), 7.07 (1H, d, J=8.7 Hz), 7.11-7.18 (2H, m), 9.20 (1H, s).
(Step 4)

The title compound was synthesized using (R)-N-(7-fluoro-1,1-dimethyl-2,3-dihydro-1H-inden-5-yl)-2,3,7,8,9,10-hexahydro-[1,4]dioxino[2,3-f]isoquinoline-7-carboxamide, by the reaction and purification in the same manner as in Step 9 of Example 252.

¹H NMR (300 MHz, CDCl₃): δ 1.30 (6H, s), 1.86 (2H, t, J=7.4 Hz), 2.01-2.12 (3H, m), 2.48 (2H, t, J=6.6 Hz), 2.54-2.68 (2H, m), 2.81 (2H, t, J=7.4 Hz), 2.85-2.92 (1H, m), 2.98 (1H, dt), 3.73-3.84 (2H, m), 4.21-4.31 (4H, m), 5.96 (1H, s), 6.77 (1H, d), 6.83 (1H, d), 6.97 (1H, s), 7.09 (1H, dd, J=11.9, 1.7 Hz), 9.10 (1H, s).

Example 286

5-((6R)-6-((3,5-difluoro-4-(trimethylsilyl)phenyl)carbamoyl)-3,6,8,9-tetrahydrofuro[2,3-f]isoquinolin-7(2H)-yl)-5-oxopentanoic acid (Step 1)

1M Borane-THF complex THF solution (193 mL, 193.35 mmol) was slowly added to a solution of 2,3-dihydrobenzofuran-7-carboxylic acid (10.58 g, 64.45 mmol) in THF (65 mL) over 30 min while the reaction solution was maintained at room temperature. The reaction mixture was stirred at 60° C. for 3.5 hr, and poured into ice (about 400 g). The mixture was stirred at room temperature for 30 min, and extracted three times with ethyl acetate. The organic layer was washed with aqueous sodium hydrogen carbonate solution and brine, and dried over magnesium sulfate, and the solvent was evaporated under reduced pressure to give (2,3-dihydrobenzofuran-7-yl)methanol (9.76 g, 65.0 mmol, quant.) as a colorless oil.

¹H NMR (300 MHz, CDCl₃): δ 2.08 (1H, brs), 3.22 (2H, t, J=8.9 Hz), 4.61 (2H, t, J=8.7 Hz), 4.67 (2H, s), 6.83 (1H, t), 7.08 (1H, d, J=7.6 Hz), 7.15 (1H, dd, J=7.4, 0.9 Hz).
(Step 2)

A mixture of (2,3-dihydrobenzofuran-7-yl)methanol (9.76 g, 64.99 mmol) and manganese dioxide (45.2 g, 519.93 mmol) in toluene (250 mL) was stirred at 60° C. for 3 hr. The manganese dioxide was filtered off, and the filtrate was concentrated under reduced pressure. The precipitate was collected by filtration and washed with cooled hexane to give 2,3-dihydrobenzofuran-7-carbaldehyde (7.43 g, 50.1 mmol, 77%) as a pale yellow solid.

¹H NMR (300 MHz, CDCl₃): δ 3.25 (2H, t, J=8.7 Hz), 4.74 (2H, t, J=8.7 Hz), 6.93 (1H, t, J=7.6 Hz), 7.41 (1H, dq, J=7.2, 1.3 Hz), 7.58 (1H, dd, J=7.9, 0.8 Hz), 10.20 (1H, s).
(Step 3)

7-(tert-Butoxycarbonyl)-2,3,6,7,8,9-hexahydrofuro[2,3-f]isoquinoline-6-carboxylic acid was synthesized using 2,3-dihydrobenzofuran-7-carbaldehyde, by the reaction and purification in the same manner as in Steps 1 to 7 of Example 254.

¹H NMR (300 MHz, CDCl₃): δ 1.43-1.50 (9H, m), 2.73-2.83 (2H, m), 3.20 (2H, t, J=8.7 Hz), 3.62-3.82 (2H, m), 4.58 (2H, t, J=9.1 Hz), 5.39-5.61 (1H, m), 6.98 (1H, d), 7.05 (1H, d).
(Step 4)

(R)-N-(7-Fluoro-1,1-dimethyl-2,3-dihydro-1H-inden-5-yl)-2,3,6,7,8,9-hexahydrofuro[2,3-f]isoquinoline-6-carboxamide was synthesized using 7-(tert-butoxycarbonyl)-2,3,6,7,8,9-hexahydrofuro[2,3-f]isoquinoline-6-carboxylic acid, by the reaction and purification in the same manner as in Steps 8 to 10 of Example 254.

¹H NMR (300 MHz, CDCl₃): δ 1.33 (6H, s), 1.90 (2H, t, J=7.4 Hz), 2.05 (1H, brs), 2.63-2.77 (2H, m), 2.86 (2H, t, J=7.4 Hz), 3.12 (2H, t), 3.19 (2H, t, J=8.7 Hz), 4.57 (2H, t, J=8.7 Hz), 4.63 (1H, s), 7.02-7.18 (4H, m), 9.18 (1H, s).
(Step 5)

The title compound was synthesized using (R)-N-(7-fluoro-1,1-dimethyl-2,3-dihydro-1H-inden-5-yl)-2,3,6,7,8,9-hexahydrofuro[2,3-f]isoquinoline-6-carboxamide, by the reaction and purification in the same manner as in Step 9 of Example 252.

¹H NMR (300 MHz, CDCl₃): δ 0.28 (9H, t, J=1.3 Hz), 2.12 (2H, quin, J=6.5 Hz), 2.43-2.65 (3H, m), 2.77-2.97 (2H, m), 3.01-3.12 (1H, m), 3.20 (2H, t, J=8.7 Hz), 3.75 (1H, ddd, J=12.3, 7.6, 4.7 Hz), 3.98 (1H, ddd, J=12.2, 7.1, 4.5 Hz), 4.58 (2H, t, J=8.7 Hz), 5.91 (1H, s), 6.81-6.89 (2H, m), 6.98 (1H, d), 7.07 (1H, d), 9.70 (1H, s).

Example 287

5-((7R)-7-((3,5-difluoro-4-(trimethylsilyl)phenyl)carbamoyl)-2,3,9,10-tetrahydro[1,4]dioxino[2,3-f]isoquinolin-8(7H)-yl)-5-oxopentanoic acid (Step 1)

(R)-N-(3,5-Difluoro-4-(trimethylsilyl)phenyl)-2,3,7,8,9,10-hexahydro-[1,4]dioxino[2,3-f]isoquinoline-7-carboxamide was synthesized using 8-(tert-butoxycarbonyl)-2,3,7,8,9,10-hexahydro-[1,4]dioxino[2,3-f]isoquinoline-7-carboxylic acid and 3,5-difluoro-4-(trimethylsilyl)aniline, by the reaction and purification in the same manner as in Steps 8 to 10 of Example 254.

¹H NMR (300 MHz, CDCl₃): δ 0.32 (9H, t, J=1.3 Hz), 1.61 (1H, brs), 2.69 (2H, t, J=5.9 Hz), 3.03-3.18 (2H, m), 4.20-4.31 (4H, m), 4.59 (1H, s), 6.76 (1H, d, J=8.3 Hz), 7.03-7.13 (3H, m), 9.42 (1H, s).
(Step 2)

The title compound was synthesized using (R)-N-(3,5-difluoro-4-(trimethylsilyl)phenyl)-2,3,7,8,9,10-hexahydro-[1,4]dioxino[2,3-f]isoquinoline-7-carboxamide, by the reaction and purification in the same manner as in Step 9 of Example 252.

¹H NMR (300 MHz, CDCl₃): δ 0.27 (9H, s), 2.08-2.17 (2H, m), 2.43-2.64 (3H, m), 2.84 (1H, dt, J=14.9, 5.9 Hz), 2.92-3.11 (2H, m), 3.73 (1H, ddd, J=12.3, 7.4, 4.9 Hz), 3.92-4.02 (1H, m), 4.20-4.30 (4H, m), 5.84 (1H, s), 6.76 (1H, d, J=8.3 Hz), 6.79-6.87 (2H, m), 6.99 (1H, d, J=8.7 Hz), 9.74 (1H, s).

Example 288

(1-(((6R)-6-((3, 5-difluoro-4-(trimethylsilyl)phenyl) carbamoyl)-3,6,8,9-tetrahydrofuro[2,3-f]isoquinolin-7(2H)-yl)carbonyl)azetidin-3-yl)acetic acid (Step 1)
(R)-N-(3,5-Difluoro-4-(trimethylsilyl)phenyl)-2,3,6,7,8,9-hexahydrofuro[2,3-f]isoquinoline-6-carboxamide was synthesized using 7-(tert-butoxycarbonyl)-2,3,6,7,8,9-hexahydrofuro[2,3-f]isoquinoline-6-carboxylic acid and 3,5-difluoro-4-(trimethylsilyl)aniline, by the reaction and purification in the same manner as in Steps 8 to 10 of Example 254.
$^1$H NMR (300 MHz, CDCl$_3$): δ 0.32 (9H, t, J=1.3 Hz), 1.90 (1H, brs), 2.70 (2H, td, J=5.7, 3.0 Hz), 3.13 (2H, t), 3.20 (2H, t, J=8.7 Hz), 4.58 (2H, t, J=8.9 Hz), 4.65 (1H, s), 7.05-7.13 (4H, m), 9.42 (1H, s).
(Step 2)
The title compound was synthesized using (R)-N-(3,5-difluoro-4-(trimethylsilyl)phenyl)-2,3,6,7,8,9-hexahydrofuro[2,3-f]isoquinoline-6-carboxamide and benzyl 2-(azetidin-3-yl)acetate, by the reaction and purification in the same manner as in Example 230 and Example 231.
$^1$H NMR (300 MHz, CDCl$_3$): δ 0.31 (9H, s), 2.72 (2H, dd, J=7.7, 1.7 Hz), 2.75-2.86 (2H, m), 2.95-3.07 (1H, m), 3.22 (2H, t, J=8.7 Hz), 3.38-3.50 (1H, m), 3.57-3.66 (1H, m), 3.70 (1H, dd, J=8.5, 5.9 Hz), 3.94 (1H, dd, J=8.5, 5.9 Hz), 4.16 (1H, t, J=8.3 Hz), 4.40 (1H, t, J=8.5 Hz), 4.59 (2H, t, J=8.7 Hz), 5.63 (1H, s), 6.68 (1H, d, J=7.9 Hz), 7.03-7.12 (3H, m), 9.92 (1H, s).

Example 289

(1-(((7R)-7-((3, 5-difluoro-4-(trimethylsilyl)phenyl) carbamoyl)-2,3,9,10-tetrahydro[1,4]dioxino[2,3-f] isoquinolin-8 (7H)-yl)carbonyl)azetidin-3-yl)acetic acid The title compound was synthesized using benzyl 2-(azetidin-3-yl)acetate and (R)-N-(3,5-difluoro-4-(trimethylsilyl) phenyl)-2,3,7,8,9,10-hexahydro-[1,4]dioxino[2,3-f]isoquinoline-7-carboxamide, by the reaction and purification in the same manner as in Example 230 and Example 231.
$^1$H NMR (300 MHz, CDCl$_3$): δ 0.31 (9H, s), 2.69-2.74 (2H, m), 2.75-2.91 (2H, m), 2.95-3.07 (1H, m), 3.37-3.48 (1H, m), 3.56-3.66 (1H, m), 3.71 (1H, dd, J=8.3, 5.7 Hz), 3.94 (1H, dd, J=8.5, 5.9 Hz), 4.16 (1H, t, J=8.5 Hz), 4.21-4.31 (4H, m), 4.39 (1H, t, J=8.5 Hz), 5.57 (1H, s), 6.68 (1H, d), 6.79 (1H, d), 7.02-7.10 (2H, m), 9.93 (1H, s).

Example 290

(1-(((1R)-1-((3,5-difluoro-4-(trimethylsilyl)phenyl) carbamoyl)-6-propyl-3,4-dihydroisoquinolin-2 (1H)-yl)carbonyl)azetidin-3-yl)acetic acid (Step 1)
A mixture of 1-(3-bromophenyl)propan-1-one (15.00 g, 70.40 mmol) and hydrazine monohydrate (8.54 mL, 176.00 mmol) in diethylene glycol (85 mL) was stirred at room temperature for 20 min. To the mixture was added powderized potassium hydroxide (13.94 g, 211.20 mmol), and the mixture was heated under reflux for 2 hr. The reaction mixture was cooled, ice water (500 mL) was added thereto, and 6N hydrochloric acid was added thereto until the pH of the mixture became 3. Then, the mixture was extracted three times with a mixed solvent of ethyl acetate/hexane (2:1). The organic layer was washed with brine, and dried over magnesium sulfate, and the solvent was evaporated under reduced pressure. The obtained residue was purified by silica gel column chromatography (solvent; 2% ethyl acetate/hexane) to give 1-bromo-3-propylbenzene (11.61 g, 58.3 mmol, 83%) as a colorless oil.
$^1$H NMR (300 MHz, CDCl$_3$): δ 0.93 (3H, t, J=7.4 Hz), 1.63 (2H, dq, J=15.0, 7.3 Hz), 2.55 (2H, t), 7.07-7.17 (2H, m), 7.28-7.34 (2H, m).
(Step 2)
2-(tert-Butoxycarbonyl)-6-propyl-1,2,3,4-tetrahydroisoquinoline-1-carboxylic acid was synthesized using 1-bromo-3-propylbenzene, by the reaction and purification in the same manner as in Steps 5 to 7 of Example 252 and Steps 3 to 7 of Example 254.
$^1$H NMR (300 MHz, CDCl$_3$): δ 0.93 (3H, t, J=7.4 Hz), 1.41-1.51 (9H, m), 1.62 (2H, sxt, J=7.5 Hz), 2.54 (2H, t, J=7.7 Hz), 2.74-2.98 (2H, m), 3.60-3.84 (2H, m), 5.36-5.56 (1H, m), 6.96 (1H, s), 7.03 (1H, d, J=7.9 Hz), 7.37 (1H, d, J=7.9 Hz).
(Step 3)
(R)-N-(3,5-Difluoro-4-(trimethylsilyl)phenyl)-6-propyl-1,2,3,4-tetrahydroisoquinoline-1-carboxamide was synthesized using 2-(tert-butoxycarbonyl)-6-propyl-1,2,3,4-tetrahydroisoquinoline-1-carboxylic acid and 3,5-difluoro-4-(trimethylsilyl)aniline, by the reaction and purification in the same manner as in Steps 8 to 10 of Example 254.
$^1$H NMR (300 MHz, CDCl$_3$): δ 0.32 (9H, t, J=1.3 Hz), 0.94 (3H, t, J=7.4 Hz), 1.62 (2H, sxt, J=7.5 Hz), 2.04 (1H, brs), 2.53 (2H, t), 2.69-2.79 (1H, m), 2.83-2.94 (1H, m), 3.14 (2H, t), 4.66 (1H, s), 6.92 (1H, s), 7.03 (1H, dd, J=7.9, 1.9 Hz), 7.06-7.13 (2H, m), 7.50 (1H, d, J=8.3 Hz), 9.56 (1H, s).
(Step 4)
The title compound was synthesized using (R)-N-(3,5-difluoro-4-(trimethylsilyl)phenyl)-6-propyl-1,2,3,4-tetrahydroisoquinoline-1-carboxamide, by the reaction and purification in the same manner as in Example 230 and Example 231.
$^1$H NMR (300 MHz, CDCl$_3$): δ 0.30 (9H, s), 0.94 (3H, t, J=7.4 Hz), 1.62 (2H, sxt, J=7.5 Hz), 2.52-2.59 (2H, m), 2.69-2.74 (2H, m), 2.83-3.05 (3H, m), 3.53-3.60 (2H, m), 3.72 (1H, dd, J=8.3, 5.7 Hz), 3.94 (1H, dd, J=8.5, 5.9 Hz), 4.18 (1H, t), 4.39 (1H, t, J=8.3 Hz), 5.62 (1H, s), 6.99 (1H, s), 7.01-7.09 (3H, m), 7.14 (1H, d), 9.98 (1H, s).

Example 291

(1-(((7R)-7-((7-fluoro-1,1-dimethyl-2,3-dihydro-1H-inden-5-yl)carbamoyl)-2,3,9,10-tetrahydro[1,4]dioxino[2,3-f]isoquinolin-8(7H)-yl)carbonyl)azetidin-3-yl)acetic acid The title compound was synthesized using (R)-N-(7-fluoro-1,1-dimethyl-2,3-dihydro-1H-inden-5-yl)-2,3,7,8,9,10-hexahydro[1,4]dioxino[2,3-f]isoquinoline-7-carboxamide and benzyl 2-(azetidin-3-yl)acetate, by the reaction and purification in the same manner as in Example 230 and Example 231.
$^1$H NMR (300 MHz, CDCl$_3$): δ 1.33 (6H, s), 1.89 (2H, t, J=7.4 Hz), 2.66-2.89 (6H, m), 2.93-3.05 (1H, m), 3.35-3.46 (1H, m), 3.57-3.65 (1H, m), 3.69 (1H, dd, J=8.5, 5.9 Hz), 3.92 (1H, dd, J=8.5, 5.9 Hz), 4.15 (1H, t), 4.21-4.30 (4H, m), 4.38 (1H, t, J=8.3 Hz), 5.57 (1H, s), 6.68 (1H, d), 6.79 (1H, d), 7.10 (1H, s), 7.17 (1H, dd, J=12.1, 1.5 Hz), 9.58 (1H, s)

Example 292 methyl 4-((1R)-1-((3,5-difluoro-4-(trimethylsilyl)phenyl)carbamoyl)-6-methoxy-3,4-dihydroisoquinolin-2(1H)-yl)butanoate Sodium triacetoxyborohydride (313 mg, 1.48 mmol) was added to a solution of (R)-N-(3,5-difluoro-4-(trimethylsilyl)phenyl)-6-methoxy-1,2,3,4-tetrahydroisoquinoline-1-carboxamide (96 mg, 0.25 mmol) and methyl 4-oxobutanoate (0.077 mL, 0.74 mmol) in ethyl acetate (4 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→75% ethyl acetate/hexane) to give the title compound (93 mg, 0.189 mmol, 77%) as a colorless oil.

$^1$H NMR (300 MHz, CDCl$_3$): δ 0.27-0.39 (9H, m), 1.81-2.17 (2H, m), 2.26-2.54 (3H, m), 2.56-2.81 (3H, m), 2.83-2.99 (1H, m), 3.15-3.27 (1H, m), 3.69 (3H, s), 3.77 (3H, s), 4.11 (1H, s), 6.63 (1H, d, J=2.6 Hz), 6.68-6.82 (1H, m), 7.08-7.23 (2H, m), 7.35-7.47 (1H, m), 9.04-9.24 (1H, m).

Example 293 methyl 4-(((1R)-1-((3, 5-difluoro-4-(trimethylsilyl)phenyl)carbamoyl)-6-methoxy-3,4-dihydroisoquinolin-2(1H)-yl) sulfonyl)butanoate TEA (0.057 mL, 0.41 mmol) was added to a solution of (R)-N-(3,5-difluoro-4-(trimethylsilyl)phenyl)-6-methoxy-1,2,3,4-tetrahydroisoquinoline-1-carboxamide (80 mg, 0.20 mmol) and methyl 4-(chlorosulfonyl)butanoate (61.7 mg, 0.31 mmol) in DMF (2.0 mL) at room temperature, and the mixture was stirred overnight at room temperature. The reaction mixture was concentrated under reduced pressure, and the obtained residue was purified by silica gel column chromatography (solvent; ethyl acetate/hexane) to give the title compound (30.0 mg, 0.054 mmol, 26.4%) as a colorless oil.

The compounds described in Examples 102 to 293 are as follows (Table 1-12-Table 1-31).

TABLE 1-12

| EXAMPLE | IUPACNAME | Structure | ADDITIVE | MS |
|---|---|---|---|---|
| 102 | (1R)-N-(6-(1-(2,2-difluoroethoxy)-2-methylpropan-2-yl)-5-fluoropyridin-3-yl)-2-((3-hydroxy-1,2-oxazol-5-yl)acetyl)-6-methoxy-1,2,3,4-tetrahydroisoquinoline-1-carboxamide | 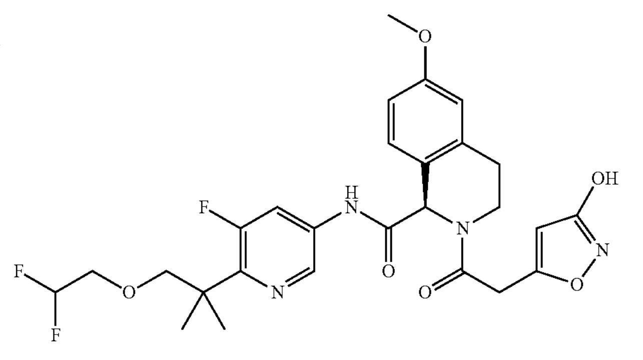 [SMILES: COc1ccc2c(c1)CCN(C(=O)Cc1cc(O)no1)[C@H]2C(=O)Nc1cnc(C(C)(C)COCC(F)F)c(F)c1] | | 563.2 (M + H) |
| 103 | (1R)-2-(cyanoacetyl)-N-(3,5-difluoro-4-(2-methyl-1-oxo-1-(pyrrolidin-1-yl)propan-2-yl)phenyl)-6-methoxy-1,2,3,4-tetrahydroisoquinoline-1-carboxamide | 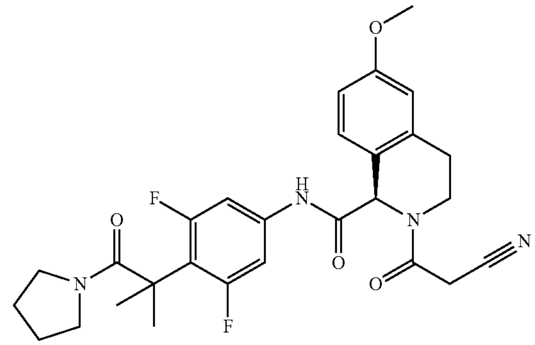 [SMILES: COc1ccc2c(c1)CCN(C(=O)CC#N)[C@H]2C(=O)Nc1cc(F)c(C(C)(C)C(=O)N2CCCC2)c(F)c1] | | 525.2 (M + H) |

TABLE 1-12-continued

| EXAMPLE | IUPACNAME | Structure | ADDITIVE | MS |
|---|---|---|---|---|
| 104 | (1R)-N-(3,5-difluoro-4-(2-methyl-1-oxo-1-(pyrrolidin-1-yl)propan-2-yl)phenyl)-6-methoxy-2-(3,3,3-trifluoropropanoyl)-1,2,3,4-tetrahydroisoquinoline-1-carboxamide | 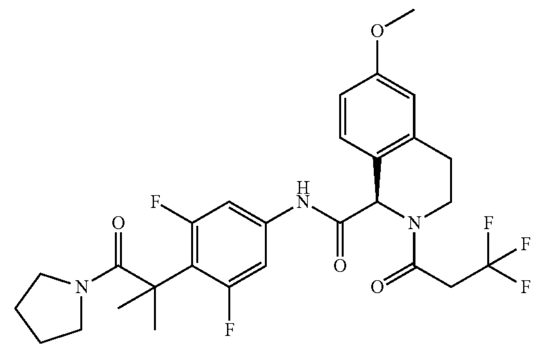 [SMILES: COc1ccc2c(c1)CCN(C(=O)CC(F)(F)F)[C@H]2C(=O)Nc1cc(F)c(C(C)(C)C(=O)N2CCCC2)c(F)c1] | | 568.1 (M + H) |
| 105 | (1R)-N-(3,5-difluoro-4-(2-methyl-1-oxo-1-(pyrrolidin-1-yl)propan-2-yl)phenyl)-6-methoxy-2-(pyridin-3-ylacetyl)-1,2,3,4-tetrahydroisoquinoline-1-carboxamide | 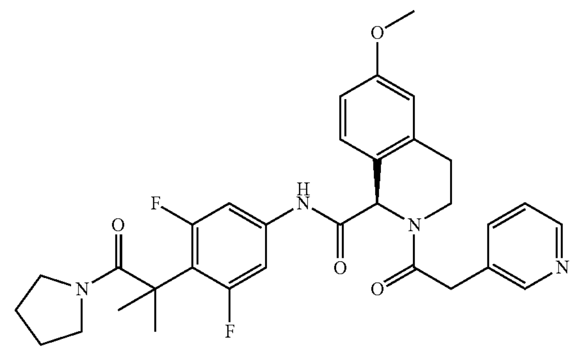 [SMILES: COc1ccc2c(c1)CCN(C(=O)Cc1cccnc1)[C@H]2C(=O)Nc1cc(F)c(C(C)(C)C(=O)N2CCCC2)c(F)c1] | | 577.2 (M + H) |
| 106 | (1R)-N-(3,5-difluoro-4-(2-methyl-1-oxo-1-(pyrrolidin-1-yl)propan-2-yl)phenyl)-6-methoxy-2-((5-methyl-1,3,4-oxadiazol-2-yl)acetyl)-1,2,3,4-tetrahydroisoquinoline-1-carboxamide | 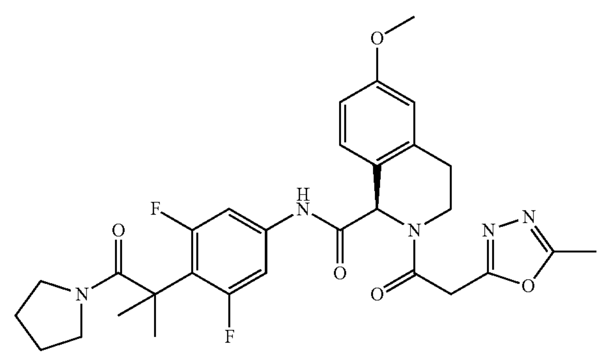 [SMILES: COc1ccc2c(c1)CCN(C(=O)Cc1nnc(C)o1)[C@H]2C(=O)Nc1cc(F)c(C(C)(C)C(=O)N2CCCC2)c(F)c1] | | 582.2 (M + H) |
| 107 | (1R)-N-(3-fluoro-4-(trimethylsilyl)phenyl)-2-((3-hydroxy-1,2-oxazol-5-yl)carbonyl)-6-(methoxymethyl)-1,2,3,4-tetrahydroisoquinoline-1-carboxamide | 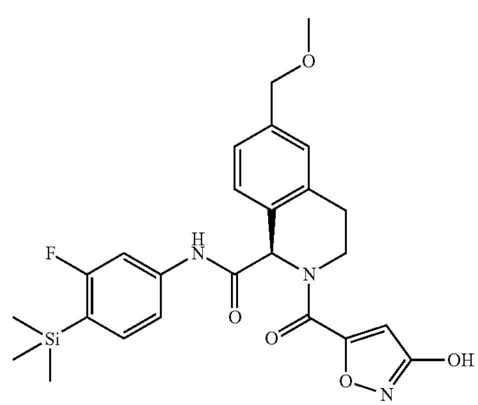 [SMILES: COCc1ccc2c(c1)CCN(C(=O)c1cc(O)no1)[C@H]2C(=O)Nc1ccc([Si](C)(C)C)c(F)c1] | | 496 (M − H) |

TABLE 1-12-continued

| EXAMPLE | IUPACNAME | Structure | ADDITIVE | MS |
|---|---|---|---|---|
| 108 | ((2-((1R)-1-((3,5-difluoro-4-(trimethylsilyl)phenyl)carbamoyl)-6-methoxy-3,4-dihydroisoquinolin-2(1H)-yl)-2-oxoethyl)(methyl)amino)acetic acid | 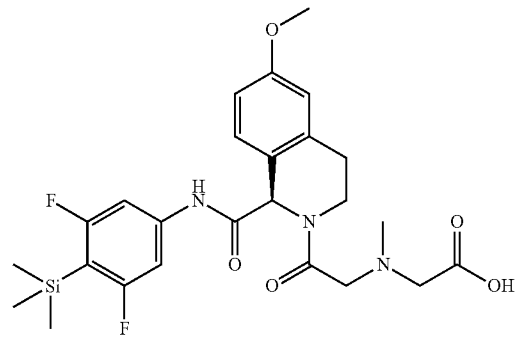 [SMILES: COc1ccc2c(c1)CCN(C(=O)CN(C)CC(=O)O)[C@H]2C(=O)Nc1cc(F)c([Si](C)(C)C)c(F)c1] | | 520.2 (M + H) |
| 109 | 5-((1R)-1-((4-tert-butyl-3,5-difluorophenyl)carbamoyl)-6-methoxy-3,4-dihydroisoquinolin-2(1H)-yl)-5-oxopentanoic acid | 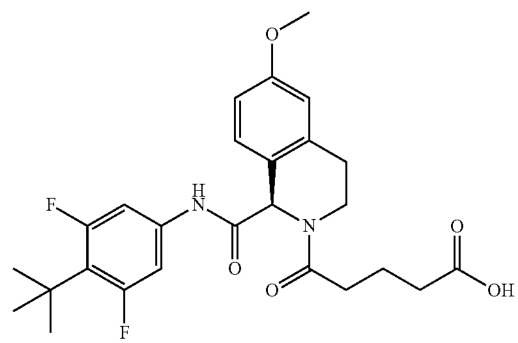 [SMILES: COc1ccc2c(c1)CCN(C(=O)CCCC(=O)O)[C@H]2C(=O)Nc1cc(F)c(C(C)(C)C)c(F)c1] | | 487.3 (M − H) |
| 110 | 5-((1R)-1-((3-fluoro-4-(trimethylsilyl)phenyl)carbamoyl)-6-(methoxymethyl)-3,4-dihydroisoquinolin-2(1H)-yl)-5-oxopentanoic acid | 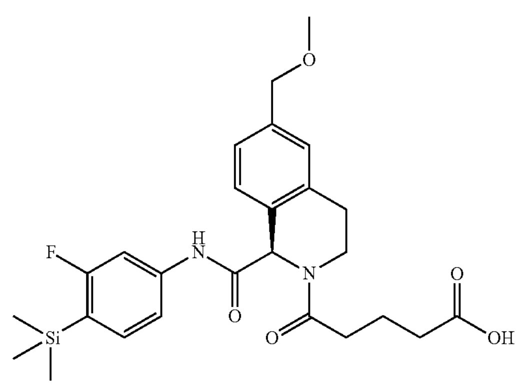 [SMILES: COCc1ccc2c(c1)CCN(C(=O)CCCC(=O)O)[C@H]2C(=O)Nc1ccc([Si](C)(C)C)c(F)c1] | | 499.1 (M − H) |
| 111 | (5R)-N-(4-(ethyl(dimethyl)silyl)-3,5-difluorophenyl)-6-((3-hydroxy-1,2-oxazol-5-yl)carbonyl)-2-methoxy-5,6,7,8-tetrahydro-1,6-naphthyridine-5-carboxamide | 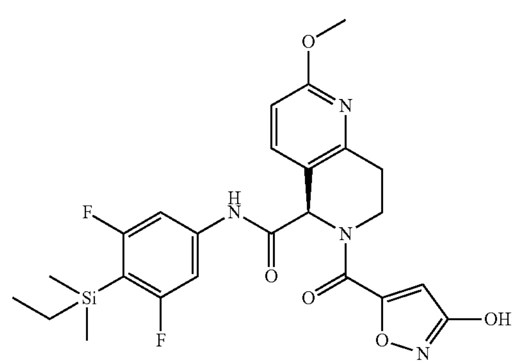 [SMILES: CC[Si](C)(C)c1c(F)cc(NC(=O)[C@H]2c3ccc(OC)nc3CCN2C(=O)c2cc(O)no2)cc1F] | | 517.1 (M + H) |

TABLE 1-13

| EXAMPLE | IUPACNAME | Structure | ADDITIVE | MS |
|---|---|---|---|---|
| 112 | (5S)-N-(4-(ethyl(dimethyl)silyl)-3,5-difluorophenyl)-6-((3-hydroxy-1,2-oxazol-5-yl)carbonyl)-2-methoxy-5,6,7,8-tetrahydro-1,6-naphthyridine-5-carboxamide | 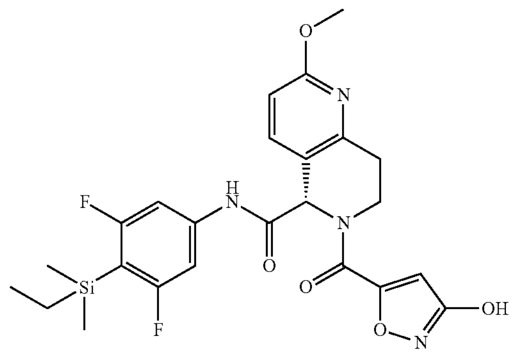 [SMILES: CC[Si](C)(C)c1c(F)cc(NC(=O)[C@@H]2c3ccc(OC)nc3CCN2C(=O)c2cc(O)no2)cc1F] | | 517.1 (M + H) |
| 113 | (5R)-N-(4-(ethyl(dimethyl)silyl)-3,5-difluorophenyl)-6-((3-hydroxy-1,2-oxazol-5-yl)acetyl)-2-methoxy-5,6,7,8-tetrahydro-1,6-naphthyridine-5-carboxamide | 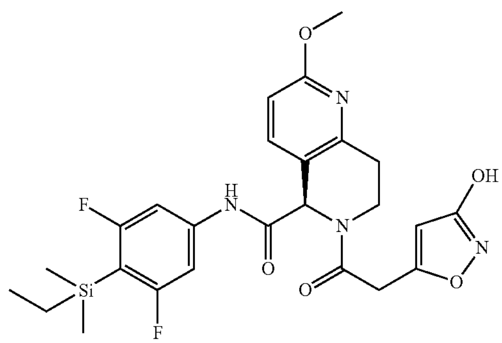 [SMILES: CC[Si](C)(C)c1c(F)cc(NC(=O)[C@H]2c3ccc(OC)nc3CCN2C(=O)Cc2cc(O)no2)cc1F] | | 531.1 (M + H) |
| 114 | 5-((5R)-5-((4-(ethyl(dimethyl)silyl)-3,5-difluorophenyl)carbamoyl)-2-methoxy-7,8-dihydro-1,6-naphthyridin-6(5H)-yl)-5-oxopentanoic acid | 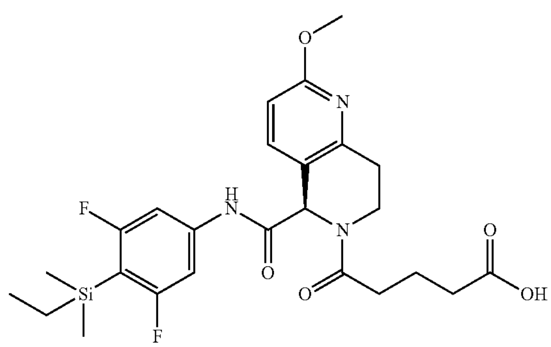 [SMILES: CC[Si](C)(C)c1c(F)cc(NC(=O)[C@H]2c3ccc(OC)nc3CCN2C(=O)CCCC(=O)O)cc1F] | | 520.2 (M + H) |
| 115 | (5R)-N-(7-fluoro-1,1-dimethyl-2,3-dihydro-1H-inden-5-yl)-6-((3-hydroxy-1,2-oxazol-5-yl)carbonyl)-2-methoxy-5,6,7,8-tetrahydro-1,6-naphthyridine-5-carboxamide | 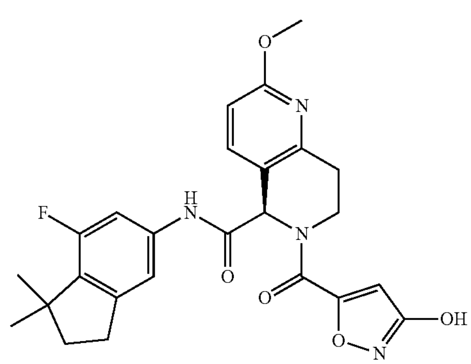 [SMILES: COc1ccc2c(n1)CCN(C(=O)c1cc(O)no1)[C@H]2C(=O)Nc1cc(F)c2c(c1)CCC2(C)C] | | 481.0 481.1 (M + H) |

TABLE 1-13-continued

| EXAMPLE | IUPACNAME | Structure | ADDITIVE | MS |
|---|---|---|---|---|
| 116 | (5S)-N-(7-fluoro-1,1-dimethyl-2,3-dihydro-1H-inden-5-yl)-6-((3-hydroxy-1,2-oxazol-5-yl)carbonyl)-2-methoxy-5,6,7,8-tetrahydro-1,6-naphthyridine-5-carboxamide | 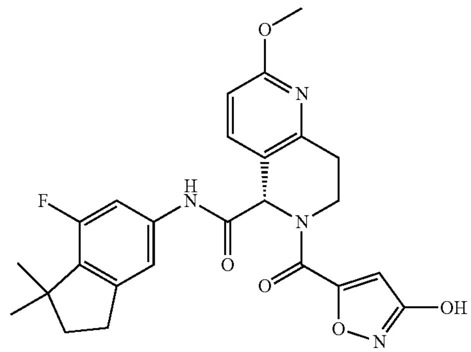 [SMILES: COc1ccc2c(n1)CCN(C(=O)c1cc(O)no1)[C@@H]2C(=O)Nc1cc(F)c2c(c1)CCC2(C)C] | | 481.2 (M + H) |
| 117 | (5R)-N-(7-fluoro-1,1-dimethyl-2,3-dihydro-1H-inden-5-yl)-6-((3-hydroxy-1,2-oxazol-5-yl)acetyl)-2-methoxy-5,6,7,8-tetrahydro-1,6-naphthyridine-5-carboxamide | 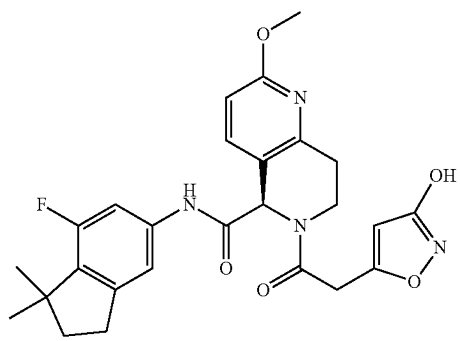 [SMILES: COc1ccc2c(n1)CCN(C(=O)Cc1cc(O)no1)[C@H]2C(=O)Nc1cc(F)c2c(c1)CCC2(C)C] | | 495.1 (M + H) |
| 118 | 5-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)-5-oxopentanoic acid | 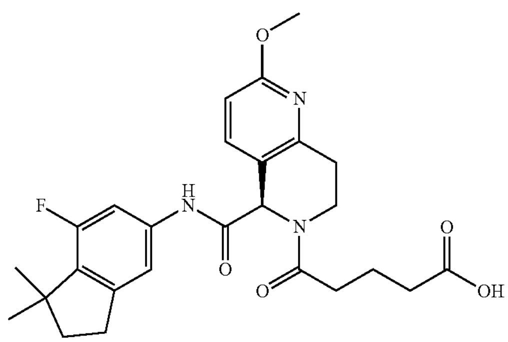 [SMILES: COc1ccc2c(n1)CCN(C(=O)CCCC(=O)O)[C@H]2C(=O)Nc1cc(F)c2c(c1)CCC2(C)C] | | 484.1 (M + H) |
| 119 | 5-((1R)-1-((3,5-difluoro-4-(1-methoxy-2-methylpropan-2-yl)phenyl)carbamoyl)-6-methoxy-3,4-dihydroisoquinolin-2(1H)-yl)-5-oxopentanoic acid | 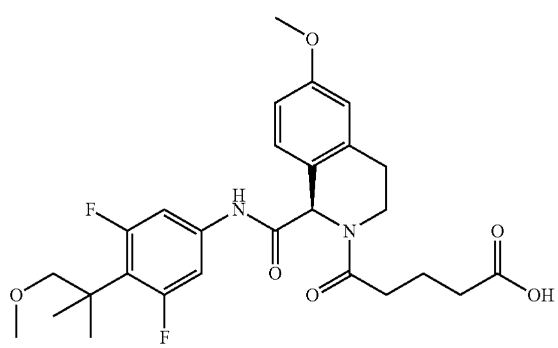 [SMILES: COCC(C)(C)c1c(F)cc(NC(=O)[C@H]2c3ccc(OC)cc3CCN2C(=O)CCCC(=O)O)cc1F] | | 517.1 (M − H) |

TABLE 1-13-continued

| EXAMPLE | IUPACNAME | Structure | ADDITIVE | MS |
|---|---|---|---|---|
| 120 | (2S)-5-((1R)-1-((4-tert-butyl-3,5-difluorophenyl)carbamoyl)-6-methoxy-3,4-dihydroisoquinolin-2(1H)-yl)-2-hydroxy-5-oxopentanoic acid | 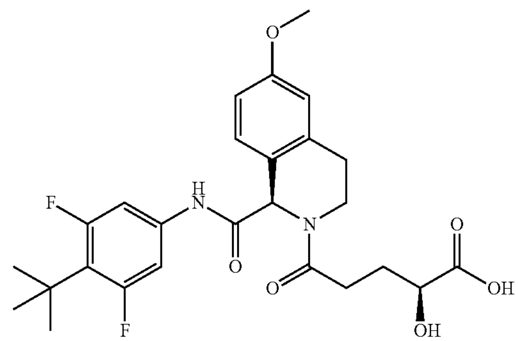 [SMILES: COc1ccc2c(c1)CCN(C(=O)CC[C@H](O)C(=O)O)[C@H]2C(=O)Nc1cc(F)c(C(C)(C)C)c(F)c1] | | 503.0 (M − H) |
| 121 | (1R)-N-(3,5-difluoro-4-(trimethylsilyl)phenyl)-2-((3-hydroxy-1,2-oxazol-5-yl)acetyl)-6-(methoxymethyl)-1,2,3,4-tetrahydroisoquinoline-1-carboxamide | 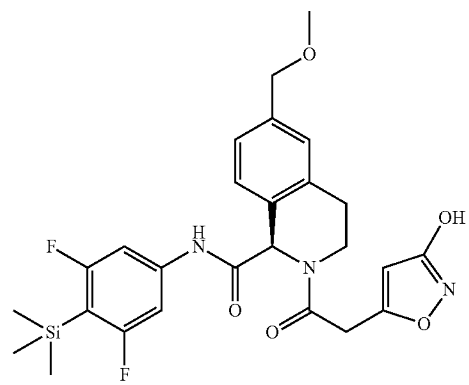 | | 528 (M − H) |

TABLE 1-14

| EXAMPLE | IUPACNAME | Structure | ADDITIVE | MS |
|---|---|---|---|---|
| 122 | (5R)-N-(3,5-difluoro-4-(trimethylsilyl)phenyl)-6-((3-hydroxy-1,2-oxazol-5-yl)carbonyl)-2-methoxy-5,6,7,8-tetrahydro-1,6-naphthyridine-5-carboxamide | 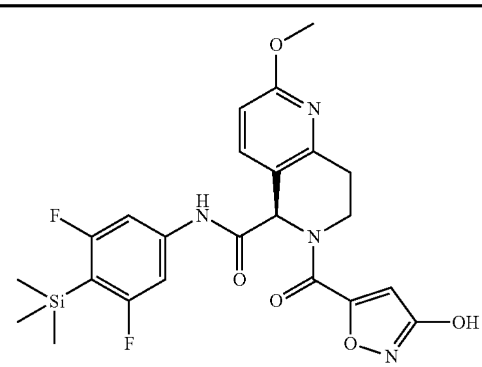 | | 503.1 (M + H) |
| 123 | (5S)-N-(3,5-difluoro-4-(trimethylsilyl)phenyl)-6-((3-hydroxy-1,2-oxazol-5-yl)carbonyl)-2-methoxy-5,6,7,8-tetrahydro-1,6-naphthyridine-5-carboxamide | 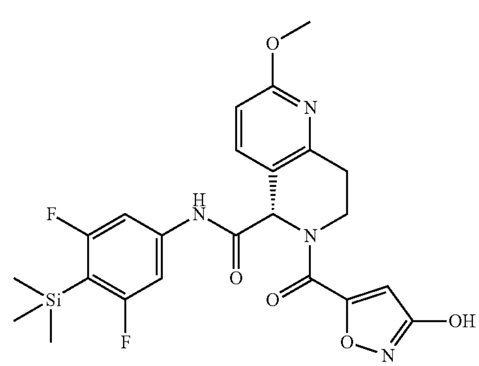 [SMILES: COc1ccc2c(n1)CCN(C(=O)c1cc(O)no1)[C@@H]2C(=O)Nc1cc(F)c([Si](C)(C)C)c(F)c1] | | 503.0 (M + H) |

TABLE 1-14-continued

| EXAMPLE | IUPACNAME | Structure | ADDITIVE | MS |
|---|---|---|---|---|
| 124 | (5R)-N-(3,5-difluoro-4-(trimethylsilyl)phenyl)-6-((3-hydroxy-1,2-oxazol-5-yl)acetyl)-2-methoxy-5,6,7,8-tetrahydro-1,6-naphthyridine-5-carboxamide | 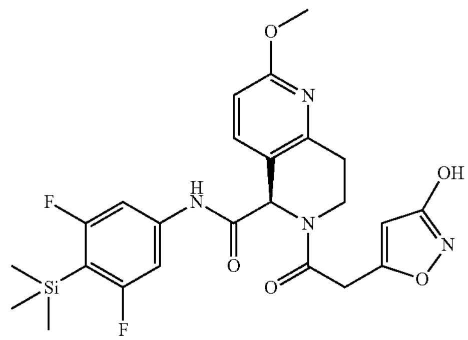 [SMILES: COc1ccc2c(n1)CCN(C(=O)Cc1cc(O)no1)[C@H]2C(=O)Nc1cc(F)c([Si](C)(C)C)c(F)c1] | | 517.1 (M + H) |
| 125 | 5-((5R)-5-((3,5-difluoro-4-(trimethylsilyl)phenyl)carbamoyl)-2-methoxy-7,8-dihydro-1,6-naphthyridin-6(5H)-yl)-5-oxopentanoic acid | 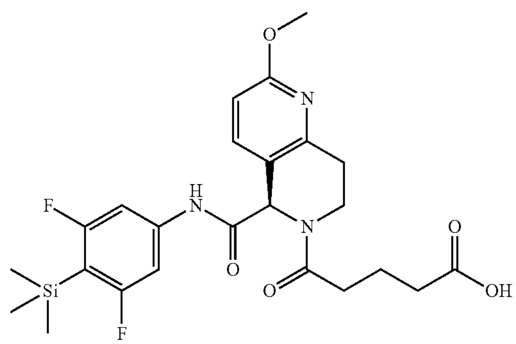 [SMILES: COc1ccc2c(n1)CCN(C(=O)CCCC(=O)O)[C@H]2C(=O)Nc1cc(F)c([Si](C)(C)C)c(F)c1] | | 504 (M − H) |
| 126 | (5R)-N-(3,5-difluoro-4-(trimethylsilyl)phenyl)-2-ethoxy-6-((3-hydroxy-1,2-oxazol-5-yl)carbonyl)-5,6,7,8-tetrahydro-1,6-naphthyridine-5-carboxamide | 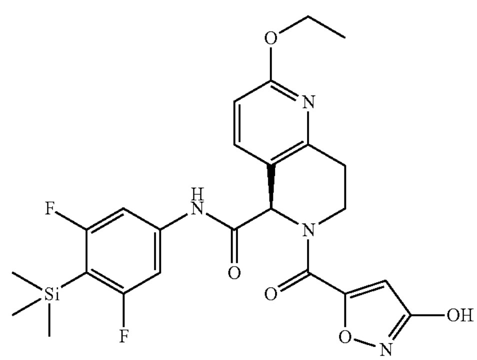 [SMILES: CCOc1ccc2c(n1)CCN(C(=O)c1cc(O)no1)[C@H]2C(=O)Nc1cc(F)c([Si](C)(C)C)c(F)c1] | | 517.1 (M + H) |
| 127 | (5S)-N-(3,5-difluoro-4-(trimethylsilyl)phenyl)-2-ethoxy-6-((3-hydroxy-1,2-oxazol-5-yl)carbonyl)-5,6,7,8-tetrahydro-1,6-naphthyridine-5-carboxamide | 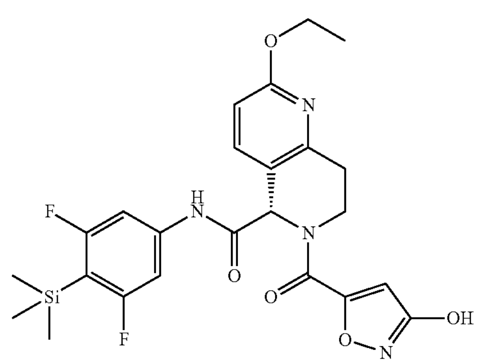 [SMILES: CCOc1ccc2c(n1)CCN(C(=O)c1cc(O)no1)[C@@H]2C(=O)Nc1cc(F)c([Si](C)(C)C)c(F)c1] | | 517.1 (M + H) |

TABLE 1-14-continued

| EXAMPLE | IUPACNAME | Structure | ADDITIVE | MS |
|---|---|---|---|---|
| 128 | (5R)-N-(3,5-difluoro-4-(trimethylsilyl)phenyl)-2-ethoxy-6-((3-hydroxy-1,2-oxazol-5-yl)acetyl)-5,6,7,8-tetrahydro-1,6-naphthyridine-5-carboxamide | 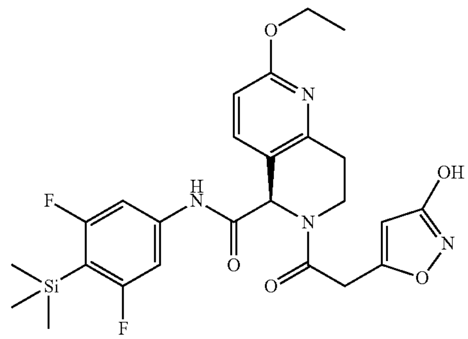 [SMILES: CCOc1ccc2c(n1)CCN(C(=O)Cc1cc(O)no1)[C@H]2C(=O)Nc1cc(F)c([Si](C)(C)C)c(F)c1] | | 531.1 (M + H) |
| 129 | 5-((5R)-5-((3,5-difluoro-4-(trimethylsilyl)phenyl)carbamoyl)-2-ethoxy-7,8-dihydro-1,6-naphthyridin-6(5H)-yl)-5-oxopentanoic acid | 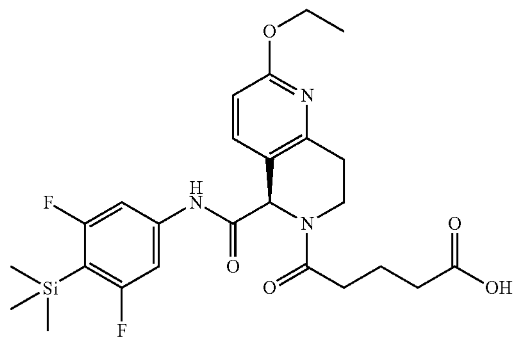 [SMILES: CCOc1ccc2c(n1)CCN(C(=O)CCCC(=O)O)[C@H]2C(=O)Nc1cc(F)c([Si](C)(C)C)c(F)c1] | | 518.1 (M − H) |
| 130 | 5-((1R)-1-((3,5-difluoro-4-(trimethylsilyl)phenyl)carbamoyl)-6-(methoxymethyl)-3,4-dihydroisoquinolin-2(1H)-yl)-5-oxopentanoic acid | 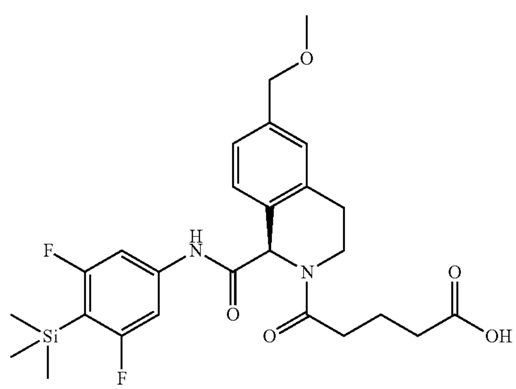 [SMILES: COCc1ccc2c(c1)CCN(C(=O)CCCC(=O)O)[C@H]2C(=O)Nc1cc(F)c([Si](C)(C)C)c(F)c1] | | 517.1 (M − H) |
| 131 | (1R)-N-(3,5-difluoro-4-(trimethylsilyl)phenyl)-2-((3-hydroxy-1,2-oxazol-5-yl)carbonyl)-6-(methoxymethyl)-1,2,3,4-tetrahydroisoquinoline-1-carboxamide | 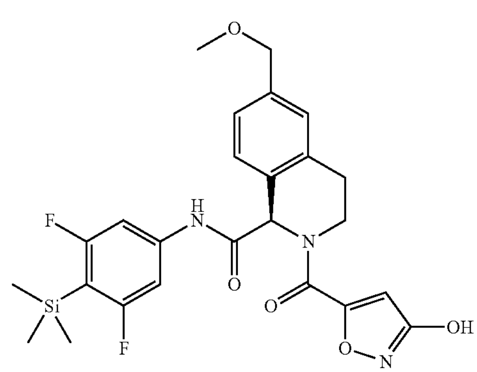 [SMILES: COCc1ccc2c(c1)CCN(C(=O)c1cc(O)no1)[C@H]2C(=O)Nc1cc(F)c([Si](C)(C)C)c(F)c1] | | 516.1 (M + H) |

TABLE 1-15

| EXAMPLE | IUPACNAME | Structure | ADDITIVE | MS |
|---|---|---|---|---|
| 132 | (1R)-N-(4-tert-butyl-3-fluorophenyl)-2-((3-hydroxy-1,2-oxazol-5-yl)acetyl)-6-(methoxymethyl)-1,2,3,4-tetrahydroisoquinoline-1-carboxamide | 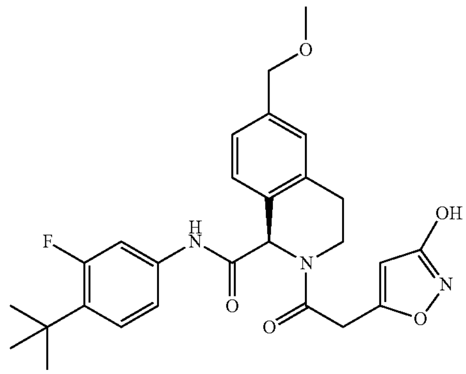 [SMILES: COCc1ccc2c(c1)CCN(C(=O)Cc1cc(O)no1)[C@H]2C(=O)Nc1ccc(C(C)(C)C)c(F)c1] | | 494.1 (M + H) |
| 133 | (1R)-N-(7-fluoro-1,1-dimethyl-2,3-dihydro-1H-inden-5-yl)-2-((3-hydroxy-1,2-oxazol-5-yl)carbonyl)-6-(methoxymethyl)-1,2,3,4-tetrahydroisoquinoline-1-carboxamide | 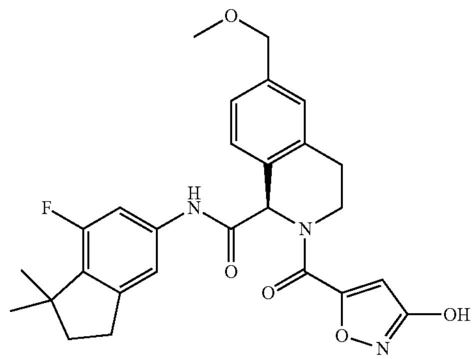 [SMILES: COCc1ccc2c(c1)CCN(C(=O)c1cc(O)no1)[C@H]2C(=O)Nc1cc(F)c2c(c1)CCC2(C)C] | | 494.2 (M + H) |
| 134 | 5-((1R)-1-((7-fluoro-1,1-dimethyl-2,3-dihydro-1H-inden-5-yl)carbamoyl)-6-(methoxymethyl)-3,4-dihydroisoquinolin-2(1H)-yl)-5-oxopentanoic acid | 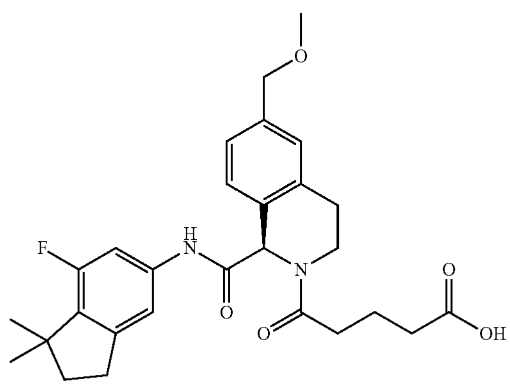 [SMILES: COCc1ccc2c(c1)CCN(C(=O)CCCC(=O)O)[C@H]2C(=O)Nc1cc(F)c2c(c1)CCC2(C)C] | | 495.1 (M − H) |
| 135 | 5-((1R)-1-((3-fluoro-4-(trimethylsilyl)phenyl)carbamoyl)-6-methoxy-3,4-dihydroisoquinolin-2(1H)-yl)-5-oxopentanoic acid | 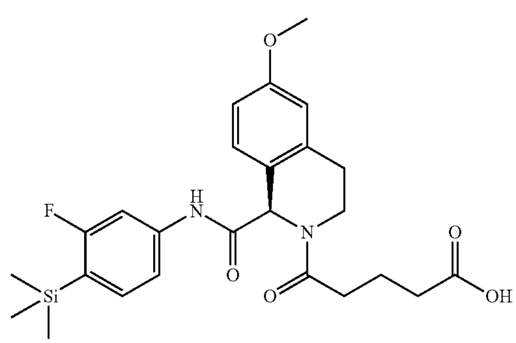 [SMILES: COc1ccc2c(c1)CCN(C(=O)CCCC(=O)O)[C@H]2C(=O)Nc1ccc([Si](C)(C)C)c(F)c1] | | 485.1 (M − H) |

TABLE 1-15-continued

| EXAMPLE | IUPACNAME | Structure | ADDITIVE | MS |
|---|---|---|---|---|
| 136 | (5R)-N-(3,5-difluoro-4-(trimethylsilyl)phenyl)-6-((3-hydroxy-1,2-oxazol-5-yl)carbonyl)-2-(methoxymethyl)-5,6,7,8-tetrahydro-1,6-naphthyridine-5-carboxamide | 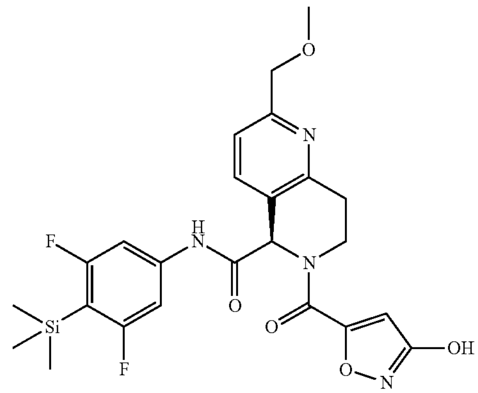 [SMILES: COCc1ccc2c(n1)CCN(C(=O)c1cc(O)no1)[C@H]2C(=O)Nc1cc(F)c([Si](C)(C)C)c(F)c1] | | 517.2 517.1 (M + H) |
| 137 | (1R)-N-(3,5-difluoro-4-(1-methoxy-2-methylpropan-2-yl)phenyl)-2-((3-hydroxy-1,2-oxazol-5-yl)carbonyl)-6-(methoxymethyl)-1,2,3,4-tetrahydroisoquinoline-1-carboxamide | 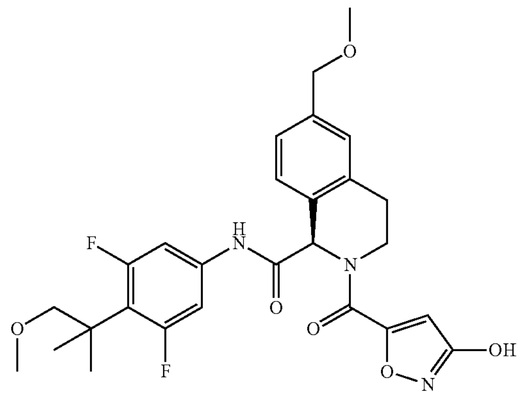 [SMILES: COCc1ccc2c(c1)CCN(C(=O)c1cc(O)no1)[C@H]2C(=O)Nc1cc(F)c(C(C)(C)COC)c(F)c1] | | 530.1 (M + H) |
| 138 | (5R)-N-(3,5-difluoro-4-(trimethylsilyl)phenyl)-6-((3-hydroxy-1,2-oxazol-5-yl)acetyl)-2-(methoxymethyl)-5,6,7,8-tetrahydro-1,6-naphthyridine-5-carboxamide | 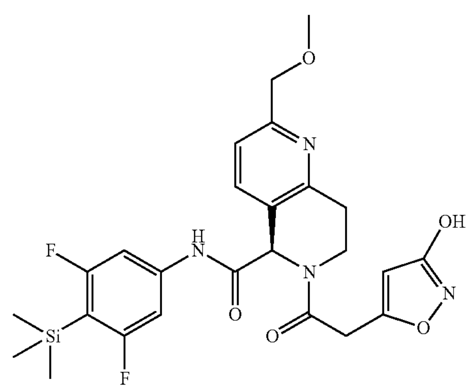 [SMILES: COCc1ccc2c(n1)CCN(C(=O)Cc1cc(O)no1)[C@H]2C(=O)Nc1cc(F)c([Si](C)(C)C)c(F)c1] | | 531.1 (M + H) |
| 139 | 5-((5R)-5-((3,5-difluoro-4-(trimethylsilyl)phenyl)carbamoyl)-2-(methoxymethyl)-7,8-dihydro-1,6-naphthyridin-6(5H)-yl)-5-oxopentanoic acid | 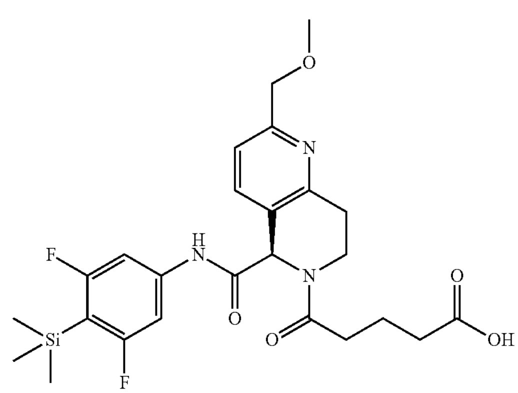 [SMILES: COCc1ccc2c(n1)CCN(C(=O)CCCC(=O)O)[C@H]2C(=O)Nc1cc(F)c([Si](C)(C)C)c(F)c1] | | 520.1 (M + H) |

TABLE 1-15-continued

| EXAMPLE | IUPACNAME | Structure | ADDITIVE | MS |
|---|---|---|---|---|
| 140 | 5-((5R)-5-((3-fluoro-4-(trimethylsilyl)phenyl)carbamoyl)-2-methoxy-7,8-dihydro-1,6-naphthyridin-6(5H)-yl)-5-oxopentanoic acid | 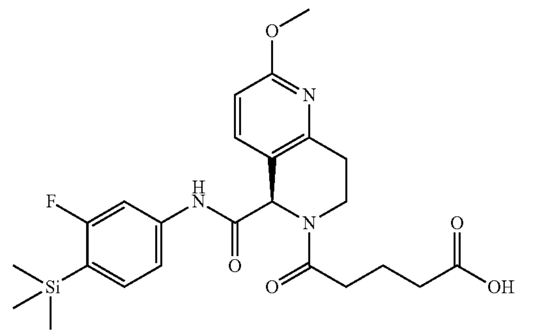 | | 488.2 (M + H) |
| 141 | 5-((1R)-1-((3,5-difluoro-4-(1-(2-methoxyethoxy)-2-methylpropan-2-yl)phenyl)carbamoyl)-6-ethoxy-3,4-dihydroisoquinolin-2(1H)-yl)-5-oxopentanoic acid | 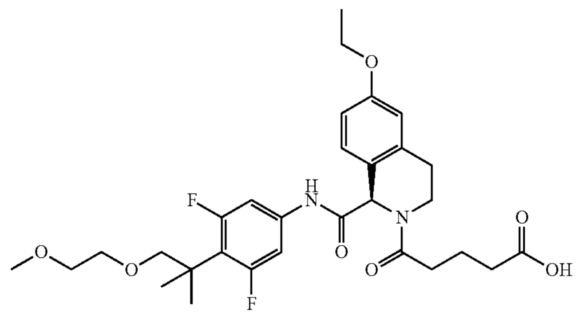 [SMILES: CCOc1ccc2c(c1)CCN(C(=O)CCCC(=O)O)[C@H]2C(=O)Nc1cc(F)c(C(C)(C)COCCOC)c(F)c1] | | 575.1 (M − H) |

TABLE 1-16

| EXAMPLE | IUPACNAME | Structure | ADDITIVE | MS |
|---|---|---|---|---|
| 142 | (1R)-N-(3,5-difluoro-4-(1-(2-methoxyethoxy)-2-methylpropan-2-yl)phenyl)-6-ethoxy-2-((3-hydroxy-1,2-oxazol-5-yl)carbonyl)-1,2,3,4-tetrahydroisoquinoline-1-carboxamide | 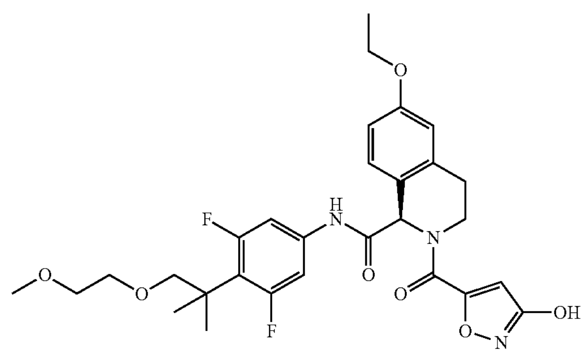 [SMILES: CCOc1ccc2c(c1)CCN(C(=O)c1cc(O)no1)[C@H]2C(=O)Nc1cc(F)c(C(C)(C)COCCOC)c(F)c1] | | 574.2 (M + H) |
| 143 | (1R)-N-(3,5-difluoro-4-(1-(2-methoxyethoxy)-2-methylpropan-2-yl)phenyl)-6-ethoxy-2-((3-hydroxy-1,2-oxazol-5-yl)acetyl)-1,2,3,4-tetrahydroisoquinoline-1-carboxamide | 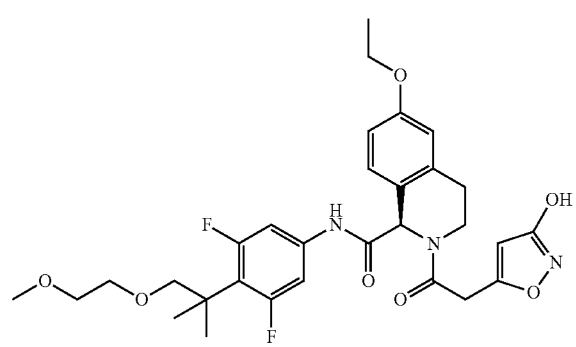 [SMILES: CCOc1ccc2c(c1)CCN(C(=O)Cc1cc(O)no1)[C@H]2C(=O)Nc1cc(F)c(C(C)(C)COCCOC)c(F)c1] | | 588.2 (M + H) |

TABLE 1-16-continued

| EXAMPLE | IUPACNAME | Structure | ADDITIVE | MS |
|---|---|---|---|---|
| 144 | 5-((1R)-1-((4-tert-butyl-3,5-difluorophenyl)carbamoyl)-6-(methoxymethyl)-3,4-dihydroisoquinolin-2(1H)-yl)-5-oxopentanoic acid | 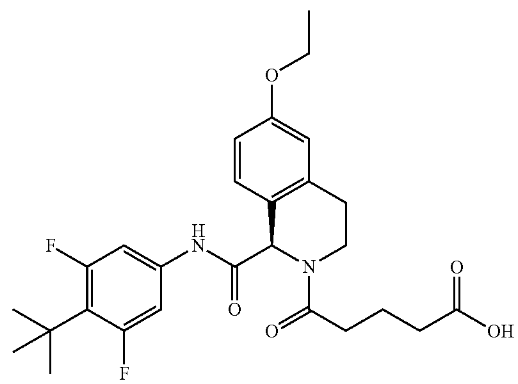 [SMILES: CCOc1ccc2c(c1)CCN(C(=O)CCCC(=O)O)[C@H]2C(=O)Nc1cc(F)c(C(C)(C)C)c(F)c1] | | 503.2 (M + H) |
| 145 | (5R)-2-ethoxy-N-(7-fluoro-1,1-dimethyl-2,3-dihydro-1H-inden-5-yl)-6-((3-hydroxy-1,2-oxazol-5-yl)carbonyl)-5,6,7,8-tetrahydro-1,6-naphthyridine-5-carboxamide | 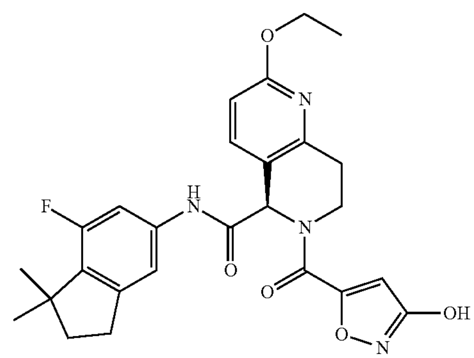 [SMILES: CCOc1ccc2c(n1)CCN(C(=O)c1cc(O)no1)[C@H]2C(=O)Nc1cc(F)c2c(c1)CCC2(C)C] | | 495.1 (M + H) |
| 146 | (5S)-2-ethoxy-N-(7-fluoro-1,1-dimethyl-2,3-dihydro-1H-inden-5-yl)-6-((3-hydroxy-1,2-oxazol-5-yl)carbonyl)-5,6,7,8-tetrahydro-1,6-naphthyridine-5-carboxamide | 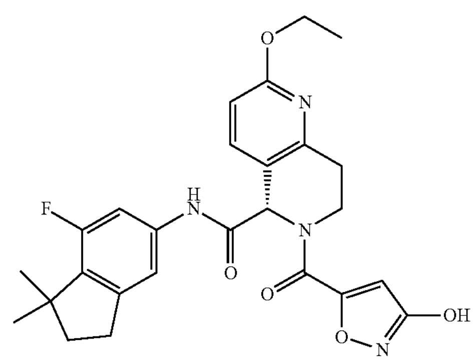 [SMILES: CCOc1ccc2c(n1)CCN(C(=O)c1cc(O)no1)[C@@H]2C(=O)Nc1cc(F)c2c(c1)CCC2(C)C] | | 495.1 (M + H) |
| 147 | (5R)-2-ethoxy-N-(7-fluoro-1,1-dimethyl-2,3-dihydro-1H-inden-5-yl)-6-((3-hydroxy-1,2-oxazol-5-yl)acetyl)-5,6,7,8-tetrahydro-1,6-naphthyridine-5-carboxamide | 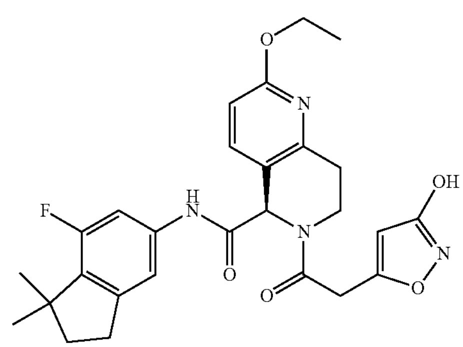 [SMILES: CCOc1ccc2c(n1)CCN(C(=O)Cc1cc(O)no1)[C@H]2C(=O)Nc1cc(F)c2c(c1)CCC2(C)C] | | 509.2 (M + H) |

TABLE 1-16-continued

| EXAMPLE | IUPACNAME | Structure | ADDITIVE | MS |
|---|---|---|---|---|
| 148 | 5-((5R)-2-ethoxy-5-((7-fluoro-1,1-dimethyl-2,3-dihydro-1H-inden-5-yl)carbamoyl)-7,8-dihydro-1,6-naphthyridin-6(5H)-yl)-5-oxopentanoic acid | 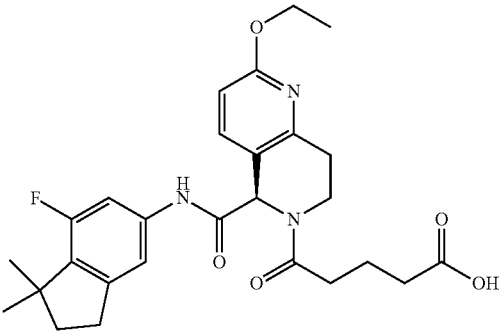 [SMILES: CCOc1ccc2c(n1)CCN(C(=O)CCCC(=O)O)[C@H]2C(=O)Nc1cc(F)c2c(c1)CCC2(C)C] | | 498.2 (M + H) |
| 149 | (5R)-2-ethoxy-N-(3-fluoro-4-(trimethylsilyl)phenyl)-6-((3-hydroxy-1,2-oxazol-5-yl)carbonyl)-5,6,7,8-tetrahydro-1,6-naphthyridine-5-carboxamide | 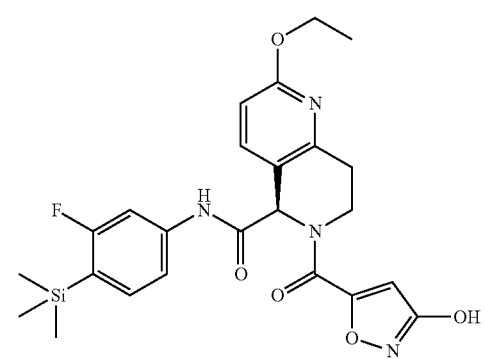 [SMILES: CCOc1ccc2c(n1)CCN(C(=O)c1cc(O)no1)[C@H]2C(=O)Nc1ccc([Si](C)(C)C)c(F)c1] | | 499.1 (M + H) |
| 150 | (5S)-2-ethoxy-N-(3-fluoro-4-(trimethylsilyl)phenyl)-6-((3-hydroxy-1,2-oxazol-5-yl)carbonyl)-5,6,7,8-tetrahydro-1,6-naphthyridine-5-carboxamide | 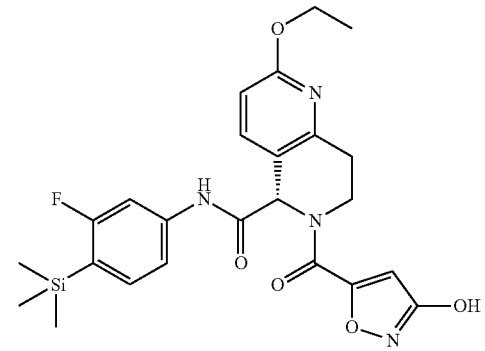 [SMILES: CCOc1ccc2c(n1)CCN(C(=O)c1cc(O)no1)[C@@H]2C(=O)Nc1ccc([Si](C)(C)C)c(F)c1] | | 499.1 (M + H) |
| 151 | (5R)-2-ethoxy-N-(3-fluoro-4-(trimethylsilyl)phenyl)-6-((3-hydroxy-1,2-oxazol-5-yl)acetyl)-5,6,7,8-tetrahydro-1,6-naphthyridine-5-carboxamide | 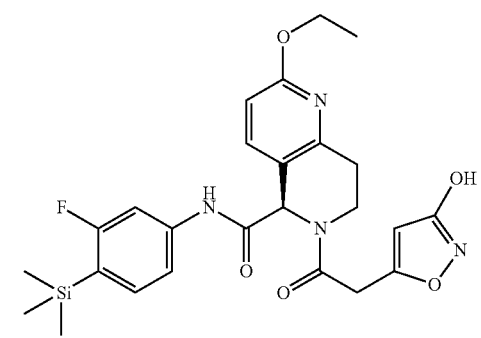 [SMILES: CCOc1ccc2c(n1)CCN(C(=O)Cc1cc(O)no1)[C@H]2C(=O)Nc1ccc([Si](C)(C)C)c(F)c1] | | 513.1 (M + H) |

TABLE 1-17

| EXAMPLE | IUPACNAME | Structure | ADDITIVE | MS |
|---|---|---|---|---|
| 152 | 5-((5R)-2-ethoxy-5-((3-fluoro-4-(trimethylsilyl)phenyl)carbamoyl)-7,8-dihydro-1,6-naphthyridin-6(5H)-yl)-5-oxopentanoic acid | 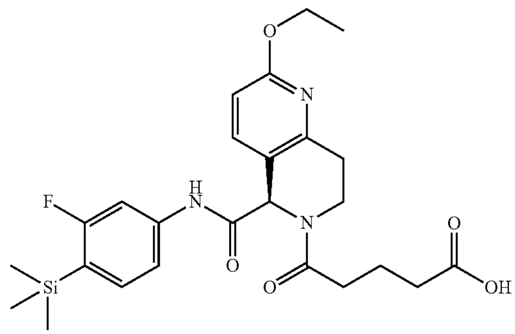 [SMILES: CCOc1ccc2c(n1)CCN(C(=O)CCCC(=O)O)[C@H]2C(=O)Nc1ccc([Si](C)(C)C)c(F)c1] | | 502.2 (M + H) |
| 153 | 5-((1R)-1-((4-(1-(2,2-difluoroethoxy)-2-methylpropan-2-yl)-3,5-difluorophenyl)carbamoyl)-6-ethoxy-3,4-dihydroisoquinolin-2(1H)-yl)-5-oxopentanoic acid | 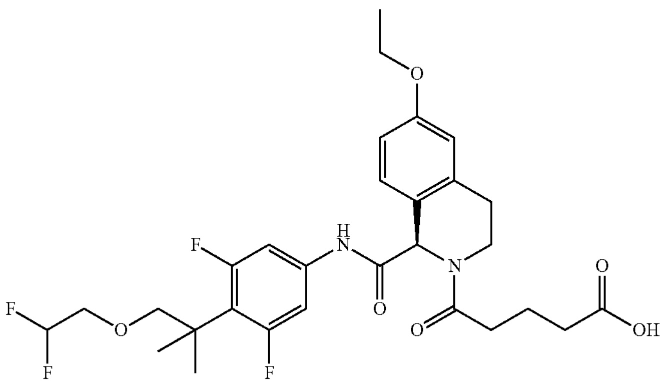 [SMILES: CCOc1ccc2c(c1)CCN(C(=O)CCCC(=O)O)[C@H]2C(=O)Nc1cc(F)c(C(C)(C)COCC(F)F)c(F)c1] | | 581.1 (M − H) |
| 154 | (1R)-N-(4-(1-(2,2-difluoroethoxy)-2-methylpropan-2-yl)-3,5-difluorophenyl)-6-ethoxy-2-((3-hydroxy-1,2-oxazol-5-yl)carbonyl)-1,2,3,4-tetrahydroisoquinoline-1-carboxamide | 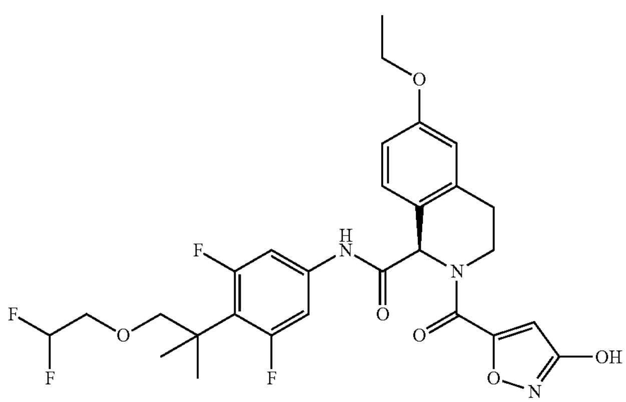 [SMILES: CCOc1ccc2c(c1)CCN(C(=O)c1cc(O)no1)[C@H]2C(=O)Nc1cc(F)c(C(C)(C)COCC(F)F)c(F)c1] | | 580.1 (M + H) |
| 155 | (1R)-N-(4-(1-(2,2-difluoroethoxy)-2-methylpropan-2-yl)-3,5-difluorophenyl)-6-ethoxy-2-((3-hydroxy-1,2-oxazol-5-yl)acetyl)-1,2,3,4-tetrahydroisoquinoline-1-carboxamide | 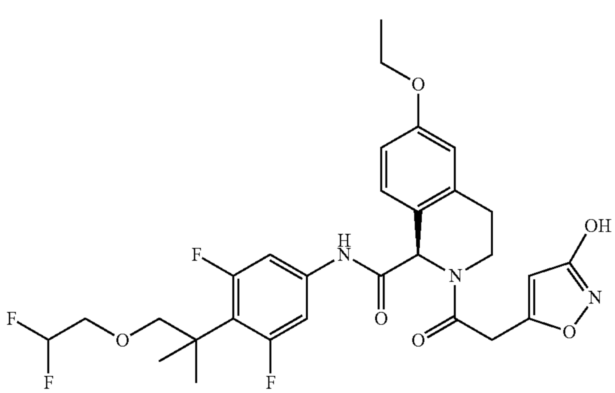 [SMILES: CCOc1ccc2c(c1)CCN(C(=O)Cc1cc(O)no1)[C@H]2C(=O)Nc1cc(F)c(C(C)(C)COCC(F)F)c(F)c1] | | 592.1 (M − H) |

TABLE 1-17-continued

| EXAMPLE | IUPACNAME | Structure | ADDITIVE | MS |
|---|---|---|---|---|
| 156 | 5-((1R)-1-((3,5-difluoro-4-(trimethylsilyl)phenyl)carbamoyl)-6-methoxy-3,4-dihydro-isoquinolin-2(1H)-yl)-3-hydroxy-3-methyl-5-oxopentanoic acid | 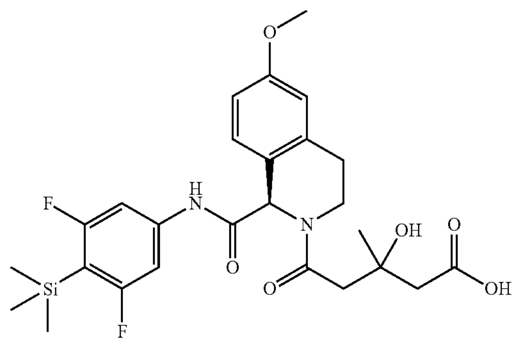 [SMILES: COc1ccc2c(c1)CCN(C(=O)CC(C)(O)CC(=O)O)[C@H]2C(=O)Nc1cc(F)c([Si](C)(C)C)c(F)c1] | | 535.1 (M + H) |
| 157 | (1R)-N-(4-(1-(cyclopropyl-methoxy)-2-methylpropan-2-yl)-3,5-difluorophenyl)-2-((3-hydroxy-1,2-oxazol-5-yl)acetyl)-6-methoxy-1,2,3,4-tetrahydro-isoquinoline-1-carboxamide | 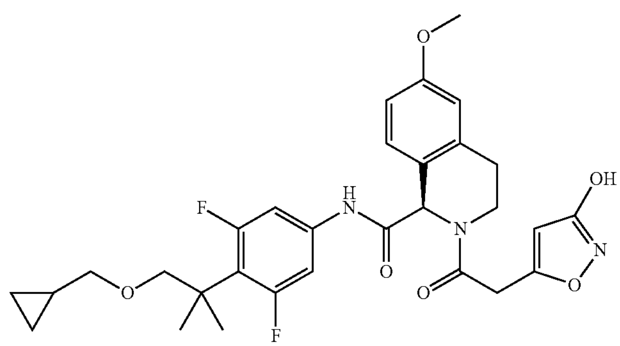 [SMILES: COc1ccc2c(c1)CCN(C(=O)Cc1cc(O)no1)[C@H]2C(=O)Nc1cc(F)c(C(C)(C)COCC2CC2)c(F)c1] | | 568.1 (M − H) |
| 158 | (1R)-N-(4-(1-(cyclopropyl-methoxy)-2-methylpropan-2-yl)-3,5-difluorophenyl)-2-((3-hydroxy-1,2-oxazol-5-yl)carbonyl)-6-methoxy-1,2,3,4-tetrahydro-isoquinoline-1-carboxamide | 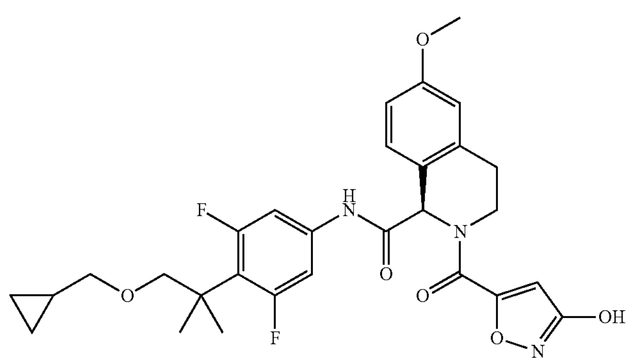 [SMILES: COc1ccc2c(c1)CCN(C(=O)c1cc(O)no1)[C@H]2C(=O)Nc1cc(F)c(C(C)(C)COCC2CC2)c(F)c1] | | 556.2 (M + H) |
| 159 | (1R)-N-(4-(1-(2,2-difluoroethoxy)-2-methylpropan-2-yl)-3,5-difluorophenyl)-2-((3-hydroxy-1,2-oxazol-5-yl)acetyl)-6-methoxy-1,2,3,4-tetrahydro-isoquinoline-1-carboxamide | 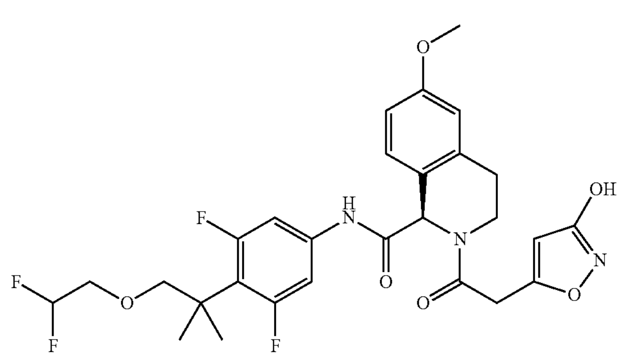 [SMILES: COc1ccc2c(c1)CCN(C(=O)Cc1cc(O)no1)[C@H]2C(=O)Nc1cc(F)c(C(C)(C)COCC(F)F)c(F)c1] | | 578.0 (M − H) |

TABLE 1-17-continued

| EXAMPLE | IUPACNAME | Structure | ADDITIVE | MS |
|---|---|---|---|---|
| 160 | (1R)-N-(4-(1-(2,2-difluoroethoxy)-2-methylpropan-2-yl)-3,5-difluorophenyl)-2-((3-hydroxy-1,2-oxazol-5-yl)carbonyl)-6-methoxy-1,2,3,4-tetrahydro-isoquinoline-1-carboxamide | 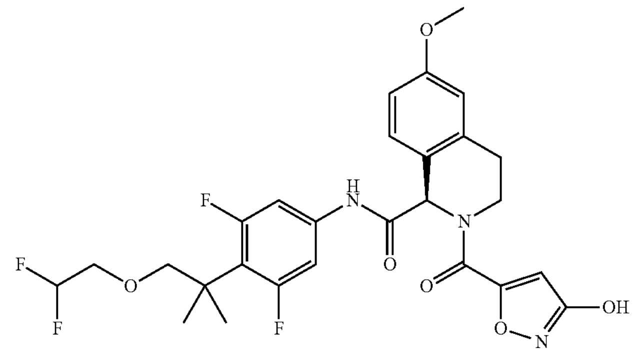 [SMILES: COc1ccc2c(c1)CCN(C(=O)c1cc(O)no1)[C@H]2C(=O)Nc1cc(F)c(C(C)(C)COCC(F)F)c(F)c1] | | 564.0 (M − H) |
| 161 | 5-((1R)-1-((4-(1-(cyclopropyl-methoxy)-2-methylpropan-2-yl)-3,5-difluorophenyl)carbamoyl)-6-methoxy-3,4-dihydro-isoquinolin-2(1H)-yl)-5-oxopentanoic acid | 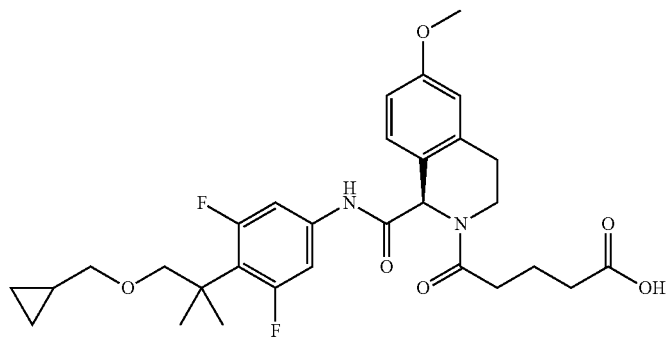 [SMILES: COc1ccc2c(c1)CCN(C(=O)CCCC(=O)O)[C@H]2C(=O)Nc1cc(F)c(C(C)(C)COCC2CC2)c(F)c1] | | 557.2 (M − H) |

TABLE 1-18

| EXAMPLE | IUPACNAME | Structure | ADDITIVE | MS |
|---|---|---|---|---|
| 162 | 5-((1R)-1-((4-(1-(2,2-difluoroethoxy)-2-methyl-propan-2-yl)-3,5-difluorophenyl)carbamoyl)-6-methoxy-3,4-dihydro-isoquinolin-2(1H)-yl)-5-oxopentanoic acid | 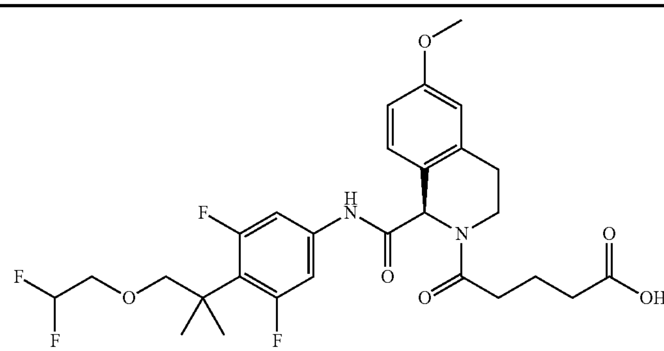 | | 567.1 (M − H) |
| 163 | (1R)-N-(3(5-difluoro-4-(1-methoxy-2-methylpropan-2-yl)phenyl)-6-ethoxy-2-((3-hydroxy-1,2-oxazol-5-yl)carbonyl)-1,2,3,4-tetrahydro-isoquinoline-1-carboxamide | 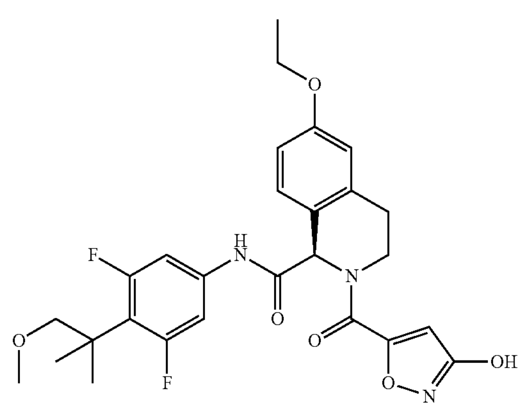 [SMILES: CCOc1ccc2c(c1)CCN(C(=O)c1cc(O)no1)[C@H]2C(=O)Nc1cc(F)c(C(C)(C)COC)c(F)c1] | | 530.1 (M + H) |

TABLE 1-18-continued

| EXAMPLE | IUPACNAME | Structure | ADDITIVE | MS |
|---|---|---|---|---|
| 164 | 5-((1R)-1-((3,5-difluoro-4-(1-methoxy-2-methylpropan-2-yl)phenyl)carbamoyl)-6-ethoxy-3,4-dihydroisoquinolin-2(1H)-yl)-5-oxopentanoic acid | 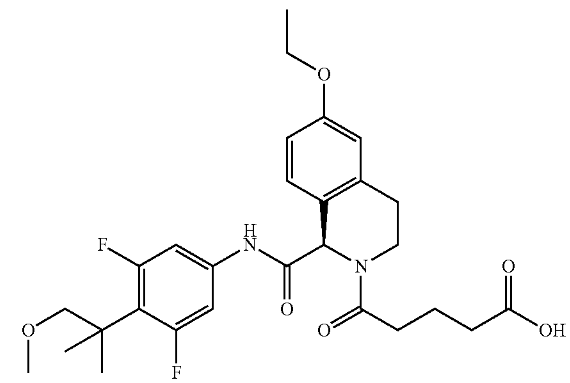 [SMILES: CCOc1ccc2c(c1)CCN(C(=O)CCCC(=O)O)[C@H]2C(=O)Nc1cc(F)c(C(C)(C)COC)c(F)c1] | | 531.1 (M − H) |
| 165 | (1R)-N-(3,5-difluoro-4-(1-methoxy-2-methylpropan-2-yl)phenyl)-6-ethoxy-2-((3-hydroxy-1,2-oxazol-5-yl)acetyl)-1,2,3,4-tetrahydroisoquinoline-1-carboxamide | 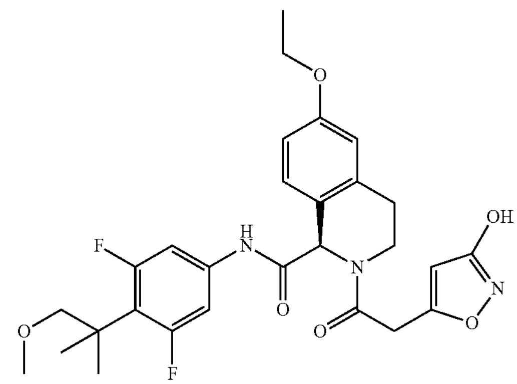 [SMILES: CCOc1ccc2c(c1)CCN(C(=O)Cc1cc(O)no1)[C@H]2C(=O)Nc1cc(F)c(C(C)(C)COC)c(F)c1] | | 542.1 (M − H) |
| 166 | 5-((1R)-6-ethoxy-1-((4-(1-ethoxy-2-methylpropan-2-yl)-3,5-difluorophenyl)carbamoyl)-3,4-dihydroisoquinolin-2(1H)-yl)-5-oxopentanoic acid | 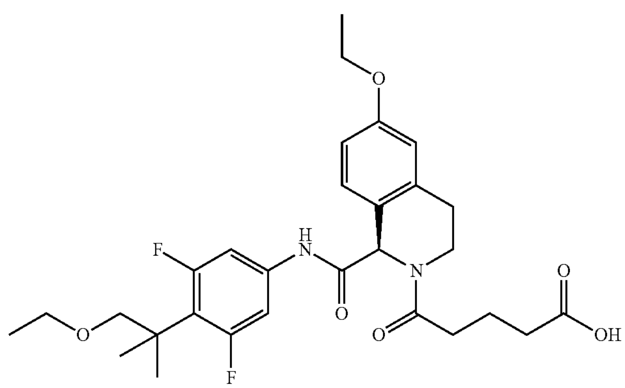 [SMILES: CCOCC(C)(C)c1c(F)cc(NC(=O)[C@H]2c3ccc(OCC)cc3CCN2C(=O)CCCC(=O)O)cc1F] | | 547.2 (M + H) |
| 167 | (1R)-6-ethoxy-N-(4-(1-ethoxy-2-methylpropan-2-yl)-3,5-difluorophenyl)-2-((3-hydroxy-1,2-oxazol-5-yl)carbonyl)-1,2,3,4-tetrahydroisoquinoline-1-carboxamide | 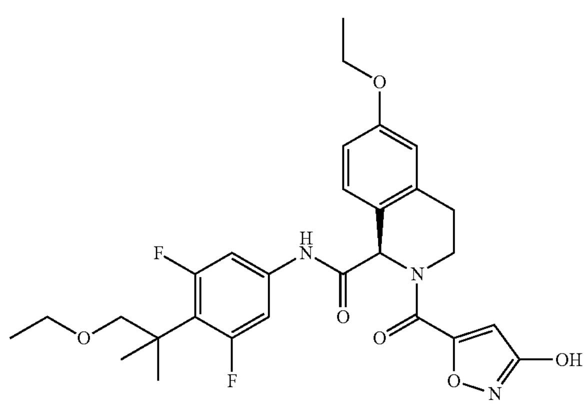 [SMILES: CCOCC(C)(C)c1c(F)cc(NC(=O)[C@H]2c3ccc(OCC)cc3CCN2C(=O)c2cc(O)no2)cc1F] | | 544.2 (M + H) |

TABLE 1-18-continued

| EXAMPLE | IUPACNAME | Structure | ADDITIVE | MS |
|---|---|---|---|---|
| 168 | (1R)-6-ethoxy-N-(4-(1-ethoxy-2-methylpropan-2-yl)-3,5-difluorophenyl)-2-((3-hydroxy-1,2-oxazol-5-yl)acetyl)-1,2,3,4-tetrahydro-isoquinoline-1-carboxamide | 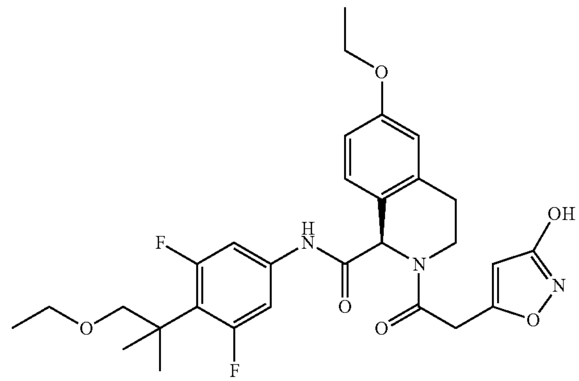 [SMILES: CCOCC(C)(C)c1c(F)cc(NC(=O)[C@H]2c3ccc(OCC)cc3CCN2C(=O)Cc2cc(O)no2)cc1F] | | 556.1 (M − H) |
| 169 | (1R)-N-(7-fluoro-1,1-dimethyl-2,3-dihydro-1H-inden-5-yl)-2-((3-hydroxy-1,2-oxazol-5-yl)acetyl)-6-(methoxymethyl)-1,2,3,4-tetrahydro-isoquinoline-1-carboxamide | 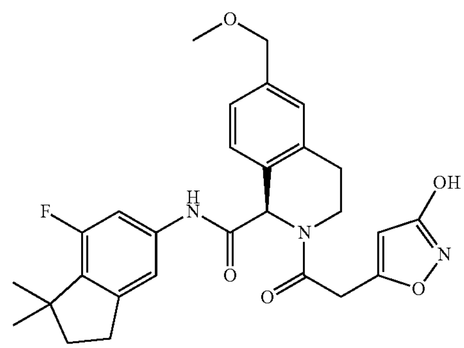 [SMILES: COCc1ccc2c(c1)CCN(C(=O)Cc1cc(O)no1)[C@H]2C(=O)Nc1cc(F)c2c(c1)CCC2(C)C] | | 506.1 (M − H) |
| 170 | (1R)-N-(4-(1-ethoxy-2-methylpropan-2-yl)-3,5-difluorophenyl)-2-((3-hydroxy-1,2-oxazol-5-yl)acetyl)-6-methoxy-1,2,3,4-tetrahydro-isoquinoline-1-carboxamide | 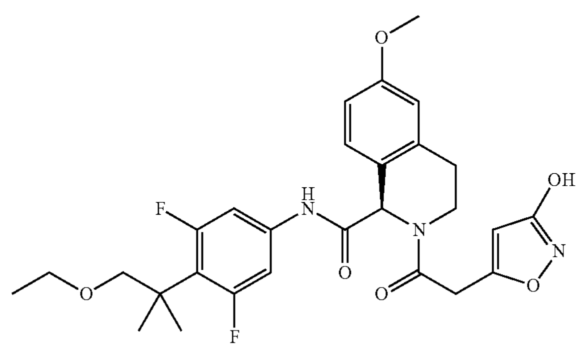 [SMILES: CCOCC(C)(C)c1c(F)cc(NC(=O)[C@H]2c3ccc(OC)cc3CCN2C(=O)Cc2cc(O)no2)cc1F] | | 542.2 (M − H) |
| 171 | (1R)-N-(4-(1-ethoxy-2-methylpropan-2-yl)-3,5-difluorophenyl)-2-((3-hydroxy-1,2-oxazol-5-yl)carbonyl)-6-methoxy-1,2,3,4-tetrahydro-isoquinoline-1-carboxamide | 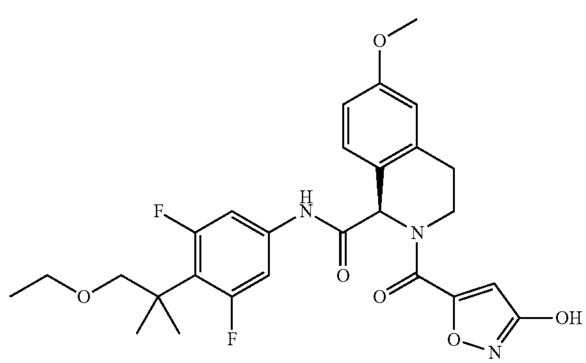 [SMILES: CCOCC(C)(C)c1c(F)cc(NC(=O)[C@H]2c3ccc(OC)cc3CCN2C(=O)c2cc(O)no2)cc1F] | | 530.1 (M + H) |

TABLE 1-19

| EXAMPLE | IUPACNAME | Structure | ADDITIVE | MS |
|---|---|---|---|---|
| 172 | 5-((1R)-1-((4-(1-ethoxy-2-methylpropan-2-yl)-3,5-difluorophenyl)carbamoyl)-6-methoxy-3,4-dihydroisoquinolin-2(1H)-yl)-5-oxopentanoic acid | 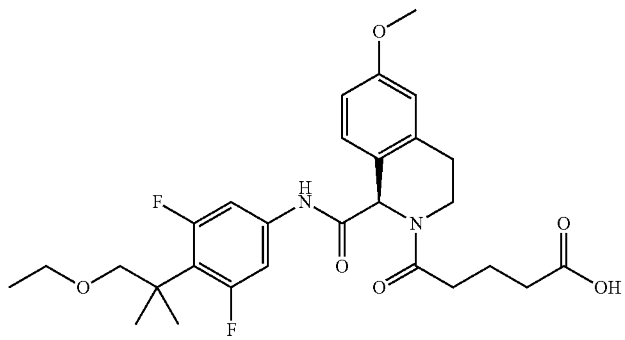 [SMILES: CCOCC(C)(C)c1c(F)cc(NC(=O)[C@H]2c3ccc(OC)cc3CCN2C(=O)CCCC(=O)O)cc1F] | | 531.1 (M − H) |
| 173 | (5R)-N-(4-(ethyl(dimethyl)silyl)-3,5-difluorophenyl)-6-((3-hydroxy-1,2-oxazol-5-yl)acetyl)-2-(methoxymethyl)-5,6,7,8-tetrahydro-1,6-naphthyridine-5-carboxamide | 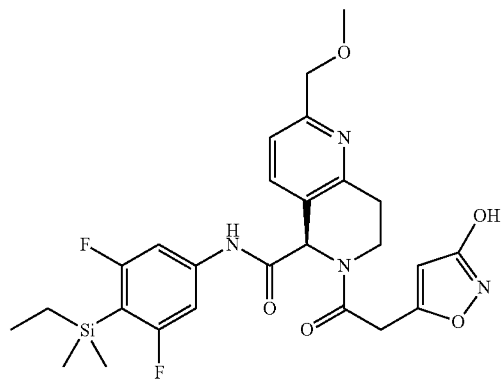 [SMILES: CC[Si](C)(C)c1c(F)cc(NC(=O)[C@H]2c3ccc(COC)nc3CCN2C(=O)Cc2cc(O)no2)cc1F] | | 545.1 (M + H) |
| 174 | (5R)-N-(4-(ethyl(dimethyl)silyl)-3,5-difluorophenyl)-6-((3-hydroxy-1,2-oxazol-5-yl)carbonyl)-2-(methoxymethyl)-5,6,7,8-tetrahydro-1,6-naphthyridine-5-carboxamide | 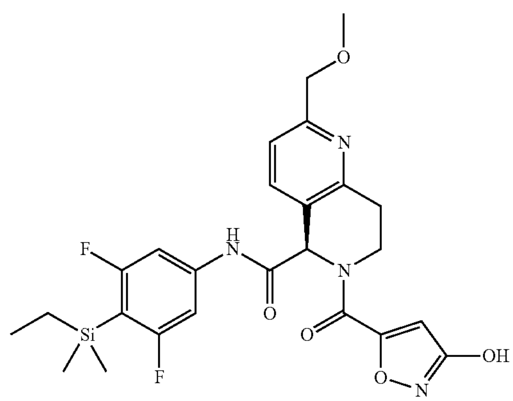 [SMILES: CC[Si](C)(C)c1c(F)cc(NC(=O)[C@H]2c3ccc(COC)nc3CCN2C(=O)c2cc(O)no2)cc1F] | | 531.1 (M + H) |
| 175 | 5-((5R)-5-((4-(ethyl(dimethyl)silyl)-3,5-difluorophenyl)carbamoyl)-2-(methoxymethyl)-7,8-dihydro-1,6-naphthyridin-6(5H)-yl)-5-oxopentanoic acid | 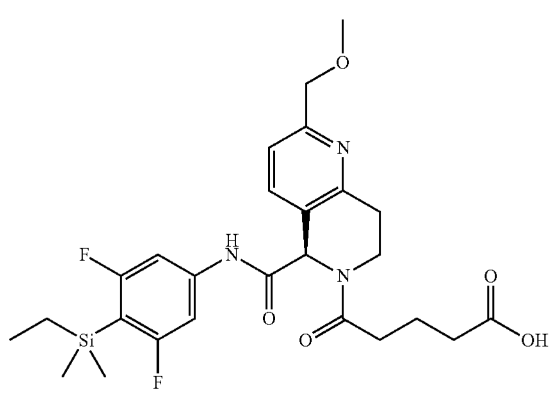 [SMILES: CC[Si](C)(C)c1c(F)cc(NC(=O)[C@H]2c3ccc(COC)nc3CCN2C(=O)CCCC(=O)O)cc1F] | | 534.2 (M + H) |

TABLE 1-19-continued

| EXAMPLE | IUPACNAME | Structure | ADDITIVE | MS |
|---|---|---|---|---|
| 176 | 5-((1R)-1-((7-fluoro-1,1-dimethyl-2,3-dihydro-1H-inden-5-yl)carbamoyl)-6-methoxy-3,4-dihydroisoquinolin-2(1H)-yl)-5-oxopentanoicacid | 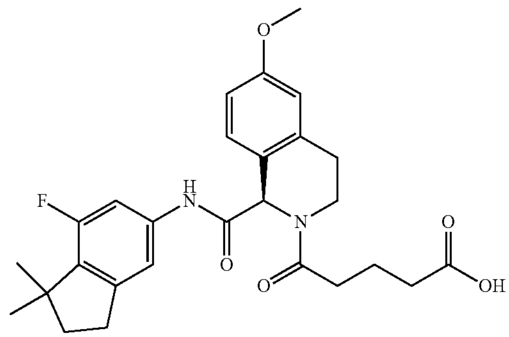 [SMILES: COc1ccc2c(c1)CCN(C(=O)CCCC(=O)O)[C@H]2C(=O)Nc1cc(F)c2c(c1)CCC2(C)C] | | 483.1 (M + H) |
| 177 | 4-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)-4-oxobutanoic acid | 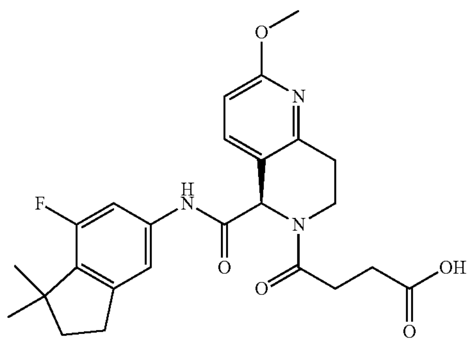 [SMILES: COc1ccc2c(n1)CCN(C(=O)CCC(=O)O)[C@H]2C(=O)Nc1cc(F)c2c(c1)CCC2(C)C] | | 470.2 (M + H) |
| 178 | 4-((5R)-5-((3,5-difluoro-4-(trimethylsilyl)phenyl)carbamoyl)-2-methoxy-7,8-dihydro-1,6-naphthyridin-6(5H)-yl)-4-oxobutanoic acid | 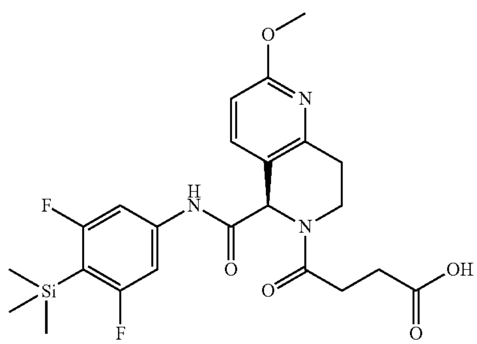 [SMILES: COc1ccc2c(n1)CCN(C(=O)CCC(=O)O)[C@H]2C(=O)Nc1cc(F)c([Si](C)(C)C)c(F)c1] | | 490.2 (M − H) |
| 179 | 5-((1R)-1-((3,5-difluoro-4-(trimethylsilyl)phenyl)carbamoyl)-6-ethoxy-3,4-dihydroisoquinolin-2(1H)-yl)-5-oxopentanoic acid | 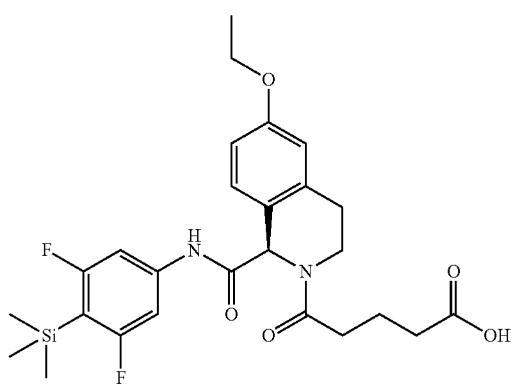 [SMILES: CCOc1ccc2c(c1)CCN(C(=O)CCCC(=O)O)[C@H]2C(=O)Nc1cc(F)c([Si](C)(C)C)c(F)c1] | | 517.1 (M − H) |

TABLE 1-19-continued

| EXAMPLE | IUPACNAME | Structure | ADDITIVE | MS |
|---|---|---|---|---|
| 180 | 4-((1R)-1-((3,5-difluoro-4-(trimethylsilyl)phenyl)carbamoyl)-6-ethoxy-3,4-dihydroisoquinolin-2(1H)-yl)-4-oxobutanoic acid | 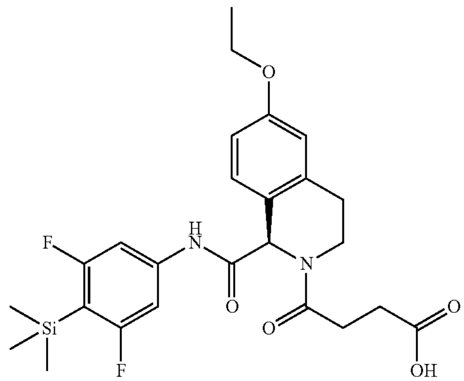 [SMILES: CCOc1ccc2c(c1)CCN(C(=O)CCC(=O)O)[C@H]2C(=O)Nc1cc(F)c([Si](C)(C)C)c(F)c1] | | 503.0 (M − H) |
| 181 | 5-((1R)-6-((difluoromethoxy)methyl)-1-((3,5-difluoro-4-(trimethylsilyl)phenyl)carbamoyl)-3,4-dihydroisoquinolin-2(1H)-yl)-5-oxopentanoic acid | 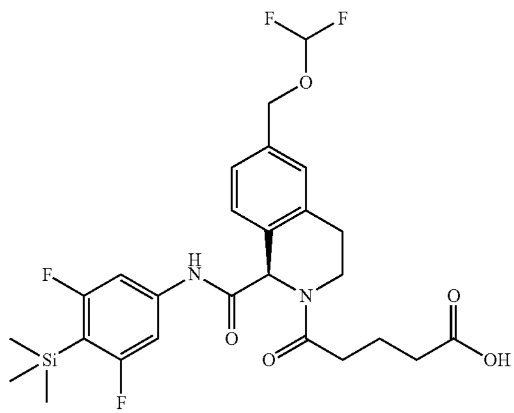 [SMILES: C[Si](C)(C)c1c(F)cc(NC(=O)[C@H]2c3ccc(COC(F)F)cc3CCN2C(=O)CCCC(=O)O)cc1F] | | 553.0 (M − H) |

TABLE 1-20

| EXAMPLE | IUPACNAME | Structure | ADDITIVE | MS |
|---|---|---|---|---|
| 182 | 5-((1R)-6-ethoxy-1-((7-fluoro-1,1-dimethyl-2,3-dihydro-1H-inden-5-yl)carbamoyl)-3,4-dihydroisoquinolin-2(1H)-yl)-5-oxopentanoic acid | 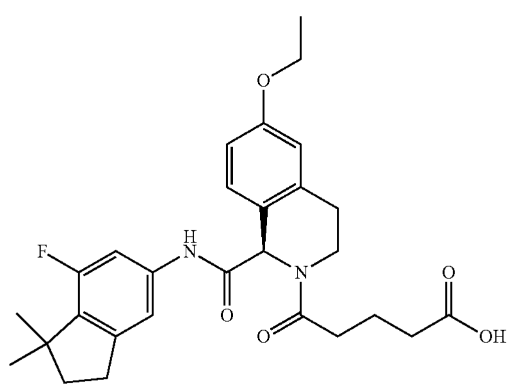 [SMILES: CCOc1ccc2c(c1)CCN(C(=O)CCCC(=O)O)[C@H]2C(=O)Nc1cc(F)c2c(c1)CCC2(C)C] | | 497.2 (M + H) |

TABLE 1-20-continued

| EXAMPLE | IUPACNAME | Structure | ADDITIVE | MS |
|---|---|---|---|---|
| 183 | 5-((1R)-6-ethoxy-1-((3-fluoro-4-(trimethylsilyl)phenyl)carbamoyl)-3,4-dihydroisoquinolin-2(1H)-yl)-5-oxopentanoic acid | 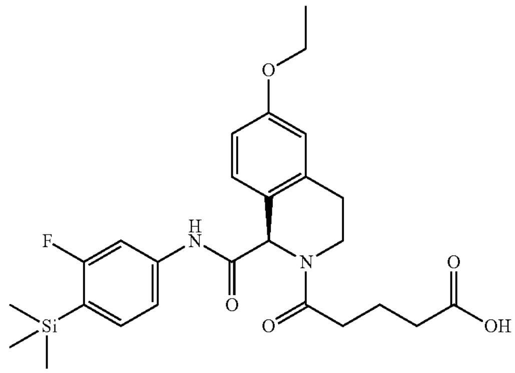 [SMILES: CCOc1ccc2c(c1)CCN(C(=O)CCCC(=O)O)[C@H]2C(=O)Nc1ccc([Si](C)(C)C)c(F)c1] | | 499.0 (M − H) |
| 184 | 5-((1R)-1-((2,5-difluoro-4-(trimethylsilyl)phenyl)carbamoyl)-6-ethoxy-3,4-dihydroisoquinolin-2(1H)-yl)-5-oxopentanoic acid | 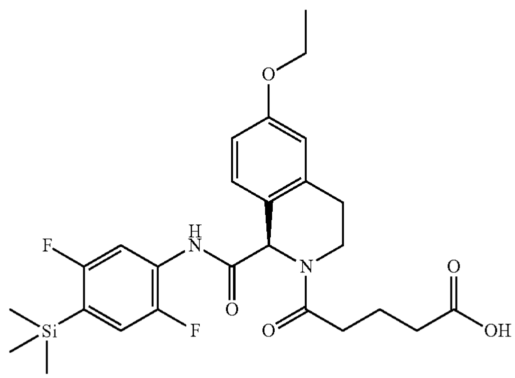 [SMILES: CCOc1ccc2c(c1)CCN(C(=O)CCCC(=O)O)[C@H]2C(=O)Nc1cc(F)c([Si](C)(C)C)cc1F] | | 517.1 (M − H) |
| 185 | 5-((1-((3(5-difluoro-4-(trimethylsilyl)phenyl)carbamoyl)-6-methoxy-3,4-dihydroisoquinolin-2(1H)-yl)carbonyl)-1-methyl-1H-pyrazole-3-carboxylic acid | 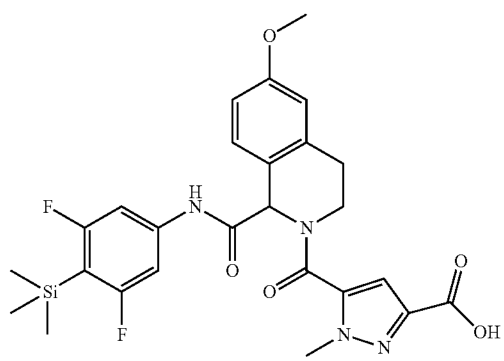 [SMILES: COc1ccc2c(c1)CCN(C(=O)c1cc(C(=O)O)nn1C)C2C(=O)Nc1cc(F)c([Si](C)(C)C)c(F)c1] | | 543.1 (M + H) |
| 186 | ethyl N-((1-((3,5-difluoro-4-(trimethylsilyl)phenyl)carbamoyl)-6-methoxy-3,4-dihydroisoquinolin-2(1H)-yl)carbonyl)-beta-alaninate | 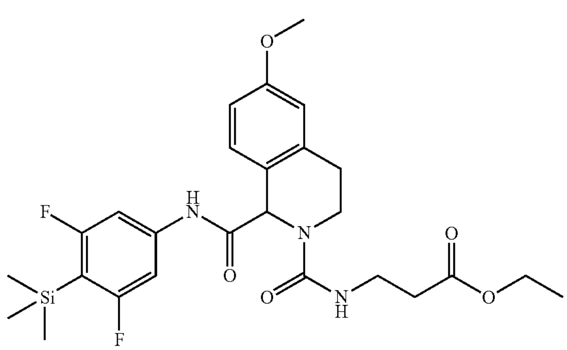 [SMILES: CCOC(=O)CCNC(=O)N1CCc2cc(OC)ccc2C1C(=O)Nc1cc(F)c([Si](C)(C)C)c(F)c1] | | 534.1 (M + H) |

TABLE 1-20-continued

| EXAMPLE | IUPACNAME | Structure | ADDITIVE | MS |
|---|---|---|---|---|
| 187 | (1R)-N-(3,5-difluoro-4-(trimethylsilyl)phenyl)-2-((2,4-dioxo-1,3-thiazolidin-5-yl)acetyl)-6-methoxy-1,2,3,4-tetrahydroisoquinoline-1-carboxamide | 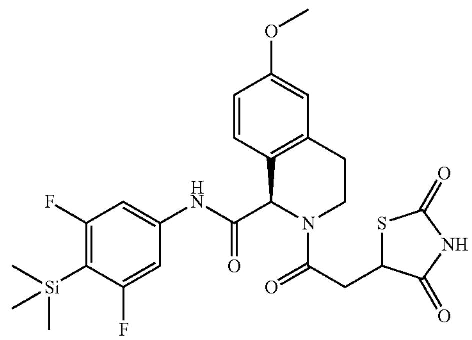 [SMILES: COc1ccc2c(c1)CCN(C(=O)CC1SC(=O)NC1=O)[C@H]2C(=O)Nc1cc(F)c([Si](C)(C)C)c(F)c1] | | 546.0 (M − H) |
| 188 | N-(((1R)-1-((3,5-difluoro-4-(trimethylsilyl)phenyl)carbamoyl)-6-methoxy-3,4-dihydroisoquinolin-2(1H)-yl)carbonyl)-beta-alanine | 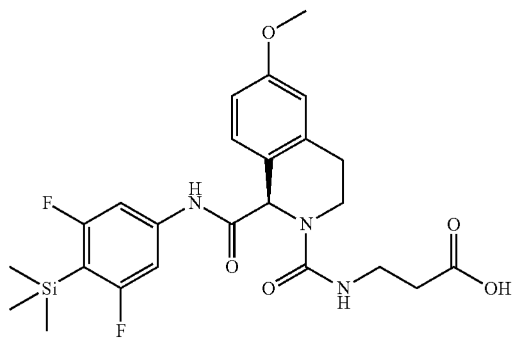 [SMILES: COc1ccc2c(c1)CCN(C(=O)NCCC(=O)O)[C@H]2C(=O)Nc1cc(F)c([Si](C)(C)C)c(F)c1] | | 506.1 (M + H) |
| 189 | 5-(2-((1R)-1-((4-tert-butyl-3,5-difluorophenyl)carbamoyl)-6-methoxy-3,4-dihydroisoquinolin-2(1H)-yl)-2-oxoethyl)-1,2-oxazole-3-carboxylic acid | 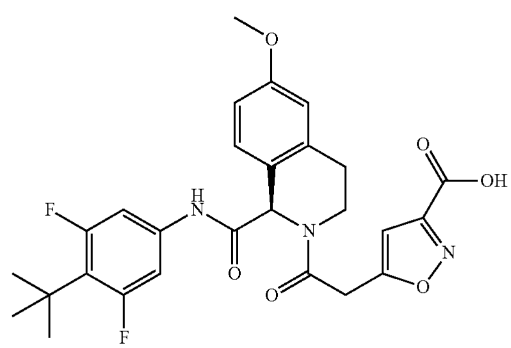 [SMILES: COc1ccc2c(c1)CCN(C(=O)Cc1cc(C(=O)O)no1)[C@H]2C(=O)Nc1cc(F)c(C(C)(C)C)c(F)c1] | | 528.0 (M + H) |
| 190 | 5-((1R)-1-((3,5-difluoro-4-(trimethylsilyl)phenyl)carbamoyl)-6-(oxetan-3-yloxy)-3,4-dihydroisoquinolin-2(1H)-yl)-5-oxopentanoic acid | 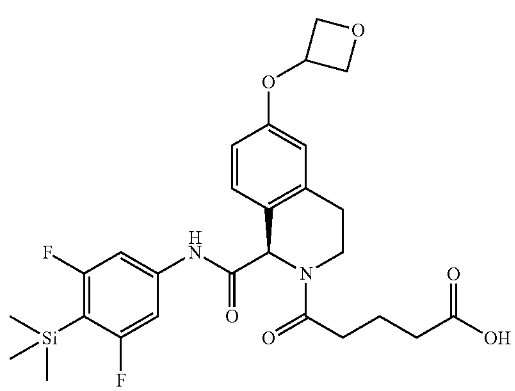 [SMILES: C[Si](C)(C)c1c(F)cc(NC(=O)[C@H]2c3ccc(OC4COC4)cc3CCN2C(=O)CCCC(=O)O)cc1F] | | 545.0 (M − H) |

TABLE 1-20-continued

| EXAMPLE | IUPACNAME | Structure | ADDITIVE | MS |
|---|---|---|---|---|
| 191 | 5-((1R)-6-(3,3-difluoroazetidin-1-yl)-1-((7-fluoro-1,1-dimethyl-2,3-dihydro-1H-inden-5-yl)carbamoyl)-3,4-dihydroisoquinolin-2(1H)-yl)-5-oxopentanoic acid | 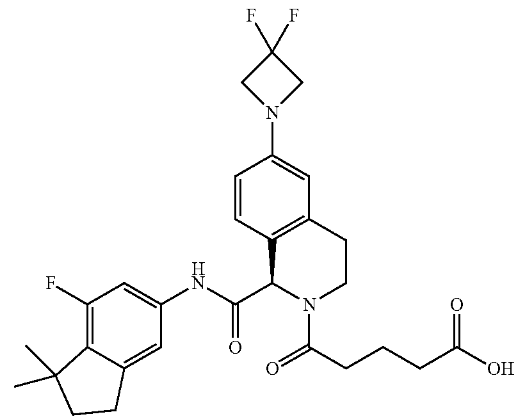 [SMILES: CC1(C)CCc2cc(NC(=O)[C@H]3c4ccc(N5CC(F)(F)C5)cc4CCN3C(=O)CCCC(=O)O)cc(F)c21] | | 544.1 (M + H) |

TABLE 1-21

| EXAMPLE | IUPACNAME | Structure | ADDITIVE | MS |
|---|---|---|---|---|
| 192 | (1R)-2-(5-amino-5-oxopentanoyl)-N-(3,5-difluoro-4-(trimethylsilyl)phenyl)-6-methoxy-1,2,3,4-tetrahydroisoquinoline-1-carboxamide | 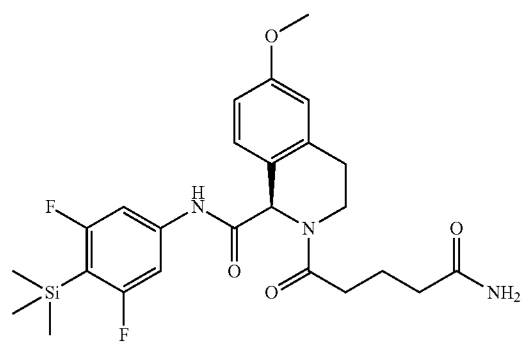 [SMILES: COc1ccc2c(c1)CCN(C(=O)CCCC(N)=O)[C@H]2C(=O)Nc1cc(F)c([Si](C)(C)C)c(F)c1] | | 504.1 (M + H) |
| 193 | 4-((1R)-6-(difluoromethoxy)-1-((3-fluoro-4-(trimethylsilyl)phenyl)carbamoyl)-3,4-dihydroisoquinolin-2(1H)-yl)-4-oxobutanoic acid | 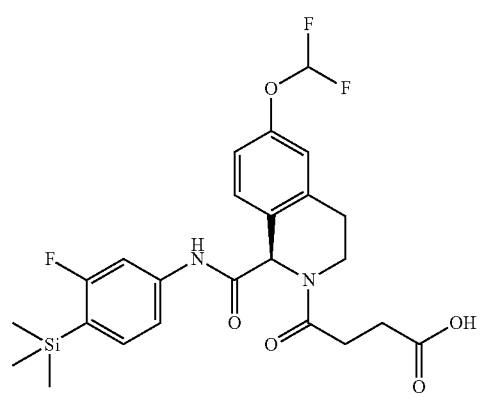 [SMILES: C[Si](C)(C)c1ccc(NC(=O)[C@H]2c3ccc(OC(F)F)cc3CCN2C(=O)CCC(=O)O)cc1F] | | 507.1 (M − H) |

TABLE 1-21-continued

| EXAMPLE | IUPACNAME | Structure | ADDITIVE | MS |
|---|---|---|---|---|
| 194 | 5-((1R)-6-(difluoromethoxy)-1-((3-fluoro-4-(trimethylsilyl)phenyl)carbamoyl)-3,4-dihydroisoquinolin-2(1H)-yl)-5-oxopentanoic acid | 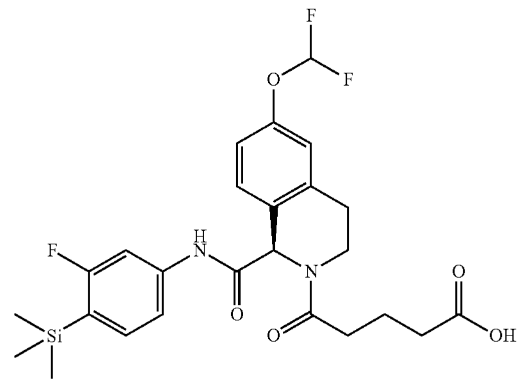 [SMILES: C[Si](C)(C)c1ccc(NC(=O)[C@H]2c3ccc(OC(F)F)cc3CCN2C(=O)CCCC(=O)O)cc1F] | | 521.0 (M − H) |
| 195 | 4-((1R)-6-(difluoromethoxy)-1-((3,5-difluoro-4-(trimethylsilyl)phenyl)carbamoyl)-3,4-dihydroisoquinolin-2(1H)-yl)-4-oxobutanoic acid | 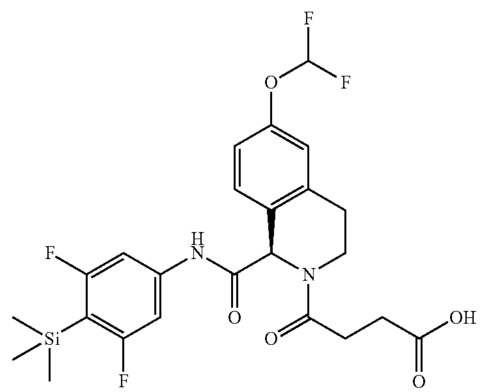 [SMILES: C[Si](C)(C)c1c(F)cc(NC(=O)[C@H]2c3ccc(OC(F)F)cc3CCN2C(=O)CCC(=O)O)cc1F] | | 525.0 (M − H) |
| 196 | 5-((1R)-6-(difluoromethoxy)-1-((3,5-difluoro-4-(trimethylsilyl)phenyl)carbamoyl)-3,4-dihydroisoquinolin-2(1H)-yl)-5-oxopentanoic acid | 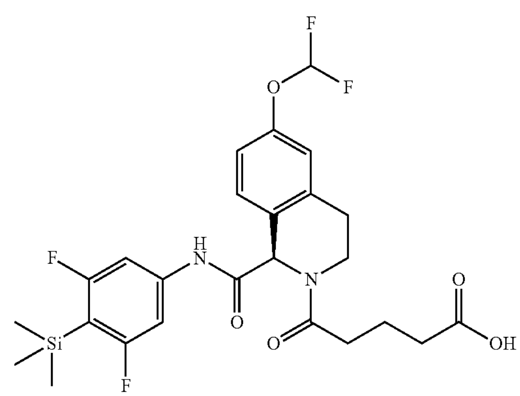 [SMILES: C[Si](C)(C)c1c(F)cc(NC(=O)[C@H]2c3ccc(OC(F)F)cc3CCN2C(=O)CCCC(=O)O)cc1F] | | 538.9 (M − H) |
| 197 | 4-((1R)-6-(2,2-difluoroethoxy)-1-((3-fluoro-4-(trimethylsilyl)phenyl)carbamoyl)-3,4-dihydroisoquinolin-2(1H)-yl)-4-oxobutanoic acid | 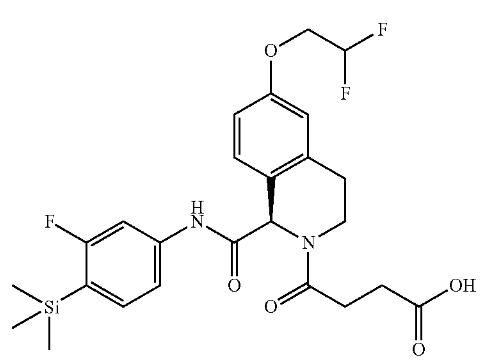 [SMILES: C[Si](C)(C)c1ccc(NC(=O)[C@H]2c3ccc(OCC(F)F)cc3CCN2C(=O)CCC(=O)O)cc1F] | | 521.0 (M − H) |

TABLE 1-21-continued

| EXAMPLE | IUPACNAME | Structure | ADDITIVE | MS |
|---|---|---|---|---|
| 198 | 5-((1R)-6-(2,2-difluoroethoxy)-1-((3-fluoro-4-(trimethylsilyl)phenyl)carbamoyl)-3,4-dihydroisoquinolin-2(1H)-yl)-5-oxopentanoic acid | 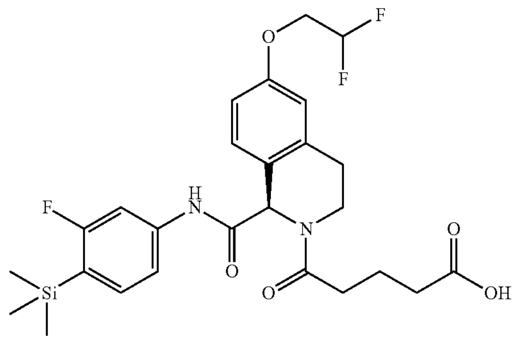 [SMILES: C[Si](C)(C)c1ccc(NC(=O)[C@H]2c3ccc(OCC(F)F)cc3CCN2C(=O)CCCC(=O)O)cc1F] | | 537.1 (M + H) |
| 199 | 4-((1R)-6-(2,2-difluoroethoxy)-1-((3,5-difluoro-4-(trimethylsilyl)phenyl)carbamoyl)-3,4-dihydroisoquinolin-2(1H)-yl)-4-oxobutanoic acid | 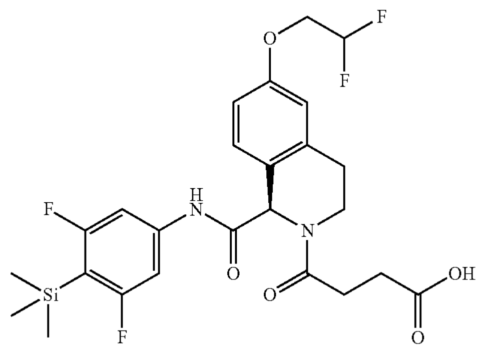 [SMILES: C[Si](C)(C)c1c(F)cc(NC(=O)[C@H]2c3ccc(OCC(F)F)cc3CCN2C(=O)CCC(=O)O)cc1F] | | 538.9 (M − H) |
| 200 | 5-((1R)-6-(2,2-difluoroethoxy)-1-((3,5-difluoro-4-(trimethylsilyl)phenyl)carbamoyl)-3,4-dihydroisoquinolin-2(1H)-yl)-5-oxopentanoic acid | 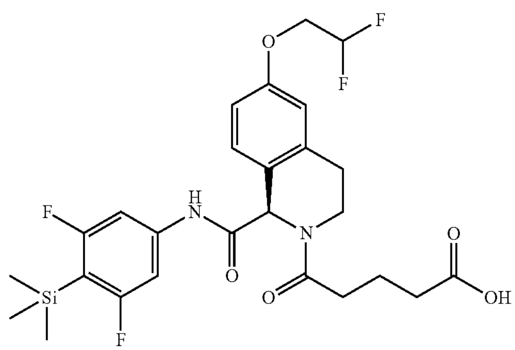 [SMILES: C[Si](C)(C)c1c(F)cc(NC(=O)[C@H]2c3ccc(OCC(F)F)cc3CCN2C(=O)CCCC(=O)O)cc1F] | | 555.0 (M + H) |
| 201 | 4-((1R)-1-((3-fluoro-4-(trimethylsilyl)phenyl)carbamoyl)-6-(2,2,2-trifluoroethoxy)-3,4-dihydroisoquinolin-2(1H)-yl)-4-oxobutanoic acid | 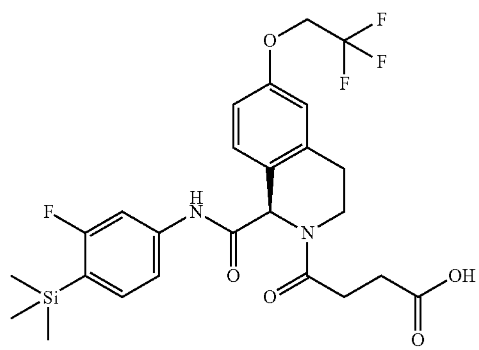 [SMILES: C[Si](C)(C)c1ccc(NC(=O)[C@H]2c3ccc(OCC(F)(F)F)cc3CCN2C(=O)CCC(=O)O)cc1F] | | 539.0 (M − H) |

TABLE 1-22

| EXAMPLE | IUPACNAME | Structure | ADDITIVE | MS |
|---|---|---|---|---|
| 202 | 5-((1R)-1-((3-fluoro-4-(trimethylsilyl)phenyl)carbamoyl)-6-(2,2,2-trifluoroethoxy)-3,4-dihydroisoquinolin-2(1H)-yl)-5-oxopentanoic acid | 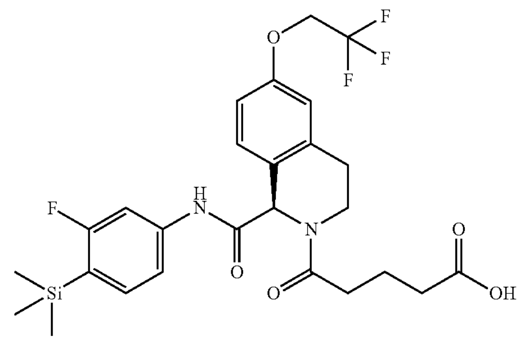 [SMILES: C[Si](C)(C)c1ccc(NC(=O)[C@H]2c3ccc(OCC(F)(F)F)cc3CCN2C(=O)CCCC(=O)O)cc1F] | | 555.0 (M + H) |
| 203 | 4-((1R)-1-((3,5-difluoro-4-(trimethylsilyl)phenyl)carbamoyl)-6-(2,2,2-trifluoroethoxy)-3,4-dihydroisoquinolin-2(1H)-yl)-4-oxobutanoic acid | 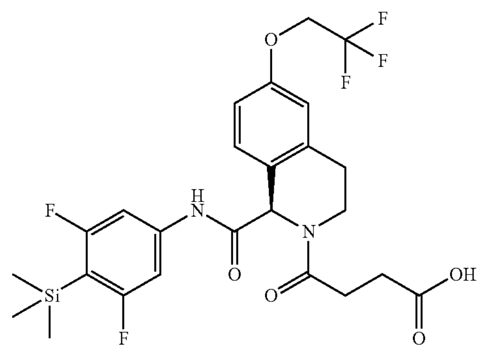 [SMILES: C[Si](C)(C)c1c(F)cc(NC(=O)[C@H]2c3ccc(OCC(F)(F)F)cc3CCN2C(=O)CCC(=O)O)cc1F] | | 559.0 (M + H) |
| 204 | 5-((1R)-1-((3,5-difluoro-4-(trimethylsilyl)phenyl)carbamoyl)-6-(2,2,2-trifluoroethoxy)-3,4-dihydroisoquinolin-2(1H)-yl)-5-oxopentanoic acid | 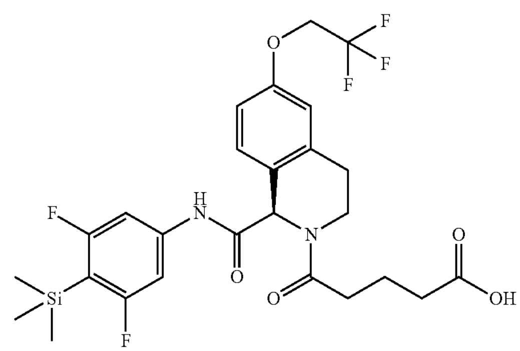 [SMILES: C[Si](C)(C)c1c(F)cc(NC(=O)[C@H]2c3ccc(OCC(F)(F)F)cc3CCN2C(=O)CCCC(=O)O)cc1F] | | 573.1 (M + H) |
| 205 | 4-((1R)-6-(difluoromethoxy)-1-((7-fluoro-1,1-dimethyl-2,3-dihydro-1H-inden-5-yl)carbamoyl)-3,4-dihydroisoquinolin-2(1H)-yl)-4-oxobutanoic acid | 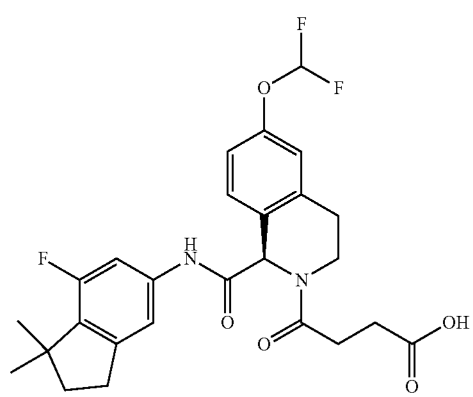 [SMILES: CC1(C)CCc2cc(NC(=O)[C@H]3c4ccc(OC(F)F)cc4CCN3C(=O)CCC(=O)O)cc(F)c21] | | 503.0 (M − H) |

TABLE 1-22-continued

| EXAMPLE | IUPACNAME | Structure | ADDITIVE | MS |
|---|---|---|---|---|
| 206 | 5-((1R)-6-(difluoromethoxy)-1-((7-fluoro-1,1-dimethyl-2,3-dihydro-1H-inden-5-yl)carbamoyl)-3,4-dihydroisoquinolin-2(1H)-yl)-5-oxopentanoic acid | 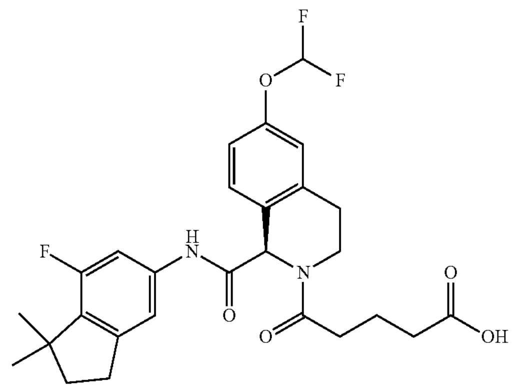 [SMILES: CC1(C)CCc2cc(NC(=O)[C@H]3c4ccc(OC(F)F)cc4CCN3C(=O)CCCC(=O)O)cc(F)c21] | | 519.1 (M + H) |
| 207 | 4-((1R)-6-(2,2-difluoroethoxy)-1-((7-fluoro-1,1-dimethyl-2,3-dihydro-1H-inden-5-yl)carbamoyl)-3,4-dihydroisoquinolin-2(1H)-yl)-4-oxobutanoic acid | 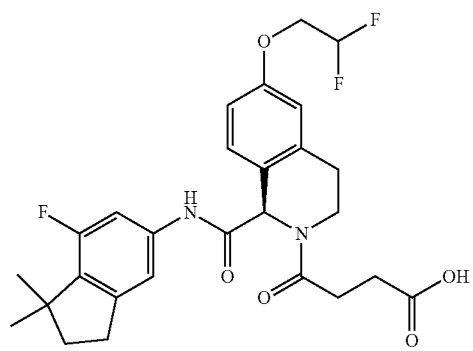 [SMILES: CC1(C)CCc2cc(NC(=O)[C@H]3c4ccc(OCC(F)F)cc4CCN3C(=O)CCC(=O)O)cc(F)c21] | | 517.0 (M − H) |
| 208 | 5-((1R)-6-(2,2-difluoroethoxy)-1-((7-fluoro-1,1-dimethyl-2,3-dihydro-1H-inden-5-yl)carbamoyl)-3,4-dihydroisoquinolin-2(1H)-yl)-5-oxopentanoic acid | 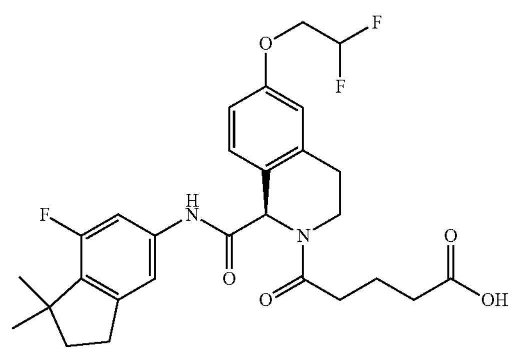 [SMILES: CC1(C)CCc2cc(NC(=O)[C@H]3c4ccc(OCC(F)F)cc4CCN3C(=O)CCCC(=O)O)cc(F)c21] | | 533.1 (M + H) |
| 209 | (4R)-5-((1R)-1-((3,5-difluoro-4-(trimethylsilyl)phenyl)carbamoyl)-6-ethoxy-3,4-dihydroisoquinolin-2(1H)-yl)-4-hydroxy-5-oxopentanoic acid | 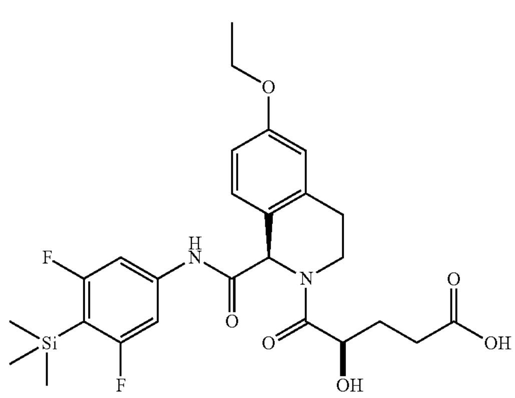 [SMILES: CCOc1ccc2c(c1)CCN(C(=O)[C@H](O)CCC(=O)O)[C@H]2C(=O)Nc1cc(F)c([Si](C)(C)C)c(F)c1] | | 535.0 (M + H) |

TABLE 1-22-continued

| EXAMPLE | IUPACNAME | Structure | ADDITIVE | MS |
|---|---|---|---|---|
| 210 | 6-((1R)-6-ethoxy-1-((7-fluoro-1,1-dimethyl-2,3-dihydro-1H-inden-5-yl)carbamoyl)-3,4-dihydroisoquinolin-2(1H)-yl)-6-oxohexanoic acid | 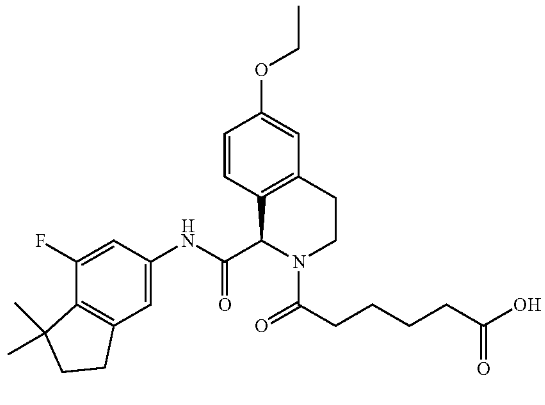 [SMILES: CCOc1ccc2c(c1)CCN(C(=O)CCCCC(=O)O)[C@H]2C(=O)Nc1cc(F)c2c(c1)CCC2(C)C] | | 511.0 (M + H) |
| 211 | 6-((1R)-6-ethoxy-1-((3-fluoro-4-(trimethylsilyl)phenyl)carbamoyl)-3,4-dihydroisoquinolin-2(1H)-yl)-6-oxohexanoic acid | 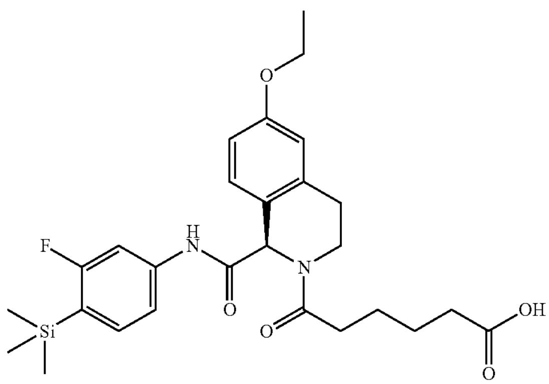 [SMILES: CCOc1ccc2c(c1)CCN(C(=O)CCCCC(=O)O)[C@H]2C(=O)Nc1ccc([Si](C)(C)C)c(F)c1] | | 513.0 (M − H) |

TABLE 1-23

| EXAMPLE | IUPACNAME | Structure | ADDITIVE | MS |
|---|---|---|---|---|
| 212 | 5-((5R)-2-(difluoromethoxy)-5-((7-fluoro-1,1-dimethyl-2,3-dihydro-1H-inden-5-yl)carbamoyl)-7,8-dihydro-1,6-naphthyridin-6(5H)-yl)-5-oxopentanoic acid | 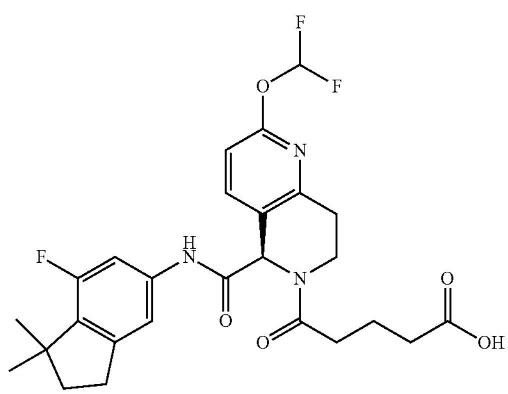 | | 518.0 (M − H) |

TABLE 1-23-continued

| EXAMPLE | IUPACNAME | Structure | ADDITIVE | MS |
|---------|-----------|-----------|----------|-----|
| 213 | (1R)-N-(3,5-difluoro-4-(trimethylsilyl)phenyl)-2-((1,1-dioxido-4-oxo-1,2,5-thiadiazolidin-2-yl)acetyl)-6-ethoxy-1,2,3,4-tetrahydroisoquinoline-1-carboxamide | 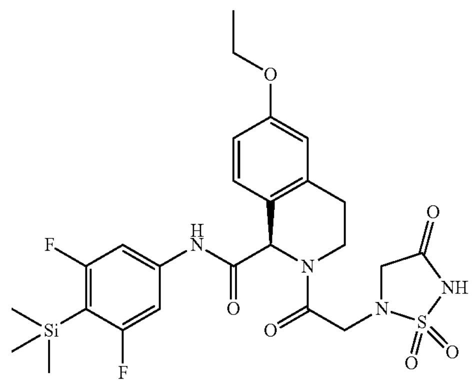 [SMILES: CCOc1ccc2c(c1)CCN(C(=O)CN1CC(=O)NS1(=O)=O)[C@H]2C(=O)Nc1cc(F)c([Si](C)(C)C)c(F)c1] | | 578.9 (M − H) |
| 214 | (5R)-6-((1,1-dioxido-4-oxo-1,2,5-thiadiazolidin-2-yl)acetyl)-N-(7-fluoro-1,1-dimethyl-2,3-dihydro-1H-inden-5-yl)-2-methoxy-5,6,7,8-tetrahydro-1,6-naphthyridine-5-carboxamide | 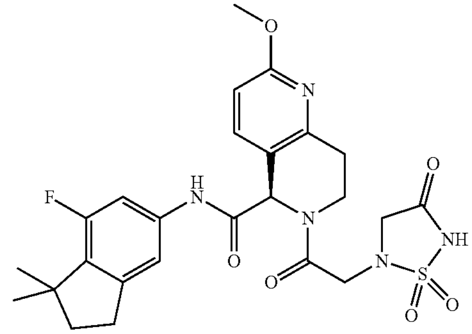 [SMILES: COc1ccc2c(n1)CCN(C(=O)CN1CC(=O)NS1(=O)=O)[C@H]2C(=O)Nc1cc(F)c2c(c1)CCC2(C)C] | | 546.0 (M + H) |
| 215 | 5-((1R)-1-((7-fluoro-1,1-dimethyl-2,3-dihydro-1H-inden-5-yl)carbamoyl)-6-(2,2,2-trifluoroethoxy)-3,4-dihydroisoquinolin-2(1H)-yl)-5-oxopentanoic acid | 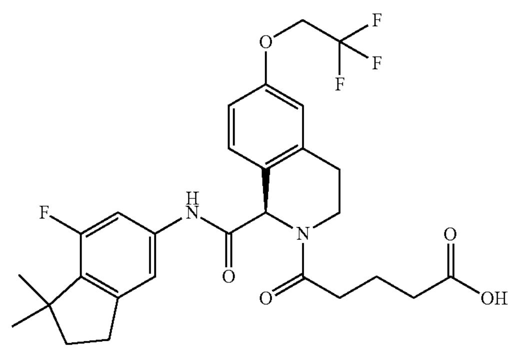 [SMILES: CC1(C)CCc2cc(NC(=O)[C@H]3c4ccc(OCC(F)(F)F)cc4CCN3C(=O)CCCC(=O)O)cc(F)c21] | | 549.0 |
| 216 | (4R)-4-amino-5-((1R)-1-((3,5-difluoro-4-(trimethylsilyl)phenyl)carbamoyl)-6-ethoxy-3,4-dihydroisoquinolin-2(1H)-yl)-5-oxopentanoic acid | 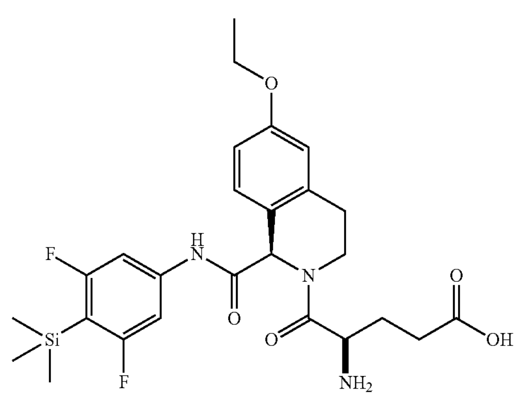 [SMILES: CCOc1ccc2c(c1)CCN(C(=O)[C@H](N)CCC(=O)O)[C@H]2C(=O)Nc1cc(F)c([Si](C)(C)C)c(F)c1] | | 534.0 (M + H) |

TABLE 1-23-continued

| EXAMPLE | IUPACNAME | Structure | ADDITIVE | MS |
|---|---|---|---|---|
| 217 | 5-((1R)-1-((7-fluoro-1,1-dimethyl-2,3-dihydro-1H-inden-5-yl)carbamoyl)-6-isopropoxy-3,4-dihydroisoquinolin-2(1H)-yl)-5-oxopentanoic acid | 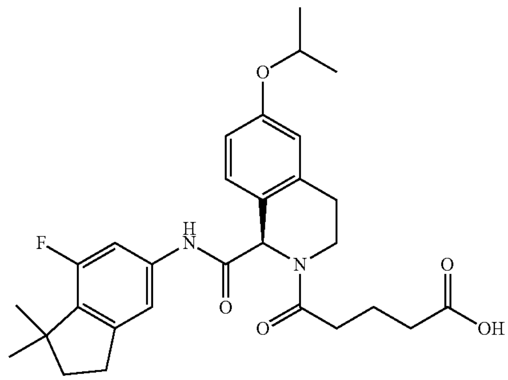 [SMILES: CC(C)Oc1ccc2c(c1)CCN(C(=O)CCCC(=O)O)[C@H]2C(=O)Nc1cc(F)c2c(c1)CCC2(C)C] | | 509.1 (M − H) |
| 218 | 5-((1R)-6-(cyclopropylmethoxy)-1-((7-fluoro-1,1-dimethyl-2,3-dihydro-1H-inden-5-yl)carbamoyl)-3,4-dihydroisoquinolin-2(1H)-yl)-5-oxopentanoic acid | 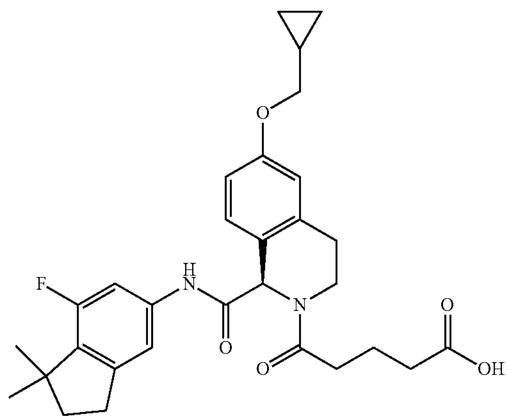 [SMILES: CC1(C)CCc2cc(NC(=O)[C@H]3c4ccc(OCC5CC5)cc4CCN3C(=O)CCCC(=O)O)cc(F)c21] | | 523.1 (M + H) |
| 219 | 5-((1R)-1-((7-fluoro-1,1-dimethyl-2,3-dihydro-1H-inden-5-yl)carbamoyl)-6-propoxy-3,4-dihydroisoquinolin-2(1H)-yl)-5-oxopentanoic acid | 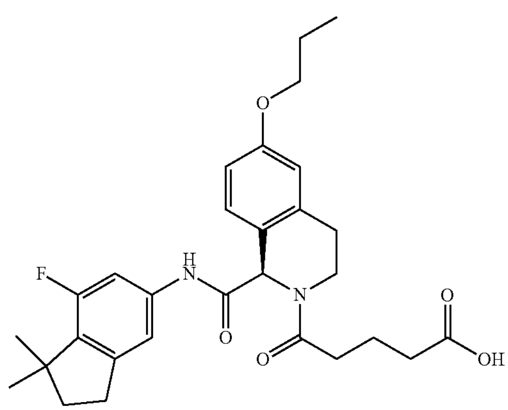 [SMILES: CCCOc1ccc2c(c1)CCN(C(=O)CCCC(=O)O)[C@H]2C(=O)Nc1cc(F)c2c(c1)CCC2(C)C] | | 508.8 (M − H) |
| 220 | (3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)azetidin-1-yl)acetic acid | 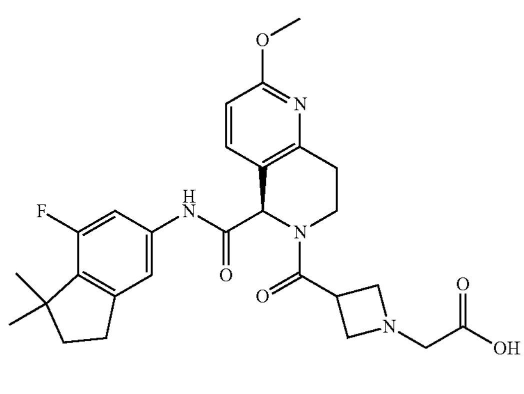 [SMILES: COc1ccc2c(n1)CCN(C(=O)C1CN(CC(=O)O)C1)[C@H]2C(=O)Nc1cc(F)c2c(c1)CCC2(C)C] | | 511.0 (M + H) |

TABLE 1-23-continued

| EXAMPLE | IUPACNAME | Structure | ADDITIVE | MS |
|---|---|---|---|---|
| 221 | 5-((1R)-1-((3-cyano-4-(trimethylsilyl)phenyl)carbamoyl)-6-ethoxy-3,4-dihydroisoquinolin-2(1H)-yl)-5-oxopentanoic acid | 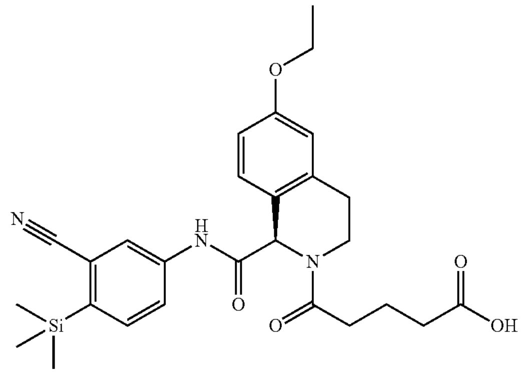 [SMILES: CCOc1ccc2c(c1)CCN(C(=O)CCCC(=O)O)[C@H]2C(=O)Nc1ccc([Si](C)(C)C)c(C#N)c1] | | 506.1 (M − H) |

TABLE 1-24

| EXAMPLE | IUPACNAME | Structure | ADDITIVE | MS |
|---|---|---|---|---|
| 222 | (2E)-4-((1R)-1-((3,5-difluoro-4-(trimethylsilyl)phenyl)carbamoyl)-6-methoxy-3,4-dihydroisoquinolin-2(1H)-yl)-4-oxobut-2-enoic acid | 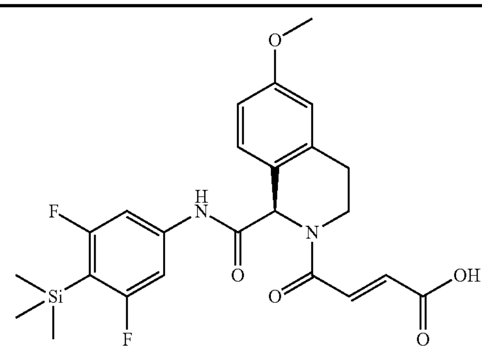 | | 486.9 (M − H) |
| 223 | (1R)-N-(3,5-difluoro-4-(trimethylsilyl)phenyl)-2-(((3S)-1,1-dioxido-4-oxo-1,2,5-thiadiazolidin-3-yl)acetyl)-6-ethoxy-1,2,3,4-tetrahydroisoquinoline-1-carboxamide | 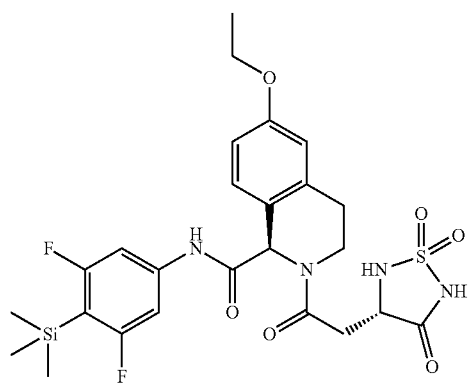 [SMILES: CCOc1ccc2c(c1)CCN(C(=O)C[C@@H]1NS(=O)(=O)NC1=O)[C@H]2C(=O)Nc1cc(F)c([Si](C)(C)C)c(F)c1] | | 578.9 (M − H) |
| 224 | (1R)-2-(((3S)-1,1-dioxido-4-oxo-1,2,5-thiadiazolidin-3-yl)acetyl)-6-ethoxy-N-(7-fluoro-1,1-dimethyl-2,3-dihydro-1H-inden-5-yl)-1,2,3,4-tetrahydroisoquinoline-1-carboxamide | 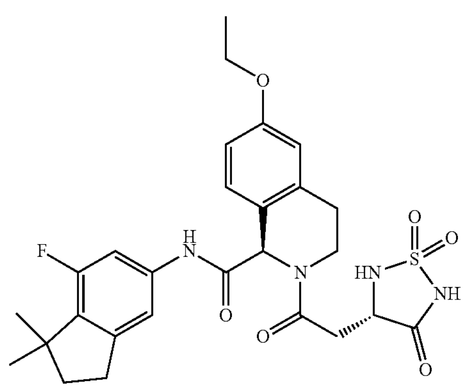 [SMILES: CCOc1ccc2c(c1)CCN(C(=O)C[C@@H]1NS(=O)(=O)NC1=O)[C@H]2C(=O)Nc1cc(F)c2c(c1)CCC2(C)C] | | 559.0 (M + H) |

TABLE 1-24-continued

| EXAMPLE | IUPACNAME | Structure | ADDITIVE | MS |
|---|---|---|---|---|
| 225 | 3-((((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)oxy)propanoic acid | 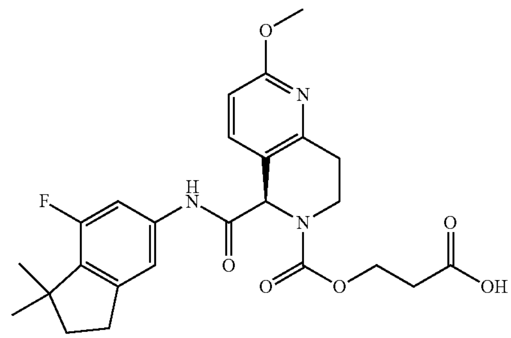 [SMILES: COc1ccc2c(n1)CCN(C(=O)OCCC(=O)O)[C@H]2C(=O)Nc1cc(F)c2c(c1)CCC2(C)C] | | 486.0 (M + H) |
| 226 | 4-((((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)oxy)butanoic acid | 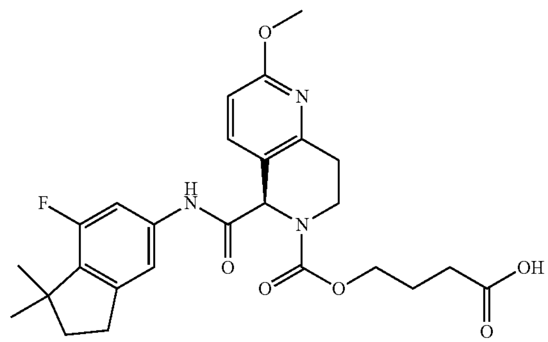 [SMILES: COc1ccc2c(n1)CCN(C(=O)OCCCC(=O)O)[C@H]2C(=O)Nc1cc(F)c2c(c1)CCC2(C)C] | | 498.0 (M − H) |
| 227 | N-(((1R)-1-((3,5-difluoro-4-(trimethylsilyl)phenyl)carbamoyl)-6-ethoxy-3,4-dihydroisoquinolin-2(1H)-yl)carbonyl)-beta-alanine | 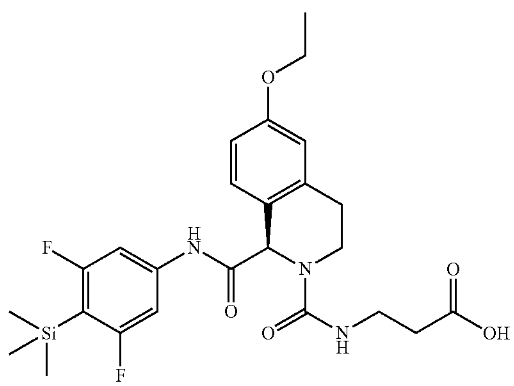 [SMILES: CCOc1ccc2c(c1)CCN(C(=O)NCCC(=O)O)[C@H]2C(=O)Nc1cc(F)c([Si](C)(C)C)c(F)c1] | | 520.1 (M + H) |
| 228 | 1-(((1R)-1-((3,5-difluoro-4-(trimethylsilyl)phenyl)carbamoyl)-6-ethoxy-3,4-dihydroisoquinolin-2(1H)-yl)carbonyl)pyrrolidine-3-carboxylic acid | 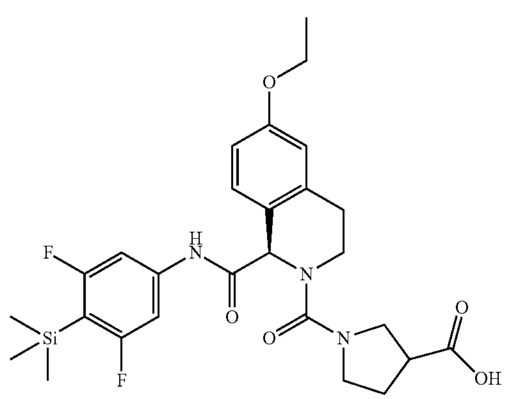 [SMILES: CCOc1ccc2c(c1)CCN(C(=O)N1CCC(C(=O)O)C1)[C@H]2C(=O)Nc1cc(F)c([Si](C)(C)C)c(F)c1] | | 546.0 (M + H) |

TABLE 1-24-continued

| EXAMPLE | IUPACNAME | Structure | ADDITIVE | MS |
|---|---|---|---|---|
| 229 | 5-((1R)-1-((3,5-difluoro-4-(trimethylsilyl)phenyl)carbamoyl)-6-ethoxy-3,4-dihydroisoquinolin-2(1H)-yl)-4,5-dioxopentanoic acid | 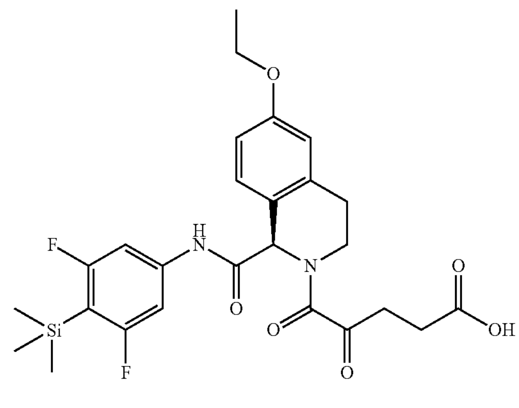 [SMILES: CCOc1ccc2c(c1)CCN(C(=O)C(=O)CCC(=O)O)[C@H]2C(=O)Nc1cc(F)c([Si](C)(C)C)c(F)c1] | | 531.1 (M − H) |
| 230 | benzyl (1-(((1R)-1-((3,5-difluoro-4-(trimethylsilyl)phenyl)carbamoyl)-6-ethoxy-3,4-dihydroisoquinolin-2(1H)-yl)carbonyl)azetidin-3-yl) acetate | 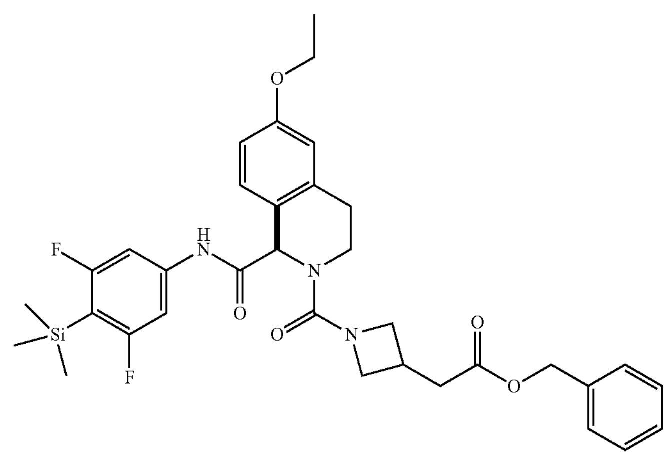 | | 636.3 (M + H) |
| 231 | (1-(((1R)-1-((3,5-difluoro-4-(trimethylsilyl)phenyl)carbamoyl)-6-ethoxy-3,4-dihydroisoquinolin-2(1H)-yl)carbonyl)azetidin-3-yl) acetic acid | 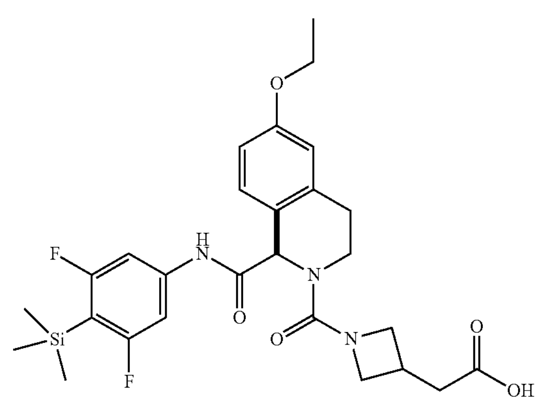 | | 546.1 (M + H) |

TABLE 1-25

| EXAMPLE | IUPACNAME | Structure | ADDITIVE | MS |
|---|---|---|---|---|
| 232 | benzyl (1-(((1R)-6-ethoxy-1-((7-fluoro-1,1-dimethyl-2,3-dihydro-1H-inden-5-yl)carbamoyl)-3,4-dihydroisoquinolin-2(1H)-yl)carbonyl)azetidin-3-yl)acetate | 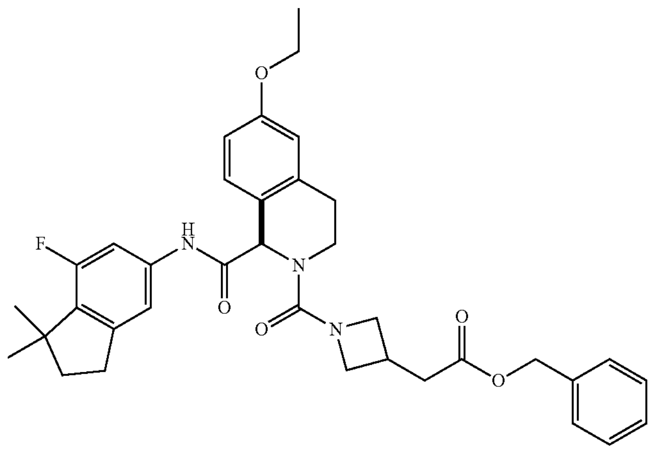 | | 614.3 (M + H) |
| 233 | (1-(((1R)-6-ethoxy-1-((7-fluoro-1,1-dimethyl-2,3-dihydro-1H-inden-5-yl)carbamoyl)-3,4-dihydroisoquinolin-2(1H)-yl)carbonyl)azetidin-3-yl)acetic acid | 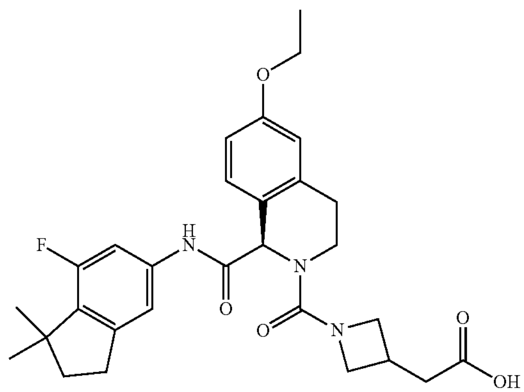 [SMILES: CCOc1ccc2c(c1)CCN(C(=O)N1CC(CC(=O)O)C1)[C@H]2C(=O)Nc1cc(F)c2c(c1)CCC2(C)C] | | 524.3 (M + H) |
| 234 | (2Z)-4-((1R)-1-((3,5-difluoro-4-(trimethylsilyl)phenyl)carbamoyl)-6-methoxy-3,4-dihydroisoquinolin-2(1H)-yl)-4-oxobut-2-enoic acid | 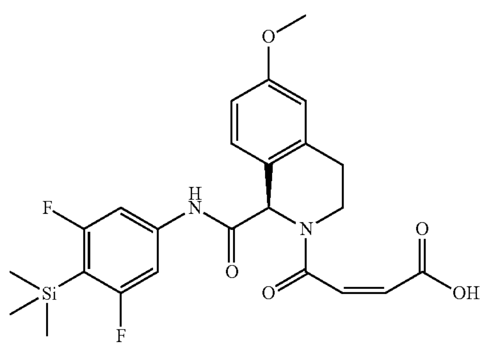 [SMILES: COc1ccc2c(c1)CCN(C(=O)/C=C\C(=O)O)[C@H]2C(=O)Nc1cc(F)c([Si](C)(C)C)c(F)c1] | | 487.1 (M − H) |
| 235 | 5-((1R)-1-((3,5-difluoro-4-(trimethylsilyl)phenyl)carbamoyl)-6-(methylsulfonyl)-3,4-dihydroisoquinolin-2(1H)-yl)-5-oxopentanoic acid | 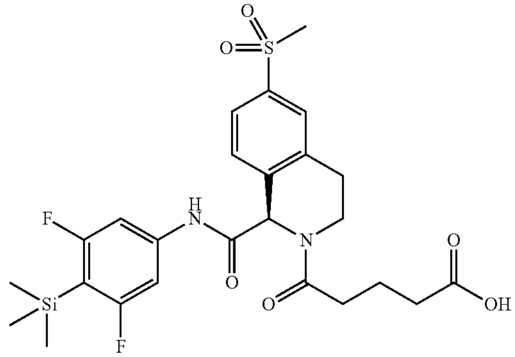 [SMILES: C[Si](C)(C)c1c(F)cc(NC(=O)[C@H]2c3ccc(S(C)(=O)=O)cc3CCN2C(=O)CCCC(=O)O)cc1F] | | 551.1 (M − H) |

TABLE 1-25-continued

| EXAMPLE | IUPACNAME | Structure | ADDITIVE | MS |
|---|---|---|---|---|
| 236 | 5-((1R)-6-ethoxy-1-((7-fluoro-1,1-dimethyl-2,3-dihydro-1H-inden-5-yl)carbamoyl)-3,4-dihydroisoquinolin-2(1H)-yl)-3-hydroxy-3-methyl-5-oxopentanoic acid | 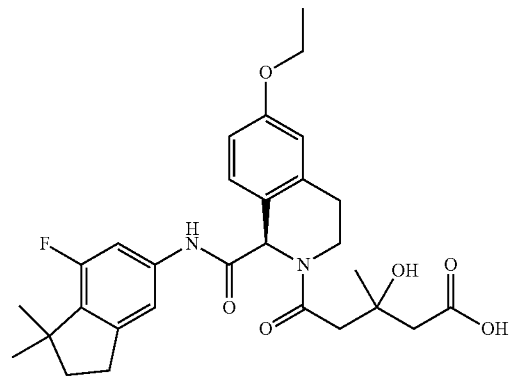 [SMILES: CCOc1ccc2c(c1)CCN(C(=O)CC(C)(O)CC(=O)O)[C@H]2C(=O)Nc1cc(F)c2c(c1)CCC2(C)C] | | 527.2 (M + H) |
| 237 | tert-butyl (((1R)-1-((3,5-difluoro-4-(trimethylsilyl)phenyl)carbamoyl)-6-ethoxy-3,4-dihydroisoquinolin-2(1H)-yl)sulfonyl)carbamate | 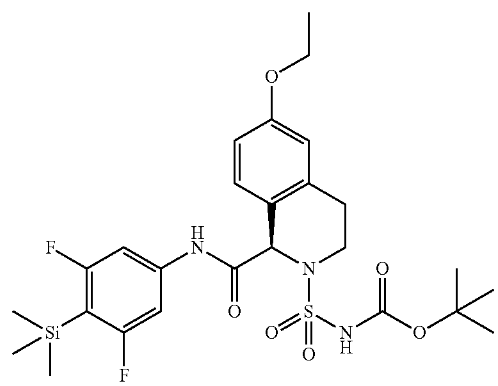 [SMILES: CCOc1ccc2c(c1)CCN(S(=O)(=O)NC(=O)OC(C)(C)C)[C@H]2C(=O)Nc1cc(F)c([Si](C)(C)C)c(F)c1] | | 582.3 (M − H) |
| 238 | 4-((((1R)-1-((3,5-difluoro-4-(trimethylsilyl)phenyl)carbamoyl)-6-ethoxy-3,4-dihydroisoquinolin-2(1H)-yl)carbonyl)amino)butanoic acid | 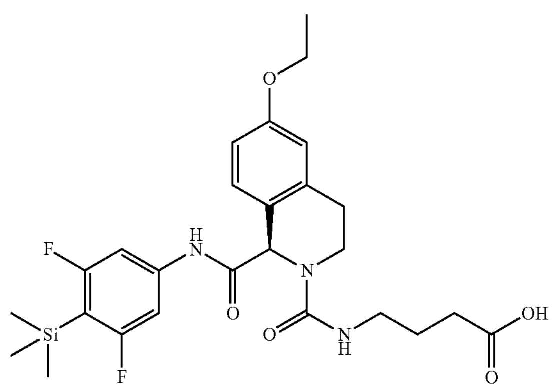 [SMILES: CCOc1ccc2c(c1)CCN(C(=O)NCCCC(=O)O)[C@H]2C(=O)Nc1cc(F)c([Si](C)(C)C)c(F)c1] | | 534.2 (M + H) |
| 239 | 4-(((1R)-1-((3,5-difluoro-4-(trimethylsilyl)phenyl)carbamoyl)-6-ethoxy-3,4-dihydroisoquinolin-2(1H)-yl)carbonyl)morpholine-2-carboxylic acid | 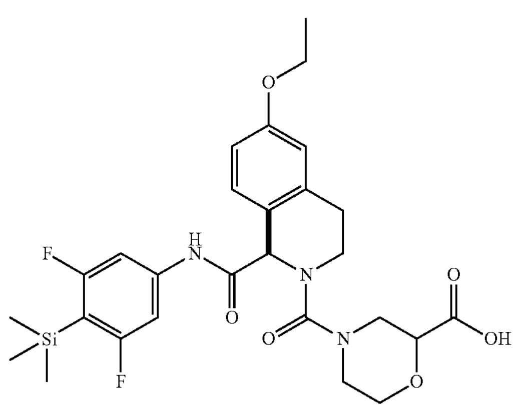 | | 562.2 (M + H) |

TABLE 1-25-continued

| EXAMPLE | IUPACNAME | Structure | ADDITIVE | MS |
|---|---|---|---|---|
| 240 | 5-((1R)-1-((3,5-difluoro-4-(trimethylsilyl)phenyl)carbamoyl)-6-ethoxy-3,4-dihydroisoquinolin-2(1H)-yl)-3-hydroxy-3-methyl-5-oxopentanoic acid | 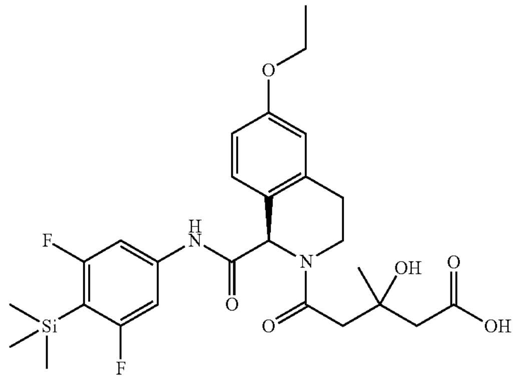 [SMILES: CCOc1ccc2c(c1)CCN(C(=O)CC(C)(O)CC(=O)O)[C@H]2C(=O)Nc1cc(F)c([Si](C)(C)C)c(F)c1] | | 549.2 (M + H) |
| 241 | 5-((1R)-6-ethoxy-1-((7-fluoro-1,1-dimethyl-2,3-dihydro-1H-inden-5-yl)carbamoyl)-3,4-dihydroisoquinolin-2(1H)-yl)-2,2-dimethyl-5-oxopentanoic acid | 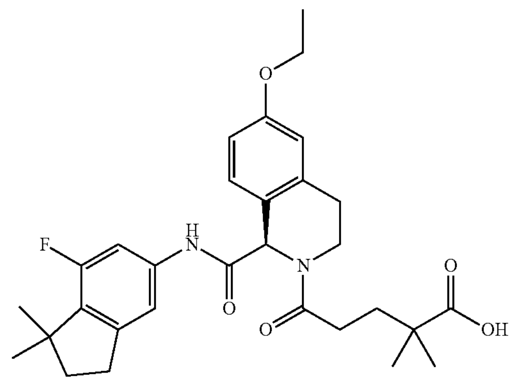 [SMILES: CCOc1ccc2c(c1)CCN(C(=O)CCC(C)(C)C(=O)O)[C@H]2C(=O)Nc1cc(F)c2c(c1)CCC2(C)C] | | 525.3 (M + H) |

TABLE 1-26

| EXAMPLE | IUPACNAME | Structure | ADDITIVE | MS |
|---|---|---|---|---|
| 242 | 4-((((1R)-1-((3,5-difluoro-4-(trimethylsilyl)phenyl)carbamoyl)-6-methoxy-3,4-dihydroisoquinolin-2(1H)-yl)carbonyl)amino)butanoic acid | 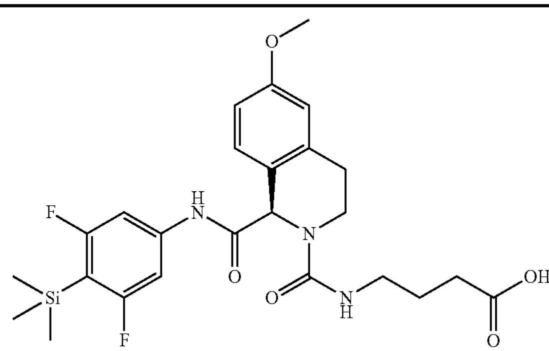 | | 520.2 (M + H) |
| 243 | 4-((((1R)-((3,5-difluoro-4-(trimethylsilyl)phenyl)carbamoyl)-6-ethoxy-3,4-dihydroisoquinolin-2(1H)-yl)sulfonyl)amino)butanoic | 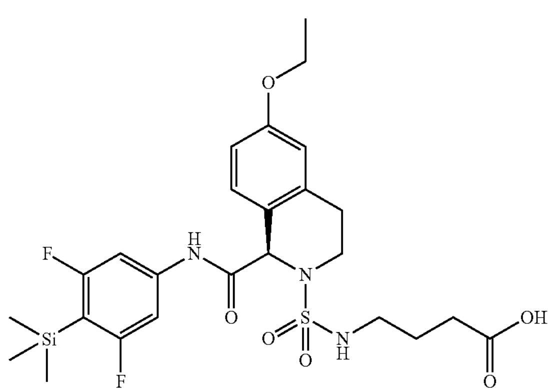 [SMILES: CCOc1ccc2c(c1)CCN(S(=O)(=O)NCCCC(=O)O)[C@H]2C(=O)Nc1cc(F)c([Si](C)(C)C)c(F)c1] | | 570.2 (M + H) |

TABLE 1-26-continued

| EXAMPLE | IUPACNAME | Structure | ADDITIVE | MS |
|---|---|---|---|---|
| 244 | N-(((1R)-1-((3,5-difluoro-4-(trimethylsilyl)phenyl)carbamoyl)-6-methoxy-3,4-dihydroisoquinolin-2(1H)-yl)carbonyl)-2-methylalanine | 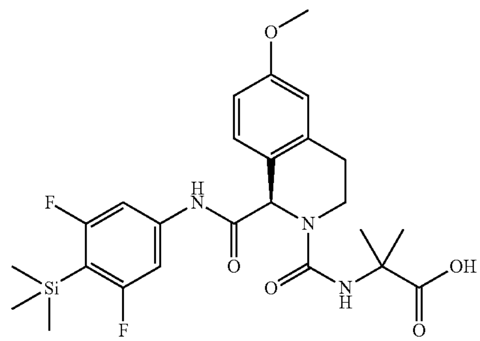 [SMILES: COc1ccc2c(c1)CCN(C(=O)NC(C)(C)C(=O)O)[C@H]2C(=O)Nc1cc(F)c([Si](C)(C)C)c(F)c1] | | 520.2 (M + H) |
| 245 | benzyl N-(((1R)-1-((3(5-difluoro-4-(trimethylsilyl)phenyl)carbamoyl)-6-methoxy-3,4-dihydroisoquinolin-2(1H)-yl)carbonyl)-D-alaninate | 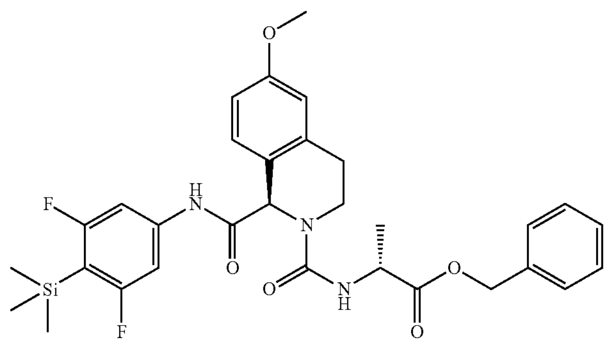 [SMILES: COc1ccc2c(c1)CCN(C(=O)N[C@H](C)C(=O)OCc1ccccc1)[C@H]2C(=O)Nc1cc(F)c([Si](C)(C)C)c(F)c1] | | 596.2 (M + H) |
| 246 | N-(((1R)-1-((3(5-difluoro-4-(trimethylsilyl)phenyl)carbamoyl)-6-methoxy-3,4-dihydroisoquinolin-2(1H)-yl)carbonyl)-D-alanine | 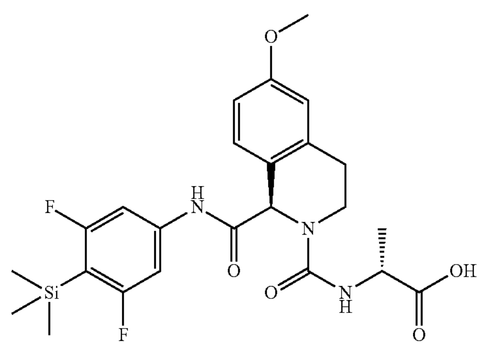 [SMILES: COc1ccc2c(c1)CCN(C(=O)N[C@H](C)C(=O)O)[C@H]2C(=O)Nc1cc(F)c([Si](C)(C)C)c(F)c1] | | 506.3 (M + H) |
| 247 | 5-((1R)-6-cyano-1-((3,5-difluoro-4-(trimethylsilyl)phenyl)carbamoyl)-3,4-dihydroisoquinolin-2(1H)-yl)-5-oxopentanoic acid | 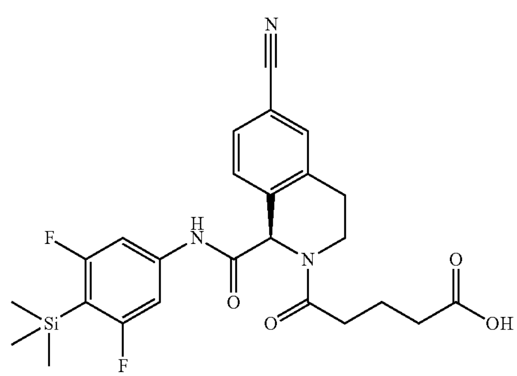 [SMILES: C[Si](C)(C)c1c(F)cc(NC(=O)[C@H]2c3ccc(C#N)cc3CCN2C(=O)CCCC(=O)O)cc1F] | | 498.2 (M − H) |

TABLE 1-26-continued

| EXAMPLE | IUPACNAME | Structure | ADDITIVE | MS |
|---|---|---|---|---|
| 248 | (4S)-5-(((1R)-1-((3,5-difluoro-4-(trimethylsilyl)phenyl)carbamoyl)-6-methoxy-3,4-dihydroisoquinolin-2(1H)-yl)-4-hydroxy-5-oxopentanoic acid | 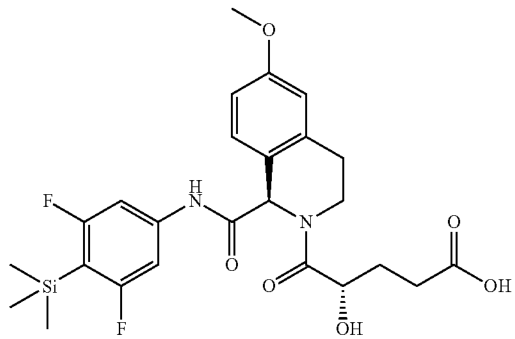 [SMILES: COc1ccc2c(c1)CCN(C(=O)[C@@H](O)CCC(=O)O)[C@H]2C(=O)Nc1cc(F)c([Si](C)(C)C)c(F)c1] | | 521.2 (M + H) |
| 249 | N-(((1R)-1-((3(5-difluoro-4-(trimethylsilyl)phenyl)carbamoyl)-6-methoxy-3,4-dihydroisoquinolin-2(1H)-yl)carbonyl)-L-alanine | 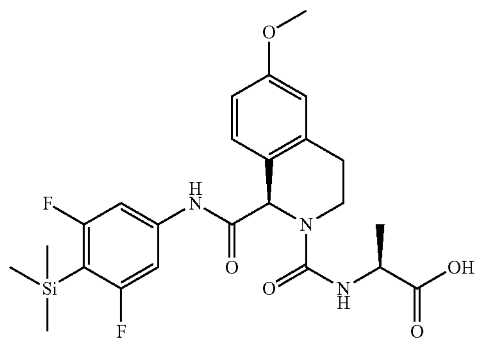 [SMILES: COc1ccc2c(c1)CCN(C(=O)N[C@@H](C)C(=O)O)[C@H]2C(=O)Nc1cc(F)c([Si](C)(C)C)c(F)c1] | | 506.3 (M + H) |
| 250 | 5-((5R)-5-((3,5-difluoro-4-(trimethylsilyl)phenyl)carbamoyl)-2-isopropyl-7,8-dihydro-1,6-naphthyridin-6(5H)-yl)-5-oxopentanoic acid | 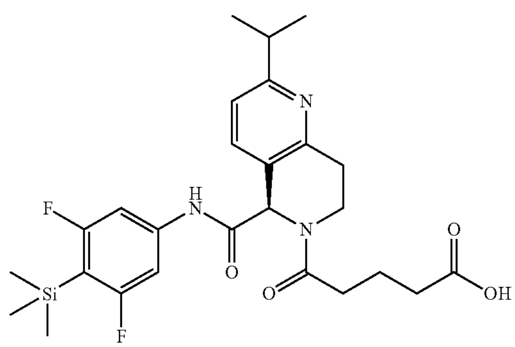 [SMILES: CC(C)c1ccc2c(n1)CCN(C(=O)CCCC(=O)O)[C@H]2C(=O)Nc1cc(F)c([Si](C)(C)C)c(F)c1] | | 518.2 (M + H) |
| 251 | 5-((5R)-5-((3,5-difluoro-4-(trimethylsilyl)phenyl)carbamoyl)-2-propyl-7,8-dihydro-1,6-naphthyridin-6(5H)-yl)-5-oxopentanoic acid | 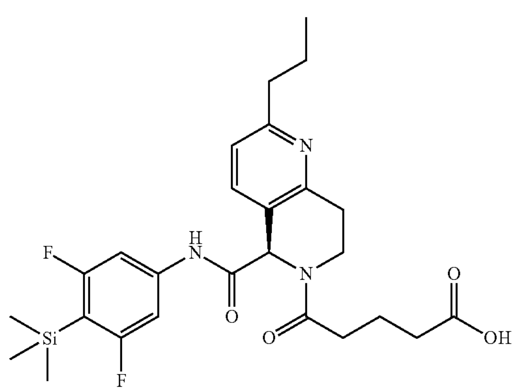 | | 518.2 (M + H) |

TABLE 1-27

| EXAMPLE | IUPACNAME | Structure | ADDITIVE | MS |
|---|---|---|---|---|
| 252 | 5-((5R)-5-((3,5-difluoro-4-(trimethylsilyl)phenyl)carbamoyl)-2,3,7,8-tetrahydrofuro[2,3-g]isoquinolin-6(5H)-yl)-5-oxopentanoic acid | 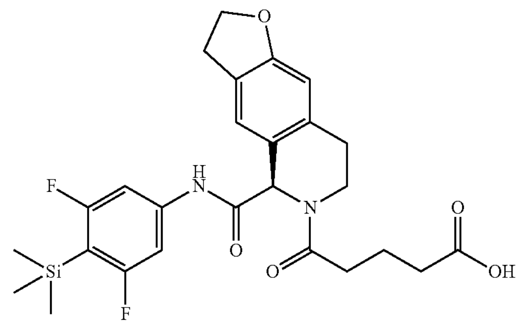 [SMILES: C[Si](C)(C)c1c(F)cc(NC(=O)[C@H]2c3cc4c(cc3CCN2C(=O)CCCC(=O)O)OCC4)cc1F] | | 515.1 (M − H) |
| 253 | 5-((1R)-1-((3,5-difluoro-4-(trimethylsilyl)phenyl)carbamoyl)-6-methoxy-5-methyl-3,4-dihydroisoquinolin-2(1H)-yl)-5-oxopentanoic acid | 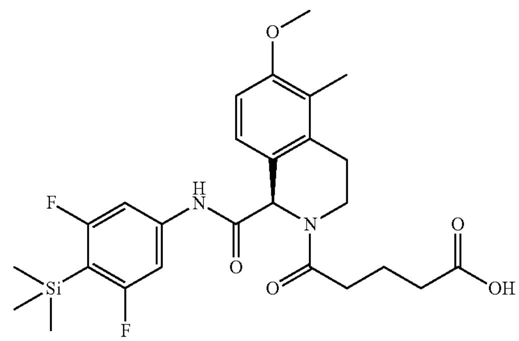 [SMILES: COc1ccc2c(c1C)CCN(C(=O)CCCC(=O)O)[C@H]2C(=O)Nc1cc(F)c([Si](C)(C)C)c(F)c1] | | 519.1 (M + H) |
| 254 | 5-((6R)-6-((3,5-difluoro-4-(trimethylsilyl)phenyl)carbamoyl)-8,9-dihydro[1,3]dioxolo[4,5-f]isoquinolin-7(6H)-yl)-5-oxopentanoic acid | 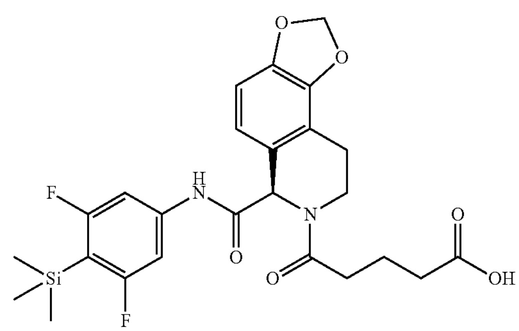 [SMILES: C[Si](C)(C)c1c(F)cc(NC(=O)[C@H]2c3ccc4c(c3CCN2C(=O)CCCC(=O)O)OCO4)cc1F] | | 519.2 (M + H) |
| 255 | 5-((5R)-5-((7-fluoro-1,1-dimethyl-2,3-dihydro-1H-inden-5-yl)carbamoyl)-2,3,7,8-tetrahydrofuro[2,3-g]isoquinolin-6(5H)-yl)-5-oxopentanoic acid | 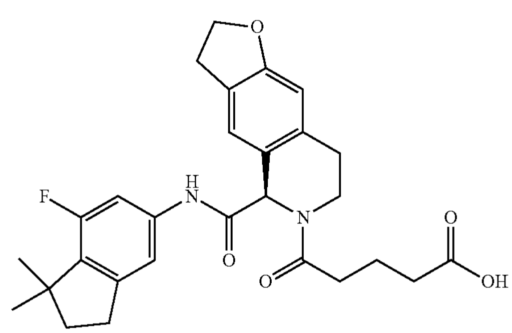 [SMILES: CC1(C)CCc2cc(NC(=O)[C@H]3c4cc5c(cc4CCN3C(=O)CCCC(=O)O)OCC5)cc(F)c21] | | 493.2 (M − H) |

TABLE 1-27-continued

| EXAMPLE | IUPACNAME | Structure | ADDITIVE | MS |
|---|---|---|---|---|
| 256 | 5-((6R)-6-((7-fluoro-1,1-dimethyl-2,3-dihydro-1H-inden-5-yl)carbamoyl)-8,9-dihydro[1,3]dioxolo[4,5-f]isoquinolin-7(6H)-yl)-5-oxopentanoic acid | 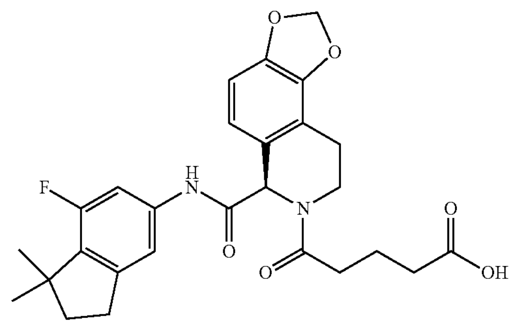 [SMILES: CC1(C)CCc2cc(NC(=O)[C@H]3c4ccc5c(c4CCN3C(=O)CCCC(=O)O)OCO5)cc(F)c21] | | 497.2 (M + H) |
| 257 | N-(((1R)-1-((3,5-difluoro-4-(trimethylsilyl)phenyl)carbamoyl)-6-methoxy-3,4-dihydroisoquinolin-2(1H)-yl)carbonyl)-N-methyl-beta-alanine | 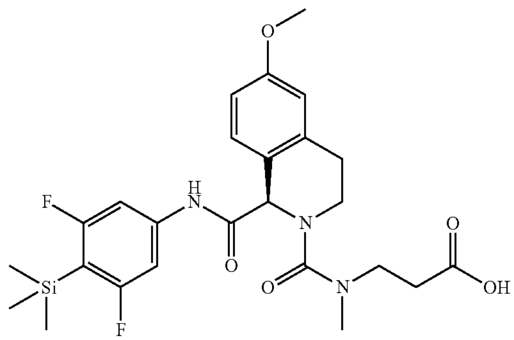 [SMILES: COc1ccc2c(c1)CCN(C(=O)N(C)CCC(=O)O)[C@H]2C(=O)Nc1cc(F)c([Si](C)(C)C)c(F)c1] | | 520.2 (M + H) |
| 258 | 1-(((1R-1-((3,5-difluoro-4-(trimethylsilyl)phenyl)carbamoyl)-6-methoxy-3,4-dihydroisoquinolin-2(1H)-yl)carbonyl)azetidine-3-carboxylic acid | 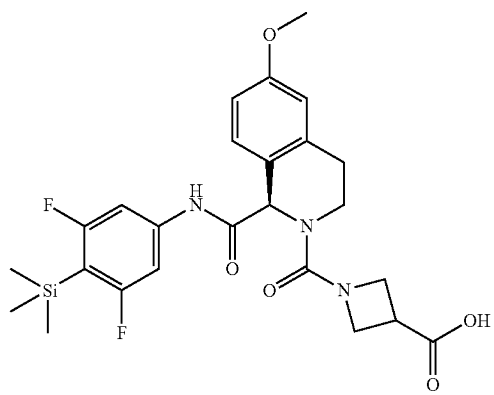 [SMILES: COc1ccc2c(c1)CCN(C(=O)N1CC(C(=O)O)C1)[C@H]2C(=O)Nc1cc(F)c([Si](C)(C)C)c(F)c1] | | 518.2 (M + H) |
| 259 | 1-(((1R)-1-((3,5-difluoro-4-(trimethylsilyl)phenyl)carbamoyl)-6-ethoxy-3,4-dihydroisoquinolin-2(1H)-yl)carbonyl)azetidine-3-carboxylic acid | 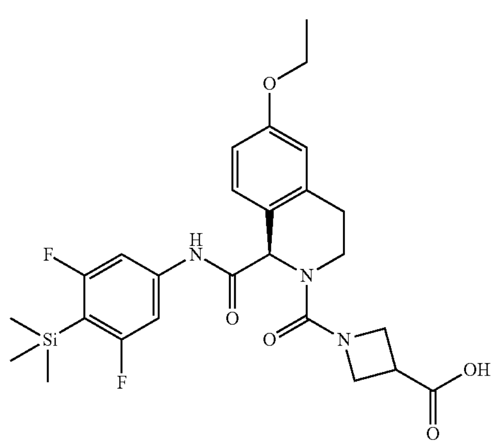 [SMILES: CCOc1ccc2c(c1)CCN(C(=O)N1CC(C(=O)O)C1)[C@H]2C(=O)Nc1cc(F)c([Si](C)(C)C)c(F)c1] | | 532.2 (M + H) |

TABLE 1-27-continued

| EXAMPLE | IUPACNAME | Structure | ADDITIVE | MS |
|---------|-----------|-----------|----------|-----|
| 260 | (1-(((1R)-1-((3,5-difluoro-4-(trimethylsilyl)phenyl)carbamoyl)-6-methoxy-3,4-dihydroisoquinolin-2(1H)-yl)carbonyl)azetidin-3-yl)acetic acid | 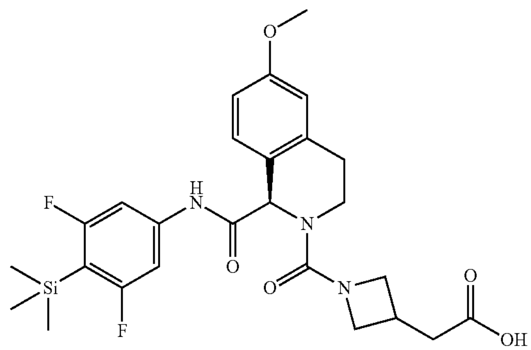 [SMILES: COc1ccc2c(c1)CCN(C(=O)N1CC(CC(=O)O)C1)[C@H]2C(=O)Nc1cc(F)c([Si](C)(C)C)c(F)c1] | | 532.1<br>532.2<br>(M + H) |
| 261 | 5-((1R)-1-((7-fluoro-1,1-dimethyl-2,3-dihydro-1H-inden-5-yl)carbamoyl)-6-methoxy-5-methyl-3,4-dihydroisoquinolin-2(1H)-yl)-5-oxopentanoic acid | 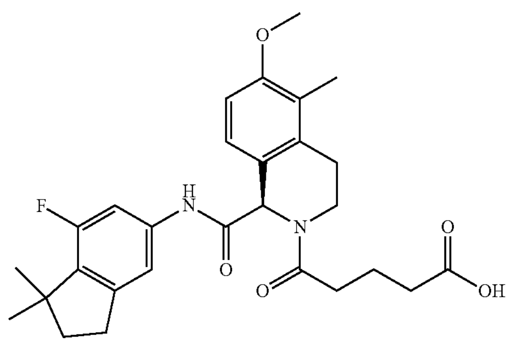 [SMILES: COc1ccc2c(c1C)CCN(C(=O)CCCC(=O)O)[C@H]2C(=O)Nc1cc(F)c2c(c1)CCC2(C)C] | | 497.2<br>(M + H) |

TABLE 1-28

| EXAMPLE | IUPACNAME | Structure | ADDITIVE | MS |
|---------|-----------|-----------|----------|-----|
| 262 | 5-((1R)-1-((7-fluoro-1,1-dimethyl-2,3-dihydro-1H-inden-5-yl)carbamoyl)-6-propyl-3,4-dihydroisoquinolin-2(1H)-yl)-5-oxopentanoic acid | 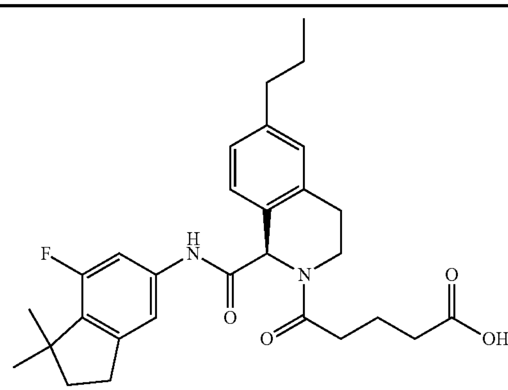 | | 495.3<br>(M + H) |
| 263 | benzyl N-(((1R)-((3,5-difluoro-4-(trimethylsilyl)phenyl)carbamoyl)-6-methoxy-3,4-dihydroisoquinolin-2(1H)-yl)carbonyl)glycinate | 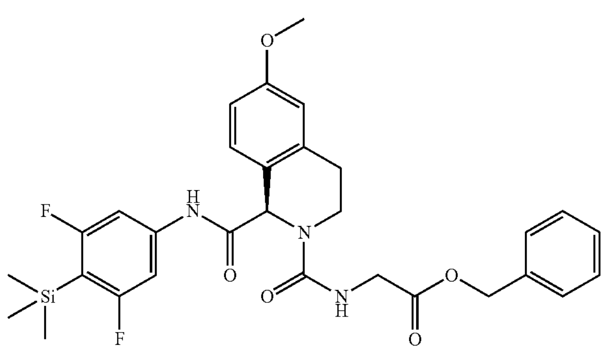 | | 582.2<br>(M + H) |

TABLE 1-28-continued

| EXAMPLE | IUPACNAME | Structure | ADDITIVE | MS |
|---|---|---|---|---|
| 264 | N-(((1R)-1-((3,5-difluoro-4-(trimethylsilyl)phenyl)carbamoyl)-6-methoxy-3,4-dihydroisoquinolin-2(1H)-yl)carbonyl)glycine | 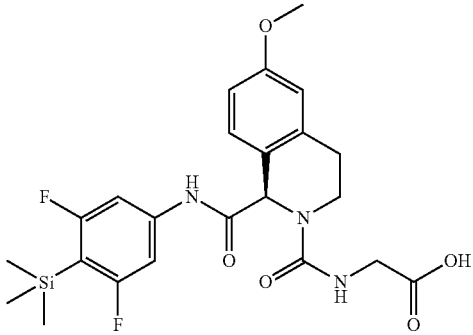 [SMILES: COc1ccc2c(c1)CCN(C(=O)NCC(=O)O)[C@H]2C(=O)Nc1cc(F)c([Si](C)(C)C)c(F)c1] | | 492.2 (M + H) |
| 265 | (4S)-5-((1R)-6-ethoxy-1-((7-fluoro-1,1-dimethyl-2,3-dihydro-1H-inden-5-yl)carbamoyl)-3,4-dihydroisoquinolin-2(1H)-yl)-4-methyl-5-oxopentanoic acid | 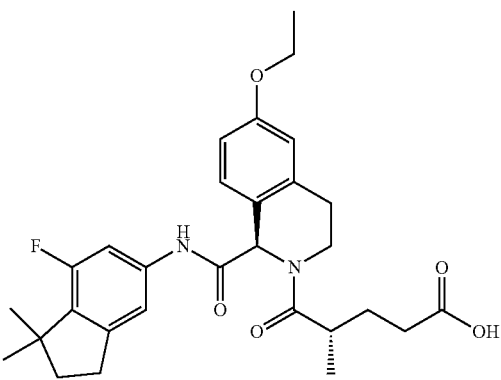 [SMILES: CCOc1ccc2c(c1)CCN(C(=O)[C@@H](C)CCC(=O)O)[C@H]2C(=O)Nc1cc(F)c2c(c1)CCC2(C)C] | | 509.3 (M − H) |
| 266 | (2S)-5-((1R)-6-ethoxy-1-((7-fluoro-1,1-dimethyl-2,3-dihydro-1H-inden-5-yl)carbamoyl)-3,4-dihydroisoquinolin-2(1H)-yl)-2-methyl-5-oxopentanoic acid | 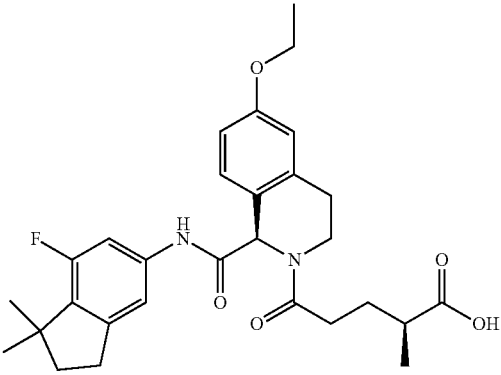 [SMILES: CCOc1ccc2c(c1)CCN(C(=O)CC[C@H](C)C(=O)O)[C@H]2C(=O)Nc1cc(F)c2c(c1)CCC2(C)C] | | 511.2 (M + H) |
| 267 | ((1-(((1R)-1-((3,5-difluoro-4-(trimethylsilyl)phenyl)carbamoyl)-6-methoxy-3,4-dihydroisoquinolin-2(1H)-yl)carbonyl)azetidin-3-yl)oxy)acetic acid | 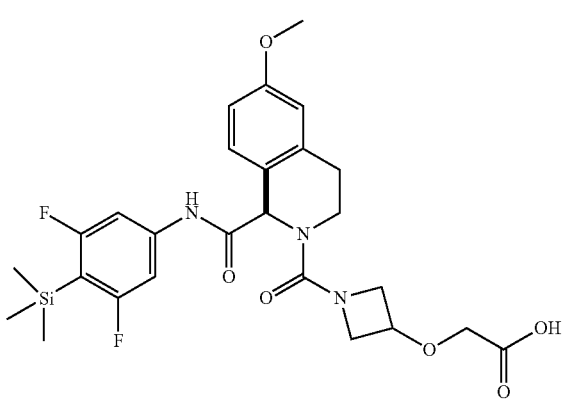 | | 548.2 (M + H) |

TABLE 1-28-continued

| EXAMPLE | IUPACNAME | Structure | ADDITIVE | MS |
|---|---|---|---|---|
| 268 | (4R)-5-((1R)-6-ethoxy-1-((7-fluoro-1,1-dimethyl-2,3-dihydro-1H-inden-5-yl)carbamoyl)-3,4-dihydroisoquinolin-2(1H)-yl)-4-methyl-5-oxopentanoic acid | 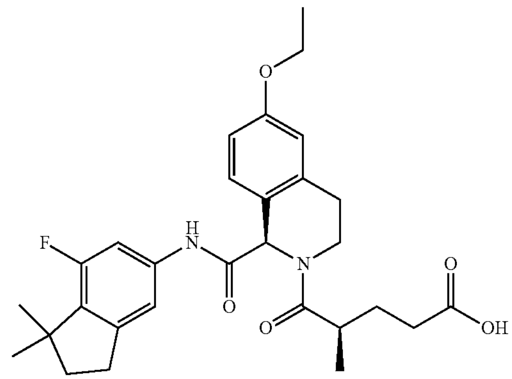 [SMILES: CCOc1ccc2c(c1)CCN(C(=O)[C@H](C)CCC(=O)O)[C@H]2C(=O)Nc1cc(F)c2c(c1)CCC2(C)C] | | 509.3 (M − H) |
| 269 | (2R)-5-((1R)-6-ethoxy-1-((7-fluoro-1,1-dimethyl-2,3-dihydro-1H-inden-5-yl)carbamoyl)-3,4-dihydroisoquinolin-2(1H)-yl)-2-methyl-5-oxopentanoic acid | 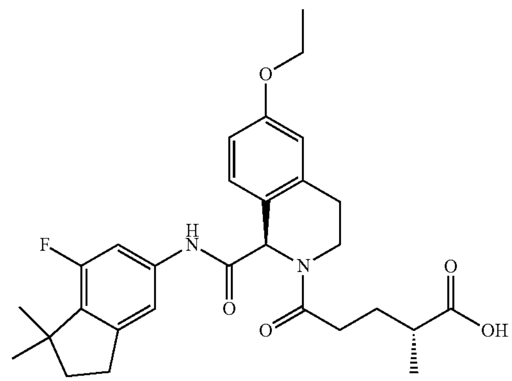 [SMILES: CCOc1ccc2c(c1)CCN(C(=O)CC[C@@H](C)C(=O)O)[C@H]2C(=O)Nc1cc(F)c2c(c1)CCC2(C)C] | | 511.1 (M + H) |
| 270 | 5-((5R)-2-(difluoromethoxy)-5-((3,5-difluoro-4-(trimethylsilyl)phenyl)carbamoyl)-7,8-dihydro-1,6-naphthyridin-6(5H)-yl)-5-oxopentanoic acid | 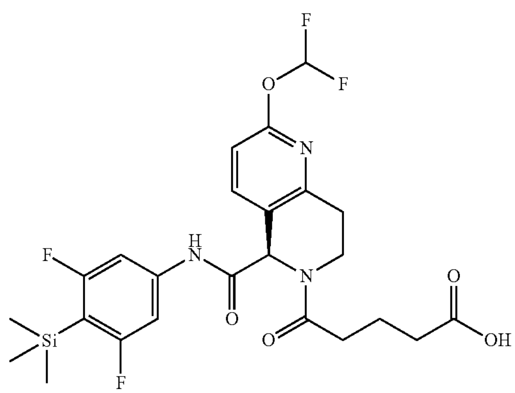 [SMILES: C[Si](C)(C)c1c(F)cc(NC(=O)[C@H]2c3ccc(OC(F)F)nc3CCN2C(=O)CCCC(=O)O)cc1F] | | 540.1 (M − H) |
| 271 | (1-(((6R)-6-((7-fluoro-1,1-dimethyl-2,3-dihydro-1H-inden-5-yl)carbamoyl)-8,9-dihydro[1,3]dioxolo[4,5-f]isoquinolin-7(6H)-yl)carbonyl)azetidin-3-yl)acetic acid | 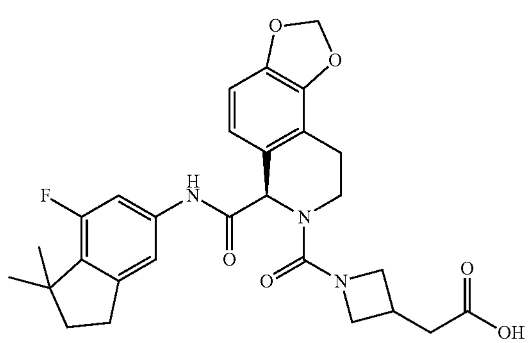 [SMILES: CC1(C)CCc2cc(NC(=O)[C@H]3c4ccc5c(c4CCN3C(=O)N3CC(CC(=O)O)C3)OCO5)cc(F)c21] | | 524.2 (M + H) |

TABLE 1-29

| EXAMPLE | IUPACNAME | Structure | ADDITIVE | MS |
|---|---|---|---|---|
| 272 | (1-(((6R)-6-((3,5-difluoro-4-(trimethylsilyl)phenyl)carbamoyl)-8,9-dihydro[1,3]dioxolo[4,5-f]isoquinolin-7(6H)-yl)carbonyl)azetidin-3-yl)acetic acid | 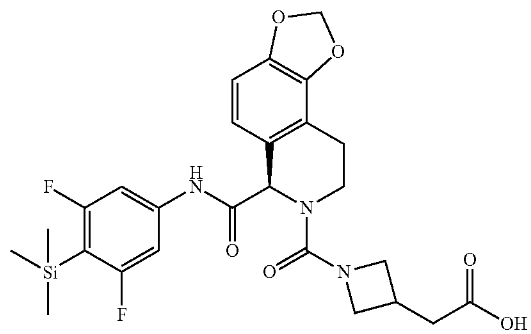 [SMILES: C[Si](C)(C)c1c(F)cc(NC(=O)[C@H]2c3ccc4c(c3CCN2C(=O)N2CC(CC(=O)O)C2)OCO4)cc1F] | | 546.1 (M + H) |
| 273 | (1-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)azetidin-3-yl)acetic acid | 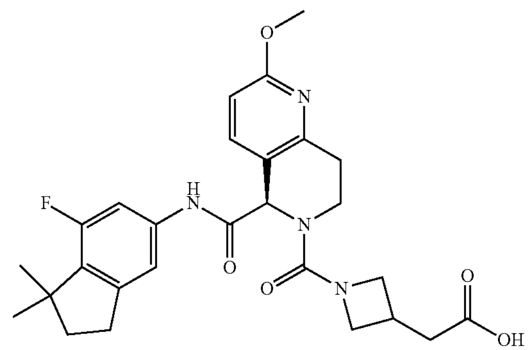 | | 511.2 (M + H) |
| 274 | (1-(((1R)-((3,5-difluoro-4-(trimethylsilyl)phenyl)carbamoyl)-6-methoxy-3,4-dihydroisoquinolin-2(1H)-yl)carbonyl)-3-hydroxyazetidin-3-yl)acetic acid | 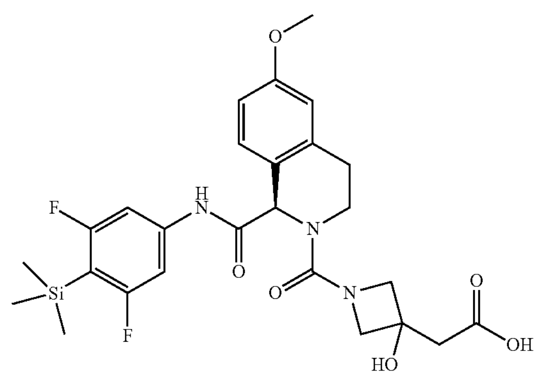 [SMILES: COc1ccc2c(c1)CCN(C(=O)N1CC(O)(CC(=O)O)C1)[C@H]2C(=O)Nc1cc(F)c([Si](C)(C)C)c(F)c1] | | 548.2 (M + H) |
| 275 | (1-(((1R)-1-((3,5-difluoro-4-(trimethylsilyl)phenyl)carbamoyl)-6-(methoxymethyl)-3,4-dihydroisoquinolin-2(1H)-yl)carbonyl)azetidin-3-yl)acetic acid | 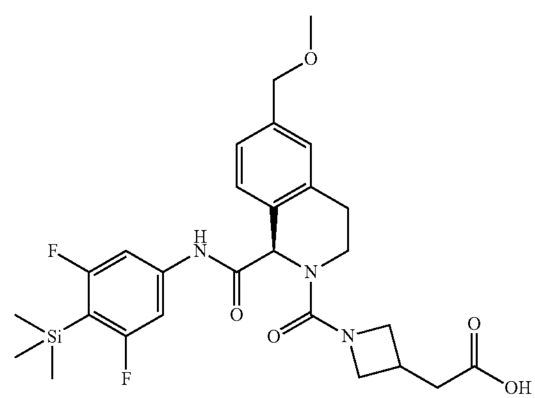 [SMILES: COCc1ccc2c(c1)CCN(C(=O)N1CC(CC(=O)O)C1)[C@H]2C(=O)Nc1cc(F)c([Si](C)(C)C)c(F)c1] | | 546.2 (M + H) |

TABLE 1-29-continued

| EXAMPLE | IUPACNAME | Structure | ADDITIVE | MS |
|---|---|---|---|---|
| 276 | 3-((((1R)-1-((3,5-difluoro-4-(trimethylsilyl)phenyl)carbamoyl)-6-methoxy-3,4-dihydroisoquinolin-2(1H)-yl)carbonyl)oxy)propanoic acid | 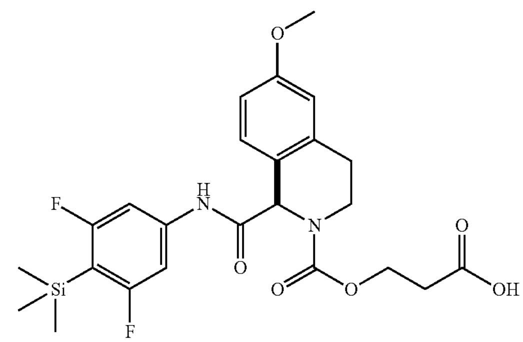 | | 507.2 (M + H) |
| 277 | 3-((((1R)-((3,5-difluoro-4-(trimethylsilyl)phenyl)carbamoyl)-6-ethoxy-3,4-dihydroisoquinolin-2(1H)-yl)carbonyl)oxy)propanoic acid | 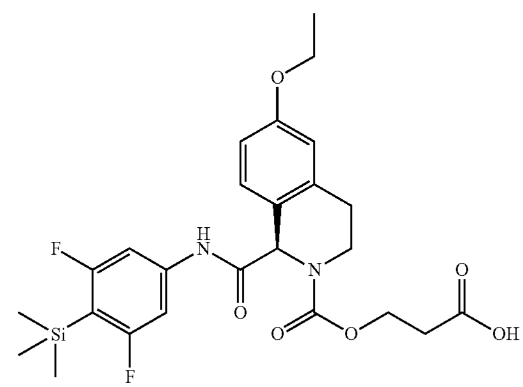 [SMILES: CCOc1ccc2c(c1)CCN(C(=O)OCCC(=O)O)[C@H]2C(=O)Nc1cc(F)c([Si](C)(C)C)c(F)c1] | | 521.2 (M + H) |
| 278 | (1-(((5R)-2-(difluoromethoxy)-5-((3,5-difluoro-4-(trimethylsilyl)phenyl)carbamoyl)-7,8-dihydro-1,6-naphthyridin-6(5H)-yl)carbonyl)azetidin-3-yl)acetic acid | 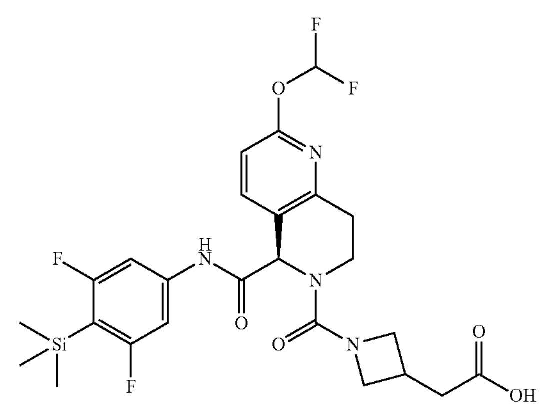 [SMILES: C[Si](C)(C)c1c(F)cc(NC(=O)[C@H]2c3ccc(OC(F)F)nc3CCN2C(=O)N2CC(CC(=O)O)C2)cc1F] | | 567.1 (M − H) |
| 279 | (1-(((1R)-1-((3-fluoro-4-(trimethylsilyl)phenyl)carbamoyl)-6-methoxy-3,4-dihydroisoquinolin-2(1H)-yl)carbonyl)azetidin-3-yl)acetic acid | 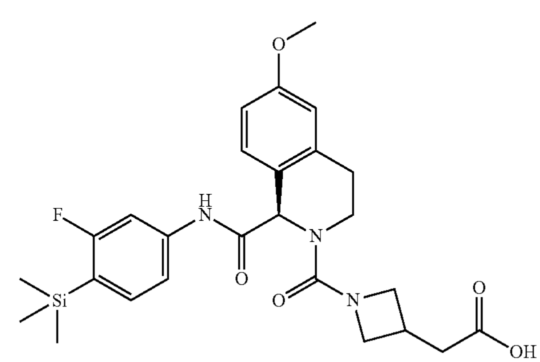 [SMILES: COc1ccc2c(c1)CCN(C(=O)N1CC(CC(=O)O)C1)[C@H]2C(=O)Nc1ccc([Si](C)(C)C)c(F)c1] | | 514.1 (M + H) |

TABLE 1-29-continued

| EXAMPLE | IUPACNAME | Structure | ADDITIVE | MS |
|---|---|---|---|---|
| 280 | (1-(((1R)-6-ethoxy-1-((3-fluoro-4-(trimethylsilyl)phenyl)carbamoyl)-3,4-dihydroisoquinolin-2(1H)-yl)carbonyl)azetidin-3-yl)acetic acid | 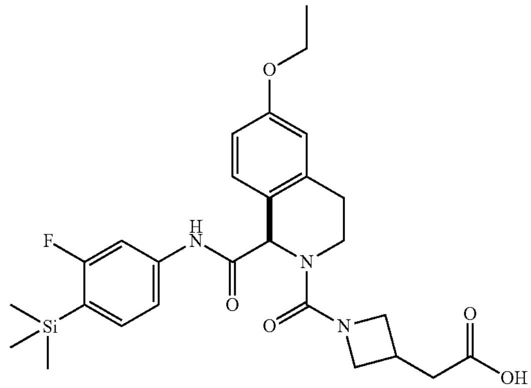 | | 528.2 (M + H) |
| 281 | (1-(((5R)-5-((3,5-difluoro-4-(trimethylsilyl)phenyl)carbamoyl)-2-methoxy-7,8-dihydro-1,6-naphthyridin-6(5H)-yl)carbonyl)azetidin-3-yl)acetic acid | 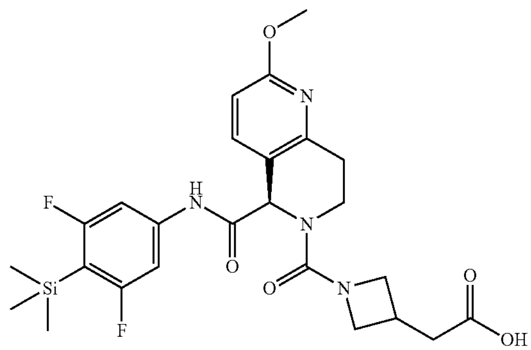 | | 533.2 (M + H) |

TABLE 1-30

| EXAMPLE | IUPACNAME | Structure | ADDITIVE | MS |
|---|---|---|---|---|
| 282 | 5-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)-5-oxopentanoic acid monosulfate dihydrate | 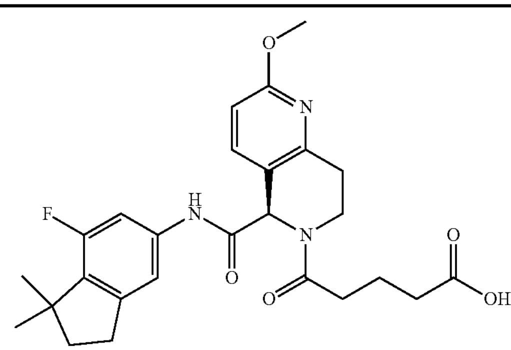 | $H_2SO_4$ $2H_2O$ | 484.3 (M + H) |
| 283 | (1-(((1R)-6-(difluoromethoxy)-1-((3,5-difluoro-4-(trimethylsilyl)phenyl)carbamoyl)-3,4-dihydroisoquinolin-2(1H)-yl)carbonyl)azetidin-3-yl)acetic acid | 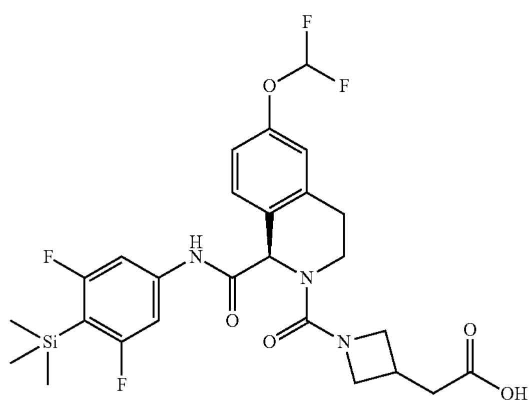 [SMILES: C[Si](C)(C)c1c(F)cc(NC(=O)[C@H]2c3ccc(OC(F)F)cc3CCN2C(=O)N2CC(CC(=O)O)C2)cc1F] | | 568.2 (M + H) |

TABLE 1-30-continued

| EXAMPLE | IUPACNAME | Structure | ADDITIVE | MS |
|---|---|---|---|---|
| 284 | 5-((6R)-6-((7-fluoro-1,1-dimethyl-2,3-dihydro-1H-inden-5-yl)carbamoyl)-3,6,8,9-tetrahydrofuro[2,3-f]isoquinolin-7(2H)-yl)-5-oxopentanoic acid | 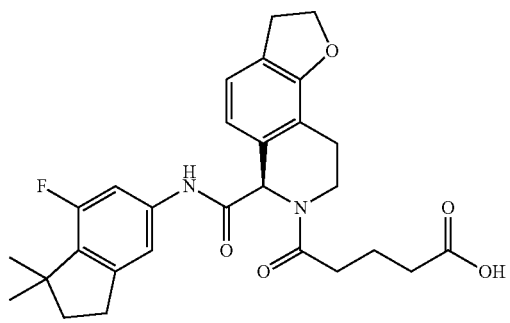 [SMILES: CC1(C)CCc2cc(NC(=O)[C@H]3c4ccc5c(c4CCN3C(=O)CCCC(=O)O)OCC5)cc(F)c21] | | 495.1 (M + H) |
| 285 | 5-((7R)-7-((7-fluoro-1,1-dimethyl-2,3-dihydro-1H-inden-5-yl)carbamoyl)-2,3,9,10-tetrahydro[1,4]dioxino[2,3-f]isoquinolin-8(7H)-yl)-5-oxopentanoic acid | 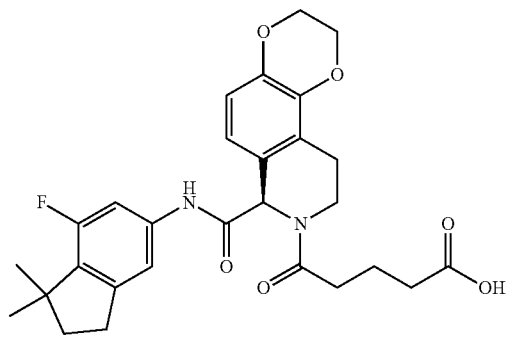 [SMILES: CC1(C)CCc2cc(NC(=O)[C@H]3c4ccc5c(c4CCN3C(=O)CCCC(=O)O)OCCO5)cc(F)c21] | | 509.2 (M − H) |
| 286 | 5-((6R)-6-((3,5-difluoro-4-(trimethylsilyl)phenyl)carbamoyl)-3,6,8,9-tetrahydrofuro[2,3-f]isoquinolin-7(2H)-yl)-5-oxopentanoic acid | 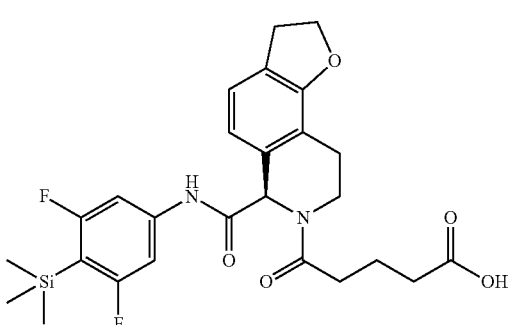 | | 517.3 (M + H) |
| 287 | 5-((7R)-7-((3,5-difluoro-4-(trimethylsilyl)phenyl)carbamoyl)-2,3,9,10-tetrahydro[1,4]dioxino[2,3-f]isoquinolin-8(7H)-yl)-5-oxopentanoic acid | 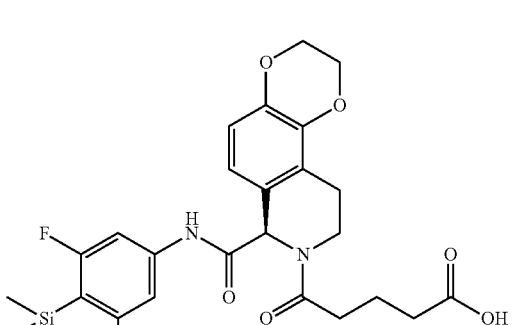 | | 533.2 (M + H) |

TABLE 1-30-continued

| EXAMPLE | IUPACNAME | Structure | ADDITIVE | MS |
|---|---|---|---|---|
| 288 | (1-(((6R)-6-((3,5-difluoro-4-(trimethylsilyl)phenyl)carbamoyl)-3,6,8,9-tetrahydrofuro[2,3-f]isoquinolin-7(2H)-yl)carbonyl)azetidin-3-yl)acetic acid | 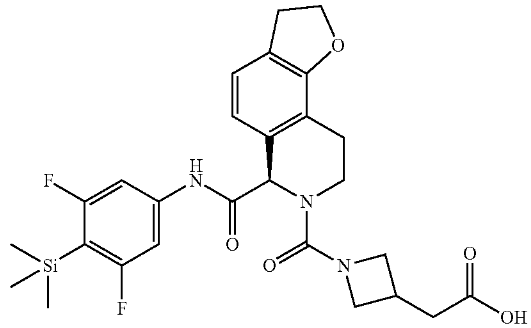 [SMILES: C[Si](C)(C)c1c(F)cc(NC(=O)[C@H]2c3ccc4c(c3CCN2C(=O)N2CC(CC(=O)O)C2)OCC4)cc1F] | | 544.2 (M + H) |
| 289 | (1-(((7R)-7-((3,5-difluoro-4-(trimethylsilyl)phenyl)carbamoyl)-2,3,9,10-tetrahydro[1,4]dioxino[2,3-f]isoquinolin-8(7H)-yl)carbonyl)azetidin-3-yl)acetic acid | 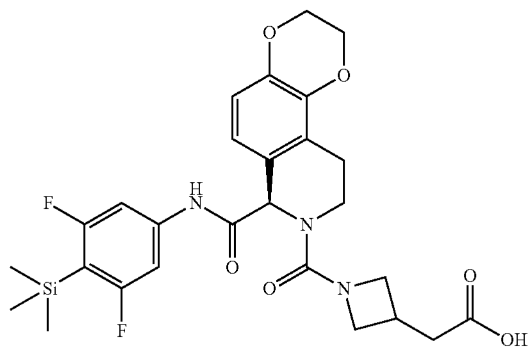 [SMILES: C[Si](C)(C)c1c(F)cc(NC(=O)[C@H]2c3ccc4c(c3CCN2C(=O)N2CC(CC(=O)O)C2)OCCO4)cc1F] | | 560.1 (M + H) |
| 290 | (1-(((1R)-1-((3,5-difluoro-4-(trimethylsilyl)phenyl)carbamoyl)-6-propyl-3,4-dihydroisoquinolin-2(1H)-yl)carbonyl)azetidin-3-yl)acetic acid | 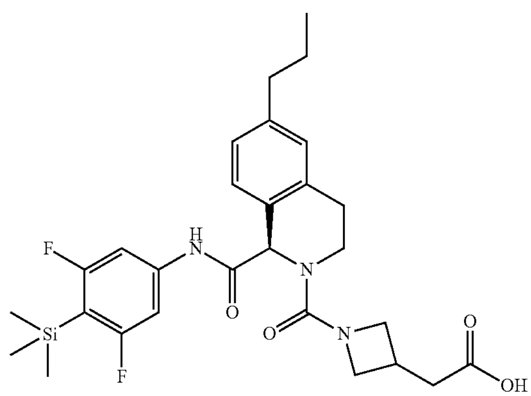 | | 544.2 (M + H) |
| 291 | (1-(((7R)-7-((7-fluoro-1,1-dimethyl-2,3-dihydro-1H-inden-5-yl)carbamoyl)-2,3,9,10-tetrahydro[1,4]dioxino[2,3-f]isoquinolin-8(7H)-yl)carbonyl)azetidin-3-yl)acetic acid | 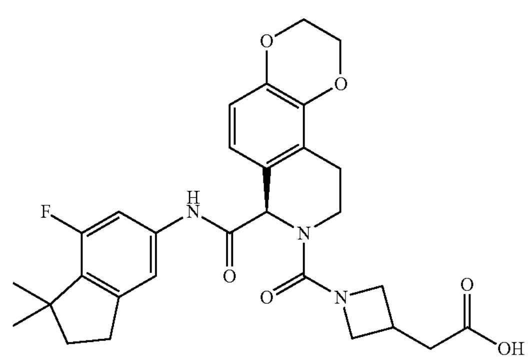 [SMILES: CC1(C)CCc2cc(NC(=O)[C@H]3c4ccc5c(c4CCN3C(=O)N3CC(CC(=O)O)C3)OCCO5)cc(F)c21] | | 538.3 (M + H) |

TABLE 1-31

| EXAMPLE | IUPACNAME | Structure | ADDITIVE | MS |
|---|---|---|---|---|
| 292 | methyl 4-((1R)-1-((3,5-difluoro-4-(trimethylsilyl)phenyl)carbamoyl)-6-methoxy-3,4-dihydroisoquinolin-2(1H)-yl)butanoate | 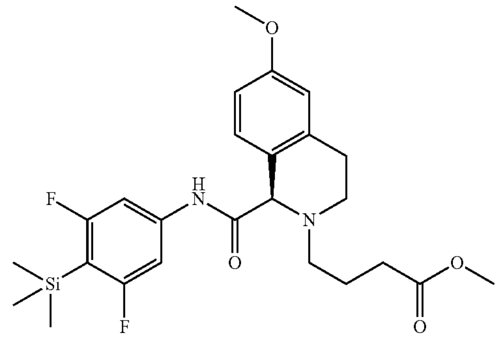 | | 491.2 (M + H) |
| 293 | methyl 4-(((1R)-1-((3,5-difluoro-4-(trimethylsilyl)phenyl)carbamoyl)-6-methoxy-3,4-dihydroisoquinolin-2(1H)-yl)sulfonyl)butanoate | 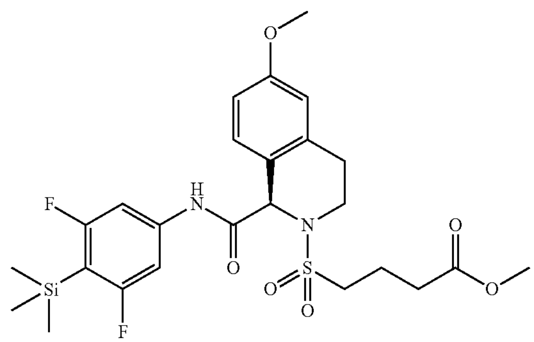 | | 555.2 (M + H) |

Experimental Example 1

RORγt Binding Test Using Fluorescent-labeled Cholesterol

The binding activity of the test compound to RORγt was measured by a time resolved fluorescence resonance energy transfer method (TR-FRET) utilizing histidine-tagged RORγt, fluorescent-labeled cholesterol (BODIPY-cholesterol, AVIVA), and terbium-labeled anti-histidine tag antibody (Invitrogen). First, a test compound diluted with an assay buffer (20 mM Tris-HCl (pH 7.5), 100 mM NaCl, 1 mM DTT, 0.1% BSA) was added to a 384 well plate by 3 μL. Then, RORγt diluted with an assay buffer to 240 nM was added by 3 μL, after which fluorescent-labeled cholesterol diluted with the assay buffer to 12 μM was added by 3 μL, and the mixture was stood at room temperature for 20 min. Thereafter, a terbium-labeled anti-histidine tag antibody diluted with the assay buffer to 8 nM was added by 3 μL. The mixture was stood at room temperature for 20 min, and fluorescence intensity (excitation wavelength 320 nm, fluorescence wavelength 520 nm, delay time 100 microseconds) was measured by Envision (PerkinElmer).

The results (binding inhibitory rate of fluorescent-labeled cholesterol to RORγt at test compound 1 μM) measured by the above-mentioned method are shown in Tables 2-1 to 2-6.

Experimental Examples 1-2

RORγt Binding Test Using Fluorescent-labeled Synthetic Ligand

The fluorescent-labeled synthetic cholesterol ligand was synthesized as follows.

(Step 1)

A solution of (4-(methoxymethyl)phenyl)boronic acid (999 mg, 6.02 mmol), glyoxylic acid monohydrate (554 mg, 6.02 mmol) and diallylamine (0.741 mL, 6.02 mmol) in acetonitrile (12 mL) stirred was at 60° C. for 5 hr. The reaction mixture was concentrated under reduced pressure. The obtained residue was purified by silica gel column chromatography (Diol, solvent; ethyl acetate), and crystallized from ethyl acetate to give 2-(diallylamino)-2-(4-(methoxymethyl)phenyl)acetic acid (200 mg, 0.726 mmol, 12.07%) as white crystals.

$^1$H NMR (300 MHz, DMSO-d$_6$): δ 3.04-3.46 (7H, m), 4.39 (2H, s), 4.43 (1H, s), 5.04-5.23 (4H, m), 5.78 (2H, ddt, J=16.9, 10.5, 6.3 Hz), 7.23-7.40 (4H, m).

(Step 2)

To a solution of 3,5-difluoro-4-(trimethylsilyl)aniline (6.69 g, 33.25 mmol), 2-(diallylamino)-2-(4-(methoxymethyl)phenyl)acetic acid (11.9 g, 43.22 mmol), DMAP (4.47 g, 36.57 mmol) and DIEA (29.0 mL, 166.23 mmol) in ethyl acetate (200 mL) was added T3P (29.3 mL, 49.87 mmol), and the mixture was stirred at 80° C. for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 3→35% ethyl acetate/hexane) to give 2-(diallylamino)-N-(3,5-difluoro-4-(trimethylsilyl)phenyl)-2-(4-(methoxymethyl)phenyl)acetamide (9.00 g, 19.62 mmol, 59.0%) as a pale yellow oil.

(Step 3)

A solution of 2-(diallylamino)-N-(3,5-difluoro-4-(trimethylsilyl)phenyl)-2-(4-(methoxymethyl)phenyl)acetamide (1.64 g, 3.58 mmol), 1,3-dimethylbarbituric acid (1.173 g, 7.51 mmol) and Pd(PPh$_3$)$_4$ (0.165 g, 0.14 mmol) in THF (15 mL) was stirred overnight under argon gas atmosphere at room temperature. The obtained residue was purified by silica gel column chromatography (NH, solvent gradient; 5→75% ethyl acetate/hexane) to give 2-amino-N-(3,5-difluoro-4-(trimethylsilyl)phenyl)-2-(4-(methoxymethyl)phenyl)acetamide (470.5 mg, 1.243 mmol, 34.8%) as a pale yellow oil.
(Step 4)

To a solution of 2-amino-N-(3,5-difluoro-4-(trimethylsilyl)phenyl)-2-(4-(methoxymethyl)phenyl)acetamide (470 mg, 1.24 mmol) and DIEA (0.651 mL, 3.73 mmol) in THF (10 mL) was added allyl chloroformate (0.158 mL, 1.49 mmol) at 0° C., and the mixture was stirred for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0-10% ethyl acetate/hexane) to give allyl (2-((3,5-difluoro-4-(trimethylsilyl)phenyl)amino)-1-(4-(methoxymethyl)phenyl)-2-oxoethyl)carbamate (297 mg, 0.641 mmol, 51.7%) as a white solid.
(Step 5)

Allyl (2-((3,5-difluoro-4-(trimethylsilyl)phenyl)amino)-1-(4-(methoxymethyl)phenyl)-2-oxoethyl)carbamate (296 mg) was resolved by chiral column chromatography. The fraction having a shorter retention time was concentrated to give allyl (R)-(2-((3,5-difluoro-4-(trimethylsilyl)phenyl)amino)-1-(4-(methoxymethyl)phenyl)-2-oxoethyl)carbamate (108.5 mg, >99.9% ee) as a white solid.
purification condition by chiral column chromatography
   column: CHIRALPAK AD (NF001) 50 mmID×500 mmL
   solvent: hexane/EtOH=600/400
   flow rate: 80 mL/min
   temperature: 30° C.
   detection method: UV 220 nm
(Step 6)

A solution of allyl (R)-(2-((3,5-difluoro-4-(trimethylsilyl)phenyl)amino)-1-(4-(methoxymethyl)phenyl)-2-oxoethyl)carbamate (109 mg, 0.24 mmol), 1,3-dimethylbarbituric acid (81 mg, 0.52 mmol) and Pd(PPh$_3$)$_4$ (10.89 mg, 9.43 μmol) in THF (1571 μL) was stirred under argon gas atmosphere at room temperature for 6 hr. The reaction solution was concentrated under reduced pressure, and the obtained residue was purified by silica gel column chromatography (NH, solvent gradient; 40→80% ethyl acetate/hexane) to give (R)-2-amino-N-(3,5-difluoro-4-(trimethylsilyl)phenyl)-2-(4-(methoxymethyl)phenyl)acetamide (100 mg, 0.263 mmol, 112%) as a yellow oil.
(Step 7)

To a solution of (R)-2-amino-N-(3,5-difluoro-4-(trimethylsilyl)phenyl)-2-(4-(methoxymethyl)phenyl)acetamide (9.07 mg, 0.02 mmol) in DMF (0.5 ml) was added 1-((5-((2Z)-2-((1-(difluoroboryl)-3,5-dimethyl-1H-pyrrol-2-yl)methylene)-2H-pyrrol-5-yl)pentanoyl)oxy)pyrrolidine-2,5-dione (BODIPY (registered trademark) FL-C5 succinimidyl ester) (5.0 mg, 0.01 mmol) at room temperature, and the mixture was stirred at room temperature for 3 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane), and then preparative HPLC (C18, mobile phase: water/acetonitrile (containing 0.1% TFA)) to give 5-((2Z)-2-((1-(difluoroboryl)-3,5-dimethyl-1H-pyrrol-2-yl)methylene)-2H-pyrrol-5-yl)-N-(1R)-2-((3,5-difluoro-4-(trimethylsilyl)phenyl)amino)-1-(4-(methoxymethyl)phenyl)-2-oxoethyl)pentanamide (3.8 mg, 5.58 μmol, 46.6%) as an orange solid, which is a fluorescent-labeled synthetic ligand.

$^1$H NMR (300 MHz, CDCl$_3$): δ 0.31 (9H, t, J=1.3 Hz), 1.71-1.87 (4H, m), 2.25 (3H, s), 2.32-2.42 (2H, m), 2.53 (3H, s), 2.91-3.03 (2H, m), 3.35 (3H, s), 4.40 (2H, s), 5.71 (1H, d, J=7.2 Hz), 6.09 (1H, s), 6.23 (1H, d, J=4.2 Hz), 6.80-6.90 (2H, m), 6.90-6.99 (2H, m), 7.06 (1H, s), 7.23-7.31 (2H, m), 7.33-7.42 (2H, m), 8.63 (1H, s).

MS(API): Calculated 680.6. Found 679.3 (M–H).

The binding activity of the test compound to RORγt was measured by a time resolved fluorescence resonance energy transfer method (TR-FRET) utilizing histidine-tagged RORγt, fluorescent-labeled synthetic ligand, and terbium-labeled anti-histidine tag antibody (Invitrogen). First, a test compound diluted with an assay buffer (20 mM Tris-HCl (pH 7.5), 100 mM NaCl, 1 mM DTT, 0.1% BSA) was added to a 384 well plate by 3 μL. Then, RORγt diluted with an assay buffer to 240 nM was added by 3 μL, after which fluorescent-labeled synthetic ligand diluted with the assay buffer to 12 μM was added by 3 μL, and the mixture was stood at room temperature for 20 min. Thereafter, a terbium-labeled anti-histidine tag antibody diluted with the assay buffer to 8 nM was added by 3 μL. The mixture was stood at room temperature for 20 min, and fluorescence intensity (excitation wavelength 320 nm, fluorescence wavelength 520 nm, delay time 100 microseconds) was measured by Envision (PerkinElmer).

The results (binding inhibitory rate of fluorescent-labeled synthetic ligand to RORγt at test compound 1 μM) measured by the above-mentioned method are shown in Tables 3-1 to 3-2.

Experimental Example 2

Cofactor Recruitment Test

Cofactor recruitment test was performed by Alpha Screen (Histidine Detection Kit, PerkinElmer) method. First, a test compound was diluted with an assay buffer (50 mM Tris-HCl (pH 7.5), 50 mM KCl, 1 mM DTT, 0.1% BSA) and added to a 384 well plate by 5 μL. Then, RORγt diluted with an assay buffer to 125 nM was added by 10 μL each, after which solutions of 25 nM biotinylated SRC-1 peptide (biotin-CLTARHKILHRLLQEGSPSD), 12.5 μg/mL acceptor beads and 12.5 μg/mL donor beads prepared with the assay buffer were added by 10 μL each. The mixture was stood in a dark place for 1 hr, and the signal value was measured by Envision (PerkinElmer).

The results (signal value inhibitory rate at test compound 1 μM) measured by the above-mentioned method are shown in Tables 2-1 to 2-6.

Experimental Example 3

Jurkat Reporter Test

The Jurkat cells used for the reporter test were cultured in a culture medium (RPMI (Invitrogen), 10% FCS (AusGeneX), 100 U/mL penicillin, 100 μg/mL streptomycin). On the day of the test, 4×10$^7$ cells were recovered by a centrifugal operation (1000 rpm, 5 min.) and suspended in PBS (phosphate buffered saline) (Invitrogen). Thereafter, the cells were recovered again by a centrifugal operation, and suspended in 2 mL of R buffer (NEON transfection kit, Invitrogen). Then, a reporter vector 53 μg wherein a human IL-17 ROR response element was inserted into the upstream of luciferase of pGL 4.28 (Promega), and a vector (27 μg) wherein RORγt sequence was inserted into the downstream of CMV promoter were added to the cell suspension. Gene transfer was performed by Electroporation apparatus (NEON, Invitrogen) under the conditions of pulse voltage 1350 V, interval 10 milliseconds, number of times 3. The cells after gene transfer were suspended in 40 mL of a reaction medium (RPMI, 10% Lipid reduced FCS (HyClone), 10 mM HEPES (pH 7.5), 100 U/mL penicillin, 100 μg/mL streptomycin, 5 μM lovastatin), and plated in a 96 well plate by 90 μL. A test compound diluted with the reaction medium was added by 10 μL, and the cells were cultured overnight in an incubator. Bright-Glo (Promega) was added by 100 μL, and the mixture was stirred at room temperature for 10 min, and the luminescence level was measured by Envision (PerkinElmer).

The results (luminescence level inhibitory rate at test compound 3 μM) measured by the above-mentioned method are shown in Tables 2-1 to 2-6.

TABLE 2-1

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 2 | 99.7 | 80.5 | 98.1 |
| 3 | 101 | 92.7 | 99.6 |
| 4 | 101 | 81.9 | 99.7 |
| 7 | 102 | 92.8 | 101 |
| 8 | 102 | 81.2 | 101 |
| 9 | 100 | 77.3 | 101 |
| 10 | 98.9 | 43.8 | 98.8 |
| 11 | 103 | 67.7 | 99.7 |
| 12 | 103 | 82.4 | 99.3 |
| 13 | 100 | 80.4 | 101 |
| 25 | 102 | 85.8 | 102 |
| 26 | 97.7 | 81.5 | 102 |
| 27 | 103 | 82.8 | 101 |
| 28 | 102 | 83.2 | 101 |
| 29 | 102 | 88 | 102 |
| 30 | 102 | 82 | 99.8 |
| 32 | 101 | 89.9 | 103 |
| 36 | 101 | 67.1 | 97.7 |
| 37 | 103 | 98.3 | 98.6 |
| 41 | 102 | 74.9 | 98.9 |
| 43 | 102 | 88.3 | 101 |
| 45 | 103 | 76.9 | 99.6 |
| 54 | 100 | 81.9 | 101 |
| 55 | 102 | 73.4 | 100 |
| 56 | 101 | 61.3 | 99.9 |

TABLE 2-2

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 63 | 100 | 70 | 99.9 |
| 65 | 102 | 98 | 100 |
| 66 | 102 | 82 | 99.5 |
| 67 | 103 | 87 | 100 |
| 68 | 103 | 73 | 99 |
| 69 | 102 | 83 | 100 |
| 70 | 102 | 82 | 99 |
| 72 | 104 | 94 | 100 |
| 73 | 102 | 90 | 100 |
| 75 | 101 | 78 | 96 |
| 77 | 101 | 91 | 100 |
| 78 | 101 | 89 | 101 |
| 79 | 102 | 97 | 102 |
| 80 | 102 | 97 | 100 |
| 82 | 102 | 98 | 100 |
| 84 | 101 | 92 | 100 |
| 85 | 103 | 99 | 101 |

TABLE 2-2-continued

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 86 | 103 | 98 | 101 |
| 87 | 102 | 98 | 102 |
| 92 | 103 | 99 | 102 |
| 94 | 103 | 99 | 103 |
| 95 | 102 | 98 | 103 |
| 97 | 102 | 96 | 102 |
| 98 | 99 | 96 | 102 |
| 101 | 102 | 99 | 103 |

TABLE 2-3

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 103 | 104 | 101 | 102 |
| 104 | 102 | 101 | 102 |
| 105 | 103 | 100 | 101 |
| 106 | 102 | 101 | 102 |
| 107 | 103 | 100 | 102 |
| 109 | 103 | 95 | 102 |
| 110 | 102 | 100 | 103 |
| 111 | 103 | 99 | 103 |
| 113 | 104 | 99 | 101 |
| 114 | 103 | 98 | 101 |
| 115 | 103 | 89 | 102 |
| 117 | 102 | 87 | 101 |
| 118 | 104 | 81 | 100 |
| 121 | 101 | 100 | 103 |
| 122 | 102 | 99 | 103 |
| 124 | 101 | 99 | 102 |
| 125 | 102 | 99 | 102 |
| 126 | 101 | 100 | 102 |
| 128 | 103 | 100 | 103 |
| 129 | 98 | 99 | 102 |
| 130 | 102 | 100 | 104 |
| 131 | 103 | 100 | 103 |
| 132 | 100 | 98 | 104 |
| 133 | 103 | 96 | 103 |
| 135 | 102 | 97 | 104 |

TABLE 2-4

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 136 | 100 | 97 | 103 |
| 137 | 102 | 98 | 103 |
| 138 | 102 | 100 | 104 |
| 140 | 100 | 95 | 102 |
| 143 | 101 | 56 | 83 |
| 144 | 101 | 97 | 101 |
| 145 | 102 | 92 | 100 |
| 147 | 101 | 89 | 101 |
| 149 | 103 | 99 | 103 |
| 151 | 99 | 99 | 102 |
| 152 | 102 | 97 | 103 |
| 153 | 100 | 84 | 97 |
| 154 | 101 | 85 | 98 |
| 155 | 101 | 84 | 99 |
| 156 | 102 | 98 | 103 |

TABLE 2-4-continued

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 157 | 99 | 74 | 94 |
| 158 | 101 | 76 | 93 |
| 159 | 100 | 80 | 97 |
| 160 | 100 | 82 | 98 |
| 161 | 100 | 76 | 90 |
| 162 | 99 | 82 | 95 |
| 163 | 100 | 97 | 101 |
| 164 | 101 | 96 | 101 |
| 165 | 101 | 96 | 101 |
| 166 | 100 | 86 | 99 |

TABLE 2-5

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 167 | 101 | 85 | 97 |
| 168 | 97 | 86 | 99 |
| 169 | 102 | 93 | 102 |
| 170 | 102 | 81 | 97 |
| 171 | 100 | 82 | 96 |
| 172 | 101 | 82 | 97 |
| 173 | 101 | 97 | 99 |
| 174 | 101 | 88 | 98 |
| 179 | NT | 94 | 102 |
| 180 | NT | 93 | 100 |
| 182 | NT | 67 | 99 |
| 183 | NT | 91 | 102 |
| 184 | NT | 93 | 100 |
| 187 | NT | 93 | 103 |
| 192 | NT | 95 | 102 |
| 194 | NT | 87 | 100 |
| 195 | NT | 89 | 101 |
| 196 | NT | 91 | 100 |
| 209 | NT | 87 | 99 |
| 210 | NT | 76 | 98 |
| 211 | NT | 92 | 101 |
| 221 | NT | 97 | 101 |
| 222 | NT | 94 | 100 |
| 227 | NT | 95 | 101 |
| 231 | NT | 96 | 101 |

TABLE 2-6

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 235 | NT | 45 | 93 |
| 238 | NT | 92 | 100 |
| 240 | NT | 91 | 101 |
| 242 | NT | 94 | 101 |
| 248 | NT | 87 | 100 |
| 254 | NT | 101 | 102 |
| 256 | NT | 102 | 83 |
| 260 | NT | 95 | 101 |
| 272 | NT | 101 | 100 |
| 273 | NT | 62 | 96 |
| 279 | NT | 89 | 100 |

TABLE 2-6-continued

| Ex. No. | Experimental Example 1 Binding inhibitory rate of fluorescent-labeled cholesterol to RORγt at test compound 1 μM (%) | Experimented Example 2 Signal value inhibitory rate at test compound 1 μM (%) | Experimental Example 3 Luminescence level inhibitory rate at test compound 3 μM (%) |
|---|---|---|---|
| 281 | NT | 89 | 102 |
| 282 | NT | 56 | 95 |

NT: Not Tested

TABLE 3-1

| Ex. No. | Experimental Example 1-2 Binding inhibitory rate of fluorescent-labeled synthetic ligand to RORγt at test compound 1 μM (%) |
|---|---|
| 7 | 101 |
| 13 | 102 |
| 25 | 101 |
| 26 | 101 |
| 27 | 101 |
| 41 | 102 |
| 43 | 102 |
| 45 | 102 |
| 56 | 102 |
| 63 | 102 |
| 65 | 101 |
| 66 | 102 |
| 67 | 102 |
| 68 | 101 |
| 69 | 101 |
| 70 | 102 |
| 72 | 102 |
| 73 | 102 |
| 75 | 102 |
| 78 | 102 |
| 79 | 102 |
| 80 | 102 |
| 82 | 102 |
| 86 | 102 |
| 88 | 102 |
| 94 | 101 |
| 97 | 101 |
| 98 | 102 |
| 101 | 102 |
| 103 | 101 |
| 104 | 101 |
| 105 | 101 |
| 106 | 101 |
| 107 | 102 |
| 109 | 102 |
| 110 | 102 |
| 111 | 101 |
| 114 | 102 |
| 115 | 101 |
| 117 | 102 |
| 118 | 102 |
| 121 | 101 |
| 125 | 101 |
| 126 | 101 |
| 129 | 101 |
| 130 | 102 |
| 131 | 101 |
| 132 | 102 |
| 133 | 101 |
| 135 | 101 |

TABLE 3-2

| Ex No. | Experimental Example 1-2 Binding inhibitory rate of fluorescent-labeled synthetic ligand to RORγt at test compound 1 μM (%) |
|---|---|
| 136 | 102 |
| 137 | 102 |
| 138 | 101 |
| 140 | 101 |
| 143 | 101 |
| 144 | 101 |
| 147 | 101 |
| 151 | 102 |
| 152 | 101 |
| 153 | 102 |
| 154 | 102 |
| 155 | 101 |
| 157 | 102 |
| 159 | 101 |
| 163 | 102 |
| 166 | 102 |
| 167 | 102 |
| 169 | 102 |
| 170 | 102 |
| 171 | 101 |
| 172 | 101 |
| 179 | 101 |
| 180 | 101 |
| 182 | 101 |
| 183 | 101 |
| 184 | 101 |
| 187 | 101 |
| 192 | 102 |
| 194 | 101 |
| 195 | 101 |
| 196 | 102 |
| 209 | 102 |
| 210 | 101 |
| 211 | 101 |
| 221 | 102 |
| 222 | 102 |
| 227 | 102 |
| 231 | 101 |
| 235 | 102 |
| 238 | 101 |
| 240 | 101 |
| 242 | 101 |
| 248 | 101 |
| 254 | 102 |
| 256 | 100 |
| 260 | 102 |
| 272 | 102 |
| 273 | 101 |
| 279 | 102 |
| 281 | 102 |
| 282 | 102 |

Experimental Example 4

Effect on IL-17 Production in Human Blood

The inhibitory effect of the test compound on IL-17 production in human blood was evaluated as follows. First, 150 μL of peripheral blood collected from healthy individuals using heparinized vacuum blood collection tubes was dispensed into each well of a 96-well plate (Corning), and 45 μL of RPMI 1640 medium (Gibco) containing 10% fetal bovine serum (FBS, Hyclone) and 30 μL of the test compound diluted with the medium was added to each well. The plate was then cultured for 30 min at 37° C. Cells were subsequently stimulated by adding 30 μL of 100 ng/mL human IL-23 (R&D) and 45 μL of Dynabeads Human (Invitrogen) to each well and culturing the plate for 3 days at 37° C. In wells without stimulation, 75 μL of RPMI 1640 medium containing 10% FBS was added instead of the IL-23 and Dynabeads solution. After culturing for 3 days, the culture supernatant was collected, and the amount of IL-17 in the supernatant was measured using an IL-17 ELISA kit (R&D).

The results of the above-described measurements (percent inhibition of IL-17 production with 10 μM of the test compound) are shown in Table 4.

TABLE 4

| Example No. | Percent Inhibition at 10 μM |
|---|---|
| 82 | 75% |
| 118 | 88% |
| 140 | 91% |
| 144 | 86% |
| 179 | 82% |
| 260 | 89% |
| 266 | 88% |
| 272 | 93% |
| 273 | 89% |

The results above showed that the example compounds inhibited IL-17 production in human blood.

Experimental Example 5

Effect on IL-23-induced Cytokine Expression in Mice

A mouse IL-23 solution (500 ng/10 μL, prepared by Takeda Pharmaceutical Company Limited) or PBS (10 μL, negative control group) was administered intradermally in the ear of Balb/c mice (Charles River Japan, male, 7 weeks old). Twenty-four hr after administration, the ear was resected under isoflurane anesthesia. The test compound was suspended in 0.5% methylcellulose and administered orally 30 min before and 8 hr after IL-23 administration.

RNA extraction from the ear tissue and quantitative PCR were performed as follows. Specifically, ear tissue 5 mm in diameter was punched from an area of the resected ear centering on the IL-23 injection site, and the tissue was immersed in RNAlater (QIAGEN) for at least 18 hr. The RNAlater-treated ear tissue was homogenized in 350 μL of RLT buffer (RNeasy mini kit, QIAGEN) and treated (55° C., 10 min) with Proteinase K (QIAGEN). Total RNA was then extracted according to the RNeasy mini kit protocol. The RNA thus obtained was then reverse transcribed into cDNA using the High-Capacity RNA-to-cDNA kit (Applied Biosystems), and the amount of each cytokine expressions was measured by real-time PCR (Viia7™, Applied Biosystems). The PCR buffer used was TaqMan Fast Advanced Master Mix (Applied Biosystems), and TaqMan Gene Expression Assays (Applied Biosystems) Mm00439618 ml (IL-17A) and 4352341E (β-actin) were used for cytokine gene detection. The IL-17A gene expression level was normalized to the R-actin gene expression level, and the percent inhibition of IL-17A gene expression with the test compound was then calculated.

The results obtained with the above-described method (percent inhibition of IL-17A gene expression with oral administration of the test compound) are shown in Table 5.

TABLE 5

| Example No. | Dose (mg/kg) | Percent inhibition of IL-17A gene expression* |
|---|---|---|
| 68 | 100 | 90% |
| 82 | 10 | 85% |
| 109 | 30 | 96% |

TABLE 5-continued

| Example No. | Dose (mg/kg) | Percent inhibition of IL-17A gene expression* |
|---|---|---|
| 118 | 10 | 87% |
| 125 | 30 | 89% |
| 135 | 30 | 68% |
| 140 | 30 | 90% |
| 176 | 30 | 91% |
| 179 | 30 | 95% |
| 260 | 10 | 76% |
| 272 | 10 | 86% |
| 273 | 10 | 77% |
| 279 | 10 | 71% |
| 281 | 10 | 93% |

*versus the negative control group

The results above showed that oral administration of the example compounds inhibited IL-17A gene expression in vivo.

Experimental Example 6

Effect in a Mouse Model of IL-23-induced Psoriasis

Mouse IL-23 (500 ng/15 μL, R&D) or PBS (15 μL, negative control group) was administered intradermally in the ear of Balb/c mice (Charles River Japan, male, 7 weeks old) 5 times every other days. Seven hr after IL-23 administration at 8 days after the initial administration (final administration), the mice were anesthetized with isoflurane, and ear thickness was measured with calipers. After the ear thickness was measured, the ear was resected, tissue 8 mm in diameter was punched from an area centering on the IL-23 injection site, and the tissue was weighed. The punched ear tissue was cut in half, and one half was immersion-fixed in 10% neutral buffer formalin solution for use in histopathological evaluation. The other half was immersed in RNAlater (QIAGEN) for at least 18 hr for use in an evaluation of the IL-17A mRNA expression level. The test compound was suspended in 0.5% methylcellulose and administered orally twice daily on consecutive days from 30 min before the initial IL-23 administration to 30 min before the final IL-23 administration.

The change in ear thickness in this model was evaluated by calculating the difference in measured thickness between before IL-23 administration and 7 hr after the final IL-23 administration. In addition, the formalin-fixed tissue was embedded and sectioned, then stained with hematoxylineosin. The degree of acanthosis was then evaluated qualitatively by microscopy (classified with a score of 0 to 4). RNA extraction from the ear tissue and quantitative PCR were performed as follows. As described above, ear tissue treated with RNAlater (QIAGEN) was homogenized in 350 μL of RLT buffer (RNeasy mini kit, QIAGEN) and treated (55° C., 10 min) with Proteinase K (QIAGEN). Total RNA was then extracted according to the RNeasy mini kit protocol. The RNA thus obtained was reverse transcribed into cDNA using the High-Capacity RNA-to-cDNA kit (Applied Biosystems), and the expression of each gene was measured by real-time PCR (Viia7™, Applied Biosystems). The PCR buffer used was TaqMan Fast Advanced Master Mix (Applied Biosystems), and TaqMan Gene Expression Assays (Applied Biosystems) Mm00439618_m1 (IL-17A) and 4352341E (β-actin) were used to detect the genes. The IL-17A gene expression level was normalized to the R-actin gene expression level, and the percent inhibition of IL-17A gene expression with the test compound was then calculated.

The measurement results obtained with the above-described method (ear thickness, acanthosis score, and percent inhibition of IL-17A gene expression with oral administration of the test compound) are shown in Table 6.

TABLE 6

| Example No. | Dose (mg/kg) | Percent Inhibition of Ear Thickness* | Percent Inhibition of Acanthosis Score* | Percent Inhibition of IL-17A Expression* |
|---|---|---|---|---|
| 118 | 30 | 61% | 80% | 111% |

*versus the negative control group

The results above showed that oral administration of the example compounds inhibited the increase in ear thickness, acanthosis, and IL-17A gene expression in the mouse model of psoriasis.

Formulation Example 1

| | |
|---|---|
| (1) the compound of Example 1 | 10.0 g |
| (2) lactose | 70.0 g |
| (3) cornstarch | 50.0 g |
| (4) soluble starch | 7.0 g |
| (5) magnesium stearate | 3.0 g |

The compound of Example 1 (10.0 g) and magnesium stearate (3.0 g) are granulated in aqueous solution (70 mL) of soluble starch (7.0 g as soluble starch) and then dried, the resulting mixture is mixed with lactose (70.0 g) and cornstarch (50.0 g) (lactose, cornstarch, soluble starch and magnesium stearate are all products in compliance with Japanese Pharmacopoeia 14$^{th}$ Edition). The mixture compressed to give tablets.

INDUSTRIAL APPLICABILITY

The compound of the present invention has a superior RORγt inhibitory action, and useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

This application is based on patent application No. 2013-140210 filed on Jul. 3, 2013 in Japan, the contents of which are encompassed in full herein.

The invention claimed is:
1. A compound represented by the following formula (I):

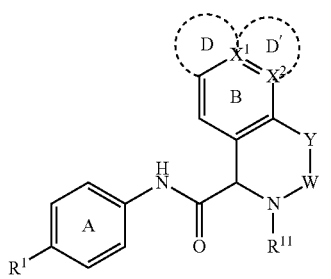

wherein
Ring A is a benzene ring optionally further substituted by 1 to 3 substituents selected from
(1) a halogen atom, and
(2) a cyano group;
$R^1$ is a group represented by the formula: $-Q(R^{1a})(R^{1b})(R^{1c})$
wherein
Q is a silicon atom, and
$R^{1a}$, $R^{1b}$ and $R^{1c}$ are each independently a $C_{1-6}$ alkyl group;
$R^{11}$ is $-CR^{12}R^{12'}-R^{12''}$, $-C(=O)-R^4$ or $-SO_2-R^{13}$;
$R^{12}$ is a $C_{1-6}$ alkyl group optionally substituted by 1 to 3 $C_{1-6}$ alkoxy-carbonyl groups and $R^{12'}$ and $R^{12''}$ are hydrogen atoms;
$R^4$ is
(1) a 5- or 6-membered monocyclic aromatic heterocyclic group optionally substituted by 1 to 5 substituents selected from
(a) a hydroxy group,
(b) a carboxy group, and
(c) a $C_{1-6}$ alkyl group,
(2) a 3- to 8-membered monocyclic non-aromatic heterocyclic group optionally substituted by 1 to 3 substituents selected from
(a) an oxo group,
(b) a $C_{1-6}$ alkyl group optionally substituted by 1 to 3 substituents selected from
(i) a carboxy group, and
(ii) a $C_{1-6}$ alkoxy-carbonyl optionally substituted by 1 to 3 $C_{6-14}$ aryl groups,
(c) a carboxy group,
(d) a hydroxy group, and
(e) a $C_{1-6}$ alkoxy group optionally substituted by 1 to 3 carboxy groups,
(3) a $C_{1-6}$ alkyl group optionally substituted by 1 to 5 substituents selected from (a) a 3- to 8-membered monocyclic non-aromatic heterocyclic group optionally substituted by 1 to 5 substituents selected from
(i) an oxo group, and
(ii) a $C_{1-6}$ alkyl group,
(b) a 5- or 6-membered monocyclic aromatic heterocyclic group optionally substituted by 1 to 3 substituents selected from
(i) a hydroxy group,
(ii) a $C_{1-6}$ alkyl group,
(iii) a $C_{1-6}$ alkoxy group, and
(iv) a carboxy group,
(c) a hydroxy group,
(d) a $C_{1-6}$ alkylsulfonyl group,
(e) a carboxy group,
(f) a 8- to 14-membered fused polycyclic aromatic heterocyclic group,
(g) a halogen atom,
(h) a cyano group,
(i) a $C_{1-6}$ alkoxy group optionally substituted by 1 to 3 carboxy groups,
(j) an amino group optionally mono- or di-substituted by $C_{1-6}$ alkyl group(s) optionally substituted by 1 to 3 carboxy groups, and
(k) a carbamoyl group,
(4) an amino group optionally mono- or di-substituted by substituent(s) selected from
(a) a 5- or 6-membered monocyclic aromatic heterocyclic group optionally substituted by 1 to 3 $C_{1-6}$ alkyl groups, and
(b) a $C_{1-6}$ alkyl group optionally substituted by 1 to 3 substituents selected from
(i) a $C_{1-6}$ alkoxy-carbonyl group optionally substituted by 1 to 3 $C_{6-14}$ aryl groups, and
(ii) a carboxy group,
(5) a carboxy group,
(6) a carbamoyl group,
(7) a $C_{2-6}$ alkenyl group optionally substituted by 1 to 3 carboxy groups,
(8) a $C_{1-6}$ alkyl-carbonyl group optionally substituted by 1 to 3 carboxy groups, or
(9) a $C_{1-6}$ alkoxy group optionally substituted by 1 to 3 carboxy groups;
$R^{13}$ is
(1) an amino group optionally mono- or di-substituted by substituent(s) selected from
(a) a $C_{1-6}$ alkoxy-carbonyl group, and
(b) a $C_{1-6}$ alkyl group optionally substituted by 1 to 3 carboxy groups, or
(2) a $C_{1-6}$ alkyl group optionally substituted by 1 to 3 substituents selected from a $C_{1-6}$ alkoxy-carbonyl group;

the partial structure represented by the formula:

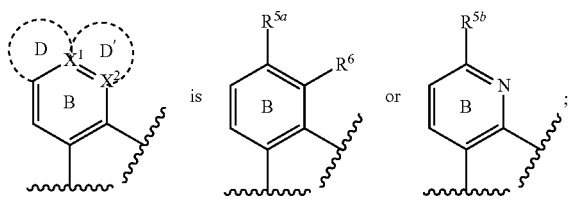

$R^{5a}$ and $R^{5b}$ are each independently
(1) a $C_{1-6}$ alkyl group optionally substituted by 1 to 3 substituents selected from a $C_{1-6}$ alkoxy group optionally substituted by 1 to 3 halogen atoms,
(2) a $C_{1-6}$ alkoxy group optionally substituted by 1 to 3 substituents selected from
  (a) a halogen atom, and
  (b) a $C_{3-10}$ cycloalkyl group,
(3) a $C_{1-6}$ alkylsulfonyl group,
(4) a cyano group,
(5) a cyclic amino group optionally substituted by 1 to 3 halogen atoms, or
(6) an oxetan-3-yloxy group;
$R^6$ is a hydrogen atom or a $C_{1-6}$ alkyl group;
$R^7$ is a $C_{1-6}$ alkyl group;
Y is a methylene group; and
W is a methylene group,
or a salt thereof.

2. The compound or salt of claim 1, wherein $R^1$ is a trimethylsilyl group or an ethyldimethylsilyl group.

3. The compound or salt of claim 1, wherein $R^4$ is
(1) a $C_{1-6}$ alkyl group optionally substituted by 1 to 3 substituents selected from (a) a halogen atom, (b) a cyano group, (c) a hydroxy group, (d) a 5- to 6-membered monocyclic aromatic heterocyclic group, (e) a 4- to 6-membered monocyclic non-aromatic heterocyclic group, and (f) a carboxy group,
(2) a 5- or 6-membered monocyclic aromatic heterocyclic group optionally substituted by 1 to 5 substituents selected from
  (a) a hydroxy group,
  (b) a carboxy group, and
  (c) a $C_{1-6}$ alkyl group,
or
(3) a 3- to 8-membered monocyclic non-aromatic heterocyclic group optionally substituted by 1 to 3 substituents selected from
  (a) an oxo group.
  (b) a $C_{1-6}$ alkyl group optionally substituted by 1 to 3 substituents selected from
    (i) a carboxy group, and
    (ii) a $C_{1-6}$ alkoxy-carbonyl optionally substituted by 1 to 3 $C_{6-14}$ aryl groups,
  (c) a carboxy group,
  (d) a hydroxy group, and
  (e) a $C_{1-6}$ alkoxy group optionally substituted by 1 to 3 carboxy groups.

4. The compound or salt of claim 1, wherein $R^{5a}$ is
(1) a $C_{1-6}$ alkyl group optionally substituted by 1 to 3 substituents selected from a $C_{1-6}$ alkoxy group optionally substituted by 1 to 3 halogen atoms,
(2) a $C_{1-6}$ alkoxy group optionally substituted by 1 to 3 substituents selected from
  (a) a halogen atom, and
  (b) a $C_{3-10}$ cycloalkyl group,
or
(3) a $C_{1-6}$ alkylsulfonyl group.

5. The compound or salt of claim 1, wherein $R^{5b}$ is
(1) a $C_{1-4}$ alkyl group optionally substituted by 1 to 3 substituents selected from a $C_{1-6}$ alkoxy group optionally substituted by 1 to 3 halogen atoms, or
(2) a $C_{1-4}$ alkoxy group optionally substituted by 1 to 3 substituents selected from
  (a) a halogen atom, and
  (b) a $C_{3-10}$ cycloalkyl group.

6. The compound or salt of claim 1, wherein $R^6$ is a hydrogen atom.

7. (1-(((5R)-5-((3,5-Difluoro-4-(trimethylsilyl)phenyl)carbamoyl)-2-methoxy-7,8-dihydro-1,6-naphthyridin-6(5H)-yl)carbonyl)azetidin-3-yl)acetic acid or a salt thereof.

8. A pharmaceutical composition comprising the compound or salt of claim 1, and a pharmaceutically acceptable carrier.

9. The pharmaceutical composition of claim 8, which is a RORγt inhibitor.

10. The pharmaceutical composition of claim 8, which is an agent for the treatment of psoriasis.

11. A method of inhibiting RORγt, which comprises administering an effective amount of the compound or salt of claim 1 to a mammal.

12. A method for the treatment of psoriasis, which comprises administering an effective amount of the compound or salt of claim 1 to a mammal.

13. 5-((1R)-1-((3,5-difluoro-4-(trimethylsilyl)phenyl)carbamoyl)-6-methoxy-3,4-dihydroisoquinolin-2(1H)-yl)-5-oxopentanoic acid or a salt thereof.

14. 5-((1R)-1-((3,5-difluoro-4-(trimethylsilyl)phenyl)carbamoyl)-6-(methoxymethyl)-3,4-dihydroisoquinolin-2(1H)-yl)-5-oxopentanoic acid or a salt thereof.

15. A compound represented by the following formula (I):

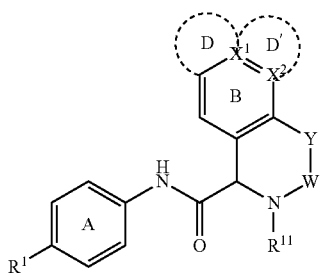

wherein
Ring A is a benzene ring optionally further substituted by 1 to 3 substituents selected from
(1) a halogen atom,
(2) a cyano group;
$R^1$ is a group represented by the formula: $-Q(R^{1a})(R^{1b})(R^{1c})$
wherein
Q is a silicon atom,
$R^{1a}$, $R^{1b}$, and $R^{1c}$ are each independently a $C_{1-6}$ alkyl group;
$R^{11}$ is $-CR^{12}R^{12'}-R_{12}''$, $-(=O)-R_4$ or $-SO_2-R^{13}$;

$R^{12'}$ is a $C_{1-6}$ alkyl group optionally substituted by 1 to 3 $C_{1-6}$ alkoxy-carbonyl groups, and $R^{12'}$ and $R^{12''}$ are hydrogen atoms;

$R^4$ is
(1) a 5- or 6-membered monocyclic aromatic heterocyclic group optionally substituted by 1 to 5 substituents selected from
  (a) a hydroxy group,
  (b) a carboxy group, and
  (c) a $C_{1-6}$ alkyl group,
(2) a 3- to 8-membered monocyclic non-aromatic heterocyclic group optionally substituted by 1 to 3 substituents selected from
  (a) an oxo group,
  (b) a $C_{1-6}$ alkyl group optionally substituted by 1 to 3 substituents selected from
    (i) a carboxy group, and
    (ii) a $C_{1-6}$ alkoxy-carbonyl optionally substituted by 1 to 3 $C_{6-14}$ aryl groups,
  (c) a carboxy group,
  (d) a hydroxy group, and
  (e) a $C_{1-6}$ alkoxy group optionally substituted by 1 to 3 carboxy groups,
(3) a $C_{1-6}$ alkyl group optionally substituted by 1 to 5 substituents selected from
  (a) a 3- to 8-membered monocyclic non-aromatic heterocyclic group optionally substituted by 1 to 5 substituents selected from
    (i) an oxo group, and
    (ii) a $C_{1-6}$ alkyl group,
  (b) a 5- or 6-membered monocyclic aromatic heterocyclic group optionally substituted by 1 to 3 substituents selected from
    (i) a hydroxy group,
    (ii) a $C_{1-6}$ alkyl group,
    (iii) a $C_{1-6}$ alkoxy group, and
    (iv) a carboxy group,
  (c) a hydroxy group,
  (d) a $C_{1-6}$ alkylsulfonyl group,
  (e) a carboxy group,
  (f) a 8- to 14-membered fused polycyclic aromatic heterocyclic group,
  (g) a halogen atom,
  (h) a cyano group,
  (i) a $C_{1-6}$ alkoxy group optionally substituted by 1 to 3 carboxy groups,
  (j) an amino group optionally mono- or di-substituted by $C_{1-6}$ alkyl group(s) optionally substituted by 1 to 3 carboxy groups, and
  (k) a carbamoyl group,
(4) an amino group optionally mono- or di-substituted by substituent(s) selected from
  (a) a 5- or 6-membered monocyclic aromatic heterocyclic group optionally substituted by 1 to 3 $C_{1-6}$ alkyl groups, and
  (b) a $C_{1-6}$ alkyl group optionally substituted by 1 to 3 substituents selected from
    (i) a $C_{1-6}$ alkoxy-carbonyl group optionally substituted by 1 to 3 $C_{6-14}$ aryl groups, and
    (ii) a carboxy group,
(5) a carboxy group,
(6) a carbamoyl group,
(7) a $C_{2-6}$ alkenyl group optionally substituted by 1 to 3 carboxy groups,
(8) a $C_{1-6}$ alkyl-carbonyl group optionally substituted by 1 to 3 carboxy groups, or (9) a $C_{1-6}$ alkoxy group optionally substituted by 1 to 3 carboxy groups;

$R^{13}$ is
(1) an amino group optionally mono- or di-substituted by substituent(s) selected from
  (a) a $C_{1-6}$ alkoxy-carbonyl group, and
  (b) a $C_{1-6}$ alkyl group optionally substituted by 1 to 3 carboxy groups, or
(2) a $C_{1-6}$ alkyl group optionally substituted by 1 to 3 substituents selected from a $C_{1-6}$ alkoxy-carbonyl group;

the partial structure represented by the formula:

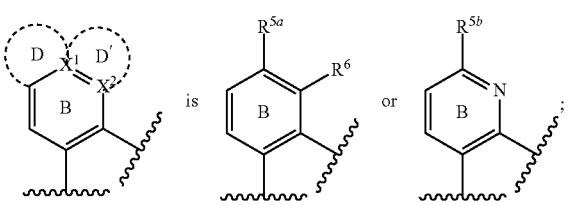

$R^{5a}$ is
(1) a $C_{1-6}$ alkyl group optionally substituted by 1 to 3 substituents selected from a $C_{1-6}$ alkoxy group optionally substituted by 1 to 3 halogen atoms,
(2) a $C_{1-6}$ alkoxy group optionally substituted by 1 to 3 substituents selected from
  (a) a halogen atom, and
  (b) a $C_{3-10}$ cycloalkyl group,
(3) a $C_{1-6}$ alkylsulfonyl group,
(4) a cyano group,
(5) a cyclic amino group optionally substituted by 1 to 3 halogen atoms, or
(6) an oxetan-3-yloxy group;

$R^{5b}$ is
(1) a $C_{1-6}$ alkyl group optionally substituted by 1 to 3 $C_{1-6}$ alkoxy groups, or
(2) a $C_{1-6}$ alkoxy group optionally substituted by 1 to 3 halogen atoms;
$R^6$ is a hydrogen atom or a $C_{1-6}$ alkyl group;
$R^7$ is a $C_{1-6}$ alkyl group;
Y is a methylene group; and
W is a methylene group,
or a salt thereof.

16. A compound represented by the following formula (I):

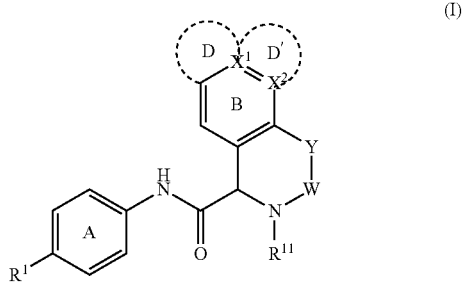

wherein
Ring A is a benzene ring optionally further substituted by 1 to 3 substituents selected from
(1) a halogen atom, and
(2) a cyano group;

R¹ is a group represented by the formula: -Q(R¹ᵃ)(R¹ᵇ)(R¹ᶜ)

wherein

Q is a silicon atom, and

R¹ᵃ, R¹ᵇ and R¹ᶜ are each independently a $C_{1-6}$ alkyl group;

R¹¹ is —C(=O)—R⁴;

R⁴ is (1) a 5- or 6-membered monocyclic aromatic heterocyclic group optionally substituted by 1 to 3 hydroxy groups, (2) a 3- to 8-membered monocyclic non-aromatic heterocyclic group optionally substituted by 1 to 3 substituents selected from
  (a) an oxo group, and
  (b) a $C_{1-6}$ alkyl group optionally substituted by 1 to 3 carboxy groups, (3) a $C_{1-6}$ alkyl group optionally substituted by 1 to 5 substituents selected from
  (a) a 3- to 8-membered monocyclic non-aromatic heterocyclic group optionally substituted by 1 to 3 oxo groups,
  (b) a 5- or 6-membered monocyclic aromatic heterocyclic group optionally substituted by 1 to 3 substituents selected from
    (i) a hydroxy group,
    (ii) a $C_{1-6}$ alkyl group, and
    (iii) a $C_{1-6}$ alkoxy group,
  (c) a hydroxy group,
  (d) a carboxy group,
  (e) a halogen atom,
  (f) a cyano group, and
  (g) a carbamoyl group, (4) an amino group optionally mono- or di-substituted by substituent(s) selected from a $C_{1-6}$ alkyl group optionally substituted by 1 to 3 carboxy groups, or (5) a $C_{2-6}$ alkenyl group optionally substituted by 1 to 3 carboxy groups;

the partial structure represented by the formula:

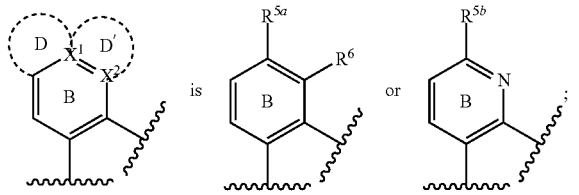

is $R^{5a}$ and $R^{5b}$ are each independently (1) a $C_{1-6}$ alkyl group optionally substituted by 1 to 3 $C_{1-6}$ alkoxy groups, (2) a $C_{1-6}$ alkoxy group optionally substituted by 1 to 3 halogen atoms, or (3) a $C_{1-6}$ alkylsulfonyl group;

R⁶ is a hydrogen atom;

Y is a methylene group; and

W is a methylene group, or a salt thereof.

17. A compound represented by the following formula (I):

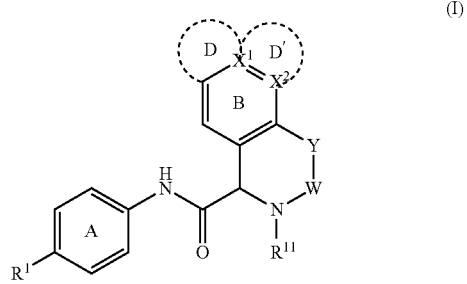

(I)

wherein

Ring A is a benzene ring optionally further substituted by 1 to 3 substituents selected from
(1) a halogen atom, and
(2) a cyano group;

R¹ is a group represented by the formula: -Q(R¹ᵃ)(R¹ᵇ)(R¹ᶜ)

wherein

Q is a silicon atom, and

R¹ᵃ, R¹ᵇ, and R¹ᶜ are each independently a $C_{1-6}$ alkyl group;

R¹¹ is —C(=O)—R⁴;

R⁴ is (1) a 5- or 6-membered monocyclic aromatic heterocyclic group optionally substituted by 1 to 3 hydroxy groups, (2) a 3- to 8-membered monocyclic non-aromatic heterocyclic group optionally substituted by 1 to 3 substituents selected from
  (a) an oxo group, and
  (b) a $C_{1-6}$ alkyl group optionally substituted by 1 to 3 carboxy groups, (3) a $C_{1-6}$ alkyl group optionally substituted by 1 to 5 substituents selected from
  (a) a 3- to 8-membered monocyclic non-aromatic heterocyclic group optionally substituted by 1 to 3 oxo groups,
  (b) a 5- or 6-membered monocyclic aromatic heterocyclic group optionally substituted by 1 to 3 substituents selected from
    (i) a hydroxy group,
    (ii) a $C_{1-6}$ alkyl group, and
    (iii) a $C_{1-6}$ alkoxy group,
  (c) a hydroxy group,
  (d) a carboxy group,
  (e) a halogen atom,
  (f) a cyano group, and
  (g) a carbamoyl group, (4) an amino group optionally mono- or di-substituted by substituent(s) selected from a $C_{1-6}$ alkyl group optionally substituted by 1 to 3 carboxy groups, or (5) a $C_{2-6}$ alkenyl group optionally substituted by 1 to 3 carboxy groups;

the partial structure represented by the formula:

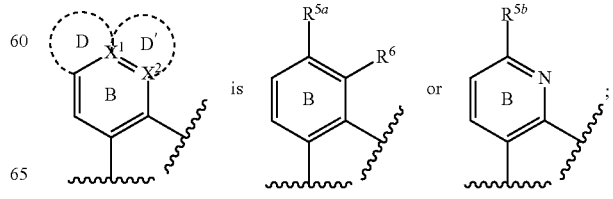

$R^{5a}$ is
(1) a $C_{1-6}$ alkyl group optionally substituted by 1 to 3 $C_{1-6}$ alkoxy groups,
(2) a $C_{1-6}$ alkoxy group optionally substituted by 1 to 3 halogen atoms, or
(3) a $C_{1-6}$ alkylsulfonyl group;
$R^{5b}$ is
(1) a $C_{1-6}$ alkyl group optionally substituted by 1 to 3 $C_{1-6}$ alkoxy groups, or
(2) a $C_{1-6}$ alkoxy group;
$R^6$ is a hydrogen atom;
Y is a methylene group; and
W is a methylene group,
or a salt thereof.

18. A compound represented by the following formula (I):

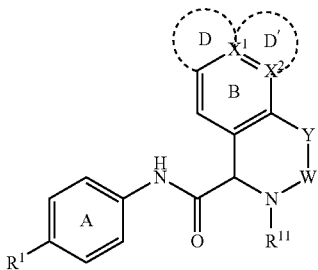

wherein
Ring A is a benzene ring optionally further substituted by 1 to 3 halogen atoms;

$R^1$ is a group represented by the formula: $-Q(R^{1a})(R^{1b})(R^{1c})$
wherein
Q is a silicon atom, and
$R^{1a}$, $R^{1b}$ and $R^{1c}$ are each independently a $C_{1-6}$ alkyl group;
$R^{11}$ is $-C(=O)-R^4$;
$R^4$ is
(1) a 3- to 8-membered monocyclic non-aromatic heterocyclic group optionally substituted by 1 to 3 substituents selected from a $C_{1-6}$ alkyl group optionally substituted by 1 to 3 carboxy groups, or
(2) a $C_{1-6}$ alkyl group optionally substituted by 1 to 3 carboxy groups;
the partial structure represented by the formula:

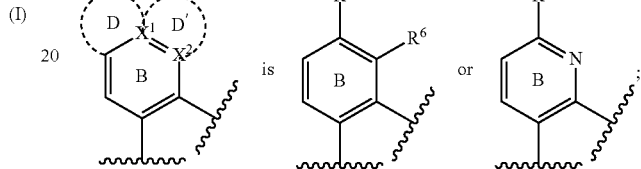

$R^{5a}$ and $R^{5b}$ are each independently a $C_{1-6}$ alkoxy group;
$R^6$ is a hydrogen atom;
Y is a methylene group; and
W is a methylene group,
or a salt thereof.

* * * * *

UNITED STATES PATENT AND TRADEMARK OFFICE
CERTIFICATE OF CORRECTION

PATENT NO.         : 10,053,468 B2                                          Page 1 of 1
APPLICATION NO.    : 14/902309
DATED              : August 21, 2018
INVENTOR(S)        : Satoshi Yamamoto et al.

It is certified that error appears in the above-identified patent and that said Letters Patent is hereby corrected as shown below:

In the Claims

In Column 504, Line 66, Claim 15, "-CR$^{12}$R$^{12'}$-R$_{12}$''" should read -- -CR$^{12}$R$^{12'}$-R$^{12''}$ --.

In Column 504, Line 66, Claim 15, "-(=O)-R$_4$" should read -- -C(=O)-R$^4$ --.

In Column 505, Line 2, Claim 15, "R$^{12}$ 40" should read -- R$^{12'}$ --.

Signed and Sealed this
Fourth Day of December, 2018

Andrei Iancu
*Director of the United States Patent and Trademark Office*

SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence

```
<220> FEATURE:
<223> OTHER INFORMATION: SRC-1 peptide

<400> SEQUENCE: 1

Cys Leu Thr Ala Arg His Lys Ile Leu His Arg Leu Leu Gln Glu Gly
1               5                   10                  15

Ser Pro Ser Asp
            20
```